United States Patent
Cirillo et al.

(10) Patent No.: US 12,325,870 B2
(45) Date of Patent: Jun. 10, 2025

(54) SOLUBILIZED APYRASES, METHODS AND USE

(71) Applicant: NOVARTIS AG, Basel (CH)

(72) Inventors: Agostino Cirillo, Basel (CH); Hilmar Ebersbach, Wallisellen (CH); Boerje Haraldsson, Basel (CH); Thomas Huber, Allschwil (CH); Guido Junge, Basel (CH); Regina Link, Münchenstein (CH); Max Warncke, Basel (CH); Chao Zou, Allschwil (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 17/261,533

(22) PCT Filed: Jul. 17, 2019

(86) PCT No.: PCT/IB2019/056117
§ 371 (c)(1),
(2) Date: Jan. 19, 2021

(87) PCT Pub. No.: WO2020/016804
PCT Pub. Date: Jan. 23, 2020

(65) Prior Publication Data
US 2022/0356455 A1    Nov. 10, 2022

(30) Foreign Application Priority Data
Jul. 18, 2018  (EP) .................... 18184269

(51) Int. Cl.
*C12N 9/14*     (2006.01)
*A61K 38/46*    (2006.01)
*A61K 45/06*    (2006.01)
*A61K 38/00*    (2006.01)

(52) U.S. Cl.
CPC .............. *C12N 9/14* (2013.01); *A61K 38/465* (2013.01); *A61K 45/06* (2013.01); *A61K 38/00* (2013.01); *C12Y 306/01005* (2013.01)

(58) Field of Classification Search
None
See application file for complete search history.

(56) References Cited

U.S. PATENT DOCUMENTS

| | | |
|---|---|---|
| 7,247,300 B1 | 7/2007 | Chen et al. |
| 2002/0002277 A1* | 1/2002 | Maliszewski .... C07K 14/70596 536/23.5 |
| 2002/0173005 A1 | 11/2002 | Ford et al. |
| 2013/0142775 A1 | 6/2013 | Chen et al. |

FOREIGN PATENT DOCUMENTS

| | | |
|---|---|---|
| WO | 0023459 A1 | 4/2000 |
| WO | 0111949 A1 | 2/2001 |
| WO | 2011/088231 A1 | 7/2011 |
| WO | 2020/016804 A1 | 1/2020 |

OTHER PUBLICATIONS

Moeckel et al., "Optimizing human apyrase to treat arterial thrombosis and limit reperfusion injury without increasing bleeding risk", Science Translational Medicine, vol. 6(248), pp. 1-24. (Year: 2014).*
Schulte, et al. Structural elements and limited proteolysis of CD39 influence ATP diphosphohydrolase activity. Biochemistry. Feb. 23, 1999;38(8):2248-58. (Year: 1999).*
Moeckel et al., Science Translational Medicine, 6(248):248ra105-248ra105 (2014).
Musi et al., Archives of Biochemistry and Biophysics, 461(1):30-39 (2007).
Drosopoulos et al., Biochemistry, 39(23):6936-6943 (2000).
Gayle et al., Journal of Clinical Investigation, (101(9):1851-1859 (1998).
Dai et al., Cell, 116(5):649-659 (2004).
Mundipharma Pharmaceuticals Limited, Internet Citation, pp. 1-14, 2013, Retrieved from the Internet: URL:http://www.medicines/ie/printfriendlydocument.aspx?documentid=14383&companyid=103.
Smith et al., Biochemistry, 38(18):5849-5857 (1999).
Yang et al., Biochemistry, 43(28):9185-9194 (2004).
Yang et al., Thrombosis Research, 122(4):541-548 (2008).
Whisstock et al., "Prediction of Protein Function From Protein Sequence and Structure," Quarterly Reviews of Biophysics, 2003, vol. 36, No. 3, pp. 307-340.
Witkowski et al., "Coversion of a beta-Ketoacyl Synthase to a Malonyl Decarboxylase by Replacement . . . ," Biochemistry, 1999, vol. 38, pp. 11643-11650.
Seffernick et al., "Melamine Deaminase and Atrazine Chlorohydrolase: 98 Percent Identical . . . ," Journal of Bacteriology, 2001, vol. 183, No. 8, pp. 2405-2410.
Roberts, et al., The Differential Effect of Apyrase Treatment and hCD39 Overexpression on Chronic Renal Fibrosis After Ischemia-Reperfusion Injury, Transplantation, Jul. 2017, e194-e204, 101(7).

* cited by examiner

*Primary Examiner* — Nghi V Nguyen
(74) *Attorney, Agent, or Firm* — David Goetz

(57) ABSTRACT

Provided herein are solubilized apyrase polypeptides, nucleotides encoding such solubilized apyrase polypeptides, pharmaceutical compositions containing such solubilized apyrase polypeptides, therapeutic uses of such solubilized apyrase polypeptides. Also provided herein are methods useful for preventing or treating tissue damage, e.g., by administering a solubilized apyrase polypeptide or pharmaceutical composition thereof, and methods for producing such solubilized apyrase polypeptides.

8 Claims, 12 Drawing Sheets

Specification includes a Sequence Listing.

```
wtCD39          1   MEDTKESNVKTFCSKNILAILGFSSIIAVIALLAVGLTQNKALPENVKYG    50
                                                       ||||||||||||||
CD39deltaMIL    1   ---------------------------------TQNKALPENVKYG      13 wtCD39         51   IVLDAGSSHTSLYIYKWPAEKENDTGVVHQVEECRVKGPGISKFVQKVNE   100
                    ||||||||||||||||||||||||||||||||||||||||||||||||||
CD39deltaMIL   14   IVLDAGSSHTSLYIYKWPAEKENDTGVVHQVEECRVKGPGISKFVQKVNE    63 wtCD39        101   IGIYLTDCMERAREVIPRSQHQETPVYLGATAGMRLLRMESEELADRVLD   150
                    ||||||||||||||||||||||||||||||||||||||||||||||||||
CD39deltaMIL   64   IGIYLTDCMERAREVIPRSQHQETPVYLGATAGMRLLRMESEELADRVLD   113 wtCD39        151   VVERSLSNYPFDFQGARIITGQEEGAYGWITINYLLGKFSQKTRWFSIVP   200
                    |||||||||||||||||||||||||||||||||||||||||
CD39deltaMIL  114   VVERSLSNYPFDFQGARIITGQEEGAYGWITINYLLGKFSQK--------   155 wtCD39        201   YETNNQETFGALDLGGASTQVTFVPQNQTIESPDNALQFRLYGKDYNVYT   250
                        ||||||||||||||||||||||||||||||||||||||||||||||
CD39deltaMIL  156   ----NQETFGALDLGGASTQVTFVPQNQTIESPDNALQFRLYGKDYNVYT   201 wtCD39        251   HSFLCYGKDQALWQKLAKDIQVASNEILRDPCFHPGYKKVVNVSDLYKTP   300
                    ||||||||||||||||||||||||||||||||||||||||||||||||||
CD39deltaMIL  202   HSFLCYGKDQALWQKLAKDIQVASNEILRDPCFHPGYKKVVNVSDLYKTP   251 wtCD39        301   CTKRFEMTLPFQQFEIQGIGNYQQCHQSILELFNTSYCPYSQCAFNGIFL   350
                    ||||||||||||||||||||||||||||||||||||||||||||||||||
CD39deltaMIL  252   CTKRFEMTLPFQQFEIQGIGNYQQCHQSILELFNTSYCPYSQCAFNGIFL   301 wtCD39        351   PPLQGDFGAFSAFYFVMKFLNLTSEKVSQEKVTEMMKKFCAQPWEEIKTS   400
                    ||||||||||||||||||||||||||||||||||||||||||||||||||
CD39deltaMIL  302   PPLQGDFGAFSAFYFVMKFLNLTSEKVSQEKVTEMMKKFCAQPWEEIKTS   351 wtCD39        401   YAGVKEKYLSEYCFSGTYILSLLLQGYHFTADSWEHIHFIGKIQGSDAGW   450
                    ||||||||||||||||||||||||||||||||||||||||||||||||||
CD39deltaMIL  352   YAGVKEKYLSEYCFSGTYILSLLLQGYHFTADSWEHIHFIGKIQGSDAGW   401 wtCD39        451   TLGYMLNLTNMIPAEQPLSTPLSHSTYVFLMVFSLVLFTVAIIGLLIFH   500
                    |||||||||||||||||||||||||||
CD39deltaMIL  402   TLGYMLNLTNMIPAEQPLSTPLSHST-----------------------   427 wtCD39        501   KPSYFWKDMV      510

CD39deltaMIL  427   ----------      427
```

FIG 1

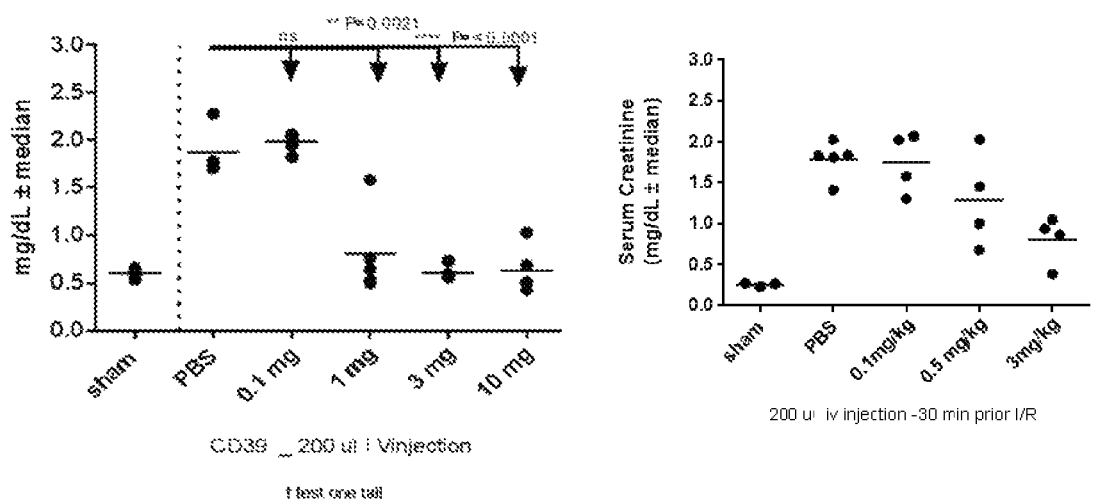
FIG 12A
FIG 12B
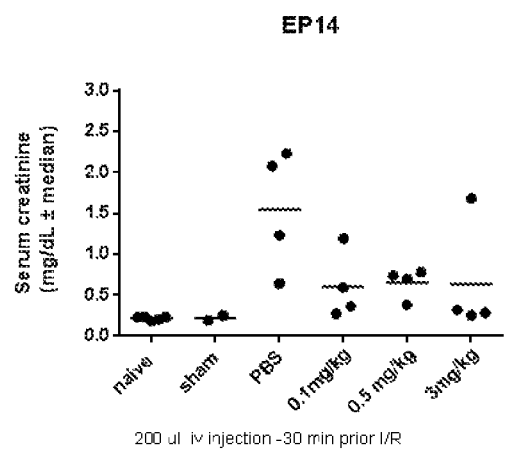
FIG 12C

SEQUENCE LISTING

<160> NUMBER OF SEQ ID NOS: 253

<210> SEQ ID NO 1
<211> LENGTH: 510
<212> TYPE: PRT
<213> ORGANISM: Homo sapiens

<400> SEQUENCE: 1

Met Glu Asp Thr Lys Glu Ser Asn Val Lys Thr Phe Cys Ser Lys Asn
1               5                   10                  15

Ile Leu Ala Ile Leu Gly Phe Ser Ser Ile Ala Val Ile Ala Leu
            20                  25                  30

Leu Ala Val Gly Leu Thr Gln Asn Lys Ala Leu Pro Glu Asn Val Lys
            35                  40                  45

Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
        115                 120                 125

Gly Ala Thr Ala Gly Met Arg Leu Leu Arg Met Glu Ser Glu Glu Leu
    130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
        195                 200                 205

Phe Gly Ala Leu Asp Leu Gly Gly Ala Ser Thr Gln Val Thr Phe Val
    210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
            260                 265                 270

Ala Ser Asn Glu Ile Leu Arg Asp Pro Cys Phe His Pro Gly Tyr Lys
        275                 280                 285

```
Lys Val Val Asn Val Ser Asp Leu Tyr Lys Thr Pro Cys Thr Lys Arg
    290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
                340                 345                 350

Leu Gln Gly Asp Phe Gly Ala Phe Ser Ala Phe Tyr Phe Val Met Lys
                355                 360                 365

Phe Leu Asn Leu Thr Ser Glu Lys Val Ser Gln Glu Lys Val Thr Glu
    370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Leu Gln Gly Tyr His Phe Thr Ala Asp
                420                 425                 430

Ser Trp Glu His Ile His Phe Ile Gly Lys Ile Gln Gly Ser Asp Ala
    435                 440                 445

Gly Trp Thr Leu Gly Tyr Met Leu Asn Leu Thr Asn Met Ile Pro Ala
    450                 455                 460

Glu Gln Pro Leu Ser Thr Pro Leu Ser His Ser Thr Tyr Val Phe Leu
465                 470                 475                 480

Met Val Leu Phe Ser Leu Val Leu Phe Thr Val Ala Ile Ile Gly Leu
                485                 490                 495

Leu Ile Phe His Lys Pro Ser Tyr Phe Trp Lys Asp Met Val
                500                 505                 510

<210> SEQ ID NO 2
<211> LENGTH: 511
<212> TYPE: PRT
<213> ORGANISM: Rattus norvegicus

<400> SEQUENCE: 2

Met Glu Asp Ile Lys Asp Ser Lys Val Lys Arg Phe Cys Ser Lys Asn
1               5                   10                  15

Ile Leu Ile Ile Leu Gly Phe Ser Ser Val Leu Ala Val Ile Ala Leu
                20                  25                  30

Ile Ala Val Gly Leu Thr His Asn Lys Pro Leu Pro Glu Asn Val Lys
                35                  40                  45

Tyr Gly Ile Val Leu Asp Ala Gly Ser Ser His Thr Asn Leu Tyr Ile
    50                  55                  60

Tyr Lys Trp Pro Ala Glu Lys Glu Asn Asp Thr Gly Val Val Gln Leu
65                  70                  75                  80

Leu Glu Glu Cys Gln Val Lys Gly Pro Gly Ile Ser Lys Tyr Ala Gln
                85                  90                  95

Lys Thr Asp Glu Ile Ala Ala Tyr Leu Ala Glu Cys Met Lys Met Ser
                100                 105                 110

Thr Glu Arg Ile Pro Ala Ser Lys Gln His Gln Thr Pro Val Tyr Leu
                115                 120                 125

Gly Ala Thr Ala Gly Met Arg Leu Leu Arg Met Glu Ser Lys Gln Ser
    130                 135                 140

Ala Asp Glu Val Leu Ala Ala Val Ser Arg Ser Leu Lys Ser Tyr Pro
```

```
                    145                 150                 155                 160
        Phe Asp Phe Gln Gly Ala Lys Ile Ile Thr Gly Gln Glu Glu Gly Ala
                        165                 170                 175

Tyr Gly Trp Ile Thr Ile Asn Tyr Leu Leu Gly Arg Phe Thr Gln Glu
                        180                 185                 190

Gln Ser Trp Leu Asn Phe Ile Ser Asp Ser Gln Lys Gln Ala Thr Phe
                        195                 200                 205

Gly Ala Leu Asp Leu Gly Gly Ser Ser Thr Gln Val Thr Phe Val Pro
                        210                 215                 220

Leu Asn Gln Thr Leu Glu Ala Pro Glu Thr Ser Leu Gln Phe Arg Leu
        225                 230                 235                 240

Tyr Gly Thr Asp Tyr Thr Val Tyr Thr His Ser Phe Leu Cys Tyr Gly
                        245                 250                 255

Lys Asp Gln Ala Leu Trp Gln Lys Leu Ala Gln Asp Ile Gln Val Ser
                        260                 265                 270

Ser Gly Gly Ile Leu Lys Asp Pro Cys Phe Tyr Pro Gly Tyr Lys Lys
                        275                 280                 285

Val Val Asn Val Ser Glu Leu Tyr Gly Thr Pro Cys Thr Lys Arg Phe
        290                 295                 300

Glu Lys Lys Leu Pro Phe Asn Gln Phe Gln Val Gln Gly Thr Gly Asp
        305                 310                 315                 320

Tyr Glu Gln Cys His Gln Ser Ile Leu Lys Phe Phe Asn Asn Ser His
                        325                 330                 335

Cys Pro Tyr Ser Gln Cys Ala Phe Asn Gly Val Phe Leu Pro Pro Leu
                        340                 345                 350

Gln Gly Ser Phe Gly Ala Phe Ser Ala Phe Tyr Phe Val Met Asp Phe
                        355                 360                 365

Phe Lys Lys Met Ala Asn Asp Ser Val Ser Ser Gln Glu Lys Met Thr
                        370                 375                 380

Glu Ile Thr Lys Asn Phe Cys Ser Lys Pro Trp Glu Glu Val Lys Ala
        385                 390                 395                 400

Ser Tyr Pro Thr Val Lys Glu Lys Tyr Leu Ser Glu Tyr Cys Phe Ser
                        405                 410                 415

Gly Thr Tyr Ile Leu Ser Leu Leu Gln Gly Tyr Asn Phe Thr Gly
                        420                 425                 430

Thr Ser Trp Asp Gln Ile His Phe Met Gly Lys Ile Lys Asp Ser Asn
                        435                 440                 445

Ala Gly Trp Thr Leu Gly Tyr Met Leu Asn Leu Thr Asn Met Ile Pro
        450                 455                 460

Ala Glu Gln Pro Leu Ser Pro Pro Leu Pro His Ser Thr Tyr Ile Ser
        465                 470                 475                 480

Leu Met Val Leu Phe Ser Leu Val Leu Val Ala Met Val Ile Thr Gly
                        485                 490                 495

Leu Phe Ile Phe Ser Lys Pro Ser Tyr Phe Trp Lys Glu Ala Val
                        500                 505                 510

<210> SEQ ID NO 3
<211> LENGTH: 441
<212> TYPE: PRT
<213> ORGANISM: Homo sapiens

<400> SEQUENCE: 3

Gln Ile His Lys Gln Glu Val Leu Pro Pro Gly Leu Lys Tyr Gly Ile
1               5                   10                  15
```

-continued

Val Leu Asp Ala Gly Ser Ser Arg Thr Val Tyr Val Tyr Gln Trp
            20                  25                  30

Pro Ala Glu Lys Glu Asn Asn Thr Gly Val Val Ser Gln Thr Phe Lys
                35                  40                  45

Cys Ser Val Lys Gly Ser Gly Ile Ser Ser Tyr Gly Asn Asn Pro Gln
 50                  55                  60

Asp Val Pro Arg Ala Phe Glu Glu Cys Met Gln Lys Val Lys Gly Gln
 65                  70                  75                  80

Val Pro Ser His Leu His Gly Ser Thr Pro Ile His Leu Gly Ala Thr
                85                  90                  95

Ala Gly Met Arg Leu Leu Arg Leu Gln Asn Glu Thr Ala Ala Asn Glu
                100                 105                 110

Val Leu Glu Ser Ile Gln Ser Tyr Phe Lys Ser Gln Pro Phe Asp Phe
            115                 120                 125

Arg Gly Ala Gln Ile Ile Ser Gly Gln Glu Glu Gly Val Tyr Gly Trp
            130                 135                 140

Ile Thr Ala Asn Tyr Leu Met Gly Asn Phe Leu Glu Lys Asn Leu Trp
145                 150                 155                 160

His Met Trp Val His Pro His Gly Val Glu Thr Thr Gly Ala Leu Asp
                165                 170                 175

Leu Gly Gly Ala Ser Thr Gln Ile Ser Phe Val Ala Gly Glu Lys Met
                180                 185                 190

Asp Leu Asn Thr Ser Asp Ile Met Gln Val Ser Leu Tyr Gly Tyr Val
            195                 200                 205

Tyr Thr Leu Tyr Thr His Ser Phe Gln Cys Tyr Gly Arg Asn Glu Ala
210                 215                 220

Glu Lys Lys Phe Leu Ala Met Leu Leu Gln Asn Ser Pro Thr Lys Asn
225                 230                 235                 240

His Leu Thr Asn Pro Cys Tyr Pro Arg Asp Tyr Ser Ile Ser Phe Thr
                245                 250                 255

Met Gly His Val Phe Asp Ser Leu Cys Thr Val Asp Gln Arg Pro Glu
            260                 265                 270

Ser Tyr Asn Pro Asn Asp Val Ile Thr Phe Glu Gly Thr Gly Asp Pro
            275                 280                 285

Ser Leu Cys Lys Glu Lys Val Ala Ser Ile Phe Asp Phe Lys Ala Cys
 290                 295                 300

His Asp Gln Glu Thr Cys Ser Phe Asp Gly Val Tyr Gln Pro Lys Ile
305                 310                 315                 320

Lys Gly Pro Phe Val Ala Phe Ala Gly Phe Tyr Tyr Thr Ala Ser Ala
                325                 330                 335

Leu Asn Leu Ser Gly Ser Phe Ser Leu Asp Thr Phe Asn Ser Ser Thr
            340                 345                 350

Trp Asn Phe Cys Ser Gln Asn Trp Ser Gln Leu Pro Leu Leu Leu Pro
            355                 360                 365

Lys Phe Asp Glu Val Tyr Ala Arg Ser Tyr Cys Phe Ser Ala Asn Tyr
 370                 375                 380

Ile Tyr His Leu Phe Val Asn Gly Tyr Lys Phe Thr Glu Glu Thr Trp
385                 390                 395                 400

Pro Gln Ile His Phe Glu Lys Glu Val Gly Asn Ser Ser Ile Ala Trp
                405                 410                 415

Ser Leu Gly Tyr Met Leu Ser Leu Thr Asn Gln Ile Pro Ala Glu Ser
            420                 425                 430

Pro Leu Ile Arg Leu Pro Ile Glu Pro

```
                    435                 440
```

<210> SEQ ID NO 4
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350
```

```
Ala Gly Val Lys Glu Lys Tyr Leu Ser Glu Tyr Cys Phe Ser Gly Thr
        355                 360                 365

Tyr Ile Leu Ser Leu Leu Leu Gln Gly Tyr His Phe Thr Ala Asp Ser
    370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425

<210> SEQ ID NO 5
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 5
acccagaaca aggccctgcc cgagaacgtg aagtacggca tcgtgctgga tgccggcagc      60
agccacacca gcctgtacat ctacaagtgg cctgccgaga agaaaacga caccggcgtg     120 gtgcatcagg tggaagagtg cagagtgaag ggccctggca tcagcaagtt cgtgcagaaa    180
gtgaacgaga tcggcatcta cctgaccgac tgcatggaac gggccaggga agtgatcccc    240
agaagccagc accaggaaac ccccgtgtat ctgggagcca ccgccggcat gagactgctg    300
agaatggaaa gcgaggaact ggccgaccgg gtgctggacg tggtggaaag aagcctgagc    360
aactacccat cgatttttca aggcgccaga atcatccacg ccaggaaga aggcgcctac    420 ggctggatca ccatcaacta cctgctgggc aagttcagcc agaagaatca ggaaaccttc    480
ggcgccctgg acctgggcgg agcttctacc caagtgacct cgtgcccca gaatcagacc    540 atcgagagcc ccgacaacgc cctgcagttc cggctgtacg gcaaggacta caatgtgtac    600
acccacagct ttctgtgcta cggaaaggac caggctctgt ggcagaagct ggccaaggac    660
atccaggtgg ccagcaacga gatcctgcgg gaccctttgct tccaccccgg ctacaagaaa    720
gtcgtgaacg tgtccgacct gtacaagacc ccctgcacca agagattcga gatgaccctg    780
cccttccagc agttcgagat ccagggcatc ggcaattacc agcagtgcca ccagagcatc    840
ctggaactgt tcaacaccag ctactgcccc tacagccagt gcgccttcaa cggcatcttc    900
ctgccacctc tgcaggggga tttcggcgcc ttcagcgcct ctacttcgt gatgaagttc    960 ctgaacctga ccagcgagaa ggtgtccag gaaaaagtga cagagatgat gaagaagttc   1020
tgcgcccagc cctgggagga aatcaagacc tcctacgctg gcgtgaaaga gaagtacctg   1080
agcgagtact gcttcagcgg cacctacatc ctgagcctgc tgctgcaggg ctaccacttc   1140
accgccgata gctgggagca catccacttc atcggcaaga ttcagggcag cgacgccggc   1200
tggacactgg gctacatgct gaatctgacc aacatgatcc ccgccgagca gcccctgagc   1260
acacctctga gccacagcac c                                             1281

<210> SEQ ID NO 6
<211> LENGTH: 427
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 6

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Met Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
        355                 360                 365

Tyr Ile Leu Ser Leu Leu Leu Gln Gly Tyr His Phe Thr Ala Asp Ser
    370                 375                 380

Trp Glu His Ile His Phe Ile Gly Lys Ile Gln Gly Ser Asp Ala Gly
385                 390                 395                 400
```

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425

<210> SEQ ID NO 7
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 7

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120
gtgcatcagg tggaagagtg cagagtgaag ggccctggca tcagcaagtt cgtgcagaaa    180
gtgaacgaga tcggcatcta cctgaccgac tgcatggaac gggccatgga agtgatcccc    240
agaagccagc accaggaaac ccccgtgtat ctgggagcca ccgccggcat gagactgctg    300
agaatggaaa gcgaggaact ggccgaccgg gtgctggacg tggtggaaag aagcctgagc    360
aactacccat cgattttca aggcgccaga atcatcaccg ccaggaaga aggcgcctac      420
ggctggatca ccatcaacta cctgctgggc aagttcagcc agaagaatca ggaaaccttc    480
ggcgccctgg acctgggcgg agcttctacc caagtgacct tcgtgcccca gaatcagacc    540
atcgagagcc ccgacaacgc cctgcagttc ggctgtacg gcaaggacta caatgtgtac    600
acccacagct ttctgtgcta cggaaaggac caggctctgt ggcagaagct ggccaaggac    660
atccaggtgg ccagcaacga gatcctgcgg gacccttgct tccaccccgg ctacaagaaa    720
gtcgtgaacg tgtccgacct gtacaagacc ccctgcacca agagattcga gatgaccctg    780
cccttccagc agttcgagat ccagggcatc ggcaattacc agcagtgcca ccagagcatc    840
ctggaactgt tcaacaccag ctactgcccc tacagccagt gcgccttcaa cggcatcttc    900
ctgccacctc tgcaggggga tttcggcgcc ttcagcgcct ctacttcgt gatgaagttc    960
ctgaacctga ccagcgagaa ggtgtcccag gaaaaagtga cagagatgat gaagaagttc   1020
tgcgcccagc cctgggagga aatcaagacc tcctacgctg gcgtgaaaga gaagtacctg   1080
agcgagtact gcttcagcgg cacctacatc ctgagcctgc tgctgcaggg ctaccacttc   1140
accgccgata gctgggagca catccacttc atcggcaaga ttcagggcag cgacgccggc   1200
tggacactgg gctacatgct gaatctgacc aacatgatcc ccgccgagca gcccctgagc   1260
acacctctga gccacagcac c                                              1281
```

<210> SEQ ID NO 8
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala

```
            20                  25                  30
Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
 50                  55                  60

Gly Ile Tyr Leu Thr Asp Cys Met Glu Arg Ala Met Glu Val Ile Pro
 65                  70                  75                  80

Arg Ser Gln His Gln Glu Thr Pro Val Tyr Leu Gly Ala Thr Ala Gly
                 85                  90                  95

Met Arg Leu Leu Arg Met Glu Ser Glu Leu Ala Asp Arg Val Met
        100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Gly Ala Tyr Gly Trp Ile Thr
        130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
        180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
        210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
        260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
        290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
        340                 345                 350

Ala Gly Val Lys Glu Lys Tyr Leu Ser Glu Tyr Cys Phe Ser Gly Thr
        355                 360                 365

Tyr Ile Leu Ser Leu Leu Leu Gln Gly Tyr His Phe Thr Ala Asp Ser
        370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
        420                 425

<210> SEQ ID NO 9
```

```
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
acccagaaca aggccctgcc cgagaacgtg aagtacggca tcgtgctgga tgccggcagc      60
agccacacca gcctgtacat ctacaagtgg cctgccgaga agaaaacga caccggcgtg     120
gtgcatcagg tggaagagtg cagagtgaag ggccctggca tcagcaagtt cgtgcagaaa     180
gtgaacgaga tcggcatcta cctgaccgac tgcatggaac gggccatgga agtgatcccc     240
agaagccagc accaggaaac ccccgtgtat ctgggagcca ccgccggcat gagactgctg     300
agaatggaaa gcgaggaact ggccgaccgg gtgatggacg tggtggaaag aagcctgagc     360
aactacccat tcgatttca aggcgccaga atcatcaccg ccaggaaga aggcgcctac      420
ggctggatca ccatcaacta cctgctgggc aagttcagcc agaagaatca ggaaaccttc     480
ggcgccctgg acctgggcgg agcttctacc caagtgacct tcgtgcccca gaatcagacc     540
atcgagagcc ccgacaacgc cctgcagttc cggctgtacg gcaaggacta caatgtgtac     600
acccacagct ttctgtgcta cggaaaggac caggctctgt ggcagaagct ggccaaggac     660
atccaggtgg ccagcaacga gatcctgcgg gacccttgct ccacccccgg ctacaagaaa     720
gtcgtgaacg tgtccgacct gtacaagacc ccctgcacca agagattcga gatgaccctg     780
cccttccagc agttcgagat ccaaggcatc ggcaattacc agcagtgcca ccagagcatc     840
ctggaactgt tcaacaccag ctactgcccc tacagccagt gcgccttcaa cggcatcttc     900
ctgccacctc tgcaggggga tttcggcgcc ttcagcgcct ctacttcgt gatgaagttc      960
ctgaacctga ccagcgagaa ggtgtcccag aaaaagtga cagagatgat gaagaagttc    1020
tgcgcccagc cctgggagga aatcaagacc tcctacgctg gcgtgaaaga agtacctg     1080
agcgagtact gcttcagcgg cacctacatc ctgagcctgc tgctgcaggg ctaccacttc    1140
accgccgata gctgggagca catccacttc atcggcaaga ttcagggcag cgacgccggc    1200
tggacactgg gctacatgct gaatctgacc aacatgatcc ccgccgagca gccccctgagc    1260
acacctctga gccacagcac c                                             1281

<210> SEQ ID NO 10
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Met Glu Val Ile Pro
```

```
                65                  70                  75                  80
Arg Ser Gln His Gln Glu Thr Pro Val Tyr Leu Gly Ala Thr Ala Gly
                    85                  90                  95
Met Arg Leu Leu Arg Met Glu Ser Glu Leu Ala Asp Arg Val Leu
                100                 105                 110
Asp Val Val Glu Arg Ser Leu Ser Asn Tyr Pro Phe Asp Phe Gln Gly
                115                 120                 125
Ala Arg Ile Ile Thr Gly Gln Glu Gly Ala Tyr Gly Trp Ile Thr
130                 135                 140
Ile Asn Tyr Leu Leu Gly Lys Phe Ser Gln Lys Asn Gln Glu Thr Phe
145                 150                 155                 160
Gly Ala Leu Asp Leu Gly Gly Ala Ser Thr Gln Val Thr Phe Val Pro
                165                 170                 175
Gln Asn Gln Thr Ile Glu Ser Pro Asp Asn Ala Leu Gln Phe Arg Leu
                180                 185                 190
Tyr Gly Lys Asp Tyr Asn Val Tyr Thr His Ser Phe Leu Cys Tyr Gly
                195                 200                 205
Lys Asp Gln Ala Leu Trp Gln Lys Leu Ala Lys Asp Ile Gln Val Ala
210                 215                 220
Ser Asn Glu Ile Leu Arg Asp Pro Cys Phe His Pro Gly Tyr Lys Lys
225                 230                 235                 240
Val Val Asn Val Ser Asp Leu Tyr Lys Thr Pro Cys Thr Lys Gly Phe
                245                 250                 255
Glu Met Thr Leu Pro Phe Gln Gln Phe Glu Ile Gln Gly Ile Gly Asn
                260                 265                 270
Tyr Gln Gln Cys His Gln Ser Ile Leu Glu Leu Phe Asn Thr Ser Tyr
                275                 280                 285
Cys Pro Tyr Ser Gln Cys Ala Phe Asn Gly Ile Phe Leu Pro Pro Leu
                290                 295                 300
Gln Gly Asp Phe Gly Ala Phe Ser Ala Phe Tyr Phe Val Met Lys Phe
305                 310                 315                 320
Leu Asn Leu Thr Ser Glu Lys Val Ser Gln Glu Lys Val Thr Glu Met
                325                 330                 335
Met Lys Lys Phe Cys Ala Gln Pro Trp Glu Ile Lys Thr Ser Tyr
                340                 345                 350
Ala Gly Val Lys Glu Lys Tyr Leu Ser Glu Tyr Cys Phe Ser Gly Thr
                355                 360                 365
Tyr Ile Leu Ser Leu Leu Leu Gln Gly Tyr His Phe Thr Ala Asp Ser
370                 375                 380
Trp Glu His Ile His Phe Ile Gly Lys Ile Gln Gly Ser Asp Ala Gly
385                 390                 395                 400
Trp Thr Leu Gly Tyr Met Leu Asn Leu Thr Asn Met Ile Pro Ala Glu
                405                 410                 415
Gln Pro Leu Arg Thr Pro Leu Ser His Ser Thr
                420                 425
```

<210> SEQ ID NO 11
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11

-continued

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120
gtgcatcagg tggaagagtg cagagtgaag ggccctggca tcagcaagtt cgtgcagaaa     180
gtgaacgaga tcggcatcta cctgaccgac tgcatggaac gggccatgga agtgatcccc     240
agaagccagc accaggaaac ccccgtgtat ctgggagcca ccgccggcat gagactgctg     300
agaatggaaa gcgaggaact ggccgaccgg gtgctggacg tggtggaaag aagcctgagc     360
aactacccat tcgattttca aggcgccaga atcatcaccg gccaggaaga aggcgcctac     420
ggctggatca ccatcaacta cctgctgggc aagttcagcc agaagaatca ggaaaccttc     480
ggcgccctgg acctgggcgg agcttctacc caagtgacct tcgtgcccca gaatcagacc     540
atcgagagcc ccgacaacgc cctgcagttc cggctgtacg caaggactac aatgtgtac     600
acccacagct ttctgtgcta cggaaaggac caggctctgt ggcagaagct ggccaaggac     660
atccaggtgg ccagcaacga gatcctgcgg gaccccttgct tccacccgg ctacaagaaa     720
gtcgtgaacg tgtccgacct gtacaagacc ccctgcacca agggattcga gatgaccctg     780
cccttccagc agttcgagat ccagggcatc ggcaattacc agcagtgcca ccagagcatc     840
ctggaactgt tcaacaccag ctactgcccc tacagccagt gcgccttcaa cggcatcttc     900
ctgccacctc tgcaggggga tttcggcgcc ttcagcgcct tctacttcgt gatgaagttc     960
ctgaacctga ccagcgagaa ggtgtcccag gaaaaagtga cagagatgat gaagaagttc    1020
tgcgcccagc cctgggagga aatcaagacc tcctacgctg gcgtgaaaga gaagtacctg    1080
agcgagtact gcttcagcgg cacctacatc ctgagcctgc tgctgcaggg ctaccacttc    1140
accgccgata gctgggagca catccacttc atcggcaaga ttcagggcag cgacgccggc    1200
tggacactgg gctacatgct gaatctgacc aacatgatcc ccgccgagca gccccctgcgc    1260
acacctctga gccacagcac c                                             1281
```

<210> SEQ ID NO 12
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 12

```
Thr Gln Asn Lys Ala Leu Pro Glu Asn Val Lys Tyr Gly Ile Val Leu
1               5                  10                  15

Asp Ala Gly Ser Ser His Thr Ser Leu Tyr Ile Tyr Lys Trp Pro Ala
                20                  25                  30

Glu Lys Glu Asn Asp Thr Gly Val Val His Gln Val Glu Glu Cys Arg
            35                  40                  45

Val Lys Gly Pro Gly Ile Ser Lys Phe Ala Gln Lys Val Asn Glu Ile
        50                  55                  60

Gly Ile Tyr Leu Thr Asp Cys Met Glu Arg Ala Met Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
```

```
            115                 120                 125
Ala Arg Ile Ile Thr Gly Gln Glu Glu Gly Ala Tyr Gly Trp Ile Thr
        130                 135                 140
Ile Asn Tyr Leu Leu Gly Lys Phe Ser Gln Lys Asn Gln Glu Thr Phe
145                 150                 155                 160
Gly Ala Leu Asp Leu Gly Gly Ala Ser Thr Gln Val Thr Phe Val Pro
                165                 170                 175
Gln Asn Gln Thr Ile Glu Ser Pro Asp Asn Ala Leu Gln Phe Arg Leu
            180                 185                 190
Tyr Gly Lys Asp Tyr Asn Val Tyr Thr His Ser Phe Leu Cys Tyr Gly
        195                 200                 205
Lys Asp Gln Ala Leu Trp Gln Lys Leu Ala Lys Asp Ile Gln Val Ala
210                 215                 220
Ser Asn Glu Ile Leu Arg Asp Pro Cys Phe His Pro Gly Tyr Lys Lys
225                 230                 235                 240
Val Val Asn Val Ser Asp Leu Tyr Lys Thr Pro Cys Thr Lys Arg Phe
                245                 250                 255
Glu Met Thr Leu Pro Phe Gln Gln Phe Glu Ile Gln Gly Ile Gly Asn
            260                 265                 270
Tyr Gln Gln Cys His Gln Ser Ile Leu Glu Leu Phe Asn Thr Ser Tyr
        275                 280                 285
Cys Pro Tyr Ser Gln Cys Ala Phe Asn Gly Ile Phe Leu Pro Pro Leu
        290                 295                 300
Gln Gly Asp Phe Gly Ala Phe Ser Ala Phe Tyr Phe Val Met Lys Phe
305                 310                 315                 320
Leu Asn Leu Thr Ser Glu Lys Val Ser Gln Glu Lys Val Thr Glu Met
                325                 330                 335
Met Lys Lys Phe Cys Ala Gln Pro Trp Glu Glu Ile Lys Thr Ser Tyr
            340                 345                 350
Ala Gly Val Lys Glu Lys Tyr Leu Ser Glu Tyr Cys Phe Ser Gly Thr
        355                 360                 365
Tyr Ile Leu Ser Leu Leu Leu Gln Gly Tyr His Phe Thr Ala Asp Ser
        370                 375                 380
Trp Glu His Ile His Phe Ile Gly Lys Ile Gln Gly Ser Asp Ala Gly
385                 390                 395                 400
Trp Thr Leu Gly Tyr Met Leu Asn Leu Thr Asn Met Ile Pro Ala Glu
                405                 410                 415
Gln Pro Leu Arg Thr Pro Leu Ser His Ser Thr
            420                 425

<210> SEQ ID NO 13
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
acccagaaca aggccctgcc cgagaacgtg aagtacggca tcgtgctgga tgccggcagc    60
agccacacca gcctgtacat ctacaagtgg cctgccgaga agaaaacgac accggcgtg   120 gtgcatcagg tggaagagtg cagagtgaag ggccctggca tcagcaagtt cgcgcagaaa   180
gtgaacgaga tcggcatcta cctgaccgac tgcatggaac gggccatgga agtgatcccc   240
```

```
agaagccagc accaggaaac ccccgtgtat ctgggagcca ccgccggcat gagactgctg    300
agaatggaaa gcgaggaact ggccgaccgg gtgctggacg tggtggaaag aagcctgagc    360
aactacccat tcgattttca aggcgccaga atcatcaccg gccaggaaga aggcgcctac    420
ggctggatca ccatcaacta cctgctgggc aagttcagcc agaagaatca ggaaaccttc    480
ggcgccctgg acctgggcgg agcttctacc caagtgacct tcgtgcccca gaatcagacc    540
atcgagagcc ccgacaacgc cctgcagttc cggctgtacg caaggacta caatgtgtac    600 acccacagct ttctgtgcta cggaaaggac caggctctgt ggcagaagct ggccaaggac    660
atccaggtgg ccagcaacga gatcctgcgg gacccttgct tccacccggg ctacaagaaa    720
gtcgtgaacg tgtccgacct gtacaagacc ccctgcacca gagattcga gatgacctg     780 cccttccagc agttcgagat ccagggcatc ggcaattacc agcagtgcca ccagagcatc    840
ctggaactgt tcaacaccag ctactgcccc tacagccagt gcgccttcaa cggcatcttc    900
ctgccacctc tgcaggggga tttcggcgcc ttcagcgcct tctacttcgt gatgaagttc    960
ctgaacctga ccagcgagaa ggtgtcccag gaaaaagtga cagagatgat gaagaagttc   1020
tgcgcccagc cctgggagga aatcaagacc tcctacgctg gcgtgaaaga gaagtacctg   1080
agcgagtact gcttcagcgg cacctacatc ctgagcctgc tgctgcaggg ctaccacttc   1140
accgccgata gctgggagca catccacttc atcggcaaga ttcagggcag cgacgccggc   1200
tggacactgg gctacatgct gaatctgacc aacatgatcc ccgccgagca gcccctgagg   1260
acacctctga gccacagcac c                                              1281

<210> SEQ ID NO 14
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Met
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
```

```
              165                 170                 175
Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
        355                 360                 365

Tyr Ile Leu Ser Leu Leu Leu Gln Gly Tyr His Phe Thr Ala Asp Ser
    370                 375                 380

Trp Glu His Ile His Phe Ile Asp Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425

<210> SEQ ID NO 15
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
acccagaaca aggccctgcc cgagaacgtg aagtacggca tcgtgctgga tgccggcagc      60
agccacacca gcctgtacat ctacaagtgg cctgccgaga agaaaacga caccggcgtg     120 gtgcatcagg tggaagagtg cagagtgaag ggccctggca tcagcaagtt cgtgcagaaa    180
gtgaacgaga tcggcatcta cctgaccgac tgcatggaac gggccaggga agtgatcccc    240
agaagccagc accaggaaac ccccgtgtat ctgggagcca ccgccggcat gagactgctg    300
agaatggaaa gcgaggaact ggccgaccgg gtgatggacg tggtggaaag aagcctgagc    360
aactacccat tcgattttca aggcgccaga atcatcaccg ccaggaagaa aggcgcctac    420
ggctggatca ccatcaacta cctgctgggc aagttcagcc agaagaatca ggaaaccttc    480
ggcgccctgg acctgggcgg agcttctacc caagtgacct tcgtgcccca gaatcagacc    540
```

-continued

```
atcgagagcc ccgacaacgc cctgcagttc cggctgtacg gcaaggacta caatgtgtac      600
acccacagct ttctgtgcta cggaaaggac caggctctgt ggcagaagct ggccaaggac      660
atccaggtgg ccagcaacga gatcctgcgg gacccttgct tccaccccgg ctacaagaaa      720
gtcgtgaacg tgtccgacct gtacaagacc ccctgcacca agagattcga gatgaccctg      780
cccttccagc agttcgagat ccagggcatc ggcaattacc agcagtgcca ccagagcatc      840
ctggaactgt tcaacaccag ctactgcccc tacagccagt gcgccttcaa cggcatcttc      900
ctgccacctc tgcaggggga tttcggcgcc ttcagcgcct tctacttcgt gatgaagttc      960
ctgaacctga ccagcgagaa ggtgtcccag gaaaaagtga cagagatgat gaagaagttc     1020
tgcgcccagc cctgggagga aatcaagacc tcctacgctg gcgtgaaaga gaagtacctg     1080
agcgagtact gcttcagcgg cacctacatc ctgagcctgc tgctgcaggg ctaccacttc     1140
accgccgata gctgggagca catccacttc atcgacaaga ttcagggcag cgacgccggc     1200
tggacactgg gctacatgct gaatctgacc aacatgatcc ccgccgagca gcccctgagc     1260
acacctctga gccacagcac c                                               1281
```

<210> SEQ ID NO 16
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 16

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Ser Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Met
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Arg Gln Lys Leu Ala Lys Asp Ile Gln Val Ala
```

```
                    210                 215                 220
Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                    245                 250                 255

Glu Met Thr Leu Pro Phe Gln Gln Phe Glu Ile Gln Gly Ile Gly Asn
                260                 265                 270

Tyr Gln Gln Cys His Gln Ser Ile Leu Glu Leu Phe Asn Thr Ser Tyr
            275                 280                 285

Cys Pro Tyr Ser Gln Cys Ala Phe Asn Gly Ile Phe Leu Pro Pro Leu
        290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
                340                 345                 350

Ala Gly Val Lys Glu Lys Tyr Leu Ser Glu Tyr Cys Phe Ser Gly Thr
            355                 360                 365

Tyr Ile Leu Ser Leu Leu Leu Gln Gly Tyr His Phe Thr Ala Asp Ser
        370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
                420                 425
```

<210> SEQ ID NO 17
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17

```
acccagaaca aggccctgcc cgagaacgtg aagtacggca tcgtgctgga tgccggcagc     60
agccacacca gcctgtacat ctacaagtgg cctgccgaga agaaaacga caccggcgtg    120 gtgcatcagg tggaagagtg cagagtgaag ggccctggca tcagcaagtt cgtgcagaaa    180
gtgaacgaga tcggcatctc cctgaccgac tgcatggaac gggccaggga agtgatcccc    240
agaagccagc accaggaaac ccccgtgtat ctgggagcca ccgccggcat gagactgctg    300
agaatggaaa gcgaggaact ggccgaccgg gtgatggacg tggtggaaag aagcctgagc    360
aactacccat cgattttca aggcgccaga atcatcaccg ccaggaaga aggcgcctac    420 ggctggatca ccatcaacta cctgctgggc aagttcagcc agaagaatca ggaaaccttc    480
ggcgccctgg acctgggcgg agcttctacc caagtgacct tcgtgcccca gaatcagacc    540
atcgagagcc ccgacaacgc cctgcagttc cggctgtacg gcaaggacta caatgtgtac    600
acccacagct ttctgtgcta cggaaaggac caggctctgc ggcagaagct ggccaaggac    660
atccaggtgg ccagcaacga gatcctgcgg gaccccttgct tccaccccgg ctacaagaaa    720
gtcgtgaacg tgtccgacct gtacaagacc ccctgcacca gagattcga gatgaccctg    780
```

-continued

| | |
|---|---|
| cccttccagc agttcgagat ccagggcatc ggcaattacc agcagtgcca ccagagcatc | 840 |
| ctggaactgt tcaacaccag ctactgcccc tacagccagt gcgccttcaa cggcatcttc | 900 |
| ctgccacctc tgcagggga tttcggcgcc ttcagcgcct tctacttcgt gatgaagttc | 960 |
| ctgaacctga ccagcgagaa ggtgtcccag gaaaaagtga cagagatgat gaagaagttc | 1020 |
| tgcgcccagc cctgggagga aatcaagacc tcctacgctg gcgtgaaaga gaagtacctg | 1080 |
| agcgagtact gcttcagcgg cacctacatc ctgagcctgc tgctgcaggg ctaccacttc | 1140 |
| accgccgata gctgggagca catccacttc atcggcaaga ttcagggcag cgacgccggc | 1200 |
| tggacactgg gctacatgct gaatctgacc aacatgatcc ccgccgagca gcccctgagc | 1260 |
| acacctctga gccacagcac c | 1281 |

<210> SEQ ID NO 18
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Glu Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Ser Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Ala Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Thr Gly Asn

```
                260             265             270
Tyr Gln Gln Cys His Gln Ser Ile Leu Glu Leu Phe Asn Thr Ser Tyr
            275                 280                 285

Cys Pro Tyr Ser Gln Cys Ala Phe Asn Gly Ile Phe Leu Pro Pro Leu
            290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
                340                 345                 350

Ala Gly Val Lys Glu Lys Tyr Leu Ser Glu Tyr Cys Phe Ser Gly Thr
            355                 360                 365

Tyr Ile Leu Ser Leu Leu Leu Gln Gly Tyr His Phe Thr Ala Asp Ser
370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
                420                 425

<210> SEQ ID NO 19
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
acccagaaca aggccctgcc cgagaacgtg aagtacggca tcgtgctgga tgccggcagc      60
agccacacca gcctgtacat ctacaagtgg cctgccgagg aagaaaacga caccggcgtg     120
gtgcatcagg tggaagagtg cagagtgaag ggccctggca tcagcaagtt cgtgcagaaa     180
gtgaacgaga tcggcatcta cctgtccgac tgcatggaac gggccaggga agtgatcccc     240
agaagccagc accaggaaac ccccgtgtat ctgggagcca ccgccggcat gagactgctg     300
agaatggaaa gcgaggaact ggccgaccgg gtgctggacg cggtggaaag aagcctgagc     360
aactacccat tcgattttca aggcgccaga atcatcaccg ccaggaaga aggcgcctac      420 ggctggatca ccatcaacta cctgctgggc aagttcagcc agaagaatca ggaaaccttc     480
ggcgccctgg acctgggcgg agcttctacc caagtgacct tcgtgcccca gaatcagacc     540
atcgagagcc ccgacaacgc cctgcagttc cggctgtacg gcaaggacta caatgtgtac     600
acccacagct ttctgtgcta cggaaaggac caggctctgt ggcagaagct ggccaaggac     660
atccaggtgg ccagcaacga gatcctgcgg gacccttgct ccacccccgg ctacaagaaa     720
gtcgtgaacg tgtccgacct gtacaagacc ccctgcacca agagattcga gatgaccctg     780
cccttccagc agttcgagat ccagggcacc ggcaattacc agcagtgcca ccagagcatc     840
ctggaactgt tcaacaccag ctactgcccc tacagccagt gcgccttcaa cggcatcttc     900
ctgccacctc tgcaggggga tttcggcgcc ttcagcgcct tctacttcgt gatgaagttc     960
ctgaacctga ccagcgagaa ggtgtcccag gaaaaagtga cagagatgat gaagaagttc    1020
tgcgcccagc cctgggagga aatcaagacc tcctacgctg gcgtgaaaga gaagtacctg    1080
```

```
agcgagtact gcttcagcgg cacctacatc ctgagcctgc tgctgcaggg ctaccacttc    1140
accgccgata gctgggagca catccacttc atcggcaaga ttcagggcag cgacgccggc    1200
tggacactgg gctacatgct gaatctgacc aacatgatcc ccgccgagca gcccctgagc    1260
acacctctga gccacagcac c                                              1281
```

<210> SEQ ID NO 20
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 20

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Ala Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Phe Val Met Lys Phe
```

```
                 305                 310                 315                 320
Leu Asn Leu Thr Ser Glu Lys Val Ser Gln Glu Lys Val Thr Glu Met
                325                 330                 335
Met Lys Lys Phe Cys Ala Gln Pro Trp Glu Ile Lys Thr Ser Tyr
                340                 345                 350
Ala Gly Val Lys Glu Lys Tyr Leu Ser Glu Tyr Cys Phe Ser Gly Thr
                355                 360                 365
Tyr Ile Leu Ser Leu Leu Leu Gln Gly Tyr His Phe Thr Ala Asp Ser
            370                 375                 380
Trp Glu His Ile His Phe Ile Gly Lys Ile Gln Gly Ser Asp Ala Gly
385                 390                 395                 400
Trp Thr Leu Gly Tyr Met Leu Asn Leu Thr Asn Met Ile Pro Ala Glu
                405                 410                 415
Gln Pro Leu Ser Thr Pro Leu Ser His Ser Thr
            420                 425
```

<210> SEQ ID NO 21
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120
gtgcatcagg tggaagagtg cagagtgaag ggccctggca tcagcaagtt cgtgcagaaa     180
gtgaacgaga tcggcatcta cctgaccgac tgcatggaac gggccaggga agtgattccc     240
agaagccagc accaggaaac ccccgtgtat ctgggagcca ccgccggcat gagactgctg     300
agaatggaaa gcgaggaact ggccgaccgg gtgctggacg cggtggaaag aagcctgagc     360
aactacccat tcgattttca aggcgccaga atcatcaccg gccaggaaga aggcgcctac     420
ggctggatca ccatcaacta cctgctgggt aagttcagcc agaagaatca ggaaaccttc     480
ggcgccctgg acctgggcgg agcttctacc caagtgacct tcgtgcccca gaatcagacc     540
atcgagagcc ccgacaacgc cctgcagttc ggctgtacg gcaaggacta caatgtgtac     600
acccacagct ttctgtgcta cggaaaggac caggctctgt ggcagaagct ggccaaggac     660
atccaggtgg ccagcaacga gatcctgcgg gacccttgct ccacccegg ctacaagaaa     720
gtagtgaacg tgtccgacct gtacaagacc ccctgcacca agagattcga gatgaccctg     780
ccattccagc agttcgagat ccagggcatc ggcaattacc agcagtgcca ccagagcatc     840
ctggaactgt tcaacaccag ctactgcccc tacagccagt gcgccttcaa cggcatcttc     900
ctgccacctc tgcagggga tttcggcgcc ttcagcgcct ctacttcgt gatgaagttc     960
ctgaacctga ccagcgagaa ggtgtcccag gaaaaagtga cagagatgat gaagaagttc    1020
tgcgcccagc cctgggagga aatcaagacc tcctacgctg gcgtgaaaga aagtacctg    1080
agcgagtact gcttcagcgg cacctacatc ctgagcctgc tgctgcaggg ctaccacttc    1140
accgccgata gctgggagca catccacttc atcggcaaga ttcagggcag cgacgccggc    1200
tggacactgg gctacatgct gaatctgacc aacatgatcc ccgccgagca gcccctgagc    1260
acacctctga gccacagcac c                                              1281
```

```
<210> SEQ ID NO 22
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Arg Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
```

```
              355                 360                 365
Tyr Ile Leu Ser Leu Leu Leu Gln Gly Tyr His Phe Thr Ala Asp Ser
    370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425
```

<210> SEQ ID NO 23
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23

| | | | | | |
|---|---|---|---|---|---|
| acccagaaca | aggccctgcc | cgagaacgtg | aagtacggca | tcgtgctgga | tgccggcagc | 60 |
| agccacacca | gcctgtacat | ctacaagtgg | cctgccgaga | agaaaacga | caccggcgtg | 120 |
| gtgcatcagg | tggaagagtg | cagagtgaag | ggccctggca | tcagcaagtt | cgtgcagaaa | 180 |
| gtgaacgaga | tcggcatcta | cctgaccgac | tgcatggaac | gggccaggga | agtgatcccc | 240 |
| agaagccagc | accaggaaac | ccccgtgtat | ctgggagcca | ccgccggcat | gagactgctg | 300 |
| agaatggaaa | gcgaggaact | ggccgaccgg | gtgctggacg | tggtggaaag | aagcctgagc | 360 |
| aactacccat | tcgattttca | aggcgccaga | atcatcaccg | gccaggaaga | aggcgcctac | 420 |
| ggctggatca | ccatcaacta | cctgctgggc | aagttcagcc | agaagaatca | ggaaaccttc | 480 |
| ggcgccctgg | acctgggcgg | agcttctacc | caagtgacct | tcgtgcccca | gaatcagacc | 540 |
| atcgagagcc | ccgacaacgc | cctgcagttc | cggctgtacg | caaggacta | caatgtgtac | 600 |
| acccacagct | ttctgtgcta | cggaaaggac | caggctctga | ggcagaagct | ggccaaggac | 660 |
| atccaggtgg | ccagcaacga | gatcctgcgg | gaccccttgct | tccacccegg | ctacaagaaa | 720 |
| gtcgtgaacg | tgtccgacct | gtacaagacc | ccctgcacca | agagattcga | gatgaccctg | 780 |
| cccttccagc | agttcgagat | ccagggcatc | ggcaattacc | agcagtgcca | ccagagcatc | 840 |
| ctggaactgt | tcaacaccag | ctactgcccc | tacagccagt | gcgccttcaa | cggcatcttc | 900 |
| ctgccacctc | tgcaggggga | tttcggcgcc | ttcagcgcct | tctacttcgt | gatgaagttc | 960 |
| ctgaacctga | ccagcgagaa | ggtgtcccag | gaaaaagtga | cagagatgat | gaagaagttc | 1020 |
| tgcgcccagc | cctgggagga | aatcaagacc | tcctacgctg | gcgtgaaaga | gaagtacctg | 1080 |
| agcgagtact | gcttcagcgg | cacctacatc | ctgagcctgc | tgctgcaggg | ctaccacttc | 1140 |
| accgccgata | gctgggagca | catccacttc | atcggcaaga | ttcagggcag | cgacgccggc | 1200 |
| tggacactgg | gctacatgct | gaatctgacc | aacatgatcc | ccgccgagca | gcccctgagc | 1260 |
| acacctctga | gccacagcac | c | | | | 1281 |

<210> SEQ ID NO 24
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65              70                  75                  80

Arg Ser Gln His Gln Glu Thr Pro Val Tyr Leu Gly Ala Thr Ala Gly
            85                  90                  95

Met Arg Leu Leu Arg Met Glu Ser Glu Leu Ala Asp Arg Val Leu
        100                 105                 110

Asp Val Val Glu Arg Ser Leu Ser Asn Tyr Pro Phe Asp Phe Gln Gly
            115                 120                 125

Ala Arg Ile Ile Thr Gly Gln Glu Gly Ala Tyr Gly Trp Ile Thr
130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
            165                 170                 175

Gln Asn Gln Thr Ile Glu Ser Pro Asp Asn Ala Leu Gln Phe Arg Leu
        180                 185                 190

Tyr Gly Lys Asp Tyr Asn Val Tyr Thr His Ser Phe Leu Cys Tyr Gly
    195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
            245                 250                 255

Glu Met Thr Leu Pro Phe Gln Gln Phe Glu Ile Gln Gly Thr Gly Asn
        260                 265                 270

Tyr Gln Gln Cys His Gln Ser Ile Leu Glu Leu Phe Asn Thr Ser Tyr
    275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
            325                 330                 335

Met Lys Lys Phe Cys Ala Gln Pro Trp Glu Ile Lys Thr Ser Tyr
        340                 345                 350

Ala Gly Val Lys Glu Lys Tyr Leu Ser Glu Tyr Cys Phe Ser Gly Thr
    355                 360                 365

Tyr Ile Leu Ser Leu Leu Leu Gln Gly Tyr His Phe Thr Ala Asp Ser
    370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
```

Gln Pro Leu Ser Thr Pro Leu Ser His Ser Thr
            420                 425

<210> SEQ ID NO 25
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120
gtgcatcagg tggaagagtg cagagtgaag ggccctggca tcagcaagtt cgtgcagaaa    180
gtgaacgaga tcggcatcta cctgaccgac tgcatggaac gggccaggga agtgatcccc    240
agaagccagc accaggaaac ccccgtgtat ctgggagcca ccgccggcat gagactgctg    300
agaatggaaa gcgaggaact ggccgaccgg gtgctggacg tggtggaaag aagcctgagc    360
aactacccat tcgattttca aggcgccaga atcatcaccg gccaggaaga aggcgcctac    420
ggctggatca ccatcaacta cctgctgggc aagttcagcc agaagaatca ggaaaccttc    480
ggcgccctgg acctgggcgg agcttctacc caagtgacct tcgtgcccca gaatcagacc    540
atcgagagcc ccgacaacgc cctgcagttc cggctgtacg gcaaggacta caatgtgtac    600
acccacagct ttctgtgcta tggaaaggac caggctctgt ggcagaagct ggccaaggac    660
atccaggtgg ccagcaacga gatcctgcgg gaccccttgct tccacccagg ctacaagaaa    720
gtcgtgaacg tgtccgacct gtacaagacc ccctgcacca gagattcga gatgaccctg    780
cccttccagc agttcgagat ccagggcacc ggcaattacc agcagtgcca ccagagcatc    840
ctggaactgt tcaacaccag ctactgcccc tacagccagt gcgccttcaa cggcatcttc    900
ctgccacctc tgcaggggga tttcggcgcc ttcagcgcct tctacttcgt gatgaagttc    960
ctgaacctga ccagcgagaa ggtgtcccag gaaaaagtga cagagatgat gaagaagttc   1020
tgcgcccagc cctgggagga aatcaagacc tcctacgctg gcgtgaaaga gaagtacctg   1080
agcgagtact gcttcagcgg cacctacatc ctgagcctgc tgctgcaggg ctaccacttc   1140
accgccgata gctgggagca catccacttc atcggcaaga ttcagggcag cgacgccggc   1200
tggacactgg gctacatgct gaatctgacc aacatgatcc ccgccgagca gcctttgagc   1260
acacctctga gccacagcac c                                             1281
```

<210> SEQ ID NO 26
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val His Gln Val Glu Cys Arg
        35                  40                  45

Val Lys Gly Pro Gly Ile Ser Lys Phe Val Gln Lys Val Asn Glu Ile
 50                  55                  60

Gly Ile Tyr Leu Thr Asp Cys Met Glu Arg Ala Met Glu Val Ile Pro
 65                  70                  75                  80

Arg Ser Gln His Gln Glu Thr Pro Val Tyr Leu Gly Ala Thr Ala Gly
                 85                  90                  95

Met Arg Leu Leu Arg Met Glu Ser Glu Leu Ala Asp Arg Val Leu
                100                 105                 110

Asp Val Val Glu Arg Ser Leu Ser Asn Tyr Pro Phe Asp Phe Gln Gly
                115                 120                 125

Ala Arg Ile Ile Thr Gly Gln Glu Gly Ala Tyr Gly Trp Ile Thr
        130                 135                 140

Ile Asn Tyr Leu Leu Gly Lys Phe Ser Gln Lys Asn Gln Glu Thr Phe
145                 150                 155                 160

Gly Ala Leu Asp Leu Gly Ala Ser Thr Gln Val Thr Phe Val Pro
                165                 170                 175

Gln Asn Gln Thr Ile Glu Ser Pro Asp Asn Ala Leu Gln Phe Arg Leu
                180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Thr Gly Asn
                260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
        340                 345                 350

Ala Gly Val Lys Glu Lys Tyr Leu Ser Glu Tyr Cys Phe Ser Gly Thr
                355                 360                 365

Tyr Ile Leu Ser Leu Leu Leu Gln Gly Tyr His Phe Thr Ala Asp Ser
370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
                420                 425

<210> SEQ ID NO 27
<211> LENGTH: 1281
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27

```
acccagaaca aggccctgcc cgagaacgtg aagtacggca tcgtgctgga tgccggcagc     60
agccacacca gcctgtacat ctacaagtgg cctgccgaga agaaaacga caccggcgtg    120
gtgcatcagg tggaagagtg cagagtgaag ggccctggca tcagcaagtt cgtgcagaaa    180
gtgaacgaga tcggcatcta cctgaccgac tgcatggaac gggccatgga agtgatcccc    240
agaagccagc accaggaaac ccccgtgtat ctgggagcca ccgccggcat gagactgctg    300
agaatggaaa gcgaggaact ggccgaccgg gtgctggacg tggtggaaag aagcctgagc    360
aactacccat tcgattttca aggcgccaga atcatcaccg gccaggaaga aggcgcctac    420
ggctggatca ccatcaacta cctgctgggc aagttcagcc agaagaatca ggaaaccttc    480
ggcgccctgg acctgggcgg agcttctacc caagtgacct tcgtgcccca gaatcagacc    540
atcgagagcc ccgacaacgc cctgcagttc cggctgtacg gcaaggacta caatgtgtac    600
acccacagct ttctgtgcta cggaaaggac caggctctgt ggcagaagct ggccaaggac    660
atccaggtgg ccagcaacga gatcctgcgg gacccttgct ccacccggg ctacaagaaa     720
gtcgtgaacg tgtccgacct gtacaagacc ccctgcacca agagattcga gatgaccctg    780
cccttccagc agttcgagat ccagggcacc ggcaattacc agcagtgcca ccagagcatc    840
ctggaactgt tcaacaccag ctactgcccc tacagccagt gcgccttcaa cggcatcttc    900
ctgccacctc tgcaggggga tttcggcgcc ttcagcgcct ctacttcgt gatgaagttc      960
ctgaacctga ctagcgagaa ggtgtcccag gaaaaagtga cagagatgat gaagaagttc   1020
tgcgcccagc cctggaagga atcaagacc tcctacgctg gcgtgaaaga gaagtacctg    1080
agcgagtact gcttcagcgg cacctacatc ctgagcctgc tgctgcaggg ctaccacttc   1140
accgccgata gctgggagca catccacttc atcggcaaga ttcagggcag cgacgccggc   1200
tggacactgg gctacatgct gaatctgacc aacatgatcc ccgccgagca gcccctgagc   1260
acacctctga gccacagcac c                                              1281
```

<210> SEQ ID NO 28
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
                20                  25                  30

Glu Lys Glu Asn Asp Thr Gly Val Val His Gln Val Glu Glu Cys Arg
            35                  40                  45

Val Lys Gly Pro Gly Ile Ser Lys Phe Val Gln Lys Val Asn Glu Ile
        50                  55                  60

Gly Ile Tyr Leu Thr Asp Cys Met Glu Arg Ala Arg Glu Val Ile Pro
65                  70                  75                  80
```

```
Arg Ser Gln His Gln Glu Thr Pro Val Tyr Leu Gly Ala Thr Ala Gly
                 85                  90                  95

Met Arg Leu Leu Arg Met Glu Ser Glu Leu Ala Asp Arg Val Leu
            100                 105                 110

Asp Val Val Glu Arg Ser Leu Ser Asn Tyr Pro Phe Asp Phe Gln Gly
            115                 120                 125

Ala Arg Ile Ile Thr Gly Gln Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
210                 215                 220

Ser Asn Asp Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Thr Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
        355                 360                 365

Tyr Ile Leu Ser Leu Leu Leu Gln Gly Tyr His Phe Thr Ala Asp Ser
370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425

<210> SEQ ID NO 29
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 29
acccagaaca aggccctgcc cgagaacgtg aagtacggca tcgtgctgga tgccggcagc      60
```

```
agccacacca gcctgtacat ctacaagtgg cctgccgaga agaaaaacga caccggcgtg    120
gtgcatcagg tggaagagtg cagagtgaag ggccctggca tcagcaagtt cgtgcagaaa    180
gtgaacgaga tcggcatcta cctgaccgac tgcatggaac gggccaggga agtgatcccc    240
agaagccagc accaggaaac ccccgtgtat ctgggagcca ccgccggcat gagactgctg    300
agaatggaaa gcgaggaact ggccgaccgg gtgctggacg tggtggaaag aagcctgagc    360
aactacccat tcgatttca aggcgccaga atcatcaccg ccaggaaga aggcgcctac       420 ggctggatca ccatcaacta cctgctgggc aagttcagcc agaagaatca ggaaaccttc    480
ggcgccctgg acctgggcgg agcttctacc caagtgacct cgtgccccca gaatcagacc    540
atcgagagcc ccgacaacgc cctgcagttc cggctgtacg gcaaggacta caatgtgtac    600
acccacagct ttctgtgcta cggaaaggac caggctctgt ggcagaagct ggccaaggac    660
atccaggtgg ccagcaacga tatcctgcgg gacccttgct tccaccccgg ctacaagaaa    720
gtcgtgaacg tgtccgacct gtacaagacc ccctgcacca agagattcga gatgaccctg    780
cccttccagc agttcgagat ccagggcacc ggcaattacc agcagtgcca ccagagcatc    840
ctggaactgt tcaacaccag ctactgcccc tacagccagt gcgccttcaa cggcatcttc    900
ctgccacctc tgcaggggga tttcggcgcc ttcagcgcct tctacttcgt gatgaagttc    960
ctgaacctga ccagcgagaa ggtgtcccag gaaaaagtga cagagatgat gaagaagttc   1020
tgcgcccagc cctgggagga aatcaagacc tcctacgctg gcgtgaaaga gaagtacctg   1080
agcgagtact gcttcagcgg cacctacatc ctgagcctgc tgctgcaggg ctaccacttc   1140
accgccgata gctgggagca catccacttc atcggcaaga ttcagggcag cgacgccggc   1200
tggacactgg gctacatgct gaatctgacc aacatgatcc ccgccgagca gcccctgagc   1260
acacctctga gccacagcac c                                             1281
```

<210> SEQ ID NO 30
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125
```

```
Ala Arg Ile Ile Thr Gly Gln Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Ser Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
        355                 360                 365

Tyr Ile Leu Ser Leu Leu Pro Gln Gly Tyr His Phe Thr Ala Asp Ser
    370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425
```

<210> SEQ ID NO 31
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 31

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120 gtgcatcagg tggaagagtg cagagtgaag ggccctggca tcagcaagtt cgtgcagaaa     180
gtgaacgaga tcggcatcta cctgaccgac tgcatggaac gggccaggga agtgatcccc     240
agaagccagc accaggaaac ccccgtgtat ctgggagcca ccgccggcat gagactgctg     300
```

```
agaatggaaa gcgaggaact ggccgaccgg gtgctggacg tggtggaaag aagcctgagc    360
aactacccat tcgattttca aggcgccaga atcatcaccg gccaggaaga aggcgcctac    420
ggctggatca ccatcaacta cctgctgggc aagttcagcc agaagaatca ggaaaccttc    480
ggcgccctgg acctgggcgg agcttctacc caagtgacct cgtgccccca gaatcagacc    540
atcgagagcc ccgacaacgc cctgcagttc cggctgtacg gcaaggacta caatgtgtac    600
acccacagct ttctgtgcta cggaaaggac caggctctgt ggcagaagct ggccaaggac    660
atccaggtgg ccagcaacga gatcctgcgg gacccttgct ccacccccgg ctacaagaaa    720
gtcgtgaacg tgtccgacct gtacaagacc ccctgcacca agagattcga gatgacccctg   780 cccttccagc agttcgagat ccagggcatc ggcaattacc agcagtgcca ccagagcatc    840
ctggaactgt tcaacaccag ctactgcccc tacagccagt gcgccttcaa cggcatcttc    900
ctgccacctc tgcaggggga tttcggcgcc ttcagcgcct ctactccgt gatgaagttc      960 ctgaacctga ccagcgagaa ggtgtcccag gaaaaagtga cagagatgat gaagaagttc   1020
tgcgcccagc cctgggagga aatcaagacc tcctacgctg gcgtgaaaga gaagtacctg   1080
agcgagtact gcttcagcgg cacctacatc ctgagcctgc tgccgcaggg ctaccacttc   1140
accgccgata gctgggagca catccacttc atcggcaaga ttcagggcag cgacgccggc   1200
tggacactgg gctacatgct gaatctgacc aacatgatcc ccgccgagca gcccctgagc   1260
acacctctga gccacagcac c                                              1281
```

<210> SEQ ID NO 32
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 32

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
            85                  90                  95

Met Arg Leu Leu Arg Met Glu Ser Glu Glu Leu Ala Asp Arg Val Leu
        100                 105                 110

Asp Val Val Glu Arg Ser Leu Ser Asn Tyr Pro Phe Asp Phe Gln Gly
    115                 120                 125

Ala Arg Ile Ile Thr Gly Gln Glu Glu Gly Ala Tyr Gly Trp Ile Thr
130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
            165                 170                 175
```

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Ser Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
        355                 360                 365

Tyr Ile Leu Ser Leu Leu Gln Gly Tyr His Phe Thr Ala Asp Ser
    370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425

<210> SEQ ID NO 33
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
acccagaaca aggccctgcc cgagaacgtg aagtacggca tcgtgctgga tgccggcagc      60
agccacacca gcctgtacat ctacaagtgg cctgccgaga agaaaacga caccggcgtg     120 gtgcatcagg tggaagagtg cagagtgaag ggccctggca tcagcaagtt cgtgcagaaa     180
gtgaacgaga tcggcatcta cctgaccgac tgcatggaac gggccaggga agtgatcccc     240
agaagccagc accaggaaac ccccgtgtat ctgggagcca ccgccggcat gagactgctg     300
agaatggaaa gcgaggaact ggccgaccgg gtgctggacg tggtggaaag aagcctgagc     360
aactacccat tcgattttca aggcgccaga atcatcaccg ccaggaaga aggcgcctac     420 ggctggatca ccatcaacta cctgctgggc aagttcagcc agaagaatca ggaaaccttc     480
ggcgccttgg acctgggcgg agcttctacc caagtgacct tcgtgcccca gaatcagacc     540
atcgagagcc ccgacaacgc cctgcagttc cggctgtacg gcaaggacta caatgtgtac     600

```
acccacagct ttctgtgcta cggaaaggac caggctctgt ggcagaagct ggccaaggac    660
atccaggtgg ccagcaacga gatcctgcgg gacccttgct tccacccggg ctacaagaaa    720
gtcgtgaacg tgtccgacct gtacaagacc ccctgcacca agagattcga gatgaccctg    780
cccttccagc agttcgagat ccagggcatc ggcaattacc agcagtgcca ccagagcatc    840
ctggaactgt tcaacaccag ctactgcccc tacagccagt gcgccttcaa cggcatcttc    900
ctgccacctc tgcaggggga tttcggcgcc ttcagcgcct tctactccgt gatgaagttc    960
ctgaacctga ccagcgagaa ggtgtcccag gaaaagtgac agagatgat gaagaagttc    1020 tgcgcccagc cctgggagga aatcaagacc tcctacgctg gcgtgaaaga gaagtacctg    1080
agcgagtact gcttcagcgg cacctacatc ctgagcctgc tgctgcaggg ctaccacttc    1140
accgccgata gctgggagca catccacttc atcggcaaga ttcagggcag cgacgccggc    1200
tggacactgg gttacatgct gaatctgacc aacatgatcc ccgccgagca gcccctgagc    1260
acacctctga gccacagcac c                                              1281
```

<210> SEQ ID NO 34
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220
```

```
Ser Asn Glu Ile Leu Arg Asp Pro Cys Phe His Pro Gly Tyr Lys Lys
225                 230                 235                 240

Val Val Lys Val Ser Asp Leu Tyr Lys Thr Pro Cys Thr Lys Arg Phe
            245                 250                 255

Glu Met Thr Leu Pro Phe Gln Gln Phe Glu Ile Gln Gly Ile Gly Asn
                260                 265                 270

Tyr Gln Gln Cys His Gln Ser Ile Leu Glu Leu Phe Asn Thr Ser Tyr
            275                 280                 285

Cys Pro Tyr Ser Gln Cys Ala Phe Asn Gly Ile Phe Leu Pro Pro Leu
        290                 295                 300

Gln Gly Asp Phe Gly Ala Phe Ser Ala Phe Tyr Ser Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Ile Lys Thr Ser Tyr
            340                 345                 350

Ala Gly Val Lys Glu Lys Tyr Leu Ser Glu Tyr Cys Phe Ser Gly Thr
        355                 360                 365

Tyr Ile Leu Ser Leu Leu Pro Gln Gly Tyr His Phe Thr Ala Asp Ser
370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Ser Ala Glu
                405                 410                 415

Gln Pro Leu Ser Thr Pro Leu Ser His Ser Thr
            420                 425
```

<210> SEQ ID NO 35
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 35

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120
gtgcatcagg tggaagagtg cagagtgaag ggccctggca tcagcaagtt cgtgcagaaa    180
gtgaacgaga tcggcatcta cctgaccgac tgcatggaac gggccaggga agtgatcccc    240
agaagccagc accaggaaac ccccgtgtat ctgggagcca ccgccggcat gagactgctg    300
agaatggaaa gcgaggaact ggccgaccgg gtgctgacg tggtggaaag aagcctgagc    360
aactacccat tcgattttca aggcgccaga atcatcaccg ccaggaaga aggcgcctac    420
ggctggatca ccatcaacta cctgctgggc aagttcagcc agaagaatca ggaaaccttc    480
ggcgccctgg acctgggcgg agcttctacc caagtgacct tcgtgcccca gaatcagacc    540
atcgagagcc ccgacaacgc cctgcagttc cggctgtacg gcaaggacta caatgtgtac    600
acccacagct ttctgtgcta cggaaaggac caggcgctgt ggcagaagct ggccaaggac    660
atccaggtgg ccagcaacga gatcctgcgg gaccccttgct tccaccccgg ctacaagaaa    720
gtcgtgaagg tgtccgacct gtacaagacc cctgcacca agagattcga gatgaccctg    780
ccccttccagc agttcgagat ccagggcatc ggcaattacc agcagtgcca ccagagcatc    840
```

-continued

```
ctggaactgt tcaacaccag ctactgccca tacagccagt gcgccttcaa cggcatcttc    900
ctgccacctc tgcaggggga tttcggcgcc ttcagcgcct tctactccgt gatgaagttc    960
ctgaacctga ccagcgagaa ggtgtcccag gaaaaagtga cagagatgat gaagaagttc   1020
tgcgcccagc cctgggagga aatcaagacc tcctacgctg gcgtgaaaga gaagtacctg   1080
agcgagtact gcttcagcgg cacctacatc ctgagcctgc tgccgcaggg ctaccacttc   1140
accgccgata gctgggagca catccacttc atcggcaaga ttcagggcag cgacgccggc   1200
tggacactgg gctacatgct gaatctgacc aacatgatct ccgccgagca gcccctgagc   1260
acacctctga gccacagcac c                                              1281
```

<210> SEQ ID NO 36
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 36

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270
```

```
Tyr Gln Gln Cys His Gln Ser Ile Leu Glu Leu Phe Asn Thr Ser Tyr
            275                 280                 285
Cys Pro Tyr Ser Gln Cys Ala Phe Asn Gly Ile Phe Leu Pro Pro Leu
        290                 295                 300
Gln Gly Asp Phe Gly Ala Phe Ser Ala Phe Tyr Phe Val Met Lys Phe
305                 310                 315                 320
Leu Asn Leu Thr Ser Glu Lys Val Ser Gln Glu Lys Val Thr Glu Met
                325                 330                 335
Met Lys Lys Phe Cys Ala Gln Pro Trp Glu Glu Ile Lys Thr Ser Tyr
            340                 345                 350
Ala Gly Val Asn Glu Lys Tyr Leu Ser Glu Phe Cys Phe Ser Gly Thr
        355                 360                 365
Tyr Ile Leu Ser Leu Leu Leu Gln Gly Tyr His Phe Thr Ala Asp Ser
    370                 375                 380
Trp Glu His Ile His Phe Ile Gly Lys Ile Gln Gly Ser Asp Ala Gly
385                 390                 395                 400
Trp Thr Leu Gly Tyr Met Leu Asn Leu Thr Asn Met Ile Pro Ala Glu
                405                 410                 415
Gln Pro Leu Ser Thr Pro Leu Ser His Ser Thr
            420                 425
```

<210> SEQ ID NO 37
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 37

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120
gtgcatcagg tggaagagtg cagagtgaag ggccctggca tcagcaagtt cgtgcagaaa     180
gtgaacgaga tcggcatcta cctgaccgac tgcatggaac gggccaggga agtgatcccc     240
agaagccagc accaggaaac ccccgtgtat ctgggagcca ccgccggcat gagactgctg     300
agaatggaaa gcgaggaact ggccgaccgg gtgctggacg tggtggaaag aagcctgagc     360
aactacccat tcgattttca aggcgccaga atcatcaccg gccaggaaga aggcgcctac     420
ggctggatca ccatcaacta cctgctgggc aagttcagcc agaagaatca ggaaaccttc     480
ggcgccctgg acctgggcgg agcttctacc caagtgacct tcgtgcccca gaatcagacc     540
atcgagagcc ccgacaacgc cctgcagttc cggctgtacg caaggacta caatgtgtac     600
acccacagct ttctgtgcta cggaaaggac caggctctgt ggcagaagct ggccaaggac     660
atccaggtgg ccagcaacga gatcctgcgg gaccccttgct tccacccggg ctacaagaaa     720
gtcgtgaacg tgtccgacct gtacaagacc ccctgcacca agagattcga gatgaccctg     780
cccttccagc agttcgagat ccagggcatc ggcaattacc agcagtgcca ccagagcatc     840
ctggaactgt tcaacaccag ctactgcccc tacagccagt gcgccttcaa cggcatcttc     900
ctgccacctc tgcagggga tttcggcgcc ttcagcgcct ctacttcgt gatgaagttc       960
ctgaacctga ccagcgagaa ggtgtcccag gaaaaagtga cagagatgat gaagaagttc    1020
tgcgcccaac cctgggagga aatcaagacc tcctacgctg gcgtgaacga agagtacctg    1080
agcgagtttt gcttcagcgg cacctacatc ctgagcctgc tgctgcaggg ctaccacttc    1140
```

```
accgccgata gctgggagca catccacttc atcggcaaga ttcagggcag cgacgccggc    1200
tggacactgg gctacatgct gaatctgacc aacatgatcc ccgccgagca gcccctgagc    1260
acacctctga gccacagcac c                                               1281
```

<210> SEQ ID NO 38
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 38

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Phe Val Met Lys Phe
305                 310                 315                 320
```

```
Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Phe Cys Phe Ser Gly Thr
        355                 360                 365

Tyr Ile Leu Ser Leu Leu Leu Gln Gly Tyr His Phe Thr Ala Asp Ser
    370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
                420                 425

<210> SEQ ID NO 39
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 39
acccagaaca aggccctgcc cgagaacgtg aagtacggca tcgtgctgga tgccggcagc      60
agccacacca gcctgtacat ctacaagtgg cctgccgaga agaaaacga caccggcgtg     120 gtgcatcagg tggaagagtg cagagtgaag ggccctggca tcagcaagtt cgtgcagaaa     180
gtgaacgaga tcggcatcta cctgaccgac tgcatggaac gggccaggga agtgatcccc     240
agaagccagc accaggaaac ccccgtgtat ctgggagcca ccgccggcat gagactgctg     300
agaatggaaa gcgaggaact ggccgaccgg gtgctggacg tggtggaaag aagcctgagc     360
aactacccat tcgattttca aggcgccaga atcatccacg gccaggaaga aggcgcctac     420
ggctggatca ccatcaacta cctgctgggc aagttcagcc agaagaatca ggaaaccttc     480
ggcgccctgg acctgggcgg agcttctacc caagtgacct tcgtgcccca gaatcagacc     540
atcgagagcc ccgacaacgc cctgcagttc cggctgtacg caaggactta caatgtgtac     600
acccacagct ttctgtgcta cggaaaggac caggctctgt ggcagaagct ggccaaggac     660
atccaggtgg ccagcaacga gatcctgcgg gacccttgct ccaccccgg ctacaagaaa     720 gtcgtgaacg tgtccgacct gtacaagacc ccctgcacca agagattcga gatgaccctg     780
cccttccagc agttcgagat ccagggcatc ggcaattacc agcagtgcca ccagagcatc     840
ctggaactgt tcaacaccag ctactgcccc tacagccagt cgccttcaa cggcatcttc     900 ctgccacctc tgcagggga tttcggcgcc ttcagcgcct ctacttcgt gatgaagttc     960 ctgaacctga ccagcgagaa ggtgtcccag gaaaaagtga cagagatgat gaagaagttc    1020
tgcgcccagc cctgggagga aatcaagacc tcctacgctg gcgtgaaaga gaagtacctg    1080
agcgagtttt gcttcagcgg cacctacatc ctgagcctgc tgctgcaggg ctaccacttc    1140
accgccgata gctgggagca catccacttc atcggcaaga ttcagggcag cgacgccggc    1200
tggacactgg gctacatgct gaatctgacc aacatgatcc ccgccgagca gcccctgagc    1260
acacctctga gccacagcac c                                              1281

<210> SEQ ID NO 40
```

```
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Cys Arg
        35                  40                  45

Val Lys Gly Pro Gly Ile Ser Lys Phe Val Gln Lys Val Asn Glu Ile
    50                  55                  60

Asp Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
        355                 360                 365
```

```
Tyr Ile Leu Ser Leu Leu Gln Gln Gly Tyr His Phe Thr Ala Asp Ser
        370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425

<210> SEQ ID NO 41
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 41
```

| | | | | | |
|---|---|---|---|---|---|
| acccagaaca | aggccctgcc | cgagaacgtg | aagtacggca | tcgtgctgga | tgccggcagc | 60 |
| agccacacca | gcctgtacat | ctacaagtgg | cctgccgaga | agaaaacga | caccggcgtg | 120 |
| gtgcatcagg | tggaagagtg | cagagtgaag | ggccctggca | tcagcaagtt | cgtgcagaaa | 180 |
| gtgaacgaga | tcgacatcta | cctgaccgac | tgcatggaac | gggccaggga | agtgatcccc | 240 |
| agaagccagc | accaggaaac | ccccgtgtat | ctgggagcca | ccgccggcat | gagactgctg | 300 |
| agaatggaaa | gcgaggaact | ggccgaccgg | gtgctggacg | tggtggaaag | aagcctgagc | 360 |
| aactacccat | cgattttca | aggcgccaga | atcatccg | ccaggaaga | aggcgcctac | 420 |
| ggctggatca | ccatcaacta | cctgctgggc | aagttcagcc | agaagaatca | ggaaaccttc | 480 |
| ggcgccctgg | acctgggcgg | agcttctacc | caagtgacct | cgtgccccca | gaatcagacc | 540 |
| atcgagagcc | ccgacaacgc | cctgcagttc | cggctgtacg | gcaaggacta | caatgtgtac | 600 |
| acccacagct | ttctgtgcta | cggaaaggac | caggctctgt | ggcagaagct | ggccaaggac | 660 |
| atccaggtgg | ccagcaacga | gatcctgcgg | gacccttgct | tccaccccgg | ctacaagaaa | 720 |
| gtcgtgaacg | tgtccgacct | gtacaagacc | ccctgcacca | agagattcga | gatgacccctg | 780 |
| ccctcaccagc | agttcgagat | ccagggcatc | ggcaattacc | agcagtgcca | ccagagcatc | 840 |
| ctggaactgt | tcaacaccag | ctactgcccc | tacagccagt | gcgccttcaa | cggcatcttc | 900 |
| ctgccacctc | tgcaggggga | tttcggcgcc | ttcagcgcct | tctacttcgt | gatgaagttc | 960 |
| ctgaacctga | ccagcgagaa | ggtgtcccag | gaaaaagtga | cagagatgat | gaagaagttc | 1020 |
| tgcgcccagc | cctgggagga | aatcaagacc | tcctacgctg | gcgtgaaaga | gaagtacctg | 1080 |
| agcgagtact | gcttcagcgg | cacctacatc | ctgagcctgc | tgcagcaggg | ctaccacttc | 1140 |
| accgccgata | gctgggagca | catccacttc | atcggcaaga | ttcagggcag | cgacgccggc | 1200 |
| tggacactgg | gctacatgct | gaatctgacc | aacatgatcc | ccgccgagca | gcccctgagc | 1260 |
| acacctctga | gccacagcac | c | | | | 1281 |

```
<210> SEQ ID NO 42
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42
```

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
                20                  25                  30

Glu Lys Glu Asn Asp Thr Gly Val Val His Gln Val Glu Cys Arg
            35                  40                  45

Val Lys Gly Pro Gly Ile Ser Lys Phe Val Gln Lys Val Asn Glu Ile
        50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
            115                 120                 125

Ala Arg Ile Ile Thr Gly Gln Glu Gly Ala Tyr Gly Trp Ile Thr
            130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
            195                 200                 205

Lys Asp Gln Ala Leu Trp Gln Lys Leu Ala Lys Asp Ile Gln Val Ala
210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
            245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
            275                 280                 285

Cys Pro Tyr Ser Gln Cys Ala Phe Asn Gly Ile Phe Leu Pro Pro Leu
            290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
            355                 360                 365

Tyr Ile Leu Ser Leu Leu Gln Gln Gly Tyr His Phe Thr Ala Asp Ser
370                 375                 380

Trp Glu Asp Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
            405                 410                 415
```

Gln Pro Leu Ser Thr Pro Leu Ser His Ser Thr
            420                 425

<210> SEQ ID NO 43
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 43

| | | | | |
|---|---|---|---|---|
| acccagaaca | aggccctgcc | cgagaacgtg | aagtacggca | tcgtgctgga  tgccggcagc | 60 |
| agccacacca | gcctgtacat | ctacaagtgg | cctgccgaga | agaaaacga  caccggcgtg | 120 |
| gtgcatcagg | tggaagagtg | cagagtgaag | ggccctggca | tcagcaagtt  cgtgcagaaa | 180 |
| gtgaacgaga | tcggcatcta | cctgaccgac | tgcatggaac | gggccaggga  agtgatcccc | 240 |
| agaagccagc | accaggaaac | ccccgtgtat | ctgggagcca | ccgccggcat  gagactgctg | 300 |
| agaatggaaa | gcgaggaact | ggccgaccgg | gtgctggacg | tggtggaaag  aagcctgagc | 360 |
| aactacccat | tcgatttca  | aggcgccaga | atcatcaccg | ccaggaaga  aggcgcctac | 420 |
| ggctggatca | ccatcaacta | cctgctgggc | aagttcagcc | agaagaatca  ggaaaccttc | 480 |
| ggcgccctgg | acctgggcgg | agcttctacc | caagtgacct | tcgtgcccca  gaatcagacc | 540 |
| atcgagagcc | ccgacaacgc | cctgcagttc | cggctgtacg | gcaaggacta  caatgtgtac | 600 |
| acccacagct | ttctgtgcta | cggaaaggac | caggctctgt | ggcagaagct  ggccaaggac | 660 |
| atccaggtgg | ccagcaacga | gatcctgcgg | gaccttgct  | tccaccccgg  ctacaagaaa | 720 |
| gtcgtgaacg | tgtccgacct | gtacaagacc | ccctgcacca | agagattcga  gatgaccctg | 780 |
| cccttccagc | agttcgagat | ccagggcatc | ggcaattacc | agcagtgcca  ccagagcatc | 840 |
| ctggaactgt | tcaacaccag | ctactgcccc | tacagccagt | gcgccttcaa  cggcatcttc | 900 |
| ctgccaccte | tgcaggggga | tttcggcgcc | ttcagcgcct | tctacttcgt  gatgaagttc | 960 |
| ctgaacctga | ccagcgagaa | ggtgtcccag | gaaaaagtga | cagagatgat  gaagaagttc | 1020 |
| tgcgcccagc | cctgggagga | aatcaagacc | tcctacgctg | gcgtgaaaga  gaagtacctg | 1080 |
| agcgagtact | gcttcagcgg | cacctacatc | ctgagcctgc | tgcagcaggg  ctaccacttc | 1140 |
| accgccgata | gctgggagga | catccacttc | atcggcaaga | ttcagggcag  cgacgccggc | 1200 |
| tggacactgg | gctacatgct | gaatctgacc | aacatgatcc | ccgccgagca  gccctgagc  | 1260 |
| acacctctga | gccacagcac | c | | | 1281 |

<210> SEQ ID NO 44
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
 50                  55                  60

Gly Ile Tyr Leu Thr Asp Cys Met Glu Arg Ala Arg Glu Val Ile Pro
 65                  70                  75                  80

Arg Ser Gln His Gln Glu Thr Pro Val Tyr Leu Gly Ala Thr Ala Gly
                 85                  90                  95

Met Arg Leu Leu Arg Met Glu Ser Glu Leu Ala Asp Arg Val Leu
                100                 105                 110

Asp Val Val Glu Arg Ser Leu Ser Asn Tyr Pro Phe Asp Phe Gln Gly
             115                 120                 125

Ala Arg Ile Ile Thr Gly Gln Glu Gly Ala Tyr Gly Trp Ile Thr
         130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
                180                 185                 190

Tyr Gly Lys Asp Tyr Asn Val Tyr Thr His Ser Phe Leu Cys Tyr Gly
            195                 200                 205

Lys Asp Gln Ala Leu Trp Gln Lys Leu Ala Lys Asp Ile Gln Val Ala
210                 215                 220

Ser Asn Gly Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
                260                 265                 270

Tyr Gln Gln Cys His Gln Ser Ile Leu Glu Leu Phe Asn Thr Ser Tyr
            275                 280                 285

Cys Pro Tyr Ser Gln Cys Ala Phe Asn Gly Ile Phe Leu Pro Pro Leu
290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Ile Lys Thr Ser Tyr
            340                 345                 350

Ala Gly Val Lys Glu Lys Tyr Leu Ser Glu Tyr Cys Phe Ser Gly Thr
            355                 360                 365

Tyr Ile Leu Ser Leu Leu Gln Gly Tyr His Phe Thr Ala Asp Ser
370                 375                 380

Trp Glu His Ile His Ser Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
                420                 425

<210> SEQ ID NO 45
<211> LENGTH: 1281
<212> TYPE: DNA
<213> ORGANISM: Artificial Sequence
<220> FEATURE:

-continued

<221> NAME/KEY: source
<223> OTHER INFORMATION: /note="Description of Artificial Sequence:
      Synthetic polynucleotide"

<400> SEQUENCE: 45

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120
gtgcatcagg tggaagagtg cagagtgaag ggccctggca tcagcaagtt cgtgcagaaa     180
gtgaacgaga tcggcatcta cctgaccgac tgcatggaac gggccaggga agtgatcccc     240
agaagccagc accaggaaac ccccgtgtat ctgggagcca ccgccggcat gagactgctg     300
agaatggaaa gcgaggaact ggccgaccgg gtgctggacg tggtggaaag aagcctgagc     360
aactacccat tcgattttca aggcgccaga atcatcaccg gccaggaaga aggcgcctac     420
ggctggatca ccatcaacta cctgctgggc aagttcagcc agaagaatca ggaaaccttc     480
ggcgccctgg acctgggcgg agcttctacc caagtgacct tcgtgcccca gaatcagacc     540
atcgagagcc ccgacaacgc cctgcagttc cggctgtacg caaggactga caatgtgtac     600
acccacagct ttctgtgcta cggaaaggac caggctctgt ggcagaagct ggccaaggac     660
atccaggtgg ccagcaacgg gatcctgcgc gaccccttgct tccacccccgg ctacaagaaa     720
gtcgtgaacg tgtccgacct gtacaagacc ccctgcacca agagattcga gatgaccctg     780
cccttccagc agttcgagat ccagggcatc ggcaattacc agcagtgcca ccagagcatc     840
ctggaactgt tcaacaccag ctactgcccc tacagccagt gcgccttcaa cggcatcttc     900
ctgccacctc tgcagggga tttcggcgcc ttcagcgcct ctacttcgt gatgaagttc     960
ctgaacctga ccagcgagaa ggtgtcccag gaaaagtga cagagatgat gaagaagttc     1020
tgcgcccagc cctgggagga aatcaagacc tcctacgctg gcgtgaaaga gaagtacctg     1080
agcgagtact gcttcagcgg cacctacatc ctgagcctgc tgctgcaggg ctaccacttc     1140
accgccgata gctgggagca catccactcc atcggcaaga ttcagggcag cgacgccggc     1200
tggacactgg gctacatgct gaatctgacc aacatgatcc ccgccgagca gcccctgagc     1260
acacctctga gccacagcac c                                              1281
```

<210> SEQ ID NO 46
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Met Glu Val Ile Pro
65                  70                  75                  80

Arg Ser Gln His Gln Glu Thr Pro Val Tyr Leu Gly Ala Thr Ala Gly
                85                  90                  95
```

Met Arg Leu Leu Arg Met Glu Ser Glu Leu Ala Asp Arg Val Leu
            100                 105                 110
Asp Val Val Glu Arg Ser Leu Ser Asn Tyr Pro Phe Asp Phe Gln Gly
            115                 120                 125
Ala Arg Ile Ile Thr Gly Gln Glu Gly Ala Tyr Gly Trp Ile Thr
130                 135                 140
Ile Asn Tyr Leu Leu Gly Lys Phe Ser Gln Lys Asn Gln Glu Thr Phe
145                 150                 155                 160
Gly Ala Leu Asp Leu Gly Gly Ala Ser Thr Gln Val Thr Phe Val Pro
                165                 170                 175
Gln Asn Gln Thr Ile Glu Ser Pro Asp Asn Ala Leu Gln Phe Arg Leu
            180                 185                 190
Tyr Gly Lys Asp Tyr Asn Val Tyr Thr His Ser Phe Leu Cys Tyr Gly
            195                 200                 205
Lys Asp Gln Ala Leu Trp Gln Lys Leu Ala Lys Asp Ile Gln Val Ala
210                 215                 220
Ser Asn Glu Ile Leu Arg Asp Pro Cys Phe His Pro Gly Tyr Lys Lys
225                 230                 235                 240
Val Val Asn Val Ser Asp Leu Tyr Lys Thr Pro Cys Thr Lys Arg Phe
                245                 250                 255
Glu Met Thr Leu Pro Phe Gln Gln Phe Glu Ile Gln Gly Ile Gly Asn
            260                 265                 270
Tyr Gln Gln Cys His Gln Ser Ile Leu Glu Leu Phe Asn Thr Ser Tyr
            275                 280                 285
Cys Pro Tyr Ser Gln Cys Ala Phe Asn Gly Ile Phe Leu Pro Pro Leu
            290                 295                 300
Gln Gly Asp Phe Gly Ala Phe Ser Ala Phe Tyr Phe Val Met Lys Phe
305                 310                 315                 320
Leu Asn Leu Thr Ser Glu Lys Val Ser Gln Glu Lys Val Thr Glu Met
                325                 330                 335
Met Lys Lys Phe Cys Ala Gln Pro Trp Glu Ile Lys Thr Ser Tyr
            340                 345                 350
Ala Gly Val Lys Glu Lys Tyr Leu Ser Gly Tyr Cys Phe Ser Gly Thr
            355                 360                 365
Tyr Ile Leu Ser Leu Leu Leu Gln Gly Tyr His Phe Thr Ala Asp Ser
370                 375                 380
Trp Glu His Ile His Phe Ile Gly Lys Ile Gln Gly Ser Asp Ala Gly
385                 390                 395                 400
Trp Thr Leu Gly Tyr Met Leu Asn Leu Thr Asn Met Ile Pro Ala Glu
                405                 410                 415
Gln Pro Leu Arg Thr Pro Leu Ser His Ser Thr
            420                 425

<210> SEQ ID NO 47
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 47
acccagaaca aggccctgcc cgagaacgtg aagtacggca tcgtgctgga tgccggcagc      60
agccacacca gcctgtacat ctacaagtgg cctgccgaga agaaaacga caccggcgtg     120

```
gtgcatcagg tggaagagtg cagagtgaag ggccctggca tcagcaagtt cgtgcagaaa    180
gtgaacgaga tcggcatcta cctgaccgac tgcatggaac gggccatgga agtgatcccc    240
agaagccagc accaggaaac ccccgtgtat ctgggagcca ccgccggcat gagactgctg    300
agaatggaaa gcgaggaact ggccgaccgg gtgctggacg tggtggaaag aagcctgagc    360
aactacccat tcgattttca aggcgccaga atcatcaccg gccaggaaga aggcgcctac    420
ggctggatca ccatcaacta cctgctgggc aagttcagcc agaagaatca ggaaaccttc    480
ggcgccctgg acctgggcgg agcttctacc caagtgacct tcgtgcccca gaatcagacc    540
atcgagagcc ccgacaacgc cctgcagttc ggctgtacg gcaaggacta caatgtgtac     600
acccacagct ttctgtgcta cggaaaggac caggctctgt ggcagaagct ggccaaggac    660
atccaggtgg ccagcaacga gatcctgcgg gaccccttgct tccacccccgg ctacaagaaa  720
gtcgtgaacg tgtccgacct gtacaagacc ccctgcacca agagattcga gatgaccctg    780
cccttccagc agttcgagat ccagggcatc ggcaattacc agcagtgcca ccagagcatc    840
ctggaactgt tcaacaccag ctactgcccc tacagccagt gcgccttcaa cggcatcttc    900
ctgccacctc tgcaggggga tttcggcgcc ttcagcgcct tctacttcgt gatgaagttc    960
ctgaacctga ccagcgagaa ggtgtcccag gaaaaagtga cagagatgat gaagaagttc   1020
tgcgcccagc cctgggagga aatcaagacc tcctacgctg gcgtgaaaga aagtacctg    1080
agcgagtact gcttcagcgg cacctacatc ctgagcctgc tgctgcaggg ctaccacttc   1140
accgccgata gctgggagca catccacttc atcggcaaga ttcagggcag cgacgccggc   1200
tggacactgg gctacatgct gaatctgacc aacatgatcc ccgccgagca gcccctgcgc   1260
acacctctga gccacagcac c                                              1281

<210> SEQ ID NO 48
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140
```

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Gly Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
        355                 360                 365

Tyr Ile Leu Ser Leu Leu Leu Gln Gly Tyr His Phe Thr Ala Asp Ser
    370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Gly Thr Pro Leu Ser His Ser Thr
            420                 425

<210> SEQ ID NO 49
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 49
acccagaaca aggccctgcc cgagaacgtg aagtacggca tcgtgctgga tgccggcagc      60
agccacacca gcctgtacat ctacaagtgg cctgccgaga agaaaacga caccggcgtg     120 gtgcatcagg tggaagagtg cagagtgaag ggccctggca tcagcaagtt cgtgcagaaa     180
gtgaacgaga tcggcatcta cctgaccgac tgcatggaac gggccaggga agtgatcccc     240
agaagccagc accaggaaac ccccgtgtat ctgggagcca ccgccggcat gagactgctg     300
agaatggaaa gcgaggaact ggccgaccgg gtgctggacg tggtggaaag aagcctgagc     360

```
aactacccat tcgattttca aggcgccaga atcatcaccg gccaggaaga aggcgcctac    420
ggctggatca ccatcaacta cctgctgggc aagttcagcc agaagaatca ggaaaccttc    480
ggcgccctgg acctgggcgg agcttctacc caagtgacct tcgtgcccca gaatcagacc    540
atcgagagcc ccgacaacgc cctgcagttc cggctgtacg caaggactac aatgtgtac     600 acccacagct ttctgtgcta cggaaaggac caggctctgt ggcagaagct ggccaaggac    660
atccaggtgg ccagcaacgg gatcctgcgg gaccccttgct tccacccccgg ctacaagaaa   720 gtcgtgaacg tgtccgacct gtacaagacc ccctgcacca agagattcga gatgaccctg    780
cccttccagc agttcgagat ccagggcatc ggcaattacc agcagtgcca ccagagcatc    840
ctggaactgt tcaacaccag ctactgcccc tacagccagt gcgccttcaa cggcatcttc    900
ctgccacctc tgcagggga tttcggcgcc ttcagcgcct tctacttcgt gatgaagttc      960
ctgaacctga ccagcgagaa ggtgtcccag gaaaaagtga cagagatgat gaagaagttc    1020
tgcgcccagc cctgggagga aatcaagacc tcctacgctg gcgtgaaaga gaagtacctg    1080
agcgagtact gcttcagcgg cacctacatc ctgagcctgc tgctgcaggg ctaccacttc    1140
accgccgata gctgggagca catccacttc atcggcaaga ttcagggcag cgacgccggc    1200
tggacactgg gctacatgtt gaatctgacc aacatgatcc ccgccgagca gccccctgggc   1260 acacctctga gccacagcac c                                              1281
```

<210> SEQ ID NO 50
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
                20                  25                  30

Glu Lys Glu Asn Asp Thr Gly Val Val His Gln Val Glu Glu Cys Arg
            35                  40                  45

Val Lys Gly Pro Gly Ile Ser Lys Phe Val Gln Lys Val Asn Glu Ile
        50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190
```

```
Tyr Gly Lys Asp Tyr Asn Val Tyr Thr His Ser Phe Met Cys Tyr Gly
        195                 200                 205

Lys Asp Gln Ala Leu Arg Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
        355                 360                 365

Tyr Ile Leu Ser Leu Leu Leu Gln Gly Tyr His Phe Thr Ala Asp Ser
    370                 375                 380

Trp Glu His Ile His Ser Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Arg Thr Pro Leu Ser His Ser Thr
            420                 425
```

<210> SEQ ID NO 51
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 51

```
acccagaaca aggccctgcc cgagaacgtg aagtacggca tcgtgctgga tgccggcagc    60
agccacacca gcctgtacat ctacaagtgg cctgccgaga agaaaacga caccggcgtg   120 gtgcatcagg tggaagagtg cagagtgaag ggccctggca tcagcaagtt cgtgcagaaa   180
gtgaacgaga tcggcatcta cctgaccgac tgcatggaac gggccaggga agtgatcccc   240
agaagccagc accaggaaac ccccgtgtat ctgggagcca ccgccggcat gagactgctg   300
agaatggaaa gcgaggaact ggccgaccgg gtgctggacg tggtggaaag aagcctgagc   360
aactacccat cgattttca aggcgccaga atcatcaccg ccaggaaga aggcgcctac   420 ggctggatca ccatcaacta cctgctgggc aagttcagcc agaagaatca ggaaaccttc   480
ggcgccctgg acctgggcgg agcttctacc caagtgacct tcgtgcccca gaatcagacc   540
atcgagagcc ccgacaacgc cctgcagttc cggctgtacg gcaaggacta caatgtgtac   600
acccacagct ttatgtgcta cggaaaggac caggctctga ggcagaagct ggccaaggac   660
```

-continued

```
atccaggtgg ccagcaacga gatcctgcgg gacccttgct tccaccccgg ctacaagaaa      720
gtcgtgaacg tgtccgacct gtacaagacc ccctgtacca agagattcga gatgaccctg      780
cccttccagc agttcgagat ccagggcatc ggcaattacc agcagtgcca ccagagcatc      840
ctggaactgt tcaacaccag ctactgcccc tacagccagt cgccttcaa cggcatcttc       900 ctgccacctc tgcaggggga tttcggcgcc ttcagcgcct tctacttcgt gatgaagttc      960
ctgaacctga ccagcgagaa ggtgtcccag gaaaaagtga cagagatgat gaagaagttc     1020
tgcgcccagc cctgggagga aatcaagacc tcctacgctg gcgtgaaaga gaagtacctg     1080
agcgagtact gcttcagcgg cacctacatc ctgagcctgc tgctgcaggg ctaccacttc     1140
accgccgata gctgggagca catccactcc atcggcaaga ttcagggcag cgacgccggc     1200
tggacactgg gctacatgct gaatctgacc aacatgatcc ccgccgagca gcccctgaga     1260
acacctctga gccacagcac c                                               1281
```

<210> SEQ ID NO 52
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Lys Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240
```

```
Val Val Asn Val Ser Asp Leu Tyr Lys Thr Pro Cys Thr Lys Arg Phe
            245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
            275                 280                 285

Cys Pro Tyr Ser Gln Cys Ala Phe Asn Gly Ile Phe Leu Pro Pro Leu
            290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
            325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
            355                 360                 365

Tyr Ile Leu Ser Leu Leu Gln Gln Gly Tyr His Phe Thr Ala Asp Ser
            370                 375                 380

Trp Glu His Asn His Phe Ile Gly Lys Ile Gly Ser Asp Ala Gly
385                 390                 395                 400

Trp Thr Leu Gly Tyr Met Leu Asn Leu Thr Asn Met Ile Pro Ala Glu
            405                 410                 415

Gln Pro Leu Ser Thr Pro Leu Ser His Ser Thr
            420                 425
```

<210> SEQ ID NO 53
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 53

```
acccagaaca aggccctgcc cgagaacgtg aagtacggca tcgtgctgga tgccggcagc    60
agccacacca gcctgtacat ctacaagtgg cctgccgaga agaaaacga caccggcgtg    120 gtgcatcagg tggaagagtg cagagtgaag ggccctggca tcagcaagtt cgtgcagaaa   180
gtgaacgaga tcggcatcta cctgaccgac tgcatggaac gggccaagga agtgatcccc   240
agaagccagc accaggaaac ccccgtgtat ctgggagcca ccgccggcat gagactgctg   300
agaatggaaa gcgaggaact ggccgaccgg gtgctggacg tggtggaaag aagcctgagc   360
aactacccat cgattttca aggcgccaga atcatcaccg ccaggaaga aggcgcctac    420 ggctggatca ccatcaacta cctgctgggc aagttcagcc agaagaatca ggaaaccttc   480
ggcgccctgg acctgggcgg agcttctacc caagtgacct tcgtgcccca gaatcagacc   540
atcgagagcc ccgacaacgc cctgcagttc cggctgtacg gcaaggacta caatgtgtac   600
acccacagct ttctgtgcta cggaaaggac caggctctgt ggcagaagct ggccaaggac   660
atccaggtgg ccagcaacga gatcctgcgg gacccttgct tccacccccgg ctacaagaaa   720 gtcgtgaacg tgtccgacct gtacaagacc ccctgcacca agagattcga gatgaccctg   780
cccttccagc agttcgagat ccagggcatc ggcaattacc agcagtgcca ccagagcatc   840
ctggaactgt tcaacaccag ctactgcccc tacagccagt gcgccttcaa cggcatcttc   900
```

```
ctgccacctc tgcaggggga tttcggcgcc ttcagcgcct tctacttcgt gatgaagttc    960
ctgaacctga ccagcgagaa ggtgtcccag gaaaaagtga cagagatgat gaagaagttc   1020
tgcgcccagc cctgggagga aatcaagacc tcctacgctg gcgtgaaaga gaagtacctg   1080
agcgagtact gcttcagcgg cacctacatc ctgagcctgc tgcagcaggg ctaccacttc   1140
accgccgata gctgggagca caaccacttc atcggcaaga ttcagggcag cgacgccggc   1200
tggacactgg gctacatgct gaatctgacc aacatgatcc ccgccgagca gcccctgagc   1260
acacctctga gccacagcac c                                             1281
```

<210> SEQ ID NO 54
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Met Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285
```

```
Cys Pro Tyr Ser Gln Cys Ala Phe Asn Gly Ile Phe Leu Pro Pro Leu
        290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
                340                 345                 350

Ala Gly Val Asn Glu Lys Tyr Leu Ser Glu Phe Cys Phe Ser Gly Thr
            355                 360                 365

Tyr Ile Leu Ser Leu Leu Leu Gln Gly Tyr His Phe Thr Ala Asp Ser
        370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425
```

<210> SEQ ID NO 55
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 55

```
acccagaaca aggccctgcc cgagaacgtg aagtacggca tcgtgctgga tgccggcagc    60
agccacacca gcctgtacat ctacaagtgg cctgccgaga agaaaacga caccggcgtg   120
gtgcatcagg tggaagagtg cagagtgaag ggccctggca tcagcaagtt cgtgcagaaa   180
gtgaacgaga tcggcatcta cctgaccgac tgcatggaac gggccatgga agtgatcccc   240
agaagccagc accaggaaac ccccgtgtat ctgggagcca ccgccggcat gagactgctg   300
agaatggaaa gcgaggaact ggccgaccgg gtgctggacg tggtggaaag aagcctgagc   360
aactacccat cgattttca aggcgccaga atcatcaccg ccaggaaga aggcgcctac   420
ggctggatca ccatcaacta cctgctgggc aagttcagcc agaagaatca ggaaaccttc   480
ggcgccctgg acctgggcgg agcttctacc caagtgacct cgtgccccca gaatcagacc   540
atcgagagcc ccgacaacgc cctgcagttc cggctgtacg gcaaggacta caatgtgtac   600
acccacagct ttctgtgcta cggaaaggac caggctctgt ggcagaagct ggccaaggac   660
atccaggtgg ccagcaacga gatcctgcgg gacccttgct ccacccggg ctacaagaaa   720
gtcgtgaacg tgtccgacct gtacaagacc ccctgcacca agagattcga gatgaccctg   780
cccttccagc agttcgagat ccagggcatc ggcaattacc agcagtgcca ccagagcatc   840
ctggaactgt tcaacaccag ctactgcccc tacagccagt gcgccttcaa cggcatcttc   900
ctgccacctc tgcaggggga tttcggcgcc ttcagcgcct tctacttcgt gatgaagttc   960
ctgaacctga ccagcgagaa ggtgtcccag gaaaaagtga cagagatgat gaagaagttc  1020
tgcgcccaac cctgggagga aatcaagacc tcctacgctg gcgtgaacga gaagtacctg  1080
agcgagtttt gcttcagcgg cacctacatc ctgagcctgc tgctgcaggg ctaccacttc  1140
accgccgata gctgggagca catccacttc atcggcaaga ttcagggcag cgacgccggc  1200
```

-continued

```
tggacactgg gctacatgct gaatctgacc aacatgatcc ccgccgagca gcccctgagc    1260
acacctctga gccacagcac c                                              1281
```

<210> SEQ ID NO 56
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Met Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335
```

```
Met Lys Lys Phe Cys Ala Gln Pro Trp Glu Glu Ile Lys Thr Ser Tyr
            340                 345                 350

Ala Gly Val Lys Glu Lys Tyr Leu Ser Glu Phe Cys Phe Ser Gly Thr
        355                 360                 365

Tyr Ile Leu Ser Leu Leu Leu Gln Gly Tyr His Phe Thr Ala Asp Ser
    370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425
```

<210> SEQ ID NO 57
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120
gtgcatcagg tggaagagtg cagagtgaag ggccctggca tcagcaagtt cgtgcagaaa     180
gtgaacgaga tcggcatcta cctgaccgac tgcatggaac gggccatgga agtgatcccc     240
agaagccagc accaggaaac ccccgtgtat ctgggagcca ccgccggcat gagactgctg     300
agaatggaaa gcgaggaact ggccgaccgg gtgctggacg tggtggaaag aagcctgagc     360
aactacccat tcgattttca aggcgccaga atcatcaccg ccaggaaga aggcgcctac     420
ggctggatca ccatcaacta cctgctgggc aagttcagcc agaagaatca ggaaaccttc     480
ggcgccctgg acctgggcgg agcttctacc caagtgacct tcgtgcccca gaatcagacc     540
atcgagagcc ccgacaacgc cctgcagttc cggctgtacg caaggacta caatgtgtac     600
acccacagct ttctgtgcta cggaaaggac caggctctgt ggcagaagct ggccaaggac     660
atccaggtgg ccagcaacga gatcctgcgg gacccttgct tccacccggg ctacaagaaa     720
gtcgtgaacg tgtccgacct gtacaagacc ccctgcacca agagattcga gatgaccctg     780
cccttccagc agttcgagat ccagggcatc ggcaattacc agcagtgcca ccagagcatc     840
ctggaactgt tcaacaccag ctactgcccc tacagccagt gcgccttcaa cggcatcttc     900
ctgccacctc tgcaggggga tttcggcgcc ttcagcgcct tctacttcgt gatgaagttc     960
ctgaacctga ccagcgagaa ggtgtcccag gaaaaagtga cagagatgat gaagaagttc    1020
tgcgcccagc cctggaggga aatcaagacc tcctacgctg gcgtgaaaga gaagtacctg    1080
agcgagtttt gcttcagcgg cacctacatc ctgagcctgc tgctgcaggg ctaccacttc    1140
accgccgata gctgggagca catccacttc atcggcaaga ttcagggcag cgacgccggc    1200
tggacactgg gctacatgct gaatctgacc aacatgatcc ccgccgagca gcccctgagc    1260
acacctctga gccacagcac c                                              1281
```

<210> SEQ ID NO 58
<211> LENGTH: 430
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 58

```
Ala Pro Thr Thr Gln Asn Lys Ala Leu Pro Glu Asn Val Lys Tyr Gly
1               5                   10                  15
Ile Val Leu Asp Ala Gly Ser Ser His Thr Ser Leu Tyr Ile Tyr Lys
            20                  25                  30
Trp Pro Ala Glu Lys Glu Asn Asp Thr Gly Val Val His Gln Val Glu
        35                  40                  45
Glu Cys Arg Val Lys Gly Pro Gly Ile Ser Lys Phe Val Gln Lys Val
    50                  55                  60
Asn Glu Ile Gly Ile Tyr Leu Thr Asp Cys Met Glu Arg Ala Arg Glu
65                  70                  75                  80
Val Ile Pro Arg Ser Gln His Gln Glu Thr Pro Val Tyr Leu Gly Ala
                85                  90                  95
Thr Ala Gly Met Arg Leu Leu Arg Met Glu Ser Glu Glu Leu Ala Asp
            100                 105                 110
Arg Val Leu Asp Val Val Glu Arg Ser Leu Ser Asn Tyr Pro Phe Asp
        115                 120                 125
Phe Gln Gly Ala Arg Ile Ile Thr Gly Gln Glu Glu Gly Ala Tyr Gly
    130                 135                 140
Trp Ile Thr Ile Asn Tyr Leu Leu Gly Lys Phe Ser Gln Lys Asn Gln
145                 150                 155                 160
Glu Thr Phe Gly Ala Leu Asp Leu Gly Gly Ala Ser Thr Gln Val Thr
                165                 170                 175
Phe Val Pro Gln Asn Gln Thr Ile Glu Ser Pro Asp Asn Ala Leu Gln
            180                 185                 190
Phe Arg Leu Tyr Gly Lys Asp Tyr Asn Val Tyr Thr His Ser Phe Leu
        195                 200                 205
Cys Tyr Gly Lys Asp Gln Ala Leu Trp Gln Lys Leu Ala Lys Asp Ile
    210                 215                 220
Gln Val Ala Ser Asn Glu Ile Leu Arg Asp Pro Cys Phe His Pro Gly
225                 230                 235                 240
Tyr Lys Lys Val Val Asn Val Ser Asp Leu Tyr Lys Thr Pro Cys Thr
                245                 250                 255
Lys Arg Phe Glu Met Thr Leu Pro Phe Gln Gln Phe Glu Ile Gln Gly
            260                 265                 270
Ile Gly Asn Tyr Gln Gln Cys His Gln Ser Ile Leu Glu Leu Phe Asn
        275                 280                 285
Thr Ser Tyr Cys Pro Tyr Ser Gln Cys Ala Phe Asn Gly Ile Phe Leu
    290                 295                 300
Pro Pro Leu Gln Gly Asp Phe Gly Ala Phe Ser Ala Phe Tyr Phe Val
305                 310                 315                 320
Met Lys Phe Leu Asn Leu Thr Ser Glu Lys Val Ser Gln Glu Lys Val
                325                 330                 335
Thr Glu Met Met Lys Lys Phe Cys Ala Gln Pro Trp Glu Glu Ile Lys
            340                 345                 350
Thr Ser Tyr Ala Gly Val Lys Glu Lys Tyr Leu Ser Glu Tyr Cys Phe
        355                 360                 365
Ser Gly Thr Tyr Ile Leu Ser Leu Leu Leu Gln Gly Tyr His Phe Thr
    370                 375                 380
```

Ala Asp Ser Trp Glu His Ile His Phe Ile Gly Lys Ile Gln Gly Ser
385                 390                 395                 400

Asp Ala Gly Trp Thr Leu Gly Tyr Met Leu Asn Leu Thr Asn Met Ile
            405                 410                 415

Pro Ala Glu Gln Pro Leu Ser Pro Leu Ser His Ser Thr
            420                 425                 430

<210> SEQ ID NO 59
<211> LENGTH: 1290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 59

| | | | | |
|---|---|---|---|---|
| gcccctacca | cccagaacaa | ggccctgccc | gagaacgtga | agtacggcat cgtgctggac | 60 |
| gccggctcct | cccacacctc | cctgtacatc | tacaagtggc | tgccgagaa agaaaacgac | 120 |
| accggcgtgg | tgcaccaagt | ggaagagtgc | agagtgaagg | ccccggcat ctccaagttc | 180 |
| gtgcagaaag | tgaacgagat | cggcatctac | ctgaccgact | gcatggaacg ggccagagaa | 240 |
| gtgatccctc | ggtcccagca | ccaggaaacc | cctgtctacc | tgggcgccac cgccggcatg | 300 |
| cggctgctgc | ggatggaatc | cgaggaactg | gccgaccggg | tgctggacgt ggtggaacgg | 360 |
| tccctgtcca | actacccatt | cgattttcaa | ggcgccagaa | tcatcaccgg ccaggaagag | 420 |
| ggcgcctacg | gctggatcac | catcaactac | ctgctgggca | gttctcccca gaagaatcag | 480 |
| gaaaccttcg | gcgccctgga | cctgggcgga | gccagcaccc | aagtcacatt cgtgccccag | 540 |
| aaccagacca | tcgagagccc | cgacaacgcc | ctgcagttcc | ggctgtacgg caaggactac | 600 |
| aacgtgtaca | cccacagctt | tctgtgctac | ggcaaggacc | aggccctgtg cagaagctg | 660 |
| gccaaggaca | tccaagtggc | ctccaacgag | atcctgcggg | accccctgctt ccaccccggc | 720 |
| tacaagaaag | tggtcaacgt | gtccgacctg | tacaagaccc | cttgcaccaa gagattcgag | 780 |
| atgacccctgc | ccttccagca | gttcgagatc | cagggcatcg | gcaactacca gcagtgccac | 840 |
| cagtccatcc | tggaactgtt | caacacctcc | tactgcccct | actcccagtg cgccttcaac | 900 |
| ggcatcttcc | tgcctccact | gcagggcgac | ttcggcgcct | ctccgcctt ctacttcgtg | 960 |
| atgaagttcc | tgaacctgac | ctccgagaaa | gtgtcccagg | aaaagtgac cgagatgatg | 1020 |
| aagaagttct | gcgcccagcc | ctgggaggaa | atcaagacct | cctacgctgg cgtgaaagag | 1080 |
| aagtacctgt | ccgagtactg | cttctccggc | acctacatcc | tgtccctgct gctgcagggc | 1140 |
| taccacttca | ccgccgacag | ctgggagcac | atccacttca | tcggcaagat ccagggatcc | 1200 |
| gacgctggct | ggaccctggg | ctacatgctg | aatctgacca | acatgatccc cgccgagcag | 1260 |
| cccctgtcca | cccctctgtc | tcactccacc | | | 1290 |

<210> SEQ ID NO 60
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Thr Gln Asn Lys Ala Leu Pro Glu Asn Val Lys Tyr Gly Ile Val Leu

```
1               5                   10                  15
Asp Ala Gly Ser Ser His Thr Ser Leu Tyr Ile Tyr Lys Trp Pro Ala
                20                  25                  30
Glu Lys Glu Asn Asp Thr Gly Val Val His Gln Val Glu Glu Cys Arg
                35                  40                  45
Val Lys Gly Pro Gly Ile Ser Lys Phe Val Gln Lys Val Asn Glu Ile
                50                  55                  60
Gly Ile Tyr Leu Thr Asp Cys Met Glu Arg Ala Arg Glu Val Ile Pro
65                  70                  75                  80
Arg Ser Gln His Gln Glu Thr Pro Val Tyr Leu Gly Ala Thr Ala Gly
                85                  90                  95
Met Arg Leu Leu Arg Met Glu Ser Glu Leu Ala Asp Arg Val Leu
                100                 105                 110
Asp Val Val Glu Arg Ser Leu Ser Asn Tyr Pro Phe Asp Phe Gln Gly
                115                 120                 125
Ala Arg Ile Ile Thr Gly Gln Glu Gly Ala Tyr Gly Trp Ile Thr
                130                 135                 140
Ile Asn Tyr Leu Leu Gly Lys Phe Ser Gln Lys Asn Gln Glu Thr Phe
145                 150                 155                 160
Gly Ala Leu Asp Leu Gly Gly Ala Ser Thr Gln Val Thr Phe Val Pro
                165                 170                 175
Gln Asn Gln Thr Ile Glu Ser Pro Asp Asn Ala Leu Gln Phe Arg Leu
                180                 185                 190
Tyr Gly Lys Asp Tyr Asn Val Tyr Thr His Ser Phe Leu Cys Tyr Gly
                195                 200                 205
Lys Asp Gln Ala Leu Trp Gln Lys Leu Ala Lys Asp Ile Gln Val Ala
                210                 215                 220
Ser Asn Glu Ile Leu Arg Asp Pro Cys Phe His Pro Gly Tyr Lys Lys
225                 230                 235                 240
Val Val Asn Val Ser Asp Leu Tyr Lys Thr Pro Cys Thr Lys Arg Phe
                245                 250                 255
Glu Met Thr Leu Pro Phe Gln Gln Phe Glu Ile Gln Gly Ile Gly Asn
                260                 265                 270
Tyr Gln Gln Cys His Gln Ser Ile Leu Glu Leu Phe Asn Thr Ser Tyr
                275                 280                 285
Cys Pro Tyr Ser Gln Cys Ala Phe Asn Gly Ile Phe Leu Pro Pro Leu
                290                 295                 300
Gln Gly Asp Phe Gly Ala Phe Ser Ala Phe Tyr Ser Val Met Lys Phe
305                 310                 315                 320
Leu Asn Leu Thr Ser Glu Lys Val Ser Gln Glu Lys Val Thr Glu Met
                325                 330                 335
Met Lys Lys Phe Cys Ala Gln Pro Trp Glu Glu Ile Lys Thr Ser Tyr
                340                 345                 350
Ala Gly Val Lys Glu Lys Tyr Leu Ser Glu Phe Cys Phe Ser Gly Thr
                355                 360                 365
Tyr Ile Leu Ser Leu Leu Leu Gln Gly Tyr His Phe Thr Ala Asp Ser
                370                 375                 380
Trp Glu His Ile His Phe Ile Gly Lys Ile Gln Gly Ser Asp Ala Gly
385                 390                 395                 400
Trp Thr Leu Gly Tyr Met Leu Asn Leu Thr Asn Met Ile Pro Ala Glu
                405                 410                 415
Gln Pro Leu Ser Thr Pro Leu Ser His Ser Thr
                420                 425
```

<210> SEQ ID NO 61
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 61

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120
gtgcatcagg tggaagagtg cagagtgaag ggccctggca tcagcaagtt cgtgcagaaa     180
gtgaacgaga tcggcatcta cctgaccgac tgcatggaac gggccaggga agtgatcccc     240
agaagccagc accaggaaac ccccgtgtat ctgggagcca ccgccggcat gagactgctg     300
agaatggaaa gcgaggaact ggccgaccgg gtgctggacg tggtggaaag aagcctgagc     360
aactacccat tcgattttca aggcgccaga atcatcaccg gccaggaaga aggcgcctac     420
ggctggatca ccatcaacta cctgctgggc aagttcagcc agaagaatca ggaaaccttc     480
ggcgccttgg acctgggcgg agcttctacc caagtgacct tcgtgcccca gaatcagacc     540
atcgagagcc ccgacaacgc cctgcagttc cggctgtacg caaggacta caatgtgtac     600
acccacagct ttctgtgcta cggaaaggac caggctctgt ggcagaagct ggccaaggac     660
atccaggtgg ccagcaacga gatcctgcgg gaccccttgct tccacccggg ctacaagaaa     720
gtcgtgaacg tgtccgacct gtacaagacc ccctgcacca agagattcga gatgaccctg     780
cccttccagc agttcgagat ccagggcatc ggcaattacc agcagtgcca ccagagcatc     840
ctggaactgt tcaacaccag ctactgcccc tacagccagt gcgccttcaa cggcatcttc     900
ctgccacctc tgcaggggga tttcggcgcc ttcagcgcct ctactccgt gatgaagttc     960
ctgaacctga ccagcgagaa ggtgtcccag gaaaaagtga cagagatgat gaagaagttc    1020
tgcgcccagc cctgggagga aatcaagacc tcctacgctg gcgtgaaaga gaagtacctg    1080
agcgagtttt gcttcagcgg cacctacatc ctgagcctgc tgctgcaggg ctaccacttc    1140
accgccgata gctgggagca catccacttc atcggcaaga ttcagggcag cgacgccggc    1200
tggacactgg gttacatgct gaatctgacc aacatgatcc ccgccgagca gcccctgagc    1260
acacctctga gccacagcac c                                             1281
```

<210> SEQ ID NO 62
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 62

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
```

```
         50                  55                  60
Gly Ile Tyr Leu Thr Asp Cys Met Glu Arg Ala Arg Glu Val Ile Pro
 65                  70                  75                  80

Arg Ser Gln His Gln Glu Thr Pro Val Tyr Leu Gly Ala Thr Ala Gly
                 85                  90                  95

Met Arg Leu Leu Arg Met Glu Ser Glu Leu Ala Asp Arg Val Leu
            100                 105                 110

Asp Val Val Glu Arg Ser Leu Ser Asn Tyr Pro Phe Asp Phe Gln Gly
            115                 120                 125

Ala Arg Ile Ile Thr Gly Gln Glu Gly Ala Tyr Gly Trp Ile Thr
            130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
            195                 200                 205

Lys Asp Gln Ala Leu Trp Gln Lys Leu Ala Lys Asp Ile Gln Val Ala
210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Thr Gly Asn
            260                 265                 270

Tyr Gln Gln Cys His Gln Ser Ile Leu Glu Leu Phe Asn Thr Ser Tyr
            275                 280                 285

Cys Pro Tyr Ser Gln Cys Ala Phe Asn Gly Ile Phe Leu Pro Pro Leu
            290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
            355                 360                 365

Tyr Ile Leu Ser Leu Leu Gln Gln Gly Tyr His Phe Thr Ala Asp Ser
            370                 375                 380

Trp Glu Asp Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425

<210> SEQ ID NO 63
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 63

| | | | | | |
|---|---|---|---|---|---|
| acccagaaca | aggccctgcc | cgagaacgtg | aagtacggca | tcgtgctgga | tgccggcagc | 60 |
| agccacacca | gcctgtacat | ctacaagtgg | cctgccgaga | agaaaacga | caccggcgtg | 120 |
| gtgcatcagg | tggaagagtg | cagagtgaag | ggccctggca | tcagcaagtt | cgtgcagaaa | 180 |
| gtgaacgaga | tcggcatcta | cctgaccgac | tgcatggaac | gggccaggga | agtgatcccc | 240 |
| agaagccagc | accaggaaac | ccccgtgtat | ctgggagcca | ccgccggcat | gagactgctg | 300 |
| agaatggaaa | gcgaggaact | ggccgaccgg | gtgctggacg | tggtggaaag | aagcctgagc | 360 |
| aactacccat | tcgattttca | aggcgccaga | atcatcaccg | gccaggaaga | aggcgcctac | 420 |
| ggctggatca | ccatcaacta | cctgctgggc | aagttcagcc | agaagaatca | ggaaaccttc | 480 |
| ggcgccctgg | aacctgggcgg | agcttctacc | caagtgacct | tcgtgcccca | gaatcagacc | 540 |
| atcgagagcc | ccgacaacgc | cctgcagttc | cggctgtacg | caaggacta | caatgtgtac | 600 |
| acccacagct | ttctgtgcta | cggaaaggac | caggctctgt | ggcagaagct | ggccaaggac | 660 |
| atccaggtgg | ccagcaacga | gatcctgcgg | gaccccttgct | tccacccccgg | ctacaagaaa | 720 |
| gtcgtgaacg | tgtccgacct | gtacaagacc | ccctgcacca | agagattcga | gatgaccctg | 780 |
| cccttccagc | agttcgagat | ccagggcacc | ggcaattacc | agcagtgcca | ccagagcatc | 840 |
| ctggaactgt | tcaacaccag | ctactgcccc | tacagccagt | gcgccttcaa | cggcatcttc | 900 |
| ctgccacctc | tgcaggggga | tttcggcgcc | ttcagcgcct | tctacttcgt | gatgaagttc | 960 |
| ctgaacctga | ccagcgagaa | ggtgtcccag | gaaaaagtga | cagagatgat | gaagaagttc | 1020 |
| tgcgcccagc | cctgggagga | aatcaagacc | tcctacgctg | gcgtgaaaga | gaagtacctg | 1080 |
| agcgagtact | gcttcagcgg | cacctacatc | ctgagcctgc | tgcagcaggg | ctaccacttc | 1140 |
| accgccgata | gctgggagga | catccacttc | atcggcaaga | ttcagggcag | cgacgccggc | 1200 |
| tggacactgg | gctacatgct | gaatctgacc | aacatgatcc | ccgccgagca | gcccctgagc | 1260 |
| acacctctga | gccacagcac | c | | | | 1281 |

<210> SEQ ID NO 64
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu

```
            100                 105                 110
Asp Val Val Glu Arg Ser Leu Ser Asn Tyr Pro Phe Asp Phe Gln Gly
            115                 120                 125

Ala Arg Ile Ile Thr Gly Gln Glu Gly Ala Tyr Gly Trp Ile Thr
            130                 135             140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
            195                 200                 205

Lys Asp Gln Ala Leu Trp Gln Lys Leu Ala Lys Asp Ile Gln Val Ala
210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Phe Glu Ile Gln Gly Ile Gly Asn
            260                 265                 270

Tyr Gln Gln Cys His Gln Ser Ile Leu Glu Leu Phe Asn Thr Ser Tyr
            275                 280                 285

Cys Pro Tyr Ser Gln Cys Ala Phe Asn Gly Ile Phe Leu Pro Pro Leu
            290                 295                 300

Gln Gly Asp Phe Gly Ala Phe Ser Ala Phe Tyr Ser Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
            355                 360                 365

Tyr Ile Leu Ser Leu Leu Gln Gln Gly Tyr His Phe Thr Ala Asp Ser
370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425
```

<210> SEQ ID NO 65
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 65
acccagaaca aggccctgcc cgagaacgtg aagtacggca tcgtgctgga tgccggcagc    60
agccacacca gcctgtacat ctacaagtgg cctgccgaga agaaaacga caccggcgtg   120 gtgcatcagg tggaagagtg cagagtgaag ggccctggca tcagcaagtt cgtgcagaaa   180

```
gtgaacgaga tcggcatcta cctgaccgac tgcatggaac gggccaggga agtgatcccc    240
agaagccagc accaggaaac ccccgtgtat ctgggagcca ccgccggcat gagactgctg    300
agaatggaaa gcgaggaact ggccgaccgg gtgctggacg tggtggaaag aagcctgagc    360
aactacccat tcgattttca aggcgccaga atcatcaccg gccaggaaga aggcgcctac    420
ggctggatca ccatcaacta cctgctgggc aagttcagcc agaagaatca ggaaaccttc    480
ggcgccttgg acctgggcgg agcttctacc caagtgacct tcgtgcccca gaatcagacc    540
atcgagagcc ccgacaacgc cctgcagttc cggctgtacg gcaaggacta caatgtgtac    600
acccacagct ttctgtgcta cggaaaggac caggctctgt ggcagaagct ggccaaggac    660
atccaggtgg ccagcaacga gatcctgcgg gacccttgct ccacccccgg ctacaagaaa    720
gtcgtgaacg tgtccgacct gtacaagacc ccctgcacca agagattcga gatgaccctg    780
cccttccagc agttcgagat ccagggcatc ggcaattacc agcagtgcca ccagagcatc    840
ctggaactgt tcaacaccag ctactgcccc tacagccagt cgccctcaa cggcatcttc    900 ctgccacctc tgcaggggga tttcggcgcc ttcagcgcct tctactccgt gatgaagttc    960
ctgaacctga ccagcgagaa ggtgtcccag gaaaaagtga cagagatgat gaagaagttc    1020
tgcgcccagc cctgggagga aatcaagacc tcctacgctg gcgtgaaaga aagtacctg    1080 agcgagtact gcttcagcgg cacctacatc ctgagcctgc tgcagcaggg ctaccacttc    1140
accgccgata gctgggagca catccacttc atcggcaaga ttcagggcag cgacgccggc    1200
tggacactgg ttacatgct gaatctgacc aacatgatcc ccgccgagca gccctgagc    1260 acacctctga gccacagcac c                                              1281
```

<210> SEQ ID NO 66  
<211> LENGTH: 442  
<212> TYPE: PRT  
<213> ORGANISM: Artificial Sequence  
<220> FEATURE:  
<221> NAME/KEY: source  
<223> OTHER INFORMATION: /note="Description of Artificial Sequence: Synthetic polypeptide"

<400> SEQUENCE: 66

```
Ala Pro Thr Ser Ser Thr Lys Lys Thr Gln Leu Thr Ser Ser Thr
1               5                   10                  15

Gln Asn Lys Ala Leu Pro Glu Asn Val Lys Tyr Gly Ile Val Leu Asp
            20                  25                  30

Ala Gly Ser Ser His Thr Ser Leu Tyr Ile Tyr Lys Trp Pro Ala Glu
        35                  40                  45

Lys Glu Asn Asp Thr Gly Val Val His Gln Val Glu Glu Cys Arg Val
    50                  55                  60

Lys Gly Pro Gly Ile Ser Lys Phe Val Gln Lys Val Asn Glu Ile Gly
65                  70                  75                  80

Ile Tyr Leu Thr Asp Cys Met Glu Arg Ala Arg Glu Val Ile Pro Arg
                85                  90                  95

Ser Gln His Gln Glu Thr Pro Val Tyr Leu Gly Ala Thr Ala Gly Met
            100                 105                 110

Arg Leu Leu Arg Met Glu Ser Glu Glu Leu Ala Asp Arg Val Leu Asp
        115                 120                 125

Val Val Glu Arg Ser Leu Ser Asn Tyr Pro Phe Asp Phe Gln Gly Ala
    130                 135                 140

Arg Ile Ile Thr Gly Gln Glu Glu Gly Ala Tyr Gly Trp Ile Thr Ile
```

```
                    145                 150                 155                 160
Asn Tyr Leu Leu Gly Lys Phe Ser Gln Lys Asn Gln Glu Thr Phe Gly
                165                 170                 175

Ala Leu Asp Leu Gly Gly Ala Ser Thr Gln Val Thr Phe Val Pro Gln
                180                 185                 190

Asn Gln Thr Ile Glu Ser Pro Asp Asn Ala Leu Gln Phe Arg Leu Tyr
                195                 200                 205

Gly Lys Asp Tyr Asn Val Tyr Thr His Ser Phe Leu Cys Tyr Gly Lys
            210                 215                 220

Asp Gln Ala Leu Trp Gln Lys Leu Ala Lys Asp Ile Gln Val Ala Ser
225                 230                 235                 240

Asn Glu Ile Leu Arg Asp Pro Cys Phe His Pro Gly Tyr Lys Lys Val
                245                 250                 255

Val Asn Val Ser Asp Leu Tyr Lys Thr Pro Cys Thr Lys Arg Phe Glu
                260                 265                 270

Met Thr Leu Pro Phe Gln Gln Phe Glu Ile Gln Gly Ile Gly Asn Tyr
            275                 280                 285

Gln Gln Cys His Gln Ser Ile Leu Glu Leu Phe Asn Thr Ser Tyr Cys
        290                 295                 300

Pro Tyr Ser Gln Cys Ala Phe Asn Gly Ile Phe Leu Pro Pro Leu Gln
305                 310                 315                 320

Gly Asp Phe Gly Ala Phe Ser Ala Phe Tyr Phe Val Met Lys Phe Leu
                325                 330                 335

Asn Leu Thr Ser Glu Lys Val Ser Gln Glu Lys Val Thr Glu Met Met
                340                 345                 350

Lys Lys Phe Cys Ala Gln Pro Trp Glu Glu Ile Lys Thr Ser Tyr Ala
            355                 360                 365

Gly Val Lys Glu Lys Tyr Leu Ser Glu Tyr Cys Phe Ser Gly Thr Tyr
        370                 375                 380

Ile Leu Ser Leu Leu Leu Gln Gly Tyr His Phe Thr Ala Asp Ser Trp
385                 390                 395                 400

Glu His Ile His Phe Ile Gly Lys Ile Gln Gly Ser Asp Ala Gly Trp
                405                 410                 415

Thr Leu Gly Tyr Met Leu Asn Leu Thr Asn Met Ile Pro Ala Glu Gln
            420                 425                 430

Pro Leu Ser Thr Pro Leu Ser His Ser Thr
        435                 440

<210> SEQ ID NO 67
<211> LENGTH: 1326
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67
gcccctacca gcagcagcac caagaaaacc cagctgacca gcagcaccca gaacaaggcc      60
ctgcccgaga cgtgaagta cggcatcgtg ctggatgccg gcagcagcca caccagcctg     120
tacatctaca gtggcctgc cgagaaagaa aacgacaccg gcgtggtgca tcaggtggaa     180
gagtgcagag tgaagggccc tggcatcagc aagttcgtgc agaaagtgaa cgagatcggc     240
atctacctga ccgactgcat ggaacgggcc agggaagtga tccccagaag ccagcaccag     300
gaaacccccg tgtatctggg agccaccgcc ggcatgagac tgctgagaat ggaaagcgag     360
```

```
gaactggccg accgggtgct ggacgtggtg gaaagaagcc tgagcaacta cccattcgat    420
tttcaaggcg ccagaatcat caccggccag gaagaaggcg cctacggctg atcaccatc    480 aactacctgc tgggcaagtt cagccagaag aatcaggaaa ccttcggcgc cctggacctg    540
ggcggagctt ctacccaagt gaccttcgtg ccccagaatc agaccatcga gagccccgac    600
aacgccctgc agttccggct gtacggcaag gactacaatg tgtacaccca gctttctg     660 tgctacggaa aggaccaggc tctgtggcag aagctggcca aggacatcca ggtggccagc    720
aacgagatcc tgcgggaccc ttgcttccac cccggctaca agaaagtcgt gaacgtgtcc    780
gacctgtaca agacccctg caccaagaga ttcgagatga ccctgccctt ccagcagttc     840
gagatccagg gcatcggcaa ttaccagcag tgccaccaga gcatcctgga actgttcaac    900
accagctact gccctacag ccagtgcgcc ttcaacggca tcttcctgcc acctctgcag     960
ggggatttcg gcgccttcag cgccttctac ttcgtgatga gttcctgaa cctgaccagc    1020 gagaaggtgt cccaggaaaa agtgacagag atgatgaaga agtctgcgc ccagcccttgg    1080 gaggaaatca agacctccta cgctggcgtg aaagagaagt acctgagcga gtactgcttc    1140
agcggcacct acatcctgag cctgctgctg cagggctacc acttcaccgc cgatagctgg    1200
gagcacatcc acttcatcgg caagattcag ggcagcgacg ccggctggac actgggctac    1260
atgctgaatc tgaccaacat gatccccgcc gagcagcccc tgagcacacc tctgagccac    1320
agcacc                                                              1326
```

<210> SEQ ID NO 68
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 68

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175
```

```
Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Phe Cys Phe Ser Gly Thr
        355                 360                 365

Tyr Ile Leu Ser Leu Leu Gln Gln Gly Tyr His Phe Thr Ala Asp Ser
    370                 375                 380

Trp Glu Asp Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425

<210> SEQ ID NO 69
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69
acccagaaca aggccctgcc cgagaacgtg aagtacggca tcgtgctgga tgccggcagc      60
agccacacca gcctgtacat ctacaagtgg cctgccgaga agaaaacga caccggcgtg     120 gtgcatcagg tggaagagtg cagagtgaag ggccctggca tcagcaagtt cgtgcagaaa    180
gtgaacgaga tcggcatcta cctgaccgac tgcatggaac gggccaggga agtgatcccc    240
agaagccagc accaggaaac ccccgtgtat ctgggagcca ccgccggcat gagactgctg    300
agaatggaaa gcgaggaact ggccgaccgg gtgctggacg tggtggaaag aagcctgagc    360
aactacccat tcgattttca aggcgccaga atcatcaccg ccaggaagaa aggcgcctac    420
ggctggatca ccatcaacta cctgctgggc aagttcagcc agaagaatca ggaaaccttc    480
ggcgccctgg acctgggcgg agcttctacc caagtgacct tcgtgcccca gaatcagacc    540
```

```
atcgagagcc ccgacaacgc cctgcagttc cggctgtacg gcaaggacta caatgtgtac    600
acccacagct ttctgtgcta cggaaaggac caggctctgt ggcagaagct ggccaaggac    660
atccaggtgg ccagcaacga gatcctgcgg gacccttgct ccacccccgg ctacaagaaa    720
gtcgtgaacg tgtccgacct gtacaagacc ccctgcacca agagattcga gatgacccctg   780 cccttccagc agttcgagat ccagggcatc ggcaattacc agcagtgcca ccagagcatc    840
ctggaactgt tcaacaccag ctactgcccc tacagccagt cgcccttcaa cggcatcttc    900
ctgccacctc tgcaggggga tttcggcgcc ttcagcgcct ctacttcgt gatgaagttc     960 ctgaacctga ccagcgagaa ggtgtcccag gaaaaagtga cagagatgat gaagaagttc   1020
tgcgcccagc cctgggagga aatcaagacc tcctacgctg gcgtgaaaga gaagtacctg   1080
agcgagtttt gcttcagcgg cacctacatc ctgagcctgc tgcagcaggg ctaccacttc   1140
accgccgata gctgggagga catccacttc atcggcaaga ttcagggcag cgacgccggc   1200
tggacactgg gctacatgct gaatctgacc aacatgatcc ccgccgagca gcccctgagc   1260
acacctctga gccacagcac c                                             1281
```

<210> SEQ ID NO 70
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220
```

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Phe Cys Phe Ser Gly Thr
        355                 360                 365

Tyr Ile Leu Ser Leu Leu Gln Gln Gly Tyr His Phe Thr Ala Asp Ser
    370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425

<210> SEQ ID NO 71
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 71
acccagaaca aggccctgcc cgagaacgtg aagtacggca tcgtgctgga tgccggcagc    60
agccacacca gcctgtacat ctacaagtgg cctgccgaga agaaaacga caccggcgtg   120 gtgcatcagg tggaagagtg cagagtgaag ggcctggca tcagcaagtt cgtgcagaaa    180
gtgaacgaga tcggcatcta cctgaccgac tgcatggaac gggccaggga agtgatcccc   240
agaagccagc accaggaaac ccccgtgtat ctgggagcca ccgccggcat gagactgctg   300
agaatggaaa gcgaggaact ggccgaccgg gtgctggacg tggtggaaag aagcctgagc   360
aactacccat tcgattttca aggcgccaga atcatcaccg ccaggaaga aggcgcctac    420 ggctggatca ccatcaacta cctgctgggc aagttcagcc agaagaatca ggaaccttc    480 ggcgccctgg acctgggcgg agcttctacc caagtgacct tcgtgcccca gaatcagacc   540
atcgagagcc ccgacaacgc cctgcagttc cggctgtacg caaggacta caatgtgtac    600 acccacagct ttctgtgcta cggaaaggac caggctctgt ggcagaagct ggccaaggac   660
atccaggtgg ccagcaacga gatcctgcgg gaccccttgct tccacccccgg ctacaagaaa   720 gtcgtgaacg tgtccgacct gtacaagacc ccctgcacca agagattcga gatgaccctg   780
cccttccagc agttcgagat ccagggcatc ggcaattacc agcagtgcca ccagagcatc   840

```
ctggaactgt tcaacaccag ctactgcccc tacagccagt gcgccttcaa cggcatcttc    900
ctgccacctc tgcagggga tttcggcgcc ttcagcgcct tctacttcgt gatgaagttc      960
ctgaacctga ccagcgagaa ggtgtcccag gaaaaagtga cagagatgat gaagaagttc   1020
tgcgcccagc cctgggagga aatcaagacc tcctacgctg gcgtgaaaga gaagtacctg   1080
agcgagtttt gcttcagcgg cacctacatc ctgagcctgc tgcagcaggg ctaccacttc   1140
accgccgata gctgggagca catccacttc atcggcaaga ttcagggcag cgacgccggc   1200
tggacactgg gctacatgct gaatctgacc aacatgatcc ccgccgagca gcccctgagc   1260
acacctctga gccacagcac c                                              1281
```

<210> SEQ ID NO 72
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 72

```
Ala Pro Thr Ser Ser Thr Lys Lys Thr Gln Leu Thr Ser Ser Gly
1               5                   10                  15

Thr Gln Asn Lys Ala Leu Pro Glu Asn Val Lys Tyr Gly Ile Val Leu
            20                  25                  30

Asp Ala Gly Ser Ser His Thr Ser Leu Tyr Ile Tyr Lys Trp Pro Ala
        35                  40                  45

Glu Lys Glu Asn Asp Thr Gly Val Val His Gln Val Glu Glu Cys Arg
    50                  55                  60

Val Lys Gly Pro Gly Ile Ser Lys Phe Val Gln Lys Val Asn Glu Ile
65                  70                  75                  80

Gly Ile Tyr Leu Thr Asp Cys Met Glu Arg Ala Arg Glu Val Ile Pro
                85                  90                  95

Arg Ser Gln His Gln Glu Thr Pro Val Tyr Leu Gly Ala Thr Ala Gly
            100                 105                 110

Met Arg Leu Leu Arg Met Glu Ser Glu Glu Leu Ala Asp Arg Val Leu
        115                 120                 125

Asp Val Val Glu Arg Ser Leu Ser Asn Tyr Pro Phe Asp Phe Gln Gly
    130                 135                 140

Ala Arg Ile Ile Thr Gly Gln Glu Glu Gly Ala Tyr Gly Trp Ile Thr
145                 150                 155                 160

Ile Asn Tyr Leu Leu Gly Lys Phe Ser Gln Lys Asn Gln Glu Thr Phe
                165                 170                 175

Gly Ala Leu Asp Leu Gly Gly Ala Ser Thr Gln Val Thr Phe Val Pro
            180                 185                 190

Gln Asn Gln Thr Ile Glu Ser Pro Asp Asn Ala Leu Gln Phe Arg Leu
        195                 200                 205

Tyr Gly Lys Asp Tyr Asn Val Tyr Thr His Ser Phe Leu Cys Tyr Gly
    210                 215                 220

Lys Asp Gln Ala Leu Trp Gln Lys Leu Ala Lys Asp Ile Gln Val Ala
225                 230                 235                 240

Ser Asn Glu Ile Leu Arg Asp Pro Cys Phe His Pro Gly Tyr Lys Lys
                245                 250                 255

Val Val Asn Val Ser Asp Leu Tyr Lys Thr Pro Cys Thr Lys Arg Phe
            260                 265                 270
```

Glu Met Thr Leu Pro Phe Gln Gln Phe Glu Ile Gln Gly Ile Gly Asn
              275                 280                 285

Tyr Gln Gln Cys His Gln Ser Ile Leu Glu Leu Phe Asn Thr Ser Tyr
    290                 295                 300

Cys Pro Tyr Ser Gln Cys Ala Phe Asn Gly Ile Phe Leu Pro Pro Leu
305                 310                 315                 320

Gln Gly Asp Phe Gly Ala Phe Ser Ala Phe Tyr Phe Val Met Lys Phe
                325                 330                 335

Leu Asn Leu Thr Ser Glu Lys Val Ser Gln Glu Lys Val Thr Glu Met
                340                 345                 350

Met Lys Lys Phe Cys Ala Gln Pro Trp Glu Glu Ile Lys Thr Ser Tyr
                355                 360                 365

Ala Gly Val Lys Glu Lys Tyr Leu Ser Glu Tyr Cys Phe Ser Gly Thr
370                 375                 380

Tyr Ile Leu Ser Leu Leu Leu Gln Gly Tyr His Phe Thr Ala Asp Ser
385                 390                 395                 400

Trp Glu His Ile His Phe Ile Gly Lys Ile Gln Gly Ser Asp Ala Gly
                405                 410                 415

Trp Thr Leu Gly Tyr Met Leu Asn Leu Thr Asn Met Ile Pro Ala Glu
                420                 425                 430

Gln Pro Leu Ser Thr Pro Leu Ser His Ser Thr
                435                 440

<210> SEQ ID NO 73
<211> LENGTH: 1329
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73

| | | | | | |
|---|---|---|---|---|---|
| gcccctacct | cctccagcac | caagaaaacc | cagctgacct | ccagcggcac | ccagaacaag | 60 |
| gccctgcccg | agaacgtgaa | gtacggcatc | gtgctggacg | ccggctcctc | ccacacctcc | 120 |
| ctgtacatct | acaagtggcc | tgccgagaaa | gaaaacgaca | ccggcgtggt | gcaccaagtg | 180 |
| gaagagtgca | gagtgaaggg | ccccggcatc | tccaagttcg | tgcagaaagt | gaacgagatc | 240 |
| ggcatctacc | tgaccgactg | catggaacgg | gccagagaag | tgatccctcg | gtcccagcac | 300 |
| caggaaaccc | ctgtctacct | gggcgccacc | gccggcatgc | ggctgctgcg | gatgaatcc | 360 |
| gaggaactgg | ccgaccgggt | gctggacgtg | gtggaacggt | ccctgtccaa | ctacccattc | 420 |
| gattttcaag | cgccagaat | catcaccggc | caggaagagg | cgcctacgg | ctggatcacc | 480 |
| atcaactacc | tgctgggcaa | gttctcccag | aagaatcagg | aaaccttcgg | cgccctggac | 540 |
| ctgggcggag | ccagcaccca | agtcacattc | gtgccccaga | accagaccat | cgagagcccc | 600 |
| gacaacgccc | tgcagttccg | gctgtacggc | aaggactaca | cgtgtacac | ccacagcttt | 660 |
| ctgtgctacg | gcaaggacca | ggccctgtgg | cagaagctgg | ccaaggacat | ccaagtggcc | 720 |
| tccaacgaga | tcctgcggga | ccctgcttc | caccccggct | acaagaaagt | ggtcaacgtg | 780 |
| tccgacctgt | acaagacccc | ttgcaccaag | agattcgaga | tgaccctgcc | cttccagcag | 840 |
| ttcgagatcc | agggcatcgg | caactaccag | cagtgccacc | agtccatcct | ggaactgttc | 900 |
| aacacctcct | actgccccta | ctcccagtgc | gccttcaacg | gcatcttcct | gcctccactg | 960 |
| cagggcgact | tcggcgcctt | ctccgccttc | tacttcgtga | tgaagttcct | gaacctgacc | 1020 |

```
tccgagaaag tgtcccagga aaaagtgacc gagatgatga agaagttctg cgcccagccc    1080
tgggaggaaa tcaagacctc ctacgctggc gtgaaagaga agtacctgtc cgagtactgc    1140
ttctccggca cctacatcct gtccctgctg ctgcagggct accacttcac cgccgacagc    1200
tgggagcaca tccacttcat cggcaagatc cagggatccg acgctggctg acccctgggc    1260
tacatgctga atctgaccaa catgatcccc gccgagcagc ccctgtccac ccctctgtct    1320
cactccacc                                                            1329
```

```
<210> SEQ ID NO 74
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74
```

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Met Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285
```

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Ser Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
        355                 360                 365

Tyr Ile Leu Ser Leu Leu Gln Gln Gly Tyr His Phe Thr Ala Asp Ser
370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425

<210> SEQ ID NO 75
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 75
acccagaaca aggccctgcc cgagaacgtg aagtacggca tcgtgctgga tgccggcagc        60
agccacacca gcctgtacat ctacaagtgg cctgccgaga agaaaacga caccggcgtg       120 gtgcatcagg tggaagagtg cagagtgaag ggccctggca tcagcaagtt cgtgcagaaa       180
gtgaacgaga tcggcatcta cctgaccgac tgcatggaac gggccatgga agtgatcccc       240
agaagccagc accaggaaac ccccgtgtat ctgggagcca ccgccggcat gagactgctg       300
agaatggaaa gcgaggaact ggccgaccgg gtgctggacg tggtggaaag aagcctgagc       360
aactacccat tcgattttca aggcgccaga atcatcaccg gccaggaaga aggcgcctac       420
ggctggatca ccatcaacta cctgctgggc aagttcagcc agaagaatca ggaaaccttc       480
ggcgccctgg acctgggcgg agcttctacc caagtgacct tcgtgcccca gaatcagacc       540
atcgagagcc ccgacaacgc cctgcagttc cggctgtacg caaggactac aatgtgtac       600 acccacagct ttctgtgcta cggaaaggac caggctctgt ggcagaagct ggccaaggac       660
atccaggtgg ccagcaacga gatcctgcgg gaccccttgct tccacccggg ctacaagaaa       720
gtcgtgaacg tgtccgacct gtacaagacc ccctgcacca agagattcga gatgaccctg       780
cccttccagc agttcgagat ccagggcatc ggcaattacc agcagtgcca ccagagcatc       840
ctggaactgt tcaacaccag ctactgcccc tacagccagt gcgccttcaa cggcatcttc       900
ctgccacctc tgcaggggga tttcggcgcc ttcagcgcct tctactccgt gatgaagttc       960
ctgaacctga ccagcgagaa ggtgtcccag gaaaaagtga cagagatgat gaagaagttc      1020
tgcgcccagc cctgggagga aatcaagacc tcctacgctg gcgtgaaaga gaagtacctg      1080
agcgagtact gcttcagcgg cacctacatc ctgagcctgc tgcagcaggg ctaccacttc      1140
accgccgata gctgggagca catccacttc atcggcaaga ttcagggcag cgacgccggc      1200

```
tggacactgg gctacatgct gaatctgacc aacatgatcc ccgccgagca gcccctgagc    1260
acacctctga gccacagcac c                                              1281
```

<210> SEQ ID NO 76
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 76

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Met Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335
```

```
Met Lys Lys Phe Cys Ala Gln Pro Trp Glu Ile Lys Thr Ser Tyr
            340                 345                 350
Ala Gly Val Lys Glu Lys Tyr Leu Ser Glu Phe Cys Phe Ser Gly Thr
        355                 360                 365
Tyr Ile Leu Ser Leu Leu Gln Gln Gly Tyr His Phe Thr Ala Asp Ser
    370                 375                 380
Trp Glu His Ile His Phe Ile Gly Lys Ile Gln Gly Ser Asp Ala Gly
385                 390                 395                 400
Trp Thr Leu Gly Tyr Met Leu Asn Leu Thr Asn Met Ile Pro Ala Glu
                405                 410                 415
Gln Pro Leu Ser Thr Pro Leu Ser His Ser Thr
            420                 425
```

<210> SEQ ID NO 77
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 77

| | | | | | |
|---|---|---|---|---|---|
| acccagaaca | aggccctgcc | cgagaacgtg | aagtacggca | tcgtgctgga | tgccggcagc | 60 |
| agccacacca | gcctgtacat | ctacaagtgg | cctgccgaga | agaaaacga | caccggcgtg | 120 |
| gtgcatcagg | tggaagagtg | cagagtgaag | ggccctggca | tcagcaagtt | cgtgcagaaa | 180 |
| gtgaacgaga | tcggcatcta | cctgaccgac | tgcatggaac | gggccatgga | agtgatcccc | 240 |
| agaagccagc | accaggaaac | ccccgtgtat | ctgggagcca | ccgccggcat | gagactgctg | 300 |
| agaatggaaa | gcgaggaact | ggccgaccgg | gtgctggacg | tggtggaaag | aagcctgagc | 360 |
| aactacccat | cgatttttca | aggcgccaga | atcatcaccg | gccaggaaga | aggcgcctac | 420 |
| ggctggatca | ccatcaacta | cctgctgggc | aagttcagcc | agaagaatca | ggaaaccttc | 480 |
| ggcgccctgg | acctgggcgg | agcttctacc | caagtgacct | tcgtgcccca | gaatcagacc | 540 |
| atcgagagcc | ccgacaacgc | cctgcagttc | cggctgtacg | gcaaggacta | caatgtgtac | 600 |
| acccacagct | ttctgtgcta | cggaaaggac | caggctctgt | ggcagaagct | ggccaaggac | 660 |
| atccaggtgg | ccagcaacga | gatcctgcgg | gaccccttgct | tccaccccgg | ctacaagaaa | 720 |
| gtcgtgaacg | tgtccgacct | gtacaagacc | ccctgcacca | agagattcga | gatgaccctg | 780 |
| cccttccagc | agttcgagat | ccagggcatc | ggcaattacc | agcagtgcca | ccagagcatc | 840 |
| ctggaactgt | tcaacaccag | ctactgcccc | tacagccagt | gcgccttcaa | cggcatcttc | 900 |
| ctgccacctc | tgcagggga | tttcggcgcc | ttcagcgcct | tctacttcgt | gatgaagttc | 960 |
| ctgaacctga | ccagcgagaa | ggtgtcccag | gaaaaagtga | cagagatgat | gaagaagttc | 1020 |
| tgcgcccagc | cctgggagga | aatcaagacc | tcctacgctg | gcgtgaaaga | gaagtacctg | 1080 |
| agcgagttct | gcttcagcgg | cacctacatc | ctgagcctgc | tgcagcaggg | ctaccacttc | 1140 |
| accgccgata | gctgggagca | catccacttc | atcggcaaga | ttcagggcag | cgacgccggc | 1200 |
| tggacactgg | gctacatgct | gaatctgacc | aacatgatcc | ccgccgagca | gcccctgagc | 1260 |
| acacctctga | gccacagcac | c | | | | 1281 |

<210> SEQ ID NO 78
<211> LENGTH: 427
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 78

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Met Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Leu Ala Asp Arg Val Leu
                100                 105                 110

Asp Val Val Glu Arg Ser Leu Ser Asn Tyr Pro Phe Asp Phe Gln Gly
            115                 120                 125

Ala Arg Ile Ile Thr Gly Gln Glu Gly Ala Tyr Gly Trp Ile Thr
        130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
290                 295                 300

Gln Gly Asp Phe Gly Ala Phe Ser Ala Phe Tyr Ser Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
        355                 360                 365

Tyr Ile Leu Ser Leu Leu Leu Gln Gly Tyr His Phe Thr Ala Asp Ser
370                 375                 380
```

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425

<210> SEQ ID NO 79
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 79
acccagaaca aggccctgcc cgagaacgtg aagtacggca tcgtgctgga tgccggcagc      60
agccacacca gcctgtacat ctacaagtgg cctgccgaga agaaaacga caccggcgtg     120 gtgcatcagg tggaagagtg cagagtgaag ggccctggca tcagcaagtt cgtgcagaaa     180
gtgaacgaga tcggcatcta cctgaccgac tgcatggaac gggccatgga agtgatcccc     240
agaagccagc accaggaaac ccccgtgtat ctgggagcca ccgccggcat gagactgctg     300
agaatggaaa gcgaggaact ggccgaccgg gtgctggacg tggtggaaag aagcctgagc     360
aactacccat tcgattttca aggcgccaga atcatcaccg gccaggaaga aggcgcctac     420
ggctggatca ccatcaacta cctgctgggc aagttcagcc agaagaatca ggaaaccttc     480
ggcgccttgg acctgggcgg agcttctacc caagtgacct tcgtgcccca gaatcagacc     540
atcgagagcc ccgacaacgc cctgcagttc cggctgtacg caaggacta caatgtgtac     600 acccacagct ttctgtgcta cggaaaggac caggctctgt ggcagaagct ggccaaggac     660
atccaggtgg ccagcaacga gatcctgcgg gacccttgct tccacccggg ctacaagaaa     720
gtcgtgaacg tgtccgacct gtacaagacc ccctgcacca agagattcga gatgaccctg     780
cccttccagc agttcgagat ccagggcatc ggcaattacc agcagtgcca ccagagcatc     840
ctggaactgt tcaacaccag ctactgcccc tacagccagt gcgccttcaa cggcatcttc     900
ctgccacctc tgcaggggga tttcggcgcc ttcagcgcct tctactccgt gatgaagttc     960
ctgaacctga ccagcgagaa ggtgtcccag gaaaaagtga cagagatgat gaagaagttc    1020
tgcgcccagc cctgggagga aatcaagacc tcctacgctg gcgtgaaaga gaagtacctg    1080
agcgagtact gcttcagcgg cacctacatc ctgagcctgc tgctgcaggg ctaccacttc    1140
accgccgata gctgggagca catccacttc atcggcaaga ttcagggcag cgacgccggc    1200
tggacactgg gttacatgct gaatctgacc aacatgatcc ccgccgagca gcccctgagc    1260
acacctctga gccacagcac c                                              1281

<210> SEQ ID NO 80
<211> LENGTH: 433
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Ala Pro Thr Ser Ser Ser Thr Gln Asn Lys Ala Leu Pro Glu Asn Val
1               5                   10                  15

```
Lys Tyr Gly Ile Val Leu Asp Ala Gly Ser Ser His Thr Ser Leu Tyr
             20                  25                  30

Ile Tyr Lys Trp Pro Ala Glu Lys Glu Asn Asp Thr Gly Val Val His
         35                  40                  45

Gln Val Glu Glu Cys Arg Val Lys Gly Pro Gly Ile Ser Lys Phe Val
 50                  55                  60

Gln Lys Val Asn Glu Ile Gly Ile Tyr Leu Thr Asp Cys Met Glu Arg
 65                  70                  75                  80

Ala Arg Glu Val Ile Pro Arg Ser Gln His Gln Glu Thr Pro Val Tyr
                 85                  90                  95

Leu Gly Ala Thr Ala Gly Met Arg Leu Leu Arg Met Glu Ser Glu Glu
             100                 105                 110

Leu Ala Asp Arg Val Leu Asp Val Val Glu Arg Ser Leu Ser Asn Tyr
             115                 120                 125

Pro Phe Asp Phe Gln Gly Ala Arg Ile Ile Thr Gly Gln Glu Glu Gly
             130                 135                 140

Ala Tyr Gly Trp Ile Thr Ile Asn Tyr Leu Leu Gly Lys Phe Ser Gln
145                 150                 155                 160

Lys Asn Gln Glu Thr Phe Gly Ala Leu Asp Leu Gly Gly Ala Ser Thr
                 165                 170                 175

Gln Val Thr Phe Val Pro Gln Asn Gln Thr Ile Glu Ser Pro Asp Asn
             180                 185                 190

Ala Leu Gln Phe Arg Leu Tyr Gly Lys Asp Tyr Asn Val Tyr Thr His
             195                 200                 205

Ser Phe Leu Cys Tyr Gly Lys Asp Gln Ala Leu Trp Gln Lys Leu Ala
    210                 215                 220

Lys Asp Ile Gln Val Ala Ser Asn Glu Ile Leu Arg Asp Pro Cys Phe
225                 230                 235                 240

His Pro Gly Tyr Lys Lys Val Val Asn Val Ser Asp Leu Tyr Lys Thr
                245                 250                 255

Pro Cys Thr Lys Arg Phe Glu Met Thr Leu Pro Phe Gln Gln Phe Glu
             260                 265                 270

Ile Gln Gly Ile Gly Asn Tyr Gln Gln Cys His Gln Ser Ile Leu Glu
             275                 280                 285

Leu Phe Asn Thr Ser Tyr Cys Pro Tyr Ser Gln Cys Ala Phe Asn Gly
    290                 295                 300

Ile Phe Leu Pro Pro Leu Gln Gly Asp Phe Gly Ala Phe Ser Ala Phe
305                 310                 315                 320

Tyr Phe Val Met Lys Phe Leu Asn Leu Thr Ser Glu Lys Val Ser Gln
                325                 330                 335

Glu Lys Val Thr Glu Met Met Lys Lys Phe Cys Ala Gln Pro Trp Glu
             340                 345                 350

Glu Ile Lys Thr Ser Tyr Ala Gly Val Lys Glu Lys Tyr Leu Ser Glu
             355                 360                 365

Tyr Cys Phe Ser Gly Thr Tyr Ile Leu Ser Leu Leu Leu Gln Gly Tyr
    370                 375                 380

His Phe Thr Ala Asp Ser Trp Glu His Ile His Phe Ile Gly Lys Ile
385                 390                 395                 400

Gln Gly Ser Asp Ala Gly Trp Thr Leu Gly Tyr Met Leu Asn Leu Thr
                405                 410                 415

Asn Met Ile Pro Ala Glu Gln Pro Leu Ser Thr Pro Leu Ser His Ser
             420                 425                 430
```

Thr

<210> SEQ ID NO 81
<211> LENGTH: 1299
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 81

```
gcccctacca gcagcagcac ccagaacaag gccctgcccg agaacgtgaa gtacggcatc      60
gtgctggatg ccggcagcag ccacaccagc ctgtacatct acaagtggcc tgccgagaaa    120
gaaaacgaca ccggcgtggt gcatcaggtg aagagtgca gagtgaaggg ccctggcatc     180
agcaagttcg tgcagaaagt gaacgagatc ggcatctacc tgaccgactg catggaacgg    240
gccagggaag tgatcccag aagccagcac caggaaaccc ccgtgtatct gggagccacc     300
gccggcatga gactgctgag aatggaaagc gaggaactgg ccgaccgggt gctggacgtg    360
gtggaaagaa gcctgagcaa ctacccattc gattttcaag cgccagaat catcaccggc     420
caggaagaag gcgcctacgg ctggatcacc atcaactacc tgctgggcaa gttcagccag    480
aagaatcagg aaaccttcgg cgccctggac ctgggcggag cttctaccca agtgaccttc    540
gtgccccaga atcagaccat cgagagcccc gacaacgccc tgcagttccg gctgtacggc    600
aaggactaca atgtgtacac ccacagcttt ctgtgctacg aaaggacca ggctctgtgg     660
cagaagctgg ccaaggacat ccaggtggcc agcaacgaga tcctgcggga ccccttgcttc    720
caccccggct acaagaaagt cgtgaacgtg tccgacctgt acaagacccc ctgcaccaag    780
agattcgaga tgaccctgcc cttccagcag ttcgagatcc agggcatcgg caattaccag    840
cagtgccacc agagcatcct ggaactgttc aacaccagct actgccccta cagccagtgc    900
gccttcaacg gcatcttcct gccacctctg caggggatt tcggcgcctt cagcgccttc    960
tacttcgtga tgaagttcct gaacctgacc agcgagaagg tgtcccagga aaaagtgaca   1020
gagatgatga agaagttctg cgcccagccc tgggaggaaa tcaagacctc ctacgctggc   1080
gtgaaagaga agtacctgag cgagtactgc ttcagcggca cctacatcct gagcctgctg   1140
ctgcagggct accacttcac cgccgatagc tgggagcaca tccacttcat cggcaagatt   1200
cagggcagcg acgccggctg gacactgggc tacatgctga atctgaccaa catgatcccc   1260
gccgagcagc ccctgagcac acctctgagc cacagcacc                         1299
```

<210> SEQ ID NO 82
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 82

```
Thr Gln Asn Lys Ala Leu Pro Glu Asn Val Lys Tyr Gly Ile Val Leu
1               5                  10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45
```

Val Lys Gly Pro Gly Ile Ser Lys Phe Val Gln Lys Val Asn Glu Ile
 50                  55                  60

Gly Ile Tyr Leu Thr Asp Cys Met Glu Arg Ala Arg Glu Val Ile Pro
 65                  70                  75                  80

Arg Ser Gln His Gln Glu Thr Pro Val Tyr Leu Gly Ala Thr Ala Gly
                 85                  90                  95

Met Arg Leu Leu Arg Met Glu Ser Glu Leu Ala Asp Arg Val Leu
                100                 105                 110

Asp Val Val Glu Arg Ser Leu Ser Asn Tyr Pro Phe Asp Phe Gln Gly
                115                 120                 125

Ala Arg Ile Ile Thr Gly Gln Glu Ala Gly Ala Tyr Gly Trp Ile Thr
130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
                180                 185                 190

Tyr Gly Lys Asp Tyr Asn Val Tyr Thr His Ser Phe Leu Cys Tyr Gly
                195                 200                 205

Lys Asp Gln Ala Leu Trp Gln Lys Leu Ala Lys Asp Ile Gln Val Ala
210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
                260                 265                 270

Tyr Gln Gln Cys His Gln Ser Ile Leu Glu Leu Phe Asn Thr Ser Tyr
                275                 280                 285

Cys Pro Tyr Ser Gln Cys Ala Phe Asn Gly Ile Phe Leu Pro Pro Leu
                290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Ile Lys Thr Ser Tyr
                340                 345                 350

Ala Gly Val Lys Glu Lys Tyr Leu Ser Glu Tyr Cys Phe Ser Gly Thr
                355                 360                 365

Tyr Ile Leu Ser Leu Leu Leu Gln Gly Tyr His Phe Thr Ala Asp Ser
                370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
                420                 425

<210> SEQ ID NO 83
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120
gtgcatcagg tggaagagtg cagagtgaag ggccctggca tcagcaagtt cgtgcagaaa     180
gtgaacgaga tcggcatcta cctgaccgac tgcatggaac gggccaggga agtgatcccc     240
agaagccagc accaggaaac ccccgtgtat ctgggagcca ccgccggcat gagactgctg     300
agaatggaaa gcgaggaact ggccgaccgg gtgctggacg tggtggaaag aagcctgagc     360
aactacccat tcgattttca aggcgccaga atcatcaccg gccaggaagc cggcgcctac     420
ggctggatca ccatcaacta cctgctgggc aagttcagcc agaagaatca ggaaaccttc     480
ggcgccctgg acctgggcgg agcttctacc caagtgacct tcgtgcccca gaatcagacc     540
atcgagagcc ccgacaacgc cctgcagttc cggctgtacg caaggacta caatgtgtac     600
acccacagct ttctgtgcta cggaaaggac caggctctgt ggcagaagct ggccaaggac     660
atccaggtgg ccagcaacga gatcctgcgg gaccccttgct tccacccegg ctacaagaaa     720
gtcgtgaacg tgtccgacct gtacaagacc ccctgcacca agagattcga gatgaccctg     780
ccccttccagc agttcgagat ccagggcatc ggcaattacc agcagtgcca ccagagcatc     840
ctggaactgt tcaacaccag ctactgcccc tacagccagt gcgccttcaa cggcatcttc     900
ctgccacctc tgcaggggga tttcggcgcc ttcagcgcct tctacttcgt gatgaagttc     960
ctgaacctga ccagcgagaa ggtgtcccag gaaaaagtga cagagatgat gaagaagttc    1020
tgcgcccagc cctgggagga aatcaagacc tcctacgctg gcgtgaaaga gaagtacctg    1080
agcgagtact gcttcagcgg cacctacatc ctgagcctgc tgctgcaggg ctaccacttc    1140
accgccgata gctgggagca catccacttc atcggcaaga ttcagggcag cgacgccggc    1200
tggacactgg gctacatgct gaatctgacc aacatgatcc ccgccgagca gcccctgagc    1260
acacctctga gccacagcac c                                              1281
```

<210> SEQ ID NO 84
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95
```

```
Met Arg Leu Leu Arg Met Glu Ser Glu Leu Ala Asp Arg Val Leu
                100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Ala Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ala Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
            195                 200                 205

Lys Asp Gln Ala Leu Trp Gln Lys Leu Ala Lys Asp Ile Gln Val Ala
210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Phe Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Ile Lys Thr Ser Tyr
            340                 345                 350

Ala Gly Val Lys Glu Lys Tyr Leu Ser Glu Tyr Cys Phe Ser Gly Thr
        355                 360                 365

Tyr Ile Leu Ser Leu Leu Leu Gln Gly Tyr His Phe Thr Ala Asp Ser
    370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425

<210> SEQ ID NO 85
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 85
acccagaaca aggccctgcc cgagaacgtg aagtacggca tcgtgctgga tgccggcagc      60
agccacacca gcctgtacat ctacaagtgg cctgccgaga agaaaacga caccggcgtg     120
```

-continued

```
gtgcatcagg tggaagagtg cagagtgaag ggccctggca tcagcaagtt cgtgcagaaa      180
gtgaacgaga tcggcatcta cctgaccgac tgcatggaac gggccaggga agtgatcccc      240
agaagccagc accaggaaac ccccgtgtat ctgggagcca ccgccggcat gagactgctg      300
agaatggaaa gcgaggaact ggccgaccgg gtgctggacg tggtggaaag aagcctgagc      360
aactacccat tcgattttca aggcgccaga atcatcaccg gccaggaagc cggcgcctac      420
ggctggatca ccatcaacta cctgctgggc aagttcagcc agaagaatca ggaaaccttc      480
ggcgccctgg acctgggcgg agctgctacc caagtgacct tcgtgcccca gaatcagacc      540
atcgagagcc ccgacaacgc cctgcagttc cggctgtacg caaggactaa caatgtgtac      600
acccacagct ttctgtgcta cggaaaggac caggctctgt ggcagaagct ggccaaggac      660
atccaggtgg ccagcaacga gatcctgcgg gaccccttgct tccacccggg ctacaagaaa      720
gtcgtgaacg tgtccgacct gtacaagacc ccctgcacca agagattcga gatgaccctg      780
cccttccagc agttcgagat ccagggcatc ggcaattacc agcagtgcca ccagagcatc      840
ctggaactgt tcaacaccag ctactgcccc tacagccagt gcgccttcaa cggcatcttc      900
ctgccacctc tgcaggggga tttcggcgcc ttcagcgcct tctacttcgt gatgaagttc      960
ctgaacctga ccagcgagaa ggtgtcccag gaaaaagtga cagagatgat gaagaagttc     1020
tgcgcccagc cctggaggga aatcaagacc tcctacgctg gcgtgaaaga aagtacctg      1080 agcgagtact gcttcagcgg cacctacatc ctgagcctgc tgctgcaggg ctaccacttc     1140
accgccgata gctgggagca catccacttc atcggcaaga ttcagggcag cgacgccggc     1200
tggacactgg gctacatgct gaatctgacc aacatgatcc ccgccgagca gcccctgagc     1260
acacctctga gccacagcac c                                                1281
```

<210> SEQ ID NO 86
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Gln Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140
```

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
            165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
            195                 200                 205

Lys Asp Gln Ala Leu Trp Gln Lys Leu Ala Lys Asp Ile Gln Val Ala
210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
            245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
            275                 280                 285

Cys Pro Tyr Ser Gln Cys Ala Phe Asn Gly Ile Phe Leu Pro Pro Leu
290                 295                 300

Gln Gly Asp Phe Gly Ala Phe Ser Ala Phe Tyr Ser Val Met Lys Phe
305                 310                 315                 320

Leu Asn Leu Thr Ser Glu Lys Val Ser Gln Glu Lys Val Thr Glu Met
            325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
            355                 360                 365

Tyr Ile Leu Ser Leu Leu Leu Gln Gly Tyr His Phe Thr Ala Asp Ser
370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
            405                 410                 415

Gln Pro Leu Ser Thr Pro Leu Ser His Ser Thr
            420                 425

<210> SEQ ID NO 87
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 87
acccagaaca aggccctgcc cgagaacgtg aagtacggca tcgtgctgga tgccggcagc    60
agccacacca gcctgtacat ctacaagtgg cctgccgaga agaacagga caccggcgtg   120 gtgcatcagg tggaagagtg cagagtgaag ggccctggca tcagcaagtt cgtgcagaaa   180
gtgaacgaga tcggcatcta cctgaccgac tgcatggaac gggccaggga agtgatcccc   240
agaagccagc accaggaaac ccccgtgtat ctgggagcca ccgccggcat gagactgctg   300
agaatggaaa gcgaggaact ggccgaccgg gtgctggacg tggtggaaag aagcctgagc   360
aactacccat tcgattttca aggcgccaga atcatcaccg gccaggaaga aggcgcctac   420

```
ggctggatca ccatcaacta cctgctgggc aagttcagcc agaagaatca ggaaaccttc    480
ggcgccctgg acctgggcgg agcttctacc aagtgacct  tcgtgcccca gaatcagacc    540
atcgagagcc ccgacaacgc cctgcagttc cggctgtacg gcaaggacta caatgtgtac    600
acccacagct ttctgtgcta cggaaaggac caggctctgt ggcagaagct ggccaaggac    660
atccaggtgg ccagcaacga gatcctgcgg gacccttgct ccacccccgg ctacaagaaa    720
gtcgtgaacg tgtccgacct gtacaagacc ccctgcacca agagattcga gatgaccctg    780
cccttccagc agttcgagat ccagggcatc ggcaattacc agcagtgcca ccagagcatc    840
ctggaactgt tcaacaccag ctactgcccc tacagccagt gcgccttcaa cggcatcttc    900
ctgccacctc tgcaggggga tttcggcgcc ttcagcgcct ctactccgt  gatgaagttc    960 ctgaacctga ccagcgagaa ggtgtcccag gaaaaagtga cagagatgat gaagaagttc   1020
tgcgcccagc cctgggagga aatcaagacc tcctacgctg gcgtgaaaga gaagtacctg   1080
agcgagtact gcttcagcgg cacctacatc ctgagcctgc tgctgcaggg ctaccacttc   1140
accgccgata gctgggagca catccacttc atcggcaaga ttcagggcag cgacgccggc   1200
tggacactgg gctacatgct gaatctgacc aacatgatcc ccgccgagca gcccctgagc   1260
acacctctga gccacagcac c                                             1281
```

<210> SEQ ID NO 88
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 88

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Ala Ile Glu Ser Pro Asp Asn Ala Leu Gln Phe Arg Leu
            180                 185                 190
```

```
Tyr Gly Lys Asp Tyr Asn Val Tyr Thr His Ser Phe Leu Cys Tyr Gly
            195                 200                 205

Lys Asp Gln Ala Leu Trp Gln Lys Leu Ala Lys Asp Ile Gln Val Ala
210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Ser Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
        355                 360                 365

Tyr Ile Leu Ser Leu Leu Leu Gln Gly Tyr His Phe Thr Ala Asp Ser
    370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425
```

<210> SEQ ID NO 89
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 89

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120 gtgcatcagg tggaagagtg cagagtgaag ggccctggca tcagcaagtt cgtgcagaaa     180
gtgaacgaga tcggcatcta cctgaccgac tgcatggaac gggccaggga agtgatcccc     240
agaagccagc accaggaaac ccccgtgtat ctgggagcca ccgccggcat gagactgctg     300
agaatggaaa gcgaggaact ggccgaccgg gtgctggacg tggtggaaag aagcctgagc     360
aactacccat tcgattttca aggcgccaga atcatcaccg ccaggaagaa aggcgcctac     420
ggctggatca ccatcaacta cctgctgggc aagttcagcc agaagaatca ggaaaccttc     480
ggcgccctgg acctgggcgg agcttctacc caagtgacct tcgtgcccca gaatcaggcc     540
atcgagagcc ccgacaacgc cctgcagttc cggctgtacg gcaaggacta caatgtgtac     600
acccacagct ttctgtgcta cggaaaggac caggctctgt ggcagaagct ggccaaggac     660
```

```
atccaggtgg ccagcaacga gatcctgcgg gacccttgct tccacccggg ctacaagaaa    720
gtcgtgaacg tgtccgacct gtacaagacc ccctgcacca agagattcga gatgaccctg    780
cccttccagc agttcgagat ccagggcatc ggcaattacc agcagtgcca ccagagcatc    840
ctggaactgt tcaacaccag ctactgcccc tacagccagt gcgccttcaa cggcatcttc    900
ctgccacctc tgcaggggga tttcggcgcc ttcagcgcct ctactccgt gatgaagttc      960
ctgaacctga ccagcgagaa ggtgtcccag gaaaaagtga cagagatgat gaagaagttc    1020
tgcgcccagc cctgggagga aatcaagacc tcctacgctg gcgtgaaaga gaagtacctg    1080
agcgagtact gcttcagcgg cacctacatc ctgagcctgc tgctgcaggg ctaccacttc    1140
accgccgata gctgggagca catccacttc atcggcaaga ttcagggcag cgacgccggc    1200
tggacactgg gctacatgct gaatctgacc aacatgatcc ccgccgagca gcccctgagc    1260
acacctctga gccacagcac c                                               1281
```

<210> SEQ ID NO 90
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 90

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240
```

Val Val Gln Val Ser Asp Leu Tyr Lys Thr Pro Cys Thr Lys Arg Phe
             245                 250                 255

Glu Met Thr Leu Pro Phe Gln Gln Phe Glu Ile Gln Gly Ile Gly Asn
         260                 265                 270

Tyr Gln Gln Cys His Gln Ser Ile Leu Glu Leu Phe Asn Thr Ser Tyr
             275                 280                 285

Cys Pro Tyr Ser Gln Cys Ala Phe Asn Gly Ile Phe Leu Pro Pro Leu
         290                 295                 300

Gln Gly Asp Phe Gly Ala Phe Ser Ala Phe Tyr Ser Val Met Lys Phe
305                 310                 315                 320

Leu Asn Leu Thr Ser Glu Lys Val Ser Gln Glu Lys Val Thr Glu Met
             325                 330                 335

Met Lys Lys Phe Cys Ala Gln Pro Trp Glu Glu Ile Lys Thr Ser Tyr
             340                 345                 350

Ala Gly Val Lys Glu Lys Tyr Leu Ser Glu Tyr Cys Phe Ser Gly Thr
             355                 360                 365

Tyr Ile Leu Ser Leu Leu Leu Gln Gly Tyr His Phe Thr Ala Asp Ser
370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
             405                 410                 415

Gln Pro Leu Ser Thr Pro Leu Ser His Ser Thr
             420                 425

<210> SEQ ID NO 91
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 91
acccagaaca aggccctgcc cgagaacgtg aagtacggca tcgtgctgga tgccggcagc      60
agccacacca gcctgtacat ctacaagtgg cctgccgaga agaaaacga caccggcgtg     120 gtgcatcagg tggaagagtg cagagtgaag ggccctggca tcagcaagtt cgtgcagaaa     180
gtgaacgaga tcggcatcta cctgaccgac tgcatggaac gggccaggga agtgatcccc     240
agaagccagc accaggaaac ccccgtgtat ctgggagcca ccgccggcat gagactgctg     300
agaatggaaa gcgaggaact ggccgaccgg gtgctggacg tggtggaaag aagcctgagc     360
aactacccat tcgattttca aggcgccaga atcatcaccg ccaggaaga aggcgcctac     420 ggctggatca ccatcaacta cctgctgggc aagttcagcc agaagaatca ggaaaccttc     480
ggcgccctgg acctgggcgg agcttctacc caagtgacct tcgtgcccca gaatcagacc     540
atcgagagcc ccgacaacgc cctgcagttc cggctgtacg gcaaggacta caatgtgtac     600
acccacagct ttctgtgcta cggaaaggac caggctctgt ggcagaagct ggccaaggac     660
atccaggtgg ccagcaacga gatcctgcgg gacccttgct ccacccggg ctacaagaaa     720 gtcgtgcagg tgtccgacct gtacaagacc ccctgcacca gagattcga gatgaccctg     780 cccttccagc agttcgagat ccagggcatc ggcaattacc agcagtgcca ccagagcatc     840
ctggaactgt tcaacaccag ctactgcccc tacagccagt gcgccttcaa cggcatcttc     900 ctgccaccctc tgcaggggga tttcggcgcc ttcagcgcct tctactccgt gatgaagttc     960

```
ctgaacctga ccagcgagaa ggtgtcccag gaaaaagtga cagagatgat gaagaagttc    1020
tgcgcccagc cctgggagga aatcaagacc tcctacgctg gcgtgaaaga gaagtacctg    1080
agcgagtact gcttcagcgg cacctacatc ctgagcctgc tgctgcaggg ctaccacttc    1140
accgccgata gctgggagca catccacttc atcggcaaga ttcagggcag cgacgccggc    1200
tggacactgg gctacatgct gaatctgacc aacatgatcc ccgccgagca gcccctgagc    1260
acacctctga gccacagcac c                                              1281
```

<210> SEQ ID NO 92
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 92

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Gln Thr Ser Tyr
        275                 280                 285
```

```
Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Ser Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
                340                 345                 350

Ala Gly Val Lys Glu Lys Tyr Leu Ser Glu Tyr Cys Phe Ser Gly Thr
            355                 360                 365

Tyr Ile Leu Ser Leu Leu Gln Gly Tyr His Phe Thr Ala Asp Ser
370                 375                 380

Trp Glu His Ile His Phe Ile Gly Lys Ile Gln Gly Ser Asp Ala Gly
385                 390                 395                 400

Trp Thr Leu Gly Tyr Met Leu Asn Leu Thr Asn Met Ile Pro Ala Glu
                405                 410                 415

Gln Pro Leu Ser Thr Pro Leu Ser His Ser Thr
            420                 425
```

<210> SEQ ID NO 93
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 93

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120
gtgcatcagg tggaagagtg cagagtgaag ggccctggca tcagcaagtt cgtgcagaaa    180
gtgaacgaga tcggcatcta cctgaccgac tgcatggaac gggccaggga agtgatcccc    240
agaagccagc accaggaaac ccccgtgtat ctgggagcca ccgccggcat gagactgctg    300
agaatggaaa gcgaggaact ggccgaccgg gtgctggacg tggtggaaag aagcctgagc    360
aactacccat tcgattttca aggcgccaga atcatcaccg ccaggaaga aggcgcctac    420
ggctggatca ccatcaacta cctgctgggc aagttcagcc agaagaatca ggaaaccttc    480
ggcgccctgg acctgggcgg agcttctacc caagtgacct tcgtgcccca gaatcagacc    540
atcgagagcc ccgacaacgc cctgcagttc cggctgtacg gcaaggacta caatgtgtac    600
acccacagct ttctgtgcta cggaaaggac caggctctgt ggcagaagct ggccaaggac    660
atccaggtgg ccagcaacga gatcctgcgg gacccttgct ccacccccgg ctacaagaaa    720
gtcgtgaacg tgtccgacct gtacaagacc ccctgcacca agagattcga gatgaccctg    780
cccttccagc agttcgagat ccagggcatc ggcaattacc agcagtgcca ccagagcatc    840
ctggaactgt tccagaccag ctactgcccc tacagccagt gcgccttcaa cggcatcttc    900
ctgccacctc tgcaggggga tttcggcgcc ttcagcgcct tctactccgt gatgaagttc    960
ctgaacctga ccagcgagaa ggtgtcccag gaaaaagtga cagagatgat gaagaagttc   1020
tgcgcccagc cctgggagga aatcaagacc tcctacgctg gcgtgaaaga gaagtacctg   1080
agcgagtact gcttcagcgg cacctacatc ctgagcctgc tgctgcaggg ctaccacttc   1140
accgccgata gctgggagca catccacttc atcggcaaga ttcagggcag cgacgccggc   1200
```

```
tggacactgg gctacatgct gaatctgacc aacatgatcc ccgccgagca gcccctgagc    1260
acacctctga gccacagcac c                                              1281
```

<210> SEQ ID NO 94
<211> LENGTH: 427
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
    210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
    290                 295                 300

Gln Gly Asp Phe Gly Ala Phe Ser Ala Phe Tyr Ser Val Met Lys Phe
305                 310                 315                 320

Leu Gln Leu Thr Ser Glu Lys Val Ser Gln Glu Lys Val Thr Glu Met
                325                 330                 335
```

```
Met Lys Lys Phe Cys Ala Gln Pro Trp Glu Ile Lys Thr Ser Tyr
            340                 345                 350
Ala Gly Val Lys Glu Lys Tyr Leu Ser Glu Tyr Cys Phe Ser Gly Thr
        355                 360                 365
Tyr Ile Leu Ser Leu Leu Leu Gln Gly Tyr His Phe Thr Ala Asp Ser
    370                 375                 380
Trp Glu His Ile His Phe Ile Gly Lys Ile Gln Gly Ser Asp Ala Gly
385                 390                 395                 400
Trp Thr Leu Gly Tyr Met Leu Asn Leu Thr Asn Met Ile Pro Ala Glu
                405                 410                 415
Gln Pro Leu Ser Thr Pro Leu Ser His Ser Thr
            420                 425
```

<210> SEQ ID NO 95
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 95

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120
gtgcatcagg tggaagagtg cagagtgaag ggccctggca tcagcaagtt cgtgcagaaa     180
gtgaacgaga tcggcatcta cctgaccgac tgcatggaac gggccaggga agtgatcccc     240
agaagccagc accaggaaac ccccgtgtat ctgggagcca ccgccggcat gagactgctg     300
agaatggaaa gcgaggaact ggccgaccgg gtgctggacg tggtggaaag aagcctgagc     360
aactacccat tcgatttcca aggcgccaga atcatcaccg gccaggaaga aggcgcctac     420
ggctggatca ccatcaacta cctgctgggc aagttcagcc agaagaatca ggaaaccttc     480
ggcgccctgg acctgggcgg agcttctacc caagtgacct tcgtgcccca gaatcagacc     540
atcgagagcc ccgacaacgc cctgcagttc cggctgtacg caaggacta caatgtgtac     600
acccacagct ttctgtgcta cggaaaggac caggctctgt ggcagaagct ggccaaggac     660
atccaggtgg ccagcaacga gatcctgcgg gaccttgct tccaccccgg ctacaagaaa     720
gtcgtgaacg tgtccgacct gtacaagacc ccctgcacca agagattcga gatgaccctg     780
cccttccagc agttcgagat ccagggcatc ggcaattacc agcagtgcca ccagagcatc     840
ctggaactgt tcaacaccag ctactgcccc tacagccagt gcgccttcaa cggcatcttc     900
ctgccacctc tgcaggggga tttcggcgcc ttcagcgcct tctactccgt gatgaagttc     960
ctgcagctga ccagcgagaa ggtgtcccag gaaaaagtga cagagatgat gaagaagttc    1020
tgcgcccagc cctgggagga aatcaagacc tcctacgctg gcgtgaaaga gaagtacctg    1080
agcgagtact gcttcagcgg cacctacatc ctgagcctgc tgctgcaggg ctaccacttc    1140
accgccgata gctgggagca catccacttc atcggcaaga ttcagggcag cgacgccggc    1200
tggacactgg gctacatgct gaatctgacc aacatgatcc ccgccgagca gcccctgagc    1260
acacctctga gccacagcac c                                             1281
```

<210> SEQ ID NO 96
<211> LENGTH: 427
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 96

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Leu Ala Asp Arg Val Leu
            100                 105                 110

Asp Val Val Glu Arg Ser Leu Ser Asn Tyr Pro Phe Asp Phe Gln Gly
            115                 120                 125

Ala Arg Ile Ile Thr Gly Gln Glu Gly Ala Tyr Gly Trp Ile Thr
        130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Lys Asp Gln Ala Leu Trp Gln Lys Leu Ala Lys Asp Ile Gln Val Ala
210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
290                 295                 300

Gln Gly Asp Phe Gly Ala Phe Ser Ala Phe Tyr Ser Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Val Lys Glu Lys Tyr Leu Ser Glu Tyr Cys Phe Ser Gly Thr
        355                 360                 365

Tyr Ile Leu Ser Leu Leu Leu Gln Gly Tyr His Phe Thr Ala Asp Ser
370                 375                 380
```

Trp Glu His Ile His Phe Ile Gly Lys Ile Gln Gly Ser Asp Ala Gly
385                 390                 395                 400

Trp Thr Leu Gly Tyr Met Leu Gln Leu Thr Asn Met Ile Pro Ala Glu
            405                 410                 415

Gln Pro Leu Ser Thr Pro Leu Ser His Ser Thr
            420                 425

<210> SEQ ID NO 97
<211> LENGTH: 1281
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 97
acccagaaca aggccctgcc cgagaacgtg aagtacggca tcgtgctgga tgccggcagc      60
agccacacca gcctgtacat ctacaagtgg cctgccgaga agaaaacga caccggcgtg     120 gtgcatcagg tggaagagtg cagagtgaag ggccctggca tcagcaagtt cgtgcagaaa     180
gtgaacgaga tcggcatcta cctgaccgac tgcatggaac gggccaggga agtgatcccc     240
agaagccagc accaggaaac ccccgtgtat ctgggagcca ccgccggcat gagactgctg     300
agaatggaaa gcgaggaact ggccgaccgg gtgctgacg tggtggaaag aagcctgagc     360
aactacccat tcgattttca aggcgccaga atcatcaccg gccaggaaga aggcgcctac     420
ggctggatca ccatcaacta cctgctgggc aagttcagcc agaagaatca ggaaaccttc     480
ggcgccctgg acctgggcgg agcttctacc caagtgacct tcgtgcccca gaatcagacc     540
atcgagagcc ccgacaacgc cctgcagttc cggctgtacg gcaaggacta caatgtgtac     600
acccacagct ttctgtgcta cggaaaggac caggctctgt ggcagaagct ggccaaggac     660
atccaggtgg ccagcaacga gatcctgcgg gaccccttgct tccacccgg ctacaagaaa     720 gtcgtgaacg tgtccgacct gtacaagacc ccctgcacca gagattcga gatgaccctg     780 cccttccagc agttcgagat ccagggcatc ggcaattacc agcagtgcca ccagagcatc     840
ctggaactgt tcaacaccag ctactgcccc tacagccagt gcgccttcaa cggcatcttc     900
ctgccacctc tgcaggggga tttcggcgcc ttcagcgcct tctactccgt gatgaagttc     960
ctgaacctga ccagcgagaa ggtgtcccag gaaaaagtga cagagatgat gaagaagttc    1020
tgcgcccagc cctgggagga aatcaagacc tcctacgctg gcgtgaaaga gaagtacctg    1080
agcgagtact gcttcagcgg cacctacatc ctgagcctgc tgctgcaggg ctaccacttc    1140
accgccgata gctgggagca catccacttc atcggcaaga ttcagggcag cgacgccggc    1200
tggacactgg gctacatgct gcagctgacc aacatgatcc ccgccgagca gcccctgagc    1260
acacctctga gccacagcac c                                              1281

<210> SEQ ID NO 98
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 98
tgccctacga gacaaacaat caggaaacct tcggcgccct ggacctgggc ggagcttcta     60
cccaagtga                                                        69

<210> SEQ ID NO 99
<211> LENGTH: 431
<212> TYPE: PRT
<213> ORGANISM: Homo sapiens

<400> SEQUENCE: 99

Gln Asn Lys Ala Leu Pro Glu Asn Val Lys Tyr Gly Ile Val Leu Asp
1               5                   10                  15

Ala Gly Ser Ser His Thr Ser Leu Tyr Ile Tyr Lys Trp Pro Ala Glu
            20                  25                  30

Lys Glu Asn Asp Thr Gly Val Val His Gln Val Glu Cys Arg Val
        35                  40                  45

Lys Gly Pro Gly Ile Ser Lys Phe Val Gln Lys Val Asn Glu Ile Gly
    50                  55                  60

Ile Tyr Leu Thr Asp Cys Met Glu Arg Ala Arg Glu Val Ile Pro Arg
65                  70                  75                  80

Ser Gln His Gln Glu Thr Pro Val Tyr Leu Gly Ala Thr Ala Gly Met
                85                  90                  95

Arg Leu Leu Arg Met Glu Ser Glu Glu Leu Ala Asp Arg Val Leu Asp
            100                 105                 110

Val Val Glu Arg Ser Leu Ser Asn Tyr Pro Phe Asp Phe Gln Gly Ala
        115                 120                 125

Arg Ile Ile Thr Gly Gln Glu Glu Gly Ala Tyr Gly Trp Ile Thr Ile
    130                 135                 140

Asn Tyr Leu Leu Gly Lys Phe Ser Gln Lys Thr Arg Trp Phe Ser Ile
145                 150                 155                 160

Val Pro Tyr Glu Thr Asn Asn Gln Glu Thr Phe Gly Ala Leu Asp Leu
                165                 170                 175

Gly Gly Ala Ser Thr Gln Val Thr Phe Val Pro Gln Asn Gln Thr Ile
            180                 185                 190

Glu Ser Pro Asp Asn Ala Leu Gln Phe Arg Leu Tyr Gly Lys Asp Tyr
        195                 200                 205

Asn Val Tyr Thr His Ser Phe Leu Cys Tyr Gly Lys Asp Gln Ala Leu
    210                 215                 220

Trp Gln Lys Leu Ala Lys Asp Ile Gln Val Ala Ser Asn Glu Ile Leu
225                 230                 235                 240

Arg Asp Pro Cys Phe His Pro Gly Tyr Lys Lys Val Val Asn Val Ser
                245                 250                 255

Asp Leu Tyr Lys Thr Pro Cys Thr Lys Arg Phe Glu Met Thr Leu Pro
            260                 265                 270

Phe Gln Gln Phe Glu Ile Gln Gly Ile Gly Asn Tyr Gln Gln Cys His
        275                 280                 285

Gln Ser Ile Leu Glu Leu Phe Asn Thr Ser Tyr Cys Pro Tyr Ser Gln
    290                 295                 300

Cys Ala Phe Asn Gly Ile Phe Leu Pro Pro Leu Gln Gly Asp Phe Gly
305                 310                 315                 320

Ala Phe Ser Ala Phe Tyr Phe Val Met Lys Phe Leu Asn Leu Thr Ser
                325                 330                 335

Glu Lys Val Ser Gln Glu Lys Val Thr Glu Met Met Lys Lys Phe Cys
            340                 345                 350

Ala Gln Pro Trp Glu Glu Ile Lys Thr Ser Tyr Ala Gly Val Lys Glu
        355                 360                 365

Lys Tyr Leu Ser Glu Tyr Cys Phe Ser Gly Thr Tyr Ile Leu Ser Leu
            370                 375                 380

Leu Leu Gln Gly Tyr His Phe Thr Ala Asp Ser Trp Glu His Ile His
    385                 390                 395                 400

Phe Ile Gly Lys Ile Gln Gly Ser Asp Ala Gly Trp Thr Leu Gly Tyr
                405                 410                 415

Met Leu Asn Leu Thr Asn Met Ile Pro Ala Glu Gln Pro Leu Ser
            420                 425                 430

<210> SEQ ID NO 100
<211> LENGTH: 1293
<212> TYPE: DNA
<213> ORGANISM: Homo sapiens

<400> SEQUENCE: 100

```
cagaacaaag ccctgcccga gaacgtgaag tacggcatcg tgctggatgc cggcagcagc      60
cacaccagcc tgtacatcta caagtggcct gccgagaaag aaaacgatac cggtgtcgtg     120
caccaggtgg aagagtgcag agtgaagggc cctggcatca gcaagttcgt gcagaaagtg     180
aacgagatcg gcatctacct gaccgactgc atggaacggg ccagagaagt gatccccaga     240
agccagcacc aggaaacccc cgtgtacctg ggagccacac ccggcatgag actgctgcgg     300
atggaaagcg aggaactggc cgacagagtg ctggacgtgg tggaaagaag cctgagcaac     360
tacccattcg attttcaagg ggccagaatc atcaccggcc aggaagaggg cgcttacggc     420
tggatcacca tcaactacct gctgggcaag ttcagccaga aaacccggtg gttcagcatc     480
gtgccctacg agacaaacaa tcaggaaacc ttcggagccc tggacctggg cggagcctct     540
acccaagtga ccttcgtgcc ccagaatcag accatcgaga gccccgacaa cgccctgcag     600
ttccggctgt acggcaagga ctacaatgtg tacacccaca gctttctgtg ctacggaaag     660
gaccaggccc tgtggcagaa gctggccaag gacatccagg tggccagcaa cgagatcctg     720
cgggacccatt gcttccaccc cggctacaag aaagtcgtga acgtgtccga cctgtacaag     780
acccctgca ccaagagatt cgagatgacc ctgcccttcc agcagttcga tccagggc       840
atcggcaact accagcagtg ccaccagagc atcctggaac tgttcaacac cagctactgc     900
ccctacagcc agtgcgcctt caacggcatc ttcctgccac tctgcaggg ggacttcggc      960
gctttcagcg ccttctactt cgtgatgaag ttcctgaacc tgaccagcga aaggtgtcc     1020
caggaaaaag tgacagagat gatgaagaag ttctgcgccc agccctggga ggaaatcaag    1080
acctcctacg ctggcgtgaa agagaagtac ctgagcgagt actgcttcag cggtacctac    1140
atcctgagcc tgctgctgca gggctaccac ttcaccgccg atagctggga gcacatccac    1200
ttcatcggca agattcaggg cagcgacgcc ggctggacac tgggctacat gctgaatctg    1260
accaacatga tccccgccga gcagcccctg agc                                 1293
```

<210> SEQ ID NO 101
<211> LENGTH: 431
<212> TYPE: PRT
<213> ORGANISM: Homo sapiens

<400> SEQUENCE: 101

Asn Val Lys Tyr Gly Ile Val Leu Asp Ala Gly Ser Ser His Thr Ser
1               5                   10                  15

Leu Tyr Ile Tyr Lys Trp Pro Ala Glu Lys Glu Asn Asp Thr Gly Val
            20                  25                  30

Val His Gln Val Glu Glu Cys Arg Val Lys Gly Pro Gly Ile Ser Lys

```
            35                  40                  45
Phe Val Gln Lys Val Asn Glu Ile Gly Ile Tyr Leu Thr Asp Cys Met
 50                  55                  60
Glu Arg Ala Arg Glu Val Ile Pro Arg Ser Gln His Gln Glu Thr Pro
 65                  70                  75                  80
Val Tyr Leu Gly Ala Thr Ala Gly Met Arg Leu Leu Arg Met Glu Ser
                 85                  90                  95
Glu Glu Leu Ala Asp Arg Val Leu Asp Val Val Glu Arg Ser Leu Ser
                100                 105                 110
Asn Tyr Pro Phe Asp Phe Gln Gly Ala Arg Ile Ile Thr Gly Gln Glu
                115                 120                 125
Glu Gly Ala Tyr Gly Trp Ile Thr Ile Asn Tyr Leu Leu Gly Lys Phe
                130                 135                 140
Ser Gln Lys Thr Arg Trp Phe Ser Ile Val Pro Tyr Glu Thr Asn Asn
145                 150                 155                 160
Gln Glu Thr Phe Gly Ala Leu Asp Leu Gly Gly Ala Ser Thr Gln Val
                165                 170                 175
Thr Phe Val Pro Gln Asn Gln Thr Ile Glu Ser Pro Asp Asn Ala Leu
                180                 185                 190
Gln Phe Arg Leu Tyr Gly Lys Asp Tyr Asn Val Tyr Thr His Ser Phe
                195                 200                 205
Leu Cys Tyr Gly Lys Asp Gln Ala Leu Trp Gln Lys Leu Ala Lys Asp
210                 215                 220
Ile Gln Val Ala Ser Asn Glu Ile Leu Arg Asp Pro Cys Phe His Pro
225                 230                 235                 240
Gly Tyr Lys Lys Val Val Asn Val Ser Asp Leu Tyr Lys Thr Pro Cys
                245                 250                 255
Thr Lys Arg Phe Glu Met Thr Leu Pro Phe Gln Gln Phe Glu Ile Gln
                260                 265                 270
Gly Ile Gly Asn Tyr Gln Gln Cys His Gln Ser Ile Leu Glu Leu Phe
                275                 280                 285
Asn Thr Ser Tyr Cys Pro Tyr Ser Gln Cys Ala Phe Asn Gly Ile Phe
290                 295                 300
Leu Pro Pro Leu Gln Gly Asp Phe Gly Ala Phe Ser Ala Phe Tyr Phe
305                 310                 315                 320
Val Met Lys Phe Leu Asn Leu Thr Ser Glu Lys Val Ser Gln Glu Lys
                325                 330                 335
Val Thr Glu Met Met Lys Lys Phe Cys Ala Gln Pro Trp Glu Glu Ile
                340                 345                 350
Lys Thr Ser Tyr Ala Gly Val Lys Glu Lys Tyr Leu Ser Glu Tyr Cys
                355                 360                 365
Phe Ser Gly Thr Tyr Ile Leu Ser Leu Leu Leu Gln Gly Tyr His Phe
                370                 375                 380
Thr Ala Asp Ser Trp Glu His Ile His Phe Ile Gly Lys Ile Gln Gly
385                 390                 395                 400
Ser Asp Ala Gly Trp Thr Leu Gly Tyr Met Leu Asn Leu Thr Asn Met
                405                 410                 415
Ile Pro Ala Glu Gln Pro Leu Ser Thr Pro Leu Ser His Ser Thr
                420                 425                 430

<210> SEQ ID NO 102
<211> LENGTH: 1293
<212> TYPE: DNA
<213> ORGANISM: Homo sapiens
```

<400> SEQUENCE: 102

```
aacgtgaagt acggcatcgt gctggatgcc ggcagcagcc acaccagcct gtacatctac    60
aagtggcctg ccgagaaaga aaacgatacc ggtgtcgtgc accaggtgga agagtgcaga   120
gtgaagggcc ctggcatcag caagttcgtg cagaaagtga acgagatcgg catctacctg   180
accgactgca tggaacgggc cagagaagtg atccccagaa gccagcacca ggaaaccccc   240
gtgtacctgg gagccacagc cggcatgaga ctgctgcgga tggaaagcga ggaactggcc   300
gacagagtgc tggacgtggt ggaaagaagc ctgagcaact acccattcga ttttcaaggg   360
gccagaatca tcaccggcca ggaagagggc gcttacggct ggatcaccat caactacctg   420
ctgggcaagt tcagccagaa acccggtggt tcagcatcg tgccctacga caaacaat     480
caggaaacct tcggagccct ggacctgggc ggagcctcta cccaagtgac cttcgtgccc   540
cagaatcaga ccatcgagag ccccgacaac gccctgcagt ccggctgta cggcaaggac   600
tacaatgtgt acacccacag ctttctgtgc tacggaaagg accaggccct gtggcagaag   660
ctggccaagg acatccaggt ggccagcaac gagatcctgc gggacccttg cttccacccc   720
ggctacaaga aagtcgtgaa cgtgtccgac ctgtacaaga ccccctgcac caagagattc   780
gagatgaccc tgcccttcca gcagttcgag atccagggca tcggcaacta ccagcagtgc   840
caccagagca tcctggaact gttcaacacc agctactgcc cctacagcca gtgcgccttc   900
aacggcatct tcctgccacc tctgcagggg gacttcggcg ctttcagcgc cttctacttc   960
gtgatgaagt tcctgaacct gaccagcgag aaggtgtccc aggaaaaagt gacagagatg  1020
atgaagaagt tctgcgccca gccctgggag gaaatcaaga cctcctacgc tggcgtgaaa  1080
gagaagtacc tgagcgagta ctgcttcagc ggtacctaca tcctgagcct gctgctgcag  1140
ggctaccact tcaccgccga tagctgggag cacatccact tcatcggcaa gattcagggc  1200
agcgacgccg ctggacact gggctacatg ctgaatctga ccaacatgat ccccgccgag  1260
cagcccctga gcacacctct gtctcacagc acc                                1293
```

<210> SEQ ID NO 103
<211> LENGTH: 416
<212> TYPE: PRT
<213> ORGANISM: Homo sapiens

<400> SEQUENCE: 103

```
Asn Val Lys Tyr Gly Ile Val Leu Asp Ala Gly Ser Ser His Thr Ser
1               5                   10                  15

Leu Tyr Ile Tyr Lys Trp Pro Ala Glu Lys Glu Asn Asp Thr Gly Val
            20                  25                  30

Val His Gln Val Glu Glu Cys Arg Val Lys Gly Pro Gly Ile Ser Lys
        35                  40                  45

Phe Val Gln Lys Val Asn Glu Ile Gly Ile Tyr Leu Thr Asp Cys Met
    50                  55                  60

Glu Arg Ala Arg Glu Val Ile Pro Arg Ser Gln His Gln Glu Thr Pro
65                  70                  75                  80

Val Tyr Leu Gly Ala Thr Ala Gly Met Arg Leu Leu Arg Met Glu Ser
                85                  90                  95

Glu Glu Leu Ala Asp Arg Val Leu Asp Val Val Glu Arg Ser Leu Ser
            100                 105                 110

Asn Tyr Pro Phe Asp Phe Gln Gly Ala Arg Ile Ile Thr Gly Gln Glu
        115                 120                 125
```

```
Glu Gly Ala Tyr Gly Trp Ile Thr Ile Asn Tyr Leu Leu Gly Lys Phe
            130                 135                 140
Ser Gln Lys Thr Arg Trp Phe Ser Ile Val Pro Tyr Glu Thr Asn Asn
145                 150                 155                 160
Gln Glu Thr Phe Gly Ala Leu Asp Leu Gly Gly Ala Ser Thr Gln Val
                165                 170                 175
Thr Phe Val Pro Gln Asn Gln Thr Ile Glu Ser Pro Asp Asn Ala Leu
            180                 185                 190
Gln Phe Arg Leu Tyr Gly Lys Asp Tyr Asn Val Tyr Thr His Ser Phe
                195                 200                 205
Leu Cys Tyr Gly Lys Asp Gln Ala Leu Trp Gln Lys Leu Ala Lys Asp
210                 215                 220
Ile Gln Val Ala Ser Asn Glu Ile Leu Arg Asp Pro Cys Phe His Pro
225                 230                 235                 240
Gly Tyr Lys Lys Val Asn Val Ser Asp Leu Tyr Lys Thr Pro Cys
                245                 250                 255
Thr Lys Arg Phe Glu Met Thr Leu Pro Phe Gln Gln Phe Glu Ile Gln
            260                 265                 270
Gly Ile Gly Asn Tyr Gln Gln Cys His Gln Ser Ile Leu Glu Leu Phe
            275                 280                 285
Asn Thr Ser Tyr Cys Pro Tyr Ser Gln Cys Ala Phe Asn Gly Ile Phe
            290                 295                 300
Leu Pro Pro Leu Gln Gly Asp Phe Gly Ala Phe Ser Ala Phe Tyr Phe
305                 310                 315                 320
Val Met Lys Phe Leu Asn Leu Thr Ser Glu Lys Val Ser Gln Glu Lys
                325                 330                 335
Val Thr Glu Met Met Lys Lys Phe Cys Ala Gln Pro Trp Glu Glu Ile
            340                 345                 350
Lys Thr Ser Tyr Ala Gly Val Lys Glu Lys Tyr Leu Ser Glu Tyr Cys
                355                 360                 365
Phe Ser Gly Thr Tyr Ile Leu Ser Leu Leu Leu Gln Gly Tyr His Phe
            370                 375                 380
Thr Ala Asp Ser Trp Glu His Ile His Phe Ile Gly Lys Ile Gln Gly
385                 390                 395                 400
Ser Asp Ala Gly Trp Thr Leu Gly Tyr Met Leu Asn Leu Thr Asn Met
                405                 410                 415

<210> SEQ ID NO 104
<211> LENGTH: 1248
<212> TYPE: DNA
<213> ORGANISM: Homo sapiens

<400> SEQUENCE: 104
aacgtgaagt acggcatcgt gctggatgcc ggcagcagcc acaccagcct gtacatctac      60
aagtggcctg ccgagaaaga aaacgatacc ggtgtcgtgc accaggtgga agagtgcaga     120
gtgaagggcc ctggcatcag caagttcgtg cagaaagtga cgagatcgg catctacctg     180 accgactgca tggaacgggc cagagaagtg atccccagaa gccagcacca ggaaaccccc     240
gtgtacctgg agccacagc cggcatgaga ctgctgcgga tggaaagcga ggaactggcc     300
gacagagtgc tggacgtggt ggaaagaagc ctgagcaact acccattcga ttttcaaggg     360
gccagaatca tcaccggcca ggaagagggc gcttacggct ggatcaccat caactacctg     420
ctgggcaagt tcagccagaa aacccggtgg ttcagcatcg tgccctacga dacaaacaat     480 caggaaaccct tcggagccct ggacctgggc ggagcctcta cccaagtgac cttcgtgccc     540
```

-continued

```
cagaatcaga ccatcgagag ccccgacaac gccctgcagt tccggctgta cggcaaggac    600
tacaatgtgt acacccacag ctttctgtgc tacggaaagg accaggccct gtggcagaag    660
ctggccaagg acatccaggt ggccagcaac gagatcctgc gggacccttg cttccacccc    720
ggctacaaga aagtcgtgaa cgtgtccgac ctgtacaaga ccccctgcac caagagattc    780
gagatgaccc tgcccttcca gcagttcgag atccagggca tcggcaacta ccagcagtgc    840
caccagagca tcctggaact gttcaacacc agctactgcc cctacagcca gtgcgccttc    900
aacggcatct tcctgccacc tctgcagggg gacttcggcg ctttcagcgc cttctacttc    960
gtgatgaagt tcctgaacct gaccagcgag aaggtgtccc aggaaaaagt gacagagatg   1020
atgaagaagt tctgcgccca gccctgggag gaaatcaaga cctcctacgc tggcgtgaaa   1080
gagaagtacc tgagcgagta ctgcttcagc ggtacctaca tcctgagcct gctgctgcag   1140
ggctaccact tcaccgccga tagctgggag cacatccact tcatcggcaa gattcagggc   1200
agcgacgccg gctggacact gggctacatg ctgaatctga ccaacatg               1248
```

<210> SEQ ID NO 105
<211> LENGTH: 404
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 105

```
Asn Val Lys Tyr Gly Ile Val Leu Asp Ala Gly Ser Ser His Thr Ser
1               5                   10                  15

Leu Tyr Ile Tyr Lys Trp Pro Ala Glu Lys Glu Asn Asp Thr Gly Val
            20                  25                  30

Val His Gln Val Glu Glu Cys Arg Val Lys Gly Pro Gly Ile Ser Lys
        35                  40                  45

Phe Val Gln Lys Val Asn Glu Ile Gly Ile Tyr Leu Thr Asp Cys Met
    50                  55                  60

Glu Arg Ala Arg Glu Val Ile Pro Arg Ser Gln His Gln Glu Thr Pro
65                  70                  75                  80

Val Tyr Leu Gly Ala Thr Ala Gly Met Arg Leu Leu Arg Met Glu Ser
                85                  90                  95

Glu Glu Leu Ala Asp Arg Val Leu Asp Val Val Glu Arg Ser Leu Ser
            100                 105                 110

Asn Tyr Pro Phe Asp Phe Gln Gly Ala Arg Ile Ile Thr Gly Gln Glu
        115                 120                 125

Glu Gly Ala Tyr Gly Trp Ile Thr Ile Asn Tyr Leu Leu Gly Lys Phe
    130                 135                 140

Ser Gln Lys Asn Gln Glu Thr Phe Gly Ala Leu Asp Leu Gly Gly Ala
145                 150                 155                 160

Ser Thr Gln Val Thr Phe Val Pro Gln Asn Gln Thr Ile Glu Ser Pro
                165                 170                 175

Asp Asn Ala Leu Gln Phe Arg Leu Tyr Gly Lys Asp Tyr Asn Val Tyr
            180                 185                 190

Thr His Ser Phe Leu Cys Tyr Gly Lys Asp Gln Ala Leu Trp Gln Lys
        195                 200                 205

Leu Ala Lys Asp Ile Gln Val Ala Ser Asn Glu Ile Leu Arg Asp Pro
    210                 215                 220
```

```
Cys Phe His Pro Gly Tyr Lys Lys Val Val Asn Val Ser Asp Leu Tyr
225                 230                 235                 240

Lys Thr Pro Cys Thr Lys Arg Phe Glu Met Thr Leu Pro Phe Gln Gln
            245                 250                 255

Phe Glu Ile Gln Gly Ile Gly Asn Tyr Gln Gln Cys His Gln Ser Ile
        260                 265                 270

Leu Glu Leu Phe Asn Thr Ser Tyr Cys Pro Tyr Ser Gln Cys Ala Phe
    275                 280                 285

Asn Gly Ile Phe Leu Pro Pro Leu Gln Gly Asp Phe Gly Ala Phe Ser
290                 295                 300

Ala Phe Tyr Phe Val Met Lys Phe Leu Asn Leu Thr Ser Glu Lys Val
305                 310                 315                 320

Ser Gln Glu Lys Val Thr Glu Met Met Lys Lys Phe Cys Ala Gln Pro
            325                 330                 335

Trp Glu Glu Ile Lys Thr Ser Tyr Ala Gly Val Lys Glu Lys Tyr Leu
        340                 345                 350

Ser Glu Tyr Cys Phe Ser Gly Thr Tyr Ile Leu Ser Leu Leu Leu Gln
    355                 360                 365

Gly Tyr His Phe Thr Ala Asp Ser Trp Glu His Ile His Phe Ile Gly
370                 375                 380

Lys Ile Gln Gly Ser Asp Ala Gly Trp Thr Leu Gly Tyr Met Leu Asn
385                 390                 395                 400

Leu Thr Asn Met
```

<210> SEQ ID NO 106
<211> LENGTH: 1212
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 106

```
aacgtgaagt acggcatcgt gctggatgcc ggcagcagcc acaccagcct gtacatctac    60
aagtggcctg ccgagaaaga aaacgatacc ggtgtcgtgc accaggtgga agagtgcaga   120
gtgaagggcc ctggcatcag caagttcgtg cagaaagtga acgagatcgg catctacctg   180
accgactgca tggaacgggc cagagaagtg atccccagaa gccagcacca ggaaaccccc   240
gtgtacctgg agccacagc cggcatgaga ctgctgcgga tggaaagcga ggaactggcc   300
gacagagtgc tggacgtggt ggaaagaagc ctgagcaact acccattcga ttttcaaggg   360
gccagaatca tcaccggcca ggaagagggc gcttacggct ggatcaccat caactacctg   420
ctgggcaagt tcagccagaa aaatcaggaa accttcggag ccctggacct gggcggagcc   480
tctacccaag tgaccttcgt gccccagaat cagaccatcg agagccccga caacgccctg   540
cagttccggc tgtacggcaa ggactacaat gtgtacaccc acagctttct gtgctacgga   600
aaggaccagg ccctgtggca gaagctggcc aaggacatcc aggtggccag caacgagatc   660
ctgcgggacc cttgcttcca ccccggctac aagaaagtcg tgaacgtgtc cgacctgtac   720 aagacccct gcaccaagag attcgagatg accctgccct ccagcagtt cgagatccag   780 ggcatcggca actaccagca gtgccaccag agcatcctgg aactgttcaa caccagctac   840
tgcccctaca gccagtgcgc cttcaacgga atcttcctgc cacctctgca gggggacttc   900
ggcgctttca gcgccttcta cttcgtgatg aagttcctga acctgaccag cgagaaggtg   960
```

```
tcccaggaaa aagtgacaga gatgatgaag aagttctgcg cccagccctg ggaggaaatc    1020
aagacctcct acgctggcgt gaaagagaag tacctgagcg agtactgctt cagcggtacc    1080
tacatcctga gcctgctgct gcagggctac cacttcaccg ccgatagctg ggagcacatc    1140
cacttcatcg gcaagattca gggcagcgac gccggctgga cactgggcta catgctgaat    1200
ctgaccaaca tg                                                        1212

<210> SEQ ID NO 107
<211> LENGTH: 416
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Asn Val Lys Tyr Gly Ile Val Leu Asp Ala Gly Ser Ser His Thr Ser
1               5                   10                  15

Leu Tyr Ile Tyr Lys Trp Pro Ala Glu Lys Glu Asn Asp Thr Gly Val
            20                  25                  30

Val His Gln Val Glu Glu Ala Arg Val Lys Gly Pro Gly Ile Ser Lys
        35                  40                  45

Phe Val Gln Lys Val Asn Glu Ile Gly Ile Tyr Leu Thr Asp Ala Met
    50                  55                  60

Glu Arg Ala Arg Glu Val Ile Pro Arg Ser Gln His Gln Glu Thr Pro
65                  70                  75                  80

Val Tyr Leu Gly Ala Thr Ala Gly Met Arg Leu Leu Arg Met Glu Ser
                85                  90                  95

Glu Glu Leu Ala Asp Arg Val Leu Asp Val Val Glu Arg Ser Leu Ser
            100                 105                 110

Asn Tyr Pro Phe Asp Phe Gln Gly Ala Arg Ile Ile Thr Gly Gln Glu
        115                 120                 125

Glu Gly Ala Tyr Gly Trp Ile Thr Ile Asn Tyr Leu Leu Gly Lys Phe
    130                 135                 140

Ser Gln Lys Thr Arg Trp Phe Ser Ile Val Pro Tyr Glu Thr Asn Asn
145                 150                 155                 160

Gln Glu Thr Phe Gly Ala Leu Asp Leu Gly Gly Ala Ser Thr Gln Val
                165                 170                 175

Thr Phe Val Pro Gln Asn Gln Thr Ile Glu Ser Pro Asp Asn Ala Leu
            180                 185                 190

Gln Phe Arg Leu Tyr Gly Lys Asp Tyr Asn Val Tyr Thr His Ser Phe
        195                 200                 205

Leu Cys Tyr Gly Lys Asp Gln Ala Leu Trp Gln Lys Leu Ala Lys Asp
    210                 215                 220

Ile Gln Val Ala Ser Asn Glu Ile Leu Arg Asp Pro Cys Phe His Pro
225                 230                 235                 240

Gly Tyr Lys Lys Val Val Asn Val Ser Asp Leu Tyr Lys Thr Pro Cys
                245                 250                 255

Thr Lys Arg Phe Glu Met Thr Leu Pro Phe Gln Gln Phe Glu Ile Gln
            260                 265                 270

Gly Ile Gly Asn Tyr Gln Gln Cys His Gln Ser Ile Leu Glu Leu Phe
        275                 280                 285

Asn Thr Ser Tyr Cys Pro Tyr Ser Gln Cys Ala Phe Asn Gly Ile Phe
    290                 295                 300
```

```
Leu Pro Pro Leu Gln Gly Asp Phe Gly Ala Phe Ser Ala Phe Tyr Phe
305                 310                 315                 320

Val Met Lys Phe Leu Asn Leu Thr Ser Glu Lys Val Ser Gln Glu Lys
                325                 330                 335

Val Thr Glu Met Met Lys Lys Phe Cys Ala Gln Pro Trp Glu Glu Ile
            340                 345                 350

Lys Thr Ser Tyr Ala Gly Val Lys Glu Lys Tyr Leu Ser Glu Tyr Cys
        355                 360                 365

Phe Ser Gly Thr Tyr Ile Leu Ser Leu Leu Leu Gln Gly Tyr His Phe
    370                 375                 380

Thr Ala Asp Ser Trp Glu His Ile His Phe Ile Gly Lys Ile Gln Gly
385                 390                 395                 400

Ser Asp Ala Gly Trp Thr Leu Gly Tyr Met Leu Asn Leu Thr Asn Met
                405                 410                 415
```

<210> SEQ ID NO 108
<211> LENGTH: 1248
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 108

```
aacgtgaagt acggcatcgt gctggatgcc ggcagcagcc acaccagcct gtacatctac      60
aagtggcctg ccgagaaaga aaacgatacc ggtgtcgtgc accaggtgga agaggccaga     120
gtgaagggcc ctggcatcag caagttcgtg cagaaagtga cgagatcgg catctacctg      180
accgacgcca tggaacgggc cagagaagtg atccccagaa gccagcacca ggaaaccccc     240
gtgtacctgg agccacagc cggcatgaga ctgctgcgga tggaaagcga ggaactggcc      300
gacagagtgc tggacgtggt ggaaagaagc ctgagcaact acccattcga ttttcaaggg     360
gccagaatca tcaccggcca ggaagagggc gcttacggct ggatcaccat caactacctg     420
ctgggcaagt tcagccagaa aacccggtgg ttcagcatcg tgccctacga gacaaacaat     480
caggaaaccct tcggagccct ggacctgggc ggagcctcta cccaagtgac cttcgtgccc     540
cagaatcaga ccatcgagag ccccgacaac gccctgcagt tccggctgta cggcaaggac     600
tacaatgtgt acacccacag ctttctgtgc tacggaaagg accaggccct gtggcagaag     660
ctggccaagg acatccaggt ggccagcaac gagatcctgc gggacccttg cttccacccc     720
ggctacaaga aagtcgtgaa cgtgtccgac ctgtacaaga ccccctgcac caagagattc     780
gagatgaccc tgcccttcca gcagttcgag atccagggca tcggcaacta ccagcagtgc     840
caccagagca tcctggaact gttcaacacc agctactgcc cctacagcca gtgcgccttc     900
aacggcatct tcctgccacc tctgcagggg gacttcggcg ctttcagcgc cttctacttc     960
gtgatgaagt tcctgaacct gaccagcgag aaggtgtccc aggaaaaagt gacagagatg    1020
atgaagaagt tctgcgccca gccctgggag gaaatcaaga cctcctacgc tggcgtgaaa    1080
gagaagtacc tgagcgagta ctgcttcagc ggtacctaca tcctgagcct gctgctgcag    1140
ggctaccact tcaccgccga tagctgggag cacatccact tcatcggcaa gattcagggc    1200
agcgacgccg gctggacact gggctacatg ctgaatctga ccaacatg              1248
```

<210> SEQ ID NO 109
<211> LENGTH: 416
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Asn Val Lys Tyr Gly Ile Val Leu Asp Ala Gly Ser Ser His Thr Ser
1               5                   10                  15

Leu Tyr Ile Tyr Lys Trp Pro Ala Glu Lys Glu Asn Asp Thr Gly Val
            20                  25                  30

Val His Gln Val Glu Glu Cys Arg Val Lys Gly Pro Gly Ile Ser Lys
        35                  40                  45

Phe Val Gln Lys Val Asn Glu Ile Gly Ile Tyr Leu Thr Asp Cys Met
50                  55                  60

Glu Arg Ala Arg Glu Val Ile Pro Arg Ser Gln His Gln Glu Thr Pro
65                  70                  75                  80

Val Tyr Leu Gly Ala Thr Ala Gly Met Arg Leu Leu Arg Met Glu Ser
                85                  90                  95

Glu Glu Leu Ala Asp Arg Val Leu Asp Val Val Glu Arg Ser Leu Ser
            100                 105                 110

Asn Tyr Pro Phe Asp Phe Gln Gly Ala Arg Ile Ile Thr Gly Gln Glu
        115                 120                 125

Glu Gly Ala Tyr Gly Trp Ile Thr Ile Asn Tyr Leu Leu Gly Lys Phe
130                 135                 140

Ser Gln Lys Thr Arg Trp Phe Ser Ile Val Pro Tyr Glu Thr Asn Asn
145                 150                 155                 160

Gln Glu Thr Phe Gly Ala Leu Asp Leu Gly Gly Ala Ser Thr Gln Val
                165                 170                 175

Thr Phe Val Pro Gln Asn Gln Thr Ile Glu Ser Pro Asp Asn Ala Leu
            180                 185                 190

Gln Phe Arg Leu Tyr Gly Lys Asp Tyr Asn Val Tyr Thr His Ser Phe
        195                 200                 205

Leu Cys Tyr Gly Lys Asp Gln Ala Leu Trp Gln Lys Leu Ala Lys Asp
210                 215                 220

Ile Gln Val Ala Ser Asn Glu Ile Leu Arg Asp Pro Ala Phe His Pro
225                 230                 235                 240

Gly Tyr Lys Lys Val Asn Val Ser Asp Leu Tyr Lys Thr Pro Cys
                245                 250                 255

Thr Lys Arg Phe Glu Met Thr Leu Pro Phe Gln Gln Phe Glu Ile Gln
            260                 265                 270

Gly Ile Gly Asn Tyr Gln Gln Ala His Gln Ser Ile Leu Glu Leu Phe
        275                 280                 285

Asn Thr Ser Tyr Cys Pro Tyr Ser Gln Cys Ala Phe Asn Gly Ile Phe
290                 295                 300

Leu Pro Pro Leu Gln Gly Asp Phe Gly Ala Phe Ser Ala Phe Tyr Phe
305                 310                 315                 320

Val Met Lys Phe Leu Asn Leu Thr Ser Glu Lys Val Ser Gln Glu Lys
                325                 330                 335

Val Thr Glu Met Met Lys Lys Phe Cys Ala Gln Pro Trp Glu Glu Ile
            340                 345                 350

Lys Thr Ser Tyr Ala Gly Val Lys Glu Lys Tyr Leu Ser Glu Tyr Cys
        355                 360                 365

Phe Ser Gly Thr Tyr Ile Leu Ser Leu Leu Leu Gln Gly Tyr His Phe
370                 375                 380
```

-continued

Thr Ala Asp Ser Trp Glu His Ile His Phe Ile Gly Lys Ile Gln Gly
385                 390                 395                 400

Ser Asp Ala Gly Trp Thr Leu Gly Tyr Met Leu Asn Leu Thr Asn Met
            405                 410                 415

<210> SEQ ID NO 110
<211> LENGTH: 1248
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 110
aacgtgaagt acggcatcgt gctggatgcc ggcagcagcc acaccagcct gtacatctac      60
aagtggcctg ccgagaaaga aaacgatacc ggtgtcgtgc accaggtgga agagtgcaga     120
gtgaagggcc ctggcatcag caagttcgtg cagaaagtga acgagatcgg catctacctg     180
accgactgca tggaacgggc cagagaagtg atccccagaa gccagcacca ggaaaccccc     240
gtgtacctgg agccacagc cggcatgaga ctgctgcgga tggaaagcga ggaactggcc      300
gacagagtgc tggacgtggt ggaaagaagc ctgagcaact acccattcga ttttcaaggg     360
gccagaatca tcaccggcca ggaagagggc gcttacggct ggatcaccat caactacctg     420
ctgggcaagt tcagccagaa aacccggtgg ttcagcatcg tgccctacga dacaaacaat     480
caggaaacct tcggagccct ggacctgggc ggagcctcta cccaagtgac cttcgtgccc     540
cagaatcaga ccatcgagag ccccgacaac gccctgcagt tccggctgta cggcaaggac     600
tacaatgtgt acacccacag ctttctgtgc tacggaaagg accaggccct gtggcagaag     660
ctggccaagg acatccaggt ggccagcaac gagatcctgc gggaccctgc cttccacccc     720
ggctacaaga aagtcgtgaa cgtgtccgac ctgtacaaga ccccctgcac caagagattc     780
gagatgaccc tgcccttcca gcagttcgag atccagggca tcggcaacta ccagcaggcc     840
caccagagca tcctggaact gttcaacacc agctactgcc cctacagcca gtgcgccttc     900
aacggcatct tcctgccacc tctgcagggg gacttcggcg cttteagcgc cttctacttc     960
gtgatgaagt tcctgaacct gaccagcgag aaggtgtccc aggaaaaagt gacagagatg    1020
atgaagaagt ctctgcgccc agccctggga gaaatcaaga cctcctacgc tggcgtgaaa    1080
gagaagtacc tgagcgagta ctgcttcagc ggtacctaca tcctgagcct gctgctgcag    1140
ggctaccact tcaccgccga tagctgggag cacatccact tcatcggcaa gattcagggc    1200
agcgacgccg gctggacact gggctacatg ctgaatctga ccaacatg                1248

<210> SEQ ID NO 111
<211> LENGTH: 416
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Asn Val Lys Tyr Gly Ile Val Leu Asp Ala Gly Ser Ser His Thr Ser
1               5                   10                  15

Leu Tyr Ile Tyr Lys Trp Pro Ala Glu Lys Glu Asn Asp Thr Gly Val
            20                  25                  30

-continued

Val His Gln Val Glu Glu Cys Arg Val Lys Gly Pro Gly Ile Ser Lys
           35                  40                  45

Phe Val Gln Lys Val Asn Glu Ile Gly Ile Tyr Leu Thr Asp Cys Met
 50                  55                  60

Glu Arg Ala Arg Glu Val Ile Pro Arg Ser Gln His Gln Glu Thr Pro
 65                  70                  75                  80

Val Tyr Leu Gly Ala Thr Ala Gly Met Arg Leu Leu Arg Met Glu Ser
                 85                  90                  95

Glu Glu Leu Ala Asp Arg Val Leu Asp Val Val Glu Arg Ser Leu Ser
            100                 105                 110

Asn Tyr Pro Phe Asp Phe Gln Gly Ala Arg Ile Ile Thr Gly Gln Glu
        115                 120                 125

Glu Gly Ala Tyr Gly Trp Ile Thr Ile Asn Tyr Leu Leu Gly Lys Phe
    130                 135                 140

Ser Gln Lys Thr Arg Trp Phe Ser Ile Val Pro Tyr Glu Thr Asn Asn
145                 150                 155                 160

Gln Glu Thr Phe Gly Ala Leu Asp Leu Gly Gly Ala Ser Thr Gln Val
                165                 170                 175

Thr Phe Val Pro Gln Asn Gln Thr Ile Glu Ser Pro Asp Asn Ala Leu
            180                 185                 190

Gln Phe Arg Leu Tyr Gly Lys Asp Tyr Asn Val Tyr Thr His Ser Phe
        195                 200                 205

Leu Ala Tyr Gly Lys Asp Gln Ala Leu Trp Gln Lys Leu Ala Lys Asp
    210                 215                 220

Ile Gln Val Ala Ser Asn Glu Ile Leu Arg Asp Pro Cys Phe His Pro
225                 230                 235                 240

Gly Tyr Lys Lys Val Val Asn Val Ser Asp Leu Tyr Lys Thr Pro Ala
                245                 250                 255

Thr Lys Arg Phe Glu Met Thr Leu Pro Phe Gln Gln Phe Glu Ile Gln
            260                 265                 270

Gly Ile Gly Asn Tyr Gln Gln Cys His Gln Ser Ile Leu Glu Leu Phe
        275                 280                 285

Asn Thr Ser Tyr Cys Pro Tyr Ser Gln Cys Ala Phe Asn Gly Ile Phe
    290                 295                 300

Leu Pro Pro Leu Gln Gly Asp Phe Gly Ala Phe Ser Ala Phe Tyr Phe
305                 310                 315                 320

Val Met Lys Phe Leu Asn Leu Thr Ser Glu Lys Val Ser Gln Glu Lys
                325                 330                 335

Val Thr Glu Met Met Lys Lys Phe Cys Ala Gln Pro Trp Glu Glu Ile
            340                 345                 350

Lys Thr Ser Tyr Ala Gly Val Lys Glu Lys Tyr Leu Ser Glu Tyr Cys
        355                 360                 365

Phe Ser Gly Thr Tyr Ile Leu Ser Leu Leu Gln Gly Tyr His Phe
370                 375                 380

Thr Ala Asp Ser Trp Glu His Ile His Phe Ile Gly Lys Ile Gln Gly
385                 390                 395                 400

Ser Asp Ala Gly Trp Thr Leu Gly Tyr Met Leu Asn Leu Thr Asn Met
                405                 410                 415

<210> SEQ ID NO 112
<211> LENGTH: 1248
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 112

```
aacgtgaagt acggcatcgt gctggatgcc ggcagcagcc acaccagcct gtacatctac      60
aagtggcctg ccgagaaaga aaacgatacc ggtgtcgtgc accaggtgga agagtgcaga     120
gtgaagggcc ctggcatcag caagttcgtg cagaaagtga acgagatcgg catctacctg     180
accgactgca tgaacgggc cagagaagtg atccccagaa gccagcacca ggaaaccccc      240
gtgtacctgg gagccacagc cggcatgaga ctgctgcgga tggaaagcga ggaactggcc     300
gacagagtgc tggacgtggt ggaaagaagc ctgagcaact acccattcga ttttcaaggg     360
gccagaatca tcaccggcca ggaagagggc gcttacggct ggatcaccat caactacctg     420
ctgggcaagt tcagccagaa aacccggtgg ttcagcatcg tgccctacga caaaacaat     480
caggaaacct tcggagccct ggacctgggc ggagcctcta cccaagtgac cttcgtgccc     540
cagaatcaga ccatcgagag ccccgacaac gccctgcagt tccggctgta cggcaaggac    600
tacaatgtgt acacccacag ctttctggcc tacggaaagg accaggccct gtggcagaag    660
ctggccaagg acatccaggt ggccagcaac gagatcctgc gggacccttg cttccacccc    720
ggctacaaga agtcgtgaa cgtgtccgac ctgtacaaga ccccgccac caagagattc      780
gagatgaccc tgcccttcca gcagttcgag atccagggca tcggcaacta ccagcagtgc    840
caccagagca tcctggaact gttcaacacc agctactgcc cctacagcca gtgcgccttc    900
aacggcatct cctgccacc tctgcagggg gacttcggcg cttttcagcgc cttctacttc    960
gtgatgaagt tcctgaacct gaccagcgag aaggtgtccc aggaaaaagt gacagagatg   1020
atgaagaagt tctgcgccca gccctgggag gaaatcaaga cctcctacgc tggcgtgaaa   1080
gagaagtacc tgagcgagta ctgcttcagc ggtacctaca tcctgagcct gctgctgcag   1140
ggctaccact tcaccgccga tagctgggag cacatccact tcatcggcaa gattcagggc   1200
agcgacgccg gctggacact gggctacatg ctgaatctga ccaacatg                1248
```

<210> SEQ ID NO 113
<211> LENGTH: 416
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 113

```
Asn Val Lys Tyr Gly Ile Val Leu Asp Ala Gly Ser Ser His Thr Ser
1               5                   10                  15

Leu Tyr Ile Tyr Lys Trp Pro Ala Glu Lys Glu Asn Asp Thr Gly Val
            20                  25                  30

Val His Gln Val Glu Glu Cys Arg Val Lys Gly Pro Gly Ile Ser Lys
        35                  40                  45

Phe Val Gln Lys Val Asn Glu Ile Gly Ile Tyr Leu Thr Asp Cys Met
    50                  55                  60

Glu Arg Ala Arg Glu Val Ile Pro Arg Ser Gln His Gln Glu Thr Pro
65                  70                  75                  80

Val Tyr Leu Gly Ala Thr Ala Gly Met Arg Leu Leu Arg Met Glu Ser
                85                  90                  95

Glu Glu Leu Ala Asp Arg Val Leu Asp Val Val Glu Arg Ser Leu Ser
            100                 105                 110
```

Asn Tyr Pro Phe Asp Phe Gln Gly Ala Arg Ile Ile Thr Gly Gln Glu
            115                 120                 125

Glu Gly Ala Tyr Gly Trp Ile Thr Ile Asn Tyr Leu Leu Gly Lys Phe
130                 135                 140

Ser Gln Lys Thr Arg Trp Phe Ser Ile Val Pro Tyr Glu Thr Asn Asn
145                 150                 155                 160

Gln Glu Thr Phe Gly Ala Leu Asp Leu Gly Ala Ser Thr Gln Val
            165                 170                 175

Thr Phe Val Pro Gln Asn Gln Thr Ile Glu Ser Pro Asp Asn Ala Leu
            180                 185                 190

Gln Phe Arg Leu Tyr Gly Lys Asp Tyr Asn Val Tyr Thr His Ser Phe
            195                 200                 205

Leu Cys Tyr Gly Lys Asp Gln Ala Leu Trp Gln Lys Leu Ala Lys Asp
210                 215                 220

Ile Gln Val Ala Ser Asn Glu Ile Leu Arg Asp Pro Cys Phe His Pro
225                 230                 235                 240

Gly Tyr Lys Lys Val Val Asn Val Ser Asp Leu Tyr Lys Thr Pro Cys
            245                 250                 255

Thr Lys Arg Phe Glu Met Thr Leu Pro Phe Gln Gln Phe Glu Ile Gln
            260                 265                 270

Gly Ile Gly Asn Tyr Gln Gln Cys His Gln Ser Ile Leu Glu Leu Phe
            275                 280                 285

Asn Thr Ser Tyr Ala Pro Tyr Ser Gln Ala Ala Phe Asn Gly Ile Phe
            290                 295                 300

Leu Pro Pro Leu Gln Gly Asp Phe Gly Ala Phe Ser Ala Phe Tyr Phe
305                 310                 315                 320

Val Met Lys Phe Leu Asn Leu Thr Ser Glu Lys Val Ser Gln Glu Lys
            325                 330                 335

Val Thr Glu Met Met Lys Lys Phe Cys Ala Gln Pro Trp Glu Glu Ile
            340                 345                 350

Lys Thr Ser Tyr Ala Gly Val Lys Glu Lys Tyr Leu Ser Glu Tyr Cys
            355                 360                 365

Phe Ser Gly Thr Tyr Ile Leu Ser Leu Leu Gln Gly Tyr His Phe
370                 375                 380

Thr Ala Asp Ser Trp Glu His Ile His Phe Ile Gly Lys Ile Gln Gly
385                 390                 395                 400

Ser Asp Ala Gly Trp Thr Leu Gly Tyr Met Leu Asn Leu Thr Asn Met
            405                 410                 415

<210> SEQ ID NO 114
<211> LENGTH: 1248
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 114
aacgtgaagt acggcatcgt gctggatgcc ggcagcagcc acaccagcct gtacatctac      60
aagtggcctg ccgagaaaga aaacgatacc ggtgtcgtgc accaggtgga agagtgcaga     120
gtgaagggcc ctggcatcag caagttcgtg cagaaagtga cgagatcgg catctacctg     180 accgactgca tggaacgggc cagagaagtg atccccagaa gccagcacca ggaaaccccc    240
gtgtacctgg agccacagc cggcatgaga ctgctgcgga tggaaagcga ggaactggcc     300

```
gacagagtgc tggacgtggt ggaaagaagc ctgagcaact acccattcga ttttcaaggg    360
gccagaatca tcaccggcca ggaagagggc gcttacggct ggatcaccat caactacctg    420
ctgggcaagt tcagccagaa aacccggtgg ttcagcatcg tgccctacga gacaaacaat    480
caggaaacct tcggagccct ggacctgggc ggagcctcta cccaagtgac cttcgtgccc    540
cagaatcaga ccatcgagag ccccgacaac gccctgcagt tccggctgta cggcaaggac    600
tacaatgtgt acacccacag ctttctgtgc tacggaaagg accaggccct gtggcagaag    660
ctggccaagg acatccaggt ggccagcaac gagatcctgc gggacccttg cttccacccc    720
ggctacaaga aagtcgtgaa cgtgtccgac ctgtacaaga ccccctgcac caagagattc    780
gagatgaccc tgcccttcca gcagttcgag atccagggca tcggcaacta ccagcagtgc    840
caccagagca tcctggaact gttcaacacc agctacgccc cctacagcca ggccgccttc    900
aacggcatct tcctgccacc tctgcagggg gacttcggcg ctttcagcgc cttctacttc    960
gtgatgaagt tcctgaacct gaccagcgag aaggtgtccc aggaaaaagt gacagagatg   1020
atgaagaagt ctgcgcccca gccctgggag gaaatcaaga cctcctacgc tggcgtgaaa   1080
gagaagtacc tgagcgagta ctgcttcagc ggtacctaca tcctgagcct gctgctgcag   1140
ggctaccact tcaccgccga tagctgggag cacatccact tcatcggcaa gattcagggc   1200
agcgacgccg gctggacact gggctacatg ctgaatctga ccaacatg              1248
```

<210> SEQ ID NO 115
<211> LENGTH: 416
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 115

```
Asn Val Lys Tyr Gly Ile Val Leu Asp Ala Gly Ser Ser His Thr Ser
1               5                   10                  15

Leu Tyr Ile Tyr Lys Trp Pro Ala Glu Lys Glu Asn Asp Thr Gly Val
            20                  25                  30

Val His Gln Val Glu Glu Cys Arg Val Lys Gly Pro Gly Ile Ser Lys
        35                  40                  45

Phe Val Gln Lys Val Asn Glu Ile Gly Ile Tyr Leu Thr Asp Cys Met
    50                  55                  60

Glu Arg Ala Arg Glu Val Ile Pro Arg Ser Gln His Gln Glu Thr Pro
65                  70                  75                  80

Val Tyr Leu Gly Ala Thr Ala Gly Met Arg Leu Leu Arg Met Glu Ser
                85                  90                  95

Glu Glu Leu Ala Asp Arg Val Leu Asp Val Val Glu Arg Ser Leu Ser
            100                 105                 110

Asn Tyr Pro Phe Asp Phe Gln Gly Ala Arg Ile Ile Thr Gly Gln Glu
        115                 120                 125

Glu Gly Ala Tyr Gly Trp Ile Thr Ile Asn Tyr Leu Leu Gly Lys Phe
    130                 135                 140

Ser Gln Lys Thr Arg Trp Phe Ser Ile Val Pro Tyr Glu Thr Asn Asn
145                 150                 155                 160

Gln Glu Thr Phe Gly Ala Leu Asp Leu Gly Gly Ala Ser Thr Gln Val
                165                 170                 175

Thr Phe Val Pro Gln Asn Gln Thr Ile Glu Ser Pro Asp Asn Ala Leu
```

```
                  180                 185                 190
Gln Phe Arg Leu Tyr Gly Lys Asp Tyr Asn Val Tyr Thr His Ser Phe
              195                 200                 205
Leu Cys Tyr Gly Lys Asp Gln Ala Leu Trp Gln Lys Leu Ala Lys Asp
          210                 215                 220
Ile Gln Val Ala Ser Asn Glu Ile Leu Arg Asp Pro Cys Phe His Pro
225                 230                 235                 240
Gly Tyr Lys Lys Val Val Asn Val Ser Asp Leu Tyr Lys Thr Pro Cys
              245                 250                 255
Thr Lys Arg Phe Glu Met Thr Leu Pro Phe Gln Gln Phe Glu Ile Gln
          260                 265                 270
Gly Ile Gly Asn Tyr Gln Gln Cys His Gln Ser Ile Leu Glu Leu Phe
      275                 280                 285
Asn Thr Ser Tyr Cys Pro Tyr Ser Gln Cys Ala Phe Asn Gly Ile Phe
  290                 295                 300
Leu Pro Pro Leu Gln Gly Asp Phe Gly Ala Phe Ser Ala Phe Tyr Phe
305                 310                 315                 320
Val Met Lys Phe Leu Asn Leu Thr Ser Glu Lys Val Ser Gln Glu Lys
              325                 330                 335
Val Thr Glu Met Met Lys Lys Phe Ala Ala Gln Pro Trp Glu Glu Ile
          340                 345                 350
Lys Thr Ser Tyr Ala Gly Val Lys Glu Lys Tyr Leu Ser Glu Tyr Ala
      355                 360                 365
Phe Ser Gly Thr Tyr Ile Leu Ser Leu Leu Gln Gly Tyr His Phe
  370                 375                 380
Thr Ala Asp Ser Trp Glu His Ile His Phe Ile Gly Lys Ile Gln Gly
385                 390                 395                 400
Ser Asp Ala Gly Trp Thr Leu Gly Tyr Met Leu Asn Leu Thr Asn Met
              405                 410                 415

<210> SEQ ID NO 116
<211> LENGTH: 1248
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 116
aacgtgaagt acggcatcgt gctggatgcc ggcagcagcc acaccagcct gtacatctac      60
aagtggcctg ccgagaaaga aaacgatacc ggtgtcgtgc accaggtgga agagtgcaga     120
gtgaagggcc ctggcatcag caagttcgtg cagaaagtga cgagatcgg catctacctg     180 accgactgca tggaacgggc cagagaagtg atccccagaa gccagcacca ggaaaccccc     240
gtgtacctgg agccacagc cggcatgaga ctgctgcgga tggaaagcga ggaactggcc     300
gacagagtgc tggacgtggt ggaaagaagc ctgagcaact cccattcga ttttcaaggg     360 gccagaatca tcaccggcca ggaagagggc gcttacggct ggatcaccat caactacctg     420
ctgggcaagt tcagccagaa aacccggtgg ttcagcatcg tgccctacga acaaacaat     480 caggaaacct tcggagccct ggacctgggc ggagcctcta cccaagtgac cttcgtgccc     540
cagaatcaga ccatcgagag ccccgacaac gccctgcagt tccggctgta cggcaaggac     600
tacaatgtgt acacccacag ctttctgtgc tacggaaagg accaggccct gtggcagaag     660
ctggccaagg acatccaggt ggccagcaac gagatcctgc gggacccttg cttccacccc     720
```

```
ggctacaaga aagtcgtgaa cgtgtccgac ctgtacaaga ccccctgcac caagagattc    780
gagatgaccc tgcccttcca gcagttcgag atccagggga tcggcaacta ccagcagtgc    840
caccagagca tcctggaact gttcaacacc agctactgcc cctacagcca gtgcgccttc    900
aacggcatct tcctgccacc tctgcagggg gacttcggcg ctttcagcgc cttctacttc    960
gtgatgaagt tcctgaacct gaccagcgag aaggtgtccc aggaaaaagt gacagagatg   1020
atgaagaagt cgccgccca gcctgggag gaaatcaaga cctcctacgc tggcgtgaaa   1080
gagaagtacc tgagcgagta cgccttcagc ggtacctaca tcctgagcct gctgctgcag   1140
ggctaccact tcaccgccga tagctgggag cacatccact tcatcggcaa gattcagggc   1200
agcgacgccg gctggacact gggctacatg ctgaatctga ccaacatg               1248
```

<210> SEQ ID NO 117
<211> LENGTH: 404
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

```
Asn Val Lys Tyr Gly Ile Val Leu Asp Ala Gly Ser Ser His Thr Ser
 1               5                  10                  15

Leu Tyr Ile Tyr Lys Trp Pro Ala Glu Lys Glu Asn Asp Thr Gly Val
            20                  25                  30

Val His Gln Val Glu Glu Ala Arg Val Lys Gly Pro Gly Ile Ser Lys
        35                  40                  45

Phe Val Gln Lys Val Asn Glu Ile Gly Ile Tyr Leu Thr Asp Ala Met
    50                  55                  60

Glu Arg Ala Arg Glu Val Ile Pro Arg Ser Gln His Gln Glu Thr Pro
65                  70                  75                  80

Val Tyr Leu Gly Ala Thr Ala Gly Met Arg Leu Leu Arg Met Glu Ser
                85                  90                  95

Glu Glu Leu Ala Asp Arg Val Leu Asp Val Val Glu Arg Ser Leu Ser
            100                 105                 110

Asn Tyr Pro Phe Asp Phe Gln Gly Ala Arg Ile Ile Thr Gly Gln Glu
        115                 120                 125

Glu Gly Ala Tyr Gly Trp Ile Thr Ile Asn Tyr Leu Leu Gly Lys Phe
    130                 135                 140

Ser Gln Lys Asn Gln Glu Thr Phe Gly Ala Leu Asp Leu Gly Gly Ala
145                 150                 155                 160

Ser Thr Gln Val Thr Phe Val Pro Gln Asn Gln Thr Ile Glu Ser Pro
                165                 170                 175

Asp Asn Ala Leu Gln Phe Arg Leu Tyr Gly Lys Asp Tyr Asn Val Tyr
            180                 185                 190

Thr His Ser Phe Leu Cys Tyr Gly Lys Asp Gln Ala Leu Trp Gln Lys
        195                 200                 205

Leu Ala Lys Asp Ile Gln Val Ala Ser Asn Glu Ile Leu Arg Asp Pro
    210                 215                 220

Cys Phe His Pro Gly Tyr Lys Lys Val Val Asn Val Ser Asp Leu Tyr
225                 230                 235                 240

Lys Thr Pro Cys Thr Lys Arg Phe Glu Met Thr Leu Pro Phe Gln Gln
                245                 250                 255
```

```
Phe Glu Ile Gln Gly Ile Gly Asn Tyr Gln Gln Cys His Gln Ser Ile
            260                 265                 270
Leu Glu Leu Phe Asn Thr Ser Tyr Cys Pro Tyr Ser Gln Cys Ala Phe
        275                 280                 285
Asn Gly Ile Phe Leu Pro Pro Leu Gln Gly Asp Phe Gly Ala Phe Ser
    290                 295                 300
Ala Phe Tyr Phe Val Met Lys Phe Leu Asn Leu Thr Ser Glu Lys Val
305                 310                 315                 320
Ser Gln Glu Lys Val Thr Glu Met Met Lys Lys Phe Cys Ala Gln Pro
                325                 330                 335
Trp Glu Glu Ile Lys Thr Ser Tyr Ala Gly Val Lys Glu Lys Tyr Leu
            340                 345                 350
Ser Glu Tyr Cys Phe Ser Gly Thr Tyr Ile Leu Ser Leu Leu Leu Gln
        355                 360                 365
Gly Tyr His Phe Thr Ala Asp Ser Trp Glu His Ile His Phe Ile Gly
    370                 375                 380
Lys Ile Gln Gly Ser Asp Ala Gly Trp Thr Leu Gly Tyr Met Leu Asn
385                 390                 395                 400
Leu Thr Asn Met
```

<210> SEQ ID NO 118
<211> LENGTH: 1212
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 118

```
aacgtgaagt acggcatcgt gctggatgcc ggcagcagcc acaccagcct gtacatctac      60
aagtggcctg ccgagaaaga aaacgatacc ggtgtcgtgc accaggtgga agaggccaga     120
gtgaagggcc ctggcatcag caagttcgtg cagaaagtga cgagatcgg catctacctg     180
accgacgcca tggaacgggc cagagaagtg atccccagaa gccagcacca ggaaaccccc     240
gtgtacctgg agccacagc cggcatgaga ctgctgcgga tggaaagcga ggaactggcc     300
gacagagtgc tggacgtggt ggaaagaagc ctgagcaact acccattcga ttttcaaggg     360
gccagaatca tcaccggcca ggaagagggc gcttacggct ggatcaccat caactacctg     420
ctgggcaagt tcagccagaa aaatcaggaa accttcggag ccctggacct gggcggagcc     480
tctacccaag tgaccttcgt gccccagaat cagaccatcg agagccccga caacgccctg     540
cagttccggc tgtacggcaa ggactacaat gtgtacaccc acagctttct gtgctacgga     600
aaggaccagg ccctgtggca gaagctggcc aaggacatcc aggtggccag caacgagatc     660
ctgcgggacc cttgcttcca ccccggctac aagaaagtcg tgaacgtgtc cgacctgtac     720
aagacccct gcaccaagag attcgagatg accctgccct ccagcagtt cgagatccag     780
ggcatcggca actaccagca gtgccaccag agcatcctgg aactgttcaa caccagctac     840
tgcccctaca gccagtgcgc cttcaacggc atcttcctgc cacctctgca ggggacttc     900
ggcgctttca gcgccttcta cttcgtgatg aagttcctga acctgaccag cgagaaggtg     960
tcccaggaaa agtgacaga gatgatgaag aagttctgcg cccagccctg gaggaaatc    1020
aagacctcct acgctggcgt gaaagagaag tacctgagcg agtactgctt cagcggtacc    1080
tacatcctga gcctgctgct gcagggctac cacttcaccg ccgatagctg ggagcacatc    1140
```

```
cacttcatcg gcaagattca gggcagcgac gccggctgga cactgggcta catgctgaat    1200
ctgaccaaca tg                                                        1212
```

<210> SEQ ID NO 119
<211> LENGTH: 404
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

```
Asn Val Lys Tyr Gly Ile Val Leu Asp Ala Gly Ser Ser His Thr Ser
1               5                   10                  15

Leu Tyr Ile Tyr Lys Trp Pro Ala Glu Lys Glu Asn Asp Thr Gly Val
            20                  25                  30

Val His Gln Val Glu Glu Cys Arg Val Lys Gly Pro Gly Ile Ser Lys
        35                  40                  45

Phe Val Gln Lys Val Asn Glu Ile Gly Ile Tyr Leu Thr Asp Cys Met
    50                  55                  60

Glu Arg Ala Arg Glu Val Ile Pro Arg Ser Gln His Gln Glu Thr Pro
65                  70                  75                  80

Val Tyr Leu Gly Ala Thr Ala Gly Met Arg Leu Leu Arg Met Glu Ser
                85                  90                  95

Glu Glu Leu Ala Asp Arg Val Leu Asp Val Val Glu Arg Ser Leu Ser
            100                 105                 110

Asn Tyr Pro Phe Asp Phe Gln Gly Ala Arg Ile Ile Thr Gly Gln Glu
        115                 120                 125

Glu Gly Ala Tyr Gly Trp Ile Thr Ile Asn Tyr Leu Leu Gly Lys Phe
    130                 135                 140

Ser Gln Lys Asn Gln Glu Thr Phe Gly Ala Leu Asp Leu Gly Gly Ala
145                 150                 155                 160

Ser Thr Gln Val Thr Phe Val Pro Gln Asn Gln Thr Ile Glu Ser Pro
                165                 170                 175

Asp Asn Ala Leu Gln Phe Arg Leu Tyr Gly Lys Asp Tyr Asn Val Tyr
            180                 185                 190

Thr His Ser Phe Leu Cys Tyr Gly Lys Asp Gln Ala Leu Trp Gln Lys
        195                 200                 205

Leu Ala Lys Asp Ile Gln Val Ala Ser Asn Glu Ile Leu Arg Asp Pro
    210                 215                 220

Ala Phe His Pro Gly Tyr Lys Lys Val Val Asn Val Ser Asp Leu Tyr
225                 230                 235                 240

Lys Thr Pro Cys Thr Lys Arg Phe Glu Met Thr Leu Pro Phe Gln Gln
                245                 250                 255

Phe Glu Ile Gln Gly Ile Gly Asn Tyr Gln Gln Ala His Gln Ser Ile
            260                 265                 270

Leu Glu Leu Phe Asn Thr Ser Tyr Cys Pro Tyr Ser Gln Cys Ala Phe
        275                 280                 285

Asn Gly Ile Phe Leu Pro Pro Leu Gln Gly Asp Phe Gly Ala Phe Ser
    290                 295                 300

Ala Phe Tyr Phe Val Met Lys Phe Leu Asn Leu Thr Ser Glu Lys Val
305                 310                 315                 320

Ser Gln Glu Lys Val Thr Glu Met Met Lys Lys Phe Cys Ala Gln Pro
                325                 330                 335
```

Trp Glu Glu Ile Lys Thr Ser Tyr Ala Gly Val Lys Glu Lys Tyr Leu
            340                 345                 350

Ser Glu Tyr Cys Phe Ser Gly Thr Tyr Ile Leu Ser Leu Leu Leu Gln
        355                 360                 365

Gly Tyr His Phe Thr Ala Asp Ser Trp Glu His Ile His Phe Ile Gly
    370                 375                 380

Lys Ile Gln Gly Ser Asp Ala Gly Trp Thr Leu Gly Tyr Met Leu Asn
385                 390                 395                 400

Leu Thr Asn Met

<210> SEQ ID NO 120
<211> LENGTH: 1212
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 120
aacgtgaagt acggcatcgt gctggatgcc ggcagcagcc acaccagcct gtacatctac      60
aagtggcctg ccgagaaaga aaacgatacc ggtgtcgtgc accaggtgga agagtgcaga     120
gtgaagggcc ctggcatcag caagttcgtg cagaaagtga cgagatcgg catctacctg     180
accgactgca tggaacgggc cagagaagtg atccccagaa gccagcacca ggaaaccccc     240
gtgtacctgg agccacagc cggcatgaga ctgctgcgga tggaaagcga ggaactggcc     300
gacagagtgc tggacgtggt ggaaagaagc ctgagcaact acccattcga ttttcaaggg     360
gccagaatca tcaccggcca ggaagagggc gcttacggct ggatcaccat caactacctg     420
ctgggcaagt tcagccagaa aaatcaggaa accttcggag ccctggacct gggcggagcc     480
tctacccaag tgaccttcgt gccccagaat cagaccatcg agagccccga caacgccctg     540
cagttccggc tgtacggcaa ggactacaat gtgtacaccc acagctttct gtgctacgga     600
aaggaccagg ccctgtggca gaagctggcc aaggacatcc aggtggccag caacgagatc     660
ctgcgggacc ctgccttcca ccccggctac aagaaagtcg tgaacgtgtc cgacctgtac     720
aagacccct gcaccaagag attcgagatg accctgccct tccagcagtt cgagatccag     780
ggcatcggca actaccagca ggcccaccag agcatcctgg aactgttcaa caccagctac     840
tgcccctaca gccagtgcgc cttcaacggc atcttcctgc acctctgca ggggacttc     900
ggcgctttca gcgccttcta cttcgtgatg aagttcctga acctgaccag cgagaaggtg     960
tcccaggaaa aagtgacaga gatgatgaag aagttctgcg cccagccctg ggaggaaatc    1020
aagacctcct acgctggcgt gaaagagaag tacctgagcg agtactgctt cagcggtacc    1080
tacatcctga gcctgctgct gcagggctac cacttcaccg ccgatagctg ggagcacatc    1140
cacttcatcg gcaagattca gggcagcgac gccggctgga cactgggcta catgctgaat    1200
ctgaccaaca tg                                                        1212

<210> SEQ ID NO 121
<211> LENGTH: 404
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

```
Asn Val Lys Tyr Gly Ile Val Leu Asp Ala Gly Ser Ser His Thr Ser
1               5                   10                  15

Leu Tyr Ile Tyr Lys Trp Pro Ala Glu Lys Glu Asn Asp Thr Gly Val
            20                  25                  30

Val His Gln Val Glu Glu Cys Arg Val Lys Gly Pro Gly Ile Ser Lys
        35                  40                  45

Phe Val Gln Lys Val Asn Glu Ile Gly Ile Tyr Leu Thr Asp Cys Met
    50                  55                  60

Glu Arg Ala Arg Glu Val Ile Pro Arg Ser Gln His Gln Glu Thr Pro
65              70                  75                  80

Val Tyr Leu Gly Ala Thr Ala Gly Met Arg Leu Leu Arg Met Glu Ser
            85                  90                  95

Glu Glu Leu Ala Asp Arg Val Leu Asp Val Val Glu Arg Ser Leu Ser
            100                 105                 110

Asn Tyr Pro Phe Asp Phe Gln Gly Ala Arg Ile Ile Thr Gly Gln Glu
        115                 120                 125

Glu Gly Ala Tyr Gly Trp Ile Thr Ile Asn Tyr Leu Leu Gly Lys Phe
    130                 135                 140

Ser Gln Lys Asn Gln Glu Thr Phe Gly Ala Leu Asp Leu Gly Gly Ala
145                 150                 155                 160

Ser Thr Gln Val Thr Phe Val Pro Gln Asn Gln Thr Ile Glu Ser Pro
            165                 170                 175

Asp Asn Ala Leu Gln Phe Arg Leu Tyr Gly Lys Asp Tyr Asn Val Tyr
        180                 185                 190

Thr His Ser Phe Leu Ala Tyr Gly Lys Asp Gln Ala Leu Trp Gln Lys
        195                 200                 205

Leu Ala Lys Asp Ile Gln Val Ala Ser Asn Glu Ile Leu Arg Asp Pro
210                 215                 220

Cys Phe His Pro Gly Tyr Lys Lys Val Val Asn Val Ser Asp Leu Tyr
225                 230                 235                 240

Lys Thr Pro Ala Thr Lys Arg Phe Glu Met Thr Leu Pro Phe Gln Gln
            245                 250                 255

Phe Glu Ile Gln Gly Ile Gly Asn Tyr Gln Gln Cys His Gln Ser Ile
        260                 265                 270

Leu Glu Leu Phe Asn Thr Ser Tyr Cys Pro Tyr Ser Gln Cys Ala Phe
        275                 280                 285

Asn Gly Ile Phe Leu Pro Pro Leu Gln Gly Asp Phe Gly Ala Phe Ser
        290                 295                 300

Ala Phe Tyr Phe Val Met Lys Phe Leu Asn Leu Thr Ser Glu Lys Val
305                 310                 315                 320

Ser Gln Glu Lys Val Thr Glu Met Met Lys Lys Phe Cys Ala Gln Pro
            325                 330                 335

Trp Glu Glu Ile Lys Thr Ser Tyr Ala Gly Val Lys Glu Lys Tyr Leu
        340                 345                 350

Ser Glu Tyr Cys Phe Ser Gly Thr Tyr Ile Leu Ser Leu Leu Leu Gln
        355                 360                 365

Gly Tyr His Phe Thr Ala Asp Ser Trp Glu His Ile His Phe Ile Gly
        370                 375                 380

Lys Ile Gln Gly Ser Asp Ala Gly Trp Thr Leu Gly Tyr Met Leu Asn
385                 390                 395                 400

Leu Thr Asn Met
```

<210> SEQ ID NO 122
<211> LENGTH: 1212
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 122

```
aacgtgaagt acggcatcgt gctggatgcc ggcagcagcc acaccagcct gtacatctac     60
aagtggcctg ccgagaaaga aaacgatacc ggtgtcgtgc accaggtgga agagtgcaga    120
gtgaagggcc ctggcatcag caagttcgtg cagaaagtga acgagatcgg catctacctg    180
accgactgca tggaacgggc cagagaagtg atccccagaa gccagcacca ggaaaccccc    240
gtgtacctgg agccacagc cggcatgaga ctgctgcgga tggaaagcga ggaactggcc    300
gacagagtgc tggacgtggt ggaaagaagc ctgagcaact acccattcga ttttcaaggg    360
gccagaatca tcaccggcca ggaagagggc gcttacggct ggatcaccat caactacctg    420
ctgggcaagt tcagccagaa aaatcaggaa accttcggag ccctggacct gggcggagcc    480
tctacccaag tgaccttcgt gccccagaat cagaccatcg agagccccga caacgccctg    540
cagttccggc tgtacggcaa ggactacaat gtgtacaccc acagctttct ggcctacgga    600
aaggaccagg ccctgtggca gaagctggcc aaggacatcc aggtggccag caacgagatc    660
ctgcgggacc cttgcttcca ccccggctac aagaaagtcg tgaacgtgtc cgacctgtac    720
aagaccccg ccaccaagag attcgagatg accctgccct ccagcagtt cgagatccag    780
ggcatcggca actaccagca gtgccaccag agcatcctgg aactgttcaa caccagctac    840
tgcccctaca ccagtgcgc cttcaacggc atcttcctgc cacctctgca ggggacttc    900
ggcgctttca gcgccttcta cttcgtgatg aagttcctga acctgaccag cgagaaggtg    960
tcccaggaaa aagtgacaga gatgatgaag aagttctgcg cccagccctg ggaggaaatc   1020
aagacctcct acgctggcgt gaaagagaag tacctgagcg agtactgctt cagcggtacc   1080
tacatcctga gcctgctgct gcagggctac cacttcaccg ccgatagctg ggagcacatc   1140
cacttcatcg gcaagattca gggcagcgac gccggctgga cactgggcta catgctgaat   1200
ctgaccaaca tg                                                        1212
```

<210> SEQ ID NO 123
<211> LENGTH: 404
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 123

```
Asn Val Lys Tyr Gly Ile Val Leu Asp Ala Gly Ser Ser His Thr Ser
1               5                   10                  15

Leu Tyr Ile Tyr Lys Trp Pro Ala Glu Lys Glu Asn Asp Thr Gly Val
            20                  25                  30

Val His Gln Val Glu Glu Cys Arg Val Lys Gly Pro Gly Ile Ser Lys
        35                  40                  45

Phe Val Gln Lys Val Asn Glu Ile Gly Ile Tyr Leu Thr Asp Cys Met
    50                  55                  60

Glu Arg Ala Arg Glu Val Ile Pro Arg Ser Gln His Gln Glu Thr Pro
65                  70                  75                  80
```

Val Tyr Leu Gly Ala Thr Ala Gly Met Arg Leu Leu Arg Met Glu Ser
                85                  90                  95

Glu Glu Leu Ala Asp Arg Val Leu Asp Val Val Glu Arg Ser Leu Ser
            100                 105                 110

Asn Tyr Pro Phe Asp Phe Gln Gly Ala Arg Ile Ile Thr Gly Gln Glu
        115                 120                 125

Glu Gly Ala Tyr Gly Trp Ile Thr Ile Asn Tyr Leu Leu Gly Lys Phe
    130                 135                 140

Ser Gln Lys Asn Gln Glu Thr Phe Gly Ala Leu Asp Leu Gly Gly Ala
145                 150                 155                 160

Ser Thr Gln Val Thr Phe Val Pro Gln Asn Gln Thr Ile Glu Ser Pro
                165                 170                 175

Asp Asn Ala Leu Gln Phe Arg Leu Tyr Gly Lys Asp Tyr Asn Val Tyr
            180                 185                 190

Thr His Ser Phe Leu Cys Tyr Gly Lys Asp Gln Ala Leu Trp Gln Lys
        195                 200                 205

Leu Ala Lys Asp Ile Gln Val Ala Ser Asn Glu Ile Leu Arg Asp Pro
    210                 215                 220

Cys Phe His Pro Gly Tyr Lys Lys Val Val Asn Val Ser Asp Leu Tyr
225                 230                 235                 240

Lys Thr Pro Cys Thr Lys Arg Phe Glu Met Thr Leu Pro Phe Gln Gln
                245                 250                 255

Phe Glu Ile Gln Gly Ile Gly Asn Tyr Gln Gln Cys His Gln Ser Ile
            260                 265                 270

Leu Glu Leu Phe Asn Thr Ser Tyr Ala Pro Tyr Ser Gln Ala Ala Phe
        275                 280                 285

Asn Gly Ile Phe Leu Pro Pro Leu Gln Gly Asp Phe Gly Ala Phe Ser
    290                 295                 300

Ala Phe Tyr Phe Val Met Lys Phe Leu Asn Leu Thr Ser Glu Lys Val
305                 310                 315                 320

Ser Gln Glu Lys Val Thr Glu Met Met Lys Lys Phe Cys Ala Gln Pro
                325                 330                 335

Trp Glu Glu Ile Lys Thr Ser Tyr Ala Gly Val Lys Glu Lys Tyr Leu
            340                 345                 350

Ser Glu Tyr Cys Phe Ser Gly Thr Tyr Ile Leu Ser Leu Leu Leu Gln
        355                 360                 365

Gly Tyr His Phe Thr Ala Asp Ser Trp Glu His Ile His Phe Ile Gly
    370                 375                 380

Lys Ile Gln Gly Ser Asp Ala Gly Trp Thr Leu Gly Tyr Met Leu Asn
385                 390                 395                 400

Leu Thr Asn Met

<210> SEQ ID NO 124
<211> LENGTH: 1212
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 124
aacgtgaagt acggcatcgt gctggatgcc ggcagcagcc acaccagcct gtacatctac    60
aagtggcctg ccgagaaaga aaacgatacc ggtgtcgtgc accaggtgga agagtgcaga   120

```
gtgaagggcc ctggcatcag caagttcgtg cagaaagtga acgagatcgg catctacctg    180
accgactgca tggaacgggc cagagaagtg atccccagaa gccagcacca ggaaaccccc    240
gtgtacctgg gagccacagc cggcatgaga ctgctgcgga tggaaagcga ggaactggcc    300
gacagagtgc tggacgtggt ggaaagaagc ctgagcaact acccattcga ttttcaaggg    360
gccagaatca tcaccggcca ggaagagggc gcttacggct ggatcaccat caactacctg    420
ctgggcaagt tcagccagaa aaatcaggaa accttcggag ccctggacct gggcggagcc    480
tctacccaag tgaccttcgt gccccagaat cagaccatcg agagcccga caacgccctg    540 cagttccggc tgtacggcaa ggactacaat gtgtacaccc acagctttct gtgctacgga    600
aaggaccagg ccctgtggca gaagctggcc aaggacatcc aggtggccag caacgagatc    660
ctgcgggacc cttgcttcca ccccggctac aagaaagtcg tgaacgtgtc cgacctgtac    720 aagacccct gcaccaagag attcgagatg accctgccct ccagcagtt cgagatccag    780 ggcatcggca actaccagca gtgccaccag agcatcctgg aactgttcaa caccagctac    840
gccccctaca gccaggccgc cttcaacggc atcttcctgc acctctgca gggggacttc    900 ggcgctttca gcgccttcta cttcgtgatg aagttcctga acctgaccag cgagaaggtg    960
tcccaggaaa agtgacaga gatgatgaag aagttctgcg cccagccctg ggaggaaatc   1020
aagacctcct acgctggcgt gaaagagaag tacctgagcg agtactgctt cagcggtacc   1080
tacatcctga gcctgctgct gcagggctac cacttcaccg ccgatagctg ggagcacatc   1140
cacttcatcg gcaagattca gggcagcgac gccggctgga cactgggcta catgctgaat   1200
ctgaccaaca tg                                                         1212
```

<210> SEQ ID NO 125
<211> LENGTH: 404
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 125

```
Asn Val Lys Tyr Gly Ile Val Leu Asp Ala Gly Ser Ser His Thr Ser
1               5                   10                  15

Leu Tyr Ile Tyr Lys Trp Pro Ala Glu Lys Glu Asn Asp Thr Gly Val
            20                  25                  30

Val His Gln Val Glu Glu Cys Arg Val Lys Gly Pro Gly Ile Ser Lys
        35                  40                  45

Phe Val Gln Lys Val Asn Glu Ile Gly Ile Tyr Leu Thr Asp Cys Met
    50                  55                  60

Glu Arg Ala Arg Glu Val Ile Pro Arg Ser Gln His Gln Glu Thr Pro
65                  70                  75                  80

Val Tyr Leu Gly Ala Thr Ala Gly Met Arg Leu Leu Arg Met Glu Ser
                85                  90                  95

Glu Glu Leu Ala Asp Arg Val Leu Asp Val Val Glu Arg Ser Leu Ser
            100                 105                 110

Asn Tyr Pro Phe Asp Phe Gln Gly Ala Arg Ile Ile Thr Gly Gln Glu
        115                 120                 125

Glu Gly Ala Tyr Gly Trp Ile Thr Ile Asn Tyr Leu Leu Gly Lys Phe
    130                 135                 140

Ser Gln Lys Asn Gln Glu Thr Phe Gly Ala Leu Asp Leu Gly Gly Ala
145                 150                 155                 160
```

Ser Thr Gln Val Thr Phe Val Pro Gln Asn Gln Thr Ile Glu Ser Pro
            165                 170                 175

Asp Asn Ala Leu Gln Phe Arg Leu Tyr Gly Lys Asp Tyr Asn Val Tyr
        180                 185                 190

Thr His Ser Phe Leu Cys Tyr Gly Lys Asp Gln Ala Leu Trp Gln Lys
            195                 200                 205

Leu Ala Lys Asp Ile Gln Val Ala Ser Asn Glu Ile Leu Arg Asp Pro
210                 215                 220

Cys Phe His Pro Gly Tyr Lys Lys Val Val Asn Val Ser Asp Leu Tyr
225                 230                 235                 240

Lys Thr Pro Cys Thr Lys Arg Phe Glu Met Thr Leu Pro Phe Gln Gln
            245                 250                 255

Phe Glu Ile Gln Gly Ile Gly Asn Tyr Gln Gln Cys His Gln Ser Ile
        260                 265                 270

Leu Glu Leu Phe Asn Thr Ser Tyr Cys Pro Tyr Ser Gln Cys Ala Phe
            275                 280                 285

Asn Gly Ile Phe Leu Pro Pro Leu Gln Gly Asp Phe Gly Ala Phe Ser
        290                 295                 300

Ala Phe Tyr Phe Val Met Lys Phe Leu Asn Leu Thr Ser Glu Lys Val
305                 310                 315                 320

Ser Gln Glu Lys Val Thr Glu Met Met Lys Lys Phe Ala Ala Gln Pro
            325                 330                 335

Trp Glu Glu Ile Lys Thr Ser Tyr Ala Gly Val Lys Glu Lys Tyr Leu
            340                 345                 350

Ser Glu Tyr Ala Phe Ser Gly Thr Tyr Ile Leu Ser Leu Leu Leu Gln
            355                 360                 365

Gly Tyr His Phe Thr Ala Asp Ser Trp Glu His Ile His Phe Ile Gly
        370                 375                 380

Lys Ile Gln Gly Ser Asp Ala Gly Trp Thr Leu Gly Tyr Met Leu Asn
385                 390                 395                 400

Leu Thr Asn Met

<210> SEQ ID NO 126
<211> LENGTH: 1212
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 126
aacgtgaagt acggcatcgt gctggatgcc ggcagcagcc acaccagcct gtacatctac      60
aagtggcctg ccgagaaaga aaacgatacc ggtgtcgtgc accaggtgga agagtgcaga     120
gtgaagggcc ctggcatcag caagttcgtg cagaaagtga acgagatcgg catctacctg     180
accgactgca tggaacgggc cagagaagtg atccccagaa gccagcacca ggaaaccccc     240
gtgtacctgg agccacagc cggcatgaga ctgctgcgga tggaaagcga ggaactggcc      300
gacagagtgc tggacgtggt ggaaagaagc ctgagcaact acccattcga ttttcaaggg     360
gccagaatca tcaccggcca ggaagagggc gcttacggct ggatcaccat caactacctg     420
ctgggcaagt tcagccagaa aaatcaggaa accttcggag ccctggacct gggcggagcc     480
tctacccaag tgaccttcgt gccccagaat cagaccatcg agagcccga caacgccctg     540 cagttccggc tgtacggcaa ggactacaat gtgtacaccc acagctttct gtgctacgga     600

-continued

```
aaggaccagg ccctgtggca gaagctggcc aaggacatcc aggtggccag caacgagatc    660
ctgcgggacc cttgcttcca ccccggctac aagaaagtcg tgaacgtgtc cgacctgtac    720
aagaccccct gcaccaagag attcgagatg accctgccct tccagcagtt cgagatccag    780
ggcatcggca actaccagca gtgccaccag agcatcctgg aactgttcaa caccagctac    840
tgcccctaca gccagtgcgc cttcaacggc atcttcctgc acctctgca gggggacttc     900 ggcgctttca gcgccttcta cttcgtgatg aagttcctga acctgaccag cgagaaggtg    960
tcccaggaaa aagtgacaga tgatgaag aagttcgccg cccagccctg ggaggaaatc     1020
aagacctcct acgctggcgt gaaagagaag tacctgagcg agtacgcctt cagcggtacc   1080
tacatcctga gcctgctgct gcagggctac cacttcaccg ccgatagctg ggagcacatc   1140
cacttcatcg gcaagattca gggcagcgac gccggctgga cactgggcta catgctgaat   1200
ctgaccaaca tg                                                       1212
```

<210> SEQ ID NO 127
<211> LENGTH: 431
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 127

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Thr Arg Trp Phe Ser
145                 150                 155                 160

Ile Val Pro Tyr Glu Thr Asn Asn Gln Glu Thr Phe Gly Ala Leu Asp
                165                 170                 175

Leu Gly Gly Ala Ser Thr Gln Val Thr Phe Val Pro Gln Asn Gln Thr
            180                 185                 190

Ile Glu Ser Pro Asp Asn Ala Leu Gln Phe Arg Leu Tyr Gly Lys Asp
        195                 200                 205

Tyr Asn Val Tyr Thr His Ser Phe Leu Cys Tyr Gly Lys Asp Gln Ala
    210                 215                 220

Leu Trp Gln Lys Leu Ala Lys Asp Ile Gln Val Ala Ser Asn Glu Ile
225                 230                 235                 240
```

Leu Arg Asp Pro Cys Phe His Pro Gly Tyr Lys Lys Val Val Asn Val
            245                 250                 255

Ser Asp Leu Tyr Lys Thr Pro Cys Thr Lys Arg Phe Glu Met Thr Leu
        260                 265                 270

Pro Phe Gln Gln Phe Glu Ile Gln Gly Ile Gly Asn Tyr Gln Gln Cys
    275                 280                 285

His Gln Ser Ile Leu Glu Leu Phe Asn Thr Ser Phe Asn Gly Ile Phe
290                 295                 300

Leu Pro Pro Leu Gln Gly Asp Phe Gly Ala Phe Ser Ala Phe Tyr Phe
305                 310                 315                 320

Val Met Lys Phe Leu Asn Leu Thr Ser Glu Lys Val Ser Gln Glu Lys
                325                 330                 335

Val Thr Glu Met Met Lys Lys Phe Cys Ala Gln Pro Trp Glu Glu Ile
            340                 345                 350

Lys Thr Ser Tyr Ala Gly Val Lys Glu Lys Tyr Leu Ser Glu Tyr Cys
        355                 360                 365

Phe Ser Gly Thr Tyr Ile Leu Ser Leu Leu Leu Gln Gly Tyr His Phe
    370                 375                 380

Thr Ala Asp Ser Trp Glu His Ile His Phe Ile Gly Lys Ile Gln Gly
385                 390                 395                 400

Ser Asp Ala Gly Trp Thr Leu Gly Tyr Met Leu Asn Leu Thr Asn Met
                405                 410                 415

Ile Pro Ala Glu Gln Pro Leu Ser Thr Pro Leu Ser His Ser Thr
            420                 425                 430

<210> SEQ ID NO 128
<211> LENGTH: 1293
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 128
acacagaaca aagccctgcc cgagaacgtg aagtacggca tcgtgctgga tgccggcagc        60
agccacacca gcctgtacat ctacaagtgg cctgccgaga agaaaacga taccggtgtc       120 gtgcaccagg tggaagagtg cagagtgaag ggccctggca tcagcaagtt cgtgcagaaa       180
gtgaacgaga tcggcatcta cctgaccgac tgcatggaac gggccagaga agtgatcccc       240
agaagccagc accaggaaac ccccgtgtac ctgggagcca cagccggcat gagactgctg       300
cggatggaaa gcgaggaact ggccgacaga gtgctggacg tggtggaaag aagcctgagc       360
aactacccat tcgattttca agggccagaa atcatcaccg ccaggaaga gggcgcttac        420 ggctggatca ccatcaacta cctgctgggc aagttcagcc agaaaacccg gtggttcagc       480
atcgtgccct acgagacaaa caatcaggaa accttcggag ccctggacct gggcggagcc       540
tctacccaag tgaccttcgt gccccagaat cagaccatcg agagcccga caacgccctg        600 cagttccggc tgtacggcaa ggactacaat gtgtacaccc acagctttct gtgctacgga       660
aaggaccagg ccctgtggca gaagctggcc aaggacatcc aggtggccag caacgagatc       720
ctgcgggacc cttgcttcca ccccggctac aagaaagtcg tgaacgtgtc cgacctgtac       780
aagaccccct gcaccaagag attcgagatg accctgccct tccagcagtt cgagatccag       840
ggcatcggca actaccagca gtgccaccag agcatcctgg aactgttcaa caccagcttc       900

```
aacggcatct tcctgccacc tctgcagggg gacttcggcg ctttcagcgc cttctacttc    960
gtgatgaagt tcctgaacct gaccagcgag aaggtgtccc aggaaaaagt gacagagatg   1020
atgaagaagt tctgcgccca gccctgggag gaaatcaaga cctcctacgc tggcgtgaaa   1080
gagaagtacc tgagcgagta ctgcttcagc ggtacctaca tcctgagcct gctgctgcag   1140
ggctaccact tcaccgccga tagctgggag cacatccact tcatcggcaa gattcagggc   1200
agcgacgccg ctggacact gggctacatg ctgaatctga ccaacatgat ccccgccgag   1260
cagcccctga gcacacctct gtctcacagc acc                                1293
```

<210> SEQ ID NO 129
<211> LENGTH: 439
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 129

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Thr Arg Trp Phe Ser
145                 150                 155                 160

Ile Val Pro Tyr Glu Thr Asn Asn Gln Glu Thr Phe Gly Ala Leu Asp
                165                 170                 175

Leu Gly Gly Ala Ser Thr Gln Val Thr Phe Val Pro Gln Asn Gln Thr
            180                 185                 190

Ile Glu Ser Pro Asp Asn Ala Leu Gln Phe Arg Leu Tyr Gly Lys Asp
        195                 200                 205

Tyr Asn Val Tyr Thr His Ser Phe Leu Cys Tyr Gly Lys Asp Gln Ala
    210                 215                 220

Leu Trp Gln Lys Leu Ala Lys Asp Ile Gln Val Ala Ser Asn Glu Ile
225                 230                 235                 240

Leu Arg Asp Pro Cys Phe His Pro Gly Tyr Lys Lys Val Val Asn Val
                245                 250                 255

Ser Asp Leu Tyr Lys Thr Pro Cys Thr Lys Arg Phe Glu Met Thr Leu
            260                 265                 270

Pro Phe Gln Gln Phe Glu Ile Gln Gly Ile Gly Asn Tyr Gln Gln Cys
        275                 280                 285
```

His Gln Ser Ile Leu Glu Leu Phe Asn Thr Ser Tyr Ala Pro Tyr Ser
    290                 295                 300

Gln Ala Ala Phe Asn Gly Ile Phe Leu Pro Pro Leu Gln Gly Asp Phe
305                 310                 315                 320

Gly Ala Phe Ser Ala Phe Tyr Phe Val Met Lys Phe Leu Asn Leu Thr
                325                 330                 335

Ser Glu Lys Val Ser Gln Glu Lys Val Thr Glu Met Met Lys Lys Phe
                340                 345                 350

Cys Ala Gln Pro Trp Glu Glu Ile Lys Thr Ser Tyr Ala Gly Val Lys
                355                 360                 365

Glu Lys Tyr Leu Ser Glu Tyr Cys Phe Ser Gly Thr Tyr Ile Leu Ser
            370                 375                 380

Leu Leu Leu Gln Gly Tyr His Phe Thr Ala Asp Ser Trp Glu His Ile
385                 390                 395                 400

His Phe Ile Gly Lys Ile Gln Gly Ser Asp Ala Gly Trp Thr Leu Gly
                405                 410                 415

Tyr Met Leu Asn Leu Thr Asn Met Ile Pro Ala Glu Gln Pro Leu Ser
                420                 425                 430

Thr Pro Leu Ser His Ser Thr
                435

<210> SEQ ID NO 130
<211> LENGTH: 1317
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 130
acacagaaca aagccctgcc cgagaacgtg aagtacggca tcgtgctgga tgccggcagc    60
agccacacca gcctgtacat ctacaagtgg cctgccgaga agaaaacga taccggtgtc   120 gtgcaccagg tggaagagtg cagagtgaag ggccctggca tcagcaagtt cgtgcagaaa   180
gtgaacgaga tcggcatcta cctgaccgac tgcatggaac gggccagaga agtgatcccc   240
agaagccagc accaggaaac ccccgtgtac ctgggagcca cagccggcat gagactgctg   300
cggatggaaa gcgaggaact ggccgacaga gtgctgacg tggtggaaag aagcctgagc   360
aactacccat tcgattttca aggggccaga atcatcaccg ccaggaagag gggcgcttac   420
ggctggatca ccatcaacta cctgctgggc aagttcagcc agaaaacccg gtggttcagc   480
atcgtgccct acgagacaaa caatcaggaa accttcggag ccctggacct gggcggagcc   540
tctacccaag tgaccttcgt gccccagaat cagaccatcg agagcccga caacgccctg   600 cagttccggc tgtacggcaa ggactacaat gtgtacaccc cagctttct gtgctacgga   660 aaggaccagg ccctgtggca gaagctggcc aaggacatcc aggtggccag caacgagatc   720
ctgcgggacc cttgcttcca ccccggctac aagaaagtcg tgaacgtgtc cgacctgtac   780
aagaccccct gcaccaagag attcgagatg accctgccct ccagcagtt cgagatccag   840 ggcatcggca actaccagca gtgccaccag agcatcctgg aactgttcaa caccagctac   900
gcccctacac gccaggccgc cttcaacggc atcttcctgc acctctgca ggggacttc   960 ggcgctttca gcgccttcta cttcgtgatg aagttcctga acctgaccag cgagaaggtg  1020
tcccaggaaa aagtgacaga gatgatgaag aagttctgcg cccagccctg ggaggaaatc  1080

```
aagacctcct acgctggcgt gaaagagaag tacctgagcg agtactgctt cagcggtacc    1140
tacatcctga gcctgctgct gcagggctac cacttcaccg ccgatagctg ggagcacatc    1200
cacttcatcg gcaagattca gggcagcgac gccggctgga cactgggcta catgctgaat    1260
ctgaccaaca tgatccccgc cgagcagccc ctgagcacac tctgtctca cagcacc        1317
```

```
<210> SEQ ID NO 131
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Ala Pro Thr Ser Ser Ser Thr Lys Lys Thr Gln Leu Thr Ser Ser Gly
1               5                   10                  15
```

```
<210> SEQ ID NO 132
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
gcccccacca gcagcagcac caagaagacc cagctgacca gcagcggc                48
```

```
<210> SEQ ID NO 133
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Ala Pro Thr Ser Ser Ser Thr Lys Lys Thr Gln Leu Thr Ser Ser
1               5                   10                  15
```

```
<210> SEQ ID NO 134
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
gcccctacca gcagcagcac caagaaaacc cagctgacca gcagc                   45
```

```
<210> SEQ ID NO 135
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Ala Pro Thr Ser Ser Ser
```

<210> SEQ ID NO 136
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 136
gcccctacca gcagcagc                                                 18

<210> SEQ ID NO 137
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 137

Ala Pro Thr
1

<210> SEQ ID NO 138
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 138 gcccctacc                                                            9

<210> SEQ ID NO 139
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 139

Ala Pro Thr Ser Ser Ser Thr Lys Lys
1               5

<210> SEQ ID NO 140
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 140
gcccctacca gcagcagcac caagaaa                                       27

<210> SEQ ID NO 141
<211> LENGTH: 12
<212> TYPE: PRT
<213> ORGANISM: Artificial Sequence -continued

```
<220> FEATURE:
<221> NAME/KEY: source
<223> OTHER INFORMATION: /note="Description of Artificial Sequence:
      Synthetic peptide"

<400> SEQUENCE: 141

Ala Pro Thr Ser Ser Thr Lys Lys Thr Gln Leu
1               5                   10

<210> SEQ ID NO 142
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
gcccctacca gcagcagcac caagaaaacc cagctg                                 36

<210> SEQ ID NO 143
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Ser Ser Ser Thr Lys Lys Thr Gln Leu
1               5

<210> SEQ ID NO 144
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
agcagcagca ccaagaaaac ccagctg                                           27

<210> SEQ ID NO 145
<211> LENGTH: 426
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 145

Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80
```

Arg Ser Gln His Gln Glu Thr Pro Val Tyr Leu Gly Ala Thr Ala Gly
                85                  90                  95

Met Arg Leu Leu Arg Met Glu Ser Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Asp Glu Gly Ala Tyr Gly Trp Ile Thr
130                 135                 140

Ile Asn Tyr Leu Leu Gly Lys Phe Ser Gln Lys Asn Gln Glu Thr Phe
145                 150                 155                 160

Gly Ala Leu Asp Leu Gly Gly Ala Ser Thr Gln Val Thr Phe Val Pro
                165                 170                 175

Gln Asn Gln Thr Ile Glu Ser Pro Asp Asn Ala Leu Gln Phe Arg Leu
            180                 185                 190

Tyr Gly Lys Asp Tyr Asn Val Tyr Thr His Ser Phe Leu Cys Tyr Gly
        195                 200                 205

Arg Asp Gln Ala Leu Trp Gln Lys Leu Ala Lys Asp Ile Gln Val Ala
210                 215                 220

Ser Asn Glu Ile Leu Arg Asp Pro Cys Phe His Pro Gly Tyr Lys Lys
225                 230                 235                 240

Val Val Asn Val Ser Asp Leu Tyr Lys Thr Pro Cys Thr Lys Arg Phe
                245                 250                 255

Glu Met Thr Leu Pro Phe Gln Gln Phe Glu Ile Gln Gly Ile Gly Asn
            260                 265                 270

Tyr Gln Gln Cys His Gln Ser Ile Leu Glu Leu Phe Asn Thr Ser Tyr
        275                 280                 285

Cys Pro Tyr Ser Gln Cys Ala Phe Asn Gly Ile Phe Leu Pro Pro Leu
290                 295                 300

Gln Gly Asp Phe Gly Ala Phe Ser Asn Phe Tyr Tyr Val Met Lys Phe
305                 310                 315                 320

Leu Asn Leu Thr Ser Glu Lys Val Ser Gln Glu Lys Val Thr Glu Met
                325                 330                 335

Met Lys Lys Phe Cys Ala Gln Pro Trp Glu Glu Ile Lys Thr Ser Tyr
            340                 345                 350

Ala Gly Gln Glu Arg Trp Leu Arg Asp Tyr Cys Phe Ser Gly Thr Tyr
        355                 360                 365

Ile Leu Ser Leu Leu Leu Gln Gly Tyr His Phe Thr Ala Asp Ser Trp
370                 375                 380

Glu His Ile His Phe Ile Gly Lys Ile Gln Gly Ser Asp Ala Gly Trp
385                 390                 395                 400

Thr Leu Gly Tyr Met Leu Asn Leu Thr Asn Met Ile Pro Ala Glu Gln
                405                 410                 415

Pro Leu Ser Thr Pro Leu Ser His Ser Thr
            420                 425

<210> SEQ ID NO 146
<211> LENGTH: 1278
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 146

```
acccagaaca aggccctgcc cgagaacgtg aagtacggca tcgtgctgga tgccggcagc      60
agccacacca gcctgtacat ctacaagtgg cctgccgaga agaaaacga caccggcgtg     120
gtgcatcagg tggaagagtg cagagtgaag ggccctggca tcagcaagtt cgtgcagaaa     180
gtgaacgaga tcggcatcta cctgaccgac tgcatggaac gggccagaga agtgatcccc     240
agaagccagc accaggaaac ccccgtgtat ctgggagcca ccgccggcat gagactgctg     300
agaatggaaa gcgaggaact ggccgaccgg gtgctggacg tggtggaaag aagcctgagc     360
aactacccat tcgattttca aggcgccaga atcatcaccg gccaggacga gggcgcctac     420
ggctggatca ccatcaacta cctgctgggc aagttcagcc agaagaatca ggaaaccttc     480
ggcgccctgg acctgggcgg agcttctacc caagtgacct tcgtgcccca gaatcagacc     540
atcgagagcc ccgacaacgc cctgcagttc cggctgtacg caaggacta caatgtgtac     600
acccacagct ttctgtgcta cggccgggac caggctctgt ggcagaagct ggccaaggac     660
atccaggtgg ccagcaacga gatcctgcgg gacccttgct ccacccggg ctacaagaaa     720
gtcgtgaacg tgtccgacct gtacaagacc ccctgcacca gagattcga gatgaccctg     780
cccttccagc agttcgagat ccagggcatc ggcaactacc agcagtgcca ccagagcatc     840
ctggaactgt tcaacaccag ctactgcccc tacagccagt cgccttcaa cggcatcttc     900
ctgccacctc tgcaggggga tttcggcgcc ttcagcaact tctactacgt gatgaagttc     960
ctgaacctga ccagcgagaa ggtgtcccag gaaaaagtga cagagatgat gaagaagttc    1020
tgcgcccagc cctgggagga aatcaagacc tcttacgccg acaggaacg gtggctgcgg    1080
gactactgtt tcagcggcac ctacatcctg tccctgctgc tgcagggcta ccacttcacc    1140
gccgatagct gggagcacat ccacttcatc ggcaagattc agggcagcga cgccggctgg    1200
acactgggct acatgctgaa tctgaccaac atgatccccg ccgagcagcc cctgagcaca    1260
cctctgtctc acagcacc                                                  1278
```

<210> SEQ ID NO 147
<211> LENGTH: 537
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 147

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Gly Gly Gly Ser Thr Gln
            100                 105                 110

Asn Lys Ala Leu Pro Glu Asn Val Lys Tyr Gly Ile Val Leu Asp Ala
        115                 120                 125
```

```
Gly Ser Ser His Thr Ser Leu Tyr Ile Tyr Lys Trp Pro Ala Glu Lys
    130                 135                 140

Glu Asn Asp Thr Gly Val Val His Gln Val Glu Glu Cys Arg Val Lys
145                 150                 155                 160

Gly Pro Gly Ile Ser Lys Phe Val Gln Lys Val Asn Glu Ile Gly Ile
                165                 170                 175

Tyr Leu Thr Asp Cys Met Glu Arg Ala Arg Glu Val Ile Pro Arg Ser
                180                 185                 190

Gln His Gln Glu Thr Pro Val Tyr Leu Gly Ala Thr Ala Gly Met Arg
            195                 200                 205

Leu Leu Arg Met Glu Ser Glu Leu Ala Asp Arg Val Leu Asp Val
210                 215                 220

Val Glu Arg Ser Leu Ser Asn Tyr Pro Phe Asp Phe Gln Gly Ala Arg
225                 230                 235                 240

Ile Ile Thr Gly Gln Glu Gly Ala Tyr Gly Trp Ile Thr Ile Asn
                245                 250                 255

Tyr Leu Gly Lys Phe Ser Gln Lys Asn Gln Glu Thr Phe Gly Ala
                260                 265                 270

Leu Asp Leu Gly Gly Ala Ser Thr Gln Val Thr Phe Val Pro Gln Asn
            275                 280                 285

Gln Thr Ile Glu Ser Pro Asp Asn Ala Leu Gln Phe Arg Leu Tyr Gly
            290                 295                 300

Lys Asp Tyr Asn Val Tyr Thr His Ser Phe Leu Cys Tyr Gly Lys Asp
305                 310                 315                 320

Gln Ala Leu Trp Gln Lys Leu Ala Lys Asp Ile Gln Val Ala Ser Asn
                325                 330                 335

Glu Ile Leu Arg Asp Pro Cys Phe His Pro Gly Tyr Lys Lys Val Val
            340                 345                 350

Asn Val Ser Asp Leu Tyr Lys Thr Pro Cys Thr Lys Arg Phe Glu Met
            355                 360                 365

Thr Leu Pro Phe Gln Gln Phe Glu Ile Gln Gly Ile Gly Asn Tyr Gln
370                 375                 380

Gln Cys His Gln Ser Ile Leu Glu Leu Phe Asn Thr Ser Tyr Cys Pro
385                 390                 395                 400

Tyr Ser Gln Cys Ala Phe Asn Gly Ile Phe Leu Pro Pro Leu Gln Gly
                405                 410                 415

Asp Phe Gly Ala Phe Ser Ala Phe Tyr Phe Val Met Lys Phe Leu Asn
                420                 425                 430

Leu Thr Ser Glu Lys Val Ser Gln Glu Lys Val Thr Glu Met Met Lys
            435                 440                 445

Lys Phe Cys Ala Gln Pro Trp Glu Glu Ile Lys Thr Ser Tyr Ala Gly
450                 455                 460

Val Lys Glu Lys Tyr Leu Ser Glu Tyr Cys Phe Ser Gly Thr Tyr Ile
465                 470                 475                 480

Leu Ser Leu Leu Leu Gln Gly Tyr His Phe Thr Ala Asp Ser Trp Glu
                485                 490                 495

His Ile His Phe Ile Gly Lys Ile Gln Gly Ser Asp Ala Gly Trp Thr
                500                 505                 510

Leu Gly Tyr Met Leu Asn Leu Thr Asn Met Ile Pro Ala Glu Gln Pro
            515                 520                 525

Leu Ser Thr Pro Leu Ser His Ser Thr
530                 535
```

<210> SEQ ID NO 148
<211> LENGTH: 1611
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 148

```
acggtggccg ctcccagcgt gttcatcttc ccccccagcg acgagcagct gaagagcggc      60
accgccagcg tggtgtgcct gctgaacaac ttctaccccc gggaggccaa ggtgcagtgg     120
aaggtggaca acgccctgca gagcggcaac agccaggaaa gcgtcaccga gcaggacagc     180
aaggactcca cctacagcct gagcagcacc ctgaccctga gcaaggccga ctacgagaag     240
cacaaggtgt acgcctgcga ggtgacccac cagggcctgt ccagcccgt gaccaagagc      300
ttcaaccggg gcgagggagg cggaggatct acccagaaca aggccctgcc cgagaacgtg     360
aagtacggca tcgtgctgga tgccggcagc agccacacca gcctgtacat ctacaagtgg     420
cctgccgaga agaaaacga caccggcgtg gtgcatcagg tggaagagtg cagagtgaag     480
ggccctggca tcagcaagtt cgtgcagaaa gtgaacgaga tcggcatcta cctgaccgac     540
tgcatggaac gggccaggga agtgatcccc agaagccagc accaggaaac ccccgtgtat     600
ctgggagcca ccgccggcat gagactgctg agaatgaaa gcgaggaact ggccgaccgg     660
gtgctggacg tggtggaaag aagcctgagc aactacccat tcgattttca aggcgccaga     720
atcatcaccg gccaggaaga aggcgcctac ggctggatca ccatcaacta cctgctgggc     780
aagttcagcc agaagaatca ggaaaccttc ggcgccctgg acctgggcgg agcttctacc     840
caagtgacct tcgtgcccca gaatcagacc atcgagagcc ccgacaacgc cctgcagttc     900
cggctgtacg gcaaggacta caatgtgtac acccacagct ttctgtgcta cggaaaggac     960
caggctctgt ggcagaagct ggccaaggac atccaggtgg ccagcaacga gatcctgcgg    1020
gaccccttgct tccaccccgg ctacaagaaa gtcgtgaacg tgtccgacct gtacaagacc    1080
ccctgcacca agagattcga gatgaccctg cccttccagc agttcgagat ccagggcatc    1140
ggcaattacc agcagtgcca ccagagcatc ctggaactgt tcaacaccag ctactgcccc    1200
tacagccagt gcgccttcaa cggcatcttc ctgccacctc tgcaggggga tttcggcgcc    1260
ttcagcgcct tctacttcgt gatgaagttc ctgaacctga ccagcgagaa ggtgtcccag    1320
gaaaaagtga cagagatgat gaagaagttc tgcgcccagc cctgggagga aatcaagacc    1380
tcctacgctg gcgtgaaaga aagtacctg agcgagtact gcttcagcgg cacctacatc     1440
ctgagcctgc tgctgcaggg ctaccacttc accgccgata gctgggagca catccacttc    1500
atcggcaaga ttcagggcag cgacgccggc tggacactgg gctacatgct gaatctgacc    1560
aacatgatcc ccgccgagca gcccctgagc acacctctga gccacagcac c             1611
```

<210> SEQ ID NO 149
<211> LENGTH: 508
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 149

Met Gln Ile Phe Val Lys Thr Leu Thr Gly Lys Thr Ile Thr Leu Glu

-continued

```
1               5                   10                  15
Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
            50                  55                  60

Ser Thr Leu His Leu Val Leu Arg Leu Arg Gly Gly Gly Gly Gly Gly
65                  70                  75                  80

Ser Thr Gln Asn Lys Ala Leu Pro Glu Asn Val Lys Tyr Gly Ile Val
            85                  90                  95

Leu Asp Ala Gly Ser Ser His Thr Ser Leu Tyr Ile Tyr Lys Trp Pro
            100                 105                 110

Ala Glu Lys Glu Asn Asp Thr Gly Val Val His Gln Val Glu Glu Cys
            115                 120                 125

Arg Val Lys Gly Pro Gly Ile Ser Lys Phe Val Gln Lys Val Asn Glu
            130                 135                 140

Ile Gly Ile Tyr Leu Thr Asp Cys Met Glu Arg Ala Arg Glu Val Ile
145                 150                 155                 160

Pro Arg Ser Gln His Gln Glu Thr Pro Val Tyr Leu Gly Ala Thr Ala
            165                 170                 175

Gly Met Arg Leu Leu Arg Met Glu Ser Glu Glu Leu Ala Asp Arg Val
            180                 185                 190

Leu Asp Val Val Glu Arg Ser Leu Ser Asn Tyr Pro Phe Asp Phe Gln
            195                 200                 205

Gly Ala Arg Ile Ile Thr Gly Gln Glu Glu Gly Ala Tyr Gly Trp Ile
            210                 215                 220

Thr Ile Asn Tyr Leu Leu Gly Lys Phe Ser Gln Lys Asn Gln Glu Thr
225                 230                 235                 240

Phe Gly Ala Leu Asp Leu Gly Gly Ala Ser Thr Gln Val Thr Phe Val
            245                 250                 255

Pro Gln Asn Gln Thr Ile Glu Ser Pro Asp Asn Ala Leu Gln Phe Arg
            260                 265                 270

Leu Tyr Gly Lys Asp Tyr Asn Val Tyr Thr His Ser Phe Leu Cys Tyr
            275                 280                 285

Gly Lys Asp Gln Ala Leu Trp Gln Lys Leu Ala Lys Asp Ile Gln Val
            290                 295                 300

Ala Ser Asn Glu Ile Leu Arg Asp Pro Cys Phe His Pro Gly Tyr Lys
305                 310                 315                 320

Lys Val Val Asn Val Ser Asp Leu Tyr Lys Thr Pro Cys Thr Lys Arg
            325                 330                 335

Phe Glu Met Thr Leu Pro Phe Gln Gln Phe Glu Ile Gln Gly Ile Gly
            340                 345                 350

Asn Tyr Gln Gln Cys His Gln Ser Ile Leu Glu Leu Phe Asn Thr Ser
            355                 360                 365

Tyr Cys Pro Tyr Ser Gln Cys Ala Phe Asn Gly Ile Phe Leu Pro Pro
            370                 375                 380

Leu Gln Gly Asp Phe Gly Ala Phe Ser Ala Phe Tyr Phe Val Met Lys
385                 390                 395                 400

Phe Leu Asn Leu Thr Ser Glu Lys Val Ser Gln Glu Lys Val Thr Glu
            405                 410                 415

Met Met Lys Lys Phe Cys Ala Gln Pro Trp Glu Glu Ile Lys Thr Ser
            420                 425                 430
```

Tyr Ala Gly Val Lys Glu Lys Tyr Leu Ser Glu Tyr Cys Phe Ser Gly
            435                 440                 445

Thr Tyr Ile Leu Ser Leu Leu Leu Gln Gly Tyr His Phe Thr Ala Asp
        450                 455                 460

Ser Trp Glu His Ile His Phe Ile Gly Lys Ile Gln Gly Ser Asp Ala
465                 470                 475                 480

Gly Trp Thr Leu Gly Tyr Met Leu Asn Leu Thr Asn Met Ile Pro Ala
                485                 490                 495

Glu Gln Pro Leu Ser Thr Pro Leu Ser His Ser Thr
            500                 505

<210> SEQ ID NO 150
<211> LENGTH: 1524
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 150

| | | |
|---|---|---|
| atgcaaatct tcgtgaagac cctgactggt aagaccatca ccctcgaggt ggagcccagt | 60 |
| gacaccatcg agaatgtcaa ggcaaagatc caagataagg aaggcatccc tcctgatcag | 120 |
| cagaggttga tctttgctgg gaaacagctg gaagatggac gcaccctgtc tgactacaac | 180 |
| atccagaaag agtccactct gcacttggtc ctgcgcttga ggggggggtgg aggcggagga | 240 |
| tctacccaga caaggcccct gcccgagaac gtgaagtacg catcgtgct ggatgccggc | 300 |
| agcagccaca ccagcctgta catctacaag tggcctgccg agaaagaaaa cgacaccggc | 360 |
| gtggtgcatc aggtggaaga gtgcagagtg aagggccctg gcatcagcaa gttcgtgcag | 420 |
| aaagtgaacg agatcggcat ctacctgacc gactgcatgg aacgggccag ggaagtgatc | 480 |
| cccagaagcc agcaccagga aaccccgtg tatctgggag ccaccgccgg catgagactg | 540 |
| ctgagaatgg aaagcgagga actggccgac cgggtgctgg acgtggtgga agaagcctg | 600 |
| agcaactacc cattcgattt caaggcgcc agaatcatca ccggccagga agaaggcgcc | 660 |
| tacggctgga tcaccatcaa ctacctgctg gcaagttca gccagaagaa tcaggaaacc | 720 |
| ttcggcgccc tggacctggg cggagcttct acccaagtga ccttcgtgcc ccagaatcag | 780 |
| accatcgaga gccccgacaa cgccctgcag ttccggctgt acggcaagga ctacaatgtg | 840 |
| tacacccaca gctttctgtg ctacggaaag gaccaggctc tgtggcagaa gctggccaag | 900 |
| gacatccagg tggccagcaa cgagatcctg cgggaccctt gcttccaccc cggctacaag | 960 |
| aaagtcgtga acgtgtccga cctgtacaag accccctgca ccaagagatt cgagatgacc | 1020 |
| ctgcccttcc agcagttcga gatccagggc atcggcaatt accagcagtg ccaccagagc | 1080 |
| atcctggaac tgttcaacac cagctactgc ccctacagcc agtgcgcctt caacggcatc | 1140 |
| ttcctgccac ctctgcaggg ggatttcggc gccttcagcg ccttctactt cgtgatgaag | 1200 |
| ttcctgaacc tgaccagcga agggtgtcc caggaaaaag tgacagagat gatgaagaag | 1260 |
| ttctgcgccc agccctggga ggaaatcaag acctcctacg ctggcgtgaa agagaagtac | 1320 |
| ctgagcgagt actgcttcag cggcacctac atcctgagcc tgctgctgca gggctaccac | 1380 |
| ttcaccgccg atagctggga gcacatccac ttcatcggca agattcaggg cagcgacgcc | 1440 |
| ggctggacac tgggctacat gctgaatctg accaacatga tccccgccga gcagcccctg | 1500 |
| agcacacctc tgagccacag cacc | 1524 |

<210> SEQ ID NO 151
<211> LENGTH: 618
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 151

```
Asp Ala His Lys Ser Glu Val Ala His Arg Phe Lys Asp Leu Gly Glu
 1               5                  10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Gly Gly Gly Ser Thr
            180                 185                 190

Gln Asn Lys Ala Leu Pro Glu Asn Val Lys Tyr Gly Ile Val Leu Asp
        195                 200                 205

Ala Gly Ser Ser His Thr Ser Leu Tyr Ile Tyr Lys Trp Pro Ala Glu
    210                 215                 220

Lys Glu Asn Asp Thr Gly Val Val His Gln Val Glu Glu Cys Arg Val
225                 230                 235                 240

Lys Gly Pro Gly Ile Ser Lys Phe Val Gln Lys Val Asn Glu Ile Gly
                245                 250                 255

Ile Tyr Leu Thr Asp Cys Met Glu Arg Ala Arg Glu Val Ile Pro Arg
            260                 265                 270

Ser Gln His Gln Glu Thr Pro Val Tyr Leu Gly Ala Thr Ala Gly Met
        275                 280                 285

Arg Leu Leu Arg Met Glu Ser Glu Leu Ala Asp Arg Val Leu Asp
    290                 295                 300

Val Val Glu Arg Ser Leu Ser Asn Tyr Pro Phe Asp Phe Gln Gly Ala
305                 310                 315                 320

Arg Ile Ile Thr Gly Gln Glu Gly Ala Tyr Gly Trp Ile Thr Ile
                325                 330                 335

Asn Tyr Leu Leu Gly Lys Phe Ser Gln Lys Asn Gln Glu Thr Phe Gly
            340                 345                 350
```

Ala Leu Asp Leu Gly Gly Ala Ser Thr Gln Val Thr Phe Val Pro Gln
355                 360                 365

Asn Gln Thr Ile Glu Ser Pro Asp Asn Ala Leu Gln Phe Arg Leu Tyr
        370                 375                 380

Gly Lys Asp Tyr Asn Val Tyr Thr His Ser Phe Leu Cys Tyr Gly Lys
385                 390                 395                 400

Asp Gln Ala Leu Trp Gln Lys Leu Ala Lys Asp Ile Gln Val Ala Ser
                405                 410                 415

Asn Glu Ile Leu Arg Asp Pro Cys Phe His Pro Gly Tyr Lys Lys Val
            420                 425                 430

Val Asn Val Ser Asp Leu Tyr Lys Thr Pro Cys Thr Lys Arg Phe Glu
        435                 440                 445

Met Thr Leu Pro Phe Gln Gln Phe Glu Ile Gln Gly Ile Gly Asn Tyr
450                 455                 460

Gln Gln Cys His Gln Ser Ile Leu Glu Leu Phe Asn Thr Ser Tyr Cys
465                 470                 475                 480

Pro Tyr Ser Gln Cys Ala Phe Asn Gly Ile Phe Leu Pro Pro Leu Gln
                485                 490                 495

Gly Asp Phe Gly Ala Phe Ser Ala Phe Tyr Phe Val Met Lys Phe Leu
            500                 505                 510

Asn Leu Thr Ser Glu Lys Val Ser Gln Glu Lys Val Thr Glu Met Met
        515                 520                 525

Lys Lys Phe Cys Ala Gln Pro Trp Glu Glu Ile Lys Thr Ser Tyr Ala
530                 535                 540

Gly Val Lys Glu Lys Tyr Leu Ser Glu Tyr Cys Phe Ser Gly Thr Tyr
545                 550                 555                 560

Ile Leu Ser Leu Leu Leu Gln Gly Tyr His Phe Thr Ala Asp Ser Trp
                565                 570                 575

Glu His Ile His Phe Ile Gly Lys Ile Gln Gly Ser Asp Ala Gly Trp
            580                 585                 590

Thr Leu Gly Tyr Met Leu Asn Leu Thr Asn Met Ile Pro Ala Glu Gln
        595                 600                 605

Pro Leu Ser Thr Pro Leu Ser His Ser Thr
610                 615

<210> SEQ ID NO 152
<211> LENGTH: 1854
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 152
gacgcccaca agagcgaggt ggcccaccgg ttcaaggacc tgggcgagga aaacttcaag      60
gccctggtgc tgatcgcctt cgcccagtac ctgcagcaga gccccttcga agatcacgta     120
aagttagtca acgaggttac ggaattcgca aagacatgcg ttgctgacga atccgctgag     180
aattgtgaca gagtttgca cactttattc ggagataagt tgtgtactgt agctactttg     240
agagagactt acggtgaaat ggctgactgc tgtgcaaaac aggaaccaga acgtaacgaa     300
tgtttccttc agcataagga tgataaccct aaccttccaa ggcttgttag gccagaagtc     360
gacgtgatgt gcaccgcctt ccatgataat gaagagactt tcttaaaaaa gtacctatac     420
gagattgcaa ggcgtcatcc atatttttac gccccagagc tgttgttttt cgcaaagaga     480

-continued

```
tacaaagctg catttactga gtgttgccaa gctgccgaca aggccgcttg tttgctacca    540
aagttggacg aattgagagg aggcggagga tctacccaga acaaggccct gcccgagaac    600
gtgaagtacg gcatcgtgct ggatgccggc agcagccaca ccagcctgta catctacaag    660
tggcctgccg agaaagaaaa cgacaccggc gtggtgcatc aggtggaaga gtgcagagtg    720
aagggccctg gcatcagcaa gttcgtgcag aaagtgaacg agatcggcat ctacctgacc    780
gactgcatgg aacgggccag ggaagtgatc cccagaagcc agcaccagga acccccgtg    840
tatctgggag ccaccgccgg catgagactg ctgagaatgg aaagcgagga actggccgac    900
cgggtgctgg acgtggtgga agaagcctg agcaactacc cattcgattt caaggcgcc    960
agaatcatca ccggccagga agaaggcgcc tacggctgga tcaccatcaa ctacctgctg   1020
ggcaagttca gccagaagaa tcaggaaacc ttcggcgccc tggacctggg cggagcttct   1080
acccaagtga ccttcgtgcc ccagaatcag accatcgaga gccccgacaa cgccctgcag   1140
ttccggctgt acggcaagga ctacaatgtg tacacccaca gctttctgtg ctacggaaag   1200
gaccaggctc tgtggcagaa gctggccaag gacatccagg tggccagcaa cgagatcctg   1260
cgggacccct gcttccaccc cggctacaag aaagtcgtga cgtgtccga cctgtacaag   1320
accccctgca ccaagagatt cgagatgacc ctgcccttcc agcagttcga gatccagggc   1380
atcggcaatt accagcagtg ccaccagagc atcctggaac tgttcaacac cagctactgc   1440
ccctacagcc agtgcgcctt caacggcatc ttcctgccac tctgcagggg ggatttcggc   1500
gccttcagcg ccttctactt cgtgatgaag ttcctgaacc tgaccagcga aggtgtcc   1560
caggaaaaag tgacagagat gatgaagaag ttctgcgccc agccctggga ggaaatcaag   1620
acctcctacg ctggcgtgaa agagaagtac ctgagcgagt actgcttcag cggcacctac   1680
atcctgagcc tgctgctgca gggctaccac ttcaccgccg atagctggga gcacatccac   1740
ttcatcggca agattcaggg cagcgacgcc ggctggacac tgggctacat gctgaatctg   1800
accaacatga tccccgccga gcagcccctg agcacacctc tgagccacag cacc         1854
```

<210> SEQ ID NO 153
<211> LENGTH: 625
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 153

```
Asp Glu Gly Lys Ala Ser Ser Ala Lys Gln Arg Leu Lys Cys Ala Ser
1               5                   10                  15

Leu Gln Lys Phe Gly Glu Arg Ala Phe Lys Ala Trp Ala Val Ala Arg
            20                  25                  30

Leu Ser Gln Arg Phe Pro Lys Ala Glu Phe Ala Glu Val Ser Lys Leu
        35                  40                  45

Val Thr Asp Leu Thr Lys Val His Thr Glu Cys Cys His Gly Asp Leu
    50                  55                  60

Leu Glu Cys Ala Asp Asp Arg Ala Asp Leu Ala Lys Tyr Ile Cys Glu
65                  70                  75                  80

Asn Gln Asp Ser Ile Ser Ser Lys Leu Lys Glu Cys Cys Glu Lys Pro
                85                  90                  95

Leu Leu Glu Lys Ser His Cys Ile Ala Glu Val Glu Asn Asp Glu Met
            100                 105                 110
```

-continued

```
Pro Ala Asp Leu Pro Ser Leu Ala Ala Asp Phe Val Glu Ser Lys Asp
            115                 120                 125

Val Cys Lys Asn Tyr Ala Glu Ala Lys Asp Val Phe Leu Gly Met Phe
    130                 135                 140

Leu Tyr Glu Tyr Ala Arg Arg His Pro Asp Tyr Ser Val Val Leu Leu
145                 150                 155                 160

Leu Arg Leu Ala Lys Thr Tyr Glu Thr Thr Leu Glu Lys Cys Cys Ala
                165                 170                 175

Ala Ala Asp Pro His Glu Cys Tyr Ala Lys Val Phe Asp Glu Phe Lys
            180                 185                 190

Pro Gly Gly Gly Ser Thr Gln Asn Lys Ala Leu Pro Glu Asn Val
        195                 200                 205

Lys Tyr Gly Ile Val Leu Asp Ala Gly Ser Ser His Thr Ser Leu Tyr
    210                 215                 220

Ile Tyr Lys Trp Pro Ala Glu Lys Glu Asn Asp Thr Gly Val Val His
225                 230                 235                 240

Gln Val Glu Glu Cys Arg Val Lys Gly Pro Gly Ile Ser Lys Phe Val
                245                 250                 255

Gln Lys Val Asn Glu Ile Gly Ile Tyr Leu Thr Asp Cys Met Glu Arg
            260                 265                 270

Ala Arg Glu Val Ile Pro Arg Ser Gln His Gln Glu Thr Pro Val Tyr
        275                 280                 285

Leu Gly Ala Thr Ala Gly Met Arg Leu Leu Arg Met Glu Ser Glu Glu
    290                 295                 300

Leu Ala Asp Arg Val Leu Asp Val Val Glu Arg Ser Leu Ser Asn Tyr
305                 310                 315                 320

Pro Phe Asp Phe Gln Gly Ala Arg Ile Ile Thr Gly Gln Glu Glu Gly
                325                 330                 335

Ala Tyr Gly Trp Ile Thr Ile Asn Tyr Leu Leu Gly Lys Phe Ser Gln
            340                 345                 350

Lys Asn Gln Glu Thr Phe Gly Ala Leu Asp Leu Gly Gly Ala Ser Thr
        355                 360                 365

Gln Val Thr Phe Val Pro Gln Asn Gln Thr Ile Glu Ser Pro Asp Asn
    370                 375                 380

Ala Leu Gln Phe Arg Leu Tyr Gly Lys Asp Tyr Asn Val Tyr Thr His
385                 390                 395                 400

Ser Phe Leu Cys Tyr Gly Lys Asp Gln Ala Leu Trp Gln Lys Leu Ala
                405                 410                 415

Lys Asp Ile Gln Val Ala Ser Asn Glu Ile Leu Arg Asp Pro Cys Phe
            420                 425                 430

His Pro Gly Tyr Lys Lys Val Val Asn Val Ser Asp Leu Tyr Lys Thr
        435                 440                 445

Pro Cys Thr Lys Arg Phe Glu Met Thr Leu Pro Phe Gln Gln Phe Glu
    450                 455                 460

Ile Gln Gly Ile Gly Asn Tyr Gln Gln Cys His Gln Ser Ile Leu Glu
465                 470                 475                 480

Leu Phe Asn Thr Ser Tyr Cys Pro Tyr Ser Gln Cys Ala Phe Asn Gly
                485                 490                 495

Ile Phe Leu Pro Pro Leu Gln Gly Asp Phe Gly Ala Phe Ser Ala Phe
            500                 505                 510

Tyr Phe Val Met Lys Phe Leu Asn Leu Thr Ser Glu Lys Val Ser Gln
        515                 520                 525

Glu Lys Val Thr Glu Met Met Lys Lys Phe Cys Ala Gln Pro Trp Glu
```

```
                530               535               540
Glu Ile Lys Thr Ser Tyr Ala Gly Val Lys Glu Lys Tyr Leu Ser Glu
545                 550                 555                 560

Tyr Cys Phe Ser Gly Thr Tyr Ile Leu Ser Leu Leu Gln Gly Tyr
                565                 570                 575

His Phe Thr Ala Asp Ser Trp Glu Ile His Phe Ile Gly Lys Ile
            580                 585                 590

Gln Gly Ser Asp Ala Gly Trp Thr Leu Gly Tyr Met Leu Asn Leu Thr
        595                 600                 605

Asn Met Ile Pro Ala Glu Gln Pro Leu Ser Thr Pro Leu Ser His Ser
    610                 615                 620

Thr
625

<210> SEQ ID NO 154
<211> LENGTH: 1875
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 154
gacgagggta aggcatcatc tgccaagcag agattaaaat gtgcatcttt gcaaaaattt      60
ggagagagag cttttaaggc atgggctgtt gcccgactaa gccaaagatt cccaaaagcc     120
gaatttgctg aagtatccaa gctggtgact gatttgacta agtacatac agaatgttgc      180 catggcgacc ttttagaatg tgctgatgac agagcagatt tggctaagta tatctgcgaa     240
aatcaagatt caatcagctc taagctgaag gaatgttgcg agaaaccact gttagaaaaa     300
tcgcattgta ttgctgaagt tgaaaatgat gagatgcctg ctgacttgcc ttctcttgcc     360
gctgattttg ttgagtcgaa ggatgtctgt aagaattatg ctgaagctaa agacgttttc     420
ctgggtatgt tcttatatga gtacgcaaga cgtcacccag attactctgt ggttctgcta     480
ctgagattgg ctaaaacata cgagacaacg ctggagaagt gctgtgctgc cgctgacCCt     540
catgagtgct atgcaaaggt ttttgatgaa ttcaaaccag gaggcggagg atctacccag     600
aacaaggccc tgcccgagaa cgtgaagtac ggcatcgtgc tggatgccgg cagcagccac     660
accagcctgt acatctacaa gtggcctgcc gagaaagaaa cgacaccgg cgtggtgcat      720 caggtggaag agtgcagagt gaagggccct ggcatcagca agttcgtgca gaaagtgaac     780
gagatcggca tctacctgac cgactgcatg gaacgggcca gggaagtgat ccccagaagc     840
cagcaccagg aaacccccgt gtatctggga gccaccgccg gcatgagact gctgagaatg     900
gaaagcgagg aactggccga ccgggtgctg acgtggtgg aaagaagcct gagcaactac      960
ccattcgatt tcaaggcgc cagaatcatc accggccagg aagaaggcgc ctacggctgg    1020
atcaccatca actacctgct gggcaagttc agccagaaga atcaggaaac cttcggcgcc    1080
ctggacctgg gcggagcttc tacccaagtg accttcgtgc cccagaatca gaccatcgag    1140
agccccgaca cgccctgca gttccggctg tacggcaagg actacaatgt gtacccccac    1200
agctttctgt gctacggaaa ggaccaggct ctgtggcaga gctggccaa ggacatccag    1260 gtggccagca acgagatcct gcgggaccct tgcttccacc ccggctacaa gaaagtcgtg    1320
aacgtgtccg acctgtacaa gacccctgc accaagagat cgagatgac cctgcccttc     1380 cagcagttcg agatccaggg catcggcaat taccagcagt gccaccagag catcctggaa    1440
```

-continued

```
ctgttcaaca ccagctactg cccctacagc cagtgcgcct tcaacggcat cttcctgcca    1500
cctctgcagg gggatttcgg cgccttcagc gccttctact tcgtgatgaa gttcctgaac    1560
ctgaccagcg agaaggtgtc ccaggaaaaa gtgacagaga tgatgaagaa gttctgcgcc    1620
cagccctggg aggaaatcaa gacctcctac gctggcgtga agagaagta ccctgagcgag    1680 tactgcttca gcggcaccta catcctgagc ctgctgctgc agggctacca cttcaccgcc    1740
gatagctggg agcacatcca cttcatcggc aagattcagg gcagcgacgc cggctggaca    1800
ctgggctaca tgctgaatct gaccaacatg atccccgccg agcagcccct gagcacacct    1860
ctgagccaca gcacc                                                    1875
```

<210> SEQ ID NO 155
<211> LENGTH: 439
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 155

```
Thr Gln Asn Lys Ala Leu Pro Glu Asn Val Lys Tyr Gly Ile Val Leu
1               5                   10                  15

Asp Ala Gly Ser Ser His Thr Ser Leu Tyr Ile Tyr Lys Trp Pro Ala
            20                  25                  30

Glu Lys Glu Asn Asp Thr Gly Val Val His Gln Val Glu Glu Cys Arg
        35                  40                  45

Val Lys Gly Pro Gly Ile Ser Lys Phe Val Gln Lys Val Asn Glu Ile
    50                  55                  60

Gly Ile Tyr Leu Thr Asp Cys Met Glu Arg Ala Arg Glu Val Ile Pro
65                  70                  75                  80

Arg Ser Gln His Gln Glu Thr Pro Val Tyr Leu Gly Ala Thr Ala Gly
                85                  90                  95

Met Arg Leu Leu Arg Met Glu Ser Glu Glu Leu Ala Asp Arg Val Leu
            100                 105                 110

Asp Val Val Glu Arg Ser Leu Ser Asn Tyr Pro Phe Asp Phe Gln Gly
        115                 120                 125

Ala Arg Ile Ile Thr Gly Gln Glu Glu Gly Ala Tyr Gly Trp Ile Thr
    130                 135                 140

Ile Asn Tyr Leu Leu Gly Lys Phe Ser Gln Lys Thr Arg Trp Phe Ser
145                 150                 155                 160

Ile Val Pro Tyr Glu Thr Asn Asn Gln Glu Thr Phe Gly Ala Leu Asp
                165                 170                 175

Leu Gly Gly Ala Ser Thr Gln Val Thr Phe Val Pro Gln Asn Gln Thr
            180                 185                 190

Ile Glu Ser Pro Asp Asn Ala Leu Gln Phe Arg Leu Tyr Gly Lys Asp
        195                 200                 205

Tyr Asn Val Tyr Thr His Ser Phe Leu Cys Tyr Gly Lys Asp Gln Ala
    210                 215                 220

Leu Trp Gln Lys Leu Ala Lys Asp Ile Gln Val Ala Ser Asn Glu Ile
225                 230                 235                 240

Leu Arg Asp Pro Cys Phe His Pro Gly Tyr Lys Lys Val Val Asn Val
                245                 250                 255

Ser Asp Leu Tyr Lys Thr Pro Cys Thr Lys Arg Phe Glu Met Thr Leu
            260                 265                 270
```

Pro Phe Gln Gln Phe Glu Ile Gln Gly Ile Gly Asn Tyr Gln Gln Cys
    275                 280                 285

His Gln Ser Ile Leu Glu Leu Phe Asn Thr Ser Tyr Cys Pro Tyr Ser
    290                 295                 300

Gln Cys Ala Phe Asn Gly Ile Phe Leu Pro Pro Leu Gln Gly Asp Phe
305                 310                 315                 320

Gly Ala Phe Ser Ala Phe Tyr Ser Val Met Lys Phe Leu Asn Leu Thr
                325                 330                 335

Ser Glu Lys Val Ser Gln Glu Lys Val Thr Glu Met Met Lys Lys Phe
                340                 345                 350

Cys Ala Gln Pro Trp Glu Glu Ile Lys Thr Ser Tyr Ala Gly Val Lys
                355                 360                 365

Glu Lys Tyr Leu Ser Glu Tyr Cys Phe Ser Gly Thr Tyr Ile Leu Ser
    370                 375                 380

Leu Leu Leu Gln Gly Tyr His Phe Thr Ala Asp Ser Trp Glu His Ile
385                 390                 395                 400

His Phe Ile Gly Lys Ile Gln Gly Ser Asp Ala Gly Trp Thr Leu Gly
                405                 410                 415

Tyr Met Leu Asn Leu Thr Asn Met Ile Pro Ala Glu Gln Pro Leu Ser
                420                 425                 430

Thr Pro Leu Ser His Ser Thr
                435

<210> SEQ ID NO 156
<211> LENGTH: 1317
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 156
acccagaaca aggccctgcc cgagaacgtg aagtacggca tcgtgctgga tgccggcagc      60
agccacacca gcctgtacat ctacaagtgg cctgccgaga agaaaacga caccggcgtg     120 gtgcatcagg tggaagagtg cagagtgaag ggccctggca tcagcaagtt cgtgcagaaa    180
gtgaacgaga tcggcatcta cctgaccgac tgcatggaac gggccaggga agtgatcccc    240
agaagccagc accaggaaac ccccgtgtat ctgggagcca ccgccggcat gagactgctg    300
agaatggaaa gcgaggaact ggccgaccgg gtgctggacg tggtggaaag aagcctgagc    360
aactacccat tcgattttca aggcgccaga atcatcaccg gccaggaaga aggcgcctac    420
ggctggatca ccatcaacta cctgctgggc aagttcagcc agaagaccag atggttcagc    480
atcgtgccct acgagacaaa caatcaggaa accttcggcg ccctggacct gggcggagct    540
tctacccaag tgaccttcgt gccccagaat cagaccatcg agagccccga caacgccctg    600
cagttccggc tgtacggcaa ggactacaat gtgtacaccc acagctttct gtgctacgga    660
aaggaccagg ctctgtggca gaagctggcc aaggacatcc aggtggccag caacgagatc    720
ctgcgggacc cttgcttcca ccccggctac aagaaagtcg tgaacgtgtc cgacctgtac    780
aagaccccct gcaccaagag attcgagatg accctgccct ccagcagtt cgagatccag    840 ggcatcggca attaccagca gtgccaccag agcatcctgg aactgttcaa caccagctac    900 tgccoctaca gccagtgcgc cttcaacggc atcttcctgc cacctctgca ggggatttc     960 ggcgccttca gcgccttcta ctccgtgatg aagttcctga acctgaccag cgagaaggtg   1020

```
tcccaggaaa aagtgacaga gatgatgaag aagttctgcg cccagccctg ggaggaaatc    1080
aagacctcct acgctggcgt gaaagagaag tacctgagcg agtactgctt cagcggcacc    1140
tacatcctga gcctgctgct gcagggctac cacttcaccg ccgatagctg ggagcacatc    1200
cacttcatcg gcaagattca gggcagcgac gccggctgga cactgggcta catgctgaat    1260
ctgaccaaca tgatccccgc cgagcagccc ctgagcacac tctgagccca cagcacc      1317
```

<210> SEQ ID NO 157  
<211> LENGTH: 90  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic primer"

<400> SEQUENCE: 157

```
tcgcgatcct ggaaggcgtg cactgcgccc taccagcag cagcaccaag aaaacccagc     60
tgaccagcag cacccagaac aaggccctgc                                     90
```

<210> SEQ ID NO 158  
<211> LENGTH: 18  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic primer"

<400> SEQUENCE: 158

```
tagaaggcac agtcgagg                                                  18
```

<210> SEQ ID NO 159  
<211> LENGTH: 66  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic primer"

<400> SEQUENCE: 159

```
ctggtcgcga tcctggaagg cgtgcactgc gcccctacca gcagcagcac ccagaacaag    60
gccctg                                                               66
```

<210> SEQ ID NO 160  
<211> LENGTH: 66  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic primer"

<400> SEQUENCE: 160

```
ctggtcgcga tcctggaagg cgtgcactgc gcccctacca gcagcagcac ccagaacaag    60
gccctg                                                               66
```

<210> SEQ ID NO 161  
<211> LENGTH: 57  
<212> TYPE: DNA  
<213> ORGANISM: Artificial Sequence  
<220> FEATURE:

```
<221> NAME/KEY: source
<223> OTHER INFORMATION: /note="Description of Artificial Sequence:
      Synthetic primer"

<400> SEQUENCE: 161
ctggtcgcga tcctggaagg cgtgcactgc gccgctacca cccagaacaa ggccctg        57

<210> SEQ ID NO 162
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 162
ctggtcgcga tcctggaagg cgtgcactgc gccgctacca gcagcagcac caagaaaacc    60
cagaacaagg ccctg                                                      75

<210> SEQ ID NO 163
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 163
ctggtcgcga tcctggaagg cgtgcactgc gccgctacca gcagcagcac caagaaaacc    60
cagctgaccc agaacaaggc cctg                                            84

<210> SEQ ID NO 164
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 164
ctggtcgcga tcctggaagg cgtgcactgc agcagcagca ccaagaaaac ccagctgacc    60
cagaacaagg ccctg                                                      75

<210> SEQ ID NO 165
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 165
catacgattt aggtga                                                     16

<210> SEQ ID NO 166
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 166
tagaaggcac agtcgagg                                                         18

<210> SEQ ID NO 167
<211> LENGTH: 76
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 167
```

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

```
<210> SEQ ID NO 168
<211> LENGTH: 105
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 168
```

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu
            100                 105

```
<210> SEQ ID NO 169
<211> LENGTH: 186
<212> TYPE: PRT
<213> ORGANISM: Homo sapiens

<400> SEQUENCE: 169
```

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

```
Gln Ser Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
 50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
             100                 105                 110

Pro Arg Leu Val Arg Pro Glu Val Asp Val Met Cys Thr Ala Phe His
         115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg
            180                 185

<210> SEQ ID NO 170
<211> LENGTH: 193
<212> TYPE: PRT
<213> ORGANISM: Homo sapiens

<400> SEQUENCE: 170

Asp Glu Gly Lys Ala Ser Ser Ala Lys Gln Arg Leu Lys Cys Ala Ser
1               5                  10                  15

Leu Gln Lys Phe Gly Glu Arg Ala Phe Lys Ala Trp Ala Val Ala Arg
             20                  25                  30

Leu Ser Gln Arg Phe Pro Lys Ala Glu Phe Ala Glu Val Ser Lys Leu
         35                  40                  45

Val Thr Asp Leu Thr Lys Val His Thr Glu Cys Cys His Gly Asp Leu
 50                  55                  60

Leu Glu Cys Ala Asp Asp Arg Ala Asp Leu Ala Lys Tyr Ile Cys Glu
 65                  70                  75                  80

Asn Gln Asp Ser Ile Ser Ser Lys Leu Lys Glu Cys Cys Glu Lys Pro
                 85                  90                  95

Leu Leu Glu Lys Ser His Cys Ile Ala Glu Val Glu Asn Asp Glu Met
             100                 105                 110

Pro Ala Asp Leu Pro Ser Leu Ala Ala Asp Phe Val Glu Ser Lys Asp
         115                 120                 125

Val Cys Lys Asn Tyr Ala Glu Ala Lys Asp Val Phe Leu Gly Met Phe
130                 135                 140

Leu Tyr Glu Tyr Ala Arg Arg His Pro Asp Tyr Ser Val Val Leu Leu
145                 150                 155                 160

Leu Arg Leu Ala Lys Thr Tyr Glu Thr Thr Leu Glu Lys Cys Cys Ala
                165                 170                 175

Ala Ala Asp Pro His Glu Cys Tyr Ala Lys Val Phe Asp Glu Phe Lys
            180                 185                 190

Pro

<210> SEQ ID NO 171
<211> LENGTH: 30
```

-continued

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 171
ctgccgagaa agaacaggac accggcgtgg                                   30

<210> SEQ ID NO 172
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 172
ccacgccggt gtcctgttct ttctcggcag                                   30

<210> SEQ ID NO 173
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 173
cgtgccccag aatcaggcca tcgagagcc                                    29

<210> SEQ ID NO 174
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 174
ggctctcgat ggcctgattc tggggcacg                                    29

<210> SEQ ID NO 175
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 175
ggctacaaga aagtcgtgca ggtgtccgac ctgtacaaga c                      41

<210> SEQ ID NO 176
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 176
```

```
gtcttgtaca ggtcggacac ctgcacgact ttcttgtagc c                   41
```

<210> SEQ ID NO 177
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 177

```
gcatcctgga actgttccag accagctact gcccc                          35
```

<210> SEQ ID NO 178
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 178

```
ggggcagtag ctggtctgga acagttccag gatgc                          35
```

<210> SEQ ID NO 179
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 179

```
ccgtgatgaa gttcctgcag ctgaccagcg agaag                          35
```

<210> SEQ ID NO 180
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 180

```
cttctcgctg gtcagctgca ggaacttcat cacgg                          35
```

<210> SEQ ID NO 181
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 181

```
cactgggcta catgctgcag ctgaccaaca tgatcc                         36
```

<210> SEQ ID NO 182
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 182
ggatcatgtt ggtcagctgc agcatgtagc ccagtg                               36

<210> SEQ ID NO 183
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 183
ctacatcctg agcctgctgc agcagggcta ccacttcac                            39

<210> SEQ ID NO 184
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 184
gtgaagtggt agccctgctg cagcaggctc aggatgtag                            39

<210> SEQ ID NO 185
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 185
gagaagtacc tgagcgagtt ttgcttcagc ggcacctaca tcc                       43

<210> SEQ ID NO 186
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 186
ggatgtaggt gccgctgaag caaaactcgc tcaggtactt ctc                       43

<210> SEQ ID NO 187
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 187
gttcgagatc cagggcaccg gcaattacca gcagtg                               36

<210> SEQ ID NO 188

```
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 188
cactgctggt aattgccggt gccctggatc tcgaac                              36

<210> SEQ ID NO 189
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 189
cgccgatagc tgggagcaca tccacttcat cggcaag                             37

<210> SEQ ID NO 190
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 190
cttgccgatg aagtggatgt gctcccagct atcggcg                             37

<210> SEQ ID NO 191
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 191
gagatcggca tctacctgac cgactgcatg gaacgggcca tggaagtgat ccccagaagc    60
cagcaccagg aaaccccccgt gtatctggga gccaccgccg gcatgagact gctgagaatg  120

<210> SEQ ID NO 192
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 192
gagatcggca tctacctgac cgact                                          25

<210> SEQ ID NO 193
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 193
cattctcagc agtctcat                                                           18

<210> SEQ ID NO 194
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 194
cttcagcgcc ttctactccg tgatgaagtt cctgaacctg accagcgaga aggtgtccca            60
ggaaaaagtg acagagatga tgaagaagtt ctgcgcccag ccctgggagg aaatcaagac          120

<210> SEQ ID NO 195
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 195
cttcagcgcc ttctactcc                                                          19

<210> SEQ ID NO 196
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 196
ggtcttgatt tcctcccag                                                          19

<210> SEQ ID NO 197
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 197
ctgggaggaa atcaagacct cctacgctgg cgtgaaagag aagtacctga gcgagttctg            60
cttcagcggc acctacatcc tgagcctgct gctgcagggc taccacttca ccgccgata           119

<210> SEQ ID NO 198
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 198
ctgggaggaa atcaagacct cctacgctgg cgtgaaagag aagtacctga gcgagtactg            60
cttcagcggc acctacatcc tgagcctgct gcagcagggc taccacttca ccgccgata    119

<210> SEQ ID NO 199
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 199
ctgggaggaa atcaagacct cctacgctgg cgtgaaagag aagtacctga gcgagttctg    60
cttcagcggc acctacatcc tgagcctgct gcagcagggc taccacttca ccgccgata    119

<210> SEQ ID NO 200
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 200
ctgggaggaa atcaagacc                                                 19

<210> SEQ ID NO 201
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 201
tatcggcggt gaagtggta                                                 19

<210> SEQ ID NO 202
<211> LENGTH: 119
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 202
ctgggaggaa atcaagacct cctacgctgg cgtgaaagag aagtacctga gcgagtactg    60
cttcagcggc acctacatcc tgagcctgct gctgcagggc taccacttca ccgccgata    119

<210> SEQ ID NO 203
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 203
caccggccag gaagccggcg cctacg                                         26

<210> SEQ ID NO 204
<211> LENGTH: 26

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 204
cgtaggcgcc ggcttcctgg ccggtg                                          26

<210> SEQ ID NO 205
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 205
ggacctgggc ggagctgcta cccaagtgac cttc                                 34

<210> SEQ ID NO 206
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 206
gaaggtcact tgggtagcag ctccgcccag gtcc                                 34

<210> SEQ ID NO 207
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 207
ctggatcacc atcaactacc tgctgggcaa gttcagccag aagaccagat ggttcagcat     60
cgtgccctac gagacaaaca                                                 80

<210> SEQ ID NO 208
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 208
tcacttgggt agaagctccg cccaggtcca gggcgccgaa ggtttcctga ttgtttgtct     60
cgtagggca                                                             69

<210> SEQ ID NO 209
<211> LENGTH: 430
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 209

```
Ala Pro Thr Thr Gln Asn Lys Ala Leu Pro Glu Asn Val Lys Tyr Gly
1               5                   10                  15
Ile Val Leu Asp Ala Gly Ser Ser His Thr Ser Leu Tyr Ile Tyr Lys
            20                  25                  30
Trp Pro Ala Glu Lys Glu Asn Asp Thr Gly Val Val His Gln Val Glu
        35                  40                  45
Glu Cys Arg Val Lys Gly Pro Gly Ile Ser Lys Phe Val Gln Lys Val
    50                  55                  60
Asn Glu Ile Gly Ile Tyr Leu Thr Asp Cys Met Glu Arg Ala Met Glu
65                  70                  75                  80
Val Ile Pro Arg Ser Gln His Gln Glu Thr Pro Val Tyr Leu Gly Ala
                85                  90                  95
Thr Ala Gly Met Arg Leu Leu Arg Met Glu Ser Glu Glu Leu Ala Asp
            100                 105                 110
Arg Val Leu Asp Val Val Glu Arg Ser Leu Ser Asn Tyr Pro Phe Asp
        115                 120                 125
Phe Gln Gly Ala Arg Ile Ile Thr Gly Gln Glu Glu Gly Ala Tyr Gly
    130                 135                 140
Trp Ile Thr Ile Asn Tyr Leu Leu Gly Lys Phe Ser Gln Lys Asn Gln
145                 150                 155                 160
Glu Thr Phe Gly Ala Leu Asp Leu Gly Gly Ala Ser Thr Gln Val Thr
                165                 170                 175
Phe Val Pro Gln Asn Gln Thr Ile Glu Ser Pro Asp Asn Ala Leu Gln
            180                 185                 190
Phe Arg Leu Tyr Gly Lys Asp Tyr Asn Val Tyr Thr His Ser Phe Leu
        195                 200                 205
Cys Tyr Gly Lys Asp Gln Ala Leu Trp Gln Lys Leu Ala Lys Asp Ile
    210                 215                 220
Gln Val Ala Ser Asn Glu Ile Leu Arg Asp Pro Cys Phe His Pro Gly
225                 230                 235                 240
Tyr Lys Lys Val Val Asn Val Ser Asp Leu Tyr Lys Thr Pro Cys Thr
                245                 250                 255
Lys Arg Phe Glu Met Thr Leu Pro Phe Gln Gln Phe Glu Ile Gln Gly
            260                 265                 270
Ile Gly Asn Tyr Gln Gln Cys His Gln Ser Ile Leu Glu Leu Phe Asn
        275                 280                 285
Thr Ser Tyr Cys Pro Tyr Ser Gln Cys Ala Phe Asn Gly Ile Phe Leu
    290                 295                 300
Pro Pro Leu Gln Gly Asp Phe Gly Ala Phe Ser Ala Phe Tyr Phe Val
305                 310                 315                 320
Met Lys Phe Leu Asn Leu Thr Ser Glu Lys Val Ser Gln Glu Lys Val
                325                 330                 335
Thr Glu Met Met Lys Lys Phe Cys Ala Gln Pro Trp Glu Glu Ile Lys
            340                 345                 350
Thr Ser Tyr Ala Gly Val Lys Glu Lys Tyr Leu Ser Glu Tyr Cys Phe
        355                 360                 365
Ser Gly Thr Tyr Ile Leu Ser Leu Leu Leu Gln Gly Tyr His Phe Thr
    370                 375                 380
Ala Asp Ser Trp Glu His Ile His Phe Ile Gly Lys Ile Gln Gly Ser
385                 390                 395                 400
```

Asp Ala Gly Trp Thr Leu Gly Tyr Met Leu Asn Leu Thr Asn Met Ile
            405                 410                 415

Pro Ala Glu Gln Pro Leu Ser Thr Pro Leu Ser His Ser Thr
        420                 425                 430

<210> SEQ ID NO 210
<211> LENGTH: 1290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 210
gcccctacca cccagaacaa ggccctgccc gagaacgtga agtacggcat cgtgctggat      60
gccggcagca gccacaccag cctgtacatc tacaagtggc ctgccgagaa agaaaacgac     120
accggcgtgg tgcatcaggt ggaagagtgc agagtgaagg ccctggcat cagcaagttc      180 gtgcagaaag tgaacgagat cggcatctac ctgaccgact gcatggaacg ggccatggaa     240
gtgatcccca agccagca ccaggaaacc cccgtgtatc tgggagccac cgccggcatg       300
agactgctga atggaaag cgaggaactg gccgaccggg tgctggacgt ggtggaaaga       360
agcctgagca actacccatt cgattttcaa ggcgccagaa tcatcaccgg ccaggaagaa     420
ggcgcctacg gctggatcac catcaactac ctgctgggca gttcagcca agaatcag       480 gaaaccttcg gcgccctgga cctgggcgga gcttctaccc aagtgaccttcgtgccccag     540 aatcagacca tcgagagccc cgacaacgcc ctgcagttcc ggctgtacgg caaggactac   600
aatgtgtaca cccacagctt tctgtgctac ggaaaggacc aggctctgtg cagaagctg     660 gccaaggaca tccaggtggc cagcaacgag atcctgcggg acccttgctt ccaccccggc    720
tacaagaaag tcgtgaacgt gtccgacctg tacaagaccc cctgcaccaa gagattcgag    780
atgaccctgc ccttccagca gttcgagatc cagggcatcg gcaattacca gcagtgccac    840
cagagcatcc tggaactgtt caacaccagc tactgcccct acagccagtg cgccttcaac    900
ggcatcttcc tgccacctct gcagggggat ttcggcgcct tcagcgcctt ctacttcgtg    960
atgaagttcc tgaacctgac cagcgagaag gtgtcccagg aaaaagtgac agagatgatg   1020
aagaagttct gcgcccagcc ctgggaggaa atcaagaccc cctacgctgg cgtgaaagag   1080
aagtacctga gcgagtactg cttcagcggc acctacatcc tgagcctgct gctgcagggc   1140
taccacttca ccgccgatag ctgggagcac atccacttca tcggcaagat tcagggcagc   1200
gacgccggct ggacactggg ctacatgctg aatctgacca catgatccc cgccgagcag    1260 cccctgagca cacctctgag ccacagcacc                                   1290

<210> SEQ ID NO 211
<211> LENGTH: 430
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 211

Ala Pro Thr Thr Gln Asn Lys Ala Leu Pro Glu Asn Val Lys Tyr Gly
1               5                   10                  15

Ile Val Leu Asp Ala Gly Ser Ser His Thr Ser Leu Tyr Ile Tyr Lys
            20                  25                  30

```
Trp Pro Ala Glu Lys Glu Asn Asp Thr Gly Val Val His Gln Val Glu
        35                  40                  45

Glu Cys Arg Val Lys Gly Pro Gly Ile Ser Lys Phe Val Gln Lys Val
    50                  55                  60

Asn Glu Ile Gly Ile Tyr Leu Thr Asp Cys Met Glu Arg Ala Met Glu
65                  70                  75                  80

Val Ile Pro Arg Ser Gln His Gln Glu Thr Pro Val Tyr Leu Gly Ala
                85                  90                  95

Thr Ala Gly Met Arg Leu Leu Arg Met Glu Ser Glu Leu Ala Asp
            100                 105                 110

Arg Val Leu Asp Val Val Glu Arg Ser Leu Ser Asn Tyr Pro Phe Asp
            115                 120                 125

Phe Gln Gly Ala Arg Ile Ile Thr Gly Gln Glu Glu Gly Ala Tyr Gly
        130                 135                 140

Trp Ile Thr Ile Asn Tyr Leu Leu Gly Lys Phe Ser Gln Lys Asn Gln
145                 150                 155                 160

Glu Thr Phe Gly Ala Leu Asp Leu Gly Ala Ser Thr Gln Val Thr
            165                 170                 175

Phe Val Pro Gln Asn Gln Thr Ile Glu Ser Pro Asp Asn Ala Leu Gln
        180                 185                 190

Phe Arg Leu Tyr Gly Lys Asp Tyr Asn Val Tyr Thr His Ser Phe Leu
    195                 200                 205

Cys Tyr Gly Lys Asp Gln Ala Leu Trp Gln Lys Leu Ala Lys Asp Ile
    210                 215                 220

Gln Val Ala Ser Asn Glu Ile Leu Arg Asp Pro Cys Phe His Pro Gly
225                 230                 235                 240

Tyr Lys Lys Val Val Asn Val Ser Asp Leu Tyr Lys Thr Pro Cys Thr
                245                 250                 255

Lys Arg Phe Glu Met Thr Leu Pro Phe Gln Gln Phe Glu Ile Gln Gly
            260                 265                 270

Ile Gly Asn Tyr Gln Gln Cys His Gln Ser Ile Leu Glu Leu Phe Asn
        275                 280                 285

Thr Ser Tyr Cys Pro Tyr Ser Gln Cys Ala Phe Asn Gly Ile Phe Leu
    290                 295                 300

Pro Pro Leu Gln Gly Asp Phe Gly Ala Phe Ser Ala Phe Tyr Phe Val
305                 310                 315                 320

Met Lys Phe Leu Asn Leu Thr Ser Glu Lys Val Ser Gln Glu Lys Val
                325                 330                 335

Thr Glu Met Met Lys Lys Phe Cys Ala Gln Pro Trp Glu Glu Ile Lys
            340                 345                 350

Thr Ser Tyr Ala Gly Val Lys Glu Lys Tyr Leu Ser Glu Phe Cys Phe
        355                 360                 365

Ser Gly Thr Tyr Ile Leu Ser Leu Leu Leu Gln Gly Tyr His Phe Thr
    370                 375                 380

Ala Asp Ser Trp Glu His Ile His Phe Ile Gly Lys Ile Gln Gly Ser
385                 390                 395                 400

Asp Ala Gly Trp Thr Leu Gly Tyr Met Leu Asn Leu Thr Asn Met Ile
                405                 410                 415

Pro Ala Glu Gln Pro Leu Ser Thr Pro Leu Ser His Ser Thr
            420                 425                 430

<210> SEQ ID NO 212
<211> LENGTH: 1290
```

<210> SEQ ID NO 213
<211> LENGTH: 433
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 212

```
gcccctacca cccagaacaa ggccctgccc gagaacgtga agtacggcat cgtgctggat      60
gccggcagca gccacaccag cctgtacatc tacaagtggc ctgccgagaa agaaaacgac     120
accggcgtgg tgcatcaggt ggaagagtgc agagtgaagg gccctggcat cagcaagttc     180
gtgcagaaag tgaacgagat cggcatctac ctgaccgact gcatggaacg ggccatggaa     240
gtgatcccca agccagca ccaggaaacc cccgtgtatc tgggagccac cgccggcatg     300
agactgctga atggaaag cgaggaactg gccgaccggg tgctggacgt ggtggaaaga     360
agcctgagca actacccatt cgattttcaa ggcgccagaa tcatcaccgg ccaggaagaa     420
ggcgcctacg gctggatcac catcaactac ctgctgggca gttcagcca agaatcag     480
gaaaccttcg gcgccctgga cctgggcgga gcttctaccc aagtgaccttt cgtgccccag     540
aatcagacca tcgagagccc cgacaacgcc ctgcagttcc ggctgtacgg caaggactac     600
aatgtgtaca cccacagctt tctgtgctac ggaaaggacc aggctctgtg cagaagctg     660
gccaaggaca tccaggtggc cagcaacgag atcctgcggg acccttgctt ccaccccggc     720
tacaagaaag tcgtgaacgt gtccgacctg tacaagaccc cctgcaccaa gagattcgag     780
atgaccctgc ccttccagca gttcgagatc cagggcatcg gcaattacca gcagtgccac     840
cagagcatcc tggaactgtt caacaccagc tactgcccct acagccagtg cgccttcaac     900
ggcatcttcc tgccacctct gcaggggat ttcggcgcct tcagcgcctt ctacttcgtg     960
atgaagttcc tgaacctgac cagcgagaag gtgtcccagg aaaaagtgac agagatgatg    1020
aagaagttct gcgcccagcc ctgggaggaa atcaagacct cctacgctgg cgtgaaagag    1080
aagtacctga gcgagttttg cttcagcggc acctacatcc tgagcctgct gctgcagggc    1140
taccacttca ccgccgatag ctgggagcac atccacttca tcggcaagat tcagggcagc    1200
gacgccggct ggacactggg ctacatgctg aatctgacca catgatccc cgccgagcag    1260
cccctgagca cacctctgag ccacagcacc                                      1290
```

<210> SEQ ID NO 213
<211> LENGTH: 433
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 213

Ala Pro Thr Ser Ser Thr Gln Asn Lys Ala Leu Pro Glu Asn Val
1               5                   10                  15

Lys Tyr Gly Ile Val Leu Asp Ala Gly Ser Ser His Thr Ser Leu Tyr
            20                  25                  30

Ile Tyr Lys Trp Pro Ala Glu Lys Glu Asn Asp Thr Gly Val Val His
        35                  40                  45

Gln Val Glu Glu Cys Arg Val Lys Gly Pro Gly Ile Ser Lys Phe Val
    50                  55                  60

Gln Lys Val Asn Glu Ile Gly Ile Tyr Leu Thr Asp Cys Met Glu Arg
65                  70                  75                  80

```
Ala Met Glu Val Ile Pro Arg Ser Gln His Gln Thr Pro Val Tyr
                85                  90                  95

Leu Gly Ala Thr Ala Gly Met Arg Leu Leu Arg Met Glu Ser Glu
            100                 105                 110

Leu Ala Asp Arg Val Leu Asp Val Val Glu Arg Ser Leu Ser Asn Tyr
        115                 120                 125

Pro Phe Asp Phe Gln Gly Ala Arg Ile Ile Thr Gly Gln Glu Glu Gly
130                 135                 140

Ala Tyr Gly Trp Ile Thr Ile Asn Tyr Leu Leu Gly Lys Phe Ser Gln
145                 150                 155                 160

Lys Asn Gln Glu Thr Phe Gly Ala Leu Asp Leu Gly Gly Ala Ser Thr
                165                 170                 175

Gln Val Thr Phe Val Pro Gln Asn Gln Thr Ile Glu Ser Pro Asp Asn
            180                 185                 190

Ala Leu Gln Phe Arg Leu Tyr Gly Lys Asp Tyr Asn Val Tyr Thr His
        195                 200                 205

Ser Phe Leu Cys Tyr Gly Lys Asp Gln Ala Leu Trp Gln Lys Leu Ala
210                 215                 220

Lys Asp Ile Gln Val Ala Ser Asn Glu Ile Leu Arg Asp Pro Cys Phe
225                 230                 235                 240

His Pro Gly Tyr Lys Lys Val Val Asn Val Ser Asp Leu Tyr Lys Thr
                245                 250                 255

Pro Cys Thr Lys Arg Phe Glu Met Thr Leu Pro Phe Gln Gln Phe Glu
            260                 265                 270

Ile Gln Gly Ile Gly Asn Tyr Gln Gln Cys His Gln Ser Ile Leu Glu
        275                 280                 285

Leu Phe Asn Thr Ser Tyr Cys Pro Tyr Ser Gln Cys Ala Phe Asn Gly
290                 295                 300

Ile Phe Leu Pro Pro Leu Gln Gly Asp Phe Gly Ala Phe Ser Ala Phe
305                 310                 315                 320

Tyr Phe Val Met Lys Phe Leu Asn Leu Thr Ser Glu Lys Val Ser Gln
                325                 330                 335

Glu Lys Val Thr Glu Met Met Lys Lys Phe Cys Ala Gln Pro Trp Glu
            340                 345                 350

Glu Ile Lys Thr Ser Tyr Ala Gly Val Lys Glu Lys Tyr Leu Ser Glu
        355                 360                 365

Phe Cys Phe Ser Gly Thr Tyr Ile Leu Ser Leu Leu Leu Gln Gly Tyr
370                 375                 380

His Phe Thr Ala Asp Ser Trp Glu His Ile His Phe Ile Gly Lys Ile
385                 390                 395                 400

Gln Gly Ser Asp Ala Gly Trp Thr Leu Gly Tyr Met Leu Asn Leu Thr
                405                 410                 415

Asn Met Ile Pro Ala Glu Gln Pro Leu Ser Thr Pro Leu Ser His Ser
            420                 425                 430

Thr
```

<210> SEQ ID NO 214
<211> LENGTH: 1299
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 214

```
gcccctacca gcagcagcac ccagaacaag gccctgcccg agaacgtgaa gtacggcatc      60
gtgctggatg ccggcagcag ccacaccagc ctgtacatct acaagtggcc tgccgagaaa     120
gaaaacgaca ccggcgtggt gcatcaggtg aagagtgca gagtgaaggg ccctggcatc     180
agcaagttcg tgcagaaagt gaacgagatc ggcatctacc tgaccgactg catggaacgg     240
gccatggaag tgatcccag aagccagcac caggaaaccc ccgtgtatct gggagccacc     300
gccggcatga gactgctgag aatggaaagc gaggaactgg ccgaccgggt gctggacgtg     360
gtggaaagaa gcctgagcaa ctacccattc gattttcaag cgccagaat catcaccggc     420
caggaagaag gcgcctacgg ctggatcacc atcaactacc tgctgggcaa gttcagccag     480
aagaatcagg aaaccttcgg cgccctggac ctgggcggag cttctaccca agtgaccttc     540
gtgccccaga atcagaccat cgagagcccc gacaacgccc tgcagttccg gctgtacggc     600
aaggactaca atgtgtacac ccacagcttt ctgtgctacg aaaggacca ggctctgtgg     660
cagaagctgg ccaaggacat ccaggtggcc agcaacgaga tcctgcggga cccttgcttc     720
cacccccggct acaagaaagt cgtgaacgtg tccgacctgt acaagacccc ctgcaccaag     780
agattcgaga tgaccctgcc cttccagcag ttcgagatcc agggcatcgg caattaccag     840
cagtgccacc agagcatcct ggaactgttc aacaccagct actgccccta cagccagtgc     900
gccttcaacg gcatcttcct gccacctctg caggggatt cggcgccttt cagcgccttc     960
tacttcgtga tgaagttcct gaacctgacc agcgagaagg tgtcccagga aaaagtgaca    1020
gagatgatga agaagttctg cgcccagccc tgggaggaaa tcaagacctc ctacgctggc    1080
gtgaaagaga agtacctgag cgagttctgc ttcagcggca cctacatcct gagcctgctg    1140
ctgcagggct accacttcac cgccgatagc tgggagcaca tccacttcat cggcaagatt    1200
cagggcagcg acgccggctg gacactgggc tacatgctga atctgaccaa catgatcccc    1260
gccgagcagc ccctgagcac acctctgagc cacagcacc                          1299
```

<210> SEQ ID NO 215
<211> LENGTH: 442
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 215

```
Ala Pro Thr Ser Ser Ser Thr Lys Lys Thr Gln Leu Thr Ser Ser Thr
1               5                   10                  15

Gln Asn Lys Ala Leu Pro Glu Asn Val Lys Tyr Gly Ile Val Leu Asp
            20                  25                  30

Ala Gly Ser Ser His Thr Ser Leu Tyr Ile Tyr Lys Trp Pro Ala Glu
        35                  40                  45

Lys Glu Asn Asp Thr Gly Val Val His Gln Val Glu Glu Cys Arg Val
    50                  55                  60

Lys Gly Pro Gly Ile Ser Lys Phe Val Gln Lys Val Asn Glu Ile Gly
65                  70                  75                  80

Ile Tyr Leu Thr Asp Cys Met Glu Arg Ala Met Glu Val Ile Pro Arg
                85                  90                  95

Ser Gln His Gln Glu Thr Pro Val Tyr Leu Gly Ala Thr Ala Gly Met
            100                 105                 110
```

```
Arg Leu Leu Arg Met Glu Ser Glu Glu Leu Ala Asp Arg Val Leu Asp
            115                 120                 125

Val Val Glu Arg Ser Leu Ser Asn Tyr Pro Phe Asp Phe Gln Gly Ala
    130                 135                 140

Arg Ile Ile Thr Gly Gln Glu Gly Ala Tyr Gly Trp Ile Thr Ile
145                 150                 155                 160

Asn Tyr Leu Leu Gly Lys Phe Ser Gln Lys Asn Gln Glu Thr Phe Gly
                165                 170                 175

Ala Leu Asp Leu Gly Gly Ala Ser Thr Gln Val Thr Phe Val Pro Gln
            180                 185                 190

Asn Gln Thr Ile Glu Ser Pro Asp Asn Ala Leu Gln Phe Arg Leu Tyr
            195                 200                 205

Gly Lys Asp Tyr Asn Val Tyr Thr His Ser Phe Leu Cys Tyr Gly Lys
    210                 215                 220

Asp Gln Ala Leu Trp Gln Lys Leu Ala Lys Asp Ile Gln Val Ala Ser
225                 230                 235                 240

Asn Glu Ile Leu Arg Asp Pro Cys Phe His Pro Gly Tyr Lys Lys Val
                245                 250                 255

Val Asn Val Ser Asp Leu Tyr Lys Thr Pro Cys Thr Lys Arg Phe Glu
            260                 265                 270

Met Thr Leu Pro Phe Gln Gln Phe Glu Ile Gln Gly Ile Gly Asn Tyr
            275                 280                 285

Gln Gln Cys His Gln Ser Ile Leu Glu Leu Phe Asn Thr Ser Tyr Cys
    290                 295                 300

Pro Tyr Ser Gln Cys Ala Phe Asn Gly Ile Phe Leu Pro Pro Leu Gln
305                 310                 315                 320

Gly Asp Phe Gly Ala Phe Ser Ala Phe Tyr Phe Val Met Lys Phe Leu
                325                 330                 335

Asn Leu Thr Ser Glu Lys Val Ser Gln Glu Lys Val Thr Glu Met Met
            340                 345                 350

Lys Lys Phe Cys Ala Gln Pro Trp Glu Glu Ile Lys Thr Ser Tyr Ala
            355                 360                 365

Gly Val Asn Glu Lys Tyr Leu Ser Glu Phe Cys Phe Ser Gly Thr Tyr
    370                 375                 380

Ile Leu Ser Leu Leu Leu Gln Gly Tyr His Phe Thr Ala Asp Ser Trp
385                 390                 395                 400

Glu His Ile His Phe Ile Gly Lys Ile Gln Gly Ser Asp Ala Gly Trp
                405                 410                 415

Thr Leu Gly Tyr Met Leu Asn Leu Thr Asn Met Ile Pro Ala Glu Gln
            420                 425                 430

Pro Leu Ser Thr Pro Leu Ser His Ser Thr
            435                 440

<210> SEQ ID NO 216
<211> LENGTH: 1326
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 216
gcccctacca gcagcagcac caagaaaacc cagctgacca gcagcaccca gaacaaggcc      60
ctgcccgaga acgtgaagta cggcatcgtg ctggatgccg gcagcagcca caccagcctg     120
```

```
tacatctaca agtggcctgc cgagaaagaa aacgacaccg gcgtggtgca tcaggtggaa      180
gagtgcagag tgaagggccc tggcatcagc aagttcgtgc agaaagtgaa cgagatcggc      240
atctacctga ccgactgcat ggaacgggcc atggaagtga tccccagaag ccagcaccag      300 gaaaccccg tgtatctggg agccaccgcc ggcatgagac tgctgagaat ggaaagcgag       360
gaactggccg accgggtgct ggacgtggtg aaagaagcc tgagcaacta cccattcgat       420
tttcaaggcg ccagaatcat caccggccag gaagaaggcg cctacggctg gatcaccatc      480
aactacctgc tgggcaagtt cagccagaag aatcaggaaa ccttcggcgc cctggacctg      540
ggcggagctt ctacccaagt gaccttcgtg ccccagaatc agaccatcga gagccccgac      600
aacgccctgc agttccggct gtacggcaag gactacaatg tgtacaccca gcttctg        660 tgctacggaa aggaccaggc tctgtggcag aagctggcca aggacatcca ggtggccagc      720
aacgagatcc tgcgggaccc ttgcttccac cccggctaca agaaagtcgt gaacgtgtcc      780
gacctgtaca agaccccctg caccaagaga ttcgagatga ccctgccctt ccagcagttc      840
gagatccagg gcatcggcaa ttaccagcag tgccaccaga gcatcctgga actgttcaac      900
accagctact gcccctacag ccagtgcgcc ttcaacggca tcttcctgcc acctctgcag      960
ggggatttcg gcgccttcag cgccttctac ttcgtgatga gttcctgaa cctgaccagc      1020 gagaaggtgt cccaggaaaa agtgacagag atgatgaaga gttctgcgc ccaaccctgg      1080 gaggaaatca gacctccta cgctggcgtg aacgagaagt acctgagcga gttttgcttc      1140
agcggcacct acatcctgag cctgctgctg cagggctacc acttcaccgc cgatagctgg      1200
gagcacatcc acttcatcgg caagattcag ggcagcgacg ccggctggac actgggctac      1260
atgctgaatc tgaccaacat gatccccgcc gagcagcccc tgagcacacc tctgagccac      1320
agcacc                                                                1326
```

<210> SEQ ID NO 217
<211> LENGTH: 430
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 217

```
Ala Pro Thr Thr Gln Asn Lys Ala Leu Pro Glu Asn Val Lys Tyr Gly
1               5                   10                  15

Ile Val Leu Asp Ala Gly Ser Ser His Thr Ser Leu Tyr Ile Tyr Lys
            20                  25                  30

Trp Pro Ala Glu Lys Glu Asn Asp Thr Gly Val Val His Gln Val Glu
        35                  40                  45

Glu Cys Arg Val Lys Gly Pro Gly Ile Ser Lys Phe Val Gln Lys Val
    50                  55                  60

Asn Glu Ile Gly Ile Tyr Leu Thr Asp Cys Met Glu Arg Ala Met Glu
65                  70                  75                  80

Val Ile Pro Arg Ser Gln His Gln Glu Thr Pro Val Tyr Leu Gly Ala
                85                  90                  95

Thr Ala Gly Met Arg Leu Leu Arg Met Glu Ser Glu Glu Leu Ala Asp
            100                 105                 110

Arg Val Leu Asp Val Val Glu Arg Ser Leu Ser Asn Tyr Pro Phe Asp
        115                 120                 125

Phe Gln Gly Ala Arg Ile Ile Thr Gly Gln Glu Glu Gly Ala Tyr Gly
```

```
        130                 135                 140
Trp Ile Thr Ile Asn Tyr Leu Leu Gly Lys Phe Ser Gln Lys Asn Gln
145                 150                 155                 160

Glu Thr Phe Gly Ala Leu Asp Leu Gly Gly Ala Ser Thr Gln Val Thr
                165                 170                 175

Phe Val Pro Gln Asn Gln Thr Ile Glu Ser Pro Asp Asn Ala Leu Gln
            180                 185                 190

Phe Arg Leu Tyr Gly Lys Asp Tyr Asn Val Tyr Thr His Ser Phe Leu
        195                 200                 205

Cys Tyr Gly Lys Asp Gln Ala Leu Trp Gln Lys Leu Ala Lys Asp Ile
    210                 215                 220

Gln Val Ala Ser Asn Glu Ile Leu Arg Asp Pro Cys Phe His Pro Gly
225                 230                 235                 240

Tyr Lys Lys Val Val Asn Val Ser Asp Leu Tyr Lys Thr Pro Cys Thr
                245                 250                 255

Lys Arg Phe Glu Met Thr Leu Pro Phe Gln Gln Phe Glu Ile Gln Gly
            260                 265                 270

Ile Gly Asn Tyr Gln Gln Cys His Gln Ser Ile Leu Glu Leu Phe Asn
        275                 280                 285

Thr Ser Tyr Cys Pro Tyr Ser Gln Cys Ala Phe Asn Gly Ile Phe Leu
    290                 295                 300

Pro Pro Leu Gln Gly Asp Phe Gly Ala Phe Ser Ala Phe Tyr Phe Val
305                 310                 315                 320

Met Lys Phe Leu Asn Leu Thr Ser Glu Lys Val Ser Gln Glu Lys Val
                325                 330                 335

Thr Glu Met Met Lys Lys Phe Cys Ala Gln Pro Trp Glu Glu Ile Lys
            340                 345                 350

Thr Ser Tyr Ala Gly Val Lys Glu Lys Tyr Leu Ser Glu Phe Cys Phe
        355                 360                 365

Ser Gly Thr Tyr Ile Leu Ser Leu Leu Gln Gln Gly Tyr His Phe Thr
    370                 375                 380

Ala Asp Ser Trp Glu His Ile His Phe Ile Gly Lys Ile Gln Gly Ser
385                 390                 395                 400

Asp Ala Gly Trp Thr Leu Gly Tyr Met Leu Asn Leu Thr Asn Met Ile
                405                 410                 415

Pro Ala Glu Gln Pro Leu Ser Thr Pro Leu Ser His Ser Thr
            420                 425                 430

<210> SEQ ID NO 218
<211> LENGTH: 1290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 218
gcccctacca cccagaacaa ggccctgccc gagaacgtga agtacggcat cgtgctggat        60
gccggcagca gccacaccag cctgtacatc tacaagtggc ctgccgagaa agaaaacgac       120
accggcgtgg tgcatcaggt ggaagagtgc agagtgaagg ccctggcat cagcaagttc        180 gtgcagaaag tgaacgagat cggcatctac ctgaccgact gcatggaacg ggccatggaa       240
gtgatcccca aagccagca ccaggaaacc cccgtgtatc tggagccac cgccggcatg         300 agactgctga gaatggaaag cgaggaactg gccgaccggg tgctggacgt ggtggaaaga       360
```

```
agcctgagca actacccatt cgattttcaa ggcgccagaa tcatcaccgg ccaggaagaa      420
ggcgcctacg gctggatcac catcaactac ctgctgggca agttcagcca agaatcag       480
gaaaccttcg gcgccctgga cctgggcgga gcttctaccc aagtgacctt cgtgccccag     540
aatcagacca tcgagagccc cgacaacgcc ctgcagttcc ggctgtacgg caaggactac     600
aatgtgtaca cccacagctt tctgtgctac ggaaaggacc aggctctgtg cagaagctg      660
gccaaggaca tccaggtggc cagcaacgag atcctgcggg acccttgctt ccaccccggc     720
tacaagaaag tcgtgaacgt gtccgacctg tacaagaccc cctgcaccaa gagattcgag     780
atgaccctgc ccttccagca gttcgagatc cagggcatcg caattacca gcagtgccac     840
cagagcatcc tggaactgtt caacaccagc tactgcccct acagccagtg cgccttcaac     900
ggcatcttcc tgccacctct gcaggggat ttcggcgcct tcagcgcctt ctacttcgtg      960
atgaagttcc tgaacctgac cagcgagaag gtgtcccagg aaaaagtgac agagatgatg    1020
aagaagttct gcgcccagcc ctgggaggaa atcaagaccc cctacgctgg cgtgaaagag    1080
aagtacctga gcgagttctg cttcagcggc acctacatcc tgagcctgct gcagcagggc    1140
taccacttca ccgccgatag ctgggagcac atccacttca tcggcaagat tcagggcagc    1200
gacgccggct ggacactggg ctacatgctg aatctgacca acatgatccc cgccgagcag    1260
ccctgagca cacctctgag ccacagcacc                                      1290
```

<210> SEQ ID NO 219
<211> LENGTH: 433
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 219

```
Ala Pro Thr Ser Ser Thr Gln Asn Lys Ala Leu Pro Glu Asn Val
1               5                   10                  15

Lys Tyr Gly Ile Val Leu Asp Ala Gly Ser Ser His Thr Ser Leu Tyr
            20                  25                  30

Ile Tyr Lys Trp Pro Ala Glu Lys Glu Asn Asp Thr Gly Val Val His
        35                  40                  45

Gln Val Glu Glu Cys Arg Val Lys Gly Pro Gly Ile Ser Lys Phe Val
    50                  55                  60

Gln Lys Val Asn Glu Ile Gly Ile Tyr Leu Thr Asp Cys Met Glu Arg
65                  70                  75                  80

Ala Met Glu Val Ile Pro Arg Ser Gln His Gln Glu Thr Pro Val Tyr
                85                  90                  95

Leu Gly Ala Thr Ala Gly Met Arg Leu Leu Arg Met Glu Ser Glu Glu
            100                 105                 110

Leu Ala Asp Arg Val Leu Asp Val Val Glu Arg Ser Leu Ser Asn Tyr
        115                 120                 125

Pro Phe Asp Phe Gln Gly Ala Arg Ile Ile Thr Gly Gln Glu Glu Gly
    130                 135                 140

Ala Tyr Gly Trp Ile Thr Ile Asn Tyr Leu Leu Gly Lys Phe Ser Gln
145                 150                 155                 160

Lys Asn Gln Glu Thr Phe Gly Ala Leu Asp Leu Gly Gly Ala Ser Thr
                165                 170                 175

Gln Val Thr Phe Val Pro Gln Asn Gln Thr Ile Glu Ser Pro Asp Asn
```

```
                180                 185                 190
Ala Leu Gln Phe Arg Leu Tyr Gly Lys Asp Tyr Asn Val Tyr Thr His
            195                 200                 205

Ser Phe Leu Cys Tyr Gly Lys Asp Gln Ala Leu Trp Gln Lys Leu Ala
        210                 215                 220

Lys Asp Ile Gln Val Ala Ser Asn Glu Ile Leu Arg Asp Pro Cys Phe
225                 230                 235                 240

His Pro Gly Tyr Lys Lys Val Val Asn Val Ser Asp Leu Tyr Lys Thr
                245                 250                 255

Pro Cys Thr Lys Arg Phe Glu Met Thr Leu Pro Phe Gln Gln Phe Glu
            260                 265                 270

Ile Gln Gly Ile Gly Asn Tyr Gln Gln Cys His Gln Ser Ile Leu Glu
        275                 280                 285

Leu Phe Asn Thr Ser Tyr Cys Pro Tyr Ser Gln Cys Ala Phe Asn Gly
        290                 295                 300

Ile Phe Leu Pro Pro Leu Gln Gly Asp Phe Gly Ala Phe Ser Ala Phe
305                 310                 315                 320

Tyr Phe Val Met Lys Phe Leu Asn Leu Thr Ser Glu Lys Val Ser Gln
                325                 330                 335

Glu Lys Val Thr Glu Met Met Lys Lys Phe Cys Ala Gln Pro Trp Glu
            340                 345                 350

Glu Ile Lys Thr Ser Tyr Ala Gly Val Lys Glu Lys Tyr Leu Ser Glu
        355                 360                 365

Phe Cys Phe Ser Gly Thr Tyr Ile Leu Ser Leu Leu Gln Gln Gly Tyr
    370                 375                 380

His Phe Thr Ala Asp Ser Trp Glu His Ile His Phe Ile Gly Lys Ile
385                 390                 395                 400

Gln Gly Ser Asp Ala Gly Trp Thr Leu Gly Tyr Met Leu Asn Leu Thr
                405                 410                 415

Asn Met Ile Pro Ala Glu Gln Pro Leu Ser Thr Pro Leu Ser His Ser
            420                 425                 430

Thr

<210> SEQ ID NO 220
<211> LENGTH: 1299
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 220
gcccctacca gcagcagcac ccagaacaag gccctgcccg agaacgtgaa gtacggcatc      60
gtgctggatg ccggcagcag ccacaccagc ctgtacatct acaagtggcc tgccgagaaa    120
gaaaacgaca ccggcgtggt gcatcaggtg aagagtgca gagtgaaggg ccctggcatc     180
agcaagttcg tgcagaaagt gaacgagatc ggcatctacc tgaccgactg catggaacgg    240
gccatggaag tgatccccag aagccagcac caggaaaccc ccgtgtatct gggagccacc    300
gccggcatga gactgctgag aatggaaagc gaggaactgg ccgaccgggt gctggacgtg    360
gtggaaagaa gcctgagcaa ctacccattc gattttcaag cgccagaat catcaccggc     420 caggaagaag cgcctacgg ctggatcacc atcaactacc tgctgggcaa gttcagccag     480
aagaatcagg aaaccttcgg cgccctggac ctgggcggag cttctaccca agtgaccttc    540
```

```
gtgccccaga atcagaccat cgagagcccc gacaacgccc tgcagttccg gctgtacggc    600
aaggactaca atgtgtacac ccacagcttt ctgtgctacg gaaaggacca ggctctgtgg    660
cagaagctgg ccaaggacat ccaggtggcc agcaacgaga tcctgcggga cccttgcttc    720 cacccccggct acaagaaagt cgtgaacgtg tccgacctgt acaagacccc ctgcaccaag    780
agattcgaga tgaccctgcc cttccagcag ttcgagatcc agggcatcgg caattaccag    840
cagtgccacc agagcatcct ggaactgttc aacaccagct actgccccta cagccagtgc    900
gccttcaacg gcatcttcct gccacctctg caggggatt tcggcgcctt cagcgccttc    960
tacttcgtga tgaagttcct gaacctgacc agcgagaagg tgtcccagga aaaagtgaca    1020
gagatgatga agaagttctg cgcccagccc tgggaggaaa tcaagacctc ctacgctggc    1080
gtgaaagaga agtacctgag cgagttctgc ttcagcggca cctacatcct gagcctgctg    1140
cagcagggct accacttcac cgccgatagc tgggagcaca tccacttcat cggcaagatt    1200
cagggcagcg acgccggctg gacactgggc tacatgctga atctgaccaa catgatcccc    1260
gccgagcagc ccctgagcac acctctgagc cacagcacc                           1299
```

<210> SEQ ID NO 221
<211> LENGTH: 430
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 221

```
Ala Pro Thr Thr Gln Asn Lys Ala Leu Pro Glu Asn Val Lys Tyr Gly
1               5                   10                  15

Ile Val Leu Asp Ala Gly Ser Ser His Thr Ser Leu Tyr Ile Tyr Lys
            20                  25                  30

Trp Pro Ala Glu Lys Glu Asn Asp Thr Gly Val Val His Gln Val Glu
        35                  40                  45

Glu Cys Arg Val Lys Gly Pro Gly Ile Ser Lys Phe Val Gln Lys Val
    50                  55                  60

Asn Glu Ile Gly Ile Tyr Leu Thr Asp Cys Met Glu Arg Ala Met Glu
65                  70                  75                  80

Val Ile Pro Arg Ser Gln His Gln Glu Thr Pro Val Tyr Leu Gly Ala
                85                  90                  95

Thr Ala Gly Met Arg Leu Leu Arg Met Glu Ser Glu Glu Leu Ala Asp
            100                 105                 110

Arg Val Leu Asp Val Val Glu Arg Ser Leu Ser Asn Tyr Pro Phe Asp
        115                 120                 125

Phe Gln Gly Ala Arg Ile Ile Thr Gly Gln Glu Gly Ala Tyr Gly
    130                 135                 140

Trp Ile Thr Ile Asn Tyr Leu Leu Gly Lys Phe Ser Gln Lys Asn Gln
145                 150                 155                 160

Glu Thr Phe Gly Ala Leu Asp Leu Gly Gly Ala Ser Thr Gln Val Thr
                165                 170                 175

Phe Val Pro Gln Asn Gln Thr Ile Glu Ser Pro Asp Asn Ala Leu Gln
            180                 185                 190

Phe Arg Leu Tyr Gly Lys Asp Tyr Asn Val Tyr Thr His Ser Phe Leu
        195                 200                 205

Cys Tyr Gly Lys Asp Gln Ala Leu Trp Gln Lys Leu Ala Lys Asp Ile
    210                 215                 220
```

```
Gln Val Ala Ser Asn Glu Ile Leu Arg Asp Pro Cys Phe His Pro Gly
225                 230                 235                 240

Tyr Lys Lys Val Val Asn Val Ser Asp Leu Tyr Lys Thr Pro Cys Thr
            245                 250                 255

Lys Arg Phe Glu Met Thr Leu Pro Phe Gln Gln Phe Glu Ile Gln Gly
        260                 265                 270

Ile Gly Asn Tyr Gln Gln Cys His Gln Ser Ile Leu Glu Leu Phe Asn
            275                 280                 285

Thr Ser Tyr Cys Pro Tyr Ser Gln Cys Ala Phe Asn Gly Ile Phe Leu
        290                 295                 300

Pro Pro Leu Gln Gly Asp Phe Gly Ala Phe Ser Ala Phe Tyr Ser Val
305                 310                 315                 320

Met Lys Phe Leu Asn Leu Thr Ser Glu Lys Val Ser Gln Glu Lys Val
                325                 330                 335

Thr Glu Met Met Lys Phe Cys Ala Gln Pro Trp Glu Glu Ile Lys
            340                 345                 350

Thr Ser Tyr Ala Gly Val Lys Glu Lys Tyr Leu Ser Glu Tyr Cys Phe
            355                 360                 365

Ser Gly Thr Tyr Ile Leu Ser Leu Leu Leu Gln Gly Tyr His Phe Thr
        370                 375                 380

Ala Asp Ser Trp Glu His Ile His Phe Ile Gly Lys Ile Gln Gly Ser
385                 390                 395                 400

Asp Ala Gly Trp Thr Leu Gly Tyr Met Leu Asn Leu Thr Asn Met Ile
            405                 410                 415

Pro Ala Glu Gln Pro Leu Ser Thr Pro Leu Ser His Ser Thr
            420                 425                 430

<210> SEQ ID NO 222
<211> LENGTH: 1290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 222
gcccctacca cccagaacaa ggccctgccc gagaacgtga agtacggcat cgtgctggat    60
gccggcagca gccacaccag cctgtacatc tacaagtggc ctgccgagaa agaaaacgac   120
accggcgtgg tgcatcaggt ggaagagtgc agagtgaagg ccctggcat cagcaagttc    180 gtgcagaaag tgaacgagat cggcatctac ctgaccgact gcatggaacg ggccatggaa   240
gtgatcccca aagccagca ccaggaaacc cccgtgtatc tgggagccac cgccggcatg    300
agactgctga atggaaag cgaggaactg gccgaccggg tgctggacgt ggtggaaaga    360
agcctgagca actacccatt cgattttcaa ggcgccagaa tcatcaccgg ccaggaagaa   420
ggcgcctacg ctggatcac catcaactac ctgctgggca gttcagcca aagaatcag    480 gaaaccttcg gcgccttgga cctgggcgga gcttctaccc aagtgacctt cgtgccccag   540
aatcagacca tcgagagccc cgacaacgcc ctgcagttcc ggctgtacgg caaggactac   600
aatgtgtaca cccacagctt tctgtgctac ggaaaggacc aggctctgtg cagaagctg    660 gccaaggaca tccaggtggc cagcaacgag atcctgcggg acccttgctt ccaccccggc   720
tacaagaaag tcgtgaacgt gtccgacctg tacaagaccc cctgcaccaa agagattcgag   780 atgaccctgc ccttccagca gttcgagatc cagggcatcg gcaattacca gcagtgccac   840
```

```
cagagcatcc tggaactgtt caacaccagc tactgcccct acagccagtg cgccttcaac    900
ggcatcttcc tgccacctct gcaggggat ttcggcgcct tcagcgcctt ctactccgtg     960
atgaagttcc tgaacctgac cagcgagaag gtgtcccagg aaaaagtgac agagatgatg   1020
aagaagttct gcgcccagcc ctgggaggaa atcaagaccc cctacgctgg cgtgaaagag   1080
aagtacctga gcgagtactg cttcagcggc acctacatcc tgagcctgct gctgcagggc   1140
taccacttca ccgccgatag ctgggagcac atccacttca tcggcaagat tcagggcagc   1200
gacgccggct ggacactggg ttacatgctg aatctgacca acatgatccc cgccgagcag   1260
cccctgagca cacctctgag ccacagcacc                                    1290

<210> SEQ ID NO 223
<211> LENGTH: 433
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 223

Ala Pro Thr Ser Ser Thr Gln Asn Lys Ala Leu Pro Glu Asn Val
1               5                   10                  15

Lys Tyr Gly Ile Val Leu Asp Ala Gly Ser Ser His Thr Ser Leu Tyr
            20                  25                  30

Ile Tyr Lys Trp Pro Ala Glu Lys Glu Asn Asp Thr Gly Val Val His
        35                  40                  45

Gln Val Glu Glu Cys Arg Val Lys Gly Pro Gly Ile Ser Lys Phe Val
    50                  55                  60

Gln Lys Val Asn Glu Ile Gly Ile Tyr Leu Thr Asp Cys Met Glu Arg
65                  70                  75                  80

Ala Met Glu Val Ile Pro Arg Ser Gln His Gln Glu Thr Pro Val Tyr
                85                  90                  95

Leu Gly Ala Thr Ala Gly Met Arg Leu Leu Arg Met Glu Ser Glu Glu
            100                 105                 110

Leu Ala Asp Arg Val Leu Asp Val Val Glu Arg Ser Leu Ser Asn Tyr
        115                 120                 125

Pro Phe Asp Phe Gln Gly Ala Arg Ile Ile Thr Gly Gln Glu Glu Gly
    130                 135                 140

Ala Tyr Gly Trp Ile Thr Ile Asn Tyr Leu Leu Gly Lys Phe Ser Gln
145                 150                 155                 160

Lys Asn Gln Glu Thr Phe Gly Ala Leu Asp Leu Gly Gly Ala Ser Thr
                165                 170                 175

Gln Val Thr Phe Val Pro Gln Asn Gln Thr Ile Glu Ser Pro Asp Asn
            180                 185                 190

Ala Leu Gln Phe Arg Leu Tyr Gly Lys Asp Tyr Asn Val Tyr Thr His
        195                 200                 205

Ser Phe Leu Cys Tyr Gly Lys Asp Gln Ala Leu Trp Gln Lys Leu Ala
    210                 215                 220

Lys Asp Ile Gln Val Ala Ser Asn Glu Ile Leu Arg Asp Pro Cys Phe
225                 230                 235                 240

His Pro Gly Tyr Lys Lys Val Val Asn Val Ser Asp Leu Tyr Lys Thr
                245                 250                 255

Pro Cys Thr Lys Arg Phe Glu Met Thr Leu Pro Phe Gln Gln Phe Glu
            260                 265                 270
```

```
Ile Gln Gly Ile Gly Asn Tyr Gln Gln Cys His Gln Ser Ile Leu Glu
            275                 280                 285

Leu Phe Asn Thr Ser Tyr Cys Pro Tyr Ser Gln Cys Ala Phe Asn Gly
        290                 295                 300

Ile Phe Leu Pro Pro Leu Gln Gly Asp Phe Gly Ala Phe Ser Ala Phe
305                 310                 315                 320

Tyr Ser Val Met Lys Phe Leu Asn Leu Thr Ser Glu Lys Val Ser Gln
                325                 330                 335

Glu Lys Val Thr Glu Met Met Lys Lys Phe Cys Ala Gln Pro Trp Glu
            340                 345                 350

Glu Ile Lys Thr Ser Tyr Ala Gly Val Lys Glu Lys Tyr Leu Ser Glu
        355                 360                 365

Tyr Cys Phe Ser Gly Thr Tyr Ile Leu Ser Leu Leu Leu Gln Gly Tyr
370                 375                 380

His Phe Thr Ala Asp Ser Trp Glu His Ile His Phe Ile Gly Lys Ile
385                 390                 395                 400

Gln Gly Ser Asp Ala Gly Trp Thr Leu Gly Tyr Met Leu Asn Leu Thr
                405                 410                 415

Asn Met Ile Pro Ala Glu Gln Pro Leu Ser Thr Pro Leu Ser His Ser
            420                 425                 430

Thr
```

```
<210> SEQ ID NO 224
<211> LENGTH: 1299
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 224
gcccctacca gcagcagcac ccagaacaag gccctgcccg agaacgtgaa gtacggcatc      60
gtgctggatg ccggcagcag ccacaccagc ctgtacatct acaagtggcc tgccgagaaa     120
gaaaacgaca ccggcgtggt gcatcaggtg aagagtgca gagtgaaggg ccctggcatc      180
agcaagttcg tgcagaaagt gaacgagatc ggcatctacc tgaccgactg catggaacgg     240
gccatggaag tgatccccag aagccagcac caggaaaccc ccgtgtatct gggagccacc     300
gccggcatga gactgctgag aatggaaagc gaggaactgg ccgaccgggt gctggacgtg     360
gtggaaagaa gcctgagcaa ctacccattc gattttcaag cgccagaat catcaccggc      420 caggaagaag gcgcctacgg ctggatcacc atcaactacc tgctgggcaa gttcagccag     480
aagaatcagg aaaccttcgg cgccttggac ctgggcggag cttctaccca gtgaccttc      540 gtgccccaga atcagaccat cgagagcccc gacaacgccc tgcagttccg gctgtacggc     600
aaggactaca atgtgtacac ccacagcttt ctgtgctacg aaaggaccaa ggctctgtgg     660
cagaagctgg ccaaggacat ccaggtggcc agcaacgaga tcctgcggga cccttgcttc     720 cacccccggct acaagaaagt cgtgaacgtg tccgacctgt acaagaccccc ctgcaccaag     780 agattcgaga tgaccctgcc cttccagcag ttcgagatcc agggcatcgg caattaccag     840
cagtgccacc agagcatcct ggaactgttc aacaccagct actgccccta cagccagtgc     900
gccttcaacg gcatcttcct gccacctctg caggggggatt cggcgccttt cagcgccttc     960
tactccgtga tgaagttcct gaacctgacc agcgagaagg tgtcccagga aaaagtgaca    1020
```

-continued

```
gagatgatga agaagttctg cgcccagccc tgggaggaaa tcaagacctc ctacgctggc    1080
gtgaaagaga agtacctgag cgagtactgc ttcagcggca cctacatcct gagcctgctg    1140
ctgcagggct accacttcac cgccgatagc tgggagcaca tccacttcat cggcaagatt    1200
cagggcagcg acgccggctg gacactgggt tacatgctga atctgaccaa catgatcccc    1260
gccgagcagc ccctgagcac acctctgagc cacagcacc                           1299
```

<210> SEQ ID NO 225
<211> LENGTH: 430
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 225

```
Ala Pro Thr Thr Gln Asn Lys Ala Leu Pro Glu Asn Val Lys Tyr Gly
1               5                   10                  15

Ile Val Leu Asp Ala Gly Ser Ser His Thr Ser Leu Tyr Ile Tyr Lys
            20                  25                  30

Trp Pro Ala Glu Lys Glu Asn Asp Thr Gly Val Val His Gln Val Glu
        35                  40                  45

Glu Cys Arg Val Lys Gly Pro Gly Ile Ser Lys Phe Val Gln Lys Val
    50                  55                  60

Asn Glu Ile Gly Ile Tyr Leu Thr Asp Cys Met Glu Arg Ala Arg Glu
65                  70                  75                  80

Val Ile Pro Arg Ser Gln His Gln Glu Thr Pro Val Tyr Leu Gly Ala
                85                  90                  95

Thr Ala Gly Met Arg Leu Leu Arg Met Glu Ser Glu Glu Leu Ala Asp
            100                 105                 110

Arg Val Leu Asp Val Val Glu Arg Ser Leu Ser Asn Tyr Pro Phe Asp
        115                 120                 125

Phe Gln Gly Ala Arg Ile Ile Thr Gly Gln Glu Glu Gly Ala Tyr Gly
    130                 135                 140

Trp Ile Thr Ile Asn Tyr Leu Leu Gly Lys Phe Ser Gln Lys Asn Gln
145                 150                 155                 160

Glu Thr Phe Gly Ala Leu Asp Leu Gly Gly Ala Ser Thr Gln Val Thr
                165                 170                 175

Phe Val Pro Gln Asn Gln Thr Ile Glu Ser Pro Asp Asn Ala Leu Gln
            180                 185                 190

Phe Arg Leu Tyr Gly Lys Asp Tyr Asn Val Tyr Thr His Ser Phe Leu
        195                 200                 205

Cys Tyr Gly Lys Asp Gln Ala Leu Trp Gln Lys Leu Ala Lys Asp Ile
    210                 215                 220

Gln Val Ala Ser Asn Glu Ile Leu Arg Asp Pro Cys Phe His Pro Gly
225                 230                 235                 240

Tyr Lys Lys Val Val Asn Val Ser Asp Leu Tyr Lys Thr Pro Cys Thr
                245                 250                 255

Lys Arg Phe Glu Met Thr Leu Pro Phe Gln Gln Phe Glu Ile Gln Gly
            260                 265                 270

Ile Gly Asn Tyr Gln Gln Cys His Gln Ser Ile Leu Glu Leu Phe Asn
        275                 280                 285

Thr Ser Tyr Cys Pro Tyr Ser Gln Cys Ala Phe Asn Gly Ile Phe Leu
    290                 295                 300
```

```
Pro Pro Leu Gln Gly Asp Phe Gly Ala Phe Ser Ala Phe Tyr Phe Val
305                 310                 315                 320

Met Lys Phe Leu Asn Leu Thr Ser Glu Lys Val Ser Gln Glu Lys Val
                325                 330                 335

Thr Glu Met Met Lys Lys Phe Cys Ala Gln Pro Trp Glu Glu Ile Lys
            340                 345                 350

Thr Ser Tyr Ala Gly Val Lys Glu Lys Tyr Leu Ser Glu Phe Cys Phe
        355                 360                 365

Ser Gly Thr Tyr Ile Leu Ser Leu Leu Gln Gln Gly Tyr His Phe Thr
    370                 375                 380

Ala Asp Ser Trp Glu His Ile His Phe Ile Gly Lys Ile Gln Gly Ser
385                 390                 395                 400

Asp Ala Gly Trp Thr Leu Gly Tyr Met Leu Asn Leu Thr Asn Met Ile
                405                 410                 415

Pro Ala Glu Gln Pro Leu Ser Thr Pro Leu Ser His Ser Thr
                420                 425                 430
```

<210> SEQ ID NO 226
<211> LENGTH: 1290
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 226

```
gcccctacca cccagaacaa ggccctgccc gagaacgtga agtacggcat cgtgctggat      60
gccggcagca gccacaccag cctgtacatc tacaagtggc ctgccgagaa agaaaacgac     120
accggcgtgg tgcatcaggt ggaagagtgc agagtgaagg ccctggcat cagcaagttc     180
gtgcagaaag tgaacgagat cggcatctac ctgaccgact gcatggaacg ggccagggaa     240
gtgatcccca aagccagca ccaggaaacc cccgtgtatc tgggagccac cgccggcatg     300
agactgctga aatggaaag cgaggaactg gccgaccggg tgctggacgt ggtggaaaga     360
agcctgagca actacccatt cgattttcaa ggcgccagaa tcatcaccgg ccaggaagaa     420
ggcgcctacg gctggatcac catcaactac ctgctgggca agttcagcca agagaatcag     480
gaaaccttcg cgccctgga cctgggcgga gcttctaccc aagtgacctt cgtgccccag     540
aatcagacca tcgagagccc cgacaacgcc ctgcagttcc ggctgtacgg caaggactac     600
aatgtgtaca cccacagctt tctgtgctac ggaaaggacc aggctctgtg cagaagctg     660
gccaaggaca tccaggtggc cagcaacgag atcctgcggg accccttgctt ccaccccggc     720
tacaagaaag tcgtgaacgt gtccgacctg tacaagaccc cctgcaccaa gagattcgag     780
atgacccctgc ccttccagca gttcgagatc cagggcatcg gcaattacca gcagtgccac     840
cagagcatcc tggaactgtt caacaccagc tactgccccct acagccagtg cgccttcaac     900
ggcatcttcc tgccacctct gcaggggat ttcggcgcct cagcgccttt ctacttcgtg     960
atgaagttcc tgaacctgac cagcgagaag gtgtcccagg aaaaagtgac agagatgatg    1020
aagaagttct gcgcccagcc ctggaggaa atcaagacct cctacgctgg cgtgaaagag    1080
aagtacctga gcgagttttg cttcagcggc acctacatcc tgagcctgct gcagcagggc    1140
taccactca ccgccgatag ctgggagcac atccacttca tcggcaagat tcagggcagc    1200
gacgccggct ggacactggg ctacatgctg aatctgacca catgatccc cgccgagcag    1260
cccctgagca cacctctgag ccacagcacc                                    1290
```

```
<210> SEQ ID NO 227
<211> LENGTH: 433
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 227

Ala Pro Thr Ser Ser Thr Gln Asn Lys Ala Leu Pro Glu Asn Val
1               5                   10                  15

Lys Tyr Gly Ile Val Leu Asp Ala Gly Ser Ser His Thr Ser Leu Tyr
            20                  25                  30

Ile Tyr Lys Trp Pro Ala Glu Lys Glu Asn Asp Thr Gly Val Val His
        35                  40                  45

Gln Val Glu Glu Cys Arg Val Lys Gly Pro Gly Ile Ser Lys Phe Val
    50                  55                  60

Gln Lys Val Asn Glu Ile Gly Ile Tyr Leu Thr Asp Cys Met Glu Arg
65                  70                  75                  80

Ala Arg Glu Val Ile Pro Arg Ser Gln His Gln Glu Thr Pro Val Tyr
                85                  90                  95

Leu Gly Ala Thr Ala Gly Met Arg Leu Leu Arg Met Glu Ser Glu Glu
            100                 105                 110

Leu Ala Asp Arg Val Leu Asp Val Val Glu Arg Ser Leu Ser Asn Tyr
        115                 120                 125

Pro Phe Asp Phe Gln Gly Ala Arg Ile Ile Thr Gly Gln Glu Glu Gly
    130                 135                 140

Ala Tyr Gly Trp Ile Thr Ile Asn Tyr Leu Leu Gly Lys Phe Ser Gln
145                 150                 155                 160

Lys Asn Gln Glu Thr Phe Gly Ala Leu Asp Leu Gly Gly Ala Ser Thr
                165                 170                 175

Gln Val Thr Phe Val Pro Gln Asn Gln Thr Ile Glu Ser Pro Asp Asn
            180                 185                 190

Ala Leu Gln Phe Arg Leu Tyr Gly Lys Asp Tyr Asn Val Tyr Thr His
        195                 200                 205

Ser Phe Leu Cys Tyr Gly Lys Asp Gln Ala Leu Trp Gln Lys Leu Ala
    210                 215                 220

Lys Asp Ile Gln Val Ala Ser Asn Glu Ile Leu Arg Asp Pro Cys Phe
225                 230                 235                 240

His Pro Gly Tyr Lys Lys Val Val Asn Val Ser Asp Leu Tyr Lys Thr
                245                 250                 255

Pro Cys Thr Lys Arg Phe Glu Met Thr Leu Pro Phe Gln Gln Phe Glu
            260                 265                 270

Ile Gln Gly Ile Gly Asn Tyr Gln Gln Cys His Gln Ser Ile Leu Glu
        275                 280                 285

Leu Phe Asn Thr Ser Tyr Cys Pro Tyr Ser Gln Cys Ala Phe Asn Gly
    290                 295                 300

Ile Phe Leu Pro Pro Leu Gln Gly Asp Phe Gly Ala Phe Ser Ala Phe
305                 310                 315                 320

Tyr Phe Val Met Lys Phe Leu Asn Leu Thr Ser Glu Lys Val Ser Gln
                325                 330                 335

Glu Lys Val Thr Glu Met Met Lys Lys Phe Cys Ala Gln Pro Trp Glu
            340                 345                 350
```

```
Glu Ile Lys Thr Ser Tyr Ala Gly Val Lys Glu Lys Tyr Leu Ser Glu
            355                 360                 365

Phe Cys Phe Ser Gly Thr Tyr Ile Leu Ser Leu Leu Gln Gln Gly Tyr
    370                 375                 380

His Phe Thr Ala Asp Ser Trp Glu His Ile His Phe Ile Gly Lys Ile
385                 390                 395                 400

Gln Gly Ser Asp Ala Gly Trp Thr Leu Gly Tyr Met Leu Asn Leu Thr
                405                 410                 415

Asn Met Ile Pro Ala Glu Gln Pro Leu Ser Thr Pro Leu Ser His Ser
            420                 425                 430

Thr
```

<210> SEQ ID NO 228
<211> LENGTH: 1299
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 228

```
gcccctacca gcagcagcac ccagaacaag gccctgcccg agaacgtgaa gtacggcatc     60
gtgctggatg ccggcagcag ccacaccagc ctgtacatct acaagtggcc tgccgagaaa    120
gaaaacgaca ccggcgtggt gcatcaggtg aagagtgca gagtgaaggg ccctggcatc     180
agcaagttcg tgcagaaagt gaacgagatc ggcatctacc tgaccgactg catggaacgg    240
gccagggaag tgatccccag aagccagcac caggaaaccc ccgtgtatct gggagccacc    300
gccggcatga gactgctgag aatggaaagc gaggaactgg ccgaccgggt gctggacgtg    360
gtggaaagaa gcctgagcaa ctacccattc gattttcaag gcgccagaat catcaccggc    420
caggaagaag cgcctacgg ctggatcacc atcaactacc tgctgggcaa gttcagccag    480
aagaatcagg aaaccttcgg cgccctggac ctgggcggag cttctaccca agtgaccttc    540
gtgccccaga tcagaccat cgagagcccc gacaacgccc tgcagttccg gctgtacggc    600
aaggactaca atgtgtacac ccacagcttt ctgtgctacg aaaggaccca ggctctgtgg    660
cagaagctgg ccaaggacat ccaggtggcc agcaacgaga tcctgcggga cccttgcttc    720
cacccccggct acaagaaagt cgtgaacgtg tccgacctgt acaagacccc ctgcaccaag    780
agattcgaga tgaccctgcc cttccagcag ttcgagatcc agggcatcgg caattaccag    840
cagtgccacc agagcatcct ggaactgttc aacaccagct actgcccta cagccagtgc    900
gccttcaacg gcatcttcct gccacctctg caggggatt tcggcgcctt cagcgccttc    960
tacttcgtga tgaagttcct gaacctgacc agcgagaagg tgtcccagga aaaagtgaca   1020
gagatgatga agaagttctg cgcccagccc tgggaggaaa tcaagacctc ctacgctggc   1080
gtgaaagaga agtacctgag cgagttttgc ttcagcggca cctacatcct gagcctgctg   1140
cagcagggct accacttcac cgccgatagc tgggagcaca tccacttcat cggcaagatt   1200
cagggcagcg acgccggctg gacactgggc tacatgctga atctgaccaa catgatcccc   1260
gccgagcagc ccctgagcac acctctgagc cacagcacc                          1299
```

<210> SEQ ID NO 229
<211> LENGTH: 430
<212> TYPE: PRT
<213> ORGANISM: Artificial Sequence
<220> FEATURE:

<221> NAME/KEY: source
<223> OTHER INFORMATION: /note="Description of Artificial Sequence: Synthetic polypeptide"

<400> SEQUENCE: 229

```
Ala Pro Thr Thr Gln Asn Lys Ala Leu Pro Glu Asn Val Lys Tyr Gly
1               5                   10                  15

Ile Val Leu Asp Ala Gly Ser Ser His Thr Ser Leu Tyr Ile Tyr Lys
            20                  25                  30

Trp Pro Ala Glu Lys Glu Asn Asp Thr Gly Val Val His Gln Val Glu
        35                  40                  45

Glu Cys Arg Val Lys Gly Pro Gly Ile Ser Lys Phe Val Gln Lys Val
    50                  55                  60

Asn Glu Ile Gly Ile Tyr Leu Thr Asp Cys Met Glu Arg Ala Arg Glu
65                  70                  75                  80

Val Ile Pro Arg Ser Gln His Gln Glu Thr Pro Val Tyr Leu Gly Ala
                85                  90                  95

Thr Ala Gly Met Arg Leu Leu Arg Met Glu Ser Glu Glu Leu Ala Asp
            100                 105                 110

Arg Val Leu Asp Val Val Glu Arg Ser Leu Ser Asn Tyr Pro Phe Asp
        115                 120                 125

Phe Gln Gly Ala Arg Ile Ile Thr Gly Gln Glu Glu Gly Ala Tyr Gly
    130                 135                 140

Trp Ile Thr Ile Asn Tyr Leu Leu Gly Lys Phe Ser Gln Lys Asn Gln
145                 150                 155                 160

Glu Thr Phe Gly Ala Leu Asp Leu Gly Gly Ala Ser Thr Gln Val Thr
                165                 170                 175

Phe Val Pro Gln Asn Gln Thr Ile Glu Ser Pro Asp Asn Ala Leu Gln
            180                 185                 190

Phe Arg Leu Tyr Gly Lys Asp Tyr Asn Val Tyr Thr His Ser Phe Leu
        195                 200                 205

Cys Tyr Gly Lys Asp Gln Ala Leu Trp Gln Lys Leu Ala Lys Asp Ile
    210                 215                 220

Gln Val Ala Ser Asn Glu Ile Leu Arg Asp Pro Cys Phe His Pro Gly
225                 230                 235                 240

Tyr Lys Lys Val Val Asn Val Ser Asp Leu Tyr Lys Thr Pro Cys Thr
                245                 250                 255

Lys Arg Phe Glu Met Thr Leu Pro Phe Gln Gln Phe Glu Ile Gln Gly
            260                 265                 270

Ile Gly Asn Tyr Gln Gln Cys His Gln Ser Ile Leu Glu Leu Phe Asn
        275                 280                 285

Thr Ser Tyr Cys Pro Tyr Ser Gln Cys Ala Phe Asn Gly Ile Phe Leu
    290                 295                 300

Pro Pro Leu Gln Gly Asp Phe Gly Ala Phe Ser Ala Phe Tyr Ser Val
305                 310                 315                 320

Met Lys Phe Leu Asn Leu Thr Ser Glu Lys Val Ser Gln Glu Lys Val
                325                 330                 335

Thr Glu Met Met Lys Lys Phe Cys Ala Gln Pro Trp Glu Glu Ile Lys
            340                 345                 350

Thr Ser Tyr Ala Gly Val Lys Glu Lys Tyr Leu Ser Glu Tyr Cys Phe
        355                 360                 365

Ser Gly Thr Tyr Ile Leu Ser Leu Leu Leu Gln Gly Tyr His Phe Thr
    370                 375                 380

Ala Asp Ser Trp Glu His Ile His Phe Ile Gly Lys Ile Gln Gly Ser
```

```
                385                 390                 395                 400
Asp Ala Gly Trp Thr Leu Gly Tyr Met Leu Asn Leu Thr Asn Met Ile
                    405                 410                 415

Pro Ala Glu Gln Pro Leu Ser Thr Pro Leu Ser His Ser Thr
                420                 425                 430

<210> SEQ ID NO 230
<211> LENGTH: 1290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 230
gcccctacca cccagaacaa ggccctgccc gagaacgtga agtacggcat cgtgctggac      60
gccggctcct cccacacctc cctgtacatc tacaagtggc ctgccgagaa agaaaacgac     120
accggcgtgg tgcaccaagt ggaagagtgc agagtgaagg ccccggcat ctccaagttc     180 gtgcagaaag tgaacgagat cggcatctac ctgaccgact gcatggaacg ggccagagaa     240
gtgatccctc ggtcccagca ccaggaaacc cctgtctacc tgggcgccac cgccggcatg     300
cggctgctgc ggatggaatc cgaggaactg gccgaccggg tgctggacgt ggtggaacgg     360
tccctgtcca actacccatt cgattttcaa ggcgccagaa tcatcaccgg ccaggaagag     420
ggcgcctacg gctggatcac catcaactac ctgctgggca gttctcccca gaagaatcag     480
gaaaccttcg cgcccctgga cctgggcgga gccagcaccc aagtcacatt cgtgccccag     540
aaccagacca tcgagagccc cgacaacgcc ctgcagttcc ggctgtacgg caaggactac     600
aacgtgtaca cccacagctt tctgtgctac ggcaaggacc aggccctgtg cagaagctg     660 gccaaggaca tccaagtggc ctccaacgag atcctgcggg accctgcttt ccaccccggc     720
tacaagaaag tggtcaacgt gtccgacctg tacaagaccc cttgcaccaa gagattcgag     780 atgacccctgc ccttccagca gttcgagatc cagggcatcg gcaactacca gcagtgccac     840
cagtccatcc tggaactgtt caacacctcc tactgcccct actcccagtg cgccttcaac     900
ggcatcttcc tgcctccact gcagggcgac ttcggcgcct ctccgccttt ctactccgtg     960
atgaagttcc tgaacctgac ctccgagaaa gtgtcccagg aaaaagtgac cgagatgatg    1020
aagaagttct gcgcccagcc ctgggaggaa atcaagacct cctacgctgg cgtgaaagag    1080 aagtaccctgt ccgagtactg cttctccggc acctacatcc tgtccctgct gctgcagggc    1140
taccacttca ccgccgacag ctgggagcac atccacttca tcggcaagat ccagggatcc    1200
gacgctggct ggaccctggg ctacatgctg aatctgacca acatgatccc cgccgagcag    1260
cccctgtcca cccctctgtc tcactccacc                                     1290

<210> SEQ ID NO 231
<211> LENGTH: 433
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 231

Ala Pro Thr Ser Ser Ser Thr Gln Asn Lys Ala Leu Pro Glu Asn Val
1               5                   10                  15
```

-continued

```
Lys Tyr Gly Ile Val Leu Asp Ala Gly Ser Ser His Thr Ser Leu Tyr
                 20                  25                  30
Ile Tyr Lys Trp Pro Ala Glu Lys Glu Asn Asp Thr Gly Val Val His
             35                  40                  45
Gln Val Glu Glu Cys Arg Val Lys Gly Pro Gly Ile Ser Lys Phe Val
 50                  55                  60
Gln Lys Val Asn Glu Ile Gly Ile Tyr Leu Thr Asp Cys Met Glu Arg
 65                  70                  75                  80
Ala Arg Glu Val Ile Pro Arg Ser Gln His Gln Glu Thr Pro Val Tyr
                 85                  90                  95
Leu Gly Ala Thr Ala Gly Met Arg Leu Leu Arg Met Glu Ser Glu Glu
                100                 105                 110
Leu Ala Asp Arg Val Leu Asp Val Val Glu Arg Ser Leu Ser Asn Tyr
                115                 120                 125
Pro Phe Asp Phe Gln Gly Ala Arg Ile Ile Thr Gly Gln Glu Glu Gly
                130                 135                 140
Ala Tyr Gly Trp Ile Thr Ile Asn Tyr Leu Leu Gly Lys Phe Ser Gln
145                 150                 155                 160
Lys Asn Gln Glu Thr Phe Gly Ala Leu Asp Leu Gly Gly Ala Ser Thr
                165                 170                 175
Gln Val Thr Phe Val Pro Gln Asn Gln Thr Ile Glu Ser Pro Asp Asn
                180                 185                 190
Ala Leu Gln Phe Arg Leu Tyr Gly Lys Asp Tyr Asn Val Tyr Thr His
                195                 200                 205
Ser Phe Leu Cys Tyr Gly Lys Asp Gln Ala Leu Trp Gln Lys Leu Ala
210                 215                 220
Lys Asp Ile Gln Val Ala Ser Asn Glu Ile Leu Arg Asp Pro Cys Phe
225                 230                 235                 240
His Pro Gly Tyr Lys Lys Val Val Asn Val Ser Asp Leu Tyr Lys Thr
                245                 250                 255
Pro Cys Thr Lys Arg Phe Glu Met Thr Leu Pro Phe Gln Gln Phe Glu
                260                 265                 270
Ile Gln Gly Ile Gly Asn Tyr Gln Gln Cys His Gln Ser Ile Leu Glu
                275                 280                 285
Leu Phe Asn Thr Ser Tyr Cys Pro Tyr Ser Gln Cys Ala Phe Asn Gly
290                 295                 300
Ile Phe Leu Pro Pro Leu Gln Gly Asp Phe Gly Ala Phe Ser Ala Phe
305                 310                 315                 320
Tyr Ser Val Met Lys Phe Leu Asn Leu Thr Ser Glu Lys Val Ser Gln
                325                 330                 335
Glu Lys Val Thr Glu Met Met Lys Lys Phe Cys Ala Gln Pro Trp Glu
                340                 345                 350
Glu Ile Lys Thr Ser Tyr Ala Gly Val Lys Glu Lys Tyr Leu Ser Glu
                355                 360                 365
Tyr Cys Phe Ser Gly Thr Tyr Ile Leu Ser Leu Leu Gln Gly Tyr
                370                 375                 380
His Phe Thr Ala Asp Ser Trp Glu His Ile His Phe Ile Gly Lys Ile
385                 390                 395                 400
Gln Gly Ser Asp Ala Gly Trp Thr Leu Gly Tyr Met Leu Asn Leu Thr
                405                 410                 415
Asn Met Ile Pro Ala Glu Gln Pro Leu Ser Thr Pro Leu Ser His Ser
                420                 425                 430

Thr
```

<210> SEQ ID NO 232
<211> LENGTH: 1299
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 232

```
gcccctacca gcagcagcac ccagaacaag gccctgcccg agaacgtgaa gtacggcatc      60
gtgctggatg ccggcagcag ccacaccagc ctgtacatct acaagtggcc tgccgagaaa     120
gaaaacgaca ccggcgtggt gcatcaggtg aagagtgca gagtgaaggg ccctggcatc      180
agcaagttcg tgcagaaagt gaacgagatc ggcatctacc tgaccgactg catggaacgg     240
gccagggaag tgatccccag aagccagcac caggaaaccc ccgtgtatct gggagccacc     300
gccggcatga ctgctgag aatggaaagc gaggaactgg ccgaccgggt gctggacgtg       360
gtggaaagaa gcctgagcaa ctacccattc gattttcaag cgccagaat catcaccggc      420
caggaagaag cgcctacgg ctggatcacc atcaactacc tgctgggcaa gttcagccag      480
aagaatcagg aaaccttcgg cgccttggac ctgggcggag cttctaccca agtgaccttc     540
gtgcccagaa tcagaccat cgagagcccc gacaacgccc tgcagttccg gctgtacggc      600
aaggactaca atgtgtacac ccacagcttt ctgtgctacg aaaggacca ggctctgtgg      660
cagaagctgg ccaaggacat ccaggtggcc agcaacgaga tcctgcggga ccccttgcttc    720
caccccggct acaagaaagt cgtgaacgtg tccgacctgt acaagacccc ctgcaccaag     780
agattcgaga tgaccctgcc cttccagcag ttcgagatcc agggcatcgg caattaccag     840
cagtgccacc agagcatcct ggaactgttc aacaccagct actgccccta cagccagtgc     900
gccttcaacg gcatcttcct gccacctctg caggggatt tcggcgcctt cagcgccttc      960
tactccgtga tgaagttcct gaacctgacc agcgagaagg tgtcccagga aaaagtgaca    1020
gagatgatga agaagttctg cgcccagccc tgggaggaaa tcaagacctc ctacgctggc    1080
gtgaaagaga agtacctgag cgagtactgc ttcagcggca cctacatcct gagcctgctg    1140
ctgcagggct accacttcac cgccgatagc tgggagcaca tccacttcat cggcaagatt    1200
cagggcagcg acgccggctg gacactgggt tacatgctga atctgaccaa catgatcccc    1260
gccgagcagc ccctgagcac acctctgagc cacagcacc                           1299
```

<210> SEQ ID NO 233
<211> LENGTH: 430
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 233

```
Ala Pro Thr Thr Gln Asn Lys Ala Leu Pro Glu Asn Val Lys Tyr Gly
1               5                   10                  15

Ile Val Leu Asp Ala Gly Ser Ser His Thr Ser Leu Tyr Ile Tyr Lys
            20                  25                  30

Trp Pro Ala Glu Lys Glu Asn Asp Thr Gly Val Val His Gln Val Glu
        35                  40                  45

Glu Cys Arg Val Lys Gly Pro Gly Ile Ser Lys Phe Val Gln Lys Val
```

```
            50                  55                  60
Asn Glu Ile Gly Ile Tyr Leu Thr Asp Cys Met Glu Arg Ala Met Glu
 65                  70                  75                  80

Val Ile Pro Arg Ser Gln His Gln Glu Thr Pro Val Tyr Leu Gly Ala
                 85                  90                  95

Thr Ala Gly Met Arg Leu Leu Arg Met Glu Ser Glu Glu Leu Ala Asp
            100                 105                 110

Arg Val Leu Asp Val Val Glu Arg Ser Leu Ser Asn Tyr Pro Phe Asp
        115                 120                 125

Phe Gln Gly Ala Arg Ile Ile Thr Gly Gln Glu Gly Ala Tyr Gly
        130                 135                 140

Trp Ile Thr Ile Asn Tyr Leu Leu Gly Lys Phe Ser Gln Lys Asn Gln
145                 150                 155                 160

Glu Thr Phe Gly Ala Leu Asp Leu Gly Gly Ala Ser Thr Gln Val Thr
                165                 170                 175

Phe Val Pro Gln Asn Gln Thr Ile Glu Ser Pro Asp Asn Ala Leu Gln
            180                 185                 190

Phe Arg Leu Tyr Gly Lys Asp Tyr Asn Val Tyr Thr His Ser Phe Leu
        195                 200                 205

Cys Tyr Gly Lys Asp Gln Ala Leu Trp Gln Lys Leu Ala Lys Asp Ile
    210                 215                 220

Gln Val Ala Ser Asn Glu Ile Leu Arg Asp Pro Cys Phe His Pro Gly
225                 230                 235                 240

Tyr Lys Lys Val Val Asn Val Ser Asp Leu Tyr Lys Thr Pro Cys Thr
                245                 250                 255

Lys Arg Phe Glu Met Thr Leu Pro Phe Gln Phe Glu Ile Gln Gly
            260                 265                 270

Ile Gly Asn Tyr Gln Gln Cys His Gln Ser Ile Leu Glu Leu Phe Asn
        275                 280                 285

Thr Ser Tyr Cys Pro Tyr Ser Gln Cys Ala Phe Asn Gly Ile Phe Leu
    290                 295                 300

Pro Pro Leu Gln Gly Asp Phe Gly Ala Phe Ser Ala Phe Tyr Ser Val
305                 310                 315                 320

Met Lys Phe Leu Asn Leu Thr Ser Glu Lys Val Ser Gln Glu Lys Val
                325                 330                 335

Thr Glu Met Met Lys Lys Phe Cys Ala Gln Pro Trp Glu Glu Ile Lys
            340                 345                 350

Thr Ser Tyr Ala Gly Val Lys Glu Lys Tyr Leu Ser Glu Tyr Cys Phe
        355                 360                 365

Ser Gly Thr Tyr Ile Leu Ser Leu Leu Gln Gln Gly Tyr His Phe Thr
    370                 375                 380

Ala Asp Ser Trp Glu His Ile His Phe Ile Gly Lys Ile Gln Gly Ser
385                 390                 395                 400

Asp Ala Gly Trp Thr Leu Gly Tyr Met Leu Asn Leu Thr Asn Met Ile
                405                 410                 415

Pro Ala Glu Gln Pro Leu Ser Thr Pro Leu Ser His Ser Thr
            420                 425                 430

<210> SEQ ID NO 234
<211> LENGTH: 1290
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic polynucleotide"

<400> SEQUENCE: 234

| | | | | |
|---|---|---|---|---|
| gcccctacca | cccagaacaa | ggccctgccc | gagaacgtga | agtacggcat cgtgctggat | 60 |
| gccggcagca | gccacaccag | cctgtacatc | tacaagtggc | ctgccgagaa agaaaacgac | 120 |
| accggcgtgg | tgcatcaggt | ggaagagtgc | agagtgaagg | gccctggcat cagcaagttc | 180 |
| gtgcagaaag | tgaacgagat | cggcatctac | ctgaccgact | gcatggaacg ggccatggaa | 240 |
| gtgatcccca | agccagca | ccaggaaacc | cccgtgtatc | tgggagccac cgccggcatg | 300 |
| agactgctga | atggaaag | cgaggaactg | gccgaccggg | tgctggacgt ggtgaaaga | 360 |
| agcctgagca | actacccatt | cgattttcaa | ggcgccagaa | tcatcaccgg ccaggaagaa | 420 |
| ggcgcctacg | gctggatcac | catcaactac | ctgctgggca | agttcagcca agaatcag | 480 |
| gaaaccttcg | gcgccctgga | cctgggcgga | gcttctaccc | aagtgacctt cgtgccccag | 540 |
| aatcagacca | tcgagagccc | cgacaacgcc | ctgcagttcc | ggctgtacgg caaggactac | 600 |
| aatgtgtaca | cccacagctt | tctgtgctac | ggaaaggacc | aggctctgtg cagaagctg | 660 |
| gccaaggaca | tccaggtggc | cagcaacgag | atcctgcggg | accttgctt ccaccccggc | 720 |
| tacaagaaag | tcgtgaacgt | gtccgacctg | tacaagaccc | cctgcaccaa gagattcgag | 780 |
| atgaccctgc | ccttccagca | gttcgagatc | cagggcatcg | gcaattacca gcagtgccac | 840 |
| cagagcatcc | tggaactgtt | caacaccagc | tactgccct | acagccagtg cgccttcaac | 900 |
| ggcatcttcc | tgccacctct | gcaggggat | tcggcgcct | cagcgcctt ctactccgtg | 960 |
| atgaagttcc | tgaacctgac | cagcgagaag | gtgtcccagg | aaaagtgac agagatgatg | 1020 |
| aagaagttct | gcgcccagcc | ctgggaggaa | atcaagacct | cctacgctgg cgtgaaagag | 1080 |
| aagtacctga | gcagtactg | cttcagcggc | acctacatcc | tgagcctgct gcagcagggc | 1140 |
| taccacttca | ccgccgatag | ctgggagcac | atccacttca | tcggcaagat tcagggcagc | 1200 |
| gacgccggct | ggacactggg | ctacatgctg | aatctgacca | catgatccc cgccgagcag | 1260 |
| cccctgagca | cacctctgag | ccacagcacc | | | 1290 |

<210> SEQ ID NO 235
<211> LENGTH: 433
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 235

Ala Pro Thr Ser Ser Thr Gln Asn Lys Ala Leu Pro Glu Asn Val
1               5                   10                  15

Lys Tyr Gly Ile Val Leu Asp Ala Gly Ser Ser His Thr Ser Leu Tyr
            20                  25                  30

Ile Tyr Lys Trp Pro Ala Glu Lys Glu Asn Asp Thr Gly Val Val His
        35                  40                  45

Gln Val Glu Glu Cys Arg Val Lys Gly Pro Gly Ile Ser Lys Phe Val
    50                  55                  60

Gln Lys Val Asn Glu Ile Gly Ile Tyr Leu Thr Asp Cys Met Glu Arg
65                  70                  75                  80

Ala Met Glu Val Ile Pro Arg Ser Gln His Gln Glu Thr Pro Val Tyr
                85                  90                  95

Leu Gly Ala Thr Ala Gly Met Arg Leu Leu Arg Met Glu Ser Glu Glu

```
                100                 105                 110
Leu Ala Asp Arg Val Leu Asp Val Val Glu Arg Ser Leu Ser Asn Tyr
            115                 120                 125
Pro Phe Asp Phe Gln Gly Ala Arg Ile Ile Thr Gly Gln Glu Glu Gly
            130                 135                 140
Ala Tyr Gly Trp Ile Thr Ile Asn Tyr Leu Leu Gly Lys Phe Ser Gln
145                 150                 155                 160
Lys Asn Gln Glu Thr Phe Gly Ala Leu Asp Leu Gly Gly Ala Ser Thr
                165                 170                 175
Gln Val Thr Phe Val Pro Gln Asn Gln Thr Ile Glu Ser Pro Asp Asn
                180                 185                 190
Ala Leu Gln Phe Arg Leu Tyr Gly Lys Asp Tyr Asn Val Tyr Thr His
                195                 200                 205
Ser Phe Leu Cys Tyr Gly Lys Asp Gln Ala Leu Trp Gln Lys Leu Ala
            210                 215                 220
Lys Asp Ile Gln Val Ala Ser Asn Glu Ile Leu Arg Asp Pro Cys Phe
225                 230                 235                 240
His Pro Gly Tyr Lys Lys Val Val Asn Val Ser Asp Leu Tyr Lys Thr
                245                 250                 255
Pro Cys Thr Lys Arg Phe Glu Met Thr Leu Pro Phe Gln Gln Phe Glu
                260                 265                 270
Ile Gln Gly Ile Gly Asn Tyr Gln Gln Cys His Gln Ser Ile Leu Glu
            275                 280                 285
Leu Phe Asn Thr Ser Tyr Cys Pro Tyr Ser Gln Cys Ala Phe Asn Gly
            290                 295                 300
Ile Phe Leu Pro Pro Leu Gln Gly Asp Phe Gly Ala Phe Ser Ala Phe
305                 310                 315                 320
Tyr Ser Val Met Lys Phe Leu Asn Leu Thr Ser Glu Lys Val Ser Gln
                325                 330                 335
Glu Lys Val Thr Glu Met Met Lys Lys Phe Cys Ala Gln Pro Trp Glu
                340                 345                 350
Glu Ile Lys Thr Ser Tyr Ala Gly Val Lys Glu Lys Tyr Leu Ser Glu
            355                 360                 365
Tyr Cys Phe Ser Gly Thr Tyr Ile Leu Ser Leu Leu Gln Gln Gly Tyr
            370                 375                 380
His Phe Thr Ala Asp Ser Trp Glu His Ile His Phe Ile Gly Lys Ile
385                 390                 395                 400
Gln Gly Ser Asp Ala Gly Trp Thr Leu Gly Tyr Met Leu Asn Leu Thr
                405                 410                 415
Asn Met Ile Pro Ala Glu Gln Pro Leu Ser Thr Pro Leu Ser His Ser
                420                 425                 430
Thr

<210> SEQ ID NO 236
<211> LENGTH: 1299
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 236
gcccctacca gcagcagcac ccagaacaag gccctgcccg agaacgtgaa gtacggcatc      60
gtgctggatg ccggcagcag ccacaccagc ctgtacatct acaagtggcc tgccgagaaa     120
```

```
gaaaacgaca ccggcgtggt gcatcaggtg gaagagtgca gagtgaaggg ccctggcatc    180
agcaagttcg tgcagaaagt gaacgagatc ggcatctacc tgaccgactg catggaacgg    240
gccatggaag tgatccccag aagccagcac caggaaaccc ccgtgtatct gggagccacc    300
gccggcatga gactgctgag aatggaaagc gaggaactgg ccgaccgggt gctggacgtg    360
gtggaaagaa gcctgagcaa ctacccattc gattttcaag gcgccagaat catcaccggc    420
caggaagaag gcgcctacgg ctggatcacc atcaactacc tgctgggcaa gttcagccag    480
aagaatcagg aaaccttcgg cgccctggac ctgggcggag cttctaccca agtgaccttc    540
gtgccccaga atcagaccat cgagagcccc gacaacgccc tgcagttccg gctgtacggc    600
aaggactaca atgtgtacac ccacagcttt ctgtgctacg aaaggaccag ggctctgtgg    660
cagaagctgg ccaaggacat ccaggtggcc agcaacgaga tcctgcggga cccttgcttc    720 cacccggct acaagaaagt cgtgaacgtg tccgacctgt acaagacccc ctgcaccaag    780
agattcgaga tgaccctgcc cttccagcag ttcgagatcc agggcatcgg caattaccag    840
cagtgccacc agagcatcct ggaactgttc aacaccagct actgccccta cagccagtgc    900
gccttcaacg gcatcttcct gccacctctg caggggggatt cggcgccctt cagcgccttc    960
tactccgtga tgaagttcct gaacctgacc agcgagaagg tgtcccagga aaaagtgaca   1020
gagatgatga gaagttctg cgcccagccc tgggaggaaa tcaagacctc ctacgctggc   1080
gtgaaagaga agtacctgag cgagtactgc ttcagcggca cctacatcct gagcctgctg   1140
cagcagggct accacttcac cgccgatagc tgggagcaca tccacttcat cggcaagatt   1200
cagggcagcg acgccggctg gacactgggc tacatgctga atctgaccaa catgatcccc   1260
gccgagcagc ccctgagcac acctctgagc cacagcacc                         1299
```

<210> SEQ ID NO 237
<211> LENGTH: 430
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 237

Ala Pro Thr Thr Gln Asn Lys Ala Leu Pro Glu Asn Val Lys Tyr Gly
1               5                   10                  15

Ile Val Leu Asp Ala Gly Ser Ser His Thr Ser Leu Tyr Ile Tyr Lys
            20                  25                  30

Trp Pro Ala Glu Lys Glu Asn Asp Thr Gly Val Val His Gln Val Glu
        35                  40                  45

Glu Cys Arg Val Lys Gly Pro Gly Ile Ser Lys Phe Val Gln Lys Val
    50                  55                  60

Asn Glu Ile Gly Ile Tyr Leu Thr Asp Cys Met Glu Arg Ala Arg Glu
65                  70                  75                  80

Val Ile Pro Arg Ser Gln His Gln Glu Thr Pro Val Tyr Leu Gly Ala
                85                  90                  95

Thr Ala Gly Met Arg Leu Leu Arg Met Glu Ser Glu Glu Leu Ala Asp
            100                 105                 110

Arg Val Leu Asp Val Val Glu Arg Ser Leu Ser Asn Tyr Pro Phe Asp
        115                 120                 125

Phe Gln Gly Ala Arg Ile Ile Thr Gly Gln Glu Glu Gly Ala Tyr Gly
    130                 135                 140

Trp Ile Thr Ile Asn Tyr Leu Leu Gly Lys Phe Ser Gln Lys Asn Gln
145                 150                 155                 160

Glu Thr Phe Gly Ala Leu Asp Leu Gly Gly Ala Ser Thr Gln Val Thr
            165                 170                 175

Phe Val Pro Gln Asn Gln Thr Ile Glu Ser Pro Asp Asn Ala Leu Gln
            180                 185                 190

Phe Arg Leu Tyr Gly Lys Asp Tyr Asn Val Tyr Thr His Ser Phe Leu
            195                 200                 205

Cys Tyr Gly Lys Asp Gln Ala Leu Trp Gln Lys Leu Ala Lys Asp Ile
210                 215                 220

Gln Val Ala Ser Asn Glu Ile Leu Arg Asp Pro Cys Phe His Pro Gly
225                 230                 235                 240

Tyr Lys Lys Val Val Asn Val Ser Asp Leu Tyr Lys Thr Pro Cys Thr
            245                 250                 255

Lys Arg Phe Glu Met Thr Leu Pro Phe Gln Gln Phe Glu Ile Gln Gly
            260                 265                 270

Ile Gly Asn Tyr Gln Gln Cys His Gln Ser Ile Leu Glu Leu Phe Asn
            275                 280                 285

Thr Ser Tyr Cys Pro Tyr Ser Gln Cys Ala Phe Asn Gly Ile Phe Leu
            290                 295                 300

Pro Pro Leu Gln Gly Asp Phe Gly Ala Phe Ser Ala Phe Tyr Phe Val
305                 310                 315                 320

Met Lys Phe Leu Asn Leu Thr Ser Glu Lys Val Ser Gln Glu Lys Val
            325                 330                 335

Thr Glu Met Met Lys Lys Phe Cys Ala Gln Pro Trp Glu Glu Ile Lys
            340                 345                 350

Thr Ser Tyr Ala Gly Val Asn Glu Lys Tyr Leu Ser Glu Phe Cys Phe
            355                 360                 365

Ser Gly Thr Tyr Ile Leu Ser Leu Leu Leu Gln Gly Tyr His Phe Thr
370                 375                 380

Ala Asp Ser Trp Glu His Ile His Phe Ile Gly Lys Ile Gln Gly Ser
385                 390                 395                 400

Asp Ala Gly Trp Thr Leu Gly Tyr Met Leu Asn Leu Thr Asn Met Ile
            405                 410                 415

Pro Ala Glu Gln Pro Leu Ser Thr Pro Leu Ser His Ser Thr
            420                 425                 430

<210> SEQ ID NO 238
<211> LENGTH: 1290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 238
gcccctacca cccagaacaa ggccctgccc gagaacgtga agtacggcat cgtgctggat    60
gccggcagca gccacaccag cctgtacatc tacaagtggc ctgccgagaa agaaaacgac   120
accggcgtgg tgcatcaggt ggaagagtgc agagtgaagg ccctggcat cagcaagttc    180 gtgcagaaag tgaacgagat cggcatctac ctgaccgact gcatggaacg ggccagggaa   240
gtgatcccca agccagca ccaggaaacc cccgtgtatc tgggagccac cgccggcatg     300
agactgctga gaatggaaag cgaggaactg gccgaccggg tgctggacgt ggtggaaaga   360

-continued

```
agcctgagca actacccatt cgattttcaa ggcgccagaa tcatcaccgg ccaggaagaa    420
ggcgcctacg gctggatcac catcaactac ctgctgggca agttcagcca agaatcag     480 gaaaccttcg gcgccctgga cctgggcgga gcttctaccc aagtgacctt cgtgccccag    540
aatcagacca tcgagagccc cgacaacgcc ctgcagttcc ggctgtacgg caaggactac    600
aatgtgtaca cccacagctt tctgtgctac ggaaaggacc aggctctgtg gcagaagctg    660
gccaaggaca tccaggtggc cagcaacgag atcctgcggg acccttgctt ccaccccggc    720
tacaagaaag tcgtgaacgt gtccgacctg tacaagaccc cctgcaccaa gagattcgag    780
atgacccctg ccttccagca gttcgagatc cagggcatcg caattacca gcagtgccac     840 cagagcatcc tggaactgtt caacaccagc tactgcccct acagccagtg cgccttcaac    900
ggcatcttcc tgccacctct gcaggggat ttcggcgcct cagcgccttc tacttcgtg      960 atgaagttcc tgaacctgac cagcgagaag gtgtcccagg aaaaagtgac agagatgatg    1020
aagaagttct gcgcccaacc ctgggaggaa atcaagacct cctacgctgg cgtgaacgag    1080
aagtacctga gcgagttttg cttcagcggc acctacatcc tgagcctgct gctgcagggc    1140
taccacttca ccgccgatag ctgggagcac atccacttca tcggcaagat tcagggcagc    1200
gacgccggct ggacactggg ctacatgctg aatctgacca catgatccc cgccgagcag    1260 ccctgagca cacctctgag ccacagcacc                                     1290
```

<210> SEQ ID NO 239
<211> LENGTH: 433
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 239

```
Ala Pro Thr Ser Ser Thr Gln Asn Lys Ala Leu Pro Glu Asn Val
1               5                   10                  15

Lys Tyr Gly Ile Val Leu Asp Ala Gly Ser Ser His Thr Ser Leu Tyr
            20                  25                  30

Ile Tyr Lys Trp Pro Ala Glu Lys Glu Asn Asp Thr Gly Val Val His
        35                  40                  45

Gln Val Glu Glu Cys Arg Val Lys Gly Pro Gly Ile Ser Lys Phe Val
    50                  55                  60

Gln Lys Val Asn Glu Ile Gly Ile Tyr Leu Thr Asp Cys Met Glu Arg
65                  70                  75                  80

Ala Arg Glu Val Ile Pro Arg Ser Gln His Gln Glu Thr Pro Val Tyr
                85                  90                  95

Leu Gly Ala Thr Ala Gly Met Arg Leu Leu Arg Met Glu Ser Glu Glu
            100                 105                 110

Leu Ala Asp Arg Val Leu Asp Val Val Glu Arg Ser Leu Ser Asn Tyr
        115                 120                 125

Pro Phe Asp Phe Gln Gly Ala Arg Ile Ile Thr Gly Gln Glu Glu Gly
    130                 135                 140

Ala Tyr Gly Trp Ile Thr Ile Asn Tyr Leu Leu Gly Lys Phe Ser Gln
145                 150                 155                 160

Lys Asn Gln Glu Thr Phe Gly Ala Leu Asp Leu Gly Gly Ala Ser Thr
                165                 170                 175

Gln Val Thr Phe Val Pro Gln Asn Gln Thr Ile Glu Ser Pro Asp Asn
            180                 185                 190
```

```
Ala Leu Gln Phe Arg Leu Tyr Gly Lys Asp Tyr Asn Val Tyr Thr His
        195                 200                 205

Ser Phe Leu Cys Tyr Gly Lys Asp Gln Ala Leu Trp Gln Lys Leu Ala
    210                 215                 220

Lys Asp Ile Gln Val Ala Ser Asn Glu Ile Leu Arg Asp Pro Cys Phe
225                 230                 235                 240

His Pro Gly Tyr Lys Lys Val Val Asn Val Ser Asp Leu Tyr Lys Thr
                245                 250                 255

Pro Cys Thr Lys Arg Phe Glu Met Thr Leu Pro Phe Gln Gln Phe Glu
            260                 265                 270

Ile Gln Gly Ile Gly Asn Tyr Gln Gln Cys His Gln Ser Ile Leu Glu
        275                 280                 285

Leu Phe Asn Thr Ser Tyr Cys Pro Tyr Ser Gln Cys Ala Phe Asn Gly
    290                 295                 300

Ile Phe Leu Pro Pro Leu Gln Gly Asp Phe Gly Ala Phe Ser Ala Phe
305                 310                 315                 320

Tyr Phe Val Met Lys Phe Leu Asn Leu Thr Ser Glu Lys Val Ser Gln
                325                 330                 335

Glu Lys Val Thr Glu Met Met Lys Lys Phe Cys Ala Gly Pro Trp Glu
            340                 345                 350

Glu Ile Lys Thr Ser Tyr Ala Gly Val Asn Glu Lys Tyr Leu Ser Glu
        355                 360                 365

Phe Cys Phe Ser Gly Thr Tyr Ile Leu Ser Leu Leu Gln Gly Tyr
    370                 375                 380

His Phe Thr Ala Asp Ser Trp Glu His Ile His Phe Ile Gly Lys Ile
385                 390                 395                 400

Gln Gly Ser Asp Ala Gly Trp Thr Leu Gly Tyr Met Leu Asn Leu Thr
                405                 410                 415

Asn Met Ile Pro Ala Glu Gln Pro Leu Ser Thr Pro Leu Ser His Ser
            420                 425                 430

Thr
```

<210> SEQ ID NO 240
<211> LENGTH: 1299
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 240

```
gcccctacca gcagcagcac ccagaacaag gccctgcccg agaacgtgaa gtacggcatc      60
gtgctggatg ccggcagcag ccacaccagc ctgtacatct acaagtggcc tgccgagaaa     120
gaaaacgaca ccggcgtggt gcatcaggtg gaagagtgca gagtgaaggg ccctggcatc     180
agcaagttcg tgcagaaagt gaacgagatc ggcatctacc tgaccgactg catggaacgg     240
gccagggaag tgatccccag aagccagcac caggaaaccc ccgtgtatct gggagccacc     300
gccggcatga gactgctgag aatggaaagc gaggaactgg ccgaccgggt gctggacgtg     360
gtggaaagaa gcctgagcaa ctacccattc gattttcaag gcgccagaat catcaccggc     420
caggaagaag cgcctacggc ctggatcacc atcaactacc tgctgggcaa gttcagccag     480
aagaatcagg aaaccttcgg cgccctggac ctggcggag cttctaccca agtgaccttc     540
gtgcccagca tcagaccat cgagagcccc gacaacgccc tgcagttccg gctgtacggc     600
```

```
aaggactaca atgtgtacac ccacagcttt ctgtgctacg gaaaggacca ggctctgtgg    660
cagaagctgg ccaaggacat ccaggtggcc agcaacgaga tcctgcggga cccttgcttc    720
cacccaggct acaagaaagt cgtgaacgtg tccgacctgt acaagacccc ctgcaccaag    780
agattcgaga tgaccctgcc cttccagcag ttcgagatcc agggcatcgg caattaccag    840
cagtgccacc agagcatcct ggaactgttc aacaccagct actgccccta cagccagtgc    900
gccttcaacg gcatcttcct gccacctctg caggggggatt tcggcgcctt cagcgccttc    960
tacttcgtga tgaagttcct gaacctgacc agcgagaagg tgtcccagga aaaagtgaca    1020
gagatgatga gaagttctg cgcccaaccc tgggaggaaa tcaagacctc ctacgctggc    1080
gtgaacgaga agtacctgag cgagttttgc ttcagcggca cctacatcct gagcctgctg    1140
ctgcagggct accacttcac cgccgatagc tgggagcaca tccacttcat cggcaagatt    1200
cagggcagcg acgccggctg gacactgggc tacatgctga atctgaccaa catgatcccc    1260
gccgagcagc ccctgagcac acctctgagc cacagcacc                          1299
```

<210> SEQ ID NO 241
<211> LENGTH: 442
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 241

```
Ala Pro Thr Ser Ser Thr Lys Lys Thr Gln Leu Thr Ser Ser Thr
1               5                   10                  15

Gln Asn Lys Ala Leu Pro Glu Asn Val Lys Tyr Gly Ile Val Leu Asp
            20                  25                  30

Ala Gly Ser Ser His Thr Ser Leu Tyr Ile Tyr Lys Trp Pro Ala Glu
        35                  40                  45

Lys Glu Asn Asp Thr Gly Val Val His Gln Val Glu Glu Cys Arg Val
    50                  55                  60

Lys Gly Pro Gly Ile Ser Lys Phe Val Gln Lys Val Asn Glu Ile Gly
65                  70                  75                  80

Ile Tyr Leu Thr Asp Cys Met Glu Arg Ala Arg Glu Val Ile Pro Arg
                85                  90                  95

Ser Gln His Gln Glu Thr Pro Val Tyr Leu Gly Ala Thr Ala Gly Met
            100                 105                 110

Arg Leu Leu Arg Met Glu Ser Glu Glu Leu Ala Asp Arg Val Leu Asp
        115                 120                 125

Val Val Glu Arg Ser Leu Ser Asn Tyr Pro Phe Asp Phe Gln Gly Ala
    130                 135                 140

Arg Ile Ile Thr Gly Gln Glu Glu Gly Ala Tyr Gly Trp Ile Thr Ile
145                 150                 155                 160

Asn Tyr Leu Leu Gly Lys Phe Ser Gln Lys Asn Gln Glu Thr Phe Gly
                165                 170                 175

Ala Leu Asp Leu Gly Gly Ala Ser Thr Gln Val Thr Phe Val Pro Gln
            180                 185                 190

Asn Gln Thr Ile Glu Ser Pro Asp Asn Ala Leu Gln Phe Arg Leu Tyr
        195                 200                 205

Gly Lys Asp Tyr Asn Val Tyr Thr His Ser Phe Leu Cys Tyr Gly Lys
    210                 215                 220
```

Asp Gln Ala Leu Trp Gln Lys Leu Ala Lys Asp Ile Gln Val Ala Ser
225                 230                 235                 240

Asn Glu Ile Leu Arg Asp Pro Cys Phe His Pro Gly Tyr Lys Lys Val
            245                 250                 255

Val Asn Val Ser Asp Leu Tyr Lys Thr Pro Cys Thr Lys Arg Phe Glu
        260                 265                 270

Met Thr Leu Pro Phe Gln Gln Phe Glu Ile Gln Gly Ile Gly Asn Tyr
    275                 280                 285

Gln Gln Cys His Gln Ser Ile Leu Glu Leu Phe Asn Thr Ser Tyr Cys
290                 295                 300

Pro Tyr Ser Gln Cys Ala Phe Asn Gly Ile Phe Leu Pro Pro Leu Gln
305                 310                 315                 320

Gly Asp Phe Gly Ala Phe Ser Ala Phe Tyr Val Met Lys Phe Leu
            325                 330                 335

Asn Leu Thr Ser Glu Lys Val Ser Gln Glu Lys Val Thr Glu Met Met
            340                 345                 350

Lys Lys Phe Cys Ala Gln Pro Trp Glu Ile Lys Ser Tyr Ala
        355                 360                 365

Gly Val Asn Glu Lys Tyr Leu Ser Glu Phe Cys Phe Ser Gly Thr Tyr
370                 375                 380

Ile Leu Ser Leu Leu Leu Gln Gly Tyr His Phe Thr Ala Asp Ser Trp
385                 390                 395                 400

Glu His Ile His Phe Ile Gly Lys Ile Gln Gly Ser Asp Ala Gly Trp
            405                 410                 415

Thr Leu Gly Tyr Met Leu Asn Leu Thr Asn Met Ile Pro Ala Glu Gln
        420                 425                 430

Pro Leu Ser Thr Pro Leu Ser His Ser Thr
        435                 440

<210> SEQ ID NO 242
<211> LENGTH: 1326
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 242
gcccctacca gcagcagcac caagaaaacc cagctgacca gcagcaccca gaacaaggcc      60
ctgcccgaga acgtgaagta cggcatcgtg ctggatgccg gcagcagcca caccagcctg     120
tacatctaca gtggcctgc cgagaaagaa acgacaccg gcgtggtgca tcaggtggaa       180
gagtgcagag tgaagggccc tggcatcagc aagttcgtgc agaaagtgaa cgagatcggc     240
atctacctga ccgactgcat ggaacgggcc agggaagtga tccccagaag ccagcaccag     300 gaaaccccg tgtatctggg agccaccgcc ggcatgagac tgctgagaat ggaaagcgag      360
gaactggccg accgggtgct ggacgtggtg gaaagaagcc tgagcaacta cccattcgat     420
tttcaaggcg ccagaatcat caccggccag gaagaaggcg cctacggctg atcaccatc     480 aactacctgc tggcaagtt cagccagaag aatcaggaaa ccttcggcgc cctggacctg    540
ggcggagctt ctacccaagt gaccttcgtg ccccagaatc agaccatcga gagccccgac    600
aacgccctgc agttccggct gtacggcaag gactacaatg tgtacaccca cagctttctg    660
tgctacggaa aggaccaggc tctgtggcag aagctggcca aggacatcca ggtgccagc    720 aacgagatcc tgcgggaccc ttgcttccac cccggctaca agaaagtcgt gaacgtgtcc    780

```
gacctgtaca agacccctg caccaagaga ttcgagatga ccctgcctt ccagcagttc      840 gagatccagg gcatcggcaa ttaccagcag tgccaccaga gcatcctgga actgttcaac      900
accagctact gccctacag ccagtgcgcc ttcaacggca tcttcctgcc acctctgcag      960
ggggatttcg gcgccttcag cgccttctac ttcgtgatga agttcctgaa cctgaccagc     1020
gagaaggtgt cccaggaaaa agtgacagag atgatgaaga agttctgcgc caaccctgg     1080 gaggaaatca agacctccta cgctggcgtg aacgagaagt acctgagcga gttttgcttc     1140
agcggcacct acatcctgag cctgctgctg cagggctacc acttcaccgc cgatagctgg     1200
gagcacatcc acttcatcgg caagattcag ggcagcgacg ccggctggac actgggctac     1260
atgctgaatc tgaccaacat gatccccgcc gagcagcccc tgagcacacc tctgagccac     1320
agcacc                                                               1326
```

<210> SEQ ID NO 243
<211> LENGTH: 430
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 243

```
Ala Pro Thr Thr Gln Asn Lys Ala Leu Pro Glu Asn Val Lys Tyr Gly
1               5                  10                  15

Ile Val Leu Asp Ala Gly Ser Ser His Thr Ser Leu Tyr Ile Tyr Lys
            20                  25                  30

Trp Pro Ala Glu Lys Glu Asn Asp Thr Gly Val Val His Gln Val Glu
        35                  40                  45

Glu Cys Arg Val Lys Gly Pro Gly Ile Ser Lys Phe Val Gln Lys Val
    50                  55                  60

Asn Glu Ile Gly Ile Tyr Leu Thr Asp Cys Met Glu Arg Ala Arg Glu
65                  70                  75                  80

Val Ile Pro Arg Ser Gln His Gln Glu Thr Pro Val Tyr Leu Gly Ala
                85                  90                  95

Thr Ala Gly Met Arg Leu Leu Arg Met Glu Ser Glu Glu Leu Ala Asp
            100                 105                 110

Arg Val Leu Asp Val Val Glu Arg Ser Leu Ser Asn Tyr Pro Phe Asp
        115                 120                 125

Phe Gln Gly Ala Arg Ile Ile Thr Gly Gln Glu Glu Gly Ala Tyr Gly
    130                 135                 140

Trp Ile Thr Ile Asn Tyr Leu Leu Gly Lys Phe Ser Gln Lys Asn Gln
145                 150                 155                 160

Glu Thr Phe Gly Ala Leu Asp Leu Gly Gly Ala Ser Thr Gln Val Thr
                165                 170                 175

Phe Val Pro Gln Asn Gln Thr Ile Glu Ser Pro Asp Asn Ala Leu Gln
            180                 185                 190

Phe Arg Leu Tyr Gly Lys Asp Tyr Asn Val Tyr Thr His Ser Phe Leu
        195                 200                 205

Cys Tyr Gly Lys Asp Gln Ala Leu Trp Gln Lys Leu Ala Lys Asp Ile
    210                 215                 220

Gln Val Ala Ser Asn Glu Ile Leu Arg Asp Pro Cys Phe His Pro Gly
225                 230                 235                 240

Tyr Lys Lys Val Val Asn Val Ser Asp Leu Tyr Lys Thr Pro Cys Thr
```

```
                245                 250                 255
Lys Arg Phe Glu Met Thr Leu Pro Phe Gln Gln Phe Glu Ile Gln Gly
            260                 265                 270

Ile Gly Asn Tyr Gln Gln Cys His Gln Ser Ile Leu Glu Leu Phe Asn
        275                 280                 285

Thr Ser Tyr Cys Pro Tyr Ser Gln Cys Ala Phe Asn Gly Ile Phe Leu
    290                 295                 300

Pro Pro Leu Gln Gly Asp Phe Gly Ala Phe Ser Ala Phe Tyr Phe Val
305                 310                 315                 320

Met Lys Phe Leu Asn Leu Thr Ser Glu Lys Val Ser Gln Glu Lys Val
                325                 330                 335

Thr Glu Met Met Lys Phe Cys Ala Gln Pro Trp Glu Glu Ile Lys
            340                 345                 350

Thr Ser Tyr Ala Gly Val Lys Glu Lys Tyr Leu Ser Glu Tyr Cys Phe
        355                 360                 365

Ser Gly Thr Tyr Ile Leu Ser Leu Leu Gln Gln Gly Tyr His Phe Thr
    370                 375                 380

Ala Asp Ser Trp Glu Asp Ile His Phe Ile Gly Lys Ile Gln Gly Ser
385                 390                 395                 400

Asp Ala Gly Trp Thr Leu Gly Tyr Met Leu Asn Leu Thr Asn Met Ile
                405                 410                 415

Pro Ala Glu Gln Pro Leu Ser Thr Pro Leu Ser His Ser Thr
            420                 425                 430

<210> SEQ ID NO 244
<211> LENGTH: 1290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 244
gcccctacca cccagaacaa ggccctgccc gagaacgtga agtacggcat cgtgctggat      60
gccggcagca gccacaccag cctgtacatc tacaagtggc ctgccgagaa agaaaacgac     120
accggcgtgg tgcatcaggt ggaagagtgc agagtgaagg ccctggcat cagcaagttc     180 gtgcagaaag tgaacgagat cggcatctac ctgaccgact gcatggaacg ggccagggaa     240
gtgatcccca aagccagca ccaggaaacc cccgtgtatc tgggagccac cgccggcatg     300
agactgctga aatggaaag cgaggaactg gccgaccggg tgctggacgt ggtggaaaga     360
agcctgagca actacccatt cgattttcaa ggcgccagaa tcatcaccgg ccaggaagaa     420
ggcgcctacg gctggatcac catcaactac ctgctgggca agttcagcca agaatcag     480 gaaaccttcg gcgccctgga cctgggcgga gcttctaccc aagtgacctt cgtgccccag     540
aatcagacca tcgagagccc cgacaacgcc ctgcagttcc ggctgtacgg caaggactac     600
aatgtgtaca cccacagctt tctgtgctac ggaaaggacc aggctctgtg cagaagctg     660 gccaaggaca tccaggtggc cagcaacgag atcctgcggg acccttgctt ccaccccggc     720
tacaagaaag tcgtgaacgt gtccgacctg tacaagaccc cctgcaccaa agattcgag     780 atgacccctgc ccttccagca gttcgagatc cagggcatcg caattacca gcagtgccac     840 cagagcatcc tgaactgtt caacaccagc tactgcccct acagccagtg cgccttcaac     900
ggcatcttcc tgccacctct gcaggggat tcggcgcct tcagcgcctt ctacttcgtg     960
```

-continued

```
atgaagttcc tgaacctgac cagcgagaag gtgtcccagg aaaaagtgac agagatgatg    1020
aagaagttct gcgcccagcc ctgggaggaa atcaagacct cctacgctgg cgtgaaagag    1080
aagtacctga gcgagtactg cttcagcggc acctacatcc tgagcctgct gcagcagggc    1140
taccacttca ccgccgatag ctgggaggac atccacttca tcggcaagat tcagggcagc    1200
gacgccggct ggacactggg ctacatgctg aatctgacca acatgatccc cgccgagcag    1260 ccctgagca cacctctgag ccacagcacc                                      1290
```

<210> SEQ ID NO 245
<211> LENGTH: 433
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 245

```
Ala Pro Thr Ser Ser Thr Gln Asn Lys Ala Leu Pro Glu Asn Val
1               5                   10                  15

Lys Tyr Gly Ile Val Leu Asp Ala Gly Ser Ser His Thr Ser Leu Tyr
            20                  25                  30

Ile Tyr Lys Trp Pro Ala Glu Lys Glu Asn Asp Thr Gly Val Val His
        35                  40                  45

Gln Val Glu Glu Cys Arg Val Lys Gly Pro Gly Ile Ser Lys Phe Val
    50                  55                  60

Gln Lys Val Asn Glu Ile Gly Ile Tyr Leu Thr Asp Cys Met Glu Arg
65                  70                  75                  80

Ala Arg Glu Val Ile Pro Arg Ser Gln His Gln Glu Thr Pro Val Tyr
                85                  90                  95

Leu Gly Ala Thr Ala Gly Met Arg Leu Leu Arg Met Glu Ser Glu Glu
            100                 105                 110

Leu Ala Asp Arg Val Leu Asp Val Val Glu Arg Ser Leu Ser Asn Tyr
        115                 120                 125

Pro Phe Asp Phe Gln Gly Ala Arg Ile Ile Thr Gly Gln Glu Glu Gly
    130                 135                 140

Ala Tyr Gly Trp Ile Thr Ile Asn Tyr Leu Leu Gly Lys Phe Ser Gln
145                 150                 155                 160

Lys Asn Gln Glu Thr Phe Gly Ala Leu Asp Leu Gly Gly Ala Ser Thr
                165                 170                 175

Gln Val Thr Phe Val Pro Gln Asn Gln Thr Ile Glu Ser Pro Asp Asn
            180                 185                 190

Ala Leu Gln Phe Arg Leu Tyr Gly Lys Asp Tyr Asn Val Tyr Thr His
        195                 200                 205

Ser Phe Leu Cys Tyr Gly Lys Asp Gln Ala Leu Trp Gln Lys Leu Ala
    210                 215                 220

Lys Asp Ile Gln Val Ala Ser Asn Glu Ile Leu Arg Asp Pro Cys Phe
225                 230                 235                 240

His Pro Gly Tyr Lys Lys Val Val Asn Val Ser Asp Leu Tyr Lys Thr
                245                 250                 255

Pro Cys Thr Lys Arg Phe Glu Met Thr Leu Pro Phe Gln Gln Phe Glu
            260                 265                 270

Ile Gln Gly Ile Gly Asn Tyr Gln Gln Cys His Gln Ser Ile Leu Glu
        275                 280                 285

Leu Phe Asn Thr Ser Tyr Cys Pro Tyr Ser Gln Cys Ala Phe Asn Gly
```

```
                    290                 295                 300
Ile Phe Leu Pro Pro Leu Gln Gly Asp Phe Gly Ala Phe Ser Ala Phe
305                 310                 315                 320

Tyr Phe Val Met Lys Phe Leu Asn Leu Thr Ser Glu Lys Val Ser Gln
                325                 330                 335

Glu Lys Val Thr Glu Met Met Lys Lys Phe Cys Ala Gln Pro Trp Glu
                340                 345                 350

Glu Ile Lys Thr Ser Tyr Ala Gly Val Lys Glu Lys Tyr Leu Ser Glu
            355                 360                 365

Tyr Cys Phe Ser Gly Thr Tyr Ile Leu Ser Leu Leu Gln Gln Gly Tyr
        370                 375                 380

His Phe Thr Ala Asp Ser Trp Glu Asp Ile His Phe Ile Gly Lys Ile
385                 390                 395                 400

Gln Gly Ser Asp Ala Gly Trp Thr Leu Gly Tyr Met Leu Asn Leu Thr
                405                 410                 415

Asn Met Ile Pro Ala Glu Gln Pro Leu Ser Thr Pro Leu Ser His Ser
                420                 425                 430

Thr
```

<210> SEQ ID NO 246
<211> LENGTH: 1299
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 246

```
gcccctacca gcagcagcac ccagaacaag gccctgcccg agaacgtgaa gtacggcatc    60
gtgctggatg ccggcagcag ccacaccagc ctgtacatct acaagtggcc tgccgagaaa   120
gaaaacgaca ccggcgtggt gcatcaggtg aagagtgca gagtgaaggg ccctggcatc   180
agcaagttcg tgcagaaagt gaacgagatc ggcatctacc tgaccgactg catggaacgg   240
gccagggaag tgatccccag aagccagcac caggaaaccc ccgtgtatct gggagccacc   300
gccggcatga gactgctgag aatggaaagc gaggaactgg ccgaccgggt gctggacgtg   360
gtggaaagaa gcctgagcaa ctacccattc gattttcaag cgccagaat catcaccggc   420
caggaagaag gcgcctacgg ctggatcacc atcaactacc tgctgggcaa gttcagccag   480
aagaatcagg aaaccttcgg cgccctggac ctgggcggag cttctaccca gtgaccttc   540
gtgccccaga tcagaccat cgagagcccc gacaacgccc tgcagttccg gctgtacggc   600
aaggactaca atgtgtacac ccacagcttt ctgtgctacg aaaggaccca ggctctgtgg   660
cagaagctgg ccaaggacat ccaggtggcc agcaacgaga tcctgcggga cccttgcttc   720
caccccggct acaagaaagt cgtgaacgtg tccgacctgt acaagacccc ctgcaccaag   780
agattcgaga tgaccctgcc cttccagcag ttcgagatcc agggcatcgg caattaccag   840
cagtgccacc agagcatcct ggaactgttc aacaccagct actgccccta cagccagtgc   900
gccttcaacg gcatcttcct gccacctctg caggggatt tcggcgcctt cagcgccttc   960
tacttcgtga tgaagttcct gaacctgacc agcgagaagg tgtcccagga aaagtgaca  1020
gagatgatga agaagttctg cgcccagccc tgggaggaaa tcaagacctc ctacgctggc  1080
gtgaaagaga agtacctgag cgagtactgc ttcagcggca cctacatcct gagcctgctg  1140
cagcagggct accacttcac cgccgatagc tgggaggaca tccacttcat cggcaagatt  1200
```

```
cagggcagcg acgccggctg gacactgggc tacatgctga atctgaccaa catgatcccc    1260
gccgagcagc ccctgagcac acctctgagc cacagcacc                           1299
```

<210> SEQ ID NO 247
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 247

Glu Phe Arg His Asp Ser
1               5

<210> SEQ ID NO 248
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248

```
gaattccggc acgacagc                                                  18
```

<210> SEQ ID NO 249
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 249

His His His His His His
1               5

<210> SEQ ID NO 250
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250

```
catcatcatc atcatcac                                                  18
```

<210> SEQ ID NO 251
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Gly Gly Gly Gly Ser
1               5

```
<210> SEQ ID NO 252
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Val Lys Glu Lys Tyr Leu Ser Glu
1               5

<210> SEQ ID NO 253
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 253

Gln Glu Arg Trp Leu Arg Asp
1               5
```

SOLUBILIZED APYRASES, METHODS AND USE

This application is a 371 of PCT Application No. PCT/IB2019/056117 filed Jul. 17, 2019 which claims priority to EP application No. 18184269.1 filed Jul. 18, 2018, the contents of which are incorporated herein by reference in the entirety.

TECHNICAL FIELD

The present invention relates to design and therapeutic use of solubilized apyrase polypeptides, pharmaceuticals compositions, and methods useful for preventing and treating tissue damage.

BACKGROUND OF THE DISCLOSURE

Apyrase (ATP-diphosphatase, adenosine diphosphatase, ADPase, or ATP diphosphohydrolase) is a plasma membrane-bound enzyme group of enzymes active against both di- and triphosphate nucleotides (NDPs and NTPs) and hydrolyze NTPs to nucleotide monophosphates (NMPs) in two distinct successive phosphate-releasing steps, with NDPs as intermediates. Most of the ecto-ATPases that occur on the cell surface and hydrolyze extracellular nucleotides belong to this enzyme family. They differ from ATPases, which specifically hydrolyze ATP, by hydrolyzing both ATP and ADP.

The first known human apyrase, ectonucleoside triphosphate diphosphohydrolase-1 (gene: ENTPD1, protein: NTPDase1), also known as cluster of differentiation 39 (CD39, UniProt P49961, or SEQ ID NO: 1) is a cell surface-located enzymes with an extracellularly facing catalytic site.

Among the known human CD39 family, the member CD39L3 is known as an ecto-apyrase (ecto-ATPDase) with biochemical activity between CD39 and CD39L1 (ecto-ATPase). Specifically human CD39L3 has been solubilized and purified for therapeutic purposes, e.g. as disclosed in U.S. Pat. No. 7,247,300B1 (incorporated herein by reference) or included herein as SEQ ID NO: 3.

SUMMARY OF THE DISCLOSURE

The present disclosure is inter alia based on the unexpected finding that certain modifications of solubilized human apyrase, such as human CD39 lead to a surprisingly active protein, which is still safe and easy to manufacture.

According to a first aspect of the invention, a solubilized human apyrase with at least two modifications selected from the list consisting of: N terminal deletion, C terminal deletion and central modification is provided.

In one embodiment the solubilized human apyrase comprises a N terminal deletion, a C terminal deletion and a modification deletion.

In one embodiment, the central modification comprises a deletion of one or more amino acids. In another embodiment, the central modification comprises a point mutation of one or more amino acids, such as a substitution mutation. In yet another embodiment, the central modification is a combination of a deletion of one or more amino acids and a point mutation, such as a substitution mutation, of one or more amino acids.

The N terminal deletion may be between 30 and 50 amino acids deleted from the N terminus of the wild type CD39 sequence according to SEQ ID NO: 1, such as a deletion of 30, 31, 32, 33, 34, 35, 36, 37, 38, 39, 40, 41, 42, 43, 44, 45, 46, 47, 48, 49 or 50 amino acids. In a preferred embodiment, the N terminal deletion is 34, 37, 38 or 45 amino acids.

The C terminal deletion may be between 20 and 40 amino acids deleted from the C terminus of the wild type CD39 sequence according to SEQ ID NO: 1, such as a deletion of 20, 21, 22, 23, 24, 25, 26, 27, 28, 29, 30, 31, 32, 33, 34, 35, 36, 37, 38, 39 or 40 amino acids. In a preferred embodiment, the C terminal deletion is 22, 29 of 37 amino acids.

The central deletion may be between 10 and 15 consecutive amino acids, deleted from the wild type CD39 sequence according to SEQ ID NO: 1, such as a deletion of 10, 11, 12, 13, 14 or 15 amino acids. In a preferred embodiment, the central deletion is 12 amino acids, such as amino acids number 193 to 204 in relation to the wild type CD39 sequence according to SEQ ID NO: 1.

In one embodiment, the solubilized human apyrase comprises one, two, three, four, or five point mutation(s) in relation to the wild type CD39 sequence according to SEQ ID NO: 1, selected from the group consisting of K71 E, N73Q, V95A, G102D, Y104S, T106S, R113M, L149M, V151A, E173D, T229A, L254M, K258R, W263R, E276D, N292Q, R304G, I319T, N327Q, A362N, F365S, N371Q, K405N, Y412F, L424Q, H436D, I437N, F439S, G441D, N457Q, P463S, and S469R.

In one embodiment the solubilized human apyrase comprises a sequence selected from the group consisting of SEQ ID NO: 4, SEQ ID NO: 6, SEQ ID NO: 32, SEQ ID NO: 54, SEQ ID NO: 56, SEQ ID NO: 70, SEQ ID NO: 76, and SEQ ID NO: 78.

In one embodiment, the solubilized human apyrase comprises a sequence selected from the group consisting of SEQ ID NO: 131, SEQ ID NO: 133, SEQ ID NO: 135, SEQ ID NO: 137, SEQ ID NO: 139 and SEQ ID NO: 141.

In one specific embodiment, the solubilized human apyrase comprises of a sequence selected from the group consisting of SEQ ID NO: 213, SEQ ID NO: 227, SEQ ID NO: 219, SEQ ID NO: 227, SEQ ID NO: 217, SEQ ID NO: 209, SEQ ID NO: 221, SEQ ID NO: 72, SEQ ID NO: 215, SEQ ID NO: 223, SEQ ID NO: 211, SEQ ID NO: 58 and SEQ ID NO: 229.

In one specific embodiment, the solubilized human apyrase consists of a sequence selected from the group consisting of SEQ ID NO: 213, SEQ ID NO: 227, SEQ ID NO: 219, SEQ ID NO: 227, SEQ ID NO: 217, SEQ ID NO: 209, SEQ ID NO: 221, SEQ ID NO: 72, SEQ ID NO: 215, SEQ ID NO: 223, SEQ ID NO: 211, SEQ ID NO: 58 and SEQ ID NO: 229.

In a preferred embodiment, the solubilized human apyrase comprises a sequence selected from the group consisting of SEQ ID NO: 58, SEQ ID NO: 72 and SEQ ID NO: 229.

In one embodiment, the solubilized human apyrase comprises SEQ ID NO: 58. In one embodiment, the solubilized human apyrase comprises SEQ ID NO: 72. In one embodiment, the solubilized human apyrase comprises SEQ ID NO: 229.

In a preferred embodiment, the solubilized human apyrase consists of a sequence selected from the group consisting of SEQ ID NO: 58, SEQ ID NO: 72 and SEQ ID NO: 229.

In one embodiment, the solubilized human apyrase consists SEQ ID NO: 58. In one embodiment, the solubilized human apyrase consists SEQ ID NO: 72. In one embodiment, the solubilized human apyrase consists SEQ ID NO: 229.

According to a second aspect of the invention, the invention relates to a pharmaceutical composition comprising a therapeutically effective dose of the apyrase according to the first aspect of the invention, and one or more pharmaceutically acceptable carriers is provided.

In one embodiment, the pharmaceutical composition further comprises one or more additional active ingredients.

According to a third aspect of the invention, an isolated apyrase according to the first aspect for use as a medicament is provided.

According to a fourth aspect of the invention, an isolated apyrase according to the first aspect for use in the treatment of tissue damage is provided.

The tissue damage may be acute brain injury (stroke); acute multi-organ failure; delayed graft function after transplantation of kidney or other solid organs; burn damage; radiation damage; acute damage due to trauma and/or hypoxia, such as acute respiratory distress syndrome (ARDS) or lung injury; acute kidney injury, such as acute kidney injury secondary to thoracic surgery (e.g. aortic valve replacement, coronary artery bypass surgery) or sepsis or rhabdomyolysis or toxic effects of antibiotics or other medication; acute myocardial injury.

In another embodiment, the fourth aspect of the disclosure relates to an isolated apyrase according to the first aspect of the invention for use in the treatment of cardiac surgery associated acute kidney injury.

In another embodiment, the fourth aspect of the disclosure relates to an isolated apyrase according to the first aspect of the invention for use in the treatment of delayed graft function (DGF), acute respiratory distress syndrome (ARDS), acute myocardial infarction (AMI), traumatic brain injury (TBI)/acute ischemic stroke (AIS), ischemia-reperfusion injury (IRI), or combinations thereof often referred to as multi-organ failures (MOF).

In one embodiment, the solubilized human apyrase used for the treatment of cardiac surgery associated acute kidney injury comprises an amino acid sequence of SEQ ID NO: 58.

In one embodiment, the solubilized human apyrase used for the treatment of cardiac surgery associated acute kidney injury comprises an amino acid sequence of SEQ ID NO: 72.

In one embodiment, the solubilized human apyrase used for the treatment of cardiac surgery associated acute kidney injury comprises an amino acid sequence of SEQ ID NO: 229.

In an additional preferred embodiment the disclosure relates to the use of an isolated apyrase according to the first aspect of the invention for the treatment of sepsis associated acute kidney injury.

In one embodiment of the fourth aspect, the solubilized human apyrase for use in the treatment of sepsis associated acute kidney injury comprises an amino acid sequence of SEQ ID NO: 58.

In one embodiment of the fourth aspect, the solubilized human apyrase for use in the treatment of sepsis associated acute kidney injury comprises an amino acid sequence of SEQ ID NO: 72.

In one embodiment of the fourth aspect, the solubilized human apyrase for use in the treatment of sepsis associated acute kidney injury comprises an amino acid sequence of SEQ ID NO: 229.

According to a fifth aspect of the invention, a method of treating tissue damage in a human subject is provided, comprising administering a therapeutically effective dose of solubilized human apyrase according to the first aspect to said subject. One embodiment of the fifth aspect of the invention relates to a method of treating cardiac surgery associated acute kidney injury comprising administering a therapeutically effective dose of an isolated apyrase according to the first aspect of the invention to a subject in need of such treatment.

Another embodiment of the fifth aspect of the invention relates to a method of treating delayed graft function (DGF), acute respiratory distress syndrome (ARDS), acute myocardial infarction (AMI), traumatic brain injury (TBI)/acute ischemic stroke (AIS) ischemia-reperfusion injury (IRI), or combinations thereof often referred to as multi-organ failures (MOF) comprising administering a therapeutically effective dose of an isolated apyrase according to the first aspect of the invention to a subject in need of such treatment.

In one embodiment of the fifth aspect, the solubilized human apyrase used in the method of treating cardiac surgery associated acute kidney injury comprises an amino acid sequence of SEQ ID NO: 58, SEQ ID NO: 72 or SEQ ID NO: 229.

One embodiment of the fifth aspect of the invention relates to a method of treating sepsis associated acute kidney injury comprising administering a therapeutically effective dose of an isolated apyrase according to the first aspect of the invention to a subject in need of such treatment.

In one embodiment of the fifth aspect, the solubilized human apyrase used in the method of treating sepsis associated acute kidney injury comprises an amino acid sequence of SEQ ID NO: 58, SEQ ID NO: 72 or SEQ ID NO: 229. The tissue damage may be acute brain injury (stroke); acute multi-organ failure; delayed graft function after transplantation of kidney or other solid organs; burn damage; radiation damage; acute damage due to trauma and/or hypoxia, such as acute respiratory distress syndrome (ARDS) or lung injury; acute kidney injury, such as acute kidney injury secondary to thoracic surgery (e.g. aortic valve replacement, coronary artery bypass surgery) or sepsis or rhabdomyolysis or toxic effects of antibiotics or other medication; acute myocardial injury.

According to a sixth aspect of the invention, an isolated nucleic acid molecule encoding any apyrase according to the first aspect is provided.

According to a seventh aspect of the invention, a cloning or expression vector comprising one or more nucleic acid sequences according to the sixth aspect is provided, wherein the vector is suitable for the recombinant production of isolated apyrase according to the first aspect.

According to an eight aspect of the invention, a host cell is provided comprising one or more cloning or expression vectors according to the seventh aspect.

According to a ninth aspect of the invention, a process for the production of an apyrase according to the first aspect is provided, comprising culturing a host cell according to the eight aspect, purifying and recovering said apyrase.

BRIEF DESCRIPTION OF THE FIGURES

FIG. 1 is a sequence alignment;

FIG. 12 are graphs showing in vivo results for proteins according to embodiments.

DETAILED DESCRIPTION OF THE DISCLOSURE

Figure 2A:
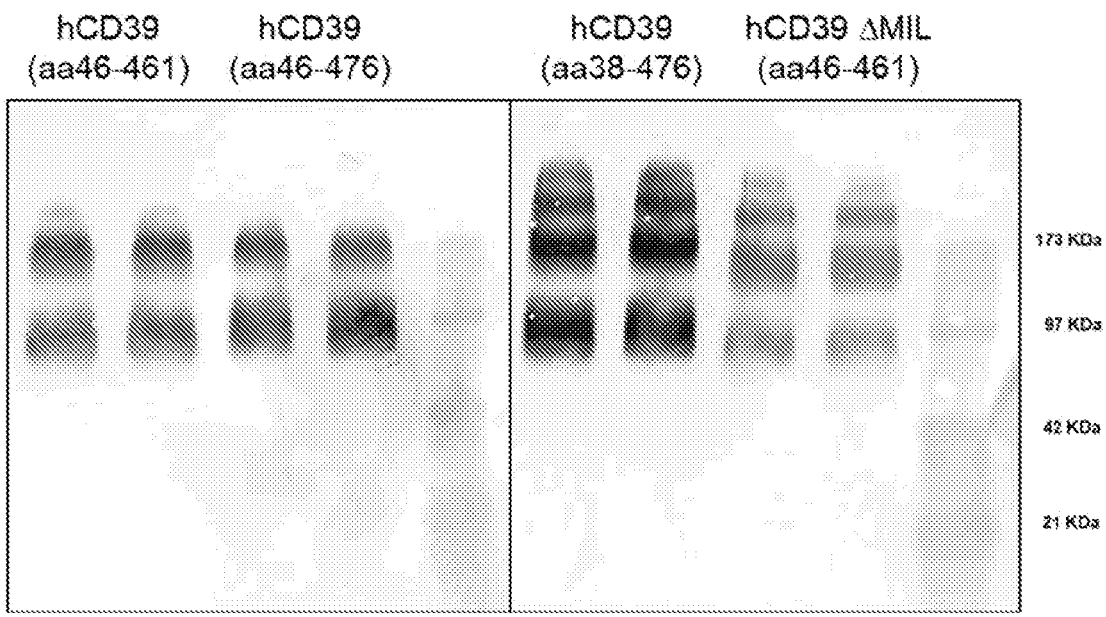
FIG. 2A is a representation of an expression level of supernatant containing human CD39 by anti-APP Western Blot according to an embodiment.

The present disclosure is inter alia based on the unexpected finding that certain modifications of solubilized CD39 lead to a surprisingly active protein, which is safe and easy to manufacture.

As will be shown in the specific examples below, a preferred embodiment is a solubilized human apyrase with at least two modifications selected from the list consisting of: N terminal deletion, C terminal deletion and central deletion, such as a solubilized human apyrase comprising a sequence selected from the group consisting of SEQ ID NO: 4, SEQ ID NO: 6, SEQ ID NO: 32, SEQ ID NO: 54, SEQ ID NO: 56, SEQ ID NO: 70, SEQ ID NO: 76, and SEQ ID NO: 78.

The inventors tried several different sequence modification strategies to achieve solubilized human apyrase with both retained activity and ability to be expressed, while still not introducing too many modifications because of the risk of increased immunogenicity and thus increased safety risk. Surprisingly, one sequence modification which was found to both increase efficiency and ability to express human apyrase was a deletion of a central section, the so called delta MIL (ΔMIL) modification, at the same time as not adding too much immunogenicity risk.

To increase the expression of the solubilized human apyrase according to embodiments of the invention, N terminal expression tags were tested. Various N terminal expression tags are known in the art, but surprisingly not all tags worked. The inventors found that a few tags worked, which could not have been foreseen.

These N terminal tags were SEQ ID NO: 131, SEQ ID NO: 133, SEQ ID NO: 135, SEQ ID NO: 137, SEQ ID NO: 139 or SEQ ID NO: 141. As is shown herein, particularly preferred tags are SEQ ID NO: 133, SEQ ID NO: 135 or SEQ ID NO: 137.

Specific details are set forth in Examples 9 to 13 below. However, in order to illustrate the unpredictable nature of these Examples, a comparative summary is presented in Table 1.

TABLE 1

Summary of preferred embodiments.

| Construct | Modifications | | Activity compared to parental EP28 | | Titer (g/L) |
| | No of N-terminal aa from SEQ ID NO: 131 | Number of point mutations | In vitro | In vivo | |
| --- | --- | --- | --- | --- | --- |
| EP1xEP17 | 6 | 2 | 1.5x | | 0.6 |
| EP17xEP19 | 6 | 2 | 1.5x | | 0.26 |
| EP1xEP17xEP19 | 6 | 3 | 1.5x | | 0.46 |
| EP17xEP19 | 3 | 2 | 1.5x | | 0.40 |
| EP1xEP17xEP19 | 3 | 3 | 1.5x | | 0.58 |
| EP1 | 3 | 1 | 1x | | 0.29 |
| EP1xEP14 | 3 | 2 | 4x | | 0.50 |
| EP28 | 16 | 0 | 1x | 1x | 0.08 |
| EP1xEP17_K405N | 15 | 3 | 1.5x | 1x | 1.4 |
| EP1xEP14 | 6 | 2 | 4x | | 0.3 |
| EP1xEP17 | 3 | 2 | 1.5x | | 0.68 |
| EP28 | 3 | 0 | 1x | | 0.10 |
| EP14 | 3 | 1 | 4x | 4x | 0.27 |

1. Definitions

To facilitate for a person skilled in the art to practice the invention, the following terms are used throughout the description.

The terms "CD39" and "hCD39" are used synonymously throughout the disclosure and unless stated otherwise means human cluster of differentiation 39 (CD39) according to UniProt P49961 or SEQ ID NO: 1.

The term "apyrase" refers to human apyrase unless stated otherwise. A "solubilized apyrase" as used herein means that that the apyrase, which as a wild type protein exist bound to a cell membrane, has been modified so that it is no longer bound to the cell membrane but exists in a soluble state i.e. no longer anchored to the cell membrane.

The abbreviation "MIL" refers to membrane interaction loop, which is a central part of the wild type (human) CD39 protein which interacts with the cell membrane, in addition to the N terminal and C terminal parts which are physically anchored through the cell membrane. The term "delta MIL", or "ΔMIL", refers to the deletion of the MIL sequence from wild type (human) CD39.

The term "about" in relation to a numerical value x means, for example, +/−10%. When used in front of a numerical range or list of numbers, the term "about" applies to each number in the series, e.g., the phrase "about 1-5" should be interpreted as "about 1-about 5", or, e.g., the phrase "about 1, 2, 3, 4" should be interpreted as "about 1, about 2, about 3, about 4, etc."

The word "substantially" does not exclude "completely," e.g., a composition which is "substantially free" from Y may be completely free from Y. Where necessary, the word "substantially" may be omitted from the definition of the disclosure.

The term "comprising" encompasses "including" as well as "consisting," e.g., a composition "comprising" X may consist exclusively of X or may include something additional, e.g., X+Y.

"Identity" with respect to a native polypeptide and its functional derivative is defined herein as the percentage of amino acid residues in the candidate sequence that are identical with the residues of a corresponding native polypeptide, after aligning the sequences and introducing gaps, if necessary, to achieve the maximum percent identity, and not considering any conservative substitutions as part of the sequence identity. Neither N- or C-terminal extensions nor insertions shall be construed as reducing identity. Methods and computer programs for the alignment are well known. The percent identity can be determined by standard alignment algorithms, for example, the Basic Local Alignment Search Tool (BLAST) described by Altshul et al. ((1990) J. Mol. Biol., 215: 403 410); the algorithm of Needleman et al. ((1970) J. Mol. Biol., 48: 444 453); or the algorithm of Meyers et al. ((1988) Comput. Appl. Biosci., 4: 11 17). A set of parameters may be the Blosum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

"Amino acid(s)" refer to all naturally occurring La-amino acids, e.g., and include D-amino acids. The phrase "amino acid sequence variant" refers to molecules with some differences in their amino acid sequences as compared to the sequences according to the present disclosure. Amino acid sequence variants of a protein according to the present disclosure, e.g., of a specified sequence, still have apyrase activity. Amino acid sequence variants include substitutional variants (those that have at least one amino acid residue removed and a different amino acid inserted in its place at the same position in a polypeptide according to the present disclosure), insertional variants (those with one or more amino acids inserted immediately adjacent to an amino acid at a particular position in a polypeptide according to the present disclosure) and deletional variants (those with one or more amino acids removed in a polypeptide according to the present disclosure).

The term "treatment" or "treat" is herein defined as the application or administration of apyrase according to the invention to a subject, or application or administration a pharmaceutical composition comprising said apyrase to a subject, or an isolated tissue or cell line from a subject, where the subject has tissue damage, a symptom associated with tissue damage, where the purpose is to alleviate, ameliorate, or improve the tissue damage or any associated symptoms of the tissue damage inter alia by reducing levels of extracellular ATP.

By "treatment" is also intended the application or administration of a pharmaceutical composition comprising an apyrase to a subject, or application or administration of a pharmaceutical composition comprising apyrase of the invention to an isolated tissue or cell line from a subject, where the subject has an tissue damage or a symptom associated with tissue damage, where the purpose is to alleviate, ameliorate, or improve the tissue damage or any associated symptoms of the tissue damage.

The term "prevent" or "preventing" refer to prophylactic or preventative treatment; it is concerned about delaying the onset of, or preventing the onset of the disease, disorders and/or symptoms associated thereto.

As used herein, a subject is "in need of" a treatment if such subject would benefit biologically, medically or in quality of life from such treatment.

The term "pharmaceutically acceptable" means a nontoxic material that does not interfere with the effectiveness of the biological activity of the active ingredient(s).

As used herein, the term "administration" or "administering" of the subject compound means providing a compound of the invention and prodrugs thereof to a subject in need of treatment. Administration "in combination with" one or more further therapeutic agents includes simultaneous (concurrent) and consecutive administration in any order, and in any route of administration.

As used herein, a "therapeutically effective dose" refers to a dose (an amount) of an apyrase that is effective, upon single or multiple dose administration to a patient (such as a human) for treating, preventing, preventing the onset of, curing, delaying, reducing the severity of, ameliorating at least one symptom of a disorder or recurring disorder, or prolonging the survival of the patient beyond that expected in the absence of such treatment. When applied to an individual active ingredient (e.g., apyrase) administered alone, the term refers to that ingredient alone. When applied to a combination, the term refers to combined doses or amounts of the active ingredients that result in the therapeutic effect, whether administered in combination, serially or simultaneously.

The phrase "dosage regimen" means the regimen used to treat an illness, e.g., the dosing protocol used during the treatment of tissue damage.

The phrase "means for administering" is used to indicate any available implement for systemically administering a drug to a patient, including, but not limited to, a pre-filled syringe, a vial and syringe, an injection pen, an autoinjector, an intravenous (i.v.) drip and bag, a pump, a patch pump, etc. With such items, a patient may self-administer the drug (i.e., administer the drug on their own behalf) or a physician may administer the drug.

2. Example 1: Membrane Free CD39

Wild type human apyrase CD39 (hCD39, UniProt P49961, or SEQ ID NO: 1) is naturally anchored in the cell membrane by a transmembrane domain at the N-terminus (putative aa 17-37), a central putative membrane interaction loop (MIL putative aa 193-204) and a C-terminal transmembrane domain (putative aa 479-499). To enable expression of a soluble variant of CD39 using a mammalian host cell, several elements of the CD39 sequence have been modified to obtain a membrane free, or solubilized, protein. The natural leader sequence and N-terminal transmembrane region were substituted by a secretion leader and a purification tag (SEQ ID NO: 133). The boundaries of the extracellular domain of CD39 have been varied to optimize expression, purification and activity parameters (amino acids no. 38-476 of SEQ ID NO: 1, amino acids no. 39-469 of SEQ ID NO: 1, amino acids 46-461 of SEQ ID NO: 1, and amino acids 46-476 of SEQ ID NO: 1, respectively). The impact of the cysteines and disulfide bridges on aggregation propensity and enzymatic activity was systematically assessed by substituting the cysteines by alanine or by shortening the loop made up by the disulfide bridge (SEQ ID 107, 109, 111, 113, and 115). A stretch of hydrophobic amino acid was described in the structural work of the rat-CD39 (Zebisch et al, J. Mol. Biol. (2012), 415, 288-306, wild type rat CD39, Uniprot P97687, set forth in SEQ ID NO: 2) and it is thought that this loop may be interacting with the cell membrane (MIL). We translated the findings to the human CD39 sequence by sequence alignment and generated CD39 variants having a loop deletion (CD39ΔMIL or EP28, as set forth in SEQ ID NO: 4). The impact of the deletion (or delta/Δ) of the MIL on expression level of functional CD39 and thermal stability was assessed.

As can be seen from FIG. 1, showing a sequence alignment of SEQ ID NO: 1 and SEQ ID NO: 4, N terminal amino acids 1 to 27, C terminal amino acids 477 to 510, and the central membrane interaction loop (MIL) amino acids 193 to 204, were deleted from wtCD39 (SEQ ID NO: 1) to form CD39ΔMIL (SEQ ID NO: 4).

zeocin marker). A list of truncated, solubilized human CD39 versions is illustrated in Table 2, with amino acid modifications numbered with reference to SEQ ID NO: 1.

TABLE 2

Truncated, solubilized human CD39 versions.

| Reference | Amino acid sequence ID | Modification(s) |
| --- | --- | --- |
| CD39(aa39-469) | SEQ ID NO: 99 | N and C terminal truncations |
| CD39(aa46-476) | SEQ ID NO: 101 | N and C terminal truncations |
| CD39(aa46-461) | SEQ ID NO: 103 | N and C terminal truncations |
| CD39(aa46-461)_dMIL(193-204) | SEQ ID NO: 105 | N and C terminal truncations, and central deletion |
| CD39(aa46-461)_delta cys1 | SEQ ID NO: 107 | N and C terminal truncations, and cysteine deletion |
| CD39(aa46-461)_delta cys2 | SEQ ID NO: 109 | N and C terminal truncations, and cysteine deletion |
| CD39(aa46-461)_delta cys3 | SEQ ID NO: 111 | N and C terminal truncations, and cysteine deletion |
| CD39(aa46-461)_delta cys4 | SEQ ID NO: 113 | N and C terminal truncations, and cysteine deletion |
| CD39(aa46-461)_delta cys5 | SEQ ID NO: 115 | N and C terminal truncations, and cysteine deletion |
| CD39(aa46-461)_dMIL(193-204)_delta cys1 | SEQ ID NO: 117 | N and C terminal truncations, central deletion and cysteine deletion |
| CD39(aa46-461)_dMIL(193-204)_delta cys2 | SEQ ID NO: 119 | N and C terminal truncations, central deletion and cysteine deletion |
| CD39(aa46-461)_dMIL(193-204)_delta cys3 | SEQ ID NO: 121 | N and C terminal truncations, central deletion and cysteine deletion |
| CD39(aa46-461)_dMIL(193-204)_delta cys4 | SEQ ID NO: 123 | N and C terminal truncations, central deletion and cysteine deletion |
| CD39(aa46-461)_dMIL(193-204)_delta cys5 | SEQ ID NO: 125 | N and C terminal truncations, central deletion and cysteine deletion |
| CD39(aa38-476)_delta337-344 | SEQ ID NO: 127 | N and C terminal truncations, and cysteine deletion |
| CD39(aa38-476)_C338A_C343A | SEQ ID NO: 129 | N and C terminal truncations, and cysteine point mutations |

The impact of the different sequences modifications on thermal stability was studied. In addition, impact of the different sequences modifications on CHO cell expression yields and monomeric content was studied.

(1) Methods (a) Generation of Expression Plasmids

DNA sequences coding for different hCD39 boundary variants and membrane interaction loop (MIL) deletion were ordered at GeneArt (Life Technologies Inc. Regensburg, Germany) including codon optimization for Homo sapiens. Sequences coding for hCD39 variants were sub cloned by standard molecular biology techniques from the GeneArt derived vectors or internally generated variants thereof into an expression vector suitable for secretion in mammalian cells. Cysteine to alanine mutations present in the cysteine bridge deleted variants were targeted by modified oligonucleotides and after a subsequent assembly PCR step the generated fragments were sub cloned into the same expression vector mentioned previously. Elements of the expression vector include a promoter (Cytomegalovirus (CMV) enhancer-promoter), a signal sequence to facilitate secretion, a polyadenylation signal and transcription terminator (Bovine Growth Hormone (BGH) gene), an element allowing episomal replication and replication in prokaryotes (e.g. SV40 origin and ColE1 or others known in the art) and elements to allow selection (ampicillin resistance gene and (b) Micro-Scale Expression of hCD39 Variants 293-6E cells (as disclosed in WO2006096989A2, incorporated herein by reference) were chosen for micro-scale experiment as one of the preferred host cell lines for transient expression of proteins in absence of serum. Transfection was performed using FuGene HD (Roche Applied Science, Cat. No. 04709705001) as transfection reagent. 293-6E cells were cultivated in suspension culture using V3 serum-free culture medium (Bioconcept, Cat. No. V3-K) for transfection and propagation of the cells. Cells were grown in Corning shake flasks (Corning, Tewksbury, MA) on an orbital shaker (100-120 rpm) in a humidified incubator at 5% $CO_2$ (seed flasks). Cells in the seed cultures should be maintained in the exponential growth phase (cell densities between $5 \times 10^5$ and $3 \times 10^6$/mL) and display a viability of >90% for transfection. Cell densities outside of this range will result in either a lag phase after dilution or reduced transfection efficiency.

For micro-scale (0.5 ml) transfections, an aliquot of cells was taken out of the seed cultures and adjusted to $0.5 \times 10^6$ cells/mL in V3 serum-free culture medium. The DNA solution (called Solution 1) was prepared by diluting 0.5 µg of hCD39 expression plasmids in 14 µl of V3 serum-free culture medium, then 2.3 µl of FuGene HD solution was also diluted in 14 µl of V3 serum-free culture medium (Solution 2). Both solutions were incubated for 5-10 min at room temperature (RD. Thereafter solution 2 was added to solution 1 with gentle mixing and incubated for another 5-15 minutes at room temperature. The transfection mix was then added to 0.5 ml of cells at $0.5 \times 10^6$ cells/mL seeded in a 48-well tissue culture plate (Corning, Tewksbury, MA) and plate placed on an orbital shaker (300 rpm) in a humidified incubator at 5% $CO_2$. The culture was harvested 3 days post transfection by centrifugation at 4000 rpm for 10 minutes at 4° C. (Heraeus, Multifuge 3 S-R, Thermo Scientific, Rockford, IL). The recovered cell supernatant was stored at 4° C. until further processing.

(c) Western-Blot Analysis on Micro-Scale Expression Supernatant

Western-Blot analysis was performed on micro-scale expression supernatant in order to check expression and correct formation of recombinant hCD39 variants. 8 μl of supernatant was diluted in E-PAGE™ Loading Buffer (4×, Invitrogen, #EPBNF-01) and loaded on E-Page 48, 8% gel (Invitrogen, #EP04808) in non-reducing conditions. Gel was run on E-base mother device (Invitrogen) for 23 min and proteins were transferred to Nitrocellulose membrane (Invitrogen 16301001) using the iBlot system (Invitrogen) according to manufacturer's instructions (7 min run). After 3 times washing in TBS/0.05 Tween20 (TBST), membrane was incubated for 1 h with 5% Milk/TBST in gentle agitation followed by 1 hr incubation with 4 μg/ml solution of anti-APP mouse antibody (Novartis internally antibody raised against a peptide stretch of amyloid precursor protein (APP) used for protein tagging) diluted in 2% Milk/TBST. After an additional 3 washing steps, membrane was incubated with 1:1000 dilution of Anti-Mouse IgG-Alkaline Phosphatase (Sigma-Aldrich, A5153-1ML) diluted in 2% Milk/TBST and washed again 3 times in TBST followed by a rinsing step in TBS. Signal was developed for 1-5 minutes using SIGMAFAST™ BCIP®/NBT (Sigma-Aldrich, #B5655-25TAB) according to manufacturer's instructions and signal stopped by rinsing the membrane with water.

(d) Solid-Phase AxPase Assay

ATPase, ADPase and AMPase activities were determined using Pi ColorLock Gold phosphate detection system (Innova Biosciences, cat n. 303-0030) on plate-captured hCD39 variants from micro-scale expression supernatant (Solid-phase Axpase assay). This method was found to be less sensitive compared to solution based assay (Liquid-phase Axpase assay) recommended by manufacturer, but would have the advantage to reduce AxPase activity mediated by host cell enzymes potentially present in the micro-scale expression supernatant. 20 μl of anti-APP mouse antibody 10 μg/ml solution antibody (Novartis internally antibody raised against a peptide stretch of amyloid precursor protein (APP) used for protein tagging) diluted in PBS was added to each well of a maxisorp 384 well clear plate (Nunc) and incubated over-night at 4° C. After three washing with TBST, wells were blocked for 1 h using 100 μl of 5% Milk/TBST at room temperature in gentle agitation. After an additional three washing steps, 20 μl of serially diluted micro-scale expression supernatant in 2% Milk/TBST was added in triplicate to the wells and incubated for 2 hrs at room temperature with gentle agitation. Wells were then washed again four times with 100 μl of TBST and twice with 80 μl of 50 mM Tris-Cl/5 mM $MgCl_2$ pH 7.5. 30 μl of 80 μM Adenosine Phosphate solutions diluted in 50 mM Tris-Cl/5 mM $MgCl_2$ pH 7.5 (ATP: SIGMA A2383, ADP: SIGMA A2754) was added to each triplicate and incubated for 24 hrs at 37° C. Signal was developed using 7.5 μl of Gold reagent mix prepared according to manufacturer's instructions for 10 minutes and reaction stopped using 3 μl of Stabilizer. Absorbance at 620 nm read using TECAN Genios Pro instrument.

Figure 2B:
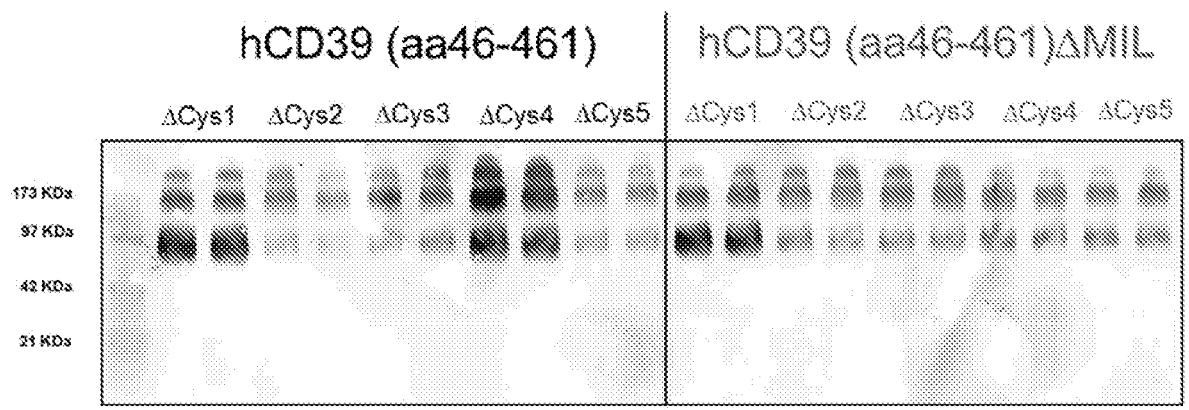
FIG. 2B is a representation of expression level of supernatant containing cysteine bridge deletion human CD39 variants by anti-APP Western Blot according to an embodiment.

(2) Results (a) Effect of Boundaries, Membrane Interaction Loop (MIL) Deletion and Cysteine Bridge Deletion on hCD39 Expression Level In order to evaluate expression level of different hCD39 variants, corresponding expression plasmids were transfected in duplicate in 0.5 ml of 293-6E cells and Western Blot (anti-APP detection Ab) performed on supernatant collected 3 days post transfection. Results are illustrated in FIG. 2A and FIG. 2B.

Results indicate a higher expression level of hCD39 starting at aa38 compared to aa46. N-terminal boundaries as well as MIL deletion seem to have no major impact on expression level. Higher expression level of hCD39 having the first or fourth cysteine-bridge deleted in the context of hCD39 (aa46-461) was also observed. Higher expression level of first cysteine bridge deletion was confirmed also using hCD39 (aa46-461) MIL backbone.

(b) Effect of Boundaries, Membrane Interaction Loop (MIL) Deletion and Cysteine Bridge Deletion on hCD39 Activity CD39 enzymatic activity was measured by solid-phase AxPase assay on the above described supernatant samples. Results are illustrated in FIG. 3 and FIG. 4, as well as Table 3.

TABLE 3

Solid-phase ATP assay on CD39 variants

Figure 3:
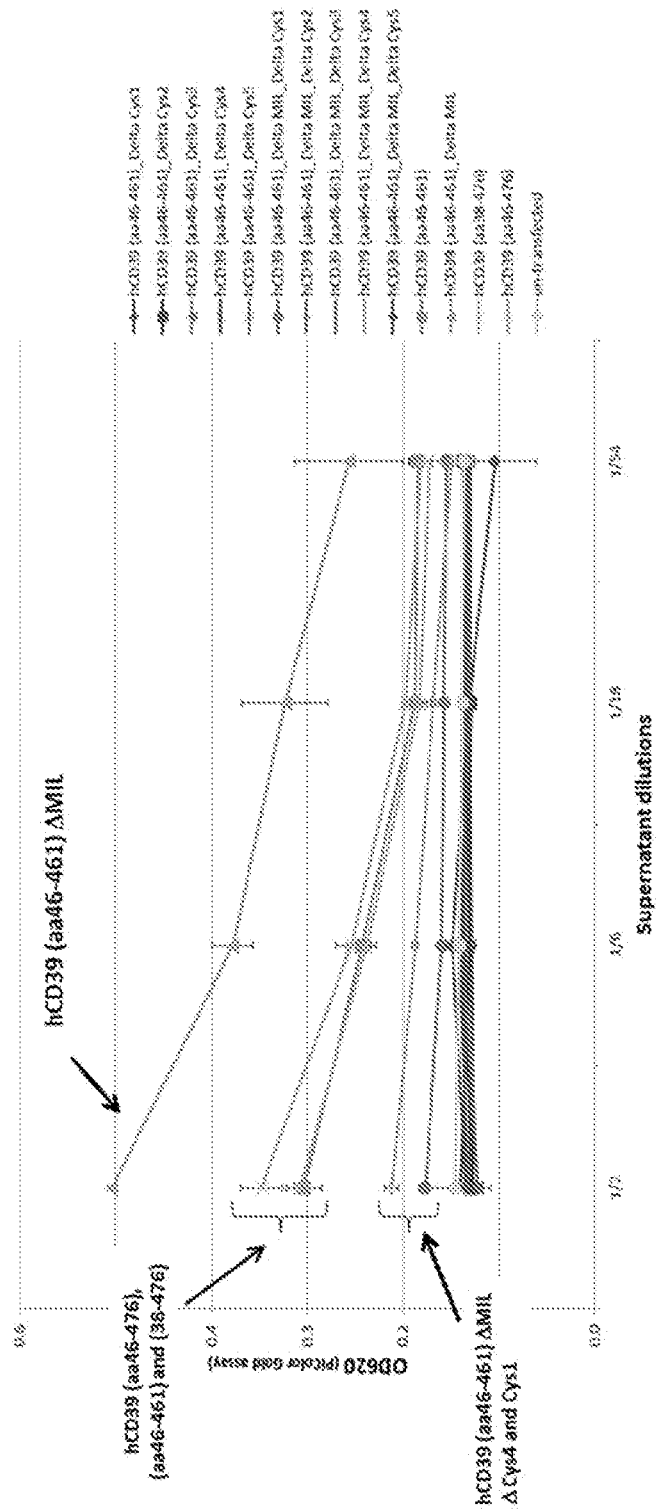
FIG. 3 is a graph showing solid-phase ATPase assay results of CD39 variants.
Figure 4:
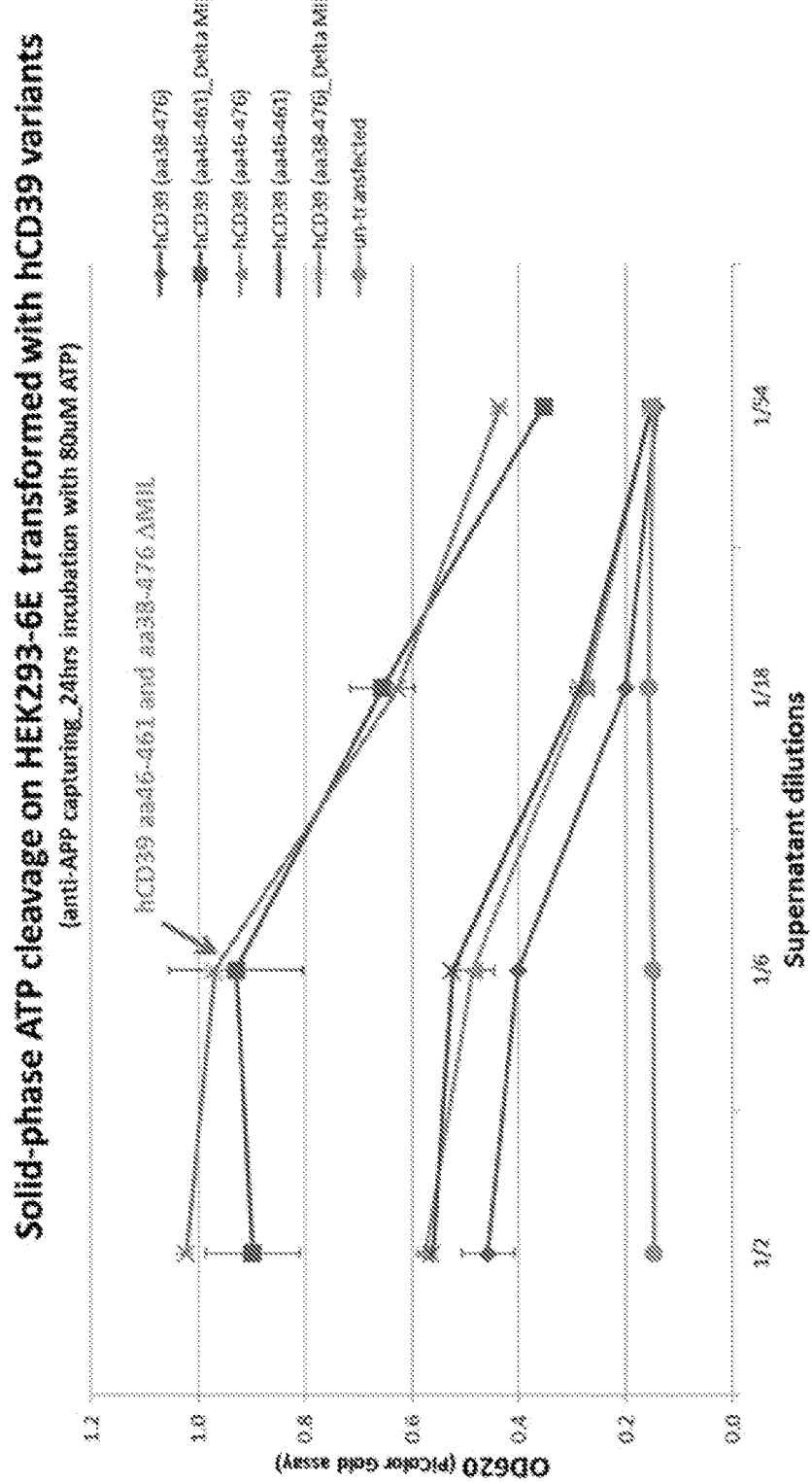
FIG. 4 is a graph showing solid-phase ATP cleavage on HEK293 cells transformed with human CD39 variants according to an embodiment.

| Sample | Sequence | Average signal Dilution 1/2 | Dilution 1/6 | Dilution 1/18 | Dilution 1/54 |
|---|---|---|---|---|---|
| FIG. 3 | | | | | |
| hCD39 (aa46-461)_Delta Cys1 | SEQ ID NO: 107 | 0.12755 | 0.12905 | 0.13155 | 0.13545 |
| hCD39 (aa46-461)_Delta Cys2 | SEQ ID NO: 109 | 0.1287 | 0.13615 | 0.12915 | 0.1375 |
| hCD39 (aa46-461)_Delta Cys3 | SEQ ID NO: 111 | 0.12265 | 0.1336 | 0.13485 | 0.1365 |
| hCD39 (aa46-461)_Delta Cys4 | SEQ ID NO: 113 | 0.14 | 0.1302 | 0.13535 | 0.1322 |
| hCD39 (aa46-461)_Delta Cys5 | SEQ ID NO: 115 | 0.1226 | 0.13865 | 0.13375 | 0.13225 |
| hCD39 (aa46-461)_Delta MIL_Delta Cys1 | SEQ ID NO: 117 | 0.17695 | 0.16 | 0.15755 | 0.1551 |

TABLE 3-continued

Solid-phase ATP assay on CD39 variants

| Sample | Sequence | Average signal Dilution 1/2 | Dilution 1/6 | Dilution 1/18 | Dilution 1/54 |
|---|---|---|---|---|---|
| hCD39 (aa46-461)_Delta MIL_Delta Cys2 | SEQ ID NO: 119 | 0.1318 | 0.1419 | 0.13065 | 0.1299 |
| hCD39 (aa46-461)_Delta MIL_Delta Cys3 | SEQ ID NO: 121 | 0.13505 | 0.1376 | 0.1347 | 0.13775 |
| hCD39 (aa46-461)_Delta MIL_Delta Cys4 | SEQ ID NO: 123 | 0.21195 | 0.18745 | 0.16915 | 0.14975 |
| hCD39 (aa46-461)_Delta MIL_Delta Cys5 | SEQ ID NO: 125 | 0.1343 | 0.1486 | 0.13135 | 0.10465 |
| hCD39 (aa46-461) | SEQ ID NO: 103 | 0.30345 | 0.2433 | 0.1879 | 0.1851 |
| hCD39 (aa46-461)_Delta MIL | SEQ ID NO: 105 | 0.5037 | 0.3779 | 0.32345 | 0.2567 |
| hCD39 (aa38-476) | Sequence not shown | 0.30745 | 0.23855 | 0.18315 | 0.17295 |
| hCD39 (aa46-476) | SEQ ID NO: 101 | 0.34815 | 0.254 | 0.1975 | 0.1817 |
| untransfected FIG. 4 | | 0.1459 | 0.14155 | 0.13855 | 0.13675 |
| hCD39 (aa38-476) | Sequence not shown | 0.45775 | 0.4007 | 0.1997 | 0.14215 |
| hCD39 (aa46-461)_Delta MIL | SEQ ID NO: 105 | 0.8983 | 0.9294 | 0.6561 | 0.35405 |
| hCD39 (aa46-476) | SEQ ID NO: 101 | 0.5756 | 0.4855 | 0.27525 | 0.153 |
| hCD39 (aa46-461) | SEQ ID NO: 103 | 0.562 | 0.52455 | 0.28625 | 0.15175 |
| hCD39 (aa38-476)_Delta MIL (EP28) | SEQ ID NO: 4 | 1.0224 | 0.9696 | 0.6263 | 0.4354 |
| untransfected | | 0.1483 | 0.1494 | 0.158 | 0.1502 |

Deletion of MIL seems to increase the fraction of functionally expressed CD39 recombinant proteins. Different boundaries do not show any major impact on active hCD39 activity. Results indicate strongly reduced or completely abolished ATPase activity of all the cysteine-bridge deleted variants. Similar results were obtained using Solid-Phase ADPase assay. Thus, surprisingly, the sequence modification which both increase efficiency and ability to express CD39 is the delta MIL (ΔMIL) modification.

3. Example 2: Expression Tags

In order to improve the expression properties of the candidates, different expression tags were tested.

Different expression tags based on the N-terminal portion of IL-2 (SEQ ID NO: 131) were tested, as set forth in Table 4. Expression tag 1-16 aa, according to SEQ ID NO: 131, was synthesized by Geneart.

TABLE 4

IL-2 expression tag variant overview

| Reference | Amino acid sequence ID | Forward primer sequence ID | Reverse primer sequence ID |
|---|---|---|---|
| Expression tag aa1-16 | SEQ ID NO: 131 | n/a | n/a |
| Expression tag aa1-15 | SEQ ID NO: 133 | SEQ ID NO: 157 | SEQ ID NO: 158 |
| Expression tag aa1-6 | SEQ ID NO: 135 | SEQ ID NO: 159 | SEQ ID NO: 158 |
| Expression tag aa1-3 | SEQ ID NO: 137 | SEQ ID NO: 161 | SEQ ID NO: 158 |
| Expression tag aa1-9 | SEQ ID NO: 139 | SEQ ID NO: 162 | SEQ ID NO: 158 |
| Expression tag aa1-12 | SEQ ID NO: 141 | SEQ ID NO: 163 | SEQ ID NO: 158 |
| Expression tag aa4-12 | SEQ ID NO: 143 | SEQ ID NO: 164 | SEQ ID NO: 158 |

All expression tags were tested in relation to CD39ΔMIL, as set forth in SEQ ID NO: 4. All the constructs included an APP tag and a His tag.

Figure 5:
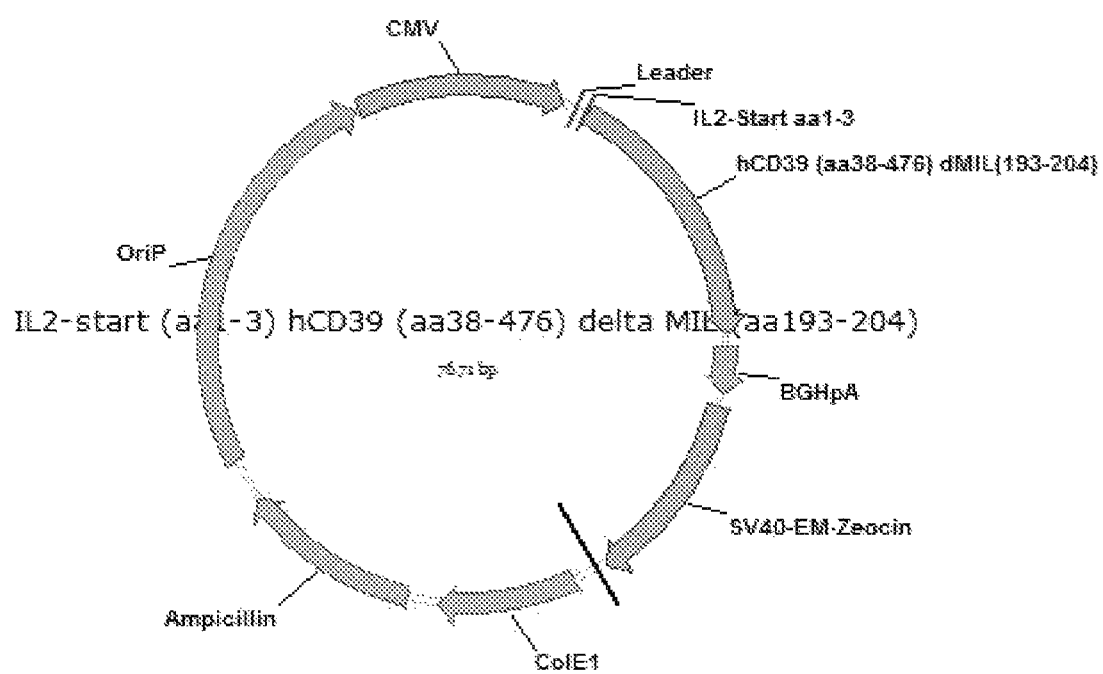
FIG. 5 is a schematic overview of a vector according to an embodiment.
Figure 6:
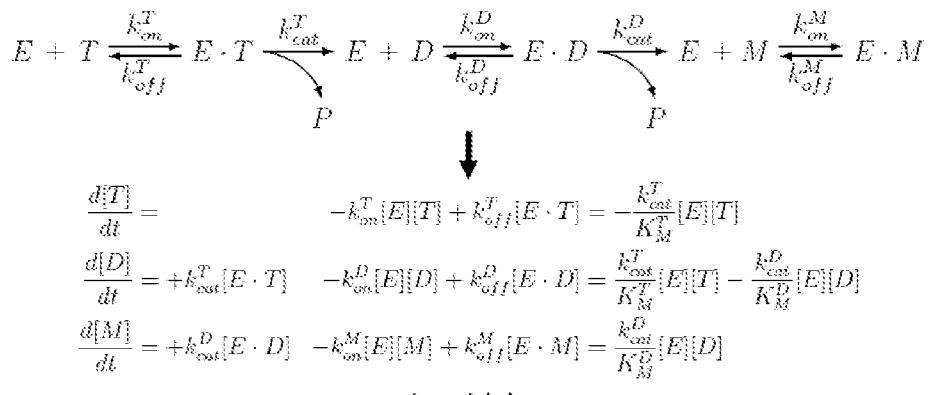
FIG. 6 is an enzymatic model based on steady state approximation.

The vector pRS5a, as set forth in FIG. 5, was used for the expression. Primer pairs were as set forth in Table 4.

Annealing temperature was 64° C. in all cases.

PCR solution was prepared by mixing 1 μl Template DNA stock, 25 μl Kapa Hifi Hotstart polymerase (from kappa Biosystems/KK2602). 1.5 μl forward Primer, 1.5 μl reverse primer, and adjusting the final volume to 50 μl with H₂O.

The PCR reaction was run according to schedule in Table 5.

TABLE 5

PCR schedule

|  | Temperature (C. °) | Time (min) | Cycles |
|---|---|---|---|
| Denaturation | 94 | 5 | 1 |
| Denaturation | 94 | 0.5 | 35 |
| Annealing | 64 | 1.5 |  |
| Polymerization | 72 | 0.5 |  |
| Final Polymerization | 72 | 5 |  |

After completion of PCR reaction, DNA extraction was performed using Wizard® SV Gel and PCR Clean-Up Kit, Promega, No. 9282, 1 column, elution in 30 µl according to the instructions of the manufacturer.

Inserts and vector were cut with enzyme supplied by New England Biolabs (NEB), NruI-HF (NEB #R3192) and NotI-HF (NEB #R3189), in CutSmart® buffer. Reaction time was 3 h at 37° C.

Ligation has been performed over night with dephosphorylated Vector with Rapid DNA Dephosphorylation and Ligation Kit, Fa. Roche, No. 04898117001 according to the valid protocol of the producer.

Next day, single colonies were picked for DNA-Miniprep and sequence analysis with forward Primer P270 (SEQ ID NO: 165) and reverse Primer P271 (SEQ ID NO: 166).

In addition, the a few protein sequences known in the art to increase expression were tested, according to Table 6.

TABLE 6

Prior art tags

| Reference | Sequence identifier |
|---|---|
| Ubiquitin | SEQ ID NO: 167 |
| CKappa | SEQ ID NO: 168 |
| HSA Domain I | SEQ ID NO: 169 |
| HSA Domain II | SEQ ID NO: 170 |

The resulting combinations tested are set forth in Table 7.

TABLE 7

Tested constructs

| Plasmid Name | Resulting amino acid sequence |
|---|---|
| pRS5a_IL2 leader -APP6-Flag- hCD39 (aa38-476)_delta MIL (aa193-204)_8M opt | SEQ ID NO: 145 |
| pRS5a_IL2 leader-hsUbiquitin- hCD39 (aa38-476)_delta MIL (aa193-204)_APP_His | SEQ ID NO: 149 |
| pRS5a_IL2 leader-hsCKappa- hCD39 (aa38-476)_delta MIL (aa193-204)_APP_His | SEQ ID NO: 147 |
| pRS5a_IL2 leader-HSA-Dom.I- hCD39 (aa38-476)_delta MIL (aa193-204)_APP_His | SEQ ID NO: 151 |
| pRS5a_IL2 leader-HSA-Dom.II- hCD39 (aa38-476)_delta MIL (aa193-204)_APP_His | SEQ ID NO: 153 |

None of the prior art tags from Table 6 gave expression of protein (data not shown). This was unexpected, since prior art teaches that these sequences should increase expression.

4. Example 3: Further Mutations

In order to improve the characteristics of soluble CD39, and make it suitable for pharmaceutical development, further modifications were introduced in the CD39ΔMIL, EP28, set forth in SEQ ID NO: 4. The different mutations and mutated variants are seen in Table 8 and are numbered according to the amino acid positions of the wild type CD39 as set forth in SEQ ID NO: 1.

TABLE 8

Point mutations

| Short name | No. Mutations | Mutation Pos. 1 | Mutation Pos. 2 | Mutation Pos. 3 | Mutation Pos. 4 | Mutation Pos. 5 | Amino acid sequence ID |
|---|---|---|---|---|---|---|---|
| EP1 | 1 | 113: R->M |  |  |  |  | SEQ ID NO: 6 |
| EP2 | 2 | 113: R->M | 149: L->M |  |  |  | SEQ ID NO: 8 |
| EP3 | 3 | 113: R->M | 304: R->G | 469: S->R |  |  | SEQ ID NO: 10 |
| EP4 | 3 | 95: V->A | 113: R->M | 469: S->R |  |  | SEQ ID NO: 12 |
| EP5 | 2 | 149: L->M | 441: G->D |  |  |  | SEQ ID NO: 14 |
| EP6 | 3 | 104: Y->S | 149: L->M | 263: W->R |  |  | SEQ ID NO: 16 |
| EP7 | 4 | 71: K->E | 106: T->S | 151: V->A | 319: I->T |  | SEQ ID NO: 18 |
| EP8 | 1 | 151: V->A |  |  |  |  | SEQ ID NO: 20 |
| EP9 | 1 | 263: W->R |  |  |  |  | SEQ ID NO: 22 |
| EP10 | 1 | 319: I->T |  |  |  |  | SEQ ID NO: 24 |
| EP11 | 2 | 113: R->M | 319: I->T |  |  |  | SEQ ID NO: 26 |
| EP12 | 2 | 276: E->D | 319: I->T |  |  |  | SEQ ID NO: 28 |
| EP13 | 2 | 365: F->S | 424: L->P |  |  |  | SEQ ID NO: 30 |
| EP14 | 1 | 365: F->S |  |  |  |  | SEQ ID NO: 32 |
| EP15 | 4 | 292: N->K | 365: F->S | 424: L->P | 463: P->S |  | SEQ ID NO: 34 |
| EP17.1 | 1 | 412: Y->F |  |  |  |  | SEQ ID NO: 38 |
| EP17 | 2 | 405: K->N | 412: Y->F |  |  |  | SEQ ID No. 36 |
| EP18 | 2 | 102: G->D | 424: L->Q |  |  |  | SEQ ID No. 40 |
| EP19 | 2 | 424: L->Q | 436: H->D |  |  |  | SEQ ID No. 42 |
| EP20 | 2 | 276: E->G | 439: F->S |  |  |  | SEQ ID No. 44 |
| EP21 | 2 | 113: R->M | 469: S->R |  |  |  | SEQ ID No. 46 |
| EP22 | 2 | 276: E->G | 469: S->G |  |  |  | SEQ ID No. 48 |
| EP23 | 4 |  | 254: L->M | 263: W->R | 439: F->S | 469: S->R | SEQ ID No. 50 |
| EP24 | 3 | 113: R->K | 424: L->Q | 437: I->N |  |  | SEQ ID No. 52 |

TABLE 8-continued

| | | Point mutations | | | | | |
|---|---|---|---|---|---|---|---|
| Short name | No. Mutations | Mutation Pos. 1 | Mutation Pos. 2 | Mutation Pos. 3 | Mutation Pos. 4 | Mutation Pos. 5 | Amino acid sequence ID |
| EP28_8M | 8 | 173: E->D | 258: K->R | 362: A->N | 365: F->Y | 404-411: VKEKYLSE-> QERWLRD | SEQ ID No. 145 |

Two mutations in active site lead to higher activity (365 and 412).

5. Example 4: Glycosylation Site Removal

Based on the EP14 variant above, the effect of glycosylation sites was checked by introducing point mutations according to Table 9, numbered according to the amino acid positions of the wild type CD39 as set forth in SEQ ID NO: 1.

TABLE 9

| Glycosylation site mutations | | |
|---|---|---|
| Mutation position | Glycosylation site | Primer |
| N73Q | NDT | P928/P929 |
| T229A | NQT | P930/P931 |
| N292Q | NVS | P932/P933 |
| N327Q | NTS | P934/P935 |
| N371Q | NLT | P936/P937 |
| N457Q | NLT | P938/P939 |

(a) Materials and Methods

The expression vector pRS5a (FIG. 5) was used for the cloning. Primers were used as set forth in Table 10.

TABLE 10

| Primer sequences | | |
|---|---|---|
| Primers | Sequence | Description |
| P928 | SEQ ID NO: 171 | Forward primer for removal of Glycosylation site N73Q |
| P929 | SEQ ID NO: 172 | Reverse primer for removal of Glycosylation site N73Q |
| P930 | SEQ ID NO: 173 | Forward primer for removal of Glycosylation site T229A |
| P931 | SEQ ID NO: 174 | Reverse primer for removal of Glycosylation site T229A |
| P932 | SEQ ID NO: 175 | Forward primer for removal of Glycosylation site N292Q |
| P933 | SEQ ID NO: 176 | Reverse primer for removal of Glycosylation site N292Q |
| P934 | SEQ ID NO: 177 | Forward primer for removal of Glycosylation site N327Q |
| P935 | SEQ ID NO: 178 | Reverse primer for removal of Glycosylation site N327Q |
| P936 | SEQ ID NO: 179 | Forward primer for removal of Glycosylation site N371Q |
| P937 | SEQ ID NO: 180 | Reverse primer for removal of Glycosylation site N371Q |
| P938 | SEQ ID NO: 181 | Forward primer for removal of Glycosylation site N457Q |
| P939 | SEQ ID NO: 182 | Reverse primer for removal of Glycosylation site N457Q |

The QuikChange Lightning Site-directed Mutagenesis Kit (Agilent, No. 210519-5) was used for the PCR, according to the manufacturer's instructions.

Next day, single colonies were picked for DNA-Miniprep and sequence analysis was performed with forward Primer P270 (SEQ ID NO: 165) and reverse Primer P271 (SEQ ID NO: 166).

To ensure the correctness of the vector backbone as well (because of mutagenesis), the sequenced insert fragment was cloned into a new vector backbone of pRS5a (FIG. 5) using the following method.

The vector was prepared using the vector backbone of SEQ ID NO: 36 with expression tag SEQ ID NO: 135, containing an APP_HIS-Tag, stock conc. 3.3 µg/µl.

Vector was digested by mixing 10 µg vector-DNA, 0.4 µl HindIII (100 U/µl, NEB), 2 µl EcoRI (20 U/µl, NEB), 5 µl Cutsmart buffer 10× conc. (NEB), $H_2O$ to final volume of 50 µl. Digestion was run for 3 h at 37° C.

Dephosphorylation was performed with Alkaline Phosphatase, Calf intestinal (CIP, NEB, No. M0290L), 10 U/µl. Directly after digestion, 3 µl of CIP was added to digested vector and incubated for 30 min. at 37° C. Digested and dephosphorylated Vector was loaded on preparative 0.8% TAE Agarose gel, correct band size of vector with ~6100 bp had been cut out. Cleanup was done with Wizard® SV Gel and PCR Clean-Up Kit, Promega, No. 9282, 1 column, elution in 100 ul. OD260 nm showed a concentration of 64 ng/µl.

Digestion of mutated Insert fragments was done by mixing 42.5 µl DNA (~3-5 ug for each DNA), 5 µl Cutsmart buffer, 10× conc., NEB no B7204S, 0.4 µl HindIII-HF, 100 U/µl, NEB no. R3104S, 2 µl EcoRI-HF, 20 U/µl, NEB no. R3103L, and adjust volume to 50 µl with $H_2O$. Digestion was carried out for 3 h at 37° C. in PCR-machine. Digested inserts were loaded on preparative 0.8% TAE Agarose gel, correct band size of vector with ~1400 bp had been cut out. Cleanup was done with Wizard® SV Gel and PCR Clean-Up Kit, Promega, No. 9282, 1 column, elution in 30 µl. OD260 nm showed a concentration of 1-25 ng/µl.

Ligation was done using (vector:insert ratio ~1:10), with Rapid DNA Ligation Kit, No. K1423, Fa. Thermo Scientific. 4 µl 5× Ligation Buffer was mixed with 1 µl Ligase, 2 µl vector fragment, HindIII/EcoRI-digested, stock conc. 64 ng/µl, 13 µl insert fragment, HindIII/EcoRI-digested, stock conc. 1-25 ng/µl. Ligation was run for 10 minutes at RT.

Transformation was done by incubation of 10 µl of ligation with 80 µl chemical competent XL1 Blue cells (Novartis, FS/RL) for 30 min on ice. Heat shock for 45 sec at 42° C. on Eppendorf incubator, followed by incubation for 2 min on ice. After that, 1 ml 2YT media was added, followed by incubation for 1.5 h at 37° C. on Eppendorf shaker (800 rpm). Cells were centrifuged for 3 min at 7000 rpm and colonies plating on LB/Carb/Gluc. Plates, followed by incubation overnight at 37° C.

Next day, single colonies were picked for DNA-Miniprep and sequence analysis was performed with forward Primer P270 (SEQ ID NO: 165) and reverse Primer P271 (SEQ ID NO: 166).

Correct sequences were transfected into HEK293 cells according to 7 days of expression, 200 ml scale.

The following material was used:

Human Embryonic Kidney cells constitutively expressing the SV40 large T antigen (HEK293-T), e.g. ATCC11268

Polyethylenimine "MAX" MW 40.000 (PEI) (Polysciences, Cat. 24765), dissolved in $H_2O$ at RT, adjusted with NaOH to pH7.05.

M11V3 serum-free culture medium (Bioconcept, CH, Cat: V3-K)

DNA: prepared with Qiagen DNA Kit, Midiprep-Kit (No. 12943) according to protocol recommended by supplier All cell culture work for the transient transfections is carried out using suspension adapted HEK293-Tcells growing in serum-free M11V3 medium.

Cells are grown in Corning shake flasks (Corning, USA) on an orbital shaker (115 rpm) in a humidified $CO_2$-incubator with 5% $CO_2$ (seed flasks).

Used Cells have been in exponential growth phase (cell density between $5 \times 10^5$ and $3 \times 10^6$/ml) and had a viability of >90%.

Transfection was performed in small scale (here 20/50 or 100 ml), using cells that have been counted and corresponding amount of cells has been adjusted to $1.4 \times 10^6$ cells/ml with M11V3-media. 36% cell suspension of the final transfection volume is used.

The DNA solution (solution 1) is prepared by diluting 1 mg/L final volume DNA in 7% final volume M11V3 and gentle mixing. To prevent contamination of the cultures because of the not steril filtrated DNA, Penc./Strep has been added to the transfection after the feeding. Then 3 mg/L final volume PEI solution is diluted in 7% final volume M11V3 and mixed gently (solution 2). Both solutions are incubated for 5-10 min at room temperature (RT). Thereafter solution 2 is added to solution 1 with gentle mixing and incubated another 5-15 minutes at RT After the incubation the transfection mix is added to the cells and the culture is cultivated for four hours (115 rpm, 37° C., 5% CO2).

Supernatant was harvested after 7 days of expression.

Centrifugation 4500 rpm., 15 min., 4° C. (Heraeus, Multifuge 3 S-R)

Clarification through a sterile filter, 0.22 µm (Stericup filter, Thermo Scientific, Cat. 567-0020))

Deliver supernatant to purification for further steps. 1 ml sample of supernatant are used for IPC on Open Access APP-column Sample vials were glass crimp vials, 2 ml Agilent, catalog number 5182-0543 and caps: crimp 11 mm, catalog number 5040-4667.

Protein was purified using immobilized metal affinity chromatography (IMAC) on Aekta Pure or Aekta Avant (GE Healthcare), according to the following protocol, using a 5 ml Histrap HP column (GE Life Sciences, Order No. 17-5248-02). The specifications are set forth in Table 11.

TABLE 11

IMAC protocol

| | CV | Flow (ml/min) | Buffer |
|---|---|---|---|
| Equilibration | 5 | 5 | IMAC A |
| Sample load | | 3 | Cell supernatant |
| Column Wash | 10 | 3 | IMAC A |
| Elution | 10 | 3 | Gradient 0-20% IMAC B |
| | 10 | 3 | 100% IMAC B |
| Fractionation | | | 2 ml fractions |

The buffers used were composed according to Table 12 and Table 13.

TABLE 12

IMAC A, equilibration- and wash buffer

| Concentration | Chemical |
|---|---|
| 10 mM | $Na_2HPO_4$ |
| 10 mM | $NaH_2PO_4$ |
| 500 mM | NaCl |
| 20 mM | Imidazol (Merck) |

TABLE 13

IMAC B, elution buffer

| Concentration | Chemical |
|---|---|
| 10 mM | $Na_2HPO_4$ |
| 10 mM | $NaH_2PO_4$ |
| 500 mM | NaCl |
| 500 mM | Imidazol (Merck) |

The resulting protein, according to Table 14, was stored.

TABLE 14

Constructs

| Construct | Mutation positions |
|---|---|
| C1140 | N73A/F365S |
| C1141 | T229A/F365S |
| C1142 | N292Q/F365S |
| C1143 | N334Q/F365S |
| C1144 | F365S/N371Q |
| C1145 | F365S/N457Q |
| C1058 | F365S |

(b) Results and Interpretation

There was no improvement of mutants concerning yield and monomeric peak of analytical SEC. The parental protein (EP14) with expression tag according to SEQ ID NO: 137 gave best yield and highest monomeric peak in analytical. Lowest yield and as well worst monomeric peak achieved with mutant N371Q.

6. Example 5: Combinations

In order to try and further improve properties, some of the mutations introduced in Example 3 above were combined according to Table 15, below. Mutations are numbered according to the amino acid positions of the wild type CD39 as set forth in SEQ ID NO: 1.

TABLE 15

Combination of constructs

| Construct | Mutation 1 | Mutation 2 | Mutation 3 | Without | Primers | SEQ ID |
|---|---|---|---|---|---|---|
| EP14xEP19 | 365: F -> S | 424: L -> Q | | 436: H -> D | P878/P879 | SEQ ID NO: 64 |
| EP17xEP19 | 424: L -> Q | 436: H -> D | 412: Y -> F | 405: K -> N | P880/P881 | SEQ ID NO: 70 |
| EP14xEP17 | 365: F -> S | 412: Y -> F | | 405: K -> N | P880/P881 | SEQ ID NO: 60 |
| EP10xEP19_H436D | 424: L -> Q | 436: H -> D | 319: I -> T | | P882/P883 | SEQ ID NO: 62 |
| EP19 w/o H436D | 424: L -> Q | | | 436: H -> D | P884/P885 | Sequence not included |

(a) Materials and Methods

The primers according to Table 16 were used.

TABLE 16

Primers

| Primer | Sequence |
|---|---|
| P878 | SEQ ID NO: 183 |
| P879 | SEQ ID NO: 184 |
| P880 | SEQ ID NO: 185 |
| P881 | SEQ ID NO: 186 |
| P882 | SEQ ID NO: 187 |
| P883 | SEQ ID NO: 188 |
| P884 | SEQ ID NO: 189 |
| P885 | SEQ ID NO: 190 |

A PCR reaction was set up using the following pipetting scheme:

5 µl of 10× reaction buffer,
1 µl ds-DNA-template (stock conc. 100 ng/µl),
1.5 µl primer 1,
1.5 µl primer 2,
1 µl dNTP mix
1.5 µl QuickSolution reagent,
35.5 µl H$_2$O (for final volume of 50 µl), and
1 µl QuickChange Lightning Enzyme.

The PCR cycling parameters according to Table 17 were used.

TABLE 17

PCR cycling parameters

| | No. of cycles | Temp | Time |
|---|---|---|---|
| 1 | 1 | 96° C. | 2 min |
| 2 | 18 | 96° C. | 20 sec |
| | | 60° C. | 10 sec |
| | | 68° C. | 3 min (30 sec/kb) |
| 3 | 1 | 68° C. | 6 min |

Directly after reaction, 2 µl DpnI-Enzyme was added to each reaction, mixed and incubated for 5 min at 37° C.

Transformation into XL10-gold ultra-competent cells was performed as follows. Cells were thawed on ice. 45 µl/transformation was used, and 2 µl B-ME was added to each vial. Then, 3 µl DpnI-digested PCR product was added, and incubated for 30 min on ice in 15 ml BD tubes. Thereafter, the samples were heat shocked for 40 seconds and incubated on ice for 2 min. Next, 950 µl SOC media was added, followed by incubation for 1.5 h at 37° C. in a shaking incubator. Finally, cells were plated on LB-carb-plates and incubated over night at 37° C. Next day, single colonies were picked for DNA-miniprep and sequence analysis.

Correct sequences were transfected into HEK293 cells as described in Example 4.

Protein was purified using immobilized metal affinity chromatography (IMAC) according to the following. 95 ml Supernatant was used (~4 ml of all is kept for analysis (IPC)).

Used Material:

Nickel-NTA Agarose, Qiagen, Cat No./ID: 30230, Poly-Prep Chromatography Columns, empty, BioRad, No. 731-1550, IMAC A Buffer pH7.4 (containing 20 mM NaPO$_4$-buffer and 50 mM Imidazol). IMAC B Buffer pH7.4 (containing 20 mM NaPO$_4$-buffer and 300 mM Imidazol). TBS (10×-conc. diluted to 1× conc. With MilliQ-Water). Amicon Ultra-4 Centrifugal Filter Unit with Ultracel-10 membrane, 10K, UFC801096.

Process Steps:

1. Columns were prepared with 1 ml Nickel-NTA-Agarose of Qiagen (=0.5 ml CV);
2. Equilibration with 10 CV IMAC A;
3. Loading of 15/45 ml SN on column (collect flow through);
4. Washing with 10 CV IMAC A (collect in 15 ml Falcon tube);
5. Elution in 6.5 CV of IMAC B;
6. Determination of concentration of eluate;
7. Concentration of 3.5 ml sample to ~400 µl with Amicon Ultra-4 Centrifugal Filter Unit 10K;
8. Buffer exchange by adding TBS and centrifugation 5000;

Samples were analyzed using analytical SEC with 40 µl of each sample and using protein gel with 12 µl of each sample.

The resulting protein was stored.

(b) Results and Interpretation

The results are shown in Table 18.

TABLE 18

Result overview

| Name | Yield (mg/l) | IPC (app, mg/l) | Aggregation (% monomeric peak) |
|---|---|---|---|
| EP14xEP19 | 6.85 | 4.5 | 75.1 |
| EP17xEP19 | 13.35 | 11.5 | 68.9 |
| EP14xEP17 | 17.27 | 11.5 | 69.2 |
| EP10xEP19_H436D | 7.42 | 4.3 | 74.3 |
| EP19 w/o H436D | 8.28 | 2.5 | 55.6 |
| EP1xEP17 | 13.46 | 13.2 | 77.4 |
| EP28 | 7.8 | 2.8 | 57.5 |

Protease Sites:

There was no/very low yield when Matriptase was inserted. With Furin site, there was ~40% yield (but for transfection only 50% of DNA has been used as well, as it was a co-transfection with Furin plasmid).

IL2-Truncations:

All truncations where aa1-3 are included give a comparable result, aa1-3 only might be slightly lower compared to the others, but this might be a variation from sample to sample. Truncation aa4-12 lead to no protein expression. No difference could be found between EP28 that contains, like all other EP-variants, a TSS linker between IL2-start and the hCD39-protein.

Combinations:

Combinations with EP19 (L424Q) did not lead to a significant improvement of protein expression.

Combination with EP1 (R113M) displayed a lower aggregation in analytical SEC. NEG726 was well expressed, but showed worst aggregation of all tested (~37%). Combination of EP14×EP17 did not lead to any further improvement (F365S+Y412F).

7. Example 6: Cloning of Final Candidates

A selection of clinical candidates as set forth in Table 19 below, were expressed for further testing.

TABLE 19

Overview of final candidates.

| Construct | Combination of clones | IL2 leader | Main Sequence |
|---|---|---|---|
| 1 | EP1×EP14×EP19aa1-3 | SEQ ID NO: 137 | SEQ ID NO: 233 |
| 2 | EP1×EP17×EP19aa1-3 | SEQ ID NO: 137 | SEQ ID NO: 217 |
| 3 | EP14aa1-3 | SEQ ID NO: 137 | SEQ ID NO: 229 |
| 4 | EP17aa1-3 | SEQ ID NO: 137 | SEQ ID NO: 237 |
| 5 | EP19aa1-3 | SEQ ID NO: 137 | SEQ ID NO: 243 |
| 6 | EP28aa1-3 (lead/parental) | SEQ ID NO: 137 | SEQ ID NO: 58 |
| 7 | EP1×EP14×EP19aa1-6 | SEQ ID NO: 135 | SEQ ID NO: 235 |
| 8 | EP1×EP17×EP19aa1-6 | SEQ ID NO: 135 | SEQ ID NO: 219 |
| 9 | EP14aa1-6 | SEQ ID NO: 135 | SEQ ID NO: 231 |
| 10 | EP17aa1-6 | SEQ ID NO: 135 | SEQ ID NO: 239 |
| 11 | EP19aa1-6 | SEQ ID NO: 135 | SEQ ID NO: 245 |
| 12 | EP28aa1-6 (lead/parental) | SEQ ID NO: 135 | SEQ ID NO: 80 |

The following primers were used:

TABLE 20

Primers

| Primer | Sequence |
|---|---|
| R113Mtempl | SEQ ID NO: 191 |
| R113MFW | SEQ ID NO: 192 |
| R113MRev | SEQ ID NO: 193 |
| F330Stempl | SEQ ID NO: 194 |
| F330SFW | SEQ ID NO: 195 |
| F330SRev | SEQ ID NO: 196 |
| Y377Ftempl | SEQ ID NO: 197 |
| L389Ctempl | SEQ ID NO: 198 |
| Y377F/L389Qtempl | SEQ ID NO: 199 |
| FW | SEQ ID NO: 200 |
| Rev | SEQ ID NO: 201 |
| WT | SEQ ID NO: 202 |

A PCR reaction was set up using the following pipetting scheme:

0.25 µl DMSO,
20 ng vector
1.5 µl insert (45 ng/µl),
2 µl 5×HF buffer,
0.1 µl Phusion pol,
0.08 µl dNTP mix
10-X µl ddH$_2$O The PCR cycling parameters according to Table 17 were used.

TABLE 21

PCR cycling parameters

| No. of cycles | Temp | Time |
|---|---|---|
| 1 | 1 | 98° C. | 3 min |
| 2 | 25 | 98° C. | 30 sec |
|  |  | 60° C. | 30 sec |
|  |  | 72° C. | 5 min 46 sec |
| 3 | 1 | 72° C. | 10 min |

Directly after reaction, 0.5 µl DpnI-Enzyme was added to each reaction, mixed and incubated for 2 h at 37° C.

Transformation into XL10-gold ultra-competent cells was performed as follows. Cells were thawed on ice. 45 µl/transformation was used, and 2 µl B-ME was added to each vial. Then, 3 µl DpnI-digested PCR product was added, and incubated for 30 min on ice in 15 ml BD tubes. Thereafter, the samples were heat shocked for 40 seconds and incubated on ice for 2 min. Next, 950 µl SOC media was added, followed by incubation for 1.5 h at 37° C. in a shaking incubator. Finally, cells were plated on LB-carb-plates and incubated over night at 37° C. Next day, single colonies were picked for DNA-miniprep and sequence analysis.

All constructs were subcloned into new vector background to ensure that sequences were correct. For this, all constructs were amplified with PCR, with G4S-linkers inserted, followed by digestion with HindIII/EcoRI.

The resulting protein was stored.

8. Example 7: Generation of Comparator Proteins (1) Null Mutations

In order to generate negative control proteins for in vivo studies, one/two mutations were inserted into the parental human CD39ΔMIL protein (EP28). This mutations have been described in the literature to remove or lower the Enzyme activity of this protein. Mutation positions are E174A and S218A.

The following primers were used:

TABLE 22

Primers

| Primer | Sequence |
|---|---|
| P910 | SEQ ID NO: 203 |
| P911 | SEQ ID NO: 204 |
| P914 | SEQ ID NO: 205 |
| P915 | SEQ ID NO: 206 |

A PCR reaction was set up using the following pipetting scheme:

5 µl of 10× reaction buffer,
1 µl ds-DNA-template (stock conc. 100 ng/µl),
1.5 µl primer 1,
1.5 µl primer 2,
1 µl dNTP mix
1.5 µl QuickSolution reagent,
35.5 µl H$_2$O (for final volume of 50 µl), and
1 µl QuickChange Lightning Enzyme.

The PCR cycling parameters according to Table 17 were used.

TABLE 23

PCR cycling parameters

|   | No. of cycles | Temp | Time |
|---|---|---|---|
| 1 | 1 | 96° C. | 2 min |
| 2 | 18 | 96° C. | 20 sec |
|   |   | 60° C. | 10 sec |
|   |   | 68° C. | 3 min (30 sec/kb) |
| 3 | 1 | 68° C. | 6 min |

Directly after reaction, 2 µl DpnI-Enzyme was added to each reaction, mixed and incubated for 5 min at 37° C.

Transformation into XL10-gold ultra-competent cells was performed as follows. Cells were thawed on ice. 45 µl/transformation was used, and 2 µl B-ME was added to each vial. Then, 3 µl DpnI-digested PCR product was added, and incubated for 30 min on ice in 15 ml BD tubes. Thereafter, the samples were heat shocked for 40 seconds and incubated on ice for 2 min. Next, 950 µl SOC media was added, followed by incubation for 1.5 h at 37° C. in a shaking incubator. Finally, cells were plated on LB-carb-plates and incubated over night at 37° C. Next day, single colonies were picked for DNA-miniprep and sequence analysis.

Correct sequences were transfected into HEK293 cells according to the following protocol.

A digestion buffer was prepared, using 10 µg vector-DNA, 0.4 µl HindIII (100 U/µl, NEB), 2 µl EcoRI (20 U/µl, NEB), 5 µl Cutsmart buffer 10× conc. (NEB), and $H_2O$ to a final volume of 50 µl. The digestion reaction was run for 3 h at 37° C.

Immediately after digestion, a dephosphorylating reaction was run. Calf intestinal alkaline phosphatase (10 U/µl, CIP, NEB, No. M0290L) was added (3 µl) to the digested vector mix and incubated for 30 min at 37° C.

The digested and dephosphorylated vector was sub cloned to check the sequence.

Correct sequences were transfected into HEK293 cells according to the following protocol.

7 days of expression was performed using the following material; 1. Human Embryonic Kidney cells constitutively expressing the SV40 large T antigen (HEK293-T, ATCC11268); 2. Polyethylenimine "MAX" MW 40.000 (PEI) (Polysciences, Cat. 24765).

The PEI solution is prepared by carefully dissolving 1 g PEI in 900 ml cell culture grade water at room temperature (RT). Then it is neutralized with NaOH for a final pH of 7.05. Finally the volume is adjusted to 1 L and the solution filtered through a 0.22 µm filter, distributed in aliquots and frozen at −80° C. until further use. Once thawed, an aliquot can be re-frozen up to 3 times at −20° C. but should not be stored long term at −20° C.

M11V3 serum-free culture medium (Bioconcept, CH, Cat: V3-K).

All cell culture work for the transient transfections is carried out using suspension adapted HEK293-Tcells growing in serum-free M11V3 medium.

For small scale (<5 L) transfections cells are grown in Corning shake flasks (Corning, USA) on an orbital shaker (100 rpm) in a humidified $CO_2$-incubator with 5% $CO_2$ (seed flasks).

In general, cells in the seed cultures should be in the exponential growth phase (cell density between $5\times10^5$ and $3\times10^6$/ml) and have a viability of >90%. Cell densities outside of this range will result in either a lag phase after splitting or reduced transfection efficacy.

For small scale (here 2 L) transfection an aliquot of cells is taken out of the seed cultures and adjusted to $1.4\times10^6$ cells/ml in 36% of the final volume with M11V3 medium.

The DNA solution (solution 1) is prepared by diluting 1 mg/L final volume DNA in 7% final volume M11V3 and gentle mixing. To prevent contamination of the cultures, this solution might be filtered using a 0.22 µm filter (e.g. Millipore Stericup). Here because of the small volume no sterile filtration has been done. Then 3 mg/L final volume PEI solution is diluted in 7% final volume M11V3 and mixed gently (solution 2). Both solutions are incubated for 5-10 min at room temperature (RT). Thereafter solution 2 is added to solution 1 with gentle mixing and incubated another 5-15 minutes at RT (do not mix again during incubation time, as PEI covers/condenses DNA into positively charged particles, which bind to anionic cell surface residues and are brought into the cell via endocytosis). After the incubation the transfection mix is added to the cells and the culture is cultivated for four hours (10 rpm, 37° C., 6% $CO_2$).

Finally the culture is fed with the remaining 50% final volume M11V3 medium according to the following example: Inoculation volume: 36 ml with $1.4\times10^6$ cells/ml.

Solution 1: 7 ml M11V3 medium with 100 µg plasmid DNA. Solution 2: 7 ml M11V3 medium with 300 µg PEI (300 µl)

Feed: 50 ml M11V3, Total 100 ml.

Protein was purified using immobilized metal affinity chromatography (IMAC) according to the following. 95 ml Supernatant was used (~4 ml of all is kept for analysis (IPC)).

Used Material:

Nickel-NTA Agarose, Qiagen, Cat No./ID: 30230, Poly-Prep Chromatography Columns, empty, BioRad, No. 731-1550, IMAC A Buffer pH7.4 (containing 20 mM $NaPO_4$-buffer and 50 mM Imidazol). IMAC B Buffer pH7.4 (containing 20 mM $NaPO_4$-buffer and 300 mM Imidazol). TBS (10×-conc. diluted to 1× conc. With MilliQ-Water). Amicon Ultra-4 Centrifugal Filter Unit with Ultracel-10 membrane, 10K, UFC801096.

Process Steps:

1. Columns were prepared with 1 ml Nickel-NTA-Agarose of Qiagen (=0.5 ml CV);
2. Equilibration with 10 CV IMAC A;
3. Loading of 15/45 ml SN on column (collect flow through);
4. Washing with 10 CV IMAC A (collect in 15 ml Falcon tube);
5. Elution in 6.5 CV of IMAC B;
6. Determination of concentration of eluate;
7. Concentration of 3.5 ml sample to ~400 µl with Amicon Ultra-4 Centrifugal Filter Unit 10K;
8. Buffer exchange by adding TBS and centrifugation 5000;

Samples were analyzed using analytical SEC with 40 µl of each sample and using protein gel with 12 µl of each sample.

The resulting protein was stored.

(2) plusMIL

Cloning of EP14aa1-3 with Membrane Interaction Loop (aa193-204) with Overlap extension PCR was performed.

The following primers were used:

TABLE 24

| Primers | |
|---|---|
| Primer | Sequence |
| FW | SEQ ID NO: 207 |
| REV | SEQ ID NO: 208 |
| Rev-sense | SEQ ID NO: 98 |

A PCR reaction was set up using the following pipetting scheme:
1.2 μl Phusion Hot Start Polymerase,
24 μl 5×HF-buffer,
0.96 μl 100 mM dNTPs (25 mM of each dNTP),
0.6 μl Fw primer,
0.6 μl Rev primer,
92.64 μl DEPC H₂O.

The PCR cycling parameters according to Table 17 were used.

TABLE 25

| PCR cycling parameters | | | |
|---|---|---|---|
| | No. of cycles | Temp | Time |
| 1 | 1 | 98° C. | 30 sec |
| 2 | 30 | 98° C. | 10 sec |
| | | 50-70° C. gradient | 30 sec |
| | | 72° C. | 30 sec |
| 3 | 1 | 72° C. | 10 min |

Directly after reaction, 2 μl DpnI-Enzyme was added to each reaction, mixed and incubated for 2 h at 37° C.

Transformation was performed by transferring 2 μl PCR product to a 96-well PCR plate and cool down on ice. 20 μl STELLAR chemical component bacteria was added and carefully mixed by pipetting once up-and-down. The samples were incubated 30 min on ice, and then 45 sec at 42° C. in a PCR machine, followed by another 60 sec incubation on ice. Finally, 90 μl SOC medium was added and incubated 1 hr at 37° C. The whole transfection mix was plated on LB-Ampicilin or LB-Carbencilin plates and grown over night at 37° C.

The resulting protein EP14_plusMIL, with an amino acid sequence according to SEQ ID NO: 155, was stored.

9. Example 8: Enzymatic Activity

The candidates generated in previous examples, were characterized using an enzymatic activity assay.

The following reagents were used: Pi free buffer, a phosphate-free physiological saline solution (140 mM NaCl, 5 mM KCl, 1 mM MgCl2, 2 mM CaCl2), 10 mM Hepes, pH7.4); and Pi free buffer+2% BSA, a phosphate-free physiological saline solution with 20 mg/ml BSA; CD39 protein (according to SEQ ID NO: 1); ATP.

Duplicate CD39 solution was prepared at 2 μg/ml. Duplicate ATP solution was prepared at 1000 μM from a 15 μl ATP stock+1185 μl buffer, total 1.2 ml.

The enzymatic reaction was studied by mixing the 60 μl ATP with 60 μl CD39 or 60 μl with Pi free buffer for the controls, in 48 well PCR plates filled with 120 μl final/well. The final concentration was 500 μM ATP and 1 μg/ml CD39.

Samples were incubated at 37° C. for 0, 5, 15, 30, 60, 90, and 150 minutes, respectively. Then, samples were evaluated either by Pi release assay or HPLC.

(1) Pi Release Assay
(a) Materials and Methods

Reagents were prepared from a standard Pi detection kit according the manufacturers instructions.

A standard curve with Pi was prepared by dilution in water. A 1:2 serial dilution of the Pi stock (100 μM) was prepared: 450 μl+450 μl water. The standard curve concentration was: 50 μM/25 μM/12.5 μM/6.25 μM/3.1 μM/1.5 μM/0 μM.

Gold reagent mix was prepared: 4 ml gold reagent+40 μl accelerator (for 3 plates). In a 96 well plate, the samples were diluted 1:10 in H₂O (Dilution in water: 10 μl sample+ 90 μl H2O). 50 μl, 1:10 diluted sample was distributed in each well of a 96 half-area well plate (Corning, 3690). 12.5 μl Gold reagent mix was added to each well (25% sample volume) and the samples were incubated 10 min at room temperature. Absorbance was read at 635 nm.

(b) Results and Interpretation
Comparative results for candidates are shown in Table 26.

TABLE 26

| Comparative results for candidates. | | | | | | |
|---|---|---|---|---|---|---|
| | Construct | IL-2 start | SEQ ID | Yield after ALC | Monomeric % after ALC | Melting Temp (° C.) | In vitro enzyme activity (relative to EP28) |
| 1 | EP14aa1-3 | SEQ ID NO: 137 | SEQ ID NO: 229 | 33.1 | 83.8 | 62 | 4 |
| 2 | EP1xEP14aa1-3 | SEQ ID NO: 137 | SEQ ID NO: 221 | 3.7 | 50.6 | 65.5 | 4 |
| 3 | EP1xEP17aa1-3 | SEQ ID NO: 137 | SEQ ID NO: 211 | 95.8 | 91.9 | 61 | 1.5 |
| 4 | EP17xEP19 aa1-3 | SEQ ID NO: 137 | SEQ ID NO: 227 | 3.5 | 38.9 | 60.5 | 1.5 |
| 5 | EP1xEP17xEP19aa1-3 | SEQ ID NO: 137 | SEQ ID NO: 217 | 153.2 | 89.7 | 60.75 | 1.5 |
| 6 | EP1 aa1-3 | SEQ ID NO: 137 | SEQ ID NO: 209 | 6.0 | 9.2 | 59.75 | 1 |
| 7 | EP1xEP14 aa1-6 | SEQ ID NO: 135 | SEQ ID NO: 223 | 148.8 | 91.8 | 64 | 4 |
| 8 | EP1xEP17 aa1-6 | SEQ ID NO: 135 | SEQ ID NO: 213 | 59.4 | 86.1 | 59.5 | 1.5 |
| 9 | EP17xEP19 aa1-6 | SEQ ID NO: 135 | SEQ ID NO: 227 | 2.7 | 13.7 | 60 | 1.5 |
| 10 | EP1xEP17xEP19aa1-6 | SEQ ID NO: 135 | SEQ ID NO: 219 | 30.9 | 88.4 | 60.75 | 1.5 |
| 11 | EP1xEP17_K405Naa1-15 | SEQ ID NO: 133 | SEQ ID NO: 215 | 156.3 | 86.4 | 62.25 | 1.5 |
| 12 | EP28aa1-3 | SEQ ID NO: 137 | SEQ ID NO: 58 | 2.7 | 10 | 60.5 | 1 |
| 13 | EP28aa1-16 | SEQ ID NO: 131 | SEQ ID NO: 72 | 4.7 | 45 | 61.8 | 1 |

Enzymatic activity was measured by adding 500 μM ATP to the enzyme and analyzing the concentration of ATP, ADP, AMP with HPLC (method description below) over time. The resulting kinetic curves where fitted with the model in FIG.

6 to obtain the enzymatic constants. In terms of the enzymatic constant Kcat the enzymes show the following order (low activity to high activity): EP28 (wt), EP17, EP14, EP15.

Figure 7:
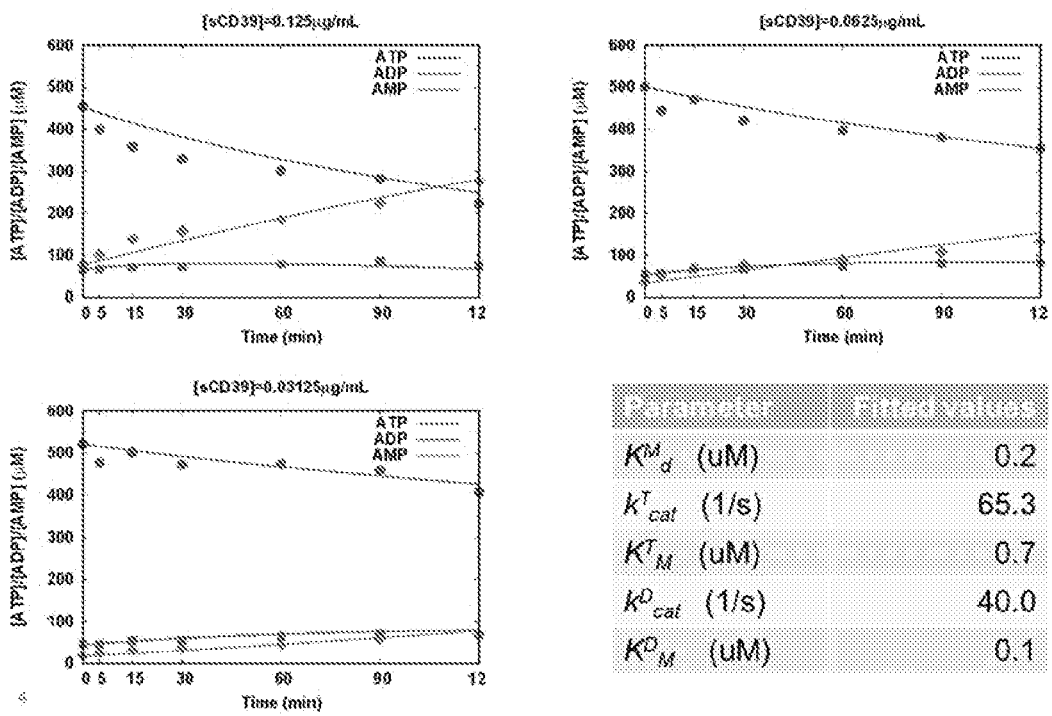
FIG. 7 is an overview of kinetic data and model fit for a protein according to an embodiment.
Figure 8:
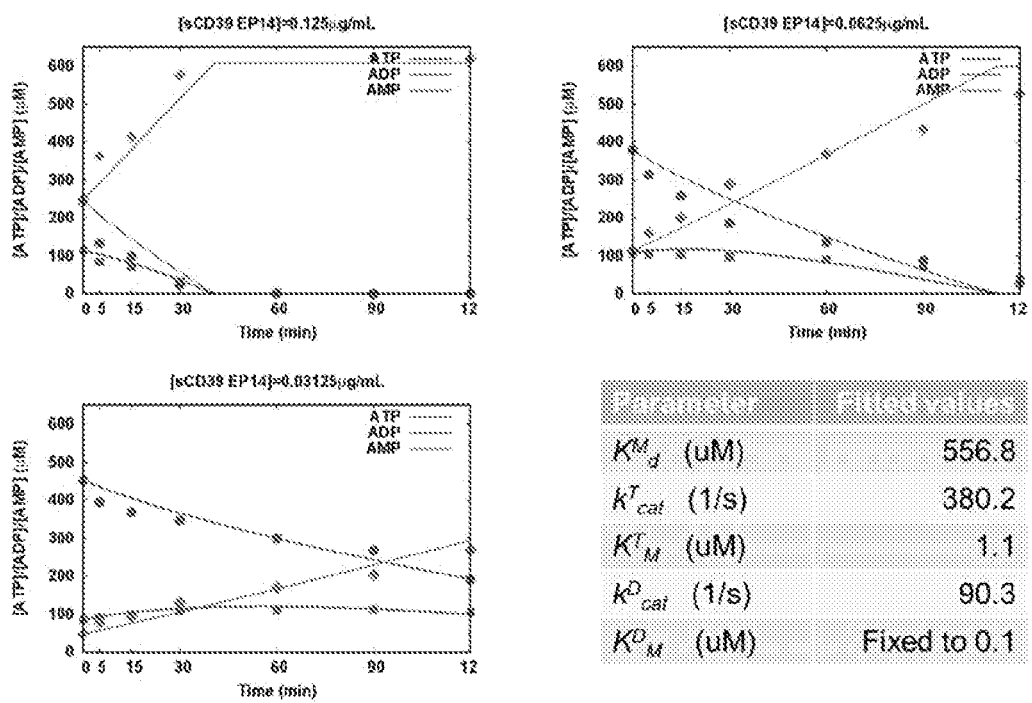
FIG. 8 is an overview of kinetic data and model fit for a protein according to an embodiment.
Figure 9:
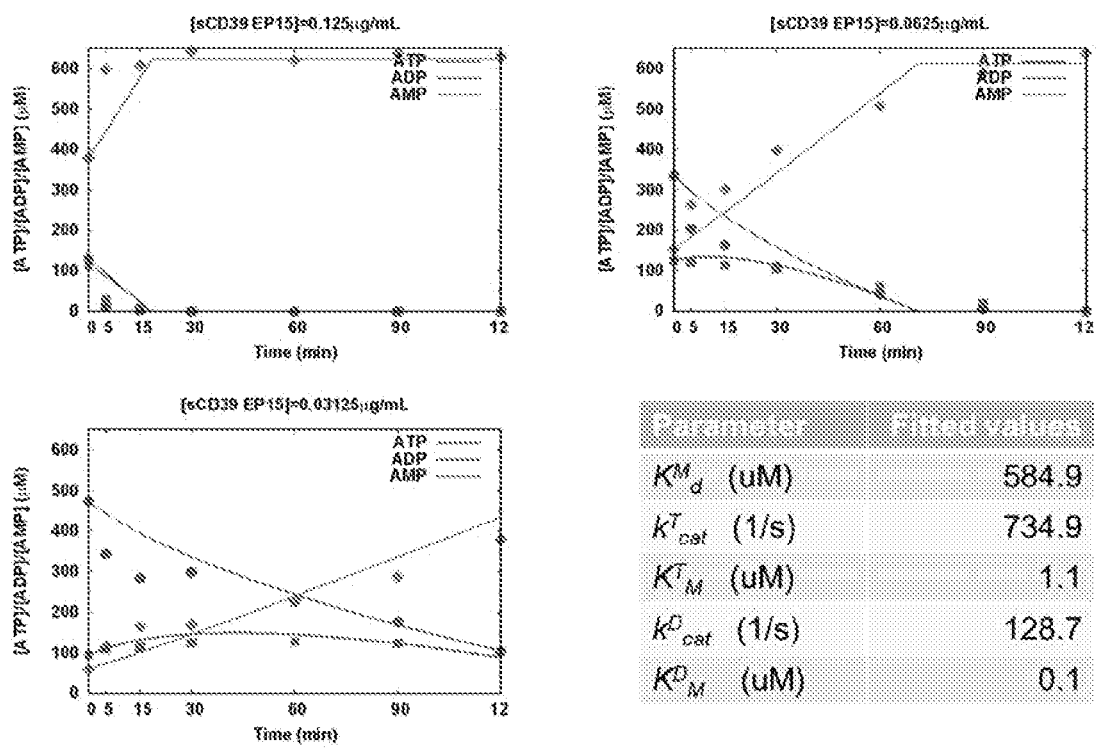
FIG. 9 is an overview of kinetic data and model fit for a protein according to an embodiment.

FIG. 7 shows kinetic data and model fit for EP28. FIG. 8 shows kinetic data and model fit for EP14. FIG. 9 shows kinetic data and model fit for EP15.

An overview of enzyme constants for EP28 (wt), EP14, EP15 and EP17 is shown in Table 27. Compared to the wild type (WT) the three novel variants show increased catalytic activity. Importantly, the new variants show a clear increase in the catalytic rate constant (kcat) catalytic efficiency (kcat/Km). As the reported ATP and ADP substrate concentration during tissue damage and thrombosis are above the reported Km, this increase in kcat and kcat/Km will likely translate in higher activity in vivo.

TABLE 27

Enzyme constants

| | ATP -> ADP + P | | | ADP -> AMP + P | | | inhibition |
|---|---|---|---|---|---|---|---|
| | $k_{cat}^T$ | $K_M^T$ | $k_{cat}^T/K_M^T$ | $k_{cat}^D$ | $K_M^D$ | $k_{cat}^D/K_M^D$ | $K_i^M$ |
| WT | 65.3 | 0.7 | 89.7 | 40.0 | 0.1 | 400.3 | 0.2 |
| EP14 | 380.2 | 1.1 | 352.6 | 90.3 | Fixed to 0.1 | 903.0 | 556.8 |
| EP15 | 734.9 | 1.1 | 658.1 | 128.7 | 0.1 | 1287.1 | 584.9 |
| EP17 | 180.7 | 1.0 | 178.1 | 67.0 | 0.1 | 670.0 | 3.0 |

(2) HPLC Validation Assay (Kinetic and Dose Response)

(a) Materials and Methods

The candidates were tested with HPLC validation assay. 70 µl of each sample was transferred into glass vials for HPLC.

Calibration samples were prepared with Stock-Solutions 5 mM as shown in Table 28.

TABLE 28

Stock solutions

| 5 mM | | weight | H$_2$O |
|---|---|---|---|
| Adenosine | 1336.2 µg/mL | 1.862 mg | 1394 µL |
| Inosine | 1341.2 µg/mL | 2.668 mg | 1989 µL |
| AMP | 1736.1 µg/mL | 2.182 mg | 1257 µL |
| ADP | 2506.6 µg/mL | 2.500 mg | 997 µL |
| ATP | 2755.7 µg/mL | 4.834 mg | 1754 µL |

| 1000 µM | 20 µL of each stock-solutions were mixed in a HPLC vial |
|---|---|
| 500 µM | 20 µL 1 mM + 20 µL H$_2$O |
| 100 µM | 10 µL 1 mM + 90 µL H$_2$O |
| 10 µM | 10 µL 100 µM + 90 µL H$_2$O |
| 1 µM | 10 µL 10 µM + 90 µL H$_2$O |

HPLC Separation was done using an Agilent 1100 System with a CapPump (G1376A), Degasser (G1379A), ALS (G1329A), Thermostat (G1330B, ColComp (G1316A) and a DAD (G1315A). Solvent A: 10 mM KH$_2$PO$_4$ (04243, Riedel-de Haën)+2 mM TBA bromide, pH7.0 (86857-10G-F, Fluka) and Solvent B: 10 mM KH2PO4/ACN 1/1+2 mM TBA bromide, pH5.5. Column: Nucleodur 300-5 C18 ec, 2×150 mm, 5 µm, Macherey-Nagel 760185.20 Batch E14100258 36654055. The column temperature was 40° C., injection volume 10 µL, flow rate was 0.3 ml/min and the gradient was 0-3': 0% B; 3-23': 0-95% B, linear; 23-28': 95% B, linear; 28-29': 95-0% B, linear; 5' Post Time". DAD: 247 nm and 259 nm.

UPLC Separation was done using a Waters UPLC I class. Solvent A: 10 mM KH$_2$PO$_4$/10 mM K$_2$HPO$_4$ 1/1+2 mM TBA bromide, pH 7.0. Solvent B: 10 mM KH$_2$PO$_4$/ACN 1/1+2 mM TBA bromide, pH 5.5. Column: Fortis Bio C18, 2.1×50 mm, 5 µm, di2chrom B10318-020301 SN H03161210-2. Column temperature was 40° C., injection volume was 10 µL, flow rate was 0.5 ml/min and gradient was 0-1': 0% B; 1-8': 0-55% B, linear; 8-10': 55% B; 10-11': 55-0% B, linear; 14' Stop Time. DAD was 247 nm and 259 nm.

(b) Results

The results can be seen in FIGS. 7, 8, 9 and 11, showing kinetic data and model fit for candidates according to different embodiments.

10. Example 9: In Vitro Activity, Initial Screen

The CD39 versions EP1 to EP24, described in previous examples, were cloned in mammalian expression vector pRS5a_Leader_APP_His (FIG. 5), without IL2-leader and without IL2-start.

(a) Materials and Methods

A small scale expression (20/50 ml scale) of EP-Hits in HEK293 (PEI-Transfection) for 7 days was performed, followed by IPC on APP-HPLC (as described supra).

Protein purification of 15/45 ml cell supernatant with Ni-NTA-columns (0.5 ml CV);

Elution with 6 CV IMAC B buffer (20 mM NaPO4-buffer, 300 mM Imidazol, pH7.4);

Concentration and rebuffering of purified protein in TBS, pH7.4;

Analysis of protein with protein gel, analytical SEC;

Delivery of all variants and three controls (parental hCD39-dMIL, or EP28, with and without IL2-start, and 8M-version without IL2-start): 90-200 ul of purified protein in TBS, pH7.4

(b) Results and Interpretation

The results are summarized in Table 29 below.

All samples are in TBS pH7.4 and have an APP- (SEQ ID N: 247) and a His-Tag (SEQ ID NO: 249)

Only parental human CD39ΔMIL (EP28) has a 15 amino acid long IL2-start, aa1-15 (SEQ ID NO: 133).

Pi release assay BOENKTH1-0252824, double det. For 60 and 180 min. values

TABLE 29

In vitro activity Pi release assay, 0.25 ug/ml + 500 uM ATP

| Date of purification | Name | conc. [mg/ml] | conc. [umolar] | total vol. [ml] | 0 min. | mean 60 min. | mean 180 min |
|---|---|---|---|---|---|---|---|
| 17 Jun. 2016 | EP1 | 0.19 | 3.7 | 0.11 | 10.35 | 20.90 | 45.99 |
| 14 Jun. 2016 | EP2 | 0.15 | 2.8 | 0.10 | 11.35 | 23.65 | 53.92 |
| 14 Jun. 2016 | EP3 | 0.11 | 2.2 | 0.10 | 8.92 | 19.22 | 40.76 |
| 14 Jun. 2016 | EP4 | 0.25 | 4.8 | 0.10 | 7.99 | 18.59 | 37.47 |
| 14 Jun. 2016 | EP5 | 0.11 | 2.1 | 0.10 | 17.36 | 39.59 | 72.09 |
| 17 Jun. 2016 | EP6 | 0.14 | 2.7 | 0.15 | 11.57 | 32.73 | 69.63 |
| 21 Jun. 2016 | EP7 | 0.41 | 7.8 | 0.11 | 9.47 | 21.19 | 43.68 |
| 21 Jun. 2016 | EP8 | 0.31 | 5.9 | 0.11 | 7.92 | 15.23 | 33.94 |
| 14 Jun. 2016 | EP9 | 0.15 | 2.9 | 0.10 | 5.56 | 13.39 | 31.38 |
| 21 Jun. 2016 | EP10 | 0.33 | 6.3 | 0.11 | 9.32 | 21.91 | 54.07 |
| 14 Jun. 2016 | EP11 | 0.23 | 4.4 | 0.10 | 10.24 | 21.27 | 46.21 |
| 21 Jun. 2016 | EP12 | 0.37 | 7.1 | 0.11 | 10.55 | 21.99 | 50.80 |
| 21 Jun. 2016 | EP13 | 0.13 | 2.5 | 0.11 | 4.93 | 3.13 | 3.54 |
| 21 Jun. 2016 | EP14 | 0.34 | 6.5 | 0.11 | 19.07 | 66.35 | 104.80 |
| 14 Jun. 2016 | EP15 | 0.19 | 3.7 | 0.10 | 11.11 | 29.26 | 89.92 |
| 14 Jun. 2016 | EP17 | 0.28 | 5.3 | 0.10 | 12.49 | 30.30 | 102.81 |
| 14 Jun. 2016 | EP18 | 0.15 | 2.9 | 0.10 | 3.91 | 9.70 | 23.49 |
| 17 Jun. 2016 | EP19 | 0.55 | 10.6 | 0.12 | 14.36 | 26.38 | 69.93 |
| 14 Jun. 2016 | EP20 | 0.14 | 2.7 | 0.10 | 3.36 | 2.22 | 3.60 |
| 14 Jun. 2016 | EP21 | 0.22 | 4.2 | 0.10 | 7.17 | 16.37 | 24.27 |
| 17 Jun. 2016 | EP22 | 0.17 | 3.3 | 0.11 | 8.06 | 15.33 | 37.30 |
| 21 Jun. 2016 | EP23.1 | 0.28 | 5.4 | 0.11 | 12.62 | 23.58 | 62.78 |
| 17 Jun. 2016 | EP24 | 0.10 | 2.0 | 0.19 | 3.10 | 3.45 | 4.83 |
| 14 Jun. 2016 | EP25 | 0.23 | 4.4 | 0.10 | 4.98 | 11.46 | 24.30 |
| 17 Jun. 2016 | EP26 hCD39-dMIL parental | 0.19 | 3.7 | 0.15 | 3.66 | 8.41 | 24.15 |
| 17 Jun. 2016 | EP28-IL2start-hCD39 par hCD39-8M | 2.19 | 42.0 | 0.14 | 10.25 | 23.48 | 52.73 |
| 21 Jun. 2016 | EP1repet. | 0.49 | 9.5 | 0.11 | 10.03 | 17.84 | 40.33 |
| 17 Jun. 2016 | EP2repet. | 0.55 | 10.6 | 0.12 | 12.80 | 28.22 | 66.88 |
| 17 Jun. 2016 | EP3repet. | 0.56 | 10.8 | 0.12 | 18.05 | 33.35 | 79.53 |
| 17 Jun. 2016 | EP4repet. | 0.61 | 11.7 | 0.16 | 15.98 | 29.47 | 68.39 |
| 17 Jun. 2016 | EP5repet. | 0.66 | 12.6 | 0.15 | 25.53 | 46.10 | 91.32 |
| 21 Jun. 2016 | EP23.4 | 0.29 | 5.5 | 0.11 | 10.43 | 22.45 | 56.53 |

11. Example 10: In Vitro Activity, Refined Screen

A subset of 12 mutants were tested a second time, but with IL-2 start allowing a larger expression scale.

(a) Materials and Methods

The mammalian expression vector pRS5a_Leader_APP_His, with a 15 amino acid long IL2-start, aa1-15 (SEQ ID NO: 133) (FIG. 5). Small scale expression (50/100 ml scale) of EP-Hits in HEK293 (PEI-Transfection) for 7 days followed by IPC on APP-HPLC (as described supra).

Protein purification of 45/95 ml cell supernatant with Ni-NTA-columns (0.5 ml CV)

Elution with 6 CV IMAC B buffer (20 mM NaPO4-buffer, 300 mM Imidazol, pH7.4)

Concentration and rebuffering of purified protein in TBS, pH7.4,

Analysis of protein with protein gel, analytical SEC

Delivery of all variants and control (parental hCD39-dMIL, or EP28, with IL2-start aa1-15 (SEQ ID NO: 133)):

500 ul of purified protein in TBS, pH7.4

(b) Results and Interpretation

The results are summarized in Table 30, Table 32 and Table 33 below.

TABLE 30

Protein purifications of EP-Hits 6 Jul. 2016, part 1

| Name | conc. [mg/ml] | conc. [umolar] | total vol. [ml] | yield/46 or 16 ml [mg] | Yield (mg/l) | IPC (APP, mg/l) |
|---|---|---|---|---|---|---|
| EP2 | 0.64 | 12.3 | 0.5 | 0.32 | 7.13 | 6.9 |
| EP3 | 0.72 | 13.9 | 0.5 | 0.36 | 8.02 | 8.6 |
| EP4 | 0.86 | 16.4 | 0.5 | 0.43 | 9.49 | 8.6 |
| EP5 | 0.89 | 17.0 | 0.5 | 0.44 | 9.84 | 10.1 |
| EP6 | 0.40 | 7.7 | 0.5 | 0.20 | 4.46 | 4.3 |
| EP9 | 0.57 | 11.0 | 0.5 | 0.29 | 6.35 | 6.0 |
| EP11 | 0.74 | 14.2 | 0.5 | 0.37 | 8.18 | 8.3 |
| EP12 | 0.85 | 16.3 | 0.5 | 0.42 | 9.40 | 8.2 |

TABLE 30-continued

Protein purifications of EP-Hits 6 Jul. 2016, part 1

| Name | conc. [mg/ml] | conc. [umolar] | total vol. [ml] | yield/46 or 16 ml [mg] | Yield (mg/l) | IPC (APP, mg/l) |
|---|---|---|---|---|---|---|
| EP14 | 0.82 | 15.7 | 0.5 | 0.41 | 9.09 | 7.8 |
| EP17 | 0.94 | 18.0 | 0.5 | 0.47 | 13.04 | 13.3 |
| EP18 | 0.70 | 13.4 | 0.5 | 0.35 | 7.75 | 6.4 |
| EP24 | 0.65 | 12.4 | 0.5 | 0.32 | 8.99 | 10.8 |
| EP28 with IL2-start | 0.27 | 5.2 | 0.5 | 0.14 | 9.01 | 6.6 |

TABLE 31

Protein purifications of EP-Hits Jun. 7, 2016, part 2

| Name | Expr. vol. (ml) | Aggregation (%) (Anal. SEC) | Monomeric peak (%) (Anal. SEC) | Degradation (%) (Anal. SEC) | Pi Assay: 1 ug/ml Enzyme, 500 uM ATP, 60 min (1:10) |
|---|---|---|---|---|---|
| EP2 | 50 | 15.7 | 69.5 | 14.9 | 53.572 |
| EP3 | 50 | 14.9 | 67.6 | 17.5 | 62.6725 |
| EP4 | 50 | 11.3 | 72.5 | 16.3 | 52.1195 |
| EP5 | 50 | 15.1 | 67.8 | 17 | 75.1995 |
| EP6 | 50 | 17.2 | 59.3 | 23.5 | 72.517 |
| EP9 | 50 | 21.7 | 57.5 | 20.8 | 63.7175 |
| EP11 | 50 | 12.3 | 72.2 | 15.6 | 59.0205 |
| EP12 | 50 | 19.9 | 63.1 | 17.1 | 48.358 |
| EP14 | 50 | 14.9 | 66.6 | 18.5 | 88.3785 |
| EP17 | 40 | 17.3 | 68.9 | 13.8 | 89.8415 |
| EP18 | 50 | 15.4 | 67.2 | 17.4 | 61.495 |
| EP24 | 40 | 8.9 | 73 | 18 | 74.713 |
| EP28 with IL2-start | 20 | 17.8 | 56.4 | 25.8 | 53.6735 |

TABLE 32

Protein purifications EP-Hits 15 Jul. 2016

| Name | MW [kD] | e [M−1*cm−1] | conc. [mg/ml] | conc. [umolar] | total volume [ml] | delivered amount | Expression volume (ml) |
|---|---|---|---|---|---|---|---|
| EP8 | 52.08 | 70875 | 0.02 | 0.5 | 0.5 | 0.01 | 50 |
| EP10 | 52.08 | 70875 | 0.76 | 14.7 | 0.5 | 0.38 | 50 |
| EP14 | 52.08 | 70875 | 0.21 | 4.0 | 0.5 | 0.10 | 50 |
| EP15 | 52.08 | 70875 | 0.81 | 15.6 | 1 | 0.81 | 100 |
| EP17 | 52.08 | 70875 | 0.22 | 4.3 | 0.5 | 0.11 | 40 |
| EP19 | 52.08 | 70875 | 1.10 | 21.2 | 0.5 | 0.55 | 50 |
| EP23 | 52.08 | 70875 | 0.46 | 8.8 | 0.5 | 0.23 | 50 |
| EP28-parental control | 52.08 | 70875 | 0.77 | 14.7 | 1 | 0.77 | 100 |

TABLE 33

Point mutations, in relation to the wild type CD39 sequence according to SEQ ID NO: 1.

| No. Mutations | Mutation Pos. 1 | Mutation Pos. 2 | Mutation Pos. 3 | Mutation Pos. 4 | Sequence found | Pi Assay: 1 ug/ml Enzyme, 500 uM ATP, 60 min., 1:10 |
|---|---|---|---|---|---|---|
| 1 | 151: V -> A | | | | 2x | 4.309 |
| 1 | 319: I -> T | | | | 2x | 54.866 |

TABLE 33-continued

Point mutations, in relation to the wild type
CD39 sequence according to SEQ ID NO: 1.

| No. Mutations | Mutation Pos. 1 | Mutation Pos. 2 | Mutation Pos. 3 | Mutation Pos. 4 | Sequence found | Pi Assay: 1 ug/ml Enzyme, 500 uM ATP, 60 min., 1:10 |
|---|---|---|---|---|---|---|
| 1 | 365: F -> S | | | | unique | 69.0195 |
| 4 | 292: N -> K | 365: F -> S | 424: L -> P | 463: P -> S | unique | 78.81 |
| 2 | 405: K -> N | 412: Y -> F | | | unique | 89.415 |
| 2 | 424: L -> Q | 436: H -> D | | | unique | 62.912 |
| 4 | 254: L -> M | 263: W -> R | 439: F -> S | 469: S -> R | unique | 88.282 |

12. Example 11: In Vivo Activity, pK (a) Materials and Methods

For in-vivo PK 10 mg/kg compound at a final concentration of 10 mg/ml in PBS buffer was administered intravenously (1 ml/kg) via the tail vein to 4 conscious female C57BL/6 mice. Mice were obtained from WIGA and had a bodyweight of around 22 g. All in-life work was conducted under the Swiss animal welfare law.
Whole blood was collected (50 µL per time point) 0.25, 3, 8, 24 and 48 h post dose in small volume serum tubes using POCT Minivettes. Serum was separated and used for concentration determination.

The Gyrolab technology is an automated immunoassay at nanoliter scale using an affinity flow-through format which works through centrifugal forces and laser-induced fluorescence detection. Streptavidin-coated beads are pre-packed in affinity columns on a Gyrolab Bioaffy CD. Each CD contains 112 columns. The affinity-capture columns per microstructure comprise 15 nl. The injected samples enter by capillary action. The biotinylated capture reagent binds to the Streptavidin coated beads. Afterwards, the analyte solution is injected, which binds to the captured molecules. Finally, the fluorophore-labeled detection reagent is applied. In the case of CD39, two different assay read-outs were used depending on the availability of an APP tag.

Figure 10A:
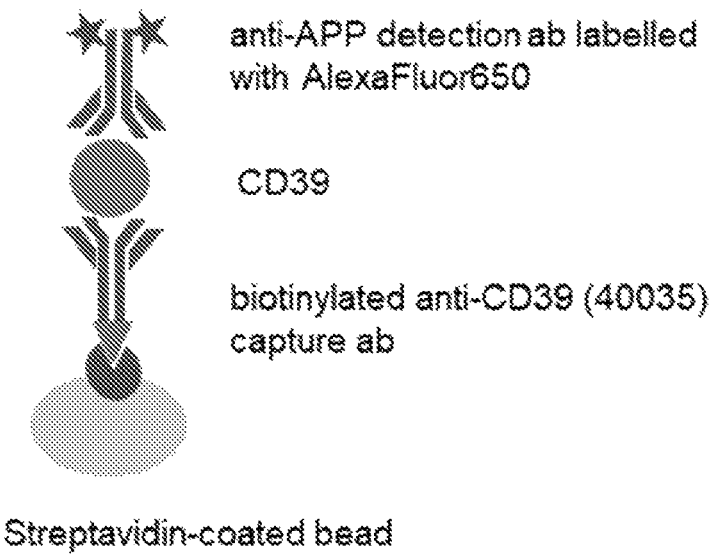
FIG. 10 is a schematic representation of experimental conditions.
Figure 10B:
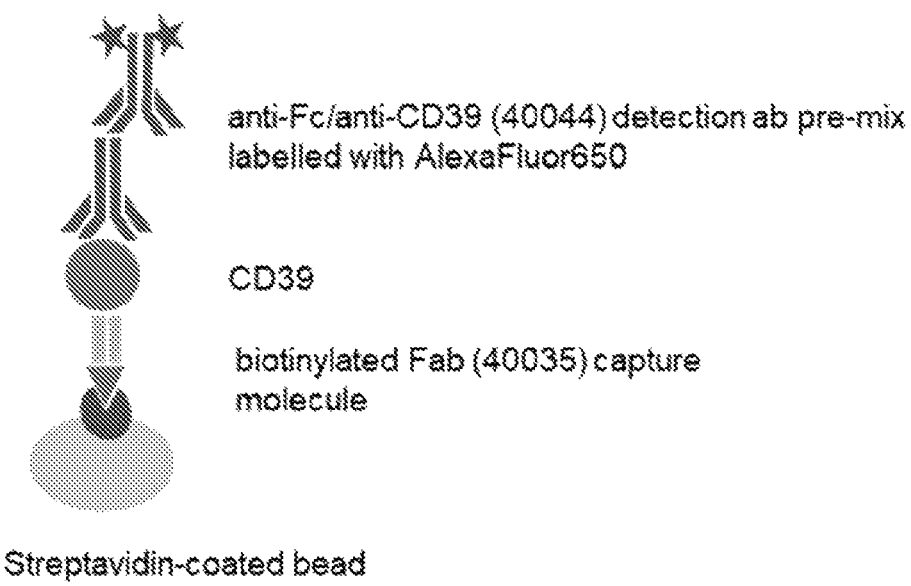
Figure 11:
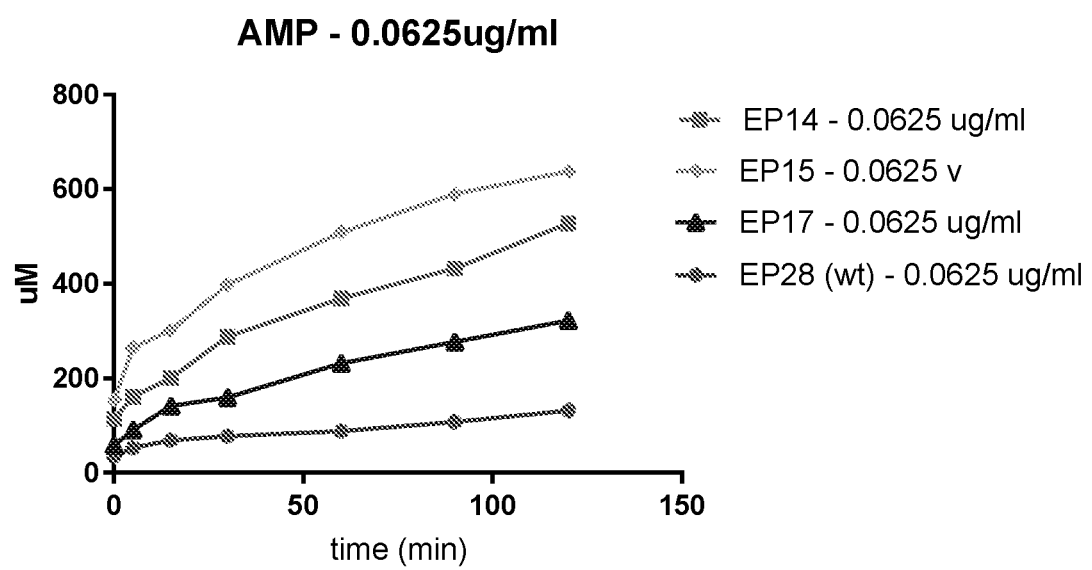
FIG. 11 is a graph showing AMP levels for proteins according to embodiments.

1) anti-CD39 (40035) and anti-APP (27431) is seen in FIG. 10A.
2) Fab (40035) and anti-Fc/anti-CD39 (40044) 1:1 pre-mix (all EP28aa1-16 constructs) is seen in FIG. 10B. Antibody 40044 loses activity when biotinylated by amine coupling, therefore, only antibody 40035 was biotinylated.

All standard curves for the CD39 constructs were diluted in Rexxip A containing 5% (v/v) mouse serum in a dilution series of 1:2. The applied concentration range for the APP tagged constructs was 5000 ng/ml-9.77 ng/ml and for EP28aa1-16 it was 10000 ng/ml-9.77 ng/ml. All mouse sera samples were diluted 1:100 in Rexxip A containing 5% (v/v) mouse serum. The QC samples of the CD39 constructs were diluted in Rexxip A containing 5% (v/v) mouse serum (50 and 500 ng/ml for constructs with APP tag, and 500 and 1000 ng/ml for EP28aa1-16). The final concentration for all biotinylated capture reagents was 0.1 mg/ml and the fluorescently labelled detection antibody was diluted to 10 nM in Rexxip F.

(b) Result and Interpretation

The results are summarized in Table 34. As can be seen, all candidates show the same PK. Therefore, the selection of the candidate was not based on PK properties.

TABLE 34 pK values

| Construct | SEQ ID | Animal 1 | Animal 2 | Animal 3 | Animal 4 | Mean t/2 (d) |
|---|---|---|---|---|---|---|
| EP28aa1-16 | SEQ ID NO: 72 | 1.1 | 1.3 | 1.0 | 1.1 | 1.1 |
| EP1xEP14aa1-6 | SEQ ID NO: 223 | 0.9 | 0.7 | 0.7 | 0.3 | 0.7 |
| EP28aa1-3 | SEQ ID NO: 58 | 0.6 | 0.7 | 0.9 | 0.8 | 0.8 |
| EP14aa1-3 | SEQ ID NO: 229 | 0.7 | 1.0 | 0.6 | 1.1 | 0.9 |
| EP14aa1-6 | SEQ ID NO: 231 | 0.7 | 0.7 | 0.7 | 0.8 | 0.7 |
| EP17aa1-3 | SEQ ID NO: 237 | 0.9 | 0.8 | 0.9 | 0.8 | 0.9 |
| EP17aa1-15 | SEQ ID NO: 241 | 0.8 | 0.9 | 0.9 | 0.6 | 0.8 |

13. Example 12: In Vivo Activity, AKI Model (a) Materials and Methods

A nephrectomy of the right kidney is performed prior to the start of I/R setting. The second kidney is removed to avoid compensatory mechanisms that change the entire dynamic of the biology. Spontaneously breathing anesthetized animals are placed on the homeothermic blanket of a homeothermic monitor system and covered by sterile gauze. The body temperature is recorded through a rectal probe and controlled in the range of 36.5-37.5° C. to avoid hypothermia. Animals are anaesthetized, shaved and disinfected (Betaseptic). Following mid-line incision/laparotomy the abdominal contents are retracted to the left and the right kidney is removed. The ureter and blood vessels are disconnected and ligated (9-0 Ethicon), the kidney is then removed.

I/R injury induction: Immediately after the nephrectomy of the right kidney abdominal contents are retracted to the right and the left renal artery is dissected free for renal ischemia induction.

Micro-aneurysm clips are used to clamp the pedicle to block the blood flow to the kidney and induce renal ischemia. The duration of the kidney ischemia starts from the time of clamping. Successful ischemia is confirmed by color change of the kidney from red to dark purple in a few seconds. After the ischemia, the micro-aneurysm clips are removed and reperfusion is indicated by a kidney color change to red.

(b) Result and Interpretation

The result is seen in FIG. 12. The candidates show a dose response in vivo which correlate to their specific in vitro activity. FIG. 12A shows results for the parental EP28, FIG. 12B shows results for EP1×EP17 and FIG. 12C shows results for EP14. As can be seen, EP28 and EP1×EP17 show similar dose responses, whereas EP14 with higher in vitro activity shows full efficacy with a lower dose.

14. Example 13: Titer, Yield and Developability

In order to manufacture selected candidates in a commercial scale, it is important to be able to express them with relatively high yield. For therapeutic proteins, this might be less straightforward compared to therapeutic antibodies, due to format complexity in addition to lack of enrichment technology which enables selection of high producing clones.

Both candidates, EP14aa1-3 and EP28aa1-3, had comparable technical characteristics, which were challenging. Particularly, low expression titers of early expression batches (data not shown) impacts production costs or might even be even lower after upscaling because of the control of host cell proteins is not robust.

In order to try to improve protein expression by early clone selection for both candidates a tailor-made purification process required was required. To this end, pools of cells expressing the candidates EP28aa1-3 and EP14aa1-3 were generated.

A parental CHO cell line was used as host cell line for the production of the EP28aa1-16/EP14aa1-3 expressing cell line. The host cell line was derived from the CHO-K1 cell line, well known to a person skilled in the art, in a way described e.g. in the patent applications WO2015092737 and WO2015092735, both incorporated by reference in their entirety. A single vial from the CHO line was used to prepare the EP28aa1-16/EP14aa1-3 recombinant cell line.

The cells were grown in chemically defined cultivation medium. One μg of SwaI linearized plasmid DNA, expression vector encoding for EP28aa1-16/EP14aa1-3, was added per transfection. The transfection reaction was performed in chemically defined cultivation medium.

Transfections were performed by electroporation using an AMAXA Gene Pulser, according to the manufactures instructions. The parental CHO cells used for transfection were in exponential growth phase with cell viabilities higher than 95%. In total, three transfections were performed with $5 \times 10^6$ cells per transfection. Immediately after transfection, cells were transferred into Shake Flasks, containing medium chemically defined cultivation medium.

Cell pools were incubated for 48 hours at 36.5° C. and 10% $CO_2$ before starting the selection process. A selection procedure was carried out using the selection marker encoded in the expression vector. 48 hours after transfection and growth under low folate conditions, additional selective pressure was applied by adding 10 nM MTX to the chemically defined cultivation medium. 21 days after the start of MTX selection, pool populations consisting predominantly of MTX resistant cells have emerged. After pool recovery cells were frozen. Standard fed batches in chemically defined cultivation medium were set up for determination of concentration of the EP28aa1-16/EP14aa1-3. A reversed phase chromatography (RPC) was used to determine the product concentration. CHO cell pools producing EP28aa1-16/EP14aa1-3 were used for a FACS single cell sorting/Cell printer procedure to obtain individualized clonal cell lines.

15. Example 14: Therapeutic Use

Extracellular ATP, activating $P2X_7R$, have been clearly linked several diseases, such as enhancing graft-versus-host disease (Wilhelm et al. Graft-versus-host disease is enhanced by extracellular ATP activating $P2X_7R$. Nature Medicine 16:12, pages 1434-1439 (2010).)

Furthermore, both in vitro and in vivo studies indicate that CD39 represents an important apyrase in cardiovascular health by regulating levels of ADP. Apyrase is known to inhibit platelet aggregation by metabolizing extracellular ADP.

Human apyrase does not covalently bind to platelets as opposed to other therapies like clopidogrel (Plavix™), which irreversibly bind to ADP receptor on the platelet. This allows a faster disappearance of the therapeutic blockade and therefore a safer approach to patients with excessive platelet activation. This provides a safer approach to patients with excessive platelet activation.

Thus, there is a clear basis for therapeutic use of compounds which reduce levels of extracellular ATP, such as the compounds according to the invention.

Specific non-limiting examples of therapeutic uses of the compounds according to the invention are acute organ damage due to trauma and/or hypoxia, such as acute respiratory distress syndrome (ARDS), lung injury, renal failure, acute kidney injury (AKI), including acute kidney injury following coronary artery bypass graft surgery, delayed graft function after transplantation (including xenotransplantation) of kidney or other solid organs, or vascular disease, such as occlusive vascular disease, transplantation, and xenotransplantation, treatment of individuals who suffer from stroke, coronary artery disease or injury resulting from myocardial infarction, atherosclerosis, arteriosclerosis, embolism, preeclampsia, angioplasty, vessel injury, transplantation, neonatal hypoxic ischemic encephalopathy, platelet-associated ischemic disorders including lung ischemia, coronary ischemia and cerebral ischemia, ischemia-reperfusion injury (IRI) thrombotic disorders including, coronary artery thrombosis, cerebral artery thrombosis, intracardiac thrombosis, peripheral artery thrombosis, and venous thrombosis delayed graft function after transplantation (including xenotransplantation) of kidney or other solid organs. Other non-limiting examples of therapeutic uses of compounds according to the invention are treatment of burns or radiation damage, sepsis, improving wound healing, decrease bleeding or the risk of bleeding, prevention organ damage, graft-versus-host disease, or prevention of transplant rejection.

Particularly preferred therapeutic uses of the compounds according to the invention is acute kidney injury (AKI), such as acute kidney injury following coronary artery bypass graft surgery or sepsis or rhabdomyolysis. This condition increases patient mortality and there is no standard of care (SoC). The main causes of AKI in the intensive care unit are: sepsis (47.5%), major surgery (34%), cardiogenic shock (27%), hypovolemia (26%) and nephrotoxic compounds (19%). Furthermore, AKI is an independent strong risk factor for developing chronic kidney disease (CKD).

20-30% of major cardiac surgeries patients acquire acute kidney injury. Another preferred embodiment relates to the use an isolated apyrase according to the invention for the treatment of cardiac surgery associated acute kidney injury.

In another embodiment, the disclosure relates to an isolated apyrase according to the invention for use in the treatment of delayed graft function (DGF), acute respiratory distress syndrome (ARDS), acute myocardial infarction (AMI), traumatic brain injury (TBI)/acute ischemic stroke (AIS), or combinations thereof often referred to as multi-organ failures (MOF).

16. Acute Kidney Injury (AKI) is a Common Complication of Sepsis. 28% of Sepsis Patients Acquire AKI. In an Additional Preferred Embodiment the Disclosure Relates to the Use an Isolated Apyrase According to the Invention for the Treatment of Sepsis Associated Acute Kidney Injury. Example 15: Therapeutic Compositions Therapeutic proteins are typically formulated either in aqueous form ready for administration or as lyophilisate for reconstitution with a suitable diluent prior to administration. A protein may be formulated either as a lyophilisate, or as an aqueous composition, for example in pre-filled syringes.

Suitable formulation can provide an aqueous pharmaceutical composition or a lyophilisate which can be reconstituted to give a solution with a high concentration of the therapeutic protein active ingredient and a low level of protein aggregation for delivery to a patient. High concentrations of protein are useful as they reduce the amount of material which must be delivered to a patient (the dose). Reduced dosing volumes minimize the time taken to deliver a fixed dose to the patient. The aqueous compositions of the invention with high concentration of proteins are particularly suitable for subcutaneous administration.

Thus the invention provides an aqueous pharmaceutical composition, suitable for administration in a subject, e.g., for subcutaneous administration, comprising a therapeutic protein.

The therapeutic protein may be used as a pharmaceutical composition when combined with a pharmaceutically acceptable carrier. Such a composition may contain, in addition to a therapeutic protein, carriers, various diluents, fillers, salts, buffers, stabilizers, solubilizers, and other materials well known in the art. The characteristics of the carrier will depend on the route of administration. The pharmaceutical compositions for use in the disclosed methods may also contain additional therapeutic agents for treatment of the particular targeted disorder.

17. Example 16: Route of Administration

Typically, the proteins according to the invention are administered by injection, for example, either intravenously, intraperitoneally, or subcutaneously. Methods to accomplish this administration are known to those of ordinary skill in the art. It may also be possible to obtain compositions that may be topically or orally administered, or which may be capable of transmission across mucous membranes. As will be appreciated by a person skilled in the art, any suitable means for administering can be used, as appropriate for a particular selected route of administration.

Examples of possible routes of administration include parenteral, (e.g., intravenous (I.V. or IV), intramuscular (IM), intradermal, subcutaneous (S.C. or SC), or infusion), oral and pulmonary (e.g., inhalation), nasal, transdermal (topical), transmucosal, intra-arterial, continuous infusion, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

An apyrase therapy can be initiated by administering a "loading dose" of the proteins according to the invention to the subject in need therapy. By "loading dose" is intended an initial dose of the proteins according to the invention that is administered to the subject, where the dose of the proteins according to the invention administered falls within the higher dosing range. The "loading dose" can be administered as a single administration, for example, a single infusion where the proteins are administered IV, or as multiple administrations, for example, multiple infusions where the proteins are administered IV, so long as the complete "loading dose" is administered within about a 24-hour period (or within the first month if multiple intravenous administration are needed, based on the severity of the disease). Following administration of the "loading dose", the subject is then administered one or more additional therapeutically effective doses of the proteins according to the invention. Subsequent therapeutically effective doses can be administered, for example, according to a weekly dosing schedule, or once every two weeks, once every three weeks, or once every four weeks. In such embodiments, the subsequent therapeutically effective doses generally fall within the lower dosing range.

Alternatively, in some embodiments, following the "loading dose", the subsequent therapeutically effective doses of the proteins according to the invention are administered according to a "maintenance schedule", wherein the therapeutically effective dose of the proteins according to the invention is administered once a month, once every 6 weeks, once every two months, once every 10 weeks, once every three months, once every 14 weeks, once every four months, once every 18 weeks, once every five months, once every 22 weeks, once every six months, once every 7 months, once every 8 months, once every 9 months, once every 10 months, once every 11 months, or once every 12 months. In such embodiments, the therapeutically effective doses of the proteins according to the invention fall within the lower dosing range, particularly when the subsequent doses are administered at more frequent intervals, for example, once every two weeks to once every month, or within the higher dosing range, particularly when the subsequent doses are administered at less frequent intervals, for example, where subsequent doses are administered one month to 12 months apart.

The timing of dosing is generally measured from the day of the first dose of the active compound, which is also known as "baseline". However, different health care providers use different naming conventions.

Notably, week zero may be referred to as week 1 by some health care providers, while day zero may be referred to as day one by some health care providers. Thus, it is possible that different physicians will designate, e.g., a dose as being given during week 3/on day 21, during week 3/on day 22, during week 4/on day 21, during week 4/on day 22, while referring to the same dosing schedule. For consistency, the first week of dosing will be referred to herein as week 0, while the first day of dosing will be referred to as day 1. However, it will be understood by a skilled artisan that this naming convention is simply used for consistency and should not be construed as limiting, i.e., weekly dosing is the provision of a weekly dose of the protein regardless of whether the physician refers to a particular week as "week 1" or "week 2". Example of dosage regimes as noted herein are found in FIGS. 1 and 2. It will be understood that a dose need not be provided at an exact time point, e.g., a dose due approximately on day 29 could be provided, e.g., on day 24 to day 34, e.g. day 30, as long as it is provided in the appropriate week.

As used herein, the phrase "container having a sufficient amount of the protein to allow delivery of [a designated dose]" is used to mean that a given container (e.g., vial, pen, syringe) has disposed therein a volume of a protein (e.g., as part of a pharmaceutical composition) that can be used to provide a desired dose. As an example, if a desired dose is 500 mg, then a clinician may use 2 ml from a container that contains a protein formulation with a concentration of 250 mg/ml, 1 ml from a container that contains a protein formulation with a concentration of 500 mg/ml, 0.5 ml from a container contains a protein formulation with a concentration of 1000 mg/ml, etc. In each such case, these containers have a sufficient amount of the protein to allow delivery of the desired 500 mg dose.

As used herein, the phrase "formulated at a dosage to allow [route of administration] delivery of [a designated dose]" is used to mean that a given pharmaceutical composition can be used to provide a desired dose of a protein via a designated route of administration (e.g., s.c. or i.v.). As an example, if a desired subcutaneous dose is 500 mg, then a clinician may use 2 ml of a protein formulation having a concentration of 250 mg/ml, 1 ml of a protein formulation having a concentration of 500 mg/ml, 0.5 ml of a protein formulation having a concentration of 1000 mg/ml, etc. In each such case, these protein formulations are at a concentration high enough to allow subcutaneous delivery of the protein. Subcutaneous delivery typically requires delivery of volumes of less than about 2 ml, preferably a volume of about 1 ml or less. However, higher volumes may be delivered over time using, e.g., a patch/pump mechanism.

Disclosed herein is the use of a protein for the manufacture of a medicament for the treatment of tissue damage in a patient, wherein the medicament is formulated to comprise containers, each container having a sufficient amount of the protein to allow delivery of at least about 75 mg, 150 mg, 300 mg or 600 mg protein per unit dose.

Disclosed herein is the use of a protein for the manufacture of a medicament for the treatment of tissue damage in a patient, wherein the medicament is formulated at a dosage to allow systemic delivery (e.g., i.v. or s.c. delivery) 75 mg, 150 mg, 300 mg of 600 mg protein per unit dose.

18. Example 17: Kits

The disclosure also encompasses kits for treating a patient with tissue damage (as the case may be) with a protein. Such kits comprise a protein (e.g., in liquid or lyophilized form) or a pharmaceutical composition comprising the protein (described supra). Additionally, such kits may comprise means for administering the protein (e.g., a syringe and vial, a prefilled syringe, a prefilled pen, a patch/pump) and instructions for use. The instructions may disclose providing the protein to the patient as part of a specific dosing regimen. These kits may also contain additional therapeutic agents (described supra) for treating psoriasis, e.g., for delivery in combination with the enclosed protein.

The phrase "means for administering" is used to indicate any available implement for systemically administering a drug top a patient, including, but not limited to, a pre-filled syringe, a vial and syringe, an injection pen, an autoinjector, an i.v. drip and bag, a pump, patch/pump, etc. With such items, a patient may self-administer the drug (i.e., administer the drug on their own behalf) or a care-giver or a physician may administer the drug.

Disclosed herein are kits for the treatment of a patient having tissue damage, comprising: a) a pharmaceutical composition comprising a therapeutically effective amount of a protein; b) means for administering the protein to the patient; and c) instructions providing subcutaneously administering a protein to a patient in need thereof.

Sequence Table

Useful amino acid and nucleotide sequences for practicing the invention are disclosed in Table 35.

TABLE 35

Sequences useful for practicing the invention.

| SEQ ID Number | Feature | Sequence |
| --- | --- | --- |
| Wild type human CD39 | | |
| SEQ ID NO: 1 | Amino acid | MEDTKESNVKTFCSKNILAILGFSSIIAVIALLAVGLTQNKALPENVKYGIVL DAGSSHTSLYIYKWPAEKENDTGVVHQVEECRVKGPGISKFVQKVNEIGI YLTDCMERAREVIPRSQHQETPVYLGATAGMRLLRMESEELADRVLDVV ERSLSNYPFDFQGARIITGQEEGAYGWITINYLLGKFSQKTRWFSIVPYET NNQETFGALDLGGASTQVTFVPQNQTIESPDNALQFRLYGKDYNVYTHS FLCYGKDQALWQKLAKDIQVASNEILRDPCFHPGYKKVVNVSDLYKTPCT KRFEMTLPFQQFEIQGIGNYQQCHQSILELFNTSYCPYSQCAFNGIFLPPL QGDFGAFSAFYFVMKFLNLTSEKVSQEKVTEMMKKFCAQPWEEIKTSYA GVKEKYLSEYCFSGTYILSLLLQGYHFTADSWEHIHFIGKIQGSDAGWTLG YMLNLTNMIPAEQPLSTPLSHSTYVFLMVLFSLVLFTVAIIGLLIFHKPSYFW KDMV |

TABLE 35-continued

Sequences useful for practicing the invention.

| SEQ ID Number | Feature | Sequence |
|---|---|---|
| Wild type rat CD39 | | |
| SEQ ID NO: 2 | Amino acid | MEDIKDSKVKRFCSKNILIILGFSSVLAVIALIAVGLTHNKPLPEN VKYGIVLD AGSSHTNLYIYKWPAEKENDTGVVQLLEECQVKGPGISKYAQKTDEIAAY LAECMKMSTERIPASKQHQTPVYLGATAGMRLLRMESKQSADEVLAAVS RSLKSYPFDFQGAKIITGQEEGAYGWITINYLLGRFTQEQSWLNFISDSQK QATFGALDLGGSSTQVTFVPLNQTLEAPETSLQFRLYGTDYTVYTHSFLC YGKDQALWQKLAQDIQVSSGGILKDPCFYPGYKKVVNVSELYGTPCTKR FEKKLPFNQFQVQGTGDYEQCHQSILKFFNNSHCPYSQCAFNGVFLPPL QGSFGAFSAFYFVMDFFKKMANDSVSSQEKMTEITKNFCSKPWEEVKAS YPTVKEKYLSEYCFSGTYILSLLLQGYNFTGTSWDQIHFMGKIKDSNAGW TLGYMLNLTNMIPAEQPLSPPLPHSTYISLMVLFSLVLVAMVITGLFIFSKPS YFWKEAV |
| CD39L3 | | |
| SEQ ID NO: 3 | Amino acid | QIHKQEVLPPGLKYGIVLDAGSSRTTVYVYQWPAEKENNTGVVSQTFKCS VKGSGISSYGNNPQDVPRAFEECMQKVKGQVPSHLHGSTPIHLGATAGM RLLRLQNETAANEVLESIQSYFKSQPFDFRGAQIISGQEEGVYGWITANYL MGNFLEKNLWHMWVHPHGVETTGALDLGGASTQISFVAGEKMDLNTSDI MQVSLYGYVYTLYTHSFQCYGRNEAEKKFLAMLLQNSPTKNHLTNPCYP RDYSISFTMGHVFDSLCTVDQRPESYNPNDVITFEGTGDPSLCKEKEVASIF DFKACHDQETCSFDGVYQPKIKGPFVAFAGFYYTASALNLSGSFSLDTFN SSTWNFCSQNWSQLPLLLPKFDEVYARSYCFSANYIYHLFVNGYKFTEET WPQIHFEKEVGNSSIAWSLGYMLSLTNQIPAESPLIRLPIEP |
| EP28 | | |
| SEQ ID NO: 4 | Amino acid | TQNKALPENVKYGIVLDAGSSHTSLYIYKWPAEKENDTGVVHQVEECRVK GPGISKFVQKVNEIGIYLTDCMERAREVIPRSQHQETPVYLGATAGMRLLR MESEELADRVLDVVERSLSNYPFDFQGARIITGQEEGAYGWITINYLLGKF SQKNQETFGALDLGGASTQVTFVPQNQTIESPDNALQFRLYGKDYNVYT HSFLCYGKDQALWQKLAKDIQVASNEILRDPCFHPGYKKVVNVSDLYKTP CTKRFEMTLPFQQFEIQGIGNYQQCHQSILELFNTSYCPYSQCAFNGIFLP PLQGDFGAFSAFYFVMKFLNLTSEKVSQEKVTEMMKKFCAQPWEEIKTS YAGVKEKYLSEYCFSGTYILSLLLQGYHFTADSWEHIHFIGKIQGSDAGWT LGYMLNLTNMIPAEQPLSTPLSHST |
| | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCAGGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGGATTTCGGCGCCTTCAGCGCCTTC TACTTCGTGATGAAGTTCCTGAACCTGACCAGCGAGAAGGTGTCCCAG GAAAAAGTGACAGAGATGATGAAGAAGTTCTGCGCCCAGCCCTGGGA GGAAATCAAGACCTCCTACGCTGGCGTGAAAGAGAAGTACCTGAGCG AGTACTGCTTCAGCGGCACCTACATCCTGAGCCTGCTGCTGCAGGGC TACCACTTCACCGCCGATAGCTGGGAGCACATCCACTTCATCGGCAA GATTCAGGGCAGCGACGCCGGCTGGACACTGGGCTACATGCTGAATC TGACCAACATGATCCCCGCCGAGCAGCCCCTGAGCACACCTCTGAGC CACAGCACC |
| EP1 | | |
| SEQ ID NO: 6 | Amino acid | TQNKALPENVKYGIVLDAGSSHTSLYIYKWPAEKENDTGVVHQVEECRVK GPGISKFVQKVNEIGIYLTDCMERAMEVIPRSQHQETPVYLGATAGMRLL RMESEELADRVLDVVERSLSNYPFDFQGARIITGQEEGAYGWITINYLLGK FSQKNQETFGALDLGGASTQVTFVPQNQTIESPDNALQFRLYGKDYNVY |

TABLE 35-continued

Sequences useful for practicing the invention.

| SEQ ID Number | Feature | Sequence |
|---|---|---|
| | | THSFLCYGKDQALWQKLAKDIQVASNEILRDPCFHPGYKKVVNVSDLYKT PCTKRFEMTLPFQQFEIQGIGNYQQCHQSILELFNTSYCPYSQCAFNGIFL PPLQGDFGAFSAFYFVMKFLNLTSEKVSQEKVTEMMKKFCAQPWEEIKT SYAGVKEKYLSEYCFSGTYILSLLLQGYHFTADSWEHIHFIGKIQGSDAGW TLGYMLNLTNMIPAEQPLSTPLSHST |
| SEQ ID NO: 7 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCATGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGATTTCGGCGCCTTCAGCGCCTTC TACTTCGTGATGAAGTTCCTGAACCTGACCAGCGAGAAGGTGTCCCAG GAAAAAGTGACAGAGATGATGAAGAAGTTCTGCGCCCAGCCCTGGGA GGAAATCAAGACCTCCTACGCTGGCGTGAAAGAGAAGTACCTGAGCG AGTACTGCTTCAGCGGCACCTACATCCTGAGCCTGCTGCTGCAGGGC TACCACTTCACCGCCGATAGCTGGGAGCACATCCACTTCATCGGCAA GATTCAGGGCAGCGACGCCGGCTGGACACTGGGCTACATGCTGAATC TGACCAACATGATCCCCGCCGAGCAGCCCCTGAGCACACCTCTGAGC CACAGCACC |

EP2

| SEQ ID Number | Feature | Sequence |
|---|---|---|
| SEQ ID NO: 8 | Amino acid | TQNKALPENVKYGIVLDAGSSHTSLYIYKWPAEKENDTGVVHQVEECRVK GPGISKFVQKVNEIGIYLTDCMERAMEVIPRSQHQETPVYLGATAGMRLL RMESEELADRVMDVVERSLSNYPFDFQGARIITGQEEGAYGWITINYLLG KFSQKNQETFGALDLGGASTQVTFVPQNQTIESPDNALQFRLYGKDYNV YTHSFLCYGKDQALWQKLAKDIQVASNEILRDPCFHPGYKKVVNVSDLYK TPCTKRFEMTLPFQQFEIQGIGNYQQCHQSILELFNTSYCPYSQCAFNGIF LPPLQGDFGAFSAFYFVMKFLNLTSEKVSQEKVTEMMKKFCAQPWEEIKT SYAGVKEKYLSEYCFSGTYILSLLLQGYHFTADSWEHIHFIGKIQGSDAGW TLGYMLNLTNMIPAEQPLSTPLSHST |
| SEQ ID NO: 9 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCATGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGATGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAAGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGATTTCGGCGCCTTCAGCGCCTTC TACTTCGTGATGAAGTTCCTGAACCTGACCAGCGAGAAGGTGTCCCAG GAAAAAGTGACAGAGATGATGAAGAAGTTCTGCGCCCAGCCCTGGGA GGAAATCAAGACCTCCTACGCTGGCGTGAAAGAGAAGTACCTGAGCG AGTACTGCTTCAGCGGCACCTACATCCTGAGCCTGCTGCTGCAGGGC TACCACTTCACCGCCGATAGCTGGGAGCACATCCACTTCATCGGCAA GATTCAGGGCAGCGACGCCGGCTGGACACTGGGCTACATGCTGAATC TGACCAACATGATCCCCGCCGAGCAGCCCCTGAGCACACCTCTGAGC CACAGCACC |

TABLE 35-continued

Sequences useful for practicing the invention.

| SEQ ID Number | Feature | Sequence |
|---|---|---|
| EP3 | | |
| SEQ ID NO: 10 | Amino acid | TQNKALPENVKYGIVLDAGSSHTSLYIYKWPAEKENDTGVVHQVEECRVK GPGISKFVQKVNEIGIYLTDCMERAMEVIPRSQHQETPVYLGATAGMRLL RMESEELADRVLDVVERSLSNYPFDFQGARIITGQEEGAYGWITINYLLGK FSQKNQETFGALDLGGASTQVTFVPQNQTIESPDNALQFRLYGKDYNVY THSFLCYGKDQALWQKLAKDIQVASNEILRDPCFHPGYKKVVNVSDLYKT PCTKGFEMTLPFQQFEIQGIGNYQQCHQSILELFNTSYCPYSQCAFNGIFL PPLQGDFGAFSAFYFVMKFLNLTSEKVSQEKVTEMMKKFCAQPWEEIKT SYAGVKEKYLSEYCFSGTYILSLLLQGYHFTADSWEHIHFIGKIQGSDAGW TLGYMLNLTNMIPAEQPLRTPLSHST |
| SEQ ID NO: 11 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCATGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGGGATTCGAGATGACCCTGCCCTTCCAGCAGTTCGAGAT CCAGGGCATCGGCAATTACCAGCAGTGCCACCAGAGCATCCTGGAAC TGTTCAACACCAGCTACTGCCCCTACAGCCAGTGCGCCTTCAACGGC ATCTTCCTGCCACCTCTGCAGGGGGATTTCGGCGCCTTCAGCGCCTT CTACTTCGTGATGAAGTTCCTGAACCTGACCAGCGAGAAGGTGTCCCA GGAAAAAGTGACAGAGATGATGAAGAAGTTCTGCGCCCAGCCCTGGG AGGAAATCAAGACCTCCTACGCTGGCGTGAAAGAGAAGTACCTGAGC GAGTACTGCTTCAGCGGCACCTACATCCTGAGCCTGCTGCTGCAGGG CTACCACTTCACCGCCGATAGCTGGGAGCACATCCACTTCATCGGCAA GATTCAGGGCAGCGACGCCGGCTGGACACTGGGCTACATGCTGAATC TGACCAACATGATCCCCGCCGAGCAGCCCCTGCGCACACCTCTGAGC CACAGCACC |
| EP4 | | |
| SEQ ID NO: 12 | Amino acid | TQNKALPENVKYGIVLDAGSSHTSLYIYKWPAEKENDTGVVHQVEECRVK GPGISKFAQKVNEIGIYLTDCMERAMEVIPRSQHQETPVYLGATAGMRLL RMESEELADRVLDVVERSLSNYPFDFQGARIITGQEEGAYGWITINYLLGK FSQKNQETFGALDLGGASTQVTFVPQNQTIESPDNALQFRLYGKDYNVY THSFLCYGKDQALWQKLAKDIQVASNEILRDPCFHPGYKKVVNVSDLYKT PCTKRFEMTLPFQQFEIQGIGNYQQCHQSILELFNTSYCPYSQCAFNGIFL PPLQGDFGAFSAFYFVMKFLNLTSEKVSQEKVTEMMKKFCAQPWEEIKT SYAGVKEKYLSEYCFSGTYILSLLLQGYHFTADSWEHIHFIGKIQGSDAGW TLGYMLNLTNMIPAEQPLRTPLSHST |
| SEQ ID NO: 13 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGCGCAGAAAGTGAACGA GATCGGCATCTACCTGACCGACTGCATGGAACGGGCCATGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGGATTTCGGCGCCTTCAGCGCCTTC TACTTCGTGATGAAGTTCCTGAACCTGACCAGCGAGAAGGTGTCCCAG |

TABLE 35-continued

Sequences useful for practicing the invention.

| SEQ ID Number | Feature | Sequence |
|---|---|---|
| | | GAAAAAGTGACAGAGATGATGAAGAAGTTCTGCGCCCAGCCCTGGGA<br>GGAAATCAAGACCTCCTACGCTGGCGTGAAAGAGAAGTACCTGAGCG<br>AGTACTGCTTCAGCGGCACCTACATCCTGAGCCTGCTGCTGCAGGGC<br>TACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGGACACCTCTGAGC<br>CACAGCACC |

EP5

| SEQ ID NO: 14 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVMDVVERSLSNYPFDFQGARIITGQEEGAYGWITINYLLGK<br>FSQKNQETFGALDLGGASTQVTFVPQNQTIESPDNALQFRLYGKDYNVY<br>THSFLCYGKDQALWQKLAKDIQVASNEILRDPCFHPGYKKVVNVSDLYKT<br>PCTKRFEMTLPFQQFEIQGIGNYQQCHQSILELFNTSYCPYSQCAFNGIFL<br>PPLQGDFGAFSAFYFVMKFLNLTSEKVSQEKVTEMMKKFCAQPWEEIKT<br>SYAGVKEKYLSEYCFSGTYILSLLLQGYHFTADSWEHIHFIDKIQGSDAGW<br>TLGYMLNLTNMIPAEQPLSTPLSHST |
| SEQ ID NO: 15 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGATGGACGTGGTGGAAAGAAGCCTGAGCAACTACCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGTGGCAGAAGCTGGCCAAGGA<br>CATCCAGGTGGCCAGCAACGAGATCCTGCGGGACCCTTGCTTCCACC<br>CCGGCTACAAGAAAGTCGTGAACGTGTCCGACCTGTACAAGACCCCC<br>TGCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCACCTCTGCAGGGGATTTCGGCGCCTTCAGCGCCTTC<br>TACTTCGTGATGAAGTTCCTGAACCTGACCAGCGAGAAGGTGTCCCAG<br>GAAAAAGTGACAGAGATGATGAAGAAGTTCTGCGCCCAGCCCTGGGA<br>GGAAATCAAGACCTCCTACGCTGGCGTGAAAGAGAAGTACCTGAGCG<br>AGTACTGCTTCAGCGGCACCTACATCCTGAGCCTGCTGCTGCAGGGC<br>TACCACTTCACCGCCGATAGCTGGGAGCACATCCACTTCATCGACAAG<br>ATTCAGGGCAGCGACGCCGGCTGGACACTGGGCTACATGCTGAATCT<br>GACCAACATGATCCCCGCCGAGCAGCCCCTGAGCACACCTCTGAGCC<br>ACAGCACC |

EP6

| SEQ ID NO: 16 | Amino acid | TQNKALPENVKYGIVLDAGSSHTSLYIYKWPAEKENDTGVVHQVEECRVK<br>GPGISKFVQKVNEIGISLTDCMERAREVIPRSQHQETPVYLGATAGMRLLR<br>MESEELADRVMDVVERSLSNYPFDFQGARIITGQEEGAYGWITINYLLGK<br>FSQKNQETFGALDLGGASTQVTFVPQNQTIESPDNALQFRLYGKDYNVY<br>THSFLCYGKDQALRQKLAKDIQVASNEILRDPCFHPGYKKVVNVSDLYKT<br>PCTKRFEMTLPFQQFEIQGIGNYQQCHQSILELFNTSYCPYSQCAFNGIFL<br>PPLQGDFGAFSAFYFVMKFLNLTSEKVSQEKVTEMMKKFCAQPWEEIKT<br>SYAGVKEKYLSEYCFSGTYILSLLLQGYHFTADSWEHIHFIGKIQGSDAGW<br>TLGYMLNLTNMIPAEQPLSTPLSHST |
| SEQ ID NO: 17 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTCCCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGATGGACGTGGTGGAAAGAAGCCTGAGCAACTACCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGCGGCAGAAGCTGGCCAAGG |

TABLE 35-continued

Sequences useful for practicing the invention.

| SEQ ID Number | Feature | Sequence |
|---|---|---|
| | | ACATCCAGGTGGCCAGCAACGAGATCCTGCGGGACCCTTGCTTCCAC<br>CCCGGCTACAAGAAAGTCGTGAACGTGTCCGACCTGTACAAGACCCC<br>CTGCACCAAGAGATTCGAGATGACCCTGCCCTTCCAGCAGTTCGAGAT<br>CCAGGGCATCGGCAATTACCAGCAGTGCCACCAGAGCATCCTGGAAC<br>TGTTCAACACCAGCTACTGCCCCTACAGCCAGTGCGCCTTCAACGGC<br>ATCTTCCTGCCACCTCTGCAGGGGATTTCGGCGCCTTCAGCGCCTT<br>CTACTTCGTGATGAAGTTCCTGAACCTGACCAGCGAGAAGGTGTCCCA<br>GGAAAAAGTGACAGAGATGATGAAGAAGTTCTGCGCCCAGCCCTGGG<br>AGGAAATCAAGACCTCCTACGCTGGCGTGAAAGAGAAGTACCTGAGC<br>GAGTACTGCTTCAGCGGCACCTACATCCTGAGCCTGCTGCTGCAGGG<br>CTACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGCACACCTCTGAGC<br>CACAGCACC |
| EP7 | | |
| SEQ ID NO: 18 | Amino acid | TQNKALPENVKYGIVLDAGSSHTSLYIYKWPAEEENDTGVVHQVEECRVK<br>GPGISKFVQKVNEIGIYLSDCMERAREVIPRSQHQETPVYLGATAGMRLL<br>RMESEELADRVLDAVERSLSNYPFDFQGARIITGQEEGAYGWITINYLLGK<br>FSQKNQETFGALDLGGASTQVTFVPQNQTIESPDNALQFRLYGKDYNVY<br>THSFLCYGKDQALWQKLAKDIQVASNEILRDPCFHPGYKKVVNVSDLYKT<br>PCTKRFEMTLPFQQFEIQGTGNYQQCHQSILELFNTSYPYSQCAFNGIF<br>LPPLQGDFGAFSAFYFVMKFLNLTSEKVSQEKVTEMMKKFCAQPWEEIKT<br>SYAGVKEKYLSEYCFSGTYILSLLLQGYHFTADSWEHIHFIGKIQGSDAGW<br>TLGYMLNLTNMIPAEQPLSTPLSHST |
| SEQ ID NO: 19 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGGAAGAAAACGACACCGGCGTGGTGCATCAGGTGGAAGAGTG<br>CAGAGTGAAGGGCCCTGGCATCAGCAAGTTCGTGCAGAAAGTGAACG<br>AGATCGGCATCTACCTGTCCGACTGCATGGAACGGGCCAGGGAAGTG<br>ATCCCCAGAAGCCAGCACCAGGAAACCCCCGTGTATCTGGGAGCCAC<br>CGCCGGCATGAGACTGCTGAGAATGGAAAGCGAGGAACTGGCCGAC<br>CGGGTGCTGGACGCGGTGGAAAGAAGCCTGAGCAACTACCCATTCGA<br>TTTTCAAGGCGCCAGAATCATCACCGGCCAGGAAGAAGGCGCCTACG<br>GCTGGATCACCATCAACTACCTGCTGGGCAAGTTCAGCCAGAAGAATC<br>AGGAAACCTTCGGCGCCCTGGACCTGGGCGGAGCTTCTACCCAAGTG<br>ACCTTCGTGCCCCAGAATCAGACCATCGAGAGCCCCGACAACGCCCT<br>GCAGTTCCGGCTGTACGGCAAGGACTACAATGTGTACACCCACAGCT<br>TTCTGTGCTACGGAAAGGACCAGGCTCTGTGGCAGAAGCTGGCCAAG<br>GACATCCAGGTGGCCAGCAACGAGATCCTGCGGGACCCTTGCTTCCA<br>CCCCGGCTACAAGAAAGTCGTGAACGTGTCCGACCTGTACAAGACCCC<br>CTGCACCAAGAGATTCGAGATGACCCTGCCCTTCCAGCAGTTCGAG<br>ATCCAGGGCACCGGCAATTACCAGCAGTGCCACCAGAGCATCCTGGA<br>ACTGTTCAACACCAGCTACTGCCCCTACAGCCAGTGCGCCTTCAACG<br>GCATCTTCCTGCCACCTCTGCAGGGGATTTCGGCGCCTTCAGCGCC<br>TTCTACTTCGTGATGAAGTTCCTGAACCTGACCAGCGAGAAGGTGTCC<br>CAGGAAAAAGTGACAGAGATGATGAAGAAGTTCTGCGCCCAGCCCTG<br>GGAGGAAATCAAGACCTCCTACGCTGGCGTGAAAGAGAAGTACCTGA<br>GCGAGTACTGCTTCAGCGGCACCTACATCCTGAGCCTGCTGCTGCAG<br>GGCTACCACTTCACCGCCGATAGCTGGGAGCACATCCACTTCATCGG<br>CAAGATTCAGGGCAGCGACGCCGGCTGGACACTGGGCTACATGCTGA<br>ATCTGACCAACATGATCCCCGCCGAGCAGCCCCTGAGCACACCTCTG<br>AGCCACAGCACC |
| EP8 | | |
| SEQ ID NO: 20 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDAVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVNVSDLYKTP<br>CTKRFEMTLPFQQFEIQGIGNYQQCHQSILELFNTSYCPYSQCAFNGIFLP<br>PLQGDFGAFSAFYFVMKFLNLTSEKVSQEKVTEMMKKFCAQPWEEIKTS<br>YAGVKEKYLSEYCFSGTYILSLLLQGYHFTADSWEHIHFIGKIQGSDAGVVT<br>LGYMLNLTNMIPAEQPLSTPLSHST |
| SEQ ID NO: 21 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TTCCCAGAAGCCAGCACCAGGAAACCCCCGTGTATCTGGGAGCCACC<br>GCCGGCATGAGACTGCTGAGAATGGAAAGCGAGGAACTGGCCGACC |

TABLE 35-continued

Sequences useful for practicing the invention.

| SEQ ID Number | Feature | Sequence |
|---|---|---|
| | | GGGTGCTGGACGCGGTGGAAAGAAGCCTGAGCAACTACCCATTCGAT<br>TTTCAAGGCGCCAGAATCATCACCGGCCAGGAAGAAGGCGCCTACGG<br>CTGGATCACCATCAACTACCTGCTGGGTAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGTGGCAGAAGCTGGCCAAGGA<br>CATCCAGGTGGCCAGCAACGAGATCCTGCGGGACCCTTGCTTCCACC<br>CCGGCTACAAGAAAGTAGTGAACGTGTCCGACCTGTACAAGACCCCC<br>TGCACCAAGAGATTCGAGATGACCCTGCCATTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCACCTCTGCAGGGGATTTCGGCGCCTTCAGCGCCTTC<br>TACTTCGTGATGAAGTTCCTGAACCTGACCAGCGAGAAGGTGTCCCAG<br>GAAAAAGTGACAGAGATGATGAAGAAGTTCTGCGCCCAGCCCTGGGA<br>GGAAATCAAGACCTCCTACGCTGGCGTGAAAGAGAAGTACCTGAGCG<br>AGTACTGCTTCAGCGGCACCTACATCCTGAGCCTGCTGCTGCAGGGC<br>TACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGCACACCTCTGAGC<br>CACAGCACC |

EP9

| SEQ ID<br>NO: 22 | Amino<br>acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALRQKLAKDIQVASNEILRDPCFHPGYKKVVNVSDLYKTP<br>CTKRFEMTLPFQQFEIQGIGNYQQCHQSILELFNTSYCPYSQCAFNGIFLP<br>PLQGDFGAFSAFYFVMKFLNLTSEKVSQEKVTEMMKKFCAQPWEEIKTS<br>YAGVKEKYLSEYCFSGTYILSLLLQGYHFTADSWEHIHFIGKIQGSDAGVVT<br>LGYMLNLTNMIPAEQPLSTPLSHST |
| SEQ ID<br>NO: 23 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGAGGCAGAAGCTGGCCAAGGA<br>CATCCAGGTGGCCAGCAACGAGATCCTGCGGGACCCTTGCTTCCACC<br>CCGGCTACAAGAAAGTCGTGAACGTGTCCGACCTGTACAAGACCCCC<br>TGCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCACCTCTGCAGGGGATTTCGGCGCCTTCAGCGCCTTC<br>TACTTCGTGATGAAGTTCCTGAACCTGACCAGCGAGAAGGTGTCCCAG<br>GAAAAAGTGACAGAGATGATGAAGAAGTTCTGCGCCCAGCCCTGGGA<br>GGAAATCAAGACCTCCTACGCTGGCGTGAAAGAGAAGTACCTGAGCG<br>AGTACTGCTTCAGCGGCACCTACATCCTGAGCCTGCTGCTGCAGGGC<br>TACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGCACACCTCTGAGC<br>CACAGCACC |

EP10

| SEQ ID<br>NO: 24 | Amino<br>acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVNVSDLYKTP<br>CTKRFEMTLPFQQFEIQGTGNYQQCHQSILELFNTSYCPYSQCAFNGIFL<br>PPLQGDFGAFSAFYFVMKFLNLTSEKVSQEKVTEMMKKFCAQPWEEIKT<br>SYAGVKEKYLSEYCFSGTYILSLLLQGYHFTADSWEHIHFIGKIQGSDAGVV<br>TLGYMLNLTNMIPAEQPLSTPLSHST |

TABLE 35-continued

Sequences useful for practicing the invention.

| SEQ ID Number | Feature | Sequence |
| --- | --- | --- |
| SEQ ID NO: 25 | DNA | ACCCAGAACAAGGCCCTGCCCGAGAACGTGAAGTACGGCATCGTGCT
GGATGCCGGCAGCAGCCACACCAGCCTGTACATCTACAAGTGGCCTG
CCGAGAAAGAAAACGACACCGGCGTGGTGCATCAGGTGGAAGAGTGC
AGAGTGAAGGGCCCTGGCATCAGCAAGTTCGTGCAGAAAGTGAACGA
GATCGGCATCTACCTGACCGACTGCATGGAACGGGCCAGGGAAGTGA
TCCCCAGAAGCCAGCACCAGGAAACCCCCGTGTATCTGGGAGCCACC
GCCGGCATGAGACTGCTGAGAATGGAAAGCGAGGAACTGGCCGACC
GGGTGCTGGACGTGGTGGAAAGAAGCCTGAGCAACTACCCATTCGAT
TTTCAAGGCGCCAGAATCATCACCGGCCAGGAAGAAGGCGCCTACGG
CTGGATCACCATCAACTACCTGCTGGGCAAGTTCAGCCAGAAGAATCA
GGAAACCTTCGGCGCCCTGGACCTGGGCGGAGCTTCTACCCAAGTGA
CCTTCGTGCCCCAGAATCAGACCATCGAGAGCCCCGACAACGCCCTG
CAGTTCCGGCTGTACGGCAAGGACTACAATGTGTACACCCACAGCTTT
CTGTGCTATGGAAAGGACCAGGCTCTGTGGCAGAAGCTGGCCAAGGA
CATCCAGGTGGCCAGCAACGAGATCCTGCGGGACCCTTGCTTCCACC
CCGGCTACAAGAAAGTCGTGAACGTGTCCGACCTGTACAAGACCCCC
GCACCAAGAGATTCGAGATGACCCTGCCCTTCCAGCAGTTCGAGATC
CAGGGCACCGGCAATTACCAGCAGTGCCACCAGAGCATCCTGGAACT
GTTCAACACCAGCTACTGCCCCTACAGCCAGTGCGCCTTCAACGGCA
TCTTCCTGCCACCTCTGCAGGGGGATTTCGGCGCCTTCAGCGCCTTC
TACTTCGTGATGAAGTTCCTGAACCTGACCAGCGAGAAGGTGTCCCAG
GAAAAAGTGACAGAGATGATGAAGAAGTTCTGCGCCCAGCCCTGGGA
GGAAATCAAGACCTCCTACGCTGGCGTGAAAGAGAAGTACCTGAGCG
AGTACTGCTTCAGCGGCACCTACATCCTGAGCCTGCTGCTGCAGGGC
TACCACTTCACCGCCGATAGCTGGGAGCACATCCACTTCATCGGCAA
GATTCAGGGCAGCGACGCCGGCTGGACACTGGGCTACATGCTGAATC
TGACCAACATGATCCCCGCCGAGCAGCCTTTGAGCACACCTCTGAGC
CACAGCACC |

EP11

| SEQ ID NO: 26 | Amino acid | TQNKALPENVKYGIVLDAGSSHTSLYIYKWPAEKENDTGVVHQVEECRVK
GPGISKFVQKVNEIGIYLTDCMERAMEVIPRSQHQETPVYLGATAGMRLL
RMESEELADRVLDVVERSLSNYPFDFQGARIITGQEEGAYGWITINYLLGK
FSQKNQETFGALDLGGASTQVTFVPQNQTIESPDNALQFRLYGKDYNVY
THSFLCYGKDQALWQKLAKDIQVASNEILRDPCFHPGYKKVVNVSDLYKT
PCTKRFEMTLPFQQFEIQGTGNYQQCHQSILELFNTSYCPYSQCAFNGIF
LPPLQGDFGAFSAFYFVMKFLNLTSEKVSQEKVTEMMKKFCAQPWEEIKT
SYAGVKEKYLSEYCFSGTYILSLLLQGYHFTADSWEHIHFIGKIQGSDAGW
TLGYMLNLTNMIPAEQPLSTPLSHST |
| SEQ ID NO: 27 | DNA | ACCCAGAACAAGGCCCTGCCCGAGAACGTGAAGTACGGCATCGTGCT
GGATGCCGGCAGCAGCCACACCAGCCTGTACATCTACAAGTGGCCTG
CCGAGAAAGAAAACGACACCGGCGTGGTGCATCAGGTGGAAGAGTGC
AGAGTGAAGGGCCCTGGCATCAGCAAGTTCGTGCAGAAAGTGAACGA
GATCGGCATCTACCTGACCGACTGCATGGAACGGGCCATGGAAGTGA
TCCCCAGAAGCCAGCACCAGGAAACCCCCGTGTATCTGGGAGCCACC
GCCGGCATGAGACTGCTGAGAATGGAAAGCGAGGAACTGGCCGACC
GGGTGCTGGACGTGGTGGAAAGAAGCCTGAGCAACTACCCATTCGAT
TTTCAAGGCGCCAGAATCATCACCGGCCAGGAAGAAGGCGCCTACGG
CTGGATCACCATCAACTACCTGCTGGGCAAGTTCAGCCAGAAGAATCA
GGAAACCTTCGGCGCCCTGGACCTGGGCGGAGCTTCTACCCAAGTGA
CCTTCGTGCCCCAGAATCAGACCATCGAGAGCCCCGACAACGCCCTG
CAGTTCCGGCTGTACGGCAAGGACTACAATGTGTACACCCACAGCTTT
CTGTGCTACGGAAAGGACCAGGCTCTGTGGCAGAAGCTGGCCAAGGA
CATCCAGGTGGCCAGCAACGAGATCCTGCGGGACCCTTGCTTCCACC
CCGGCTACAAGAAAGTCGTGAACGTGTCCGACCTGTACAAGACCCCC
TGCACCAAGAGATTCGAGATGACCCTGCCCTTCCAGCAGTTCGAGATC
CAGGGCACCGGCAATTACCAGCAGTGCCACCAGAGCATCCTGGAACT
GTTCAACACCAGCTACTGCCCCTACAGCCAGTGCGCCTTCAACGGCA
TCTTCCTGCCACCTCTGCAGGGGGATTTCGGCGCCTTCAGCGCCTTC
TACTTCGTGATGAAGTTCCTGAACCTGACTAGCGAGAAGGTGTCCCAG
GAAAAAGTGACAGAGATGATGAAGAAGTTCTGCGCCCAGCCCTGGGA
GGAAATCAAGACCTCCTACGCTGGCGTGAAAGAGAAGTACCTGAGCG
AGTACTGCTTCAGCGGCACCTACATCCTGAGCCTGCTGCTGCAGGGC
TACCACTTCACCGCCGATAGCTGGGAGCACATCCACTTCATCGGCAA
GATTCAGGGCAGCGACGCCGGCTGGACACTGGGCTACATGCTGAATC
TGACCAACATGATCCCCGCCGAGCAGCCCCTGAGCACACCTCTGAGC
CACAGCACC |

EP12

| SEQ ID NO: 28 | Amino acid | TQNKALPENVKYGIVLDAGSSHTSLYIYKWPAEKENDTGVVHQVEECRVK
GPGISKFVQKVNEIGIYLTDCMERARAEVIPRSQHQETPVYLGATAGMRLLR
MESEELADRVLDVVERSLSNYPFDFQGARIITGQEEGAYGWITINYLLGKF |

TABLE 35-continued

Sequences useful for practicing the invention.

| SEQ ID Number | Feature | Sequence |
|---|---|---|
| | | SQKNQETFGALDLGGASTQVTFVPQNQTIESPDNALQFRLYGKDYNVYT HSFLCYGKDQALWQKLAKDIQVASNDILRDPCFHPGYKKVVNVSDLYKTP CTKRFEMTLPFQQFEIQGTGNYQQCHQSILELFNTSYCPYSQCAFNGIFL PPLQGDFGAFSAFYFVMKFLNLTSEKVSQEKVTEMMKKFCAQPWEEIKT SYAGVKEKYLSEYCFSGTYILSLLLQGYHFTADSWEHIHFIGKIQGSDAGW TLGYMLNLTNMIPAEQPLSTPLSHST |
| SEQ ID NO: 29 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCAGGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGATATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCACCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGATTTCGGCGCCTTCAGCGCCTTC TACTTCGTGATGAAGTTCCTGAACCTGACCAGCGAGAAGGTGTCCCAG GAAAAAGTGACAGAGATGATGAAGAAGTTCTGCGCCCAGCCCTGGGA GGAAATCAAGACCTCCTACGCTGGCGTGAAAGAGAAGTACCTGAGCG AGTACTGCTTCAGCGGCACCTACATCCTGAGCCTGCTGCTGCAGGGC TACCACTTCACCGCCGATAGCTGGGAGCACATCCACTTCATCGGCAA GATTCAGGGCAGCGACGCCGGCTGGACACTGGGCTACATGCTGAATC TGACCAACATGATCCCCGCCGAGCAGCCCCTGAGCACACCTCTGAGC CACAGCACC |

EP13

| SEQ ID NO: 30 | Amino acid | TQNKALPENVKYGIVLDAGSSHTSLYIYKWPAEKENDTGVVHQVEECRVK GPGISKFVQKVNEIGIYLTDCMERAREVIPRSQHQETPVYLGATAGMRLLR MESEELADRVLDVVERSLSNYPFDFQGARIITGQEEGAYGWITINYLLGKF SQKNQETFGALDLGGASTQVTFVPQNQTIESPDNALQFRLYGKDYNVYT HSFLCYGKDQALWQKLAKDIQVASNEILRDPCFHPGYKKVVNVSDLYKTP CTKRFEMTLPFQQFEIQGIGNYQQCHQSILELFNTSYCPYSQCAFNGIFLP PLQGDFGAFSVMKFLNLTSEKVSQEKVTEMMKKFCAQPWEEIKTS YAGVKEKYLSEYCFSGTYILSLLPQGYHFTADSWEHIHFIGKIQGSDAGWT LGYMLNLTNMIPAEQPLSTPLSHST |
| SEQ ID NO: 31 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCAGGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGATTTCGGCGCCTTCAGCGCCTTC TACTCCGTGATGAAGTTCCTGAACCTGACCAGCGAGAAGGTGTCCCA GGAAAAAGTGACAGAGATGATGAAGAAGTTCTGCGCCCAGCCCTGGG AGGAAATCAAGACCTCCTACGCTGGCGTGAAAGAGAAGTACCTGAGC |

TABLE 35-continued

Sequences useful for practicing the invention.

| SEQ ID Number | Feature | Sequence |
|---|---|---|
| | | GAGTACTGCTTCAGCGGCACCTACATCCTGAGCCTGCTGCCGCAGGG<br>CTACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGCACACCTCTGAGC<br>CACAGCACC |

EP14

| SEQ ID NO: 32 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVNVSDLYKTP<br>CTKRFEMTLPFQQFEIQGIGNYQQCHQSILELFNTSYCPYSQCAFNGIFLP<br>PLQGDFGAFSAFYSVMKFLNLTSEKVSQEKVTEMMKKFCAQPWEEIKTS<br>YAGVKEKYLSEYCFSGTYILSLLLQGYHFTADSWEHIHFIGKIQGSDAGWT<br>LGYMLNLTNMIPAEQPLSTPLSHST |
| SEQ ID NO: 33 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCTTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGTGGCAGAAGCTGGCCAAGGA<br>CATCCAGGTGGCCAGCAACGAGATCCTGCGGGACCCTTGCTTCCACC<br>CCGGCTACAAGAAAGTCGTGAACGTGTCCGACCTGTACAAGACCCCC<br>TGCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCACCTCTGCAGGGGGATTTCGGCGCCTTCAGCGCCTTC<br>TACTCCGTGATGAAGTTCCTGAACCTGACCAGCGAGAAGGTGTCCCA<br>GGAAAAAGTGACAGAGATGATGAAGAAGTTCTGCGCCCAGCCCTGGG<br>AGGAAATCAAGACCTCCTACGCTGGCGTGAAAGAGAAGTACCTGAGC<br>GAGTACTGCTTCAGCGGCACCTACATCCTGAGCCTGCTGCTGCAGGG<br>CTACCACTTCACCGCCGATAGCTGGGAGCACATCCACTTCATCGGCAA<br>GATTCAGGGCAGCGACGCCGGCTGGACACTGGGTTACATGCTGAATC<br>TGACCAACATGATCCCCGCCGAGCAGCCCCTGAGCACACCTCTGAGC<br>CACAGCACC |

EP15

| SEQ ID NO: 34 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVKVSDLYKTP<br>CTKRFEMTLPFQQFEIQGIGNYQQCHQSILELFNTSYCPYSQCAFNGIFLP<br>PLQGDFGAFSAFYSVMKFLNLTSEKVSQEKVTEMMKKFCAQPWEEIKTS<br>YAGVKEKYLSEYCFSGTYILSLLPQGYHFTADSWEHIHFIGKIQGSDAGWT<br>LGYMLNLTNMISAEQPLSTPLSHST |
| SEQ ID NO: 35 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCTTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCGCTGTGGCAGAAGCTGGCCAAGG<br>ACATCCAGGTGGCCAGCAACGAGATCCTGCGGGACCCTTGCTTCCAC<br>CCCGGCTACAAGAAAGTCGTGAAGGTGTCCGACCTGTACAAGACCCCC |

TABLE 35-continued

Sequences useful for practicing the invention.

| SEQ ID Number | Feature | Sequence |
|---|---|---|
| | | CTGCACCAAGAGATTCGAGATGACCCTGCCCTTCCAGCAGTTCGAGAT<br>CCAGGGCATCGGCAATTACCAGCAGTGCCACCAGAGCATCCTGGAAC<br>TGTTCAACACCAGCTACTGCCCATACAGCCAGTGCGCCTTCAACGGCA<br>TCTTCCTGCCCACCTCTGCAGGGGGATTTCGGCGCCTTCAGCGCCTTC<br>TACTCCGTGATGAAGTTCCTGAACCTGACCAGCGAGAAGGTGTCCCA<br>GGAAAAAGTGACAGAGATGATGAAGAAGTTCTGCGCCCAGCCCTGGG<br>AGGAAATCAAGACCTCCTACGCTGGCGTGAAAGAGAAGTACCTGAGC<br>GAGTACTGCTTCAGCGGCACCTACATCCTGAGCCTGCTGCCGCAGGG<br>CTACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCTCCGCCGAGCAGCCCCTGAGCACACCTCTGAGC<br>CACAGCACC |

EP17

| SEQ ID NO: 36 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVNVSDLYKTP<br>CTKRFEMTLPFQQFEIQGIGNYQQCHQSILELFNTSYCPYSQCAFNGIFLP<br>PLQGDFGAFSAFYFVMKFLNLTSEKVSQEKVTEMMKKFCAQPWEEIKTS<br>YAGVNEKYLSEFCFSGTYILSLLLQGYHFTADSWEHIHFIGKIQGSDAGWT<br>LGYMLNLTNMIPAEQPLSTPLSHST |
| SEQ ID NO: 37 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGTGGCAGAAGCTGGCCAAGGA<br>CATCCAGGTGGCCAGCAACGAGATCCTGCGGGACCCTTGCTTCCACC<br>CCGGCTACAAGAAAGTCGTGAACGTGTCCGACCTGTACAAGACCCCC<br>TGCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCCACCTCTGCAGGGGGATTTCGGCGCCTTCAGCGCCTTC<br>TACTTCGTGATGAAGTTCCTGAACCTGACCAGCGAGAAGGTGTCCCAG<br>GAAAAAGTGACAGAGATGATGAAGAAGTTCTGCGCCCAACCCTGGGA<br>GGAAATCAAGACCTCCTACGCTGGCGTGAACGAGAAGTACCTGAGCG<br>AGTTTTGCTTCAGCGGCACCTACATCCTGAGCCTGCTGCTGCAGGGC<br>TACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGCACACCTCTGAGC<br>CACAGCACC |

EP17.1

| SEQ ID NO: 38 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVNVSDLYKTP<br>CTKRFEMTLPFQQFEIQGIGNYQQCHQSILELFNTSYCPYSQCAFNGIFLP<br>PLQGDFGAFSAFYFVMKFLNLTSEKVSQEKVTEMMKKFCAQPWEEIKTS<br>YAGVKEKYLSEFCFSGTYILSLLLQGYHFTADSWEHIHFIGKIQGSDAGWT<br>LGYMLNLTNMIPAEQPLSTPLSHST |
| SEQ ID NO: 39 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCATTCGAT<br>TTTCAAGGCGCCAGAATCATCACCGGCCAGGAAGAAGGCGCCTACGG |

TABLE 35-continued

Sequences useful for practicing the invention.

| SEQ ID Number | Feature | Sequence |
|---|---|---|
| | | CTGGATCACCATCAACTACCTGCTGGGCAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGTGGCAGAAGCTGGCCAAGGA<br>CATCCAGGTGGCCAGCAACGAGATCCTGCGGGACCCTTGCTTCCACC<br>CCGGCTACAAGAAAGTCGTGAACGTGTCCGACCTGTACAAGACCCCC<br>TGCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCACCTCTGCAGGGGATTTCGGCGCCTTCAGCGCCTTC<br>TACTTCGTGATGAAGTTCCTGAACCTGACCAGCGAGAAGGTGTCCCAG<br>GAAAAAGTGACAGAGATGATGAAGAAGTTCTGCGCCCAGCCCTGGGA<br>GGAAATCAAGACCTCCTACGCTGGCGTGAAAGAGAAGTACCTGAGCG<br>AGTTTTGCTTCAGCGGCACCTACATCCTGAGCCTGCTGCTGCAGGGC<br>TACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGCACACCTCTGAGC<br>CACAGCACC |

EP18

| SEQ ID NO: 40 | Amino acid | TQNKALPENVKYGIVLDAGSSHTSLYIYKWPAEKENDTGVVHQVEECRVK<br>GPGISKFVQKVNEIDIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVNVSDLYKTP<br>CTKRFEMTLPFQQFEIQGIGNYQQCHQSILELFNTSYCPYSQCAFNGIFLP<br>PLQGDFGAFSAFYFVMKFLNLTSEKVSQEKVTEMMKKFCAQPWEEIKTS<br>YAGVKEKYLSEYCFSGTYILSLLQQGYHFTADSWEHIHFIGKIQGSDAGW<br>TLGYMLNLTNMIPAEQPLSTPLSHST |
| SEQ ID NO: 41 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGACATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGTGGCAGAAGCTGGCCAAGGA<br>CATCCAGGTGGCCAGCAACGAGATCCTGCGGGACCCTTGCTTCCACC<br>CCGGCTACAAGAAAGTCGTGAACGTGTCCGACCTGTACAAGACCCCC<br>TGCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCACCTCTGCAGGGGATTTCGGCGCCTTCAGCGCCTTC<br>TACTTCGTGATGAAGTTCCTGAACCTGACCAGCGAGAAGGTGTCCCAG<br>GAAAAAGTGACAGAGATGATGAAGAAGTTCTGCGCCCAGCCCTGGGA<br>GGAAATCAAGACCTCCTACGCTGGCGTGAAAGAGAAGTACCTGAGCG<br>AGTACTGCTTCAGCGGCACCTACATCCTGAGCCTGCTGCTGCAGCAGGGC<br>TACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGCACACCTCTGAGC<br>CACAGCACC |

EP19

| SEQ ID NO: 42 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVNVSDLYKTP<br>CTKRFEMTLPFQQFEIQGIGNYQQCHQSILELFNTSYCPYSQCAFNGIFLP<br>PLQGDFGAFSAFYFVMKFLNLTSEKVSQEKVTEMMKKFCAQPWEEIKTS<br>YAGVKEKYLSEYCFSGTYILSLLQQGYHFTADSWEDIHFIGKIQGSDAGW<br>TLGYMLNLTNMIPAEQPLSTPLSHST |
| SEQ ID NO: 43 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG |

TABLE 35-continued

Sequences useful for practicing the invention.

| SEQ ID Number | Feature | Sequence |
|---|---|---|
| | | CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCAGGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGGATTTCGGCGCCTTCAGCGCCTTC TACTTCGTGATGAAGTTCCTGAACCTGACCAGCGAGAAGGTGTCCCAG GAAAAAGTGACAGAGATGATGAAGAAGTTCTGCGCCCAGCCCTGGGA GGAAATCAAGACCTCCTACGCTGGCGTGAAAGAGAAGTACCTGAGCG AGTACTGCTTCAGCGGCACCTACATCCTGAGCCTGCTGCAGCAGGGC TACCACTTCACCGCCGATAGCTGGGAGCACATCCACTTCATCGGCAA GATTCAGGGCAGCGACGCCGGCTGGACACTGGGCTACATGCTGAATC TGACCAACATGATCCCCGCCGAGCAGCCCCTGAGCACACCTCTGAGC CACAGCACC |
| EP20 | | |
| SEQ ID NO: 44 | Amino acid | TQNKALPENVKYGIVLDAGSSHTSLYIYKWPAEKENDTGVVHQVEECRVK GPGISKFVQKVNEIGIYLTDCMERAREVIPRSQHQETPVYLGATAGMRLLR MESEELADRVLDVVERSLSNYPFDFQGARIITGQEEGAYGWITINYLLGKF SQKNQETFGALDLGGASTQVTFVPQNQTIESPDNALQFRLYGKDYNVYT HSFLCYGKDQALWQKLAKDIQVASNGILRDPCFHPGYKKVVNVSDLYKTP CTKRFEMTLPFQQFEIQGIGNYQQCHQSILELFNTSYCPYSQCAFNGIFLP PLQGDFGAFSAFYFVMKFLNLTSEKVSQEKVTEMMKKFCAQPWEEIKTS YAGVKEKYLSEYCFSGTYILSLLLQGYHFTADSWEHIHSIGKIQGSDAGWT LGYMLNLTNMIPAEQPLSTPLSHST |
| SEQ ID NO: 45 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCAGGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGGGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGGATTTCGGCGCCTTCAGCGCCTTC TACTTCGTGATGAAGTTCCTGAACCTGACCAGCGAGAAGGTGTCCCAG GAAAAAGTGACAGAGATGATGAAGAAGTTCTGCGCCCAGCCCTGGGA GGAAATCAAGACCTCCTACGCTGGCGTGAAAGAGAAGTACCTGAGCG AGTACTGCTTCAGCGGCACCTACATCCTGAGCCTGCTGCAGCAGGGC TACCACTTCACCGCCGATAGCTGGGAGCACATCCACTTCATCGGCAA GATTCAGGGCAGCGACGCCGGCTGGACACTGGGCTACATGCTGAATC TGACCAACATGATCCCCGCCGAGCAGCCCCTGAGCACACCTCTGAGC CACAGCACC |
| EP21 | | |
| SEQ ID NO: 46 | Amino acid | TQNKALPENVKYGIVLDAGSSHTSLYIYKWPAEKENDTGVVHQVEECRVK GPGISKFVQKVNEIGIYLTDCMERAMEVIPRSQHQETPVYLGATAGMRLL RMESEELADRVLDVVERSLSNYPFDFQGARIITGQEEGAYGWITINYLLGK FSQKNQETFGALDLGGASTQVTFVPQNQTIESPDNALQFRLYGKDYNVY THSFLCYGKDQALWQKLAKDIQVASNEILRDPCFHPGYKKVVNVSDLYKT |

TABLE 35-continued

Sequences useful for practicing the invention.

| SEQ ID Number | Feature | Sequence |
|---|---|---|
| | | PCTKRFEMTLPFQQFEIQGIGNYQQCHQSILELFNTSYCPYSQCAFNGIFL<br>PPLQGDFGAFSAFYFVMKFLNLTSEKVSQEKVTEMMKKFCAQPWEEIKT<br>SYAGVKEKYLSEYCFSGTYILSLLLQGYHFTADSWEHIHFIGKIQGSDAGW<br>TLGYMLNLTNMIPAEQPLRTPLSHST |
| SEQ ID NO: 47 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCATGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGTGGCAGAAGCTGGCCAAGGA<br>CATCCAGGTGGCCAGCAACGAGATCCTGCGGGACCCTTGCTTCCACC<br>CCGGCTACAAGAAAGTCGTGAACGTGTCCGACCTGTACAAGACCCCC<br>TGCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCACCTCTGCAGGGGATTTCGGCGCCTTCAGCGCCTTC<br>TACTTCGTGATGAAGTTCCTGAACCTGACCAGCGAGAAGGTGTCCCAG<br>GAAAAAGTGACAGAGATGATGAAGAAGTTCTGCGCCCAGCCCTGGGA<br>GGAAATCAAGACCTCCTACGCTGGCGTGAAAGAGAAGTACCTGAGCG<br>AGTACTGCTTCAGCGGCACCTACATCCTGAGCCTGCTGCTGCAGGGC<br>TACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGCGCACACCTCTGAGC<br>CACAGCACC |

EP22

| SEQ ID NO: 48 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNGILRDPCFHPGYKKVVNVSDLYKTP<br>CTKRFEMTLPFQQFEIQGIGNYQQCHQSILELFNTSYCPYSQCAFNGIFLP<br>PLQGDFGAFSAFYFVMKFLNLTSEKVSQEKVTEMMKKFCAQPWEEIKTS<br>YAGVKEKYLSEYCFSGTYILSLLLQGYHFTADSWEHIHFIGKIQGSDAGWT<br>LGYMLNLTNMIPAEQPLGTPLSHST |
| SEQ ID NO: 49 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGTGGCAGAAGCTGGCCAAGGA<br>CATCCAGGTGGCCAGCAACGGGATCCTGCGGGACCCTTGCTTCCACC<br>CCGGCTACAAGAAAGTCGTGAACGTGTCCGACCTGTACAAGACCCCC<br>TGCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCACCTCTGCAGGGGATTTCGGCGCCTTCAGCGCCTTC<br>TACTTCGTGATGAAGTTCCTGAACCTGACCAGCGAGAAGGTGTCCCAG<br>GAAAAAGTGACAGAGATGATGAAGAAGTTCTGCGCCCAGCCCTGGGA<br>GGAAATCAAGACCTCCTACGCTGGCGTGAAAGAGAAGTACCTGAGCG<br>AGTACTGCTTCAGCGGCACCTACATCCTGAGCCTGCTGCTGCAGGGC<br>TACCACTTCACCGCCGATAGCTGGGAGCACATCCACTTCATCGGCAA<br>GATTCAGGGCAGCGACGCCGGCTGGACACTGGGCTACATGTTGAATC<br>TGACCAACATGATCCCCGCCGAGCAGCCCCTGGGCACACCTCTGAGC<br>CACAGCACC |

TABLE 35-continued

Sequences useful for practicing the invention.

| SEQ ID Number | Feature | Sequence |
|---|---|---|
| EP23 | | |
| SEQ ID NO: 50 | Amino acid | TQNKALPENVKYGIVLDAGSSHTSLYIYKWPAEKENDTGVVHQVEECRVK GPGISKFVQKVNEIGIYLTDCMERAREVIPRSQHQETPVYLGATAGMRLLR MESEELADRVLDVVERSLSNYPFDFQGARIITGQEEGAYGWITINYLLGKF SQKNQETFGALDLGGASTQVTFVPQNQTIESPDNALQFRLYGKDYNVYT HSFMCYGKDQALRQKLAKDIQVASNEILRDPCFHPGYKKVVNVSDLYKTP CTKRFEMTLPFQQFEIQGIGNYQQCHQSILELFNTSYCPYSQCAFNGIFLP PLQGDFGAFSAFYFVMKFLNLTSEKVSQEKVTEMMKKFCAQPWEEIKTS YAGVKEKYLSEYCFSGTYILSLLLQGYHFTADSWEHIHSIGKIQGSDAGWT LGYMLNLTNMIPAEQPLRTPLSHST |
| SEQ ID NO: 51 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCAGGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT ATGTGCTACGGAAAGGACCAGGCTCTGAGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGTACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGGATTTCGGCGCCTTCAGCGCCTTC TACTTCGTGATGAAGTTCCTGAACCTGACCAGCGAGAAGGTGTCCCAG GAAAAAGTGACAGAGATGATGAAGAAGTTCTGCGCCCAGCCCTGGGA GGAAATCAAGACCTCCTACGCTGGCGTGAAAGAGAAGTACCTGAGCG AGTACTGCTTCAGCGGCACCTACATCCTGAGCCTGCTGCTGCAGGGC TACCACTTCACCGCCGATAGCTGGGAGCACATCCACTCCATCGGCAA GATTCAGGGCAGCGACGCCGGCTGGACACTGGGCTACATGCTGAATC TGACCAACATGATCCCCGCCGAGCAGCCCCTGAGAACACCTCTGAGC CACAGCACC |
| EP24 | | |
| SEQ ID NO: 52 | Amino acid | TQNKALPENVKYGIVLDAGSSHTSLYIYKWPAEKENDTGVVHQVEECRVK GPGISKFVQKVNEIGIYLTDCMERAKEVIPRSQHQETPVYLGATAGMRLLR MESEELADRVLDVVERSLSNYPFDFQGARIITGQEEGAYGWITINYLLGKF SQKNQETFGALDLGGASTQVTFVPQNQTIESPDNALQFRLYGKDYNVYT HSFLCYGKDQALWQKLAKDIQVASNEILRDPCFHPGYKKVVNVSDLYKTP CTKRFEMTLPFQQFEIQGIGNYQQCHQSILELFNTSYCPYSQCAFNG IFLP PLQGDFGAFSAFYFVMKFLNLTSEKVSQEKVTEMMKKFCAQPWEEIKTS YAGVKEKYLSEYCFSGTYILSLLQQGYHFTADSVVEHNHFIGKIQGSDAGW TLGYMLNLTNMIPAEQPLSTPLSHST |
| SEQ ID NO: 53 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCAAGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGTACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGGATTTCGGCGCCTTCAGCGCCTTC TACTTCGTGATGAAGTTCCTGAACCTGACCAGCGAGAAGGTGTCCCAG GAAAAAGTGACAGAGATGATGAAGAAGTTCTGCGCCCAGCCCTGGGA |

TABLE 35-continued

Sequences useful for practicing the invention.

| SEQ ID Number | Feature | Sequence |
|---|---|---|
| | | GGAAATCAAGACCTCCTACGCTGGCGTGAAAGAGAAGTACCTGAGCG AGTACTGCTTCAGCGGCACCTACATCCTGAGCCTGCTGCAGCAGGGC TACCACTTCACCGCCGATAGCTGGGAGCACAACCACTTCATCGGCAA GATTCAGGGCAGCGACGCCGGCTGGACACTGGGCTACATGCTGAATC TGACCAACATGATCCCCGCCGAGCAGCCCCTGAGCACACCTCTGAGC CACAGCACC |

EP1xEP17_K405N

| SEQ ID NO: 54 | Amino acid | TQNKALPENVKYGIVLDAGSSHTSLYIYKWPAEKENDTGVVHQVEECRVK GPGISKFVQKVNEIGIYLTDCMERAMEVIPRSQHQETPVYLGATAGMRLL RMESEELADRVLDVVERSLSNYPFDFQGARIITGQEEGAYGWITINYLLGK FSQKNQETFGALDLGGASTQVTFVPQNQTIESPDNALQFRLYGKDYNVY THSFLCYGKDQALWQKLAKDIQVASNEILRDPCFHPGYKKVVNVSDLYKT PCTKRFEMTLPFQQFEIQGIGNYQQCHQSILELFNTSYCPYSQCAFNGIFL PPLQGDFGAFSAFYFVMKFLNLTSEKVSQEKVTEMMKKFCAQPWEEIKT SYAGVNEKYLSEFCFSGTYILSLLLQGYHFTADSVVEHIHFIGKIQGSDAGW TLGYMLNLTNMIPAEQPLSTPLSHST |
| SEQ ID NO: 55 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCATGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGGATTTCGGCGCCTTCAGCGCCTTC TACTTCGTGATGAAGTTCCTGAACCTGACCAGCGAGAAGGTGTCCCAG GAAAAAGTGACAGAGATGATGAAGAAGTTCTGCGCCCAACCCTGGGA GGAAATCAAGACCTCCTACGCTGGCGTGAACGAGAAGTACCTGAGCG AGTTTTGCTTCAGCGGCACCTACATCCTGAGCCTGCTGCTGCAGGGC TACCACTTCACCGCCGATAGCTGGGAGCACATCCACTTCATCGGCAA GATTCAGGGCAGCGACGCCGGCTGGACACTGGGCTACATGCTGAATC TGACCAACATGATCCCCGCCGAGCAGCCCCTGAGCACACCTCTGAGC CACAGCACC |

EP1xEP17

| SEQ ID NO: 56 | Amino acid | TQNKALPENVKYGIVLDAGSSHTSLYIYKWPAEKENDTGVVHQVEECRVK GPGISKFVQKVNEIGIYLTDCMERAMEVIPRSQHQETPVYLGATAGMRLL RMESEELADRVLDVVERSLSNYPFDFQGARIITGQEEGAYGWITINYLLGK FSQKNQETFGALDLGGASTQVTFVPQNQTIESPDNALQFRLYGKDYNVY THSFLCYGKDQALWQKLAKDIQVASNEILRDPCFHPGYKKVVNVSDLYKT PCTKRFEMTLPFQQFEIQGIGNYQQCHQSILELFNTSYCPYSQCAFNGIFL PPLQGDFGAFSAFYFVMKFLNLTSEKVSQEKVTEMMKKFCAQPWEEIKT SYAGVKEKYLSEFCFSGTYILSLLLQGYHFTADSWEHIHFIGKIQGSDAGW TLGYMLNLTNMIPAEQPLSTPLSHST |
| SEQ ID NO: 57 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCATGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC |

TABLE 35-continued

Sequences useful for practicing the invention.

| SEQ ID Number | Feature | Sequence |
|---|---|---|
| | | CCGGCTACAAGAAAGTCGTGAACGTGTCCGACCTGTACAAGACCCCC<br>TGCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCACCTCTGCAGGGGGATTTCGGCGCCTTCAGCGCCTTC<br>TACTTCGTGATGAAGTTCCTGAACCTGACCAGCGAGAAGGTGTCCCAG<br>GAAAAAGTGACAGAGATGATGAAGAAGTTCTGCGCCCAGCCCTGGGA<br>GGAAATCAAGACCTCCTACGCTGGCGTGAAAGAGAAGTACCTGAGCG<br>AGTTTTGCTTCAGCGGCACCTACATCCTGAGCCTGCTGCTGCAGGGC<br>TACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGCACACCTCTGAGC<br>CACAGCACC |

EP28aa1-3

| SEQ ID NO: 58 | Amino acid | APTTQNKALPENVKYGIVLDAGSSHTSLYIYKWPAEKENDTGVVHQVEEC<br>RVKGPGISKFVQKVNEIGIYLTDCMERAREVIPRSQHQETPVYLGATAGM<br>RLLRMESEELADRVLDVVERSLSNYPFDFQGARIITGQEEGAYGWITINYL<br>LGKFSQKNQETFGALDLGGASTQVTFVPQNQTIESPDNALQFRLYGKDY<br>NVYTHSFLCYGKDQALWQKLAKDIQVASNEILRDPCFHPGYKKVVNVSDL<br>YKTPCTKRFEMTLPFQQFEIQGIGNYQQCHQSILELFNTSYCPYSQCAFN<br>GIFLPPLQGDFGAFSAFYFVMKFLNLTSEKVSQEKVTEMMKKFCAQPWE<br>EIKTSYAGVKEKYLSEYCFSGTYILSLLLQGYHFTADSWEHIHFIGKIQGSD<br>AGWTLGYMLNLTNMIPAEQPLSTPLSHST |
| SEQ ID NO: 59 | DNA | GCCCCTACCACCCAGAACAAGGCCCTGCCCGAGAACGTGAAGTACGG<br>CATCGTGCTGGACGCCGGCTCCTCCCACACCTCCCTGTACATCTACAA<br>GTGGCCTGCCGAGAAAGAAAACGACACCGGCGTGGTGCACCAAGTG<br>GAAGAGTGCAGAGTGAAGGGCCCCGGCATCTCCAAGTTCGTGCAGAA<br>AGTGAACGAGATCGGCATCTACCTGACCGACTGCATGGAACGGGCCA<br>GAGAAGTGATCCCTCGGTCCCAGCACCAGGAAACCCCTGTCTACCTG<br>GGCGCCACCGCCGGCATGCGGCTGCTGCGGATGGAATCCGAGGAAC<br>TGGCCGACCGGGTGCTGGACGTGGTGGAACGGTCCCTGTCCAACTAC<br>CCATTCGATTTTCAAGGCGCCAGAATCATCACCGGCCAGGAAGAGGG<br>CGCCTACGGCTGGATCACCATCAACTACCTGCTGGGCAAGTTCTCCC<br>AGAAGAATCAGGAAACCTTCGGCGCCCTGGACCTGGGCGGAGCCAG<br>CACCCAAGTCACATTCGTGCCCCAGAACCAGACCATCGAGAGCCCCG<br>ACAACGCCCTGCAGTTCCGGCTGTACGGCAAGGACTACAACGTGTAC<br>ACCCACAGCTTTCTGTGCTACGGCAAGGACCAGGCCCTGTGGCAGAA<br>GCTGGCCAAGGACATCCAAGTGGCCTCCAACGAGATCCTGCGGGACC<br>CCTGCTTCCACCCCGGCTACAAGAAAGTGGTCAACGTGTCCGACCTG<br>TACAAGACCCCTTGCACCAAGAGATTCGAGATGACCCTGCCCTTCCAG<br>CAGTTCGAGATCCAGGGCATCGGCAACTACCAGCAGTGCCACCAGTC<br>CATCCTGGAACTGTTCAACACCTCCTACTGCCCCTACTCCCAGTGCGC<br>CTTCAACGGCATCTTCCTGCCTCCACTGCAGGGCGACTTCGGCGCCT<br>TCTCCGCCTTCTACTTCGTGATGAAGTTCCTGAACCTGACCTCCGAGA<br>AGTGTCCCAGGAAAAAGTGACCGAGATGATGAAGAAGTTCTGCGCC<br>CAGCCCTGGGAGGAAATCAAGACCTCCTACGCTGGCGTGAAAGAGAA<br>GTACCTGTCCGAGTACTGCTTCTCCGGCACCTACATCCTGTCCCTGCT<br>GCTGCAGGGCTACCACTTCACCGCCGACAGCTGGGAGCACATCCACT<br>TCATCGGCAAGATCCAGGGATCCGACGCTGGCTGGACCCTGGGCTAC<br>ATGCTGAATCTGACCAACATGATCCCCGCCGAGCAGCCCCTGTCCAC<br>CCCTCTGTCTCACTCCACC |

EP14xEP17

| SEQ ID NO: 60 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVNVSDLYKTP<br>CTKRFEMTLPFQQFEIQGIGNYQQCHQSILELFNTSYCPYSQCAFNGIFLP<br>PLQGDFGAFSAFYSVMKFLNLTSEKVSQEKVTEMMKKFCAQPWEEIKTS<br>YAGVKEKYLSEFCFSGTYILSLLLQGYHFTADSWEHIHFIGKIQGSDAGWT<br>LGYMLNLTNMIPAEQPLSTPLSHST |
| SEQ ID NO: 61 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAAGAAGCCTGAGCAACTACCCATTCGAT |

TABLE 35-continued

Sequences useful for practicing the invention.

| SEQ ID Number | Feature | Sequence |
|---|---|---|
| | | TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCTTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGTGGCAGAAGCTGGCCAAGGA<br>CATCCAGGTGGCCAGCAACGAGATCCTGCGGGACCCTTGCTTCCACC<br>CCGGCTACAAGAAAGTCGTGAACGTGTCCGACCTGTACAAGACCCCC<br>TGCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCCACCTCTGCAGGGGGATTTCGGCGCCTTCAGCGCCTTC<br>TACTCCGTGATGAAGTTCCTGAACCTGACCAGCGAGAAGGTGTCCCA<br>GGAAAAAGTGACAGAGATGATGAAGAAGTTCTGCGCCCAGCCCTGGG<br>AGGAAATCAAGACCTCCTACGCTGGCGTGAAAGAAGTACCTGAGC<br>GAGTTTTGCTTCAGCGGCACCTACATCCTGAGCCTGCTGCTGCAGGG<br>CTACCACTTCACCGCCGATAGCTGGGAGCACATCCACTTCATCGGCAA<br>GATTCAGGGCAGCGACGCCGGCTGGACACTGGGTTACATGCTGAATC<br>TGACCAACATGATCCCCGCCGAGCAGCCCCTGAGCACACCTCTGAGC<br>CACAGCACC |

EP10xEP19_H436D

| SEQ ID NO: 62 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVNVSDLYKTP<br>CTKRFEMTLPFQQFEIQGTGNYQQCHQSILELFNTSYCPYSQCAFNGIFL<br>PPLQGDFGAFSAFYFVMKFLNLTSEKVSQEKVTEMMKKFCAQPWEEIKT<br>SYAGVKEKYLSEYCFSGTYILSLLQQGYHFTADSWEDIHFIGKIQGSDAG<br>WTLGYMLNLTNMIPAEQPLSTPLSHST |
| SEQ ID NO: 63 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGTGGCAGAAGCTGGCCAAGGA<br>CATCCAGGTGGCCAGCAACGAGATCCTGCGGGACCCTTGCTTCCACC<br>CCGGCTACAAGAAAGTCGTGAACGTGTCCGACCTGTACAAGACCCCC<br>TGCACCAAGAGATTCGAGATGACCCTGCCCTTCCAGCAGTTCGAGATC<br>CAGGGCACCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCCACCTCTGCAGGGGGATTTCGGCGCCTTCAGCGCCTTC<br>TACTTCGTGATGAAGTTCCTGAACCTGACCAGCGAGAAGGTGTCCCAG<br>GAAAAAGTGACAGAGATGATGAAGAAGTTCTGCGCCCAGCCCTGGGA<br>GGAAATCAAGACCTCCTACGCTGGCGTGAAAGAGAAGTACCTGAGCG<br>AGTACTGCTTCAGCGGCACCTACATCCTGAGCCTGCTGCAGCAGGGC<br>TACCACTTCACCGCCGATAGCTGGGAGGACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGCACACCTCTGAGC<br>CACAGCACC |

EP14xEP19

| SEQ ID NO: 64 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVNVSDLYKTP<br>CTKRFEMTLPFQQFEIQGIGNYQQCHQSILELFNTSYCPYSQCAFNGIFLP<br>PLQGDFGAFSAFYSVMKFLNLTSEKVSQEKVTEMMKKFCAQPWEEIKTS<br>YAGVKEKYLSEYCFSGTYILSLLQQGYHFTADSWEHIHFIGKIQGSDAGW<br>TLGYMLNLTNMIPAEQPLSTPLSHST |

TABLE 35-continued

Sequences useful for practicing the invention.

| SEQ ID Number | Feature | Sequence |
|---|---|---|
| SEQ ID NO: 65 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCAGGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCTTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCCACCTCTGCAGGGGGATTTCGGCGCCTTCAGCGCCTTC TACTCCGTGATGAAGTTCCTGAACCTGACCAGCGAGAAGGTGTCCCA GGAAAAAGTGACAGAGATGATGAAGAAGTTCTGCGCCCAGCCCTGGG AGGAAATCAAGACCTCCTACGCTGGCGTGAAAGAGAAGTACCTGAGC GAGTACTGCTTCAGCGGCACCTACATCCTGAGCCTGCTGCTGCAGGG CTACCACTTCACCGCCGATAGCTGGGAGCACATCCACTTCATCGGCAA GATTCAGGGCAGCGACGCCGGCTGGACACTGGGTTACATGCTGAATC TGACCAACATGATCCCCGCCGAGCAGCCCCTGAGCACACCTCTGAGC CACAGCACC |

EP28aa1-15

| SEQ ID NO: 66 | Amino acid | APTSSSTKKTQLTSSTQNKALPENVKYGIVLDAGSSHTSLYIYKWPAEKEN DTGVVHQVEECRVKGPGISKFVQKVNEIGIYLTDCMERAREVIPRSQHQE TPVYLGATAGMRLLRMESEELADRVLDVVERSLSNYPFDFQGARIITGQE EGAYGWITINYLLGKFSQKNQETFGALDLGGASTQVTFVPQNQTIESPDN ALQFRLYGKDYNVYTHSFLCYGKDQALWQKLAKDIQVASNEILRDPCFHP GYKKVVNVSDLYKTPCTKRFEMTLPFQQFEIQGIGNYQQCHQSILELFNT SYCPYSQCAFNGIFLPPLQGDFGAFSAFYFVMKFLNLTSEKVSQEKVTEM MKKFCAQPWEEIKTSYAGVKEKYLSEYCFSGTYILSLLLQGYHFTADSWE HIHFIGKIQGSDAGVVTLGYMLNLTNMIPAEQPLSTPLSHST |
| SEQ ID NO: 67 | DNA | GCCCCTACCAGCAGCAGCACCAAGAAAACCCAGCTGACCAGCAGCAC CCAGAACAAGGCCCTGCCCGAGAACGTGAAGTACGGCATCGTGCTGG ATGCCGGCAGCAGCCACACCAGCCTGTACATCTACAAGTGGCCTGCC GAGAAAGAAAACGACACCGGCGTGGTGCATCAGGTGGAAGAGTGCAG AGTGAAGGGCCCTGGCATCAGCAAGTTCGTGCAGAAAGTGAACGAGA TCGGCATCTACCTGACCGACTGCATGGAACGGGCCAGGGAAGTGATC CCCAGAAGCCAGCACCAGGAAACCCCCGTGTATCTGGGAGCCACCGC CGGCATGAGACTGCTGAGAATGGAAAGCGAGGAACTGGCCGACCGG GTGCTGGACGTGGTGGAAAGAAGCCTGAGCAACTACCCATTCGATTTT CAAGGCGCCAGAATCATCACCGGCCAGGAAGAAGGCGCCTACGGCT GGATCACCATCAACTACCTGCTGGGCAAGTTCAGCCAGAAGAATCAG GAAACCTTCGGCGCCCTGGACCTGGGCGGAGCTTCTACCCAAGTGAC CTTCGTGCCCCAGAATCAGACCATCGAGAGCCCCGACAACGCCCTGC AGTTCCGGCTGTACGGCAAGGACTACAATGTGTACACCCACAGCTTTC TGTGCTACGGAAAGGACCAGGCTCTGTGGCAGAAGCTGGCCAAGGAC ATCCAGGTGGCCAGCAACGAGATCCTGCGGGACCCTTGCTTCCACCC CGGCTACAAGAAAGTCGTGAACGTGTCCGACCTGTACAAGACCCCCT GCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCCACCTCTGCAGGGGGATTTCGGCGCCTTCAGCGCCTTC TACTTCGTGATGAAGTTCCTGAACCTGACCAGCGAGAAGGTGTCCCAG GAAAAAGTGACAGAGATGATGAAGAAGTTCTGCGCCCAGCCCTGGGA GGAAATCAAGACCTCCTACGCTGGCGTGAAAGAGAAGTACCTGAGCG AGTACTGCTTCAGCGGCACCTACATCCTGAGCCTGCTGCTGCAGGGC TACCACTTCACCGCCGATAGCTGGGAGCACATCCACTTCATCGGCAA GATTCAGGGCAGCGACGCCGGCTGGACACTGGGCTACATGCTGAATC TGACCAACATGATCCCCGCCGAGCAGCCCCTGAGCACACCTCTGAGC CACAGCACC |

EP17xE19_H436D

| SEQ ID NO: 68 | Amino acid | TQNKALPENVKYGIVLDAGSSHTSLYIYKWPAEKENDTGVVHQVEECRVK GPGISKFVQKVNEIGIYLTDCMERAREVIPRSQHQETPVYLGATAGMRLLR |

TABLE 35-continued

Sequences useful for practicing the invention.

| SEQ ID Number | Feature | Sequence |
|---|---|---|
| | | MESEELADRVLDVVERSLSNYPFDFQGARIITGQEEGAYGWITINYLLGKF SQKNQETFGALDLGGASTQVTFVPQNQTIESPDNALQFRLYGKDYNVYT HSFLCYGKDQALWQKLAKDIQVASNEILRDPCFHPGYKKVVNVSDLYKTP CTKRFEMTLPFQQFEIQGIGNYQQCHQSILELFNTSYCPYSQCAFNGIFLP PLQGDFGAFSAFYFVMKFLNLTSEKVSQEKVTEMMKKFCAQPWEEIKTS YAGVKEKYLSEFCFSGTYILSLLQQGYHFTADSWEDIHFIGKIQGSDAGWT LGYMLNLTNMIPAEQPLSTPLSHST |
| SEQ ID NO: 69 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCAGGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGATTTCGGCGCCTTCAGCGCCTTC TACTTCGTGATGAAGTTCCTGAACCTGACCAGCGAGAAGGTGTCCCAG GAAAAAGTGACAGAGATGATGAAGAAGTTCTGCGCCCAGCCCTGGGA GGAAATCAAGACCTCCTACGCTGGCGTGAAAGAGAAGTACCTGAGCG AGTTTTGCTTCAGCGGCACCTACATCCTGAGCCTGCTGCAGCAGGGC TACCACTTCACCGCCGATAGCTGGGAGGACATCCACTTCATCGGCAA GATTCAGGGCAGCGACGCCGGCTGGACACTGGGCTACATGCTGAATC TGACCAACATGATCCCCGCCGAGCAGCCCCTGAGCACACCTCTGAGC CACAGCACC |

EP17xEP19

| SEQ ID NO: 70 | Amino acid | TQNKALPENVKYGIVLDAGSSHTSLYIYKWPAEKENDTGVVHQVEECRVK GPGISKFVQKVNEIGIYLTDCMERAREVIPRSQHQETPVYLGATAGMRLLR MESEELADRVLDVVERSLSNYPFDFQGARIITGQEEGAYGWITINYLLGKF SQKNQETFGALDLGGASTQVTFVPQNQTIESPDNALQFRLYGKDYNVYT HSFLCYGKDQALWQKLAKDIQVASNEILRDPCFHPGYKKVVNVSDLYKTP CTKRFEMTLPFQQFEIQGIGNYQQCHQSILELFNTSYCPYSQCAFNGIFLP PLQGDFGAFSAFYFVMKFLNLTSEKVSQEKVTEMMKKFCAQPWEEIKTS YAGVKEKYLSEFCFSGTYILSLLQQGYHFTADSWEHIHFIGKIQGSDAGVVT LGYMLNLTNMIPAEQPLSTPLSHST |
| SEQ ID NO: 71 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCAGGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGATTTCGGCGCCTTCAGCGCCTTC TACTTCGTGATGAAGTTCCTGAACCTGACCAGCGAGAAGGTGTCCCAG |

TABLE 35-continued

Sequences useful for practicing the invention.

| SEQ ID Number | Feature | Sequence |
|---|---|---|
| | | GAAAAAGTGACAGAGATGATGAAGAAGTTCTGCGCCCAGCCCTGGGA<br>GGAAATCAAGACCTCCTACGCTGGCGTGAAAGAGAAGTACCTGAGCG<br>AGTTTTGCTTCAGCGGCACCTACATCCTGAGCCTGCTGCAGCAGGGC<br>TACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGCACACCTCTGAGC<br>CACAGCACC |

EP28aa1-16

| SEQ ID NO: 72 | Amino acid | APTSSSTKKTQLTSSGTQNKALPENVKYGIVLDAGSSHTSLYIYKWPAEKE<br>NDTGVVHQVEECRVKGPGISKFVQKVNEIGIYLTDCMERAREVIPRSQHQ<br>ETPVYLGATAGMRLLRMESEELADRVLDVVERSLSNYPFDFQGARIITGQ<br>EEGAYGWITINYLLGKFSQKNQETFGALDLGGASTQVTFVPQNQTIESPD<br>NALQFRLYGKDYNVYTHSFLCYGKDQALWQKLAKDIQVASNEILRDPCFH<br>PGYKKVVNVSDLYKTPCTKRFEMTLPFQQFEIQGIGNYQQCHQSILELFN<br>TSYCPYSQCAFNGIFLPPLQGDFGAFSAFYFVMKFLNLTSEKVSQEKVTE<br>MMKKFCAQPWEEIKTSYAGVKEKYLSEYCFSGTYILSLLLQGYHFTADSW<br>EHIHFIGKIQGSDAGVVTLGYMLNLTNMIPAEQPLSTPLSHST |
| SEQ ID NO: 73 | DNA | GCCCCTACCTCCTCCAGCACCAAGAAAACCCAGCTGACCTCCAGCGG<br>CACCCAGAACAAGGCCCTGCCCGAGAACGTGAAGTACGGCATCGTGC<br>TGGACGCCGGCTCCTCCCACACCTCCCTGTACATCTACAAGTGGCCT<br>GCCGAGAAAGAAAACGACACCGGCGTGGTGCACCAAGTGGAAGAGT<br>GCAGAGTGAAGGGCCCCGGCATCTCCAAGTTCGTGCAGAAAGTGAAC<br>GAGATCGGCATCTACCTGACCGACTGCATGGAACGGGCCAGAGAAGT<br>GATCCCTCGGTCCCAGCACCAGGAAACCCCTGTCTACCTGGGCGCCA<br>CCGCCGGCATGCGGCTGCTGCGGATGGAATCCGAGGAACTGGCCGA<br>CCGGGTGCTGGACGTGGTGGAACGGTCCCTGTCCAACTACCCATTCG<br>ATTTTCAAGGCGCCAGAATCATCACCGGCCAGGAAGAGGGCGCCTAC<br>GGCTGGATCACCATCAACTACCTGCTGGGCAAGTTCTCCCAGAAGAAT<br>CAGGAAACCTTCGGCGCCCTGGACCTGGGCGGAGCCAGCACCCAAG<br>TCACATTCGTGCCCCAGAACCAGACCATCGAGAGCCCCGACAACGCC<br>CTGCAGTTCCGGCTGTACGGCAAGGACTACAACGTGTACACCCACAG<br>CTTTCTGTGCTACGGCAAGGACCAGGCCCTGTGGCAGAAGCTGGCCA<br>AGGACATCCAAGTGGCCTCCAACGAGATCCTGCGGGACCCCTGCTTC<br>CACCCCGGCTACAAGAAAGTGGTCAACGTGTCCGACCTGTACAAGAC<br>CCCCTTGCACCAAGAGATTCGAGATGACCCTGCCCTTCCAGCAGTTCGA<br>GATCCAGGGCATCGGCAACTACCAGCAGTGCCACCAGTCCATCCTGG<br>AACTGTTCAACACCTCCTACTGCCCCTACTCCCAGTGCGCCTTCAACG<br>GCATCTTCCTGCCTCCACTGCAGGGCGACTTCGGCGCCTTCTCCGCC<br>TTCTACTTCGTGATGAAGTTCCTGAACCTGACCTCCGAGAAAGTGTCC<br>CAGGAAAAAGTGACCGAGATGATGAAGAAGTTCTGCGCCCAGCCCTG<br>GGAGGAAATCAAGACCTCCTACGCTGGCGTGAAAGAGAAGTACCTGT<br>CCGAGTACTGCTTCTCCGGCACCTACATCCTGTCCCTGCTGCTGCAG<br>GGCTACCACTTCACCGCCGACAGCTGGGAGCACATCCACTTCATCGG<br>CAAGATCCAGGGATCCGACGCTGGCTGGACCCTGGGCTACATGCTGA<br>ATCTGACCAACATGATCCCCGCCGAGCAGCCCCTGTCCACCCCTCTG<br>TCTCACTCCACC |

EP1xEP14xEP19

| SEQ ID NO: 74 | Amino acid | TQNKALPENVKYGIVLDAGSSHTSLYIYKWPAEKENDTGVVHQVEECRVK<br>GPGISKFVQKVNEIGIYLTDCMERAMEVIPRSQHQETPVYLGATAGMRLL<br>RMESEELADRVLDVVERSLSNYPFDFQGARIITGQEEGAYGWITINYLLGK<br>FSQKNQETFGALDLGGASTQVTFVPQNQTIESPDNALQFRLYGKDYNVY<br>THSFLCYGKDQALWQKLAKDIQVASNEILRDPCFHPGYKKVVNVSDLYKT<br>PCTKRFEMTLPFQQFEIQGIGNYQQCHQSILELFNTSYCPYSQCAFNGIFL<br>PPLQGDFGAFSAFYSVMKFLNLTSEKVSQEKVTEMMKKFCAQPWEEIKT<br>SYAGVKEKYLSEYCFSGTYILSLLQQGYHFTADSWEHIHFIGKIQGSDAG<br>WTLGYMLNLTNMIPAEQPLSTPLSHST |
| SEQ ID NO: 75 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCATGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT |

TABLE 35-continued

Sequences useful for practicing the invention.

| SEQ ID Number | Feature | Sequence |
|---|---|---|
| | | CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGATTTCGGCGCCTTCAGCGCCTTC TACTCCGTGATGAAGTTCCTGAACCTGACCAGCGAGAAGGTGTCCCA GGAAAAAGTGACAGAGATGATGAAGAAGTTCTGCGCCCAGCCCTGGG AGGAAATCAAGACCTCCTACGCTGGCGTGAAAGAAGTACCTGAGC GAGTACTGCTTCAGCGGCACCTACATCCTGAGCCTGCTGCAGCAGGG CTACCACTTCACCGCCGATAGCTGGGAGCACATCCACTTCATCGGCAA GATTCAGGGCAGCGACGCCGGCTGGACACTGGGCTACATGCTGAATC TGACCAACATGATCCCCGCCGAGCAGCCCCTGAGCACACCTCTGAGC CACAGCACC |
| EP1xEP17xEP19 | | |
| SEQ ID NO: 76 | Amino acid | TQNKALPENVKYGIVLDAGSSHTSLYIYKWPAEKENDTGVVHQVEECRVK GPGISKFVQKVNEIGIYLTDCMERAMEVIPRSQHQETPVYLGATAGMRLL RMESEELADRVLDVVERSLSNYPFDFQGARIITGQEEGAYGWITINYLLGK FSQKNQETFGALDLGGASTQVTFVPQNQTIESPDNALQFRLYGKDYNVY THSFLCYGKDQALWQKLAKDIQVASNEILRDPCFHPGYKKVVNVSDLYKT PCTKRFEMTLPFQQFEIQGIGNYQQCHQSILELFNTSYCPYSQCAFNGIFL PPLQGDFGAFSAFYFVMKFLNLTSEKVSQEKVTEMMKKFCAQPWEEIKT SYAGVKEKYLSEFCFSGTYILSLLQQGYHFTADSWEHIHFIGKIQGSDAG VVTLGYMLNLTNMIPAEQPLSTPLSHST |
| SEQ ID NO: 77 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCATGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGGATTTCGGCGCCTTCAGCGCCTTC TACTTCGTGATGAAGTTCCTGAACCTGACCAGCGAGAAGGTGTCCCAG GAAAAAGTGACAGAGATGATGAAGAAGTTCTGCGCCCAGCCCTGGGA GGAAATCAAGACCTCCTACGCTGGCGTGAAAGAGAAGTACCTGAGCG AGTTCTGCTTCAGCGGCACCTACATCCTGAGCCTGCTGCAGCAGGGC TACCACTTCACCGCCGATAGCTGGGAGCACATCCACTTCATCGGCAA GATTCAGGGCAGCGACGCCGGCTGGACACTGGGCTACATGCTGAATC TGACCAACATGATCCCCGCCGAGCAGCCCCTGAGCACACCTCTGAGC CACAGCACC |
| EP1xEP14 | | |
| SEQ ID NO: 78 | Amino acid | TQNKALPENVKYGIVLDAGSSHTSLYIYKWPAEKENDTGVVHQVEECRVK GPGISKFVQKVNEIGIYLTDCMERAMEVIPRSQHQETPVYLGATAGMRLL RMESEELADRVLDVVERSLSNYPFDFQGARIITGQEEGAYGWITINYLLGK FSQKNQETFGALDLGGASTQVTFVPQNQTIESPDNALQFRLYGKDYNVY THSFLCYGKDQALWQKLAKDIQVASNEILRDPCFHPGYKKVVNVSDLYKT PCTKRFEMTLPFQQFEIQGIGNYQQCHQSILELFNTSYCPYSQCAFNGIFL PPLQGDFGAFSAFYSVMKFLNLTSEKVSQEKVTEMMKKFCAQPWEEIKT SYAGVKEKYLSEYCFSGTYILSLLLQGYHFTADSWEHIHFIGKIQGSDAGW TLGYMLNLTNMIPAEQPLSTPLSHST |
| SEQ ID NO: 79 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCATGGAAGTGA TCCCCAGAAGCCAGCACCAGGAAACCCCCGTGTATCTGGGAGCCACC |

TABLE 35-continued

Sequences useful for practicing the invention.

| SEQ ID Number | Feature | Sequence |
|---|---|---|
| | | GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCTTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGATTTCGGCGCCTTCAGCGCCTTC TACTCCGTGATGAAGTTCCTGAACCTGACCAGCGAGAAGGTGTCCCA GGAAAAAGTGACAGAGATGATGAAGAAGTTCTGCGCCCAGCCCTGGG AGGAAATCAAGACCTCCTACGCTGGCGTGAAAGAGAAGTACCTGAGC GAGTACTGCTTCAGCGGCACCTACATCCTGAGCCTGCTGCTGCAGGG CTACCACTTCACCGCCGATAGCTGGGAGCACATCCACTTCATCGGCAA GATTCAGGGCAGCGACGCCGGCTGGACACTGGGTTACATGCTGAATC TGACCAACATGATCCCCGCCGAGCAGCCCCTGAGCACACCTCTGAGC CACAGCACC |

EP28aa1-6

| SEQ ID NO: 80 | Amino acid | APTSSSTQNKALPENVKYGIVLDAGSSHTSLYIYKWPAEKENDTGVVHQV EECRVKGPGISKFVQKVNEIGIYLTDCMERAREVIPRSQHQETPVYLGATA GMRLLRMESEELADRVLDVVERSLSNYPFDFQGARIITGQEEGAYGWITI NYLLGKFSQKNQETFGALDLGGASTQVTFVPQNQTIESPDNALQFRLYGK DYNVYTHSFLCYGKDQALWQKLAKDIQVASNEILRDPCFHPGYKKVVNVS DLYKTPCTKRFEMTLPFQQFEIQGIGNYQQCHQSILELFNTSYCPYSQCA FNGIFLPPLQGDFGAFSAFYFVMKFLNLTSEKVSQEKVTEMMKKFCAQP WEEIKTSYAGVKEKYLSEYCFSGTYILSLLLQGYHFTADSWEHIHFIGKIQG SDAGWTLGYMLNLTNMIPAEQPLSTPLSHST |
| SEQ ID NO: 81 | DNA | GCCCCTACCAGCAGCAGCACCCAGAACAAGGCCCTGCCCGAGAACGT GAAGTACGGCATCGTGCTGGATGCCGGCAGCAGCCACACCAGCCTGT ACATCTACAAGTGGCCTGCCGAGAAGAAAACGACACCGGCGTGGTG CATCAGGTGGAAGAGTGCAGAGTGAAGGGCCCTGGCATCAGCAAGTT CGTGCAGAAAGTGAACGAGATCGGCATCTACCTGACCGACTGCATGG AACGGGCCAGGGAAGTGATCCCCAGAAGCCAGCACCAGGAAACCCC CGTGTATCTGGGAGCCACCGCCGGCATGAGACTGCTGAGAATGGAAA GCGAGGAACTGGCCGACCGGGTGCTGGACGTGGTGGAAAGAAGCCT GAGCAACTACCCATTCGATTTTCAAGGCGCCAGAATCATCACCGGCCA GGAAGAAGGCGCCTACGGCTGGATCACCATCAACTACCTGCTGGGCA AGTTCAGCCAGAAGAATCAGGAAACCTTCGGCGCCCTGGACCTGGGC GGAGCTTCTACCCAAGTGACCTTCGTGCCCCAGAATCAGACCATCGA GAGCCCCGACAACGCCCTGCAGTTCCGGCTGTACGGCAAGGACTACA ATGTGTACACCCACAGCTTTCTGTGCTACGGAAAGGACCAGGCTCTGT GGCAGAAGCTGGCCAAGGACATCCAGGTGGCCAGCAACGAGATCCT GCGGGACCCTTGCTTCCACCCCGGCTACAAGAAAGTCGTGAACGTGT CCGACCTGTACAAGACCCCCTGCACCAAGAGATTCGAGATGACCCTG CCCTTCCAGCAGTTCGAGATCCAGGGCATCGGCAATTACCAGCAGTG CCACCAGAGCATCCTGGAACTGTTCAACACCAGCTACTGCCCCTACAG CCAGTGCGCCTTCAACGGCATCTTCCTGCCACCTCTGCAGGGGGATT TCGGCGCCTTCAGCGCCTTCTACTTCGTGATGAAGTTCCTGAACCTGA CCAGCGAGAAGGTGTCCCAGGAAAAAGTGACAGAGATGATGAAGAAG TTCTGCGCCCAGCCCTGGGAGGAAATCAAGACCTCCTACGCTGGCGT GAAAGAGAAGTACCTGAGCGAGTACTGCTTCAGCGGCACCTACATCC TGAGCCTGCTGCTGCAGGGCTACCACTTCACCGCCGATAGCTGGGAG CACATCCACTTCATCGGCAAGATTCAGGGCAGCGACGCCGGCTGGAC ACTGGGCTACATGCTGAATCTGACCAACATGATCCCCGCCGAGCAGC CCCTGAGCACACCTCTGAGCCACAGCACC |

EP28_E174A

| SEQ ID NO: 82 | Amino acid | TQNKALPENVKYGIVLDAGSSHTSLYIYKWPAEKENDTGVVHQVEECRVK GPGISKFVQKVNEIGIYLTDCMERAREVIPRSQHQETPVYLGATAGMRLLR MESEELADRVLDVVERSLSNYPFDFQGARIITGQEAGAYGWITINYLLGKF SQKNQETFGALDLGGASTQVTFVPQNQTIESPDNALQFRLYGKDYNVYT HSFLCYGKDQALWQKLAKDIQVASNEILRDPCFHPGYKKVVNVSDLYKTP CTKRFEMTLPFQQFEIQGIGNYQQCHQSILELFNTSYCPYSQCAFNGIFLP PLQGDFGAFSAFYFVMKFLNLTSEKVSQEKVTEMMKKFCAQPWEEIKTS YAGVKEKYLSEYCFSGTYILSLLLQGYHFTADSWEHIHFIGKIQGSDAGWT LGYMLNLTNMIPAEQPLSTPLSHST |

TABLE 35-continued

Sequences useful for practicing the invention.

| SEQ ID Number | Feature | Sequence |
|---|---|---|
| SEQ ID NO: 83 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCAGGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCCATTCGAT TTTCAAGGCGCCAGAATCATCACCGGCCAGGAAGCCGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGGATTTCGGCGCCTTCAGCGCCTTC TACTTCGTGATGAAGTTCCTGAACCTGACCAGCGAGAAGGTGTCCCAG GAAAAAGTGACAGAGATGATGAAGAAGTTCTGCGCCCAGCCCTGGGA GGAAATCAAGACCTCCTACGCTGGCGTGAAAGAGAAGTACCTGAGCG AGTACTGCTTCAGCGGCACCTACATCCTGAGCCTGCTGCTGCAGGGC TACCACTTCACCGCCGATAGCTGGGAGCACATCCACTTCATCGGCAA GATTCAGGGCAGCGACGCCGGCTGGACACTGGGCTACATGCTGAATC TGACCAACATGATCCCCGCCGAGCAGCCCCTGAGCACACCTCTGAGC CACAGCACC |

EP28_E174A_S218A

| SEQ ID NO: 84 | Amino acid | TQNKALPENVKYGIVLDAGSSHTSLYIYKWPAEKENDTGVVHQVEECRVK GPGISKFVQKVNEIGIYLTDCMERAREVIPRSQHQETPVYLGATAGMRLLR MESEELADRVLDVVERSLSNYPFDFQGARIITGQEAGAYGWITINYLLGKF SQKNQETFGALDLGGAATQVTFVPQNQTIESPDNALQFRLYGKDYNVYT HSFLCYGKDQALWQKLAKDIQVASNEILRDPCFHPGYKKVVNVSDLYKTP CTKRFEMTLPFQQFEIQGIGNYQQCHQSILELFNTSYCPYSQCAFNGIFLP PLQGDFGAFSAFYFVMKFLNLTSEKVSQEKVTEMMKKFCAQPWEEIKTS YAGVKEKYLSEYCFSGTYILSLLLQGYHFTADSWEHIHFIGKIQGSDAGWT LGYMLNLTNMIPAEQPLSTPLSHST |

| SEQ ID NO: 85 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCAGGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCCATTCGAT TTTCAAGGCGCCAGAATCATCACCGGCCAGGAAGCCGGCGCCTACGG CTGGATCACCATCAACTACCTGCTGGGCAAGTTCAGCCAGAAGAATCA GGAAACCTTCGGCGCCCTGGACCTGGGCGGAGCTGCTACCCAAGTG ACCTTCGTGCCCCAGAATCAGACCATCGAGAGCCCCGACAACGCCCT GCAGTTCCGGCTGTACGGCAAGGACTACAATGTGTACACCCACAGCT TTCTGTGCTACGGAAAGGACCAGGCTCTGTGGCAGAAGCTGGCCAAG GACATCCAGGTGGCCAGCAACGAGATCCTGCGCGGGACCCTTGCTTCCA CCCCGGCTACAAGAAAGTCGTGAACGTGTCCGACCTGTACAAGACCC CTGCACCAAGAGATTCGAGATGACCCTGCCCTTCCAGCAGTTCGAG ATCCAGGGCATCGGCAATTACCAGCAGTGCCACCAGAGCATCCTGGA ACTGTTCAACACCAGCTACTGCCCCTACAGCCAGTGCGCCTTCAACG GCATCTTCCTGCCACCTCTGCAGGGGGATTTCGGCGCCTTCAGCGCC TTCTACTTCGTGATGAAGTTCCTGAACCTGACCAGCGAGAAGGTGTCC CAGGAAAAAGTGACAGAGATGATGAAGAAGTTCTGCGCCCAGCCCTG GGAGGAAATCAAGACCTCCTACGCTGGCGTGAAAGAGAAGTACCTGA GCGAGTACTGCTTCAGCGGCACCTACATCCTGAGCCTGCTGCTGCAG GGCTACCACTTCACCGCCGATAGCTGGGAGCACATCCACTTCATCGG CAAGATTCAGGGCAGCGACGCCGGCTGGACACTGGGCTACATGCTGA ATCTGACCAACATGATCCCCGCCGAGCAGCCCCTGAGCACACCTCTG AGCCACAGCACC |

EP14_N73Q

| SEQ ID NO: 86 | Amino acid | TQNKALPENVKYGIVLDAGSSHTSLYIYKWPAEKEQDTGVVHQVEECRVK GPGISKFVQKVNEIGIYLTDCMERAREVIPRSQHQETPVYLGATAGMRLLR |

TABLE 35-continued

Sequences useful for practicing the invention.

| SEQ ID Number | Feature | Sequence |
|---|---|---|
| | | MESEELADRVLDVVERSLSNYPFDFQGARIITGQEEGAYGWITINYLLGKF SQKNQETFGALDLGGASTQVTFVPQNQTIESPDNALQFRLYGKDYNVYT HSFLCYGKDQALWQKLAKDIQVASNEILRDPCFHPGYKKVVNVSDLYKTP CTKRFEMTLPFQQFEIQGIGNYQQCHQSILELFNTSYCPYSQCAFNGIFLP PLQGDFGAFSAFYSVMKFLNLTSEKVSQEKVTEMMKKFCAQPWEEIKTS YAGVKEKYLSEYCFSGTYILSLLLQGYHFTADSWEHIHFIGKIQGSDAGVVT LGYMLNLTNMIPAEQPLSTPLSHST |
| SEQ ID NO: 87 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAGAACAGGACACCGGCGTGGTGCATCAGGTGGAAGAGTG CAGAGTGAAGGGCCCTGGCATCAGCAAGTTCGTGCAGAAAGTGAACG AGATCGGCATCTACCTGACCGACTGCATGGAACGGGCCAGGGAAGTG ATCCCCAGAAGCCAGCACCAGGAAACCCCCGTGTATCTGGGAGCCAC CGCCGGCATGAGACTGCTGAGAATGGAAAGCGAGGAACTGGCCGAC CGGGTGCTGGACGTGGTGGAAAGAAGCCTGAGCAACTACCCATTCGA TTTTCAAGGCGCCAGAATCATCACCGGCCAGGAAGAAGGCGCCTACG GCTGGATCACCATCAACTACCTGCTGGGCAAGTTCAGCCAGAAGAATC AGGAAACCTTCGGCGCCCTGGACCTGGGCGGAGCTTCTACCCAAGTG ACCTTCGTGCCCCAGAATCAGACCATCGAGAGCCCCGACAACGCCCT GCAGTTCCGGCTGTACGGCAAGGACTACAATGTGTACACCCACAGCT TTCTGTGCTACGGAAAGGACCAGGCTCTGTGGCAGAAGCTGGCCAAG GACATCCAGGTGGCCAGCAACGAGATCCTGCGGGACCCTTGCTTCCA CCCCGGCTACAAGAAAGTCGTGAACGTGTCCGACCTGTACAAGACCC CCTGCACCAAGAGATTCGAGATGACCCTGCCCTTCCAGCAGTTCGAG ATCCAGGGCATCGGCAATTACCAGCAGTGCCACCAGAGCATCCTGGA ACTGTTCAACACCAGCTACTGCCCCTACAGCCAGTGCGCCTTCAACG GCATCTTCCTGCCACCTCTGCAGGGGGATTTCGGCGCCTTCAGCGCC TTCTACTCCGTGATGAAGTTCCTGAACCTGACCAGCGAGAAGGTGTCC CAGGAAAAAGTGACAGAGATGATGAAGAAGTTCTGCGCCCAGCCCTG GGAGGAAATCAAGACCTCCTACGCTGGCGTGAAAGAGAAGTACCTGA GCGAGTACTGCTTCAGCGGCACCTACATCCTGAGCCTGCTGCTGCAG GGCTACCACTTCACCGCCGATAGCTGGGAGCACATCCATTTCATCGG CAAGATTCAGGGCAGCGACGCCGGCTGGACACTGGGCTACATGCTGA ATCTGACCAACATGATCCCCGCCGAGCAGCCCCTGAGCACACCTCTG AGCCACAGCACC |

EP14_T229A

| SEQ ID NO: 88 | Amino acid | TQNKALPENVKYGIVLDAGSSHTSLYIYKWPAEKENDTGVVHQVEECRVK GPGISKFVQKVNEIGIYLTDCMERAREVIPRSQHQETPVYLGATAGMRLLR MESEELADRVLDVVERSLSNYPFDFQGARIITGQEEGAYGWITINYLLGKF SQKNQETFGALDLGGASTQVTFVPQNQAIESPDNALQFRLYGKDYNVYT HSFLCYGKDQALWQKLAKDIQVASNEILRDPCFHPGYKKVVNVSDLYKTP CTKRFEMTLPFQQFEIQGIGNYQQCHQSILELFNTSYCPYSQCAFNGIFLP PLQGDFGAFSAFYSVMKFLNLTSEKVSQEKVTEMMKKFCAQPWEEIKTS YAGVKEKYLSEYCFSGTYILSLLLQGYHFTADSWEHIHFIGKIQGSDAGWT LGYMLNLTNMIPAEQPLSTPLSHST |
| SEQ ID NO: 89 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCAGGGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGAAGAAGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGGCCATCGAGAGCCCCGACAACGCCCTG CAGTTCCGGCTGTACGGCAAGGACTACAATGTGTACACCCACAGCTTT CTGTGCTACGGAAAGGACCAGGCTCTGTGGCAGAAGCTGGCCAAGGA CATCCAGGTGGCCAGCAACGAGATCCTGCGGGACCCTTGCTTCCACC CCGGCTACAAGAAAGTCGTGAACGTGTCCGACCTGTACAAGACCCCC TGCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGGATTTCGGCGCCTTCAGCGCCTTC TACTCCGTGATGAAGTTCCTGAACCTGACCAGCGAGAAGGTGTCCCA GGAAAAAGTGACAGAGATGATGAAGAAGTTCTGCGCCCAGCCCTGGG AGGAAATCAAGACCTCCTACGCTGGCGTGAAAGAGAAGTACCTGAGC GAGTACTGCTTCAGCGGCACCTACATCCTGAGCCTGCTGCTGCAGGG CTACCACTTCACCGCCGATAGCTGGGAGCACATCCATTTCATCGGCAA GATTCAGGGCAGCGACGCCGGCTGGACACTGGGCTACATGCTGAATC |

TABLE 35-continued

Sequences useful for practicing the invention.

| SEQ ID Number | Feature | Sequence |
|---|---|---|
| | | TGACCAACATGATCCCCGCCGAGCAGCCCCTGAGCACACCTCTGAGC<br>CACAGCACC |
| EP14_N292Q | | |
| SEQ ID NO: 90 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVQVSDLYKTP<br>CTKRFEMTLPFQQFEIQGIGNYQQCHQSILELFNTSYCPYSQCAFNGIFLP<br>PLQGDFGAFSAFYSVMKFLNLTSEKVSQEKVTEMMKKFCAQPWEEIKTS<br>YAGVKEKYLSEYCFSGTYILSLLLQGYHFTADSWEHIHFIGKIQGSDAGWT<br>LGYMLNLTNMIPAEQPLSTPLSHST |
| SEQ ID NO: 91 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGTGGCAGAAGCTGGCCAAGGA<br>CATCCAGGTGGCCAGCAACGAGATCCTGCGGGACCCTTGCTTCCACC<br>CCGGCTACAAGAAAGTCGTGCAGGTGTCCGACCTGTACAAGACCCCC<br>TGCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCCACCTCTGCAGGGGGATTTCGGCGCCTTCAGCGCCTTC<br>TACTCCGTGATGAAGTTCCTGAACCTGACCAGCGAGAAGGTGTCCCA<br>GGAAAAAGTGACAGAGATGATGAAGAAGTTCTGCGCCCAGCCCTGGG<br>AGGAAATCAAGACCTCCTACGCTGGCGTGAAAGAAGTACCTGAGC<br>GAGTACTGCTTCAGCGGCACCTACATCCTGAGCCTGCTGCTGCAGGG<br>CTACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGCACACCTCTGAGC<br>CACAGCACC |
| EP14_N327Q | | |
| SEQ ID NO: 92 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVNVSDLYKTP<br>CTKRFEMTLPFQQFEIQGIGNYQQCHQSILELFQTSYCPYSQCAFNGIFLP<br>PLQGDFGAFSAFYSVMKFLNLTSEKVSQEKVTEMMKKFCAQPWEEIKTS<br>YAGVKEKYLSEYCFSGTYILSLLLQGYHFTADSWEHIHFIGKIQGSDAGWT<br>LGYMLNLTNMIPAEQPLSTPLSHST |
| SEQ ID NO: 93 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGTGGCAGAAGCTGGCCAAGGA<br>CATCCAGGTGGCCAGCAACGAGATCCTGCGGGACCCTTGCTTCCACC<br>CCGGCTACAAGAAAGTCGTGAACGTGTCCGACCTGTACAAGACCCCC |

TABLE 35-continued

Sequences useful for practicing the invention.

| SEQ ID Number | Feature | Sequence |
|---|---|---|
| | | TGCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCCAGACCAGCTACTGCCCCTACAGCCAGTGCGCCTTCAACGGCA<br>TCTTCCTGCCCACCTCTGCAGGGGGATTTCGGCGCCTTCAGCGCCTTC<br>TACTCCGTGATGAAGTTCCTGAACCTGACCAGCGAGAAGGTGTCCCA<br>GGAAAAAGTGACAGAGATGATGAAGAAGTTCTGCGCCCAGCCCTGGG<br>AGGAAATCAAGACCTCCTACGCTGGCGTGAAAGAGAAGTACCTGAGC<br>GAGTACTGCTTCAGCGGCACCTACATCCTGAGCCTGCTGCTGCAGGG<br>CTACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGCACACCTCTGAGC<br>CACAGCACC |

EP14_N371Q

| SEQ ID NO: 94 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVNVSDLYKTP<br>CTKRFEMTLPFQQFEIQGIGNYQQCHQSILELFNTSYCPYSQCAFNGIFLP<br>PLQGDFGAFSAFYSVMKFLQLTSEKVSQEKVTEMMKKFCAQPWEEIKTS<br>YAGVKEKYLSEYCFSGTYILSLLLQGYHFTADSWEHIHFIGKIQGSDAGWT<br>LGYMLNLTNMIPAEQPLSTPLSHST |
| SEQ ID NO: 95 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGTGGCAGAAGCTGGCCAAGGA<br>CATCCAGGTGGCCAGCAACGAGATCCTGCGGGACCCTTGCTTCCACC<br>CCGGCTACAAGAAAGTCGTGAACGTGTCCGACCTGTACAAGACCCCC<br>TGCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCCACCTCTGCAGGGGGATTTCGGCGCCTTCAGCGCCTTC<br>TACTCCGTGATGAAGTTCCTGCAGCTGACCAGCGAGAAGGTGTCCCA<br>GGAAAAAGTGACAGAGATGATGAAGAAGTTCTGCGCCCAGCCCTGGG<br>AGGAAATCAAGACCTCCTACGCTGGCGTGAAAGAGAAGTACCTGAGC<br>GAGTACTGCTTCAGCGGCACCTACATCCTGAGCCTGCTGCTGCAGGG<br>CTACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGCACACCTCTGAGC<br>CACAGCACC |

EP14_N457Q

| SEQ ID NO: 96 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT<br>HSFLCYGKDQALWQKLAKDIQVASNEILRDPCFHPGYKKVVNVSDLYKTP<br>CTKRFEMTLPFQQFEIQGIGNYQQCHQSILELFNTSYCPYSQCAFNGIFLP<br>PLQGDFGAFSAFYSVMKFLNLTSEKVSQEKVTEMMKKFCAQPWEEIKTS<br>YAGVKEKYLSEYCFSGTYILSLLLQGYHFTADSWEHIHFIGKIQGSDAGWT<br>LGYMLQLTNMIPAEQPLSTPLSHST |
| SEQ ID NO: 97 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCATTCGAT<br>TTTCAAGGCGCCAGAATCATCACCGGCCAGGAAGAAGGCGCCTACGG |

TABLE 35-continued

Sequences useful for practicing the invention.

| SEQ ID Number | Feature | Sequence |
|---|---|---|
| | | CTGGATCACCATCAACTACCTGCTGGGCAAGTTCAGCCAGAAGAATCA<br>GGAAACCTTCGGCGCCCTGGACCTGGGCGGAGCTTCTACCCAAGTGA<br>CCTTCGTGCCCCAGAATCAGACCATCGAGAGCCCCGACAACGCCCTG<br>CAGTTCCGGCTGTACGGCAAGGACTACAATGTGTACACCCACAGCTTT<br>CTGTGCTACGGAAAGGACCAGGCTCTGTGGCAGAAGCTGGCCAAGGA<br>CATCCAGGTGGCCAGCAACGAGATCCTGCGGGACCCTTGCTTCCACC<br>CCGGCTACAAGAAAGTCGTGAACGTGTCCGACCTGTACAAGACCCCC<br>TGCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCACCTCTGCAGGGGATTTCGGCGCCTTCAGCGCCTTC<br>TACTCCGTGATGAAGTTCCTGAACCTGACCAGCGAGAAGGTGTCCCA<br>GGAAAAAGTGACAGAGATGATGAAGAAGTTCTGCGCCCAGCCCTGGG<br>AGGAAATCAAGACCTCCTACGCTGGCGTGAAAGAAGTACCTGAGC<br>GAGTACTGCTTCAGCGGCACCTACATCCTGAGCCTGCTGCTGCAGGG<br>CTACCACTTCACCGCCGATAGCTGGGAGCACATCCACTTCATCGGCAA<br>GATTCAGGGCAGCGACGCCGGCTGGACACTGGGCTACATGCTGCAG<br>CTGACCAACATGATCCCCGCCGAGCAGCCCCTGAGCACACCTCTGAG<br>CCACAGCACC |
| SEQ ID NO: 98 | plusMILrevsense primer | TGCCCTACGAGACAAACAATCAGGAAACCTTCGGCGCCCTGGACCTG<br>GGCGGAGCTTCTACCCAAGTGA |

CD39(aa39-469)

| SEQ ID NO: 99 | Amino acid | QNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKTRWFSIVPYETNNQETFGALDLGGASTQVTFVPQNQTIESPDNALQF<br>RLYGKDYNVYTHSFLCYGKDQALWQKLAKDIQVASNEILRDPCFHPGYKK<br>VVNVSDLYKTPCTKRFEMTLPFQQFEIQGIGNYQQCHQSILELFNTSYCPY<br>SQCAFNGIFLPPLQGDFGAFSAFYFVMKFLNLTSEKVSQEKVTEMMKKFC<br>AQPVVEEIKTSYAGVKEKYLSEYCFSGTYILSLLLQGYHFTADSVVEHIHFIG<br>KIQGSDAGVVTLGYMLNLTNMIPAEQPLS |
| SEQ ID NO: 100 | DNA | CAGAACAAAGCCCTGCCCGAGAACGTGAAGTACGGCATCGTGCTGGA<br>TGCCGGCAGCAGCCACACCAGCCTGTACATCTACAAGTGGCCTGCCG<br>AGAAAGAAAACGATACCGGTGTCGTGCACCAGGTGGAAGAGTGCAGA<br>GTGAAGGGCCCTGGCATCAGCAAGTTCGTGCAGAAAGTGAACGAGAT<br>CGGCATCTACCTGACCGACTGCATGGAACGGGCCAGAGAAGTGATCC<br>CCAGAAGCCAGCACCAGGAAACCCCCGTGTACCTGGGAGCCACAGC<br>CGGCATGAGACTGCTGCGGATGGAAAGCGAGGAACTGGCCGACAGA<br>GTGCTGGACGTGGTGGAAAGAAGCCTGAGCAACTACCCATTCGATTTT<br>CAAGGGGCCAGAATCATCACCGGCCAGGAAGAGGGCGCTTACGGCT<br>GGATCACCATCAACTACCTGCTGGGCAAGTTCAGCCAGAAAACCCGG<br>TGGTTCAGCATCGTGCCCTACGAGACAAACAATCAGGAAACCTTCGGA<br>GCCCTGGACCTGGGCGGAGCCTCTACCCAAGTGACCTTCGTGCCCCA<br>GAATCAGACCATCGAGAGCCCCGACAACGCCCTGCAGTTCCGGCTGT<br>ACGGCAAGGACTACAATGTGTACACCCACAGCTTTCTGTGCTACGGAA<br>AGGACCAGGCCCTGTGGCAGAAGCTGGCCAAGGACATCCAGGTGGC<br>CAGCAACGAGATCCTGCGGGACCCTTGCTTCCACCCCGGCTACAAGA<br>AAGTCGTGAACGTGTCCGACCTGTACAAGACCCCCTGCACCAAGAGA<br>TTCGAGATGACCCTGCCCTTCCAGCAGTTCGAGATCCAGGGCATCGG<br>CAACTACCAGCAGTGCCACCAGAGCATCCTGGAACTGTTCAACACCA<br>GCTACTGCCCCTACAGCCAGTGCGCCTTCAACGGCATCTTCCTGCCA<br>CCTCTGCAGGGGACTTCGGCGCTTTCAGCGCCTTCTACTTCGTGAT<br>GAAGTTCCTGAACCTGACCAGCGAGAAGGTGTCCCAGGAAAAAGTGA<br>CAGAGATGATGAAGAAGTTCTGCGCCCAGCCCTGGGAGGAAATCAAG<br>ACCTCCTACGCTGGCGTGAAAGAAGTACCTGAGCGAGTACTGCTT<br>CAGCGGTACCTACATCCTGAGCCTGCTGCTGCAGGGCTACCACTTCA<br>CCGCCGATAGCTGGGAGCACATCCACTTCATCGGCAAGATTCAGGGC<br>AGCGACGCCGGCTGGACACTGGGCTACATGCTGAATCTGACCAACAT<br>GATCCCCGCCGAGCAGCCCCTGAGC |

CD39(aa46-476)

| SEQ ID NO: 101 | Amino acid | NVKYGIVLDAGSSHTSLYIYKWPAEKENDTGVVHQVEECRVKGPGISKFV<br>QKVNEIGIYLTDCMERAREVIPRSQHQETPVYLGATAGMRLLRMESEELA<br>DRVLDVVERSLSNYPFDFQGARIITGQEEGAYGWITINYLLGKFSQKTRW<br>FSNPYETNNQETFGALDLGGASTQVTFVPQNQTESPDNALQFRLYGKD<br>YNVYTHSFLCYGKDQALWQKLAKDIQVASNEILRDPCFHPGYKKVVNVSD<br>LYKTPCTKRFEMTLPFQQFEIQGIGNYQQCHQSILELFNTSYCPYSQCAF<br>NGIFLPPLQGDFGAFSAFYFVMKFLNLTSEKVSQEKVTEMMKKFCAQPW<br>EEIKTSYAGVKEKYLSEYCFSGTYILSLLLQGYHFTADSWEHIHFIGKIQGS<br>DAGVVTLGYMLNLTNMIPAEQPLSTPLSHST |

TABLE 35-continued

Sequences useful for practicing the invention.

| SEQ ID Number | Feature | Sequence |
|---|---|---|
| SEQ ID NO: 102 | DNA | AACGTGAAGTACGGCATCGTGCTGGATGCCGGCAGCAGCCACACCAG<br>CCTGTACATCTACAAGTGGCCTGCCGAGAAAGAAAACGATACCGGTGT<br>CGTGCACCAGGTGGAAGAGTGCAGAGTGAAGGGCCCTGGCATCAGC<br>AAGTTCGTGCAGAAAGTGAACGAGATCGGCATCTACCTGACCGACTG<br>CATGGAACGGGCCAGAGAAGTGATCCCCAGAAGCCAGCACCAGGAAA<br>CCCCCGTGTACCTGGGAGCCACAGCCGGCATGAGACTGCTGCGGAT<br>GGAAAGCGAGGAACTGGCCGACAGAGTGCTGGACGTGGTGGAAAGA<br>AGCCTGAGCAACTACCCATTCGATTTTCAAGGGGCCAGAATCATCACC<br>GGCCAGGAAGAGGGCGCTTACGGCTGGATCACCATCAACTACCTGCT<br>GGGCAAGTTCAGCCAGAAACCCGGTGGTTCAGCATCGTGCCCTACG<br>AGACAAACAATCAGGAAACCTTCGGAGCCCTGGACCTGGGCGGAGCC<br>TCTACCCAAGTGACCTTCGTGCCCCAGAATCAGACCATCGAGAGCCC<br>CGACAACGCCCTGCAGTTCCGGCTGTACGGCAAGGACTACAATGTGT<br>ACACCCACAGCTTTCTGTGCTACGGAAAGGACCAGGCCCTGTGGCAG<br>AAGCTGGCCAAGGACATCCAGGTGGCCAGCAACGAGATCCTGCGGG<br>ACCCTTGCTTCCACCCCGGCTACAAGAAAGTCGTGAACGTGTCCGAC<br>CTGTACAAGACCCCCTGCACCAAGAGATTCGAGATGACCCTGCCCTTC<br>CAGCAGTTCGAGATCCAGGGCATCGGCAACTACCAGCAGTGCCACCA<br>GAGCATCCTGGAACTGTTCAACACCAGCTACTGCCCCTACAGCCAGT<br>GCGCCTTCAACGGCATCTTCCTGCCACCTCTGCAGGGGGACTTCGGC<br>GCTTTCAGCGCCTTCTACTTCGTGATGAAGTTCCTGAACCTGACCAGC<br>GAGAAGGTGTCCCAGGAAAAAGTGACAGAGATGATGAAGAAGTTCTG<br>CGCCCAGCCCTGGGAGGAAATCAAGACCTCCTACGCTGGCGTGAAAG<br>AGAAGTACCTGAGCGAGTACTGCTTCAGCGGTACCTACATCCTGAGC<br>CTGCTGCTGCAGGGCTACCACTTCACCGCCGATAGCTGGGAGCACAT<br>CCACTTCATCGGCAAGATTCAGGGCAGCGACGCCGGCTGGACACTGG<br>GCTACATGCTGAATCTGACCAACATGATCCCCGCCGAGCAGCCCCTG<br>AGCACACCTCTGTCTCACAGCACC |

CD39(aa46-461)

| SEQ ID NO: 103 | Amino acid | NVKYGIVLDAGSSHTSLYIYKVVPAEKENDTGVVHQVEECRVKGPGISKFV<br>QKVNEIGIYLTDCMERAREVIPRSQHQETPVYLGATAGMRLLRMESEELA<br>DRVLDVVERSLSNYPFDFQGARIITGQEEGAYGWITINYLLGKFSQKTRW<br>FSNPYETNNQETFGALDLGGASTQVTFVPQNQTESPDNALQFRLYGKD<br>YNVYTHSFLCYGKDQALWQKLAKDIQVASNEILRDPCFHPGYKKVVNVSD<br>LYKTPCTKRFEMTLPFQQFEIQGIGNYQQCHQSILELFNTSYCPYSQCAF<br>NGIFLPPLQGDFGAFSAFYFVMKFLNLTSEKVSQEKVTEMMKKFCAQPW<br>EEIKTSYAGVKEKYLSEYCFSGTYILSLLLQGYHFTADSWEHIHFIGKIQGS<br>DAGWTLGYMLNLTNM |

| SEQ ID NO: 104 | DNA | AACGTGAAGTACGGCATCGTGCTGGATGCCGGCAGCAGCCACACCAG<br>CCTGTACATCTACAAGTGGCCTGCCGAGAAAGAAAACGATACCGGTGT<br>CGTGCACCAGGTGGAAGAGTGCAGAGTGAAGGGCCCTGGCATCAGC<br>AAGTTCGTGCAGAAAGTGAACGAGATCGGCATCTACCTGACCGACTG<br>CATGGAACGGGCCAGAGAAGTGATCCCCAGAAGCCAGCACCAGGAAA<br>CCCCCGTGTACCTGGGAGCCACAGCCGGCATGAGACTGCTGCGGAT<br>GGAAAGCGAGGAACTGGCCGACAGAGTGCTGGACGTGGTGGAAAGA<br>AGCCTGAGCAACTACCCATTCGATTTTCAAGGGGCCAGAATCATCACC<br>GGCCAGGAAGAGGGCGCTTACGGCTGGATCACCATCAACTACCTGCT<br>GGGCAAGTTCAGCCAGAAACCCGGTGGTTCAGCATCGTGCCCTACG<br>AGACAAACAATCAGGAAACCTTCGGAGCCCTGGACCTGGGCGGAGCC<br>TCTACCCAAGTGACCTTCGTGCCCCAGAATCAGACCATCGAGAGCCC<br>CGACAACGCCCTGCAGTTCCGGCTGTACGGCAAGGACTACAATGTGT<br>ACACCCACAGCTTTCTGTGCTACGGAAAGGACCAGGCCCTGTGGCAG<br>AAGCTGGCCAAGGACATCCAGGTGGCCAGCAACGAGATCCTGCGGG<br>ACCCTTGCTTCCACCCCGGCTACAAGAAAGTCGTGAACGTGTCCGAC<br>CTGTACAAGACCCCCTGCACCAAGAGATTCGAGATGACCCTGCCCTTC<br>CAGCAGTTCGAGATCCAGGGCATCGGCAACTACCAGCAGTGCCACCA<br>GAGCATCCTGGAACTGTTCAACACCAGCTACTGCCCCTACAGCCAGT<br>GCGCCTTCAACGGCATCTTCCTGCCACCTCTGCAGGGGGACTTCGGC<br>GCTTTCAGCGCCTTCTACTTCGTGATGAAGTTCCTGAACCTGACCAGC<br>GAGAAGGTGTCCCAGGAAAAAGTGACAGAGATGATGAAGAAGTTCTG<br>CGCCCAGCCCTGGGAGGAAATCAAGACCTCCTACGCTGGCGTGAAAG<br>AGAAGTACCTGAGCGAGTACTGCTTCAGCGGTACCTACATCCTGAGC<br>CTGCTGCTGCAGGGCTACCACTTCACCGCCGATAGCTGGGAGCACAT<br>CCACTTCATCGGCAAGATTCAGGGCAGCGACGCCGGCTGGACACTGG<br>GCTACATGCTGAATCTGACCAACATG |

CD39(aa46-461)_dMIL(193-204)

| SEQ ID NO: 105 | Amino acid | NVKYGIVLDAGSSHTSLYIYKVVPAEKENDTGVVHQVEECRVKGPGISKFV<br>QKVNEIGIYLTDCMERAREVIPRSQHQETPVYLGATAGMRLLRMESEELA |

TABLE 35-continued

Sequences useful for practicing the invention.

| SEQ ID Number | Feature | Sequence |
|---|---|---|
| | | DRVLDVVERSLSNYPFDFQGARMTGQEEGAYGWITINYLLGKFSQKNQET FGALDLGGASTQVTFVPQNQTESPDNALQFRLYGKDYNVYTHSFLCYGK DQALWQKLAKDIQVASNEILRDPCFHPGYKKVVNVSDLYKTPCTKRFEMT LPFQQFEIQGIGNYQQCHQSILELFNTSYCPYSQCAFNGIFLPPLQGDFGA FSAFYFVMKFLNLTSEKVSQEKVTEMMKKFCAQPWEEIKTSYAGVKEKYL SEYCFSGTYILSLLLQGYHFTADSWEHIHFIGKIQGSDAGVVTLGYMLNLTN M |
| SEQ ID NO: 106 | DNA | AACGTGAAGTACGGCATCGTGCTGGATGCCGGCAGCAGCCACACCAG CCTGTACATCTACAAGTGGCCTGCCGAGAAAGAAAACGATACCGGTGT CGTGCACCAGGTGGAAGAGTGCAGAGTGAAGGGCCCTGGCATCAGC AAGTTCGTGCAGAAAGTGAACGAGATCGGCATCTACCTGACCGACTG CATGGAACGGGCCAGAGAAGTGATCCCCAGAAGCCAGCACCAGGAAA CCCCCGTGTACCTGGGAGCCACAGCCGGCATGAGACTGCTGCGGAT GGAAAGCGAGGAACTGGCCGACAGAGTGCTGGACGTGGTGGAAAGA AGCCTGAGCAACTACCCATTCGATTTTCAAGGGGCCAGAATCATCACC GGCCAGGAAGAGGGCGCTTACGGCTGGATCACCATCAACTACCTGCT GGGCAAGTTCAGCCAGAAAAATCAGGAAACCTTCGGAGCCCTGGACC TGGGCGGAGCCTCTACCCAAGTGACCTTCGTGCCCCAGAATCAGACC ATCGAGAGCCCCGACAACGCCCTGCAGTTCCGGCTGTACGGCAAGGA CTACAATGTGTACACCCACAGCTTTCTGTGCTACGGAAAGGACCAGGC CCTGTGGCAGAAGCTGGCCAAGGACATCCAGGTGGCCAGCAACGAG ATCCTGCGGGACCCTTGCTTCCACCCCGGCTACAAGAAAGTCGTGAA CGTGTCCGACCTGTACAAGACCCCCTGCACCAAGAGATTCGAGATGA CCCTGCCCTTCCAGCAGTTCGAGATCCAGGGCATCGGCAACTACCAG CAGTGCCACCAGAGCATCCTGGAACTGTTCAACACCAGCTACTGCCCC CTACAGCCAGTGCGCCTTCAACGGCATCTTCCTGCCACCTCTGCAGG GGGACTTCGGCGCTTTCAGCGCCTTCTACTTCGTGATGAAGTTCCTGA ACCTGACCAGCGAGAAGGTGTCCCAGGAAAAAGTGACAGAGATGATG AAGAAGTTCTGCGCCCAGCCCTGGGAGGAAATCAAGACCTCCTACGC TGGCGTGAAAGAGAAGTACCTGAGCGAGTACTGCTTCAGCGGTACCT ACATCCTGAGCCTGCTGCTGCAGGGCTACCACTTCACCGCCGATAGC TGGGAGCACATCCACTTCATCGGCAAGATTCAGGGCAGCGACGCCGG CTGGACACTGGGCTACATGCTGAATCTGACCAACATG |

CD39(aa46-461)_delta cys1

| SEQ ID NO: 107 | Amino acid | NVKYGIVLDAGSSHTSLYIYKVVPAEKENDTGVVHQVEEARVKGPGISKFV QKVNEIGIYLTDAMERAREVIPRSQHQETPVYLGATAGMRLLRMESEELA DRVLDVVERSLSNYPFDFQGARIITGQEEGAYGWITINYLLGKFSQKTRW FSNPYETNNQETFGALDLGGASTQVTFVPQNQTESPDNALQFRLYGKD YNVYTHSFLCYGKDQALWQKLAKDIQVASNEILRDPCFHPGYKKVVNVSD LYKTPCTKRFEMTLPFQQFEIQGIGNYQQCHQSILELFNTSYCPYSQCAF NGIFLPPLQGDFGAFSAFYFVMKFLNLTSEKVSQEKVTEMMKKFCAQPW EEIKTSYAGVKEKYLSEYCFSGTYILSLLLQGYHFTADSWEHIHFIGKIQGS DAGWTLGYMLNLTNM |
| SEQ ID NO: 108 | DNA | AACGTGAAGTACGGCATCGTGCTGGATGCCGGCAGCAGCCACACCAG CCTGTACATCTACAAGTGGCCTGCCGAGAAAGAAAACGATACCGGTGT CGTGCACCAGGTGGAAGAGGCCAGAGTGAAGGGCCCTGGCATCAGC AAGTTCGTGCAGAAAGTGAACGAGATCGGCATCTACCTGACCGACGC CATGGAACGGGCCAGAGAAGTGATCCCCAGAAGCCAGCACCAGGAAA CCCCCGTGTACCTGGGAGCCACAGCCGGCATGAGACTGCTGCGGAT GGAAAGCGAGGAACTGGCCGACAGAGTGCTGGACGTGGTGGAAAGA AGCCTGAGCAACTACCCATTCGATTTTCAAGGGGCCAGAATCATCACC GGCCAGGAAGAGGGCGCTTACGGCTGGATCACCATCAACTACCTGCT GGGCAAGTTCAGCCAGAAAACCCGGTGGTTCAGCATCGTGCCCTACG AGACAAACAATCAGGAAACCTTCGGAGCCCTGGACCTGGGCGGAGCC TCTACCCAAGTGACCTTCGTGCCCCAGAATCAGACCATCGAGAGCCC CGACAACGCCCTGCAGTTCCGGCTGTACGGCAAGGACTACAATGTGT ACACCCACAGCTTTCTGTGCTACGGAAAGGACCAGGCCCTGTGGCAG AAGCTGGCCAAGGACATCCAGGTGGCCAGCAACGAGATCCTGCGGG ACCCTTGCTTCCACCCCGGCTACAAGAAAGTCGTGAACGTGTCCGAC CTGTACAAGACCCCCTGCACCAAGAGATTCGAGATGACCCTGCCCTTC CAGCAGTTCGAGATCCAGGGCATCGGCAACTACCAGCAGTGCCACCA GAGCATCCTGGAACTGTTCAACACCAGCTACTGCCCCTACAGCCAGT GCGCCTTCAACGGCATCTTCCTGCCACCTCTGCAGGGGGACTTCGGC GCTTTCAGCGCCTTCTACTTCGTGATGAAGTTCCTGAACCTGACCAGC GAGAAGGTGTCCCAGGAAAAAGTGACAGAGATGATGAAGAAGTTCTG |

TABLE 35-continued

Sequences useful for practicing the invention.

| SEQ ID Number | Feature | Sequence |
|---|---|---|
| | | CGCCCAGCCCTGGGAGGAAATCAAGACCTCCTACGCTGGCGTGAAAG AGAAGTACCTGAGCGAGTACTGCTTCAGCGGTACCTACATCCTGAGC CTGCTGCTGCAGGGCTACCACTTCACCGCCGATAGCTGGGAGCACAT CCACTTCATCGGCAAGATTCAGGGCAGCGACGCCGGCTGGACACTGG GCTACATGCTGAATCTGACCAACATG |

CD39(aa46-461)_delta cys2

| SEQ ID NO: 109 | Amino acid | NVKYGIVLDAGSSHTSLYIYKVVPAEKENDTGVVHQVEECRVKGPGISKFV QKVNEIGIYLTDCMERAREVIPRSQHQETPVYLGATAGMRLLRMESEELA DRVLDVVERSLSNYPFDFQGARIITGQEEGAYGWITINYLLGKFSQKTRW FSIVPYETNNQETFGALDLGGASTQVTFVPQNQTESPDNALQFRLYGKD YNVYTHSFLCYGKDQALWQKLAKDIQVASNEILRDPAFHPGYKKVVNVSD LYKTPCTKRFEMTLPFQQFEIQGIGNYQQAHQSILELFNTSYCPYSQCAFN GIFLPPLQGDFGAFSAFYFVMKFLNLTSEKVSQEKVTEMMKKFCAQPWE EIKTSYAGVKEKYLSEYCFSGTYILSLLLQGYHFTADSWEHIHFIGKIQGSD AGWTLGYMLNLTNM |
| SEQ ID NO: 110 | DNA | AACGTGAAGTACGGCATCGTGCTGGATGCCGGCAGCAGCCACACCAG CCTGTACATCTACAAGTGGCCTGCCGAGAAAGAAAACGATACCGGTGT CGTGCACCAGGTGGAAGAGTGCAGAGTGAAGGGCCCTGGCATCAGC AAGTTCGTGCAGAAAGTGAACGAGATCGGCATCTACCTGACCGACTG CATGGAACGGGCCAGAGAAGTGATCCCCAGAAGCCAGCACCAGGAAA CCCCCGTGTACCTGGGAGCCACAGCCGGCATGAGACTGCTGCGGAT GGAAAGCGAGGAACTGGCCGACAGAGTGCTGGACGTGGTGGAAAGA AGCCTGAGCAACTACCCATTCGATTTTCAAGGGGCCAGAATCATCACC GGCCAGGAAGAGGGCGCTTACGGCTGGATCACCATCAACTACCTGCT GGGCAAGTTCAGCCAGAAAACCCGGTGGTTCAGCATCGTGCCCTACG AGACAAACAATCAGGAAACCTTCGGAGCCCTGGACCTGGGCGGAGCC TCTACCCAAGTGACCTTCGTGCCCCAGAATCAGACCATCGAGAGCCC CGACAACGCCCTGCAGTTCCGGCTGTACGGCAAGGACTACAATGTGT ACACCCACAGCTTTCTGTGCTACGGAAAGGACCAGGCCCTGTGGCAG AAGCTGGCCAAGGACATCCAGGTGGCCAGCAACGAGATCCTGCGGG ACCCTGCCTTCCACCCCGGCTACAAGAAAGTCGTGAACGTGTCCGAC CTGTACAAGACCCCCTGCACCAAGAGATTCGAGATGACCCTGCCCTTC CAGCAGTTCGAGATCCAGGGCATCGGCAACTACCAGCAGGCCCACCA GAGCATCCTGGAACTGTTCAACACCAGCTACTGCCCCTACAGCCAGT GCGCCTTCAACGGCATCTTCCTGCCACCTCTGCAGGGGGACTTCGGC GCTTTCAGCGCCTTCTACTTCGTGATGAAGTTCCTGAACCTGACCAGC GAGAAGGTGTCCCAGGAAAAAGTGACAGAGATGATGAAGAAGTTCTG CGCCCAGCCCTGGGAGGAAATCAAGACCTCCTACGCTGGCGTGAAAG AGAAGTACCTGAGCGAGTACTGCTTCAGCGGTACCTACATCCTGAGC CTGCTGCTGCAGGGCTACCACTTCACCGCCGATAGCTGGGAGCACAT CCACTTCATCGGCAAGATTCAGGGCAGCGACGCCGGCTGGACACTGG GCTACATGCTGAATCTGACCAACATG |

CD39(aa46-461)_delta cys3

| SEQ ID NO: 111 | Amino acid | NVKYGIVLDAGSSHTSLYIYKVVPAEKENDTGVVHQVEECRVKGPGISKFV QKVNEIGIYLTDCMERAREVIPRSQHQETPVYLGATAGMRLLRMESEELA DRVLDVVERSLSNYPFDFQGARIITGQEEGAYGWITINYLLGKFSQKTRW FSIVPYETNNQETFGALDLGGASTQVTFVPQNQTIESPDNALQFRLYGKD YNVYTHSFLAYGKDQALWQKLAKDIQVASNEILRDPCFHPGYKKVVNVSD LYKTPATKRFEMTLPFQQFEIQGIGNYQQCHQSILELFNTSYCPYSQCAFN GIFLPPLQGDFGAFSAFYFVMKFLNLTSEKVSQEKVTEMMKKFCAQPWE EIKTSYAGVKEKYLSEYCFSGTYILSLLLQGYHFTADSWEHIHFIGKIQGSD AGWTLGYMLNLTNM |
| SEQ ID NO: 112 | DNA | AACGTGAAGTACGGCATCGTGCTGGATGCCGGCAGCAGCCACACCAG CCTGTACATCTACAAGTGGCCTGCCGAGAAAGAAAACGATACCGGTGT CGTGCACCAGGTGGAAGAGTGCAGAGTGAAGGGCCCTGGCATCAGC AAGTTCGTGCAGAAAGTGAACGAGATCGGCATCTACCTGACCGACTG CATGGAACGGGCCAGAGAAGTGATCCCCAGAAGCCAGCACCAGGAAA CCCCCGTGTACCTGGGAGCCACAGCCGGCATGAGACTGCTGCGGAT GGAAAGCGAGGAACTGGCCGACAGAGTGCTGGACGTGGTGGAAAGA AGCCTGAGCAACTACCCATTCGATTTTCAAGGGCCAGAATCATCACC GGCCAGGAAGAGGGCGCTTACGGCTGGATCACCATCAACTACCTGCT GGGCAAGTTCAGCCAGAAAACCCGGTGGTTCAGCATCGTGCCCTACG AGACAAACAATCAGGAAACCTTCGGAGCCCTGGACCTGGGCGGAGCC TCTACCCAAGTGACCTTCGTGCCCCAGAATCAGACCATCGAGAGCCC CGACAACGCCCTGCAGTTCCGGCTGTACGGCAAGGACTACAATGTGT |

TABLE 35-continued

Sequences useful for practicing the invention.

| SEQ ID Number | Feature | Sequence |
|---|---|---|
| | | ACACCCACAGCTTTCTGGCCTACGGAAAGGACCAGGCCCTGTGGCAG<br>AAGCTGGCCAAGGACATCCAGGTGGCCAGCAACGAGATCCTGCGGG<br>ACCCTTGCTTCCACCCCGGCTACAAGAAAGTCGTGAACGTGTCCGAC<br>CTGTACAAGACCCCCGCCACCAAGAGATTCGAGATGACCCTGCCCTT<br>CCAGCAGTTCGAGATCCAGGGCATCGGCAACTACCAGCAGTGCCACC<br>AGAGCATCCTGGAACTGTTCAACACCAGCTACGCCCCTACAGCCAGT<br>GCGCCTTCAACGGCATCTTCCTGCCACCTCTGCAGGGGGACTTCGGC<br>GCTTTCAGCGCCTTCTACTTCGTGATGAAGTTCCTGAACCTGACCAGC<br>GAGAAGGTGTCCCAGGAAAAAGTGACAGAGATGATGAAGAAGTTCTG<br>CGCCCAGCCCTGGGAGGAAATCAAGACCTCCTACGCTGGCGTGAAAG<br>AGAAGTACCTGAGCGAGTACTGCTTCAGCGGTACCTACATCCTGAGC<br>CTGCTGCTGCAGGGCTACCACTTCACCGCCGATAGCTGGGAGCACAT<br>CCACTTCATCGGCAAGATTCAGGGCAGCGACGCCGGCTGGACACTGG<br>GCTACATGCTGAATCTGACCAACATG |
| CD39(aa46-461)_delta cys4 | | |
| SEQ ID NO: 113 | Amino acid | NVKYGIVLDAGSSHTSLYIYKVVPAEKENDTGVVHQVEECRVKGPGISKFV<br>QKVNEIGIYLTDCMERAREVIPRSHQETPVYLGATAGMRLLRMESEELA<br>DRVLDVVERSLSNYPFDFQGARIITGQEEGAYGWITINYLLGKFSQKTRW<br>FSIVPYETNNQETFGALDLGGASTQVTFVPQNQTIESPDNALQFRLYGKD<br>YNVYTHSFLCYGKDQALWQKLAKDIQVASNEILRDPCFHPGYKKVVNVSD<br>LYKTPCTKRFEMTLPFQQFEIQGIGNYQQCHQSILELFNTSYAPYSQAAFN<br>GIFLPPLQGDFGAFSAFYFVMKFLNLTSEKVSQEKVTEMMKKFCAQPWE<br>EIKTSYAGVKEKYLSEYCFSGTYILSLLLQGYHFTADSWEHIHFIGKIQGSD<br>AGWTLGYMLNLTNM |
| SEQ ID NO: 114 | DNA | AACGTGAAGTACGGCATCGTGCTGGATGCCGGCAGCAGCCACACCAG<br>CCTGTACATCTACAAGTGGCCTGCCGAGAAAGAAAACGATACCGGTGT<br>CGTGCACCAGGTGGAAGAGTGCAGAGTGAAGGGCCCTGGCATCAGC<br>AAGTTCGTGCAGAAAGTGAACGAGATCGGCATCTACCTGACCGACTG<br>CATGGAACGGGCCAGAGAAGTGATCCCCAGAAGCCAGCACCAGGAAA<br>CCCCCGTGTACCTGGGAGCCACAGCCGGCATGAGACTGCTGCGCGAT<br>GGAAAGCGAGGAACTGGCCGACAGAGTGCTGGACGTGGTGGAAAGA<br>AGCCTGAGCAACTACCCATTCGATTTTCAAGGGGCCAGAATCATCACC<br>GGCCAGGAAGAGGGCGCTTACGGCTGGATCACCATCAACTACCTGCT<br>GGGCAAGTTCAGCCAGAAAACCCGGTGGTTCAGCATCGTGCCCTACG<br>AGACAAACAATCAGGAAACCTTCGGAGCCCTGGACCTGGGCGGAGCC<br>TCTACCCAAGTGACCTTCGTGCCCCAGAATCAGACCATCGAGAGCCC<br>CGACAACGCCCTGCAGTTCCGGCTGTACGGCAAGGACTACAATGTGT<br>ACACCCACAGCTTTCTGTGCTACGGAAAGGACCAGGCCCTGTGGCAG<br>AAGCTGGCCAAGGACATCCAGGTGGCCAGCAACGAGATCCTGCGGG<br>ACCCTTGCTTCCACCCCGGCTACAAGAAAGTCGTGAACGTGTCCGAC<br>CTGTACAAGACCCCCTGCACCAAGAGATTCGAGATGACCCTGCCCTTC<br>CAGCAGTTCGAGATCCAGGGCATCGGCAACTACCAGCAGTGCCACCA<br>GAGCATCCTGGAACTGTTCAACACCAGCTACGCCCCCTACAGCCAGG<br>CCGCCTTCAACGGCATCTTCCTGCCACCTCTGCAGGGGGACTTCGGC<br>GCTTTCAGCGCCTTCTACTTCGTGATGAAGTTCCTGAACCTGACCAGC<br>GAGAAGGTGTCCCAGGAAAAAGTGACAGAGATGATGAAGAAGTTCTG<br>CGCCCAGCCCTGGGAGGAAATCAAGACCTCCTACGCTGGCGTGAAAG<br>AGAAGTACCTGAGCGAGTACTGCTTCAGCGGTACCTACATCCTGAGC<br>CTGCTGCTGCAGGGCTACCACTTCACCGCCGATAGCTGGGAGCACAT<br>CCACTTCATCGGCAAGATTCAGGGCAGCGACGCCGGCTGGACACTGG<br>GCTACATGCTGAATCTGACCAACATG |
| CD39(aa46-461)_delta cys5 | | |
| SEQ ID NO: 115 | Amino acid | NVKYGIVLDAGSSHTSLYIYKVVPAEKENDTGVVHQVEECRVKGPGISKFV<br>QKVNEIGIYLTDCMERAREVIPRSHQETPVYLGATAGMRLLRMESEELA<br>DRVLDVVERSLSNYPFDFQGARIITGQEEGAYGWITINYLLGKFSQKTRW<br>FSIVPYETNNQETFGALDLGGASTQVTFVPQNQTIESPDNALQFRLYGKD<br>YNVYTHSFLCYGKDQALWQKLAKDIQVASNEILRDPCFHPGYKKVVNVSD<br>LYKTPCTKRFEMTLPFQQFEIQGIGNYQQCHQSILELFNTSYCPYSQCAF<br>NGIFLPPLQGDFGAFSAFYFVMKFLNLTSEKVSQEKVTEMMKKFAAQPW<br>EEIKTSYAGVKEKYLSEYAFSGTYILSLLLQGYHFTADSWEHIHFIGKIQGS<br>DAGWTLGYMLNLTNM |
| SEQ ID NO: 116 | DNA | AACGTGAAGTACGGCATCGTGCTGGATGCCGGCAGCAGCCACACCAG<br>CCTGTACATCTACAAGTGGCCTGCCGAGAAAGAAAACGATACCGGTGT<br>CGTGCACCAGGTGGAAGAGTGCAGAGTGAAGGGCCCTGGCATCAGC<br>AAGTTCGTGCAGAAAGTGAACGAGATCGGCATCTACCTGACCGACTG |

TABLE 35-continued

Sequences useful for practicing the invention.

| SEQ ID Number | Feature | Sequence |
|---|---|---|
| | | CATGGAACGGGCCAGAGAAGTGATCCCCAGAAGCCAGCACCAGGAAA<br>CCCCCGTGTACCTGGGAGCCACAGCCGGCATGAGACTGCTGCGGAT<br>GGAAAGCGAGGAACTGGCCGACAGAGTGCTGGACGTGGTGGAAAGA<br>AGCCTGAGCAACTACCCATTCGATTTTCAAGGGGCCAGAATCATCACC<br>GGCCAGGAAGAGGGCGCTTACGGCTGGATCACCATCAACTACCTGCT<br>GGGCAAGTTCAGCCAGAAAACCCGGTGGTTCAGCATCGTGCCCTACG<br>AGACAAACAATCAGGAAACCTTCGGAGCCCTGGACCTGGGCGGAGCC<br>TCTACCCAAGTGACCTTCGTGCCCCAGAATCAGACCATCGAGAGCCC<br>CGACAACGCCCTGCAGTTCCGGCTGTACGGCAAGGACTACAATGTGT<br>ACACCCACAGCTTTCTGTGCTACGGAAAGGACCAGGCCCTGTGGCAG<br>AAGCTGGCCAAGGACATCCAGGTGGCCAGCAACGAGATCCTGCGGG<br>ACCCCTTGCTTCCACCCCGGCTACAAGAAAGTCGTGAACGTGTCCGAC<br>CTGTACAAGACCCCCTGCACCAAGAGATTCGAGATGACCCTGCCCTTC<br>CAGCAGTTCGAGATCCAGGGCATCGGCAACTACCAGCAGTGCCACCA<br>GAGCATCCTGGAACTGTTCAACACCAGCTACTGCCCCTACAGCCAGT<br>GCGCCTTCAACGGCATCTTCCTGCCACCTCTGCAGGGGGACTTCGGC<br>GCTTTCAGCGCCTTCTACTTCGTGATGAAGTTCCTGAACCTGACCAGC<br>GAGAAGGTGTCCCAGGAAAAAGTGACAGAGATGATGAAGAAGTTCGC<br>CGCCCAGCCCTGGGAGGAAATCAAGACCTCCTACGCTGGCGTGAAAG<br>AGAAGTACCTGAGCGAGTACGCCTTCAGCGGTACCTACATCCTGAGC<br>CTGCTGCTGCAGGGCTACCACTTCACCGCCGATAGCTGGGAGCACAT<br>CCACTTCATCGGCAAGATTCAGGGCAGCGACGCCGGCTGGACACTGG<br>GCTACATGCTGAATCTGACCAACATG |
| CD39(aa46-461)_dMIL(193-204)_delta cys1 | | |
| SEQ ID NO: 117 | Amino acid | NVKYGIVLDAGSSHTSLYIYKVVPAEKENDTGVVHQVEEARVKGPGISKFV<br>QKVNEIGIYLTDAMERAREVIPRSQHQETPVYLGATAGMRLLRMESEELA<br>DRVLDVVERSLSNYPFDFQGARIITGQEEGAYGWITINYLLGKFSQKNQET<br>FGALDLGGASTQVTFVPQNQTIESPDNALQFRLYGKDYNVYTHSFLCYGK<br>DQALWQKLAKDIQVASNEILRDPCFHPGYKKVVNVSDLYKTPCTKRFEMT<br>LPFQQFEIQGIGNYQQCHQSILELFNTSYCPYSQCAFNGIFLPPLQGDFGA<br>FSAFYFVMKFLNLTSEKVSQEKVTEMMKKFCAQPWEEIKTSYAGVKEKYL<br>SEYCFSGTYILSLLLQGYHFTADSWEHIHFIGKIQGSDAGWTLGYMLNLTN<br>M |
| SEQ ID NO: 118 | DNA | AACGTGAAGTACGGCATCGTGCTGGATGCCGGCAGCAGCCACACCAG<br>CCTGTACATCTACAAGGTGGCCTGCCGAGAAAGAAAACGATACCGGTGT<br>CGTGCACCAGGTGGAAGAGGCCAGAGTGAAGGGCCCTGGCATCAGC<br>AAGTTCGTGCAGAAAGTGAACGAGATCGGCATCTACCTGACCGACGC<br>CATGGAACGGGCCAGAGAAGTGATCCCCAGAAGCCAGCACCAGGAAA<br>CCCCCGTGTACCTGGGAGCCACAGCCGGCATGAGACTGCTGCGGAT<br>GGAAAGCGAGGAACTGGCCGACAGAGTGCTGGACGTGGTGGAAAGA<br>AGCCTGAGCAACTACCCATTCGATTTTCAAGGGGCCAGAATCATCACC<br>GGCCAGGAAGAGGGCGCTTACGGCTGGATCACCATCAACTACCTGCT<br>GGGCAAGTTCAGCCAGAAAAATCAGGAAACCTTCGGAGCCCTGGACC<br>TGGGCGGAGCCTCTACCCAAGTGACCTTCGTGCCCCAGAATCAGACC<br>ATCGAGAGCCCCGACAACGCCCTGCAGTTCCGGCTGTACGGCAAGGA<br>CTACAATGTGTACACCCACAGCTTTCTGTGCTACGGAAAGGACCAGGC<br>CCTGTGGCAGAAGCTGGCCAAGGACATCCAGGTGGCCAGCAACGAG<br>ATCCTGCGGGACCCTTGCTTCCACCCCGGCTACAAGAAAGTCGTGAA<br>CGTGTCCGACCTGTACAAGACCCCCTGCACCAAGAGATTCGAGATGA<br>CCCTGCCCTTCCAGCAGTTCGAGATCCAGGGCATCGGCAACTACCAG<br>CAGTGCCACCAGAGCATCCTGGAACTGTTCAACACCAGCTACTGCCCC<br>TACAGCCAGTGCGCCTTCAACGGCATCTTCCTGCCACCTCTGCAGG<br>GGGACTTCGGCGCTTTCAGCGCCTTCTACTTCGTGATGAAGTTCCTGA<br>ACCTGACCAGCGAGAAGGTGTCCCAGGAAAAAGTGACAGAGATGATG<br>AAGAAGTTCTGCGCCCAGCCCTGGGAGGAAATCAAGACCTCCTACGC<br>TGGCGTGAAAGAGAAGTACCTGAGCGAGTACTGCTTCAGCGGTACCT<br>ACATCCTGAGCCTGCTGCTGCAGGGCTACCACTTCACCGCCGATAGC<br>TGGGAGCACATCCACTTCATCGGCAAGATTCAGGGCAGCGACGCCGG<br>CTGGACACTGGGCTACATGCTGAATCTGACCAACATG |
| CD39(aa46-461)_dMIL(193-204)_delta cys2 | | |
| SEQ ID NO: 119 | Amino acid | NVKYGIVLDAGSSHTSLYIYKVVPAEKENDTGVVHQVEECRVKGPGISKFV<br>QKVNEIGIYLTDCMERAREVIPRSQHQETPVYLGATAGMRLLRMESEELA<br>DRVLDVVERSLSNYPFDFQGARIITGQEEGAYGWITINYLLGKFSQKNQET<br>FGALDLGGASTQVTFVPQNQTIESPDNALQFRLYGKDYNVYTHSFLCYGK |

TABLE 35-continued

Sequences useful for practicing the invention.

| SEQ ID Number | Feature | Sequence |
| --- | --- | --- |
| | | DQALWQKLAKDIQVASNEILRDPAFHPGYKKVVNVSDLYKTPCTKRFEMT LPFQQFEIQGIGNYQQAHQSILELFNTSYCPYSQCAFNGIFLPPLQGDFGA FSAFYFVMKFLNLTSEKVSQEKVTEMMKKFCAQPWEEIKTSYAGVKEKYL SEYCFSGTYILSLLLQGYHFTADSWEHIHFIGKIQGSDAGVVTLGYMLNLTN M |
| SEQ ID NO: 120 | DNA | AACGTGAAGTACGGCATCGTGCTGGATGCCGGCAGCAGCCACACCAG CCTGTACATCTACAAGTGGCCTGCCGAGAAAGAAAACGATACCGGTGT CGTGCACCAGGTGGAAGAGTGCAGAGTGAAGGGCCCTGGCATCAGC AAGTTCGTGCAGAAAGTGAACGAGATCGGCATCTACCTGACCGACTG CATGGAACGGGCCAGAGAAGTGATCCCCAGAAGCCAGCACCAGGAAA CCCCCGTGTACCTGGGAGCCACAGCCGGCATGAGACTGCTGCGGAT GGAAAGCGAGGAACTGGCCGACAGAGTGCTGGACGTGGTGGAAAGA AGCCTGAGCAACTACCCATTCGATTTTCAAGGGGCCAGAATCATCACC GGCCAGGAAGAGGGCGCTTACGGCTGGATCACCATCAACTACCTGCT GGGCAAGTTCAGCCAGAAAAATCAGGAAACCTTCGGAGCCCTGGACC TGGGCGGAGCCTCTACCCAAGTGACCTTCGTGCCCCAGAATCAGACC ATCGAGAGCCCCGACAACGCCCTGCAGTTCCGGCTGTACGGCAAGGA CTACAATGTGTACACCCACAGCTTTCTGTGCTACGGAAAGGACCAGGC CCTGTGGCAGAAGCTGGCCAAGGACATCCAGGTGGCCAGCAACGAG ATCCTGCGGGACCCTGCCTTCCACCCCGGCTACAAGAAAGTCGTGAA CGTGTCCGACCTGTACAAGACCCCCTGCACCAAGAGATTCGAGATGA CCCTGCCCTTCCAGCAGTTCGAGATCCAGGGCATCGGCAACTACCAG CAGGCCCACCAGAGCATCCTGGAACTGTTCAACACCAGCTACTGCCC CTACAGCCAGTGCGCCTTCAACGGCATCTTCCTGCCACCTCTGCAGG GGGACTTCGGCGCTTTCAGCGCCTTCTACTTCGTGATGAAGTTCCTGA ACCTGACCAGCGAGAAGGTGTCCCAGGAAAAAGTGACAGAGATGATG AAGAAGTTCTGCGCCCAGCCCTGGGAGGAAATCAAGACCTCCTACGC TGGCGTGAAAGAGAAGTACCTGAGCGAGTACTGCTTCAGCGGTACCT ACATCCTGAGCCTGCTGCTGCAGGGCTACCACTTCACCGCCGATAGC TGGGAGCACATCCACTTCATCGGCAAGATTCAGGGCAGCGACGCCGG CTGGACACTGGGCTACATGCTGAATCTGACCAACATG |

CD39(aa46-461)_dMIL(193-204)_delta cys3

| SEQ ID Number | Feature | Sequence |
| --- | --- | --- |
| SEQ ID NO: 121 | Amino acid | NVKYGIVLDAGSSHTSLYIYKVVPAEKENDTGVVHQVEECRVKGPGISKFV QKVNEIGIYLTDCMERAREVIPRSQHQETPVYLGATAGMRLLRMESEELA DRVLDVVERSLSNYPFDFQGARMTGQEEGAYGWITINYLLGKFSQKNQET FGALDLGGASTQVTFVPQNQTESPDNALQFRLYGKDYNVYTHSFLAYGK DQALWQKLAKDIQVASNEILRDPCFHPGYKKVVNVSDLYKTPATKRFEMT LPFQQFEIQGIGNYQQCHQSILELFNTSYCPYSQCAFNGIFLPPLQGDFGA FSAFYFVMKFLNLTSEKVSQEKVTEMMKKFCAQPWEEIKTSYAGVKEKYL SEYCFSGTYILSLLLQGYHFTADSWEHIHFIGKIQGSDAGVVTLGYMLNLTN M |
| SEQ ID NO: 122 | DNA | AACGTGAAGTACGGCATCGTGCTGGATGCCGGCAGCAGCCACACCAG CCTGTACATCTACAAGTGGCCTGCCGAGAAAGAAAACGATACCGGTGT CGTGCACCAGGTGGAAGAGTGCAGAGTGAAGGGCCCTGGCATCAGC AAGTTCGTGCAGAAAGTGAACGAGATCGGCATCTACCTGACCGACTG CATGGAACGGGCCAGAGAAGTGATCCCCAGAAGCCAGCACCAGGAAA CCCCCGTGTACCTGGGAGCCACAGCCGGCATGAGACTGCTGCGGAT GGAAAGCGAGGAACTGGCCGACAGAGTGCTGGACGTGGTGGAAAGA AGCCTGAGCAACTACCCATTCGATTTTCAAGGGGCCAGAATCATCACC GGCCAGGAAGAGGGCGCTTACGGCTGGATCACCATCAACTACCTGCT GGGCAAGTTCAGCCAGAAAAATCAGGAAACCTTCGGAGCCCTGGACC TGGGCGGAGCCTCTACCCAAGTGACCTTCGTGCCCCAGAATCAGACC ATCGAGAGCCCCGACAACGCCCTGCAGTTCCGGCTGTACGGCAAGGA CTACAATGTGTACACCCACAGCTTTCTGGCCTACGGAAAGGACCAGG CCCTGTGGCAGAAGCTGGCCAAGGACATCCAGGTGGCCAGCAACGA GATCCTGCGGGACCCTTGCTTCCACCCCGGCTACAAGAAAGTCGTGA ACGTGTCCGACCTGTACAAGACCCCCGCCACCAAGAGATTCGAGATG ACCCTGCCCTTCCAGCAGTTCGAGATCCAGGGCATCGGCAACTACCA GCAGGCCCACCAGAGCATCCTGGAACTGTTCAACACCAGCTACTGCC CCTACAGCCAGTGCGCCTTCAACGGCATCTTCCTGCCACCTCTGCAG GGGGACTTCGGCGCTTTCAGCGCCTTCTACTTCGTGATGAAGTTCCTG AACCTGACCAGCGAGAAGGTGTCCCAGGAAAAAGTGACAGAGATGAT GAAGAAGTTCTGCGCCCAGCCCTGGGAGGAAATCAAGACCTCCTACG CTGGCGTGAAAGAGAAGTACCTGAGCGAGTACTGCTTCAGCGGTACC TACATCCTGAGCCTGCTGCTGCAGGGCTACCACTTCACCGCCGATAG CTGGGAGCACATCCACTTCATCGGCAAGATTCAGGGCAGCGACGCCG GCTGGACACTGGGCTACATGCTGAATCTGACCAACATG |

TABLE 35-continued

Sequences useful for practicing the invention.

| SEQ ID Number | Feature | Sequence |
|---|---|---|
| CD39(aa46-461)_dMIL(193-204)_delta cys4 | | |
| SEQ ID NO: 123 | Amino acid | NVKYGIVLDAGSSHTSLYIYKWPAEKENDTGVVHQVEECRVKGPGISKFV<br>QKVNEIGIYLTDCMERAREVIPRSQHQETPVYLGATAGMRLLRMESEELA<br>DRVLDVVERSLSNYPFDFQGARIITGQEEGAYGWITINYLLGKFSQKNQET<br>FGALDLGGASTQVTFVPQNQTESPDNALQFRLYGKDYNVYTHSFLCYGK<br>DQALWQKLAKDIQVASNEILRDPCFHPGYKKVVNVSDLYKTPCTKRFEMT<br>LPFQQFEIQGIGNYQQCHQSILELFNTSYAPYSQAAFNGIFLPPLQGDFGA<br>FSAFYFVMKFLNLTSEKVSQEKVTEMMKKFCAQPWEEIKTSYAGVKEKYL<br>SEYCFSGTYILSLLLQGYHFTADSWEHIHFIGKIQGSDAGWTLGYMLNLTN<br>M |
| SEQ ID NO: 124 | DNA | AACGTGAAGTACGGCATCGTGCTGGATGCCGGCAGCAGCCACACCAG<br>CCTGTACATCTACAAGTGGCCTGCCGAGAAAGAAAACGATACCGGTGT<br>CGTGCACCAGGTGGAAGAGTGCAGAGTGAAGGGCCCTGGCATCAGC<br>AAGTTCGTGCAGAAAGTGAACGAGATCGGCATCTACCTGACCGACTG<br>CATGGAACGGGCCAGAGAAGTGATCCCCAGAAGCCAGCACCAGGAAA<br>CCCCCGTGTACCTGGGAGCCACAGCCGGCATGAGACTGCTGCGGAT<br>GGAAAGCGAGGAACTGGCCGACAGAGTGCTGGACGTGGTGGAAAGA<br>AGCCTGAGCAACTACCCATTCGATTTTCAAGGGGCCAGAATCATCACC<br>GGCCAGGAAGAGGGCGCTTACGGCTGGATCACCATCAACTACCTGCT<br>GGGCAAGTTCAGCCAGAAAAATCAGGAAACCTTCGGAGCCCTGGACC<br>TGGGCGGAGCCTCTACCCAAGTGACCTTCGTGCCCCAGAATCAGACC<br>ATCGAGAGCCCCGACAACGCCCTGCAGTTCCGGCTGTACGGCAAGGA<br>CTACAATGTGTACACCCACAGCTTTCTGTGCTACGGAAAGGACCAGGC<br>CCTGTGGCAGAAGCTGGCCAAGGACATCCAGGTGGCCAGCAACGAG<br>ATCCTGCGGGACCCTTGCTTCCACCCCGGCTACAAGAAAGTCGTGAA<br>CGTGTCCGACCTGTACAAGACCCCCTGCACCAAGAGATTCGAGATGA<br>CCCTGCCCTTCCAGCAGTTCGAGATCCAGGGCATCGGCAACTACCAG<br>CAGTGCCACCAGAGCATCCTGGAACTGTTCAACACCAGCTACGCCCC<br>CTACAGCCAGGCCGCCTTCAACGGCATCTTCCTGCCACCTCTGCAGG<br>GGGACTTCGGCGCTTTCAGCGCCTTCTACTTCGTGATGAAGTTCCTGA<br>ACCTGACCAGCGAGAAGGTGTCCCAGGAAAAAGTGACAGAGATGATG<br>AAGAAGTTCTGCGCCCAGCCCTGGGAGGAAATCAAGACCTCCTACGC<br>TGGCGTGAAAGAGAAGTACCTGAGCGAGTACTGCTTCAGCGGTACCT<br>ACATCCTGAGCCTGCTGCTGCAGGGCTACCACTTCACCGCCGATAGC<br>TGGGAGCACATCCACTTCATCGGCAAGATTCAGGGCAGCGACGCCGG<br>CTGGACACTGGGCTACATGCTGAATCTGACCAACATG |
| CD39(aa46-461)_dMIL(193-204)_delta cys5 | | |
| SEQ ID NO: 125 | Amino acid | NVKYGIVLDAGSSHTSLYIYKWPAEKENDTGVVHQVEECRVKGPGISKFV<br>QKVNEIGIYLTDCMERAREVIPRSQHQETPVYLGATAGMRLLRMESEELA<br>DRVLDVVERSLSNYPFDFQGARIITGQEEGAYGWITINYLLGKFSQKNQET<br>FGALDLGGASTQVTFVPQNQTESPDNALQFRLYGKDYNVYTHSFLCYGK<br>DQALWQKLAKDIQVASNEILRDPCFHPGYKKVVNVSDLYKTPCTKRFEMT<br>LPFQQFEIQGIGNYQQCHQSILELFNTSYCPYSQCAFNGIFLPPLQGDFGA<br>FSAFYFVMKFLNLTSEKVSQEKVTEMMKKFAAQPWEEIKTSYAGVKEKYL<br>SEYAFSGTYILSLLLQGYHFTADSWEHIHFIGKIQGSDAGWTLGYMLNLTN<br>M |
| SEQ ID NO: 126 | DNA | AACGTGAAGTACGGCATCGTGCTGGATGCCGGCAGCAGCCACACCAG<br>CCTGTACATCTACAAGTGGCCTGCCGAGAAAGAAAACGATACCGGTGT<br>CGTGCACCAGGTGGAAGAGTGCAGAGTGAAGGGCCCTGGCATCAGC<br>AAGTTCGTGCAGAAAGTGAACGAGATCGGCATCTACCTGACCGACTG<br>CATGGAACGGGCCAGAGAAGTGATCCCCAGAAGCCAGCACCAGGAAA<br>CCCCCGTGTACCTGGGAGCCACAGCCGGCATGAGACTGCTGCGGAT<br>GGAAAGCGAGGAACTGGCCGACAGAGTGCTGGACGTGGTGGAAAGA<br>AGCCTGAGCAACTACCCATTCGATTTTCAAGGGGCCAGAATCATCACC<br>GGCCAGGAAGAGGGCGCTTACGGCTGGATCACCATCAACTACCTGCT<br>GGGCAAGTTCAGCCAGAAAAATCAGGAAACCTTCGGAGCCCTGGACC<br>TGGGCGGAGCCTCTACCCAAGTGACCTTCGTGCCCCAGAATCAGACC<br>ATCGAGAGCCCCGACAACGCCCTGCAGTTCCGGCTGTACGGCAAGGA<br>CTACAATGTGTACACCCACAGCTTTCTGTGCTACGGAAAGGACCAGGC<br>CCTGTGGCAGAAGCTGGCCAAGGACATCCAGGTGGCCAGCAACGAG<br>ATCCTGCGGGACCCTTGCTTCCACCCCGGCTACAAGAAAGTCGTGAA<br>CGTGTCCGACCTGTACAAGACCCCCTGCACCAAGAGATTCGAGATGA<br>CCCTGCCCTTCCAGCAGTTCGAGATCCAGGGCATCGGCAACTACCAG<br>CAGTGCCACCAGAGCATCCTGGAACTGTTCAACACCAGCTACGCCCC |

TABLE 35-continued

Sequences useful for practicing the invention.

| SEQ ID Number | Feature | Sequence |
|---|---|---|
| | | CTACAGCCAGTGCGCCTTCAACGGCATCTTCCTGCCACCTCTGCAGG<br>GGGACTTCGGCGCTTTCAGCGCCTTCTACTTCGTGATGAAGTTCCTGA<br>ACCTGACCAGCGAGAAGGTGTCCCAGGAAAAAGTGACAGAGATGATG<br>AAGAAGTTCGCCGCCCAGCCCTGGGAGGAAATCAAGACCTCCTACGC<br>TGGCGTGAAAGAGAAGTACCTGAGCGAGTACGCCTTCAGCGGTACCT<br>ACATCCTGAGCCTGCTGCTGCAGGGCTACCACTTCACCGCCGATAGC<br>TGGGAGCACATCCACTTCATCGGCAAGATTCAGGGCAGCGACGCCGG<br>CTGGACACTGGGCTACATGCTGAATCTGACCAACATG |

CD39(aa38-476)_delta337-344

| SEQ ID NO: 127 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKTRWFSIVPYETNNQETFGALDLGGASTQVTFVPQNQTIESPDNALQF<br>RLYGKDYNVYTHSFLCYGKDQALWQKLAKDIQVASNEILRDPCFHPGYKK<br>VVNVSDLYKTPCTKRFEMTLPFQQFEIQGIGNYQQCHQSILELFNTSFNGI<br>FLPPLQGDFGAFSAFYFVMKFLNLTSEKVSQEKVTEMMKKFCAQPWEEIK<br>TSYAGVKEKYLSEYCFSGTYILSLLLQGYHFTADSWEHIHFIGKIQGSDAG<br>VVTLGYMLNLTNMIPAEQPLSTPLSHST |
| SEQ ID NO: 128 | DNA | ACACAGAACAAAGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGATACCGGTGTCGTGCACCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGAGAAGTGA<br>TCCCCAGAAGCCAGCACCAGGAAACCCCCGTGTACCTGGGAGCCACA<br>GCCGGCATGAGACTGCTGCGGATGGAAAGCGAGGAACTGGCCGACA<br>GAGTGCTGGACGTGGTGGAAAGAAGCCTGAGCAACTACCCATTCGAT<br>TTTCAAGGGGCCAGAATCATCACCGGCCAGGAAGAGGGCGCTTACGG<br>CTGGATCACCATCAACTACCTGCTGGGCAAGTTCAGCCAGAAAAACCC<br>GGTGGTTCAGCATCGTGCCCTACGAGACAAACAATCAGGAAACCTTC<br>GGAGCCCTGGACCTGGGCGGAGCCTCTACCCAAGTGACCTTCGTGCC<br>CCAGAATCAGACCATCGAGAGCCCCGACAACGCCCTGCAGTTCCGGC<br>TGTACGGCAAGGACTACAATGTGTACACCCACAGCTTTCTGTGCTACG<br>GAAAGGACCAGGCCCTGTGGCAGAAGCTGGCCAAGGACATCCAGGT<br>GGCCAGCAACGAGATCCTGCGGGACCCTTGCTTCCACCCCGGCTACA<br>AGAAAGTCGTGAACGTGTCCGACCTGTACAAGACCCCCTGCACCAAG<br>AGATTCGAGATGACCCTGCCCTTCCAGCAGTTCGAGATCCAGGGCAT<br>CGGCAACTACCAGCAGTGCCACCAGAGCATCCTGGAACTGTTCAACA<br>CCAGCTTCAACGGCATCTTCCTGCCACCTCTGCAGGGGGACTTCGGC<br>GCTTTCAGCGCCTTCTACTTCGTGATGAAGTTCCTGAACCTGACCAGC<br>GAGAAGGTGTCCCAGGAAAAAGTGACAGAGATGATGAAGAAGTTCTG<br>CGCCCAGCCCTGGGAGGAAATCAAGACCTCCTACGCTGGCGTGAAAG<br>AGAAGTACCTGAGCGAGTACTGCTTCAGCGGTACCTACATCCTGAGC<br>CTGCTGCTGCAGGGCTACCACTTCACCGCCGATAGCTGGGAGCACAT<br>CCACTTCATCGGCAAGATTCAGGGCAGCGACGCCGGCTGGACACTGG<br>GCTACATGCTGAATCTGACCAACATGATCCCCGCCGAGCAGCCCCTG<br>AGCACACCTCTGTCTCACAGCACC |

CD39(aa38-476)_C338A_C343A

| SEQ ID NO: 129 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKTRWFSIVPYETNNQETFGALDLGGASTQVTFVPQNQTIESPDNALQF<br>RLYGKDYNVYTHSFLCYGKDQALWQKLAKDIQVASNEILRDPCFHPGYKK<br>VVNVSDLYKTPCTKRFEMTLPFQQFEIQGIGNYQQCHQSILELFNTSYAPY<br>SQAAFNGIFLPPLQGDFGAFSAFYFVMKFLNLTSEKVSQEKVTEMMKKFC<br>AQPWEEIKTSYAGVKEKYLSEYCFSGTYILSLLLQGYHFTADSWEHIHFIG<br>KIQGSDAGWTLGYMLNLTNMIPAEQPLSTPLSHST |
| SEQ ID NO: 130 | DNA | ACACAGAACAAAGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGATACCGGTGTCGTGCACCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGAGAAGTGA<br>TCCCCAGAAGCCAGCACCAGGAAACCCCCGTGTACCTGGGAGCCACA<br>GCCGGCATGAGACTGCTGCGGATGGAAAGCGAGGAACTGGCCGACA<br>GAGTGCTGGACGTGGTGGAAAGAAGCCTGAGCAACTACCCATTCGAT<br>TTTCAAGGGGCCAGAATCATCACCGGCCAGGAAGAGGGCGCTTACGG<br>CTGGATCACCATCAACTACCTGCTGGGCAAGTTCAGCCAGAAAAACCC<br>GGTGGTTCAGCATCGTGCCCTACGAGACAAACAATCAGGAAACCTTC |

TABLE 35-continued

Sequences useful for practicing the invention.

| SEQ ID Number | Feature | Sequence |
|---|---|---|
| | | GGAGCCCTGGACCTGGGCGGAGCCTCTACCCAAGTGACCTTCGTGCC<br>CCAGAATCAGACCATCGAGAGCCCCGACAACGCCCTGCAGTTCCGGC<br>TGTACGGCAAGGACTACAATGTGTACACCCACAGCTTTCTGTGCTACG<br>GAAAGGACCAGGCCCTGTGGCAGAAGCTGGCCAAGGACATCCAGGT<br>GGCCAGCAACGAGATCCTGCGGGACCCTTGCTTCCACCCCGGCTACA<br>AGAAAGTCGTGAACGTGTCCGACCTGTACAAGACCCCCTGCACCAAG<br>AGATTCGAGATGACCCTGCCCTTCCAGCAGTTCGAGATCCAGGGCAT<br>CGGCAACTACCAGCAGTGCCACCAGAGCATCCTGGAACTGTTCAACA<br>CCAGCTACGCCCCCTACAGCCAGGCCGCCTTCAACGGCATCTTCCTG<br>CCACCTCTGCAGGGGACTTCGGCGCTTTCAGCGCCTTCTACTTCGT<br>GATGAAGTTCCTGAACCTGACCAGCGAGAAGGTGTCCCAGGAAAAAG<br>TGACAGAGATGATGAAGAAGTTCTGCGCCCAGCCCTGGGAGGAAATC<br>AAGACCTCCTACGCTGGCGTGAAAGAGAAGTACCTGAGCGAGTACTG<br>CTTCAGCGGTACCTACATCCTGAGCCTGCTGCTGCAGGGCTACCACTT<br>CACCGCCGATAGCTGGGAGCACATCCACTTCATCGGCAAGATTCAGG<br>GCAGCGACGCCGGCTGGACACTGGGCTACATGCTGAATCTGACCAAC<br>ATGATCCCCGCCGAGCAGCCCCTGAGCACACCTCTGTCTCACAGCAC<br>C |
| Expression tag aa1-16 | | |
| SEQ ID NO: 131 | Amino acid | APTSSSTKKTQLTSSG |
| SEQ ID NO: 132 | DNA GC | GCCCCCACCAGCAGCAGCACCAAGAAGACCCAGCTGACCAGCAGCG |
| Expression tag aa1-15 | | |
| SEQ ID NO: 133 | Amino acid | APTSSSTKKTQLTSS |
| SEQ ID NO: 134 | DNA | GCCCCTACCAGCAGCAGCACCAAGAAAACCCAGCTGACCAGCAGC |
| Expression tag aa1-6 | | |
| SEQ ID NO: 135 | Amino acid | APTSSS |
| SEQ ID NO: 136 | DNA | GCCCCTACCAGCAGCAGC |
| Expression tag aa1-3 | | |
| SEQ ID NO: 137 | Amino acid | APT |
| SEQ ID NO: 138 | DNA | GCCCCTACC |
| Expression tag aa1-9 | | |
| SEQ ID NO: 139 | Amino acid | APTSSSTKK |
| SEQ ID NO: 140 | DNA | GCCCCTACCAGCAGCAGCACCAAGAAA |
| Expression tag aa1-12 | | |
| SEQ ID NO: 141 | Amino acid | APTSSSTKKTQL |
| SEQ ID NO: 142 | DNA | GCCCCTACCAGCAGCAGCACCAAGAAAACCCAGCTG |

TABLE 35-continued

Sequences useful for practicing the invention.

| SEQ ID Number | Feature | Sequence |
|---|---|---|
| Expression tag aa4-12 | | |
| SEQ ID NO: 143 | Amino acid | SSSTKKTQL |
| SEQ ID NO: 144 | DNA | AGCAGCAGCACCAAGAAAACCCAGCTG |
| EP28_8M | | |
| SEQ ID NO: 145 | Amino acid | TQNKALPENVKYGIVLDAGSSHTSLYIYKWPAEKENDTGVVHQVEECRVK GPGISKFVQKVNEIGIYLTDCMERAREVIPRSQHQETPVYLGATAGMRLLR MESEELADRVLDVVERSLSNYPFDFQGARIITGQDEGAYGWITINYLLGKF SQKNQETFGALDLGGASTQVTFVPQNQTIESPDNALQFRLYGKDYNVYT HSFLCYGRDQALWQKLAKDIQVASNEILRDPCFHPGYKKVVNVSDLYKTP CTKRFEMTLPFQQFEIQGIGNYQQCHQSILELFNTSYCPYSQCAFNGIFLP PLQGDFGAFSNFYYVMKFLNLTSEKVSQEKVTEMMKKFCAQPWEEIKTS YAGQERWLRDYCFSGTYILSLLLQGYHFTADSWEHIHFIGKIQGSDAGWT LGYMLNLTNMIPAEQPLSTPLSHST |
| SEQ ID NO: 146 | DNA | ACCCAGAACAAGGCCCTGCCCGAGAACGTGAAGTACGGCATCGTGCT GGATGCCGGCAGCAGCCACACCAGCCTGTACATCTACAAGTGGCCTG CCGAGAAAGAAAACGACACCGGCGTGGTGCATCAGGTGGAAGAGTGC AGAGTGAAGGGCCCTGGCATCAGCAAGTTCGTGCAGAAAGTGAACGA GATCGGCATCTACCTGACCGACTGCATGGAACGGGCCAGAGAAGTGA TCCCCAGAAGCCAGCACCAGGAAACCCCCGTGTATCTGGGAGCCACC GCCGGCATGAGACTGCTGAGAATGGAAAGCGAGGAACTGGCCGACC GGGTGCTGGACGTGGTGGAAAGAAGCCTGAGCAACTACCCATTCGAT TTTCAAGGCGCCAGAATCATCACCGGCCAGGACGAGGGCGCCTACGG CTGGATCACCATCAACTACCTGCTGGGCAAGTTCAGCCAGAAGAATCA GGAAACCTTCGGCGCCCTGGACCTGGGCGGAGCTTCTACCCAAGTGA CCTTCGTGCCCCAGAATCAGACCATCGAGAGCCCCGACAACGCCCTG CAGTTCCGGCTGTACGGCAAGGACTACAATGTGTACACCCACAGCTTT CTGTGCTACGGCCGGGACCAGGCTCTGTGGCAGAAGCTGGCCAAGG ACATCCAGGTGGCCAGCAACGAGATCCTGCGGGACCCTTGCTTCCAC CCCGGCTACAAGAAAGTCGTGAACGTGTCCGACCTGTACAAGACCCC CTGCACCAAGAGATTCGAGATGACCCTGCCCTTCCAGCAGTTCGAGAT CCAGGGCATCGGCAACTACCAGCAGTGCCACCAGAGCATCCTGGAAC TGTTCAACACCAGCTACTGCCCCTACAGCCAGTGCGCCTTCAACGGC ATCTTCCTGCCCACCTCTGCAGGGGATTTCGGCGCCTTCAGCAACTTC TACTACGTGATGAAGTTCCTGAACCTGACCAGCGAGAAGGTGTCCCA GGAAAAAGTGACAGAGATGATGAAGAAGTTCTGCGCCCAGCCCTGGG AGGAAATCAAGACCTCTTACGCCGGACAGGAACGGTGGCTGCGGGAC TACTGTTTCAGCGGCACCTACATCCTGTCCCTGCTGCTGCAGGGCTAC CACTTCACCGCCGATAGCTGGGAGCACATCCACTTCATCGGCAAGATT CAGGGCAGCGACGCCGGCTGGACACTGGGCTACATGCTGAATCTGAC CAACATGATCCCCGCCGAGCAGCCCCTGAGCACACCTCTGTCTCACA GCACC |
| CD39(aa38-476)_dMIL(193-204)_CKAPPA | | |
| SEQ ID NO: 147 | Amino acid | TVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKS FNRGEGGGGSTQNKALPENVKYGIVLDAGSSHTSLYIYKWPAEKENDTG VVHQVEECRVKGPGISKFVQKVNEIGIYLTDCMERAREVIPRSQHQETPV YLGATAGMRLLRMESEELADRVLDVVERSLSNYPFDFQGARIITGQEEGA YGWITINYLLGKFSQKNQETFGALDLGGASTQVTFVPQNQTIESPDNALQ FRLYGKDYNVYTHSFLCYGKDQALWQKLAKDIQVASNEILRDPCFHPGYK KVVNVSDLYKTPCTKRFEMTLPFQQFEIQGIGNYQQCHQSILELFNTSYCP YSQCAFNGIFLPPLQGDFGAFSAFYFVMKFLNLTSEKVSQEKVTEMMKKF CAQPWEEIKTSYAGVKEKYLSEYCFSGTYILSLLLQGYHFTADSVVEHIHFI GKIQGSDAGVVTLGYMLNLTNMIPAEQPLSTPLSHST |
| SEQ ID NO: 148 | DNA | ACGGTGGCCGCTCCCAGCGTGTTCATCTTCCCCCCCAGCGACGAGCA GCTGAAGAGCGGCACCGCCAGCGTGGTGTGCCTGCTGAACAACTTCT ACCCCCGGGAGGCCAAGGTGCAGTGGAAGGTGGACAACGCCCTGCA GAGCGGCAACAGCCAGGAAAGCGTCACCGAGCAGGACAGCAAGGAC TCCACCTACAGCCTGAGCAGCACCCTGACCCTGAGCAAGGCCGACTA CGAGAAGCACAAGGTGTACGCCTGCGAGGTGACCCACCAGGGCCTG TCCAGCCCCGTGACCAAGAGCTTCAACCGGGGCGAGGGAGGCGGAG GATCTACCCAGAACAAGGCCCTGCCCGAGAACGTGAAGTACGGCATC GTGCTGGATGCCGGCAGCAGCCACACCAGCCTGTACATCTACAAGTG |

TABLE 35-continued

Sequences useful for practicing the invention.

| SEQ ID Number | Feature | Sequence |
|---|---|---|
| | | GCCTGCCGAGAAAGAAAACGACACCGGCGTGGTGCATCAGGTGGAA<br>GAGTGCAGAGTGAAGGGCCCTGGCATCAGCAAGTTCGTGCAGAAAGT<br>GAACGAGATCGGCATCTACCTGACCGACTGCATGGAACGGGCCAGGG<br>AAGTGATCCCCAGAAGCCAGCACCAGGAAACCCCCGTGTATCTGGGA<br>GCCACCGCCGGCATGAGACTGCTGAGAATGGAAAGCGAGGAACTGG<br>CCGACCGGGTGCTGGACGTGGTGGAAAGAAGCCTGAGCAACTACCCA<br>TTCGATTTTCAAGGCGCCAGAATCATCACCGGCCAGGAAGAAGGCGC<br>CTACGGCTGGATCACCATCAACTACCTGCTGGGCAAGTTCAGCCAGA<br>AGAATCAGGAAACCTTCGGCGCCCTGGACCTGGGCGGAGCTTCTACC<br>CAAGTGACCTTCGTGCCCCAGAATCAGACCATCGAGAGCCCCGACAA<br>CGCCCTGCAGTTCCGGCTGTACGGCAAGGACTACAATGTGTACACCC<br>ACAGCTTTCTGTGCTACGGAAAGGACCAGGCTCTGTGGCAGAAGCTG<br>GCCAAGGACATCCAGGTGGCCAGCAACGAGATCCTGCGGGACCCTTG<br>CTTCCACCCCGGCTACAAGAAAGTCGTGAACGTGTCCGACCTGTACA<br>AGACCCCCTGCACCAAGAGATTCGAGATGACCCTGCCCTTCCAGCAGT<br>TCGAGATCCAGGGCATCGGCAATTACCAGCAGTGCCACCAGAGCATC<br>CTGGAACTGTTCAACACCAGCTACTGCCCCTACAGCCAGTGCGCCTTC<br>AACGGCATCTTCCTGCCACCTCTGCAGGGGGATTTCGGCGCCTTCAG<br>CGCCTTCTACTTCGTGATGAAGTTCCTGAACCTGACCAGCGAGAAGGT<br>GTCCCAGGAAAAAGTGACAGAGATGATGAAGAAGTTCTGCGCCCAGC<br>CCTGGGAGGAAATCAAGACCTCCTACGCTGGCGTGAAAGAGAAGTAC<br>CTGAGCGAGTACTGCTTCAGCGGCACCTACATCCTGAGCCTGCTGCT<br>GCAGGGCTACCACTTCACCGCCGATAGCTGGGAGCACATCCACTTCA<br>TCGGCAAGATTCAGGGCAGCGACGCCGGCTGGACACTGGGCTACAT<br>GCTGAATCTGACCAACATGATCCCCGCCGAGCAGCCCCTGAGCACAC<br>CTCTGAGCCACAGCACC |
| CD39(aa38-476)_dMIL(193-204)_UBI | | |
| SEQ ID NO: 149 | Amino acid | MQIFVKTLTGKTITLEVEPSDTIENVKAKIQDKEGIPPDQQRLIFAGKQLED<br>GRTLSDYNIQKESTLHLVLRLRGGGGGSTQNKALPENVKYGIVLDAGSS<br>HTSLYIYKWPAEKENDTGVVHQVEECRVKGPGISKFVQKVNEIGIYLTDC<br>MERAREVIPRSQHQETPVYLGATAGMRLLRMESEELADRVLDVVERSLS<br>NYPFDFQGARIITGQEEGAYGWITINYLLGKFSQKNQETFGALDLGGAST<br>QVTFVPQNQTESPDNALQFRLYGKDYNVYTHSFLCYGKDQALWQKLAK<br>DIQVASNEILRDPCFHPGYKKVVNVSDLYKTPCTKRFEMTLPFQQFEIQGI<br>GNYQQCHQSILELFNTSYCPYSQCAFNGIFLPPLQGDFGAFSAFYFVMKF<br>LNLTSEKVSQEKVTEMMKKFCAQPWEEIKTSYAGVKEKYLSEYCFSGTYI<br>LSLLLQGYHFTADSWEHIHFIGKIQGSDAGWTLGYMLNLTNMIPAEQPLST<br>PLSHST |
| SEQ ID NO: 150 | DNA | ATGCAAATCTTCGTGAAGACCCTGACTGGTAAGACCATCACCCTCGAG<br>GTGGAGCCCAGTGACACCATCGAGAATGTCAAGGCAAAGATCCAAGA<br>TAAGGAAGGCATCCCTCCTGATCAGCAGAGGTTGATCTTTGCTGGGAA<br>ACAGCTGGAAGATGGACGCACCCTGTCTGACTACAACATCCAGAAAG<br>AGTCCACTCTGCACTTGGTCCTGCGCTTGAGGGGGGGTGGAGGCGG<br>AGGATCTACCCAGAACAAGGCCCTGCCCGAGAACGTGAAGTACGGCA<br>TCGTGCTGGATGCCGGCAGCAGCCACACCAGCCTGTACATCTACAAG<br>TGGCCTGCCGAGAAAGAAAACGACACCGGCGTGGTGCATCAGGTGGA<br>AGAGTGCAGAGTGAAGGGCCCTGGCATCAGCAAGTTCGTGCAGAAAG<br>TGAACGAGATCGGCATCTACCTGACCGACTGCATGGAACGGGCCAGG<br>GAAGTGATCCCCAGAAGCCAGCACCAGGAAACCCCCGTGTATCTGGG<br>AGCCACCGCCGGCATGAGACTGCTGAGAATGGAAAGCGAGGAACTG<br>GCCGACCGGGTGCTGGACGTGGTGGAAAGAAGCCTGAGCAACTACC<br>CATTCGATTTTCAAGGCGCCAGAATCATCACCGGCCAGGAAGAAGGC<br>GCCTACGGCTGGATCACCATCAACTACCTGCTGGGCAAGTTCAGCCA<br>GAAGAATCAGGAAACCTTCGGCGCCCTGGACCTGGGCGGAGCTTCTA<br>CCCAAGTGACCTTCGTGCCCCAGAATCAGACCATCGAGAGCCCCGAC<br>AACGCCCTGCAGTTCCGGCTGTACGGCAAGGACTACAATGTGTACAC<br>CCACAGCTTTCTGTGCTACGGAAAGGACCAGGCTCTGTGGCAGAAGC<br>TGGCCAAGGACATCCAGGTGGCCAGCAACGAGATCCTGCGGGACCCT<br>TGCTTCCACCCCGGCTACAAGAAAGTCGTGAACGTGTCCGACCTGTA<br>CAAGACCCCCTGCACCAAGAGATTCGAGATGACCCTGCCCTTCCAGC<br>AGTTCGAGATCCAGGGCATCGGCAATTACCAGCAGTGCCACCAGAGC<br>ATCCTGGAACTGTTCAACACCAGCTACTGCCCCTACAGCCAGTGCGC<br>CTTCAACGGCATCTTCCTGCCACCTCTGCAGGGGGATTTCGGCGCCT<br>TCAGCGCCTTCTACTTCGTGATGAAGTTCCTGAACCTGACCAGCGAGA<br>AGGTGTCCCAGGAAAAAGTGACAGAGATGATGAAGAAGTTCTGCGCC<br>CAGCCCTGGGAGGAAATCAAGACCTCCTACGCTGGCGTGAAAGAGAA<br>GTACCTGAGCGAGTACTGCTTCAGCGGCACCTACATCCTGAGCCTGC |

TABLE 35-continued

Sequences useful for practicing the invention.

| SEQ ID Number | Feature | Sequence |
|---|---|---|
| | | TGCTGCAGGGCTACCACTTCACCGCCGATAGCTGGGAGCACATCCAC<br>TTCATCGGCAAGATTCAGGGCAGCGACGCCGGCTGGACACTGGGCTA<br>CATGCTGAATCTGACCAACATGATCCCCGCCGAGCAGCCCCTGAGCA<br>CACCTCTGAGCCACAGCACC |
| CD39(aa38-476_dMIL(193-)204)_HSAI<br>SEQ ID NO: 151 | HSA Domain I-G4S-CD39-dMIL Amino acid | DAHKSEVAHRFKDLGEENFKALVLIAFAQYLQQSPFEDHVKLVNEVTEFA<br>KTCVADESAENCDKSLHTLFGDKLCTVATLRETYGEMADCCAKQEPERN<br>ECFLQHKDDNPNLPRLVRPEVDVMCTAFHDNEETFLKKYLYEIARRHPYF<br>YAPELLFFAKRYKAAFTECCQAADKAACLLPKLDELRGGGGSTQNKALPE<br>NVKYGIVLDAGSSHTSLYIYKWPAEKENDTGVVHQVEECRVKGPGISKFV<br>QKVNEIGIYLTDCMERAREVIPRSQHQETPVYLGATAGMRLLRMESEELA<br>DRVLDVVERSLSNYPFDFQGARIITGQEEGAYGWITINYLLGKFSQKNQET<br>FGALDLGGASTQVTFVPQNQTIESPDNALQFRLYGKDYNVYTHSFLCYGK<br>DQALWQKLAKDIQVASNEILRDPCFHPGYKKVVNVSDLYKTPCTKRFEMT<br>LPFQQFEIQGIGNYQQCHQSILELFNTSYCPYSQCAFNGIFLPPLQGDFGA<br>FSAFYFVMKFLNLTSEKVSQEKVTEMMKKFCAQPWEEIKTSYAGVKEKYL<br>SEYCFSGTYILSLLLQGYHFTADSWEHIHFIGKIQGSDAGVVTLGYMLNLTN<br>MIPAEQPLSTPLSHST |
| SEQ ID NO: 152 | DNA | GACGCCCACAAGAGCGAGGTGGCCCACCGGTTCAAGGACCTGGGCG<br>AGGAAAACTTCAAGGCCCTGGTGCTGATCGCCTTCGCCCAGTACCTG<br>CAGCAGAGCCCCTTCGAAGATCACGTAAAGTTAGTCAACGAGGTTACG<br>GAATTCGCAAAGACATGCGTTGCTGACGAATCCGCTGAGAATTGTGAC<br>AAGAGTTTGCACACTTTATTCGGAGATAAGTTGTGTACTGTAGCTACTT<br>TGAGAGAGACTTACGGTGAAATGGCTGACTGCTGTGCAAAACAGGAA<br>CCAGAACGTAACGAATGTTTCCTTCAGCATAAGGATGATAACCCTAAC<br>CTTCCAAGGCTTGTTAGGCCAGAAGTCGACGTGATGTGCACCGCCTT<br>CCATGATAATGAAGAGACTTTTCTTAAAAAGTACCTATACGAGATTGCA<br>AGGCGTCATCCATATTTTTACGCCCCAGAGCTGTTGTTTTTCGCAAAG<br>AGATACAAAGCTGCATTTACTGAGTGTTGCCAAGCTGCCGACAAGGCC<br>GCTTGTTTGCTACCAAAGTTGGACGAATTGAGAGGAGGCGGAGGATC<br>TACCCAGAACAAGGCCCTGCCCGAGAACGTGAAGTACGGCATCGTGC<br>TGGATGCCGGCAGCAGCCACACCAGCCTGTACATCTACAAGTGGCCT<br>GCCGAGAAAGAAAACGACACCGGCGTGGTGCATCAGGTGGAAGAGT<br>GCAGAGTGAAGGGCCCTGGCATCAGCAAGTTCGTGCAGAAAGTGAAC<br>GAGATCGGCATCTACCTGACCGACTGCATGGAACGGGCCAGGGAAGT<br>GATCCCCAGAAGCCAGCACCAGGAAACCCCCGTGTATCTGGGAGCCA<br>CCGCCGGCATGAGACTGCTGAGAATGGAAAGCGAGGAACTGGCCGA<br>CCGGGTGCTGGACGTGGTGGAAAGAAGCCTGAGCAACTACCCATTCG<br>ATTTTCAAGGCGCCAGAATCATCACCGGCCAGGAAGAAGGCGCCTAC<br>GGCTGGATCACCATCAACTACCTGCTGGGCAAGTTCAGCCAGAAGAA<br>TCAGGAAACCTTCGGCGCCCTGGACCTGGGCGGAGCTTCTACCCAAG<br>TGACCTTCGTGCCCCAGAATCAGACCATCGAGAGCCCCGACAACGCC<br>CTGCAGTTCCGGCTGTACGGCAAGGACTACAATGTGTACACCCACAG<br>CTTTCTGTGCTACGGAAAGGACCAGGCTCTGTGGCAGAAGCTGGCCA<br>AGGACATCCAGGTGGCCAGCAACGAGATCCTGCGGGACCCTTGCTTC<br>CACCCCGGCTACAAGAAAGTCGTGAACGTGTCCGACCTGTACAAGAC<br>CCCCTGCACCAAGAGATTCGAGATGACCCTGCCCTTCCAGCAGTTCG<br>AGATCCAGGGCATCGGCAATTACCAGCAGTGCCACCAGAGCATCCTG<br>GAACTGTTCAACACCAGCTACTGCCCCTACAGCCAGTGCGCCTTCAAC<br>GGCATCTTCCTGCCACCTCTGCAGGGGGATTTCGGCGCCTTCAGCGC<br>CTTCTACTTCGTGATGAAGTTCCTGAACCTGACCAGCGAGAAGGTGTC<br>CCAGGAAAAGTGACAGAGATGATGAAGAAGTTCTGCGCCCAGCCCT<br>GGGAGGAAATCAAGACCTCCTACGCTGGCGTGAAAGAGAAGTACCTG<br>AGCGAGTACTGCTTCAGCGGCACCTACATCCTGAGCCTGCTGCTGCA<br>GGGCTACCACTTCACCGCCGATAGCTGGGAGCACATCCACTTCATCG<br>GCAAGATTCAGGGCAGCGACGCCGGCTGGACACTGGGCTACATGCT<br>GAATCTGACCAACATGATCCCCGCCGAGCAGCCCCTGAGCACACCTC<br>TGAGCCACAGCACC |
| CD39(aa38-476)_dMIL(193-204)_HSAII | | |
| SEQ ID NO: 153 | Amino acid | DEGKASSAKQRLKCASLQKFGERAFKAWAVARLSQRFPKAEFAEVSKLV<br>TDLTKVHTECCHGDLLECADDRADLAKYICENQDSISSKLKECCEKPLLEK<br>SHCIAEVENDEMPADLPSLAADFVESKDVCKNYAEAKDVFLGMFLYEYAR<br>RHPDYSVVLLLRLAKTYETTLEKCCAAADPHECYAKVFDEFKPGGGGST<br>QNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKNQETFGALDLGGASTQVTFVPQNQTIESPDNALQFRLYGKDYNVYT |

TABLE 35-continued

Sequences useful for practicing the invention.

| SEQ ID Number | Feature | Sequence |
|---|---|---|
| | | HSFLCYGKDQALWQKLAKDIQVASNEILRDPCFHPGYKKVVNVSDLYKTP<br>CTKRFEMTLPFQQFEIQGIGNYQQCHQSILELFNTSYCPYSQCAFNGIFLP<br>PLQGDFGAFSAFYFVMKFLNLTSEKVSQEKVTEMMKKFCAQPWEEIKTS<br>YAGVKEKYLSEYCFSGTYILSLLLQGYHFTADSWEHIHFIGKIQGSDAGWT<br>LGYMLNLTNMIPAEQPLSTPLSHST |
| SEQ ID NO: 154 | DNA | GACGAGGGTAAGGCATCATCTGCCAAGCAGAGATTAAAATGTGCATCT<br>TTGCAAAAATTTGGAGAGAGAGCTTTTAAGGCATGGGCTGTTGCCCGA<br>CTAAGCCAAAGATTCCCAAAAGCCGAATTTGCTGAAGTATCCAAGCTG<br>GTGACTGATTTGACTAAAGTACATACAGAATGTTGCCATGGCGACCTT<br>TTAGAATGTGCTGATGACAGAGCAGATTTGGCTAAGTATATCTGCGAA<br>AATCAAGATTCAATCAGCTCTAAGCTGAAGGAATGTTGCGAGAAACCA<br>CTGTTAGAAAAATCGCATTGTATTGCTGAAGTTGAAAATGATGAGATGC<br>CTGCTGACTTGCCTTCTCTTGCCGCTGATTTTGTTGAGTCGAAGGATG<br>TCTGTAAGAATTATGCTGAAGCTAAAGACGTTTTCCTGGGTATGTTCTT<br>ATATGAGTACGCAAGACGTCACCCAGATTACTCTGTGGTTCTGCTACT<br>GAGATTGGCTAAAACATACGAGACAACGCTGGAGAAGTGCTGTGCTG<br>CCGCTGACCCTCATGAGTGCTATGCAAAGGTTTTTGATGAATTCAAAC<br>CAGGAGGCGGAGGATCTACCCAGAACAAGGCCCTGCCCGAGAACGT<br>GAAGTACGGCATCGTGCTGGATGCCGGCAGCAGCCACACCAGCCTGT<br>ACATCTACAAGTGGCCTGCCGAGAAAGAAAACGACACCGGCGTGGTG<br>CATCAGGTGGAAGAGTGCAGAGTGAAGGGCCCTGGCATCAGCAAGTT<br>CGTGCAGAAAGTGAACGAGATCGGCATCTACCTGACCGACTGCATGG<br>AACGGGCCAGGGAAGTGATCCCCAGAAGCCAGCACCAGGAAACCCC<br>CGTGTATCTGGGAGCCACCGCCGGCATGAGACTGCTGAGAATGGAAA<br>GCGAGGAACTGGCCGACCGGGTGCTGGACGTGGTGGAAAGAAGCCT<br>GAGCAACTACCCATTCGATTTTCAAGGCGCCAGAATCATCACCGGCCA<br>GGAAGAAGGCGCCTACGGCTGGATCACCATCAACTACCTGCTGGGCA<br>AGTTCAGCCAGAAGAATCAGGAAACCTTCGGCGCCCTGGACCTGGGC<br>GGAGCTTCTACCCAAGTGACCTTCGTGCCCCAGAATCAGACCATCGA<br>GAGCCCCGACAACGCCCTGCAGTTCCGGCTGTACGGCAAGGACTACA<br>ATGTGTACACCCACAGCTTTCTGTGCTACGGAAAGGACCAGGCTCTGT<br>GGCAGAAGCTGGCCAAGGACATCCAGGTGGCCAGCAACGAGATCCT<br>GCGGGACCCTTGCTTCCACCCCGGCTACAAGAAAGTCGTGAACGTGT<br>CCGACCTGTACAAGACCCCCTGCACCAAGAGATTCGAGATGACCCTG<br>CCCTTCCAGCAGTTCGAGATCCAGGGCATCGGCAATTACCAGCAGTG<br>CCACCAGAGCATCCTGGAACTGTTCAACACCAGCTACTGCCCCTACAG<br>CCAGTGCGCCTTCAACGGCATCTTCCTGCCACCTCTGCAGGGGGATT<br>TCGGCGCCTTCAGCGCCTTCTACTTCGTGATGAAGTTCCTGAACCTGA<br>CCAGCGAGAAGGTGTCCCAGGAAAAAGTGACAGAGATGATGAAGAAG<br>TTCTGCGCCCAGCCCTGGGAGGAAATCAAGACCTCCTACGCTGGCGT<br>GAAAGAGAAGTACCTGAGCGAGTACTGCTTCAGCGGCACCTACATCC<br>TGAGCCTGCTGCTGCAGGGCTACCACTTCACCGCCGATAGCTGGGAG<br>CACATCCACTTCATCGGCAAGATTCAGGGCAGCGACGCCGGCTGGAC<br>ACTGGGCTACATGCTGAATCTGACCAACATGATCCCCGCCGAGCAGC<br>CCCTGAGCACACCTCTGAGCCACAGCACC |

EP14_plusMIL

| SEQ ID NO: 155 | Amino acid | TQNKALPENVKYGIVLDAGSSHTSLYIYKWPAEKENDTGVVHQVEECRVK<br>GPGISKFVQKVNEIGIYLTDCMERAREVIPRSQHQETPVYLGATAGMRLLR<br>MESEELADRVLDVVERSLSNYPFDFQGARIITGQEEGAYGWITINYLLGKF<br>SQKTRWFSIVPYETNNQETFGALDLGGASTQVTFVPQNQTIESPDNALQF<br>RLYGKDYNVYTHSFLCYGKDQALWQKLAKDIQVASNEILRDPCFHPGYKK<br>VVNVSDLYKTPCTKRFEMTLPFQQFEIQGIGNYQQCHQSILELFNTSYCPY<br>SQCAFNGIFLPPLQGDFGAFSAFYSVMKFLNLTSEKVSQEKVTEMMKKFC<br>AQPWEEIKTSYAGVKEKYLSEYCFSGTYILSLLLQGYHFTADSWEHIHFIG<br>KIQGSDAGWTLGYMLNLTNMIPAEQPLSTPLSHST |
| SEQ ID NO: 156 | DNA | ACCCAGAACAAGGCCCTGCCCGAGAACGTGAAGTACGGCATCGTGCT<br>GGATGCCGGCAGCAGCCACACCAGCCTGTACATCTACAAGTGGCCTG<br>CCGAGAAAGAAAACGACACCGGCGTGGTGCATCAGGTGGAAGAGTGC<br>AGAGTGAAGGGCCCTGGCATCAGCAAGTTCGTGCAGAAAGTGAACGA<br>GATCGGCATCTACCTGACCGACTGCATGGAACGGGCCAGGGAAGTGA<br>TCCCCAGAAGCCAGCACCAGGAAACCCCCGTGTATCTGGGAGCCACC<br>GCCGGCATGAGACTGCTGAGAATGGAAAGCGAGGAACTGGCCGACC<br>GGGTGCTGGACGTGGTGGAAAGAAGCCTGAGCAACTACCCATTCGAT<br>TTTCAAGGCGCCAGAATCATCACCGGCCAGGAAGAAGGCGCCTACGG<br>CTGGATCACCATCAACTACCTGCTGGGCAAGTTCAGCCAGAAGACCA<br>GATGGTTCAGCATCGTGCCCTACGAGACAAACAATCAGGAAACCTTCG<br>GCGCCCTGGACCTGGGCGGAGCTTCTACCCAAGTGACCTTCGTGCCC<br>CAGAATCAGACCATCGAGAGCCCCGACAACGCCCTGCAGTTCCGGCT<br>GTACGGCAAGGACTACAATGTGTACACCCACAGCTTTCTGTGCTACGG<br>AAAGGACCAGGCTCTGTGGCAGAAGCTGGCCAAGGACATCCAGGTGG<br>CCAGCAACGAGATCCTGCGGGACCCTTGCTTCCACCCCGGCTACAAG |

TABLE 35-continued

Sequences useful for practicing the invention.

| SEQ ID Number | Feature | Sequence |
|---|---|---|
| | | AAAGTCGTGAACGTGTCCGACCTGTACAAGACCCCCTGCACCAAGAG<br>ATTCGAGATGACCCTGCCCTTCCAGCAGTTCGAGATCCAGGGCATCG<br>GCAATTACCAGCAGTGCCACCAGAGCATCCTGGAACTGTTCAACACCA<br>GCTACTGCCCCTACAGCCAGTGCGCCTTCAACGGCATCTTCCTGCCA<br>CCTCTGCAGGGGGATTTCGGCGCCTTCAGCGCCTTCTACTCCGTGAT<br>GAAGTTCCTGAACCTGACCAGCGAGAAGGTGTCCCAGGAAAAAGTGA<br>CAGAGATGATGAAGAAGTTCTGCGCCCAGCCCTGGGAGGAAATCAAG<br>ACCTCCTACGCTGGCGTGAAAGAGAAGTACCTGAGCGAGTACTGCTT<br>CAGCGGCACCTACATCCTGAGCCTGCTGCTGCAGGGCTACCACTTCA<br>CCGCCGATAGCTGGGAGCACATCCACTTCATCGGCAAGATTCAGGGC<br>AGCGACGCCGGCTGGACACTGGGCTACATGCTGAATCTGACCAACAT<br>GATCCCCGCCGAGCAGCCCCTGAGCACACCTCTGAGCCACAGCACC |
| SEQ ID NO: 157 | Forward primer | TCGCGATCCTGGAAGGCGTGCACTGCGCCCCTACCAGCAGCAGCACC<br>AAGAAAACCCAGCTGACCAGCAGCACCCAGAACAAGGCCCTGC |
| SEQ ID NO: 158 | Reverse primer | TAGAAGGCACAGTCGAGG |
| SEQ ID NO: 159 | Forward primer | CTGGTCGCGATCCTGGAAGGCGTGCACTGCGCCCCTACCAGCAGCA<br>GCACCCAGAACAAGGCCCTG |
| SEQ ID NO: 160 | Forward primer | CTGGTCGCGATCCTGGAAGGCGTGCACTGCGCCCCTACCAGCAGCA<br>GCACCCAGAACAAGGCCCTG |
| SEQ ID NO: 161 | Forward primer | CTGGTCGCGATCCTGGAAGGCGTGCACTGCGCCCCTACCACCCAGAA<br>CAAGGCCCTG |
| SEQ ID NO: 162 | Forward primer | CTGGTCGCGATCCTGGAAGGCGTGCACTGCGCCCCTACCAGCAGCA<br>GCACCAAGAAAACCCAGAACAAGGCCCTG |
| SEQ ID NO: 163 | Forward primer | CTGGTCGCGATCCTGGAAGGCGTGCACTGCGCCCCTACCAGCAGCA<br>GCACCAAGAAAACCCAGCTGACCCAGAACAAGGCCCTG |
| SEQ ID NO: 164 | Forward primer | CTGGTCGCGATCCTGGAAGGCGTGCACTGCAGCAGCAGCACCAAGAA<br>AACCCAGCTGACCCAGAACAAGGCCCTG |
| SEQ ID NO: 165 | Primer P270 | CATACGATTTAGGTGA |
| SEQ ID NO: 166 | Primer P271 | TAGAAGGCACAGTCGAGG |
| SEQ ID NO: 167 | Ubiquitin tag | MQIFVKTLTGKTITLEVEPSDTIENVKAKIQDKEGIPPDQQRLIFAGKQLED<br>GRTLSDYNIQKESTLHLVLRLRGG |
| SEQ ID NO: 168 | CKappa tag | TVAAPSVFIFPPSDEQLKSGTASVVCLLNNFYPREAKVQWKVDNALQSGN<br>SQESVTEQDSKDSTYSLSSTLTLSKADYEKHKVYACEVTHQGLSSPVTKS<br>FNRGE |
| SEQ ID NO: 169 | HSA Domain I tag | DAHKSEVAHRFKDLGEENFKALVLIAFAQYLQQSPFEDHVKLVNEVTEFA<br>KTCVADESAENCDKSLHTLFGDKLCTVATLRETYGEMADCCAKQEPERN<br>ECFLQHKDDNPNLPRLVRPEVDVMCTAFHDNEETFLKKYLYEIARRHPYF<br>YAPELLFFAKRYKAAFTECCQAADKAACLLPKLDELR |
| SEQ ID NO: 170 | HSA Domain II tag | DEGKASSAKQRLKCASLQKFGERAFKAWAVARLSQRFPKAEFAEVSKLV<br>TDLTKVHTECCHGDLLECADDRADLAKYICENQDSISSKLKECCEKPLLEK<br>SHCIAEVENDEMPADLPSLAADFVESKDVCKNYAEAKDVFLGMFLYEYAR<br>RHPDYSVVLLLRLAKTYETTLEKCCAAADPHECYAKVFDEFKP |
| SEQ ID NO: 171 | P928 primer | CTGCCGAGAAAGAACAGGACACCGGCGTGG |
| SEQ ID NO: 172 | P929 primer | CCACGCCGGTGTCCTGTTCTTTCTCGGCAG |
| SEQ ID NO: 173 | P930 primer | CGTGCCCCAGAATCAGGCCATCGAGAGCC |
| SEQ ID NO: 174 | P931 primer | GGCTCTCGATGGCCTGATTCTGGGGCACG |
| SEQ ID NO: 175 | P932 primer | GGCTACAAGAAAGTCGTGCAGGTGTCCGACCTGTACAAGAC |

TABLE 35-continued

Sequences useful for practicing the invention.

| SEQ ID Number | Feature | Sequence |
|---|---|---|
| SEQ ID NO: 176 | P933 primer | GTCTTGTACAGGTCGGACACCTGCACGACTTTCTTGTAGCC |
| SEQ ID NO: 177 | P934 primer | GCATCCTGGAACTGTTCCAGACCAGCTACTGCCCC |
| SEQ ID NO: 178 | P935 primer | GGGGCAGTAGCTGGTCTGGAACAGTTCCAGGATGC |
| SEQ ID NO: 179 | P936 primer | CCGTGATGAAGTTCCTGCAGCTGACCAGCGAGAAG |
| SEQ ID NO: 180 | P937 primer | CTTCTCGCTGGTCAGCTGCAGGAACTTCATCACGG |
| SEQ ID NO: 181 | P938 primer | CACTGGGCTACATGCTGCAGCTGACCAACATGATCC |
| SEQ ID NO: 182 | P939 primer | GGATCATGTTGGTCAGCTGCAGCATGTAGCCCAGTG |
| SEQ ID NO: 183 | P878 primer | CTACATCCTGAGCCTGCTGCAGCAGGGCTACCACTTCAC |
| SEQ ID NO: 184 | P879 primer | GTGAAGTGGTAGCCCTGCTGCAGCAGGCTCAGGATGTAG |
| SEQ ID NO: 185 | P880 primer | GAGAAGTACCTGAGCGAGTTTTGCTTCAGCGGCACCTACATCC |
| SEQ ID NO: 186 | P881 primer | GGATGTAGGTGCCGCTGAAGCAAAACTCGCTCAGGTACTTCTC |
| SEQ ID NO: 187 | P882 primer | GTTCGAGATCCAGGGCACCGGCAATTACCAGCAGTG |
| SEQ ID NO: 188 | P883 primer | CACTGCTGGTAATTGCCGGTGCCCTGGATCTCGAAC |
| SEQ ID NO: 189 | P884 primer | CGCCGATAGCTGGGAGCACATCCACTTCATCGGCAAG |
| SEQ ID NO: 190 | P885 primer | CTTGCCGATGAAGTGGATGTGCTCCCAGCTATCGGCG |
| SEQ ID NO: 191 | R113Mt empl | GAGATCGGCATCTACCTGACCGACTGCATGGAACGGGCCATGGAAGTGATCCCCAGAAGCCAGCACCAGGAAACCCCCGTGTATCTGGGAGCCACCGCCGGCATGAGACTGCTGAGAATG |
| SEQ ID NO: 192 | R113MFW | GAGATCGGCATCTACCTGACCGACT |
| SEQ ID NO: 193 | R113M Rev | CATTCTCAGCAGTCTCAT |
| SEQ ID NO: 194 | F330Ste mpl | CTTCAGCGCCTTCTACTcCGTGATGAAGTTCCTGAACCTGACCAGCGAGAAGGTGTCCCAGGAAAAAGTGACAGAGATGATGAAGAAGTTCTGCGCCCAGCCCTGGGAGGAAATCAAGAC |
| SEQ ID NO: 195 | F330S FW | CTTCAGCGCCTTCTACTCC |
| SEQ ID NO: 196 | F330S Rev | GGTCTTGATTTCCTCCCAG |
| SEQ ID NO: 197 | Y377F templ | CTGGGAGGAAATCAAGACCTCCTACGCTGGCGTGAAAGAGAAGTACCTGAGCGAGTtCTGCTTCAGCGGCACCTACATCCTGAGCCTGCTGCTGCAGGGCTACCACTTCACCGCCGATA |
| SEQ ID NO: 198 | L389C templ | CTGGGAGGAAATCAAGACCTCCTACGCTGGCGTGAAAGAGAAGTACCTGAGCGAGTACTGCTTCAGCGGCACCTACATCCTGAGCCTGCTGCaGCAGGGCTACCACTTCACCGCCGATA |

TABLE 35-continued

Sequences useful for practicing the invention.

| SEQ ID Number | Feature | Sequence |
| --- | --- | --- |
| SEQ ID NO: 199 | Y377F/L 389Q templ | CTGGGAGGAAATCAAGACCTCCTACGCTGGCGTGAAAGAGAAGTACC TGAGCGAGTTCTGCTTCAGCGGCACCTACATCCTGAGCCTGCTGCaG CAGGGCTACCACTTCACCGCCGATA |
| SEQ ID NO: 200 | FW primer | CTGGGAGGAAATCAAGACC |
| SEQ ID NO: 201 | Rev primer | TATCGGCGGTGAAGTGGTA |
| SEQ ID NO: 202 | WT primer | CTGGGAGGAAATCAAGACCTCCTACGCTGGCGTGAAAGAGAAGTACC TGAGCGAGTACTGCTTCAGCGGCACCTACATCCTGAGCCTGCTGCTG CAGGGCTACCACTTCACCGCCGATA |
| SEQ ID NO: 203 | fwMut174 | CACCGGCCAGGAAGCCGGCGCCTACG |
| SEQ ID NO: 204 | revMut174 | CGTAGGCGCCGGCTTCCTGGCCGGTG |
| SEQ ID NO: 205 | fwMut218 | GGACCTGGGCGGAGCTGCTACCCAAGTGACCTTC |
| SEQ ID NO: 206 | revMut218 | GAAGGTCACTTGGGTAGCAGCTCCGCCCAGGTCC |
| SEQ ID NO: 207 | plusMILfw | CTGGATCACCATCAACTACCTGCTGGGCAAGTTCAGCCAGAAGACCA GATGGTTCAGCATCGTGCCCTACGAGACAAACA |
| SEQ ID NO: 208 | plusMILrev | TCACTTGGGTAGAAGCTCCGCCCAGGTCCAGGGCGCCGAAGGTTTCC TGATTGTTTGTCTCGTAGGGCA |
| EP1aa1-3 | | |
| SEQ ID NO: 209 | Amino acid | APTTQNKALPENVKYGIVLDAGSSHTSLYIYKWPAEKENDTGVVHQVEEC RVKGPGISKFVQKVNEIGIYLTDCMERAMEVIPRSQHQETPVYLGATAGM RLLRMESEELADRVLDVVERSLSNYPFDFQGARIITGQEEGAYGWITINYL LGKFSQKNQETFGALDLGGASTQVTFVPQNQTIESPDNALQFRLYGKDY NVYTHSFLCYGKDQALWQKLAKDIQVASNEILRDPCFHPGYKKVVNVSDL YKTPCTKRFEMTLPFQQFEIQGIGNYQQCHQSILELFNTSYCPYSQCAFN GIFLPPLQGDFGAFSAFYFVMKFLNLTSEKVSQEKVTEMMKKFCAQPWE EIKTSYAGVKEKYLSEYCFSGTYILSLLLQGYHFTADSWEHIHFIGKIQGSD AGWTLGYMLNLTNMIPAEQPLSTPLSHST |
| SEQ ID NO: 210 | DNA | GCCCCTACCACCCAGAACAAGGCCCTGCCCGAGAACGTGAAGTACGG CATCGTGCTGGATGCCGGCAGCAGCCACACCAGCCTGTACATCTACA AGTGGCCTGCCGAGAAAGAAAACGACACCGGCGTGGTGCATCAGGTG GAAGAGTGCAGAGTGAAGGGCCCTGGCATCAGCAAGTTCGTGCAGAA AGTGAACGAGATCGGCATCTACCTGACCGACTGCATGGAACGGGCCA TGGAAGTGATCCCCAGAAGCCAGCACCAGGAAACCCCCGTGTATCTG GGAGCCACCGCCGGCATGAGACTGCTGAGAATGGAAAGCGAGGAAC TGGCCGACCGGGTGCTGGACGTGGTGGAAAGAAGCCTGAGCAACTA CCCATTCGATTTTCAAGGCGCCAGAATCATCACCGGCCAGGAAGAAG GCGCCTACGGCTGGATCACCATCAACTACCTGCTGGGCAAGTTCAGC CAGAAGAATCAGGAAACCTTCGGCGCCCTGGACCTGGGCGGAGCTTC TACCCAAGTGACCTTCGTGCCCCAGAATCAGACCATCGAGAGCCCCG ACAACGCCCTGCAGTTCCGGCTGTACGGCAAGGACTACAATGTGTAC ACCCACAGCTTTCTGTGCTACGGAAAGGACCAGGCTCTGTGGCAGAA GCTGGCCAAGGACATCCAGGTGGCCAGCAACGAGATCCTGCGGGAC CCTTGCTTCCACCCCGGCTACAAGAAAGTCGTGAACGTGTCCGACCT GTACAAGACCCCCTGCACCAAGAGATTCGAGATGACCCTGCCCTTCC AGCAGTTCGAGATCCAGGGCATCGGCAATTACCAGCAGTGCCACCAG AGCATCCTGGAACTGTTCAACACCAGCTACTGCCCCTACAGCCAGTGC GCCTTCAACGGCATCTTCCTGCCACCTCTGCAGGGGATTTCGGCGC CTTCAGCGCCTTCTACTTCGTGATGAAGTTCCTGAACCTGACCAGCGA GAAGGTGTCCCAGGAAAAGTGACAGAGATGATGAAGAAGTTCTGCG CCCAGCCCTGGGAGGAAATCAAGACCTCCTACGCTGGCGTGAAAGAG AAGTACCTGAGCGAGTACTGCTTCAGCGGCACCTACATCCTGAGCCT GCTGCTGCAGGGCTACCACTTCACCGCCGATAGCTGGGAGCACATCC ACTTCATCGGCAAGATTCAGGGCAGCGACGCCGGCTGGACACTGGGC TACATGCTGAATCTGACCAACATGATCCCCGCCGAGCAGCCCCTGAG CACACCTCTGAGCCACAGCACC |

TABLE 35-continued

Sequences useful for practicing the invention.

| SEQ ID Number | Feature | Sequence |
|---|---|---|
| EP1xEP17aa1-3 | | |
| SEQ ID NO: 211 | Amino acid | APTTQNKALPENVKYGIVLDAGSSHTSLYIYKWPAEKENDTGVVHQVEEC RVKGPGISKFVQKVNEIGIYLTDCMERAMEVIPRSQHQETPVYLGATAGM RLLRMESEELADRVLDVVERSLSNYPFDFQGARIITGQEEGAYGWITINYL LGKFSQKNQETFGALDLGGASTQVTFVPQNQTIESPDNALQFRLYGKDY NVYTHSFLCYGKDQALWQKLAKDIQVASNEILRDPCFHPGYKKVVNVSDL YKTPCTKRFEMTLPFQQFEIQGIGNYQQCHQSILELFNTSYCPYSQCAFN GIFLPPLQGDFGAFSAFYFVMKFLNLTSEKVSQEKVTEMMKKFCAQPWE EIKTSYAGVKEKYLSEFCFSGTYILSLLLQGYHFTADSWEHIHFIGKIQGSD AGWTLGYMLNLTNMIPAEQPLSTPLSHST |
| SEQ ID NO: 212 | DNA | GCCCCTACCACCCAGAACAAGGCCCTGCCCGAGAACGTGAAGTACGG CATCGTGCTGGATGCCGGCAGCAGCCACACCAGCCTGTACATCTACA AGTGGCCTGCCGAGAAGAAAACGACACCGGCGTGGTGCATCAGGTG GAAGAGTGCAGAGTGAAGGGCCCTGGCATCAGCAAGTTCGTGCAGAA AGTGAACGAGATCGGCATCTACCTGACCGACTGCATGGAACGGGCCA TGGAAGTGATCCCCAGAAGCCAGCACCAGGAAACCCCCGTGTATCTG GGAGCCACCGCCGGCATGAGACTGCTGAGAATGGAAAGCGAGGAAC TGGCCGACCGGGTGCTGGACGTGGTGGAAAGAAGCCTGAGCAACTA CCCATTCGATTTTCAAGGCGCCAGAATCATCACCGGCCAGGAAGAAG GCGCCTACGGCTGGATCACCATCAACTACCTGCTGGGCAAGTTCAGC CAGAAGAATCAGGAAACCTTCGGCGCCCTGGACCTGGGCGGAGCTTC TACCCAAGTGACCTTCGTGCCCCAGAATCAGACCATCGAGAGCCCCG ACAACGCCCTGCAGTTCCGGCTGTACGGCAAGGACTACAATGTGTAC ACCCACAGCTTTCTGTGCTACGGAAAGGACCAGGCTCTGTGGCAGAA GCTGGCCAAGGACATCCAGGTGGCCAGCAACGAGATCCTGCGGGAC CCTTGCTTCCACCCCGGCTACAAGAAAGTCGTGAACGTGTCCGACCT GTACAAGACCCCCTGCACCAAGAGATTCGAGATGACCCTGCCCTTCC AGCAGTTCGAGATCCAGGGCATCGGCAATTACCAGCAGTGCCACCAG AGCATCCTGGAACTGTTCAACACCAGCTACTGCCCCTACAGCCAGTGC GCCTTCAACGGCATCTTCCTGCCACCTCTGCAGGGGGATTTCGGCGC CTTCAGCGCCTTCTACTTCGTGATGAAGTTCCTGAACCTGACCAGCGA GAAGGTGTCCCAGGAAAAGTGACAGAGATGATGAAGAAGTTCTGCG CCCAGCCCTGGGAGGAAATCAAGACCTCCTACGCTGGCGTGAAAGAG AAGTACCTGAGCGAGTTTTGCTTCAGCGGCACCTACATCCTGAGCCTG CTGCTGCAGGGCTACCACTTCACCGCCGATAGCTGGGAGCACATCCA CTTCATCGGCAAGATTCAGGGCAGCGACGCCGGCTGGACACTGGGCT ACATGCTGAATCTGACCAACATGATCCCCGCCGAGCAGCCCCTGAGC ACACCTCTGAGCCACAGCACC |
| EP1xEP17aa1-6 | | |
| SEQ ID NO: 213 | Amino acid | APTSSSTQNKALPENVKYGIVLDAGSSHTSLYIYKWPAEKENDTGVVHQV EECRVKGPGISKFVQKVNEIGIYLTDCMERAMEVIPRSQHQETPVYLGAT AGMRLLRMESEELADRVLDVVERSLSNYPFDFQGARIITGQEEGAYGWIT INYLLGKFSQKNQETFGALDLGGASTQVTFVPQNQTIESPDNALQFRLYG KDYNVYTHSFLCYGKDQALWQKLAKDIQVASNEILRDPCFHPGYKKVVNV SDLYKTPCTKRFEMTLPFQQFEIQGIGNYQQCHQSILELFNTSYCPYSQC AFNGIFLPPLQGDFGAFSAFYFVMKFLNLTSEKVSQEKVTEMMKKFCAQP WEEIKTSYAGVKEKYLSEFCFSGTYILSLLLQGYHFTADSWEHIHFIGKIQG SDAGWTLGYMLNLTNMIPAEQPLSTPLSHST |
| SEQ ID NO: 214 | DNA | GCCCCTACCAGCAGCAGCACCCAGAACAAGGCCCTGCCCGAGAACGT GAAGTACGGCATCGTGCTGGATGCCGGCAGCAGCCACACCAGCCTGT ACATCTACAAGTGGCCTGCCGAGAAGAAAACGACACCGGCGTGGTG CATCAGGTGGAAGAGTGCAGAGTGAAGGGCCCTGGCATCAGCAAGTT CGTGCAGAAAGTGAACGAGATCGGCATCTACCTGACCGACTGCATGG AACGGGCCATGGAAGTGATCCCCAGAAGCCAGCACCAGGAAACCCCC GTGTATCTGGGAGCCACCGCCGGCATGAGACTGCTGAGAATGGAAAG CGAGGAACTGGCCGACCGGGTGCTGGACGTGGTGGAAAGAAGCCTG AGCAACTACCCATTCGATTTTCAAGGCGCCAGAATCATCACCGGCCAG GAAGAAGGCGCCTACGGCTGGATCACCATCAACTACCTGCTGGGCAA GTTCAGCCAGAAGAATCAGGAAACCTTCGGCGCCCTGGACCTGGGCG GAGCTTCTACCCAAGTGACCTTCGTGCCCCAGAATCAGACCATCGAGA GCCCCGACAACGCCCTGCAGTTCCGGCTGTACGGCAAGGACTACAAT GTGTACACCCACAGCTTTCTGTGCTACGGAAAGGACCAGGCTCTGTG GCAGAAGCTGGCCAAGGACATCCAGGTGGCCAGCAACGAGATCCTGC GGGACCCTTGCTTCCACCCCGGCTACAAGAAAGTCGTGAACGTGTCC GACCTGTACAAGACCCCCTGCACCAAGAGATTCGAGATGACCCTGCC CTTCCAGCAGTTCGAGATCCAGGGCATCGGCAATTACCAGCAGTGCC ACCAGAGCATCCTGGAACTGTTCAACACCAGCTACTGCCCCTACAGCC AGTGCGCCTTCAACGGCATCTTCCTGCCACCTCTGCAGGGGGATTTC GGCGCCTTCAGCGCCTTCTACTTCGTGATGAAGTTCCTGAACCTGACC AGCGAGAAGGTGTCCCAGGAAAAGTGACAGAGATGATGAAGAAGTT |

TABLE 35-continued

Sequences useful for practicing the invention.

| SEQ ID Number | Feature | Sequence |
|---|---|---|
| | | CTGCGCCCAGCCCTGGGAGGAAATCAAGACCTCCTACGCTGGCGTGA<br>AAGAGAAGTACCTGAGCGAGTTCTGCTTCAGCGGCACCTACATCCTGA<br>GCCTGCTGCTGCAGGGCTACCACTTCACCGCCGATAGCTGGGAGCAC<br>ATCCACTTCATCGGCAAGATTCAGGGCAGCGACGCCGGCTGGACACT<br>GGGCTACATGCTGAATCTGACCAACATGATCCCCGCCGAGCAGCCCC<br>TGAGCACACCTCTGAGCCACAGCACC |
| EP1xEP17_K405Naa1-15 | | |
| SEQ ID NO: 215 | Amino acid | APTSSSTKKTQLTSSTQNKALPENVKYGIVLDAGSSHTSLYIYKWPAEKEN<br>DTGVVHQVEECRVKGPGISKFVQKVNEIGIYLTDCMERAMEVIPRSQHQE<br>TPVYLGATAGMRLLRMESEELADRVLDVVERSLSNYPFDFQGARIITGQE<br>EGAYGWITINYLLGKFSQKNQETFGALDLGGASTQVTFVPQNQTIESPDN<br>ALQFRLYGKDYNVYTHSFLCYGKDQALWQKLAKDIQVASNEILRDPCFHP<br>GYKKVVNVSDLYKTPCTKRFEMTLPFQQFEIQGIGNYQQCHQSILELFNT<br>SYCPYSQCAFNGIFLPPLQGDFGAFSAFYFVMKFLNLTSEKVSQEKVTEM<br>MKKFCAQPWEEIKTSYAGVNEKYLSEFCFSGTYILSLLLQGYHFTADSWE<br>HIHFIGKIQGSDAGWTLGYMLNLTNMIPAEQPLSTPLSHST |
| SEQ ID NO: 216 | DNA | GCCCCTACCAGCAGCAGCACCAAGAAAACCCAGCTGACCAGCAGCAC<br>CCAGAACAAGGCCCTGCCCGAGAACGTGAAGTACGGCATCGTGCTGG<br>ATGCCGGCAGCAGCCACACCAGCCTGTACATCTACAAGTGGCCTGCC<br>GAGAAAGAAAACGACACCGGCGTGGTGCATCAGGTGGAAGAGTGCAG<br>AGTGAAGGGCCCTGGCATCAGCAAGTTCGTGCAGAAAGTGAACGAGA<br>TCGGCATCTACCTGACCGACTGCATGGAACGGGCCATGGAAGTGATC<br>CCCAGAAGCCAGCACCAGGAAACCCCCGTGTATCTGGGAGCCACCGC<br>CGGCATGAGACTGCTGAGAATGGAAAGCGAGGAACTGGCCGACCGG<br>GTGCTGGACGTGGTGGAAAGAAGCCTGAGCAACTACCCATTCGATTTT<br>CAAGGCGCCAGAATCATCACCGGCCAGGAAGAAGGCGCCTACGGCT<br>GGATCACCATCAACTACCTGCTGGGCAAGTTCAGCCAGAAGAATCAG<br>GAAACCTTCGGCGCCCTGGACCTGGGCGGAGCTTCTACCCAAGTGAC<br>CTTCGTGCCCCAGAATCAGACCATCGAGAGCCCCGACAACGCCCTGC<br>AGTTCCGGCTGTACGGCAAGGACTACAATGTGTACACCCACAGCTTTC<br>TGTGCTACGGAAAGGACCAGGCTCTGTGGCAGAAGCTGGCCAAGGAC<br>ATCCAGGTGGCCAGCAACGAGATCCTGCGGGACCCTTGCTTCCACCC<br>CGGCTACAAGAAAGTCGTGAACGTGTCCGACCTGTACAAGACCCCCT<br>GCACCAAGAGATTCGAGATGACCCTGCCCTTCCAGCAGTTCGAGATC<br>CAGGGCATCGGCAATTACCAGCAGTGCCACCAGAGCATCCTGGAACT<br>GTTCAACACCAGCTACTGCCCCTACAGCCAGTGCGCCTTCAACGGCA<br>TCTTCCTGCCACCTCTGCAGGGGATTTCGGCGCCTTCAGCGCCTTC<br>TACTTCGTGATGAAGTTCCTGAACCTGACCAGCGAGAAGGTGTCCCAG<br>GAAAAAGTGACAGAGATGATGAAGAAGTTCTGCGCCCAACCCTGGGA<br>GGAAATCAAGACCTCCTACGCTGGCGTGAACGAGAAGTACCTGAGCG<br>AGTTTTGCTTCAGCGGCACCTACATCCTGAGCCTGCTGCTGCAGGGC<br>TACCACTTCACCGCCGATAGCTGGGAGCACATCCACTTCATCGGCAA<br>GATTCAGGGCAGCGACGCCGGCTGGACACTGGGCTACATGCTGAATC<br>TGACCAACATGATCCCCGCCGAGCAGCCCCTGAGCACACCTCTGAGC<br>CACAGCACC |
| EP1xEP17xEP19aa1-3 | | |
| SEQ ID NO: 217 | Amino acid | APTTQNKALPENVKYGIVLDAGSSHTSLYIYKWPAEKENDTGVVHQVEEC<br>RVKGPGISKFVQKVNEIGIYLTDCMERAMEVIPRSQHQETPVYLGATAGM<br>RLLRMESEELADRVLDVVERSLSNYPFDFQGARITGQEEGAYGWITINYL<br>LGKFSQKNQETFGALDLGGASTQVTFVPQNQTIESPDNALQFRLYGKDY<br>NVYTHSFLCYGKDQALWQKLAKDIQVASNEILRDPCFHPGYKKVVNVSDL<br>YKTPCTKRFEMTLPFQQFEIQGIGNYQQCHQSILELFNTSYCPYSQCAFN<br>GIFLPPLQGDFGAFSAFYFVMKFLNLTSEKVSQEKVTEMMKKFCAQPWE<br>EIKTSYAGVKEKYLSEFCFSGTYILSLLQQGYHFTADSWEHIHFIGKIQGSD<br>AGWTLGYMLNLTNMIPAEQPLSTPLSHST |
| SEQ ID NO: 218 | DNA | GCCCCTACCACCCAGAACAAGGCCCTGCCCGAGAACGTGAAGTACGG<br>CATCGTGCTGGATGCCGGCAGCAGCCACACCAGCCTGTACATCTACA<br>AGTGGCCTGCCGAGAAAGAAAACGACACCGGCGTGGTGCATCAGGTG<br>GAAGAGTGCAGAGTGAAGGGCCCTGGCATCAGCAAGTTCGTGCAGAA<br>AGTGAACGAGATCGGCATCTACCTGACCGACTGCATGGAACGGGCCA<br>TGGAAGTGATCCCCAGAAGCCAGCACCAGGAAACCCCCGTGTATCTG<br>GGAGCCACCGCCGGCATGAGACTGCTGAGAATGGAAAGCGAGGAAC<br>TGGCCGACCGGGTGCTGGACGTGGTGGAAAGAAGCCTGAGCAACTA<br>CCCATTCGATTTTCAAGGCGCCAGAATCATCACCGGCCAGGAAGAAG<br>GCGCCTACGGCTGGATCACCATCAACTACCTGCTGGGCAAGTTCAGC<br>CAGAAGAATCAGGAAACCTTCGGCGCCCTGGACCTGGGCGGAGCTTC<br>TACCCAAGTGACCTTCGTGCCCCAGAATCAGACCATCGAGAGCCCCG<br>ACAACGCCCTGCAGTTCCGGCTGTACGGCAAGGACTACAATGTGTAC<br>ACCCACAGCTTTCTGTGCTACGGAAAGGACCAGGCTCTGTGGCAGAA |

TABLE 35-continued

Sequences useful for practicing the invention.

| SEQ ID Number | Feature | Sequence |
|---|---|---|
| | | GCTGGCCAAGGACATCCAGGTGGCCAGCAACGAGATCCTGCGGGAC<br>CCTTGCTTCCACCCCGGCTACAAGAAAGTCGTGAACGTGTCCGACCT<br>GTACAAGACCCCCTGCACCAAGAGATTCGAGATGACCCTGCCCTTCC<br>AGCAGTTCGAGATCCAGGGCATCGGCAATTACCAGCAGTGCCACCAG<br>AGCATCCTGGAACTGTTCAACACCAGCTACTGCCCCTACAGCCAGTGC<br>GCCTTCAACGGCATCTTCCTGCCACCTCTGCAGGGGGATTTCGGCGC<br>CTTCAGCGCCTTCTACTTCGTGATGAAGTTCCTGAACCTGACCAGCGA<br>GAAGGTGTCCCAGGAAAAAGTGACAGAGATGATGAAGAAGTTCTGCG<br>CCCAGCCCTGGGAGGAAATCAAGACCTCCTACGCTGGCGTGAAAGAG<br>AAGTACCTGAGCGAGTTCTGCTTCAGCGGCACCTACATCCTGAGCCT<br>GCTGCAGCAGGGCTACCACTTCACCGCCGATAGCTGGGAGCACATCC<br>ACTTCATCGGCAAGATTCAGGGCAGCGACGCCGGCTGGACACTGGGC<br>TACATGCTGAATCTGACCAACATGATCCCCGCCGAGCAGCCCCTGAG<br>CACACCTCTGAGCCACAGCACC |

EP1xEP17xEP19aa1-6

| SEQ ID NO: 219 | Amino acid | APTSSSTQNKALPENVKYGIVLDAGSSHTSLYIYKWPAEKENDTGVVHQV<br>EECRVKGPGISKFVQKVNEIGIYLTDCMERAMEVIPRSQHQETPVYLGAT<br>AGMRLLRMESEELADRVLDVVERSLSNYPFDFQGARIITGQEEGAYGWIT<br>INYLLGKFSQKNQETFGALDLGGASTQVTFVPQNQTIESPDNALQFRLYG<br>KDYNVYTHSFLCYGKDQALWQKLAKDIQVASNEILRDPCFHPGYKKVVNV<br>SDLYKTPCTKRFEMTLPFQQFEIQGIGNYQQCHQSILELFNTSYCPYSQC<br>AFNGIFLPPLQGDFGAFSAFYFVMKFLNLTSEKVSQEKVTEMMKKFCAQP<br>WEEIKTSYAGVKEKYLSEFCFSGTYILSLLQQGYHFTADSWEHIHFIGKIQ<br>GSDAGWTLGYMLNLTNMIPAEQPLSTPLSHST |
| SEQ ID NO: 220 | DNA | GCCCCTACCAGCAGCAGCACCCAGAACAAGGCCCTGCCCGAGAACGT<br>GAAGTACGGCATCGTGCTGGATGCCGGCAGCAGCCACACCAGCCTGT<br>ACATCTACAAGTGGCCTGCCGAGAAAGAAAACGACACCGGCGTGGTG<br>CATCAGGTGGAAGAGTGCAGAGTGAAGGGCCCTGGCATCAGCAAGTT<br>CGTGCAGAAAGTGAACGAGATCGGCATCTACCTGACCGACTGCATGG<br>AACGGGCCATGGAAGTGATCCCCAGAAGCCAGCACCAGGAAACCCCC<br>GTGTATCTGGGAGCCACCGCCGGCATGAGACTGCTGAGAATGGAAAG<br>CGAGGAACTGGCCGACCGGGTGCTGGACGTGGTGGAAAGAAGCCTG<br>AGCAACTACCCATTCGATTTTCAAGGCGCCAGAATCATCACCGGCCAG<br>GAAGAAGGCGCCTACGGCTGGATCACCATCAACTACCTGCTGGGCAA<br>GTTCAGCCAGAAGAATCAGGAAACCTTCGGCGCCCTGGACCTGGGCG<br>GAGCTTCTACCCAAGTGACCTTCGTGCCCCAGAATCAGACCATCGAGA<br>GCCCCGACAACGCCCTGCAGTTCCGGCTGTACGGCAAGGACTACAAT<br>GTGTACACCCACAGCTTTCTGTGCTACGGAAAGGACCAGGCTCTGTG<br>GCAGAAGCTGGCCAAGGACATCCAGGTGGCCAGCAACGAGATCCTGC<br>GGGACCCTTGCTTCCACCCCGGCTACAAGAAAGTCGTGAACGTGTCC<br>GACCTGTACAAGACCCCCTGCACCAAGAGATTCGAGATGACCCTGCC<br>CTTCCAGCAGTTCGAGATCCAGGGCATCGGCAATTACCAGCAGTGCC<br>ACCAGAGCATCCTGGAACTGTTCAACACCAGCTACTGCCCCTACAGCC<br>AGTGCGCCTTCAACGGCATCTTCCTGCCACCTCTGCAGGGGGATTTC<br>GGCGCCTTCAGCGCCTTCTACTTCGTGATGAAGTTCCTGAACCTGACC<br>AGCGAGAAGGTGTCCCAGGAAAAAGTGACAGAGATGATGAAGAAGTT<br>CTGCGCCCAGCCCTGGGAGGAAATCAAGACCTCCTACGCTGGCGTGA<br>AAGAGAAGTACCTGAGCGAGTTCTGCTTCAGCGGCACCTACATCCTGA<br>GCCTGCTGCAGCAGGGCTACCACTTCACCGCCGATAGCTGGGAGCAC<br>ATCCACTTCATCGGCAAGATTCAGGGCAGCGACGCCGGCTGGACACT<br>GGGCTACATGCTGAATCTGACCAACATGATCCCCGCCGAGCAGCCCC<br>TGAGCACACCTCTGAGCCACAGCACC |

EP1xEP14aa1-3

| SEQ ID NO: 221 | Amino acid | APTTQNKALPENVKYGIVLDAGSSHTSLYIYKWPAEKENDTGVVHQVEEC<br>RVKGPGISKFVQKVNEIGIYLTDCMERAMEVIPRSQHQETPVYLGATAGM<br>RLLRMESEELADRVLDVVERSLSNYPFDFQGARIITGQEEGAYGWITINYL<br>LGKFSQKNQETFGALDLGGASTQVTFVPQNQTIESPDNALQFRLYGKDY<br>NVYTHSFLCYGKDQALWQKLAKDIQVASNEILRDPCFHPGYKKVVNVSDL<br>YKTPCTKRFEMTLPFQQFEIQGIGNYQQCHQSILELFNTSYCPYSQCAFN<br>GIFLPPLQGDFGAFSAFYSVMKFLNLTSEKVSQEKVTEMMKKFCAQPVVE<br>EIKTSYAGVKEKYLSEYCFSGTYILSLLLQGYHFTADSWEHIHFIGKIQGSD<br>AGWTLGYMLNLTNMIPAEQPLSTPLSHST |
| SEQ ID NO: 222 | DNA | GCCCCTACCACCCAGAACAAGGCCCTGCCCGAGAACGTGAAGTACGG<br>CATCGTGCTGGATGCCGGCAGCAGCCACACCAGCCTGTACATCTACA<br>AGTGGCCTGCCGAGAAAGAAAACGACACCGGCGTGGTGCATCAGGTG<br>GAAGAGTGCAGAGTGAAGGGCCCTGGCATCAGCAAGTTCGTGCAGAA<br>AGTGAACGAGATCGGCATCTACCTGACCGACTGCATGGAACGGGCCA<br>TGGAAGTGATCCCCAGAAGCCAGCACCAGGAAACCCCCGTGTATCTG<br>GGAGCCACCGCCGGCATGAGACTGCTGAGAATGGAAAGCGAGGAAC |

TABLE 35-continued

Sequences useful for practicing the invention.

| SEQ ID Number | Feature | Sequence |
|---|---|---|
| | | TGGCCGACCGGGTGCTGGACGTGGTGGAAAGAAGCCTGAGCAACTA<br>CCCATTCGATTTTCAAGGCGCCAGAATCATCACCGGCCAGGAAGAAG<br>GCGCCTACGGCTGGATCACCATCAACTACCTGCTGGGCAAGTTCAGC<br>CAGAAGAATCAGGAAACCTTCGGCGCCTTGGACCTGGGCGGAGCTTC<br>TACCCAAGTGACCTTCGTGCCCCAGAATCAGACCATCGAGAGCCCCG<br>ACAACGCCCTGCAGTTCCGGCTGTACGGCAAGGACTACAATGTGTAC<br>ACCCACAGCTTTCTGTGCTACGGAAAGGACCAGGCTCTGTGGCAGAA<br>GCTGGCCAAGGACATCCAGGTGGCCAGCAACGAGATCCTGCGGGAC<br>CCTTGCTTCCACCCCGGCTACAAGAAAGTCGTGAACGTGTCCGACCT<br>GTACAAGACCCCCTGCACCAAGAGATTCGAGATGACCCTGCCCTTCC<br>AGCAGTTCGAGATCCAGGGCATCGGCAATTACCAGCAGTGCCACCAG<br>AGCATCCTGGAACTGTTCAACACCAGCTACTGCCCCTACAGCCAGTGC<br>GCCTTCAACGGCATCTTCCTGCCACCTCTGCAGGGGGATTTCGGCGC<br>CTTCAGCGCCTTCTACTCCGTGATGAAGTTCCTGAACCTGACCAGCGA<br>GAAGGTGTCCCAGGAAAAGTGACAGAGATGATGAAGAAGTTCTGCG<br>CCCAGCCCTGGGAGGAAATCAAGACCTCCTACGCTGGCGTGAAAGAG<br>AAGTACCTGAGCGAGTACTGCTTCAGCGGCACCTACATCCTGAGCCT<br>GCTGCTGCAGGGCTACCACTTCACCGCCGATAGCTGGGAGCACATCC<br>ACTTCATCGGCAAGATTCAGGGCAGCGACGCCGGCTGGACACTGGGT<br>TACATGCTGAATCTGACCAACATGATCCCCGCCGAGCAGCCCCTGAG<br>CACACCTCTGAGCCACAGCACC |

EP1xEP14aa1-6

| SEQ ID NO: 223 | Amino acid | APTSSSTQNKALPENVKYGIVLDAGSSHTSLYIYKWPAEKENDTGVVHQV<br>EECRVKGPGISKFVQKVNEIGIYLTDCMERAMEVIPRSQHQETPVVLGAT<br>AGMRLLRMESEELADRVLDVVERSLSNYPFDFQGARIITGQEEGAYGWIT<br>INYLLGKFSQKNQETFGALDLGGASTQVTFVPQNQTIESPDNALQFRLYG<br>KDYNVYTHSFLCYGKDQALWQKLAKDIQVASNEILRDPCFHPGYKKVVNV<br>SDLYKTPCTKRFEMTLPFQQFEIQGIGNYQQCHQSILELFNTSYCPYSQC<br>AFNGIFLPPLQGDFGAFSAFYSVMKFLNLTSEKVSQEKVTEMMKKFCAQP<br>WEEIKTSYAGVKEKYLSEYCFSGTYILSLLLQGYHFTADSWEHIHFIGKIQG<br>SDAGWTLGYMLNLTNMIPAEQPLSTPLSHST |
| SEQ ID NO: 224 | DNA | GCCCCTACCAGCAGCAGCACCCAGAACAAGGCCCTGCCCGAGAACGT<br>GAAGTACGGCATCGTGCTGGATGCCGGCAGCAGCCACACCAGCCTGT<br>ACATCTACAAGTGGCCTGCCGAGAAAGAAAACGACACCGGCGTGGTG<br>CATCAGGTGGAAGAGTGCAGAGTGAAGGGCCCTGGCATCAGCAAGTT<br>CGTGCAGAAAGTGAACGAGATCGGCATCTACCTGACCGACTGCATGG<br>AACGGGCCATGGAAGTGATCCCCAGAAGCCAGCACCAGGAAACCCCC<br>GTGGTATCTGGGAGCCACCGCCGGCATGAGACTGCTGAGAATGGAAAG<br>CGAGGAACTGGCCGACGGGTGCTGGACGTGGTGGAAAGAAGCCTG<br>AGCAACTACCCATTCGATTTTCAAGGCGCCAGAATCATCACCGGCCAG<br>GAAGAAGGCGCCTACGGCTGGATCACCATCAACTACCTGCTGGGCAA<br>GTTCAGCCAGAAGAATCAGGAAACCTTCGGCGCCTTGGACCTGGGCG<br>GAGCTTCTACCCAAGTGACCTTCGTGCCCCAGAATCAGACCATCGAGA<br>GCCCCGACAACGCCCTGCAGTTCCGGCTGTACGGCAAGGACTACAAT<br>GTGTACACCCACAGCTTTCTGTGCTACGGAAAGGACCAGGCTCTGTGG<br>CAGAAGCTGGCCAAGGACATCCAGGTGGCCAGCAACGAGATCCTGC<br>GGGACCCTTGCTTCCACCCCGGCTACAAGAAAGTCGTGAACGTGTCC<br>GACCTGTACAAGACCCCCTGCACCAAGAGATTCGAGATGACCCTGCC<br>CTTCCAGCAGTTCGAGATCCAGGGCATCGGCAATTACCAGCAGTGCC<br>ACCAGAGCATCCTGGAACTGTTCAACACCAGCTACTGCCCCTACAGCC<br>AGTGCGCCTTCAACGGCATCTTCCTGCCACCTCTGCAGGGGGATTTC<br>GGCGCCTTCAGCGCCTTCTACTCCGTGATGAAGTTCCTGAACCTGACC<br>AGCGAGAAGGTGTCCCAGGAAAAGTGACAGAGATGATGAAGAAGTT<br>CTGCGCCCAGCCCTGGGAGGAAATCAAGACCTCCTACGCTGGCGTGA<br>AAGAGAAGTACCTGAGCGAGTACTGCTTCAGCGGCACCTACATCCTG<br>AGCCTGCTGCTGCAGGGCTACCACTTCACCGCCGATAGCTGGGAGCA<br>CATCCACTTCATCGGCAAGATTCAGGGCAGCGACGCCGGCTGGACAC<br>TGGGTTACATGCTGAATCTGACCAACATGATCCCCGCCGAGCAGCCC<br>CTGAGCACACCTCTGAGCCACAGCACC |

EP17xEP19aa1-3

| SEQ ID NO: 225 | Amino acid | APTTQNKALPENVKYGIVLDAGSSHTSLYIYKWPAEKENDTGVVHQVEEC<br>RVKGPGISKFVQKVNEIGIYLTDCMERAREVIPRSQHQETPVVLGATAGM<br>RLLRMESEELADRVLDVVERSLSNYPPDFQGARIITGQEEGAYGWITINYL<br>LGKFSQKNQETFGALDLGGASTQVTFVPQNQTIESPDNALQFRLYGKDY<br>NVYTHSFLCYGKDQALWQKLAKDIQVASNEILRDPCFHPGYKKVVNVSDL<br>YKTPCTKRFEMTLPFQQFEIQGIGNYQQCHQSILELFNTSYCPYSQCAFN<br>GIFLPPLQGDFGAFSAFYFVMKFLNLTSEKVSQEKVTEMMKKFCAQPWE<br>EIKTSYAGVKEKYLSEFCFSGTYILSLLQQGYHFTADSWEHIHFIGKIQGSD<br>AGWTLGYMLNLTNMIPAEQPLSTPLSHST |

TABLE 35-continued

Sequences useful for practicing the invention.

| SEQ ID Number | Feature | Sequence |
|---|---|---|
| SEQ ID NO: 226 | DNA | GCCCCTACCACCCAGAACAAGGCCCTGCCCGAGAACGTGAAGTACGG<br>CATCGTGCTGGATGCCGGCAGCAGCCACACCAGCCTGTACATCTACA<br>AGTGGCCTGCCGAGAAAGAAAACGACACCGGCGTGGTGCATCAGGTG<br>GAAGAGTGCAGAGTGAAGGGCCCTGGCATCAGCAAGTTCGTGCAGAA<br>AGTGAACGAGATCGGCATCTACCTGACCGACTGCATGGAACGGGCCA<br>GGGAAGTGATCCCCAGAAGCCAGCACCAGGAAACCCCCGTGTATCTG<br>GGAGCCACCGCCGGCATGAGACTGCTGAGAATGGAAAGCGAGGAAC<br>TGGCCGACCGGGTGCTGGACGTGGTGGAAAGAAGCCTGAGCAACTA<br>CCCATTCGATTTTCAAGGCGCCAGAATCATCACCGGCCAGGAAGAAG<br>GCGCCTACGGCTGGATCACCATCAACTACCTGCTGGGCAAGTTCAGC<br>CAGAAGAATCAGGAAACCTTCGGCGCCCTGGACCTGGGCGGAGCTTC<br>TACCCAAGTGACCTTCGTGCCCCAGAATCAGACCATCGAGAGCCCCG<br>ACAACGCCCTGCAGTTCCGGCTGTACGGCAAGGACTACAATGTGTAC<br>ACCCACAGCTTTCTGTGCTACGGAAAGGACCAGGCTCTGTGGCAGAA<br>GCTGGCCAAGGACATCCAGGTGGCCAGCAACGAGATCCTGCGGGAC<br>CCTTGCTTCCACCCCGGCTACAAGAAAGTCGTGAACGTGTCCGACCT<br>GTACAAGACCCCCTGCACCAAGAGATTCGAGATGACCCTGCCCTTCC<br>AGCAGTTCGAGATCCAGGGCATCGGCAATTACCAGCAGTGCCACCAG<br>AGCATCCTGGAACTGTTCAACACCAGCTACTGCCCCTACAGCCAGTGC<br>GCCTTCAACGGCATCTTCCTGCCACCTCTGCAGGGGGATTCGGCGC<br>CTTCAGCGCCTTCTACTTCGTGATGAAGTTCCTGAACCTGACCAGCGA<br>GAAGGTGTCCCAGGAAAAGTGACAGAGATGATGAAGAAGTTCTGCG<br>CCCAGCCCTGGGAGGAAATCAAGACCTCCTACGCTGGCGTGAAAGAG<br>AAGTACCTGAGCGAGTTTTGCTTCAGCGGCACCTACATCCTGAGCCTG<br>CTGCAGCAGGGCTACCACTTCACCGCCGATAGCTGGGAGCACATCCA<br>CTTCATCGGCAAGATTCAGGGCAGCGACGCCGGCTGGACACTGGGCT<br>ACATGCTGAATCTGACCAACATGATCCCCGCCGAGCAGCCCCTGAGC<br>ACACCTCTGAGCCACAGCACC |

EP17xEP19aa1-6

| SEQ ID NO: 227 | Amino acid | APTSSSTQNKALPENVKYGIVLDAGSSHTSLYIYKWPAEKENDTGVVHQV<br>EECRVKGPGISKFVQKVNEIGIYLTDCMERAREVIPRSQHQETPVYLGATA<br>GMRLLRMESEELADRVLDVVERSLSNYPFDFQGARIITGQEEGAYGWITI<br>NYLLGKFSQKNQETFGALDLGGASTQVTFVPQNQTIESPDNALQFRLYGK<br>DYNVYTHSFLCYGKDQALWQKLAKDIQVASNEILRDPCFHPGYKKVVNVS<br>DLYKTPCTKRFEMTLPFQQFEIQGIGNYQQCHQSILELFNTSYCPYSQCA<br>FNGIFLPPLQGDFGAFSAFYFVMKFLNLTSEKVSQEKVTEMMKKFCAQP<br>WEEIKTSYAGVKEKYLSEFCFSGTYILSLLQQGYHFTADSWEHIHFIGKIQ<br>GSDAGVVTLGYMLNLTNMIPAEQPLSTPLSHST |
| SEQ ID NO: 228 | DNA | GCCCCTACCAGCAGCAGCACCCAGAACAAGGCCCTGCCCGAGAACGT<br>GAAGTACGGCATCGTGCTGGATGCCGGCAGCAGCCACACCAGCCTGT<br>ACATCTACAAGTGGCCTGCCGAGAAAGAAAACGACACCGGCGTGGTG<br>CATCAGGTGGAAGAGTGCAGAGTGAAGGGCCCTGGCATCAGCAAGTT<br>CGTGCAGAAAGTGAACGAGATCGGCATCTACCTGACCGACTGCATGG<br>AACGGGCCAGGGAAGTGATCCCCAGAAGCCAGCACCAGGAAACCCC<br>CGTGTATCTGGGAGCCACCGCCGGCATGAGACTGCTGAGAATGGAAA<br>GCGAGGAACTGGCCGACCGGGTGCTGGACGTGGTGGAAAGAAGCCT<br>GAGCAACTACCCATTCGATTTTCAAGGCGCCAGAATCATCACCGGCCA<br>GGAAGAAGGCGCCTACGGCTGGATCACCATCAACTACCTGCTGGGCA<br>AGTTCAGCCAGAAGAATCAGGAAACCTTCGGCGCCCTGGACCTGGGC<br>GGAGCTTCTACCCAAGTGACCTTCGTGCCCCAGAATCAGACCATCGA<br>GAGCCCCGACAACGCCCTGCAGTTCCGGCTGTACGGCAAGGACTACA<br>ATGTGTACACCCACAGCTTTCTGTGCTACGGAAAGGACCAGGCTCTGT<br>GGCAGAAGCTGGCCAAGGACATCCAGGTGGCCAGCAACGAGATCCT<br>GCGGGACCCTTGCTTCCACCCCGGCTACAAGAAAGTCGTGAACGTGT<br>CCGACCTGTACAAGACCCCCTGCACCAAGAGATTCGAGATGACCCTG<br>CCCTTCCAGCAGTTCGAGATCCAGGGCATCGGCAATTACCAGCAGTG<br>CCACCAGAGCATCCTGGAACTGTTCAACACCAGCTACTGCCCCTACAG<br>CCAGTGCGCCTTCAACGGCATCTTCCTGCCACCTCTGCAGGGGGATT<br>TCGGCGCCTTCAGCGCCTTCTACTTCGTGATGAAGTTCCTGAACCTGA<br>CCAGCGAGAAGGTGTCCCAGGAAAAGTGACAGAGATGATGAAGAAG<br>TTCTGCGCCCAGCCCTGGGAGGAAATCAAGACCTCCTACGCTGGCGT<br>GAAAGAGAAGTACCTGAGCGAGTTTTGCTTCAGCGGCACCTACATCCT<br>GAGCCTGCTGCAGCAGGGCTACCACTTCACCGCCGATAGCTGGGAGC<br>ACATCCACTTCATCGGCAAGATTCAGGGCAGCGACGCCGGCTGGACA<br>CTGGGCTACATGCTGAATCTGACCAACATGATCCCCGCCGAGCAGCC<br>CCTGAGCACACCTCTGAGCCACAGCACC |

EP14aa1-3

| SEQ ID NO: 229 | Amino acid | APTTQNKALPENVKYGIVLDAGSSHTSLYIYKWPAEKENDTGVVHQVEEC<br>RVKGPGISKFVQKVNEIGIYLTDCMERAREVIPRSQHQETPVYLGATAGM<br>RLLRMESEELADRVLDVVERSLSNYPFDFQGARIITGQEEGAYGWITINYL |

TABLE 35-continued

Sequences useful for practicing the invention.

| SEQ ID Number | Feature | Sequence |
|---|---|---|
| | | LGKFSQKNQETFGALDLGGASTQVTFVPQNQTIESPDNALQFRLYGKDY NVYTHSFLCYGKDQALWQKLAKDIQVASNEILRDPCFHPGYKKVVNVSDL YKTPCTKRFEMTLPFQQFEIQGIGNYQQCHQSILELFNTSYCPYSQCAFN GIFLPPLQGDFGAFSAFYSVMKFLNLTSEKVSQEKVTEMMKKFCAQPWE EIKTSYAGVKEKYLSEYCFSGTYILSLLLQGYHFTADSWEHIHFIGKIQGSD AGWTLGYMLNLTNMIPAEQPLSTPLSHST |
| SEQ ID NO: 230 | DNA | GCCCCTACCACCCAGAACAAGGCCCTGCCCGAGAACGTGAAGTACGG CATCGTGCTGGACGCCGGCTCCTCCCACACCTCCCTGTACATCTACAA GTGGCCTGCCGAGAAAGAAAACGACACCGGCGTGGTGCACCAAGTG GAAGAGTGCAGAGTGAAGGGCCCCGGCATCTCCAAGTTCGTGCAGAA AGTGAACGAGATCGGCATCTACCTGACCGACTGCATGGAACGGGCCA GAGAAGTGATCCCTCGGTCCCAGCACCAGGAAACCCCTGTCTACCTG GGCGCCACCGCCGGCATGCGGCTGCTGCGGATGGAATCCGAGGAAC TGGCCGACCGGGTGCTGGACGTGGTGGAACGGTCCCTGTCCAACTAC CCATTCGATTTTCAAGGCGCCAGAATCATCACCGGCCAGGAAGAGGG CGCCTACGGCTGGATCACCATCAACTACCTGCTGGGCAAGTTCTCCC AGAAGAATCAGGAAACCTTCGGCGCCCTGGACCTGGGCGGAGCCAG CACCCAAGTCACATTCGTGCCCCAGAACCAGACCATCGAGAGCCCCG ACAACGCCCTGCAGTTCCGGCTGTACGGCAAGGACTACAACGTGTAC ACCCACAGCTTTCTGTGCTACGGCAAGGACCAGGCCCTGTGGCAGAA GCTGGCCAAGGACATCCAAGTGGCCTCCAACGAGATCCTGCGGGACC CCTGCTTCCACCCCGGCTACAAGAAAGTGGTCAACGTGTCCGACCTG TACAAGACCCCTTGCACCAAGAGATTCGAGATGACCCTGCCCTTCCAG CAGTTCGAGATCCAGGGCATCGGCAACTACCAGCAGTGCCACCAGTC CATCCTGGAACTGTTCAACACCTCCTACTGCCCCTACTCCCAGTGCGC CTTCAACGGCATCTTCCTGCCTCCACTGCAGGGCGACTTCGGCGCCT TCTCCGCCTTCTACTCCGTGATGAAGTTCCTGAACCTGACCTCCGAGA AGTGTCCCAGGAAAAAGTGACCGAGATGATGAAGAAGTTCTGCGCC CAGCCCTGGGAGGAAATCAAGACCTCCTACGCTGGCGTGAAAGAGAA GTACCTGTCCGAGTACTGCTTCTCCGGCACCTACATCCTGTCCCTGCT GCTGCAGGGCTACCACTTCACCGCCGACAGCTGGGAGCACATCCACT TCATCGGCAAGATCCAGGGATCCGACGCTGGCTGGACCCTGGGCTAC ATGCTGAATCTGACCAACATGATCCCCGCCGAGCAGCCCCTGTCCAC CCCTCTGTCTCACTCCACC |

EP14aa1-6

| SEQ ID NO: 231 | Amino acid | APTSSSTQNKALPENVKYGIVLDAGSSHTSLYIYKWPAEKENDTGVVHQV EECRVKGPGISKFVQKVNEIGIYLTDCMERAREVIPRSQHQETPVYLGATA GMRLLRMESEELADRVLDVVERSLSNYPFDFQGARIITGQEEGAYGWITI NYLLGKFSQKNQETFGALDLGGASTQVTFVPQNQTIESPDNALQFRLYGK DYNVYTHSFLCYGKDQALWQKLAKDIQVASNEILRDPCFHPGYKKVVNVS DLYKTPCTKRFEMTLPFQQFEIQGIGNYQQCHQSILELFNTSYCPYSQCA FNGIFLPPLQGDFGAFSAFYSVMKFLNLTSEKVSQEKVTEMMKKFCAQP WEEIKTSYAGVKEKYLSEYCFSGTYILSLLLQGYHFTADSWEHIHFIGKIQG SDAGWTLGYMLNLTNMIPAEQPLSTPLSHST |
| SEQ ID NO: 232 | DNA | GCCCCTACCAGCAGCAGCACCCAGAACAAGGCCCTGCCCGAGAACGT GAAGTACGGCATCGTGCTGGATGCCGGCAGCAGCCACACCAGCCTGT ACATCTACAAGTGGCCTGCCGAGAAAGAAAACGACACCGGCGTGGTG CATCAGGTGGAAGAGTGCAGAGTGAAGGGCCCTGGCATCAGCAAGTT CGTGCAGAAAGTGAACGAGATCGGCATCTACCTGACCGACTGCATGG AACGGGCCAGGGAAGTGATCCCCAGAAGCCAGCACCAGGAAACCCC CGTGTATCTGGGAGCCACCGCCGGCATGAGACTGCTGAGAATGGAAA GCGAGGAACTGGCCGACCGGGTGCTGGACGTGGTGGAAAGAAGCCT GAGCAACTACCCATTCGATTTTCAAGGCGCCAGAATCATCACCGGCCA GGAAGAAGGCGCCTACGGCTGGATCACCATCAACTACCTGCTGGGCA AGTTCAGCCAGAAGAATCAGGAAACCTTCGGCGCCTTGGACCTGGGC GGAGCTTCTACCCAAGTGACCTTCGTGCCCCAGAATCAGACCATCGA GAGCCCCGACAACGCCCTGCAGTTCCGGCTGTACGGCAAGGACTACA ATGTGTACACCCACAGCTTTCTGTGCTACGGAAAGGACCAGGCTCTGT GGCAGAAGCTGGCCAAGGACATCCAGGTGGCCAGCAACGAGATCCT GCGGGACCCTTGCTTCCACCCCGGCTACAAGAAAGTCGTGAACGTGT CCGACCTGTACAAGACCCCTGCACCAAGAGATTCGAGATGACCCTG CCCTTCCAGCAGTTCGAGATCCAGGGCATCGGCAATTACCAGCAGTG CCACCAGAGCATCCTGGAACTGTTCAACACCAGCTACTGCCCCTACAG CCAGTGCGCCTTCAACGGCATCTTCCTGCCACCTCTGCAGGGGGATT TCGGCGCCTTCAGCGCCTTCTACTCCGTGATGAAGTTCCTGAACCTGA CCAGCGAGAAGGTGTCCCAGGAAAAAGTGACAGAGATGATGAAGAAG TTCTGCGCCCAGCCCTGGGAGGAAATCAAGACCTCCTACGCTGGCGT |

TABLE 35-continued

Sequences useful for practicing the invention.

| SEQ ID Number | Feature | Sequence |
|---|---|---|
| | | GAAAGAGAAGTACCTGAGCGAGTACTGCTTCAGCGGCACCTACATCC<br>TGAGCCTGCTGCTGCAGGGCTACCACTTCACCGCCGATAGCTGGGAG<br>CACATCCACTTCATCGGCAAGATTCAGGGCAGCGACGCCGGCTGGAC<br>ACTGGGTTACATGCTGAATCTGACCAACATGATCCCCGCCGAGCAGC<br>CCCTGAGCACACCTCTGAGCCACAGCACC |

EP1xEP14xEP19aa1-3

| SEQ ID NO: 233 | Amino acid | APTTQNKALPENVKYGIVLDAGSSHTSLYIYKWPAEKENDTGVVHQVEEC<br>RVKGPGISKFVQKVNEIGIYLTDCMERAMEVIPRSQHQETPVYLGATAGM<br>RLLRMESEELADRVLDVVERSLSNYPFDFQGARIITGQEEGAYGWITINYL<br>LGKFSQKNQETFGALDLGGASTQVTFVPQNQTIESPDNALQFRLYGKDY<br>NVYTHSFLCYGKDQALWQKLAKDIQVASNEILRDPCFHPGYKKVVNVSDL<br>YKTPCTKRFEMTLPFQQFEIQGIGNYQQCHQSILELFNTSYCPYSQCAFN<br>GIFLPPLQGDFGAFSAFYSVMKFLNLTSEKVSQEKVTEMMKKFCAQPWE<br>EIKTSYAGVKEKYLSEYCFSGTYILSLLQQGYHFTADSWEHIHFIGKIQGSD<br>AGWTLGYMLNLTNMIPAEQPLSTPLSHST |
| SEQ ID NO: 234 | DNA | GCCCCTACCACCCAGAACAAGGCCCTGCCCGAGAACGTGAAGTACGG<br>CATCGTGCTGGATGCCGGCAGCAGCCACACCAGCCTGTACATCTACA<br>AGTGGCCTGCCGAGAAAGAAAACGACACCGGCGTGGTGCATCAGGTG<br>GAAGAGTGCAGAGTGAAGGGCCCTGGCATCAGCAAGTTCGTGCAGAA<br>AGTGAACGAGATCGGCATCTACCTGACCGACTGCATGGAACGGGCCA<br>TGGAAGTGATCCCCAGAAGCCAGCACCAGGAAACCCCCGTGTATCTG<br>GGAGCCACCGCCGGCATGAGACTGCTGAGAATGGAAAGCGAGGAAC<br>TGGCCGACCGGGTGCTGGACGTGGTGGAAAGAAGCCTGAGCAACTA<br>CCCATTCGATTTTCAAGGCGCCAGAATCATCACCGGCCAGGAAGAAG<br>GCGCCTACGGCTGGATCACCATCAACTACCTGCTGGGCAAGTTCAGC<br>CAGAAGAATCAGGAAACCTTCGGCGCCCTGGACCTGGGCGGAGCTTC<br>TACCCAAGTGACCTTCGTGCCCCAGAATCAGACCATCGAGAGCCCCG<br>ACAACGCCCTGCAGTTCCGGCTGTACGGCAAGGACTACAATGTGTAC<br>ACCCACAGCTTTCTGTGCTACGGAAAGGACCAGGCTCTGTGGCAGAA<br>GCTGGCCAAGGACATCCAGGTGGCCAGCAACGAGATCCTGCGGGAC<br>CCTTGCTTCCACCCCGGCTACAAGAAAGTCGTGAACGTGTCCGACCT<br>GTACAAGACCCCCTGCACCAAGAGATTCGAGATGACCCTGCCCTTCC<br>AGCAGTTCGAGATCCAGGGCATCGGCAATTACCAGCAGTGCCACCAG<br>AGCATCCTGGAACTGTTCAACACCAGCTACTGCCCCTACAGCCAGTGC<br>GCCTTCAACGGCATCTTCCTGCCACCTCTGCAGGGGGATTTCGGCGC<br>CTTCAGCGCCTTCTACTCCGTGATGAAGTTCCTGAACCTGACCAGCGA<br>GAAGGTGTCCCAGGAAAAGTGACAGAGATGATGAAGAAGTTCTGCG<br>CCCAGCCCTGGGAGGAAATCAAGACCTCCTACGCTGGCGTGAAAGAG<br>AAGTACCTGAGCGAGTACTGCTTCAGCGGCACCTACATCCTGAGCCT<br>GCTGCAGCAGGGCTACCACTTCACCGCCGATAGCTGGGAGCACATCC<br>ACTTCATCGGCAAGATTCAGGGCAGCGACGCCGGCTGGACACTGGGC<br>TACATGCTGAATCTGACCAACATGATCCCCGCCGAGCAGCCCCTGAG<br>CACACCTCTGAGCCACAGCACC |

EP1xEP14xEP19aa1-6

| SEQ ID NO: 235 | Amino acid | APTSSSTQNKALPENVKYGIVLDAGSSHTSLYIYKWPAEKENDTGVVHQV<br>EECRVKGPGISKFVQKVNEIGIYLTDCMERAMEVIPRSQHQETPVYLGAT<br>AGMRLLRMESEELADRVLDVVERSLSNYPFDFQGARIITGQEEGAYGWIT<br>INYLLGKFSQKNQETFGALDLGGASTQVTFVPQNQTIESPDNALQFRLYG<br>KDYNVYTHSFLCYGKDQALWQKLAKDIQVASNEILRDPCFHPGYKKVVNV<br>SDLYKTPCTKRFEMTLPFQQFEIQGIGNYQQCHQSILELFNTSYCPYSQC<br>AFNGIFLPPLQGDFGAFSAFYSVMKFLNLTSEKVSQEKVTEMMKKFCAQP<br>WEEIKTSYAGVKEKYLSEYCFSGTYILSLLQQGYHFTADSWEHIHFIGKIQ<br>GSDAGWTLGYMLNLTNMIPAEQPLSTPLSHST |
| SEQ ID NO: 236 | DNA | GCCCCTACCAGCAGCAGCACCCAGAACAAGGCCCTGCCCGAGAACGT<br>GAAGTACGGCATCGTGCTGGATGCCGGCAGCAGCCACACCAGCCTGT<br>ACATCTACAAGTGGCCTGCCGAGAAAGAAAACGACACCGGCGTGGTG<br>CATCAGGTGGAAGAGTGCAGAGTGAAGGGCCCTGGCATCAGCAAGTT<br>CGTGCAGAAAGTGAACGAGATCGGCATCTACCTGACCGACTGCATGG<br>AACGGGCCATGGAAGTGATCCCCAGAAGCCAGCACCAGGAAACCCCC<br>GTGTATCTGGGAGCCACCGCCGGCATGAGACTGCTGAGAATGGAAAG<br>CGAGGAACTGGCCGACCGGGTGCTGGACGTGGTGGAAAGAAGCCTG<br>AGCAACTACCCATTCGATTTTCAAGGCGCCAGAATCATCACCGGCCAG<br>GAAGAAGGCGCCTACGGCTGGATCACCATCAACTACCTGCTGGGCAA<br>GTTCAGCCAGAAGAATCAGGAAACCTTCGGCGCCCTGGACCTGGGCG<br>GAGCTTCTACCCAAGTGACCTTCGTGCCCCAGAATCAGACCATCGAGA<br>GCCCCGACAACGCCCTGCAGTTCCGGCTGTACGGCAAGGACTACAAT<br>GTGTACACCCACAGCTTTCTGTGCTACGGAAAGGACCAGGCTCTGTG<br>GCAGAAGCTGGCCAAGGACATCCAGGTGGCCAGCAACGAGATCCTGC<br>GGGACCCTTGCTTCCACCCCGGCTACAAGAAAGTCGTGAACGTGTCC |

TABLE 35-continued

Sequences useful for practicing the invention.

| SEQ ID Number | Feature | Sequence |
|---|---|---|
| | | GACCTGTACAAGACCCCTGCACCAAGAGATTCGAGATGACCCTGCC<br>CTTCCAGCAGTTCGAGATCCAGGGCATCGGCAATTACCAGCAGTGCC<br>ACCAGAGCATCCTGGAACTGTTCAACACCAGCTACTGCCCCTACAGC<br>AGTGCGCCTTCAACGGCATCTTCCTGCCCACCTCTGCAGGGGGATTTC<br>GGCGCCTTCAGCGCCTTCTACTCCGTGATGAAGTTCCTGAACCTGACC<br>AGCGAGAAGGTGTCCCAGGAAAAAGTGACAGAGATGATGAAGAAGTT<br>CTGCGCCCAGCCCTGGGAGGAAATCAAGACCTCCTACGCTGGCGTGA<br>AAGAGAAGTACCTGAGCGAGTACTGCTTCAGCGGCACCTACATCCTG<br>AGCCTGCTGCAGCAGGGCTACCACTTCACCGCCGATAGCTGGGAGCA<br>CATCCACTTCATCGGCAAGATTCAGGGCAGCGACGCCGGCTGGACAC<br>TGGGCTACATGCTGAATCTGACCAACATGATCCCCGCCGAGCAGCCC<br>CTGAGCACACCTCTGAGCCACAGCACC |

EP17aa1-3

| SEQ ID NO: 237 | Amino acid | APTTQNKALPENVKYGIVLDAGSSHTSLYIYKWPAEKENDTGVVHQVEEC<br>RVKGPGISKFVQKVNEIGIYLTDCMERAREVIPRSQHQETPVYLGATAGM<br>RLLRMESEELADRVLDVVERSLSNYPFDFQGARIITGQEEGAYGWITINYL<br>LGKFSQKNQETFGALDLGGASTQVTFVPQNQTIESPDNALQFRLYGKDY<br>NVYTHSFLCYGKDQALWQKLAKDIQVASNEILRDPCFHPGYKKVVNVSDL<br>YKTPCTKRFEMTLPFQQFEIQGIGNYQQCHQSILELFNTSYCPYSQCAFN<br>GIFLPPLQGDFGAFSAFYFVMKFLNLTSEKVSQEKVTEMMKKFCAQPWE<br>EIKTSYAGVNEKYLSEFCFSGTYILSLLLQGYHFTADSWEHIHFIGKIQGSD<br>AGWTLGYMLNLTNMIPAEQPLSTPLSHST |
| SEQ ID NO: 238 | DNA | GCCCCTACCACCCAGAACAAGGCCCTGCCCGAGAACGTGAAGTACGG<br>CATCGTGCTGGATGCCGGCAGCAGCCACACCAGCCTGTACATCTACA<br>AGTGGCCTGCCGAGAAGAAAACGACACCGGCGTGGTGCATCAGGTG<br>GAAGAGTGCAGAGTGAAGGGCCCTGGCATCAGCAAGTTCGTGCAGAA<br>AGTGAACGAGATCGGCATCTACCTGACCGACTGCATGGAACGGGCCA<br>GGGAAGTGATCCCCAGAAGCCAGCACCAGGAAACCCCCGTGTATCTG<br>GGAGCCACCGCCGGCATGAGACTGCTGAGAATGGAAAGCGAGGAAC<br>TGGCCGACCGGGTGCTGGACGTGGTGGAAAGAAGCCTGAGCAACTA<br>CCCATTCGATTTTCAAGGCGCCAGAATCATCACCGGCCAGGAAGAAG<br>GCGCCTACGGCTGGATCACCATCAACTACCTGCTGGGCAAGTTCAGC<br>CAGAAGAATCAGGAAACCTTCGGCGCCCTGGACCTGGGCGGAGCTTC<br>TACCCAAGTGACCTTCGTGCCCCAGAATCAGACCATCGAGAGCCCCG<br>ACAACGCCCTGCAGTTCCGGCTGTACGGCAAGGACTACAATGTGTAC<br>ACCCACAGCTTTCTGTGCTACGGAAAGGACCAGGCTCTGTGGCAGAA<br>GCTGGCCAAGGACATCCAGGTGGCCAGCAACGAGATCCTGCGGGAC<br>CCTTGCTTCCACCCCGGCTACAAGAAAGTCGTGAACGTGTCCGACCT<br>GTACAAGACCCCCTGCACCAAGAGATTCGAGATGACCCTGCCCTTCC<br>AGCAGTTCGAGATCCAGGGCATCGGCAATTACCAGCAGTGCCACCAG<br>AGCATCCTGGAACTGTTCAACACCAGCTACTGCCCCTACAGCCAGTGC<br>GCCTTCAACGGCATCTTCCTGCCCACCTCTGCAGGGGGATTTCGGCGC<br>CTTCAGCGCCTTCTACTTCGTGATGAAGTTCCTGAACCTGACCAGCGA<br>GAAGGTGTCCCAGGAAAAAGTGACAGAGATGATGAAGAAGTTCTGCG<br>CCCAACCCTGGGAGGAAATCAAGACCTCCTACGCTGGCGTGAACGAG<br>AAGTACCTGAGCGAGTTTTGCTTCAGCGGCACCTACATCCTGAGCCTG<br>CTGCAGGGCTACCACTTCACCGCCGATAGCTGGGAGCACATCCA<br>CTTCATCGGCAAGATTCAGGGCAGCGACGCCGGCTGGACACTGGGCT<br>ACATGCTGAATCTGACCAACATGATCCCCGCCGAGCAGCCCCTGAGC<br>ACACCTCTGAGCCACAGCACC |

EP17aa1-6

| SEQ ID NO: 239 | Amino acid | APTSSSTQNKALPENVKYGIVLDAGSSHTSLYIYKWPAEKENDTGVVHQV<br>EECRVKGPGISKFVQKVNEIGIYLTDCMERAREVIPRSQHQETPVYLGATA<br>GMRLLRMESEELADRVLDVVERSLSNYPFDFQGARIITGQEEGAYGWITI<br>NYLLGKFSQKNQETFGALDLGGASTQVTFVPQNQTIESPDNALQFRLYGK<br>DYNVYTHSFLCYGKDQALWQKLAKDIQVASNEILRDPCFHPGYKKVVNVS<br>DLYKTPCTKRFEMTLPFQQFEIQGIGNYQQCHQSILELFNTSYCPYSQCA<br>FNGIFLPPLQGDFGAFSAFYFVMKFLNLTSEKVSQEKVTEMMKKFCAQP<br>WEEIKTSYAGVNEKYLSEFCFSGTYILSLLLQGYHFTADSWEHIHFIGKIQG<br>SDAGWTLGYMLNLTNMIPAEQPLSTPLSHST |
| SEQ ID NO: 240 | DNA | GCCCCTACCAGCAGCAGCACCCAGAACAAGGCCCTGCCCGAGAACGT<br>GAAGTACGGCATCGTGCTGGATGCCGGCAGCAGCCACACCAGCCTGT<br>ACATCTACAAGTGGCCTGCCGAGAAGAAAACGACACCGGCGTGGTG<br>CATCAGGTGGAAGAGTGCAGAGTGAAGGGCCCTGGCATCAGCAAGTT<br>CGTGCAGAAAGTGAACGAGATCGGCATCTACCTGACCGACTGCATGG<br>AACGGGCCAGGGAAGTGATCCCCAGAAGCCAGCACCAGGAAACCCC<br>CGTGTATCTGGGAGCCACCGCCGGCATGAGACTGCTGAGAATGGAAA<br>GCGAGGAACTGGCCGACCGGGTGCTGGACGTGGTGGAAAGAAGCCT<br>GAGCAACTACCCATTCGATTTTCAAGGCGCCAGAATCATCACCGGCCA |

TABLE 35-continued

Sequences useful for practicing the invention.

| SEQ ID Number | Feature | Sequence |
|---|---|---|
| | | GGAAGAAGGCGCCTACGGCTGGATCACCATCAACTACCTGCTGGGCA AGTTCAGCCAGAAGAATCAGGAAACCTTCGGCGCCCTGGACCTGGGC GGAGCTTCTACCCAAGTGACCTTCGTGCCCCAGAATCAGACCATCGA GAGCCCCGACAACGCCCTGCAGTTCCGGCTGTACGGCAAGGACTACA ATGTGTACACCCACAGCTTTCTGTGCTACGGAAAGGACCAGGCTCTGT GGCAGAAGCTGGCCAAGGACATCCAGGTGGCCAGCAACGAGATCCT GCGGGACCCTTGCTTCCACCCCGGCTACAAGAAAGTCGTGAACGTGT CCGACCTGTACAAGACCCCCTGCACCAAGAGATTCGAGATGACCCTG CCCTTCCAGCAGTTCGAGATCCAGGGCATCGGCAATTACCAGCAGTG CCACCAGAGCATCCTGGAACTGTTCAACACCAGCTACTGCCCCTACAG CCAGTGCGCCTTCAACGGCATCTTCCTGCCACCTCTGCAGGGGGATT TCGGCGCCTTCAGCGCCTTCTACTTCGTGATGAAGTTCCTGAACCTGA CCAGCGAGAAGGTGTCCCAGGAAAAAGTGACAGAGATGATGAAGAAG TTCTGCGCCCAACCCTGGGAGGAAATCAAGACCTCCTACGCTGGCGT GAACGAGAAGTACCTGAGCGAGTTTTGCTTCAGCGGCACCTACATCCT GAGCCTGCTGCTGCAGGGCTACCACTTCACCGCCGATAGCTGGGAGC ACATCCACTTCATCGGCAAGATTCAGGGCAGCGACGCCGGCTGGACA CTGGGCTACATGCTGAATCTGACCAACATGATCCCCGCCGAGCAGCC CCTGAGCACACCTCTGAGCCACAGCACC |

EP17aa1-15

| SEQ ID NO: 241 | Amino acid | APTSSSTKKTQLTSSTQNKALPENVKYGIVLDAGSSHTSLYIYKWPAEKEN DTGVVHQVEECRVKGPGISKFVQKVNEIGIYLTDCMERAREVIPRSQHQE TPVYLGATAGMRLLRMESEELADRVLDVVERSLSNYPFDFQGARIITGQE EGAYGWITINYLLGKFSQKNQETFGALDLGGASTQVTFVPQNQTIESPDN ALQFRLYGKDYNVYTHSFLCYGKDQALWQKLAKDIQVASNEILRDPCFHP GYKKVVNVSDLYKTPCTKRFEMTLPFQQFEIQGIGNYQQCHQSILELFNT SYCPYSQCAFNGIFLPPLQGDFGAFSAFYFVMKFLNLTSEKVSQEKVTEM MKKFCAQPWEEIKTSYAGVNEKYLSEFCFSGTYILSLLLQGYHFTADSWE HIHFIGKIQGSDAGWTLGYMLNLTNMIPAEQPLSTPLSHST |
| SEQ ID NO: 242 | DNA | GCCCCTACCAGCAGCAGCACCAAGAAAACCCAGCTGACCAGCAGCAC CCAGAACAAGGCCCTGCCCGAGAACGTGAAGTACGGCATCGTGCTGG ATGCCGGCAGCAGCCACACCAGCCTGTACATCTACAAGTGGCCTGCC GAGAAAGAAAACGACACCGGCGTGGTGCATCAGGTGGAAGAGTGCAG AGTGAAGGGCCCTGGCATCAGCAAGTTCGTGCAGAAAGTGAACGAGA TCGGCATCTACCTGACCGACTGCATGGAACGGGCCAGGGAAGTGATC CCCAGAAGCCAGCACCAGGAAACCCCCGTGTATCTGGGAGCCACCGC CGGCATGAGACTGCTGAGAATGGAAAGCGAGGAACTGGCCGACCGG GTGCTGGACGTGGTGGAAAGAAGCCTGAGCAACTACCCATTCGATTTT CAAGGCGCCAGAATCATCACCGGCCAGGAAGAAGGCGCCTACGGCT GGATCACCATCAACTACCTGCTGGGCAAGTTCAGCCAGAAGAATCAG GAAACCTTCGGCGCCCTGGACCTGGGCGGAGCTTCTACCCAAGTGAC CTTCGTGCCCCAGAATCAGACCATCGAGAGCCCCGACAACGCCCTGC AGTTCCGGCTGTACGGCAAGGACTACAATGTGTACACCCACAGCTTTC TGTGCTACGGAAAGGACCAGGCTCTGTGGCAGAAGCTGGCCAAGGAC ATCCAGGTGGCCAGCAACGAGATCCTGCGGGACCCTTGCTTCCACCC CGGCTACAAGAAAGTCGTGAACGTGTCCGACCTGTACAAGACCCCCT GCACCAAGAGATTCGAGATGACCCTGCCCTTCCAGCAGTTCGAGATC CAGGGCATCGGCAATTACCAGCAGTGCCACCAGAGCATCCTGGAACT GTTCAACACCAGCTACTGCCCCTACAGCCAGTGCGCCTTCAACGGCA TCTTCCTGCCACCTCTGCAGGGGGATTTCGGCGCCTTCAGCGCCTTC TACTTCGTGATGAAGTTCCTGAACCTGACCAGCGAGAAGGTGTCCCAG GAAAAAGTGACAGAGATGATGAAGAAGTTCTGCGCCCAACCCTGGGA GGAAATCAAGACCTCCTACGCTGGCGTGAACGAGAAGTACCTGAGCG AGTTTTGCTTCAGCGGCACCTACATCCTGAGCCTGCTGCTGCAGGGC TACCACTTCACCGCCGATAGCTGGGAGCACATCCACTTCATCGGCAA GATTCAGGGCAGCGACGCCGGCTGGACACTGGGCTACATGCTGAATC TGACCAACATGATCCCCGCCGAGCAGCCCCTGAGCACACCTCTGAGC CACAGCACC |

EP19aa1-3

| SEQ ID NO: 243 | Amino acid | APTTQNKALPENVKYGIVLDAGSSHTSLYIYKWPAEKENDTGVVHQVEEC RVKGPGISKFVQKVNEIGIYLTDCMERAREVIPRSQHQETPVYLGATAGM RLLRMESEELADRVLDVVERSLSNYPFDFQGARIITGQEEGAYGWITINYL LGKFSQKNQETFGALDLGGASTQVTFVPQNQTIESPDNALQFRLYGKDY NVYTHSFLCYGKDQALWQKLAKDIQVASNEILRDPCFHPGYKKVVNVSDL YKTPCTKRFEMTLPFQQFEIQGIGNYQQCHQSILELFNTSYCPYSQCAFN GIFLPPLQGDFGAFSAFYFVMKFLNLTSEKVSQEKVTEMMKKFCAQPWE EIKTSYAGVKEKYLSEYCFSGTYILSLLQQGYHFTADSWEDIHFIGKIQGSD AGWTLGYMLNLTNMIPAEQPLSTPLSHST |

TABLE 35-continued

Sequences useful for practicing the invention.

| SEQ ID Number | Feature | Sequence |
|---|---|---|
| SEQ ID NO: 244 | DNA | GCCCCTACCACCCAGAACAAGGCCCTGCCCGAGAACGTGAAGTACGG<br>CATCGTGCTGGATGCCGGCAGCAGCCACACCAGCCTGTACATCTACA<br>AGTGGCCTGCCGAGAAAGAAAACGACACCGGCGTGGTGCATCAGGTG<br>GAAGAGTGCAGAGTGAAGGGCCCTGGCATCAGCAAGTTCGTGCAGAA<br>AGTGAACGAGATCGGCATCTACCTGACCGACTGCATGGAACGGGCCA<br>GGGAAGTGATCCCCAGAAGCCAGCACCAGGAAACCCCCGTGTATCTG<br>GGAGCCACCGCCGGCATGAGACTGCTGAGAATGGAAAGCGAGGAAC<br>TGGCCGACCGGGTGCTGGACGTGGTGGAAAGAAGCCTGAGCAACTA<br>CCCATTCGATTTTCAAGGCGCCAGAATCATCACCGGCCAGGAAGAAG<br>GCGCCTACGGCTGGATCACCATCAACTACCTGCTGGGCAAGTTCAGC<br>CAGAAGAATCAGGAAACCTTCGGCGCCCTGGACCTGGGCGGAGCTTC<br>TACCCAAGTGACCTTCGTGCCCCAGAATCAGACCATCGAGAGCCCCG<br>ACAACGCCCTGCAGTTCCGGCTGTACGGCAAGGACTACAATGTGTAC<br>ACCCACAGCTTTCTGTGCTACGGAAAGGACCAGGCTCTGTGGCAGAA<br>GCTGGCCAAGGACATCCAGGTGGCCAGCAACGAGATCCTGCGGGAC<br>CCTTGCTTCCACCCCGGCTACAAGAAAGTCGTGAACGTGTCCGACCT<br>GTACAAGACCCCCTGCACCAAGAGATTCGAGATGACCCTGCCCTTCC<br>AGCAGTTCGAGATCCAGGGCATCGGCAATTACCAGCAGTGCCACCAG<br>AGCATCCTGGAACTGTTCAACACCAGCTACTGCCCCTACAGCCAGTGC<br>GCCTTCAACGGCATCTTCCTGCCACCTCTGCAGGGGGATTTCGGCGC<br>CTTCAGCGCCTTCTACTTCGTGATGAAGTTCCTGAACCTGACCAGCGA<br>GAAGGTGTCCCAGGAAAAGTGACAGAGATGATGAAGAAGTTCTGCG<br>CCCAGCCCTGGGAGGAAATCAAGACCTCCTACGCTGGCGTGAAAGAG<br>AAGTACCTGAGCGAGTACTGCTTCAGCGGCACCTACATCCTGAGCCT<br>GCTGCAGCAGGGCTACCACTTCACCGCCGATAGCTGGGAGGACATCC<br>ACTTCATCGGCAAGATTCAGGGCAGCGACGCCGGCTGGACACTGGGC<br>TACATGCTGAATCTGACCAACATGATCCCCGCCGAGCAGCCCCTGAG<br>CACACCTCTGAGCCACAGCACC |

EP19aa1-6

| SEQ ID NO: 245 | Amino acid | APTSSSTQNKALPENVKYGIVLDAGSSHTSLYIYKWPAEKENDTGVVHQV<br>EECRVKGPGISKFVQKVNEIGIYLTDCMERAREVIPRSQHQETPVYLGATA<br>GMRLLRMESEELADRVLDVVERSLSNYPFDFQGARIITGQEEGAYGWITI<br>NYLLGKFSQKNQETFGALDLGGASTQVTFVPQNQTIESPDNALQFRLYGK<br>DYNVYTHSFLCYGKDQALWQKLAKDIQVASNEILRDPCFHPGYKKVVNVS<br>DLYKTPCTKRFEMTLPFQQFEIQGIGNYQQCHQSILELFNTSYCPYSQCA<br>FNGIFLPPLQGDFGAFSAFYFVMKFLNLTSEKVSQEKVTEMMKKFCAQP<br>WEEIKTSYAGVKEKYLSEYCFSGTYILSLLQQGYHFTADSWEDIHFIGKIQ<br>GSDAGWTLGYMLNLTNMIPAEQPLSTPLSHST |
| SEQ ID NO: 246 | DNA | GCCCCTACCAGCAGCAGCACCCAGAACAAGGCCCTGCCCGAGAACGT<br>GAAGTACGGCATCGTGCTGGATGCCGGCAGCAGCCACACCAGCCTGT<br>ACATCTACAAGTGGCCTGCCGAGAAAGAAAACGACACCGGCGTGGTG<br>CATCAGGTGGAAGAGTGCAGAGTGAAGGGCCCTGGCATCAGCAAGTT<br>CGTGCAGAAAGTGAACGAGATCGGCATCTACCTGACCGACTGCATGG<br>AACGGGCCAGGGAAGTGATCCCCAGAAGCCAGCACCAGGAAACCCC<br>CGTGTATCTGGGAGCCACCGCCGGCATGAGACTGCTGAGAATGGAAA<br>GCGAGGAACTGGCCGACCGGGTGCTGGACGTGGTGGAAAGAAGCCT<br>GAGCAACTACCCATTCGATTTTCAAGGCGCCAGAATCATCACCGGCCA<br>GGAAGAAGGCGCCTACGGCTGGATCACCATCAACTACCTGCTGGGCA<br>AGTTCAGCCAGAAGAATCAGGAAACCTTCGGCGCCCTGGACCTGGGC<br>GGAGCTTCTACCCAAGTGACCTTCGTGCCCCAGAATCAGACCATCGA<br>GAGCCCCGACAACGCCCTGCAGTTCCGGCTGTACGGCAAGGACTACA<br>ATGTGTACACCCACAGCTTTCTGTGCTACGGAAAGGACCAGGCTCTGT<br>GGCAGAAGCTGGCCAAGGACATCCAGGTGGCCAGCAACGAGATCCT<br>GCGGGACCCTTGCTTCCACCCCGGCTACAAGAAAGTCGTGAACGTGT<br>CCGACCTGTACAAGACCCCCTGCACCAAGAGATTCGAGATGACCCTG<br>CCCTTCCAGCAGTTCGAGATCCAGGGCATCGGCAATTACCAGCAGTG<br>CCACCAGAGCATCCTGGAACTGTTCAACACCAGCTACTGCCCCTACAG<br>CCAGTGCGCCTTCAACGGCATCTTCCTGCCACCTCTGCAGGGGGATT<br>TCGGCGCCTTCAGCGCCTTCTACTTCGTGATGAAGTTCCTGAACCTGA<br>CCAGCGAGAAGGTGTCCCAGGAAAAGTGACAGAGATGATGAAGAAG<br>TTCTGCGCCCAGCCCTGGGAGGAAATCAAGACCTCCTACGCTGGCGT<br>GAAAGAGAAGTACCTGAGCGAGTACTGCTTCAGCGGCACCTACATCC<br>TGAGCCTGCTGCAGCAGGGCTACCACTTCACCGCCGATAGCTGGGAG<br>GACATCCACTTCATCGGCAAGATTCAGGGCAGCGACGCCGGCTGGAC<br>ACTGGGCTACATGCTGAATCTGACCAACATGATCCCCGCCGAGCAGC<br>CCCTGAGCACACCTCTGAGCCACAGCACC |
| SEQ ID NO: 247 | Amino acid | EFRHDS |
| SEQ ID NO: 248 | DNA | GAATTCCGGCACGACAGC |

TABLE 35-continued

Sequences useful for practicing the invention.

| SEQ ID Number | Feature | Sequence |
|---|---|---|
| SEQ ID NO: 249 | Amino acid | HHHHHH |
| SEQ ID NO: 250 | DNA | CATCATCATCATCATCAC |

The invention claimed is:

1. A solubilized human apyrase comprising an amino acid sequence selected from the group consisting of SEQ ID NO: 58, SEQ ID NO: 74, and SEQ ID NO: 229.

2. The solubilized human apyrase of claim 1, comprising the amino acid sequence set forth in SEQ ID. No. 58.

3. The solubilized human apyrase of claim 1, comprising the amino acid sequence set forth in SEQ ID NO. 74.

4. The solubilized human apyrase of claim 1, comprising the amino acid sequence set forth in SEQ ID NO. 229.

5. A pharmaceutical composition comprising a solubilized human apyrase and one or more pharmaceutically acceptable carriers, wherein the solubilized human apyrase comprises an amino acid sequence selected from the group consisting of SEQ ID NO. 58, SEQ ID NO. 74, and SEQ ID NO. 229.

6. The pharmaceutical composition of claim 5, wherein the solubilized human apyrase comprises the amino acid sequence set forth in SEQ ID NO. 58.

7. The pharmaceutical composition of claim 5, wherein the solubilized human apyrase comprises the amino acid sequence set forth in SEQ ID NO. 74.

8. The pharmaceutical composition of claim 5, wherein the solubilized human apyrase comprises the amino acid sequence set forth in SEQ ID NO. 229.

* * * * *